(12) United States Patent
Toledo-Sherman et al.

(10) Patent No.: US 11,685,734 B2
(45) Date of Patent: Jun. 27, 2023

(54) ATM KINASE INHIBITORS AND COMPOSITIONS AND METHODS OF USE THEREOF

(71) Applicant: CHDI Foundation, Inc., New York, NY (US)

(72) Inventors: Leticia M. Toledo-Sherman, Santa Monica, CA (US); Celia Dominguez, Los Angeles, CA (US); Perla Breccia, Cambridge (GB); Amanda J. Van De Poël, Saffron Walden (GB); Grant Wishart, Airdrie (GB); Huw D. Vater, Saffron Walden (GB); William R. K. Esmieu, Cambridge (GB); Cole Clissold, Cambridge (GB); Wesley P. Blackaby, Longstowe (GB)

(73) Assignee: CHDI Foundation, Inc., New York, NY (US)

( * ) Notice: Subject to any disclaimer, the term of this patent is extended or adjusted under 35 U.S.C. 154(b) by 232 days.

(21) Appl. No.: 17/111,307

(22) Filed: Dec. 3, 2020

(65) Prior Publication Data

US 2021/0188827 A1    Jun. 24, 2021

Related U.S. Application Data

(60) Provisional application No. 62/943,694, filed on Dec. 4, 2019.

(51) Int. Cl.

| | | |
|---|---|---|
| *C07D 401/04* | (2006.01) |
| *C07D 401/14* | (2006.01) |
| *C07D 403/14* | (2006.01) |
| *C07D 405/14* | (2006.01) |
| *C07D 407/14* | (2006.01) |
| *C07D 409/14* | (2006.01) |
| *C07D 413/04* | (2006.01) |
| *C07D 413/14* | (2006.01) |
| *C07D 417/14* | (2006.01) |
| *A61K 31/55* | (2006.01) |
| *A61K 31/5377* | (2006.01) |
| *A61K 31/505* | (2006.01) |
| *A61P 21/00* | (2006.01) |
| *A61P 25/08* | (2006.01) |
| *A61P 25/14* | (2006.01) |
| *A61P 25/16* | (2006.01) |
| *A61P 27/02* | (2006.01) |

(52) U.S. Cl.
CPC ......... *C07D 413/14* (2013.01); *C07D 401/04* (2013.01); *C07D 401/14* (2013.01); *C07D 403/14* (2013.01); *C07D 405/14* (2013.01); *C07D 409/14* (2013.01); *C07D 413/04* (2013.01)

(58) Field of Classification Search
CPC .. C07D 401/04; C07D 401/14; C07D 403/14; C07D 405/14; C07D 407/14; C07D 409/14; C07D 413/04; C07D 413/14; C07D 417/14; A61K 31/55; A61K 31/5377; A61K 31/505; A61P 21/00; A61P 25/08; A61P 25/14; A61P 25/16; A61P 27/02
See application file for complete search history.

(56) References Cited

U.S. PATENT DOCUMENTS

2021/0161906 A1* 6/2021 Martinsson ............. A61P 25/00

FOREIGN PATENT DOCUMENTS

| WO | WO 2016/155884 A1 | 10/2016 |
| WO | WO 2017/140843 A1 | 8/2017 |
| WO | WO 2017/162611 A1 | 9/2017 |
| WO | WO 2018/153365 A1 | 8/2018 |

OTHER PUBLICATIONS

International Search Report and Written Opinion dated Mar. 10, 2021 for PCT/US2020/063103, 9 pages.
Flemming, A., "Huntington disease: Banking on ATM", Nature Reviews Drug Discovery, vol. 14, No. 2, p. 93 (Feb. 2015).

* cited by examiner

*Primary Examiner* — Bruck Kifle
(74) *Attorney, Agent, or Firm* — Sheppard Mullin Richter & Hampton LLP

(57) ABSTRACT

Provided are certain ATM kinase inhibitors of Formula I:

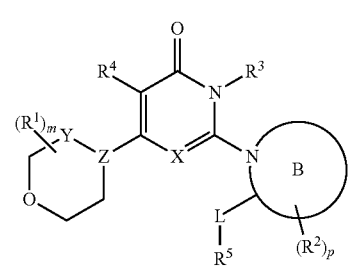

Also provided herein are compositions of such compounds, and methods of their use.

35 Claims, No Drawings

ATM KINASE INHIBITORS AND COMPOSITIONS AND METHODS OF USE THEREOF

CROSS-REFERENCE TO RELATED PATENT APPLICATIONS

This application claims the benefit under 35 U.S.C. § 119(e) of U.S. Provisional Application No. 62/943,694 filed Dec. 4, 2019, which is hereby incorporated by reference in its entirety.

FIELD

Provided herein are certain inhibitors of ataxia telangiectasia mutated ("ATM") kinase, compositions thereof, and methods of their use.

BACKGROUND

ATM is a serine/threonine protein kinase that is recruited and activated by DNA double-strand breaks. It phosphorylates several key proteins that initiate activation of the DNA damage checkpoint, leading to cell cycle arrest, DNA repair or apoptosis. The protein was named for the disorder ataxia-telangiectasia caused by mutations of ATM.

ATM plays a central role in maintaining genome integrity by regulating the detection and repair of DNA double-strand breaks. Genetic and pharmacological reduction of ATM signaling can ameliorate mutant huntingtin ("mHTT") toxicity in cellular and animal models of Huntington's disease ("HD"). Additionally, ATM kinase signaling has been shown to be altered in the post-mortem brains of HD patients. Selective inhibition of ATM could therefore provide a novel clinical intervention strategy for the treatment of HD. Accordingly, there is a need for inhibitors of ATM kinase.

SUMMARY

The present disclosure relates to compounds useful for inhibiting ATM kinase. Some embodiments provide for a compound of Formula I:

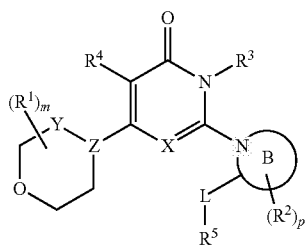

I or a deuterated analog, pharmaceutically acceptable salt, solvate, prodrug, stereoisomer, or mixture of stereoisomers thereof;
wherein:
ring B is a heterocycloalkyl ring optionally having 1 to 3 additional heteroatoms selected from O, N, and S;
X is CH or N;
(i) Z is N and Y is —CH($R^1$)— or —$CH_2$—; or
(ii) Z—Y is —C=C($R^1$)— or —C=C(H)—;
L is $C_{1-3}$alkylene optionally substituted with $C_{1-4}$alkoxy;
each $R^1$ is independently $C_{1-4}$alkyl, halo-$C_{1-4}$alkyl, $C_{1-4}$alkoxy, halo-$C_{1-4}$alkoxy, or $C_{3-6}$cycloalkyl;
or two $R^1$, together with the carbon atoms to which they are attached, join to form a cycloalkyl ring;
each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;
or two $R^2$, when present on the same carbon atom, join to form oxo;
or two $R^2$, together with the carbon atoms to which they are attached, join to form a ring optionally substituted with 1 to 3 halo;
$R^3$ is H, $C_{1-6}$alkyl optionally substituted with —N($R^8$)($R^9$), $C_{1-4}$alkoxy, or $C_{3-6}$cycloalkyl;
$R^4$ is H or halo;
$R^5$ is an aryl or heteroaryl ring, each of which is optionally substituted with 1 to 3 $R^6$.
each $R^6$ is independently halo, $C_{1-6}$alkyl, halo-$C_{1-4}$alkyl, or —$OR^7$;
each $R^7$ is independently selected from heterocycloalkyl and $C_{1-6}$alkyl optionally substituted with $C_{1-4}$alkoxy or halo;
$R^8$ and $R^9$ are each independently selected from H and $C_{1-6}$alkyl;
p is 0, 1, 2, or 3; and
m is 0, 1, 2, or 3.

Also provided is a pharmaceutical composition comprising a compound, or a deuterated analog, pharmaceutically acceptable salt, solvate, prodrug, stereoisomer, or mixture of stereoisomers thereof, described herein and a pharmaceutically acceptable carrier.

Also provided is a process for preparing a pharmaceutical composition comprising admixing a compound, or a deuterated analog, pharmaceutically acceptable salt, solvate, prodrug, stereoisomer, or mixture of stereoisomers thereof, described herein and a pharmaceutically acceptable carrier.

Also provided is a method for treating a condition or disorder mediated by an ATM kinase in a patient in need thereof comprising administering to the patient a therapeutically effective amount of a compound, or a deuterated analog, pharmaceutically acceptable salt, solvate, prodrug, stereoisomer, or mixture of stereoisomers thereof, described herein.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)$NH_2$ is attached through the carbon atom.

By "optional" or "optionally" is meant that the subsequently described event or circumstance may or may not occur, and that the description includes instances where the event or circumstance occurs and instances in which it does not. An "optionally substituted" group is one that may be unsubstituted or may be substituted with the indicated or defined groups. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain hydrocarbon groups having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkylene" encompasses straight chain and branched chain di-radical hydrocarbon groups having the indicated number of carbon atoms, usually from 1 to 20 carbon atoms, for example 1 to 8 carbon atoms, such as 1 to 6 carbon atoms, or 1 to 4 carbon atoms. For example, a $C_1$ alkylene is a methylene group. Additional examples of $C_1$-$C_4$ alkylene include 1,1-ethylene, 1,2-ethylene, 1,1-propylene, 1,2-propylene, 1,3-propylene, 1,1-butylene, 1,2-butylene, 1,3-butylene, 1,4-butylene, 2-methyl-1,2-propylene, and 2-methyl-1,3-propylene.

By "alkoxy" is meant an alkyl group of the indicated number of carbon atoms attached through an oxygen atom. Examples include methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic carbon ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated or partially unsaturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged, spirocyclic, and caged ring groups (e.g., norbornane, bicyclo [2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group, i.e., it is considered an aryl group.

"Cycloalkoxy" means a cycloalkyl group of the indicated number of carbon atoms attached through an oxygen atom. Examples include cyclopropoxy, cyclopentoxy, cyclohexoxy, and the like.

The term "halo" includes fluoro, chloro, bromo, and iodo, and the term "halogen" includes fluorine, chlorine, bromine, and iodine.

The term "haloalkyl" denotes an $C_{1-6}$ alkyl group wherein the alkyl is substituted with one halogen up to a fully substituted ("perhaloalkyl") group. A fully substituted $C_{1-6}$ haloalkyl can be represented by the formula $C_nL_{2n+1}$ wherein L is a halogen and "n" is 1, 2, 3, 4, 5, or 6; when more than one halogen is present then each halogen may be the same or different and selected from the group consisting of F, Cl, Br and I, such as F. Examples of $C_{1-6}$ haloalkyl groups include, but are not limited to, fluoromethyl, difluoromethyl, trifluoromethyl, chlorodifluoromethyl, 2,2,2-trifluoroethyl, pentafluoroethyl, perfluoropentyl and the like.

The term "haloalkoxy" denotes a haloalkyl which is attached to the parent structure through an oxygen atom. Examples include, but are not limited to, difluoromethoxy, trifluoromethoxy, 2,2,2-trifluoroethoxy, pentafluoroethoxy and the like.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include, but are not limited to, pyrrole, pyrazole, imidazole, triazole (e.g., 1,2,3-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include, but are not limited to, indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, saturated or partially unsaturated ring having the indicated number of atoms (e.g., 3 to 10, or 3 to 7, membered heterocycloalkyl) including one or more heteroatoms (e.g., 1, 2, 3 or 4 heteroatoms) selected from N, O and S, and with the remaining ring atoms being carbon. The term "heterocycloalkyl" includes heterocycloalkenyl groups (i.e. the heterocycloalkyl group having at least one double bond) and may comprise one or more oxo (=O) or N-oxide (—O⁻) moieties. Heterocycloalkyl groups may be monocyclic (i.e., heteromonocyclic) or polycyclic (e.g., bicyclic (i.e., heterobicyclic), including spirocyclic and bridged ring systems).

The definition of heterocycloalkyl encompasses ring systems wherein a ring is 1,2- or 1,3-fused to another cycloalkyl or heterocycloalkyl ring (where a carbon or nitrogen atom can form the ring junction (where the structure is chemically feasible)), as well as ring systems wherein a ring has a $C_1$-$C_2$ alkyl bridge, as well as ring systems wherein a ring is 1,2-fused to an aromatic or heteroaromatic ring, provided that the moiety is bound to the parent structure via a non-aromatic carbon or nitrogen atom.

Examples of heterocycloalkyl groups include oxiranyl, aziridinyl, azetidinyl, oxetanyl, pyrrolidinyl, imidazolidinyl, pyrazolidinyl, piperidinyl, piperazinyl, morpholinyl and thiomorpholinyl, 3-azabicyclo[3.1.0]hexan-3-yl, indolin-1-yl, isoindolin-2-yl, 1,2,3,4-tetrahydroquinolin-2-yl, 3,4-dihydroquinolin-1(2H)-yl, and 7,8-dihydro-1,6-naphthyridin-6(5H)-yl, 1-oxa-5-azaspiro[3.3]heptan-5-yl, 1-oxa-6-azaspiro[3.3]heptan-6-yl, 6-oxa-1-azaspiro[3.3]heptan-1-yl, 2-oxa-6-azaspiro[3.3]heptan-6-yl, 1,5-diazaspiro[3.3]heptan-1-yl, 1,6-diazaspiro[3.3]heptan-6-yl, 1,6-diazaspiro[3.3]heptan-1-yl, 2,6-diazaspiro[3.3]heptan-2-yl, 1-oxa-5-azaspiro[3.4]octan-5-yl, 1-oxa-6-azaspiro[3.4]octan-6-yl, 2-oxa-5-azaspiro[3.4]octan-5-yl, 2-oxa-6-azaspiro[3.4]octan-6-yl, 1,5-diazaspiro[3.4]octan-5-yl, 1,6-diazaspiro[3.4]octan-6-yl, 2,5-diazaspiro[3.4]octan-5-yl, 2,6-diazaspiro[3.4]octan-6-yl, 1-oxa-5-azaspiro[3.5]nonan-5-yl, 1-oxa-6-azaspiro[3.5]nonan-6-yl, 1-oxa-7-azaspiro[3.5]nonan-7-yl, 2-oxa-5-azaspiro[3.5]nonan-5-yl, 2-oxa-6-azaspiro[3.5]nonan-6-yl, 2-oxa-7-azaspiro[3.5]nonan-7-yl, 1,5-diazaspiro[3.5]nonan-5-yl, 1,6-diazaspiro[3.5]nonan-6-yl, 1,7-diazaspiro[3.5]nonan-7-yl, 2,5-diazaspiro[3.5]nonan-5-yl, 2,6-diazaspiro[3.5]nonan-6-yl, 2,7-diazaspiro[3.5]nonan-7-yl, 1-oxa-5-azaspiro[3.6]decan-5-yl, 1-oxa-6-azaspiro[3.6]decan-6-yl, 1-oxa-7-azaspiro[3.6]decan-7-yl, 2-oxa-5-azaspiro[3.6]decan-5-yl, 2-oxa-6-azaspiro[3.6]decan-6-yl, 2-oxa-7-azaspiro[3.6]decan-7-yl, 1,5-diazaspiro[3.6]decan-5-yl, 1,6-diazaspiro[3.6]decan-6-yl, 1,7-diazaspiro[3.6]decan-7-yl 2,5-diazaspiro[3.6]decan-5-yl, 2,6-diazaspiro[3.6]decan-6-yl, 2,7-diazaspiro[3.6]decan-7-yl, 2-azabicyclo[2.2.1]heptan-2-yl, 2-azabicyclo[3.2.1]octan-2-yl, 3-azabicyclo[3.2.1]octan-3-yl, and 6-azabicyclo[3.2.1]octan-6-yl.

When nitrogen is present in a heterocycloalkyl ring, it may, where the nature of the adjacent atoms and groups permits, exist in an oxidized state (i.e., N⁺—O⁻). Examples include pyridinyl N-oxide, piperidinyl N-oxide and morpholinyl-N-oxide. Additionally, when sulfur is present in a heterocycloalkyl ring, it may, where the nature of the adjacent atoms and groups permits, exist in an oxidized state (i.e., S⁺—O⁻ or —SO₂—). Examples include thiomorpholine S-oxide and thiomorpholine S,S-dioxide.

A "solvate" refers to an association or complex of one or more solvent molecules and a compound described herein. Examples of solvents that form solvates include, but are not limited to, water, isopropanol, ethanol, methanol, dimethylsulfoxide, ethyl acetate, acetic acid and ethanolamine.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives at a hydroxy group), amides (e.g., at an amino group), guanidines (e.g., at an amino group), carbamates (e.g., N,N-dimethylaminocarbonyl at a hydroxy group) derived from functional groups in compounds described herein, and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "substituted," as used herein, means that any one or more hydrogens on the designated atom or group is replaced with a moiety from the indicated group, provided that no atom's valence is exceeded. When the substituent is oxo (i.e., =O) then 2 hydrogen atoms on the atom are replaced. Substitution is permissible only if it results in a stable compound or useful synthetic intermediate. A stable compound or stable structure is meant to imply a compound that is sufficiently robust to survive isolation from a reaction mixture, and subsequent formulation as an agent having at least practical utility. It is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —$O(C_1$-$C_2$ alkyl) O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl; $R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2$NH$_2$, —$SO_2$NH($C_1$-$C_4$ alkyl), —$SO_2$NH(phenyl), —NHSO$_2$($C_1$-$C_4$ alkyl), —NHSO$_2$(phenyl), and —NHSO$_2$($C_1$-$C_4$ haloalkyl).

A "stereoisomer" refers to one of a set of compounds made up of the same atoms bonded by the same bonds but having different three-dimensional structures, which are not interchangeable. The term "enantiomer" refers to one of a pair of stereoisomers that are nonsuperimposeable mirror images of one another. It is intended that a compound drawn as a single stereoisomer encompasses a mixture of stereoisomers. In particular, an asymmetric ("chiral") carbon center, with respect to each such center in a compound, may be an enriched mixture or may be a racemic mixture.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) or supercritical fluid chromatograph (SFC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, a "salt" of a compound is intended to include all tautomeric forms and crystal forms of the salt of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_q$—COOH where q is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group," "radical," or "fragment" are synonymous and are intended to indicate a moiety or fragment that may be appended by a bond.

The present disclosure includes all isotopes of atoms occurring in the compounds and pharmaceutically acceptable salts thereof described herein. Isotopes include those atoms having the same atomic number but different mass numbers. The present disclosure also includes every combination of one or more atoms in the compounds and pharmaceutically acceptable salts thereof described herein that is replaced with an atom having the same atomic number but a different mass number. One such example is the replacement of an atom that is the most naturally abundant isotope, such as $^1$H or $^{12}$C, found in one of the compounds and pharmaceutically acceptable salts thereof described herein, with a different atom that is not the most naturally abundant isotope, such as $^2$H (i.e., deuterium) or $^3$H replacing $^1$H, or $^{11}$C, $^{13}$C, or $^{14}$C replacing $^{12}$C. A compound wherein such a replacement has taken place is commonly referred to as being isotopically-labeled. Isotopically labeled compounds and pharmaceutically acceptable salts thereof described herein can generally be prepared by following procedures analogous to those disclosed in the Examples infra, by substituting an isotopically labeled reagent for a non-isotopically labeled reagent. A compound in which one or more hydrogen atoms are replaced by deuterium atoms is termed a "deuterated analog" of the compound.

Accordingly, a compound described herein is intended to encompass a deuterated analog, pharmaceutically acceptable salt, solvate, prodrug, stereoisomer, or mixture of stereoisomers thereof.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of ATM activity.

As used herein, the terms "ATM," "ATM kinase" or "ATM serine/threonine kinase" and "ataxia-telangiectasia mutated protein" refer to a 350 kDa protein consisting of 3056 amino acids belonging to the family of phosphatidylinositol 3-kinase-related kinases (PIKKs). ATM and its isoforms have sequences according to NP_000042, NP_000042.3, NP_001338763, NP_001338764, NP_001338765, and NP_031525. ATM kinase plays a role in cell cycle delay after DNA damage, especially after double-strand breaks (DSBs).

The terms "ATM inhibitor" and "inhibitor of ATM" are intended to mean a compound, or a deuterated analog, pharmaceutically acceptable salt, solvate, prodrug, stereoisomer, or mixture of stereoisomers thereof, described herein which is capable of interacting with an ATM kinase and inhibiting its enzymatic activity.

The term "a condition or disorder mediated by ATM" as used herein refers to a condition or disorder in which ATM and/or the action of ATM is important or necessary, e.g., for the onset, progress, expression, etc. of that condition, or a condition which is known to be treated by ATM inhibitors.

The term "inhibiting ATM enzymatic activity" is intended to mean reducing the enzymatic activity of ATM. The enzymatic activity may comprise phosphorylation of a target protein. The concentration of inhibitor which reduces the activity of an ATM protein to 50% of that of the uninhibited enzyme is determined as the $IC_{50}$ value. In some embodiments, such reduction of an ATM protein activity is at least 50%, such as at least about 75%, for example, at least about 90%. In some embodiments, an ATM protein activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

"Treatment" or "treating" means any treatment of a disease state in a patient, including a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal. In some embodiments the subject is human.

A compound described herein refers to a compound, or a deuterated analog, pharmaceutically acceptable salt, solvate, prodrug, stereoisomer, or mixture of stereoisomers thereof, of any of Formula I, Formula II, Formula II(a), Formula II(b), Formula II(a)(i), Formula II(a)(ii), Formula II(b)(i), Formula II(b)(ii), Formula III, Formula III(a), Formula III(b), Formula III(a)(i), Formula III(a)(ii), Formula III(b)(i), Formula III(b)(ii), or Formula IV, or a compound of the Examples, or a compound of Table 1.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, are specifically embraced by herein just as if each and every combination was individually and explicitly recited, to the extent that such combinations embrace feature compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, such as those conditions or disorders mediated by ATM kinase, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| BINAP | (2,2'-Bis(diphenylphosphino)-1,1'-binaphthyl) |
| Boc | tert-butyloxycarbonyl |
| BuLi | Butyl lithium |
| Cbz | Carboxybenzyl |
| DAST | Diethylaminosulfur trifluoride |
| DBU | 1,8-Diazabicyclo[5.4.0]undec-7-ene |
| DCM | Dichloromethane |

-continued

| List of Abbreviations and Acronyms | |
|---|---|
| DIAD | Diisopropyl azodiformate |
| DIPEA | Diisopropylethylamine |
| DMAP | Dimethylaminopyridine |
| DME | Dimethoxyethane |
| DMF | Dimethylformamide |
| DMSO | Dimethylsulfoxide |
| EDC | N-Ethyl-N'-(3-dimethylaminopropyl)carbodiimide |
| ES+ | Electrospray Positive Ionization |
| h | Hour |
| HOBt | 1-Hydroxybenzotriazole |
| HPLC | High Performance Liquid Chromatography |
| LCMS | Liquid Chromatography Mass Spectrometry |
| M | Mass |
| Me | Methyl |
| MeCN | Acetonitrile |
| NMR | Nuclear Magnetic Resonance |
| $PdCL_2(tBu_2Pferrocene)_2$ | [1,1'-Bis(di-tert-butylphosphino)ferrocene]dichloropalladium(II) |
| Ph | Phenyl |
| PMB | Para-methoxy benzyl |
| rt | Room temperature |
| RT | Retention time |
| RuPhos | 2-Dicyclohexylphosphino-2',6'-di-iso-propoxy-1,1'-biphenyl |
| RuPhos palladacycle G1 | Chloro-(2-Dicyclohexylphosphino-2',6'-diisopropoxy-1,1'-biphenyl)[2-(2-aminoethyl)phenyl]palladium(II) |
| RuPhos palladacycle G3 | (2-Dicyclohexylphosphino-2',6'-diisopropoxy-1,1'-biphenyl) [2-(2'-amino-1,1'-biphenyl)]palladium(II) methanesulfonate |
| SCX | Strong Cation Exchange |
| SFC | Supercritical Fluid |
| TFA | Trifluoroacetic acid |
| TFAA | Trifluoroacetic anhydride |
| THF | Tetrahydrofuran |
| XPhos PdG2 | Chloro(2-dicyclohexylphosphino-2',4',6'-triisopropyl-1,1'-biphenyl) [2-(2'-amino-1,1'-biphenyl)]palladium(II) |

Compounds

Provided herein is a compound of Formula I:

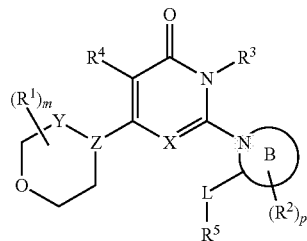

I or a deuterated analog, pharmaceutically acceptable salt, solvate, prodrug, stereoisomer, or mixture of stereoisomers thereof;
wherein:
ring B is a heterocycloalkyl ring optionally having 1 to 3 additional heteroatoms selected from O, N, and S;
X is CH or N;
(i) Z is N and Y is —CH($R^1$)— or —CH$_2$—; or
(ii) Z—Y is —C═C($R^1$)— or —C═C(H)—;
L is $C_{1-3}$alkylene optionally substituted with $C_{1-4}$alkoxy;
each $R^1$ is independently $C_{1-4}$alkyl, halo-$C_{1-4}$alkyl, $C_{1-4}$alkoxy, halo-$C_{1-4}$alkoxy, or $C_{3-6}$ cycloalkyl;
or two $R^1$, together with the carbon atoms to which they are attached, join to form a cycloalkyl ring;
each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;

or two $R^2$, when present on the same carbon atom, join to form oxo;
or two $R^2$, together with the carbon atoms to which they are attached, join to form a ring optionally substituted with 1 to 3 halo;
$R^3$ is H or $C_{1-6}$alkyl optionally substituted with —N($R^8$)($R^9$), $C_{1-4}$alkoxy, or $C_{3-6}$cycloalkyl;
$R^4$ is H or halo;
$R^5$ is an aryl or heteroaryl ring, each of which is optionally substituted with 1 to 3 $R^6$;
each $R^6$ is independently halo, $C_{1-6}$alkyl, halo-$C_{1-6}$alkyl, or —O$R^7$;
each $R^7$ is independently selected from heterocycloalkyl and $C_{1-6}$alkyl optionally substituted with $C_{1-4}$alkoxy or halo;
$R^8$ and $R^9$ are each independently selected from H and $C_{1-6}$alkyl;
p is 0, 1, 2, or 3; and
m is 0, 1, 2, or 3.

In some embodiments, provided is a compound of Formula II:

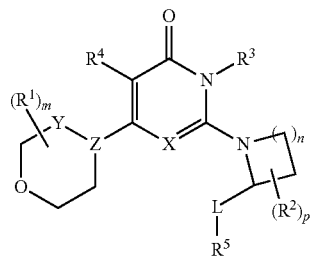

II or a deuterated analog, pharmaceutically acceptable salt, solvate, prodrug, stereoisomer, or mixture of stereoisomers thereof;

wherein:

X is CH or N;

(i) Z is N and Y is —CH($R^1$)— or —CH$_2$—; or (ii) Z—Y is —C=C($R^1$)— or —C=C(H)—;

L is $C_{1-3}$alkylene optionally substituted with $C_{1-4}$alkoxy;

each $R^1$ is independently $C_{1-4}$alkyl, halo-$C_{1-4}$alkyl, $C_{1-4}$alkoxy, halo-$C_{1-4}$alkoxy, or $C_{3-6}$ cycloalkyl;

or two $R^1$, together with the carbon atoms to which they are attached, join to form a cycloalkyl ring;

each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;

or two $R^2$, when present on the same carbon atom, join to form oxo;

or two $R^2$, together with the carbon atoms to which they are attached, join to form a ring optionally substituted with 1 to 3 halo;

$R^3$ is H or $C_{1-6}$alkyl optionally substituted with —N($R^8$)($R^9$), $C_{1-4}$alkoxy, or $C_{3-6}$cycloalkyl;

$R^4$ is H or halo;

$R^5$ is an aryl or heteroaryl ring, each of which is optionally substituted with 1 to 3 $R^6$;

each $R^6$ is independently halo, $C_{1-6}$alkyl, halo-$C_{1-6}$alkyl, or —O$R^7$;

each $R^7$ is independently selected from heterocycloalkyl and $C_{1-6}$alkyl optionally substituted with $C_{1-4}$alkoxy or halo;

$R^8$ and $R^9$ are each independently selected from H and $C_{1-6}$alkyl;

p is 0, 1, 2, or 3;

m is 0, 1, 2, or 3; and n is 0, 1, 2, 3, or 4.

In some embodiments, the compound of Formula II is a compound of Formula II(a):

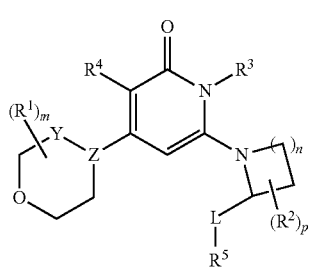

II(a)

or a deuterated analog, pharmaceutically acceptable salt, solvate, prodrug, stereoisomer, or mixture of stereoisomers thereof.

In some embodiments, the compound of Formula II is a compound of Formula II(b):

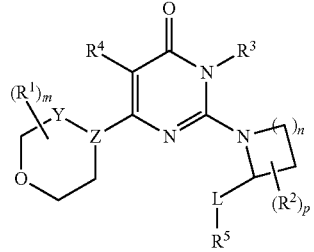

II(b)

or a deuterated analog, pharmaceutically acceptable salt, solvate, prodrug, stereoisomer, or mixture of stereoisomers thereof.

In some embodiments, the compound of Formula II is a compound of Formula II(a)(i):

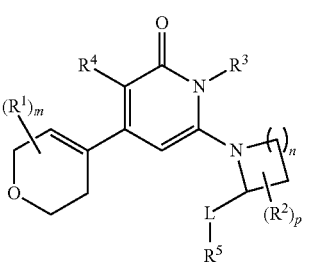

II(a)(i)

or a deuterated analog, pharmaceutically acceptable salt, solvate, prodrug, stereoisomer, or mixture of stereoisomers thereof.

In some embodiments, the compound of Formula II is a compound of Formula II(a)(ii):

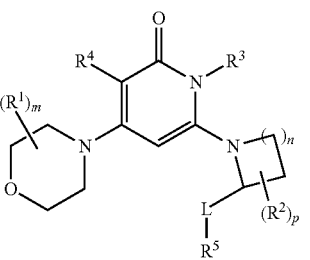

II(a)(ii)

or a deuterated analog, pharmaceutically acceptable salt, solvate, prodrug, stereoisomer, or mixture of stereoisomers thereof.

In some embodiments, the compound of Formula II is a compound of Formula II(b)(i):

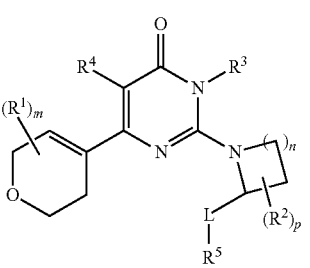

II(b)(i)

or a deuterated analog, pharmaceutically acceptable salt, solvate, prodrug, stereoisomer, or mixture of stereoisomers thereof.

In some embodiments, the compound of Formula II is a compound of Formula II(b)(ii):

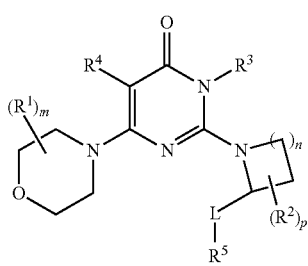

II(b)(ii)

or a deuterated analog, pharmaceutically acceptable salt, solvate, prodrug, stereoisomer, or mixture of stereoisomers thereof.

Also provided is a compound of Formula III:

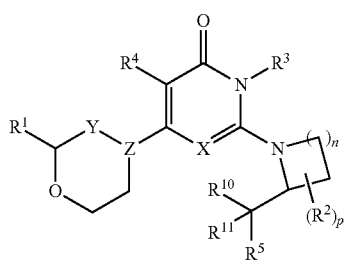

III or a deuterated analog, pharmaceutically acceptable salt, solvate, prodrug, stereoisomer, or mixture of stereoisomers thereof;
wherein:
X is CH or N;
(i) Z is N and Y is —CH($R^1$)— or —CH$_2$—; or
(ii) Z—Y is —C=C($R^1$)—;
$R^1$ is H, $C_{1-4}$alkyl, halo-$C_{1-4}$alkyl, $C_{1-4}$alkoxy, halo-$C_{1-4}$alkoxy, or $C_{3-6}$ cycloalkyl;
or two $R^1$, together with the carbon atoms to which they are attached, join to form a cycloalkyl ring;
each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;
or two $R^2$, when present on the same carbon atom, join to form oxo;
or two $R^2$, together with the carbon atoms to which they are attached, join to form a ring optionally substituted with 1 to 3 halo;
$R^3$ is H or $C_{1-3}$alkyl optionally substituted with —N($R^8$)($R^9$), $C_{1-4}$alkoxy, or $C_{3-6}$cycloalkyl;
$R^4$ is H or halo;
$R^5$ is an aryl or heteroaryl ring, each of which is optionally substituted with 1 to 3 $R^6$;
each $R^6$ is independently halo, $C_{1-6}$alkyl, halo-$C_{1-6}$alkyl, or —O$R^7$;
each $R^7$ is independently selected from heterocycloalkyl and $C_{1-6}$alkyl optionally substituted with $C_{1-4}$alkoxy or halo;

$R^8$ and $R^9$ are each independently selected from H and $C_{1-6}$alkyl;
$R^{10}$ and $R^{11}$ are each independently selected from H or $C_{1-3}$alkyl;
p is 0, 1, 2, or 3; and
n is 0, 1, 2, 3, or 4.

In some embodiments, the compound of Formula III is a compound of Formula III(a):

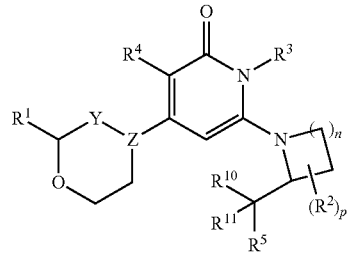

III(a)

or a deuterated analog, pharmaceutically acceptable salt, solvate, prodrug, stereoisomer, or mixture of stereoisomers thereof.

In some embodiments, the compound of Formula III is a compound of Formula III(b):

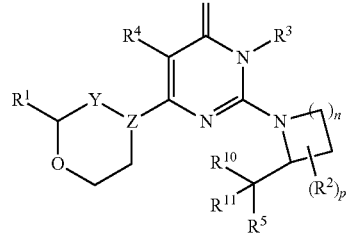

III(b)

or a deuterated analog, pharmaceutically acceptable salt, solvate, prodrug, stereoisomer, or mixture of stereoisomers thereof.

In some embodiments, the compound of Formula III is a compound of Formula III(a)(i):

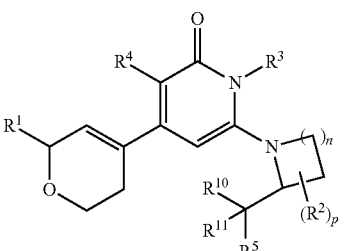

III(a)(i)

or a deuterated analog, pharmaceutically acceptable salt, solvate, prodrug, stereoisomer, or mixture of stereoisomers thereof.

In some embodiments, the compound of Formula III is a compound of Formula III(a)(ii):

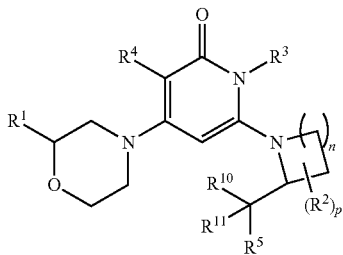

III(a)(ii)

or a deuterated analog, pharmaceutically acceptable salt, solvate, prodrug, stereoisomer, or mixture of stereoisomers thereof.

In some embodiments, the compound of Formula III is a compound of Formula III(b)(i):

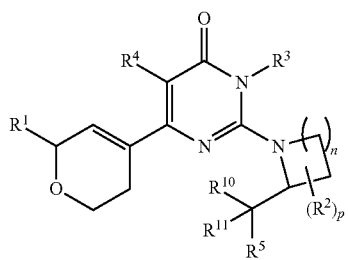

III(b)(i)

or a deuterated analog, pharmaceutically acceptable salt, solvate, prodrug, stereoisomer, or mixture of stereoisomers thereof.

In some embodiments, the compound of Formula III is a compound of Formula III(b)(ii):

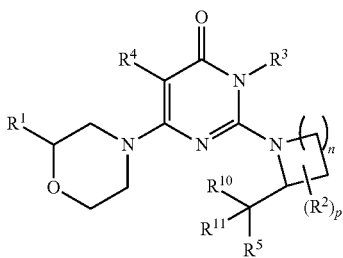

III(b)(ii)

or a deuterated analog, pharmaceutically acceptable salt, solvate, prodrug, stereoisomer, or mixture of stereoisomers thereof.

Also provided is a compound of Formula IV:

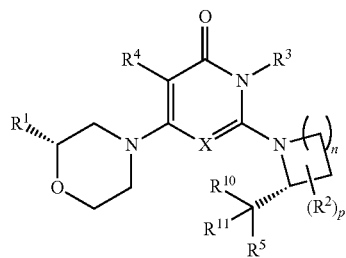

IV or a deuterated analog, pharmaceutically acceptable salt, solvate, prodrug, stereoisomer, or mixture of stereoisomers thereof;

wherein:

X is CH or N;

$R^1$ is H or $C_{1-3}$alkyl;

each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;

or two $R^2$, when present on the same carbon atom, join to form oxo;

or two $R^2$, together with the carbon atoms to which they are attached, join to form a ring optionally substituted with 1 to 3 halo;

$R^3$ is H or $C_{1-3}$alkyl;

$R^4$ is H or halo;

$R^5$ is an aryl or heteroaryl ring, each of which is optionally substituted with 1 to 3 $R^6$;

each $R^6$ is independently halo, $C_{1-6}$alkyl, halo-$C_{1-6}$alkyl, or —$OR^7$;

each $R^7$ is independently selected from heterocycloalkyl and $C_{1-6}$alkyl optionally substituted with $C_{1-4}$alkoxy or halo;

$R^{10}$ and $R^{11}$ are each independently selected from H or methyl;

p is 0, 1, 2, or 3; and n is 2, 3, or 4.

In some embodiments, m is 1, and $R^1$ is methyl.

In some embodiments, m is 0.

In some embodiments, $R^1$ is H or methyl. In some embodiments, $R^1$ is methyl.

In some embodiments, $R^1$ is H.

In some embodiments, $R^3$ is H or methyl.

In some embodiments, $R^3$ is H.

In some embodiments, $R^4$ is H or fluoro.

In some embodiments, $R^5$ is aryl optionally substituted with 1 to 3 $R^6$.

In some embodiments, $R^5$ is aryl.

In some embodiments, $R^5$ is phenyl.

In some embodiments, $R^5$ is phenyl optionally substituted with 1 to 3 $R^6$

In some embodiments, n is 2, 3, or 4. In some embodiment, n is 2. In some embodiment, n is 3.

In some embodiment, n is 4.

In some embodiments, two $R^2$, together with the carbon atoms to which they are attached, join to form a ring optionally substituted with 1 to 3 halo. In some embodiments, the ring is a saturated ring. In some embodiments, the ring is a saturated 3- to 7-membered fused, bridged, or spiro ring that optionally contains 1 to 3 heteroatoms selected from N, O, and S. In some embodiments, the ring is a saturated 3- to 7-membered fused, bridged, or spiro cycloalkyl ring.

In some embodiments, two $R^2$, together with the carbon atoms to which they are attached, join to form a 3- to-7-membered cycloalkyl ring optionally substituted with 1 to 3 halo. In some embodiments, two $R^2$, together with the carbon atoms to which they are attached, join to form a 3-to-7-membered heterocycloalkyl ring optionally substituted with 1 to 3 halo, wherein the heterocycloalkyl ring contains 1 to 3 heteroatoms selected from N, O, and S.

In some embodiments, two $R^2$, together with the carbon atoms to which they are attached, join to form a bridging ring optionally substituted with 1 to 3 halo. In some embodiments, the bridging ring is a 3- to 7-membered cycloalkyl ring. In some embodiments, two $R^2$, together with the carbon atoms to which they are attached, join to form a cyclopropyl ring optionally substituted with 1 to 3 halo.

In some embodiments, provided is a pharmaceutical composition comprising a compound described herein, or a deuterated analog, pharmaceutically acceptable salt, solvate, prodrug, stereoisomer, or mixture of stereoisomers thereof, and a pharmaceutically acceptable carrier.

In some embodiments, provided is a method for treating a condition or disorder mediated by an ATM kinase in a patient in need thereof comprising administering to the patient a therapeutically effective amount of a compound, or a deuterated analog, pharmaceutically acceptable salt, solvate, prodrug, stereoisomer, or mixture of stereoisomers thereof, described herein.

In some embodiments, the condition or disorder is Huntington's disease, Alzheimer's disease, Parkinson's disease, neuronal intranuclear inclusion disease (NIID), dentatorubral pallidolusyian atrophy (DRPLA), Friedreich's ataxia, Rubenstein-Taubi syndrome, a polyglutamine disease such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, or mixed connective tissue disease.

In some embodiments, the condition or disorder is Huntington's disease.

In some embodiments, the condition or disorder is cancer.

In some embodiments, a compound, or a deuterated analog, pharmaceutically acceptable salt, solvate, prodrug, stereoisomer, or mixture of stereoisomers thereof, may be selected from those compounds described in one or more Examples. In certain embodiments, provided are compounds described in one or more Examples for use in the methods described herein.

Also provided is a compound, or a deuterated analog, pharmaceutically acceptable salt, solvate, prodrug, stereoisomer, or mixture of stereoisomers thereof, selected from those in Table 1:

TABLE 1

| Example | Structure |
|---------|-----------|
| 1 | 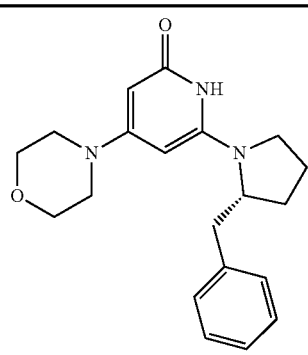 |
| 2 | 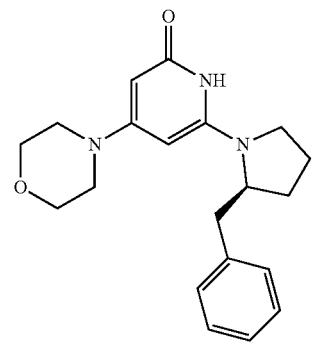 [SMILES: O=c1cc(N2CCOCC2)cc(N2CCC[C@H]2Cc2ccccc2)[nH]1] |
| 3 | 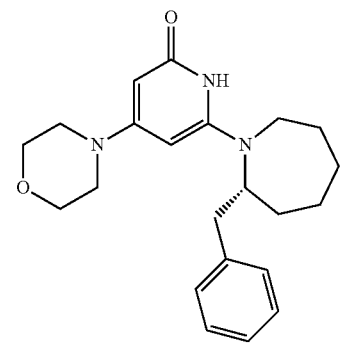 [SMILES: O=c1cc(N2CCOCC2)cc(N2CCCCC[C@@H]2Cc2ccccc2)[nH]1] |
| 4 | 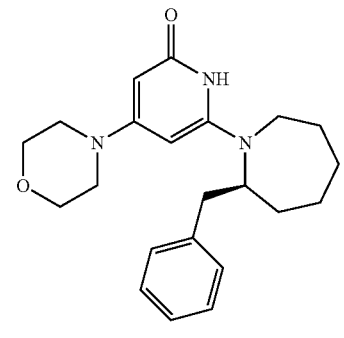 [SMILES: O=c1cc(N2CCOCC2)cc(N2CCCCC[C@H]2Cc2ccccc2)[nH]1] |
| 5 | 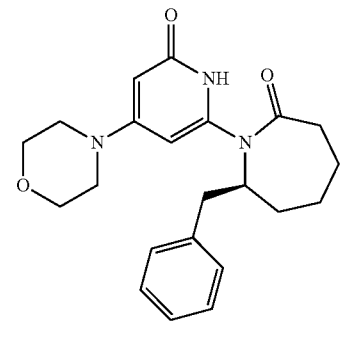 [SMILES: O=C1CCCC[C@@H](Cc2ccccc2)N1c1cc(N2CCOCC2)cc(=O)[nH]1] |

TABLE 1-continued
| Example | Structure |
|---|---|
| 6 | 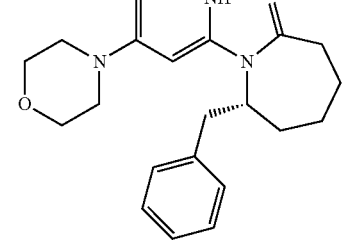 |
| 7 | 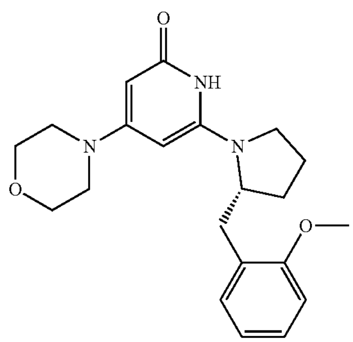 [SMILES: COc1ccccc1C[C@H]1CCCN1c1cc(N2CCOCC2)cc(=O)[nH]1] |
| 8 | 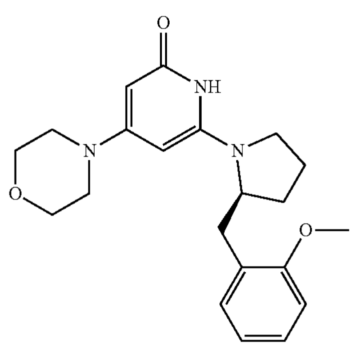 [SMILES: COc1ccccc1C[C@@H]1CCCN1c1cc(N2CCOCC2)cc(=O)[nH]1] |
| 9 | 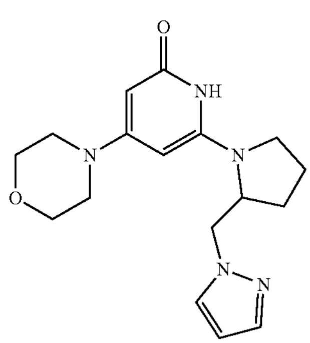 [SMILES: O=c1cc(N2CCOCC2)cc(N2CCCC2Cn2cccn2)[nH]1] |
| 10 | 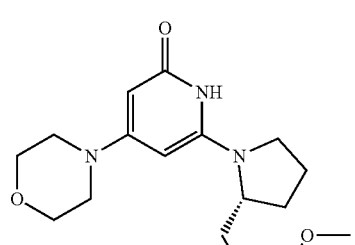 |
| 11 | |
| 12 | |
| 13 | |

TABLE 1-continued

| Example | Structure |
|---------|-----------|
| 14 | 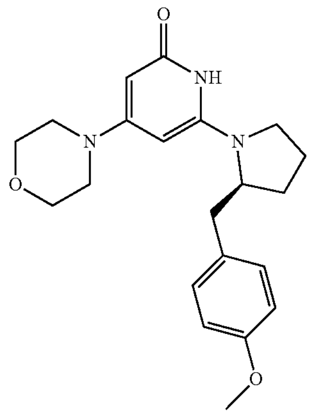 [SMILES: COc1ccc(C[C@@H]2CCCN2c2cc(N3CCOCC3)cc(=O)[nH]2)cc1] |
| 15 | 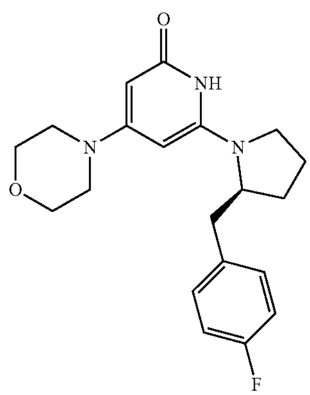 [SMILES: O=c1cc(N2CCOCC2)cc(N2CCC[C@H]2Cc2ccc(F)cc2)[nH]1] |
| 16 | 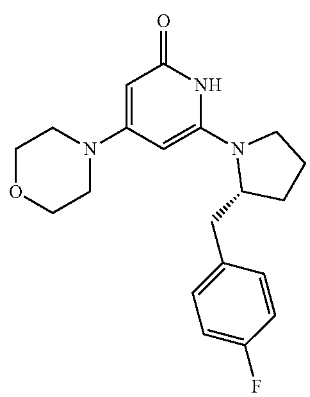 [SMILES: O=c1cc(N2CCOCC2)cc(N2CCC[C@@H]2Cc2ccc(F)cc2)[nH]1] |
| 17 | 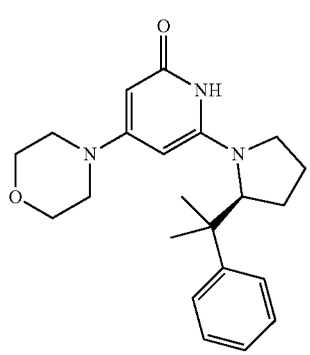 [SMILES: CC(C)(c1ccccc1)[C@@H]1CCCN1c1cc(N2CCOCC2)cc(=O)[nH]1] |
| 18 | |
| 19 | |
| 20 | |
| 21 | |

TABLE 1-continued

| Example | Structure |
|---------|-----------|
| 22 | 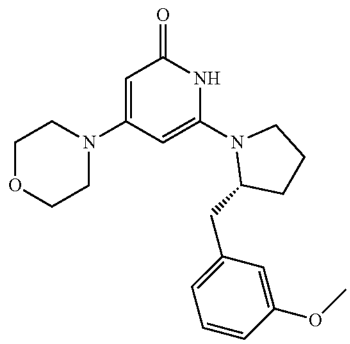 [SMILES: COc1cccc(C[C@H]2CCCN2c2cc(N3CCOCC3)cc(=O)[nH]2)c1] |
| 23 | 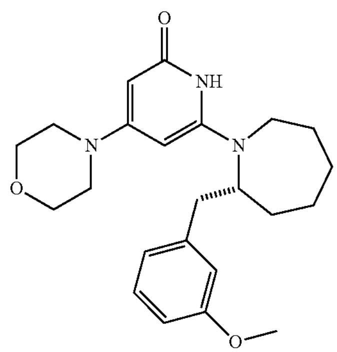 [SMILES: COc1cccc(C[C@H]2CCCCCN2c2cc(N3CCOCC3)cc(=O)[nH]2)c1] |
| 24 | 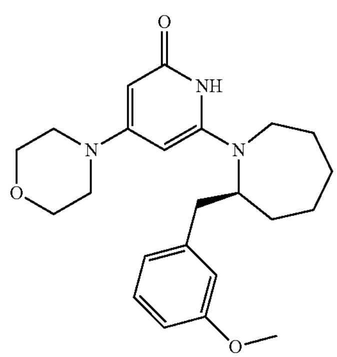 [SMILES: COc1cccc(C[C@@H]2CCCCCN2c2cc(N3CCOCC3)cc(=O)[nH]2)c1] |
| 25 | 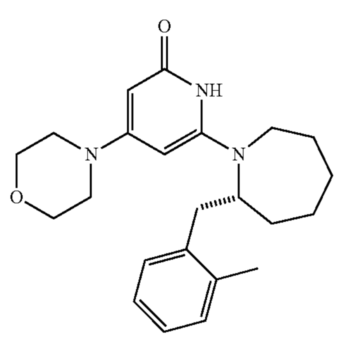 [SMILES: Cc1ccccc1C[C@H]1CCCCCN1c1cc(N2CCOCC2)cc(=O)[nH]1] |
| 26 | |
| 27 | |
| 28 | |
| 29 | |

TABLE 1-continued

| Example | Structure |
|---|---|
| 30 | 4-morpholino-6-[(2S)-2-(4-methoxybenzyl)azepan-1-yl]pyridin-2(1H)-one |
| 31 | 4-morpholino-6-[(2S)-2-(thiophen-2-ylmethyl)azepan-1-yl]pyridin-2(1H)-one |
| 32 | 4-morpholino-6-[(2R)-2-(thiophen-2-ylmethyl)azepan-1-yl]pyridin-2(1H)-one |
| 33 | 4-morpholino-6-[(2S)-2-(pyridin-2-ylmethyl)azepan-1-yl]pyridin-2(1H)-one |
| 34 | 4-morpholino-6-[(2R)-2-(pyridin-2-ylmethyl)azepan-1-yl]pyridin-2(1H)-one |
| 35 | 4-morpholino-6-[(2S)-2-benzylpiperidin-1-yl]pyridin-2(1H)-one |
| 36 | 4-morpholino-6-[(2R)-2-benzylpiperidin-1-yl]pyridin-2(1H)-one |
| 37 | 4-morpholino-6-[(3S)-3-benzylmorpholin-4-yl]pyridin-2(1H)-one |

TABLE 1-continued
| Example | Structure |
|---|---|
| 38 | 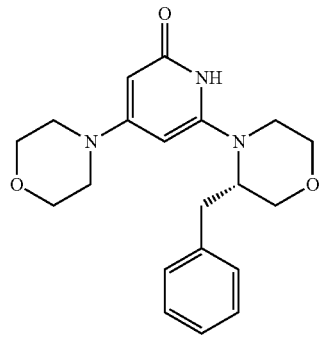 [SMILES: O=c1cc(N2CCOCC2)cc(N2CCOC[C@@H]2Cc2ccccc2)[nH]1] |
| 39 | 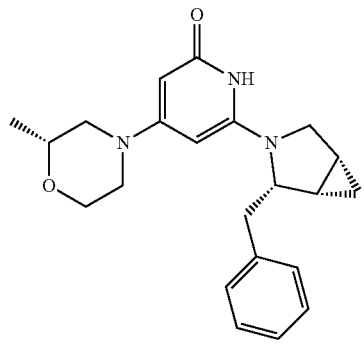 [SMILES: C[C@@H]1CN(c2cc(N3C[C@@H]4C[C@@H]4[C@@H]3Cc3ccccc3)[nH]c(=O)c2)CCO1] |
| 40 | 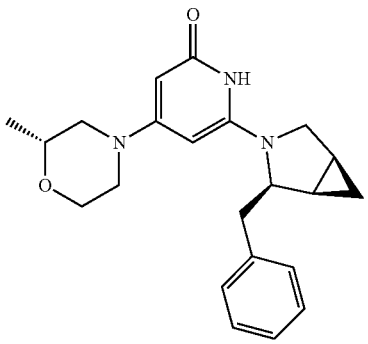 [SMILES: C[C@@H]1CN(c2cc(N3C[C@H]4C[C@H]4[C@H]3Cc3ccccc3)[nH]c(=O)c2)CCO1] |
| 41 | 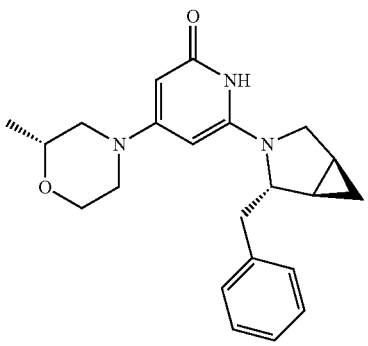 [SMILES: C[C@@H]1CN(c2cc(N3C[C@H]4C[C@H]4[C@@H]3Cc3ccccc3)[nH]c(=O)c2)CCO1] |
| 42 | 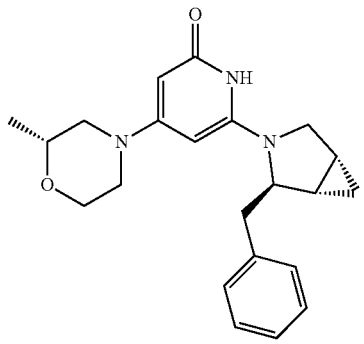 [SMILES: C[C@@H]1CN(c2cc(N3C[C@@H]4C[C@@H]4[C@H]3Cc3ccccc3)[nH]c(=O)c2)CCO1] |
| 43 | 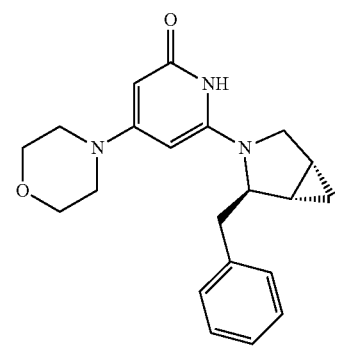 [SMILES: O=c1cc(N2CCOCC2)cc(N2C[C@@H]3C[C@@H]3[C@H]2Cc2ccccc2)[nH]1] |
| 44 | 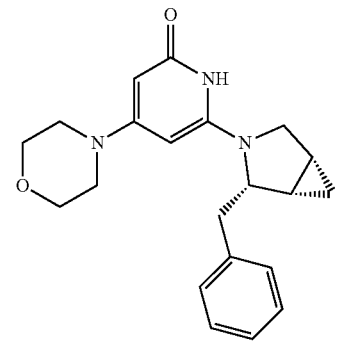 [SMILES: O=c1cc(N2CCOCC2)cc(N2C[C@@H]3C[C@@H]3[C@@H]2Cc2ccccc2)[nH]1] |
| 45 | 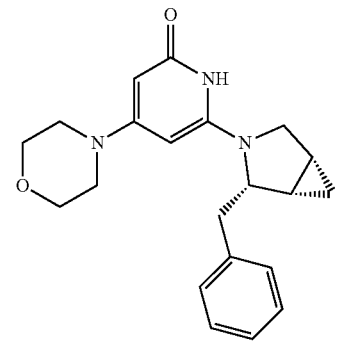 [SMILES: O=c1cc(N2CCOCC2)cc(N2C[C@@H]3C[C@@H]3[C@@H]2Cc2ccccc2)[nH]1] |

TABLE 1-continued
| Example | Structure |
|---------|-----------|
| 46 | 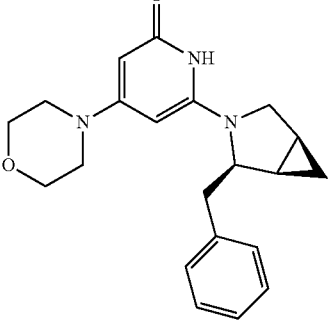 |
| 47 | 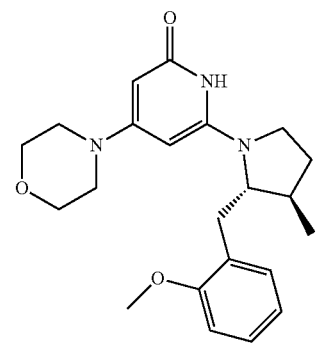 [SMILES: COc1ccccc1C[C@H]1[C@H](C)CCN1c1cc(N2CCOCC2)cc(=O)[nH]1] |
| 48 | 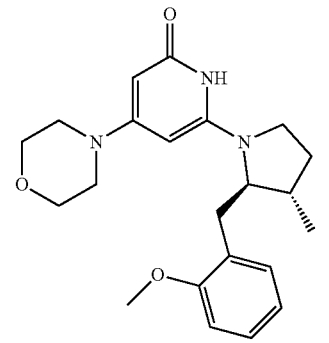 [SMILES: COc1ccccc1C[C@@H]1[C@@H](C)CCN1c1cc(N2CCOCC2)cc(=O)[nH]1] |
| 49 | 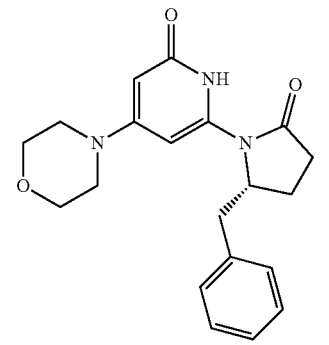 [SMILES: O=C1CC[C@H](Cc2ccccc2)N1c1cc(N2CCOCC2)cc(=O)[nH]1] |
| 50 | 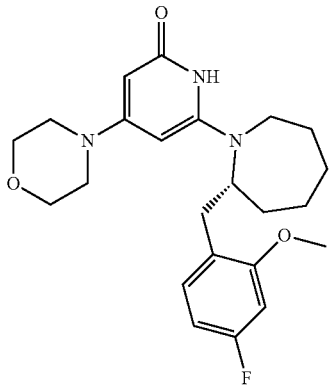 [SMILES: COc1cc(F)ccc1C[C@H]1CCCCCN1c1cc(N2CCOCC2)cc(=O)[nH]1] |
| 51 | 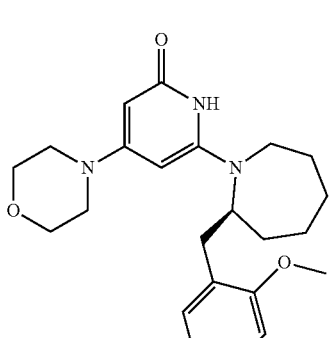 |
| 52 |  |
| 53 | 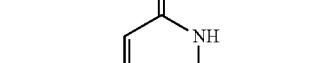 |

TABLE 1-continued

| Example | Structure |
|---------|-----------|
| 54 | 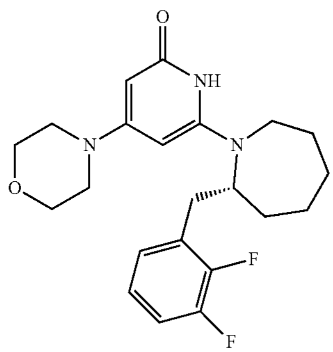 [SMILES: O=c1cc(N2CCOCC2)cc(N2CCCCC[C@@H]2Cc2cccc(F)c2F)[nH]1] |
| 55 | 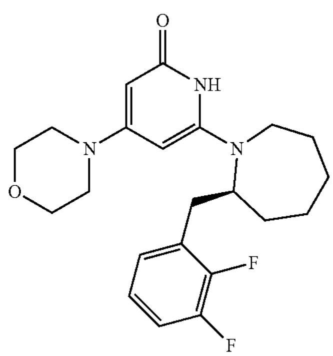 [SMILES: O=c1cc(N2CCOCC2)cc(N2CCCCC[C@H]2Cc2cccc(F)c2F)[nH]1] |
| 56 | 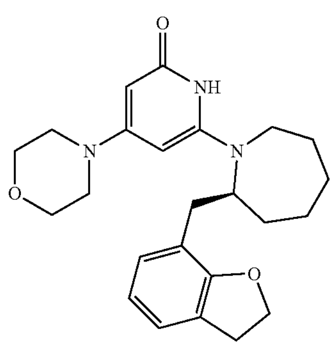 [SMILES: O=c1cc(N2CCOCC2)cc(N2CCCCC[C@H]2Cc2cccc3c2OCC3)[nH]1] |
| 57 | 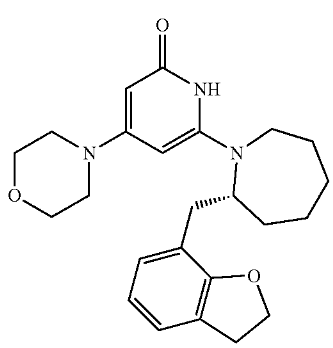 [SMILES: O=c1cc(N2CCOCC2)cc(N2CCCCC[C@@H]2Cc2cccc3c2OCC3)[nH]1] |
| 58 | |
| 59 | |
| 60 | |
| 61 | |

TABLE 1-continued

| Example | Structure |
|---------|-----------|
| 62 | 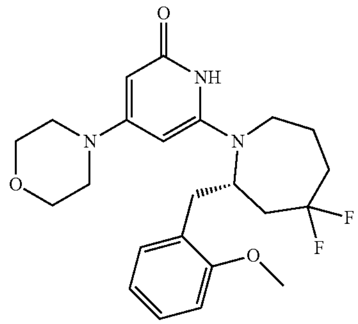 [SMILES: COc1ccccc1C[C@H]1CC(F)(F)CCCN1c1cc(N2CCOCC2)cc(=O)[nH]1] |
| 63 | 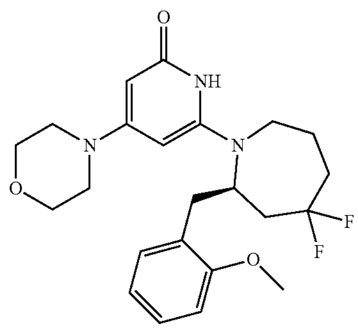 [SMILES: COc1ccccc1C[C@@H]1CC(F)(F)CCCN1c1cc(N2CCOCC2)cc(=O)[nH]1] |
| 64 | 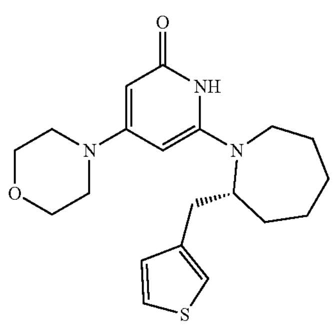 [SMILES: O=c1cc(N2CCOCC2)cc(N2CCCCC[C@@H]2Cc2ccsc2)[nH]1] |
| 65 | 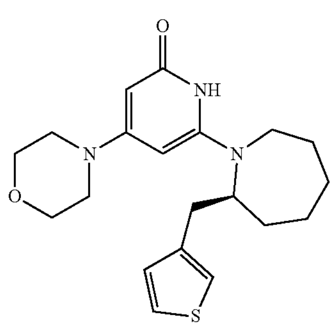 [SMILES: O=c1cc(N2CCOCC2)cc(N2CCCCC[C@H]2Cc2ccsc2)[nH]1] |
| 66 | |
| 67 | |
| 68 | |
| 69 | |

TABLE 1-continued
| Example | Structure |
|---|---|
| 70 | 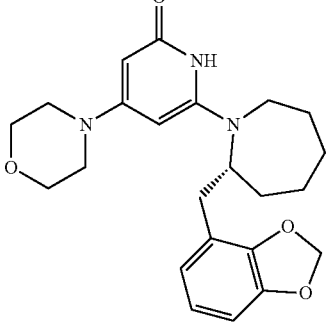 |
| 71 | 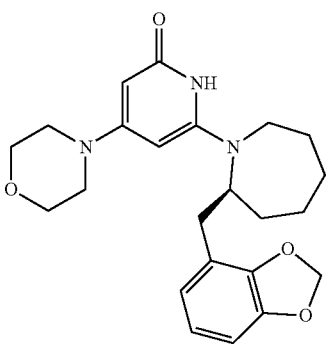 [SMILES: O=c1cc(N2CCOCC2)cc(N2CCCCC[C@H]2Cc2cccc3c2OCO3)[nH]1] |
| 72 | 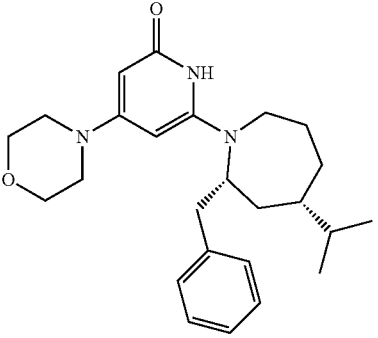 [SMILES: CC(C)[C@H]1CCCN(c2cc(N3CCOCC3)cc(=O)[nH]2)[C@@H](Cc2ccccc2)C1] |
| 73 | 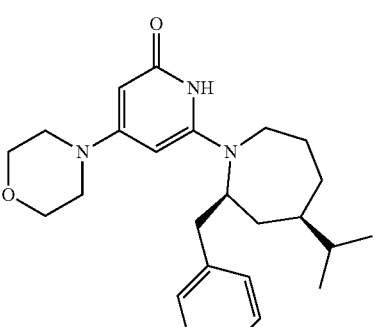 |
| 74 | 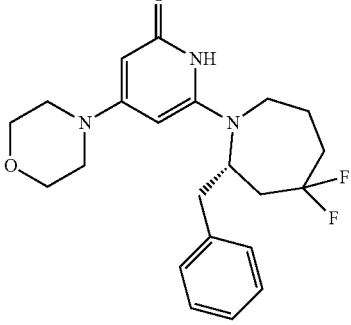 |
| 75 | 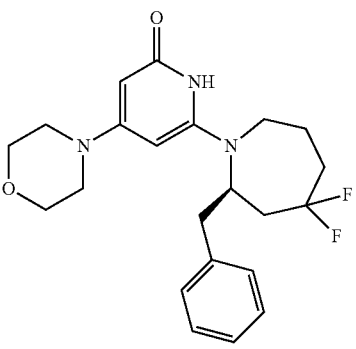 [SMILES: O=c1cc(N2CCOCC2)cc(N2CCCC(F)(F)C[C@H]2Cc2ccccc2)[nH]1] |
| 76 | 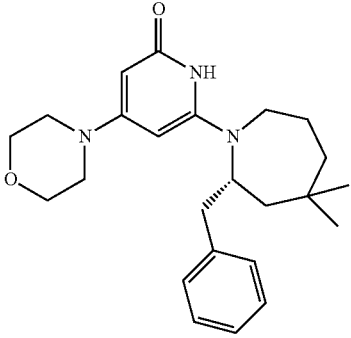 [SMILES: CC1(C)CCCN(c2cc(N3CCOCC3)cc(=O)[nH]2)[C@@H](Cc2ccccc2)C1] |
| 77 | 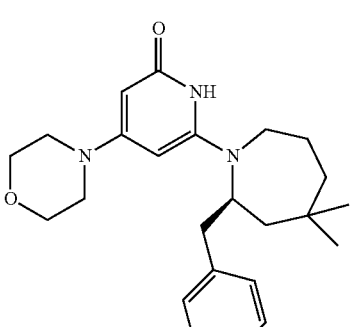 |

TABLE 1-continued
| Example | Structure |
|---|---|
| 78 | 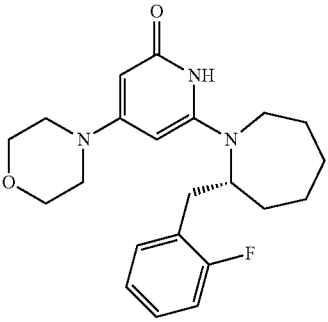 [SMILES: O=c1cc(N2CCOCC2)cc(N2CCCCC[C@@H]2Cc2ccccc2F)[nH]1] |
| 79 | 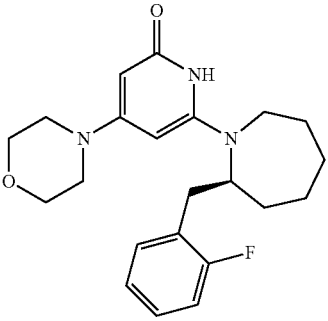 [SMILES: O=c1cc(N2CCOCC2)cc(N2CCCCC[C@H]2Cc2ccccc2F)[nH]1] |
| 80 | 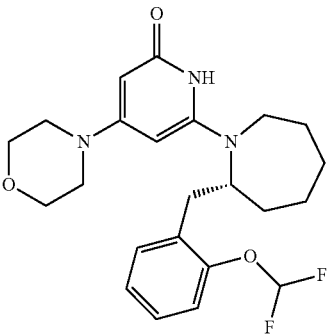 [SMILES: O=c1cc(N2CCOCC2)cc(N2CCCCC[C@@H]2Cc2ccccc2OC(F)F)[nH]1] |
| 81 | 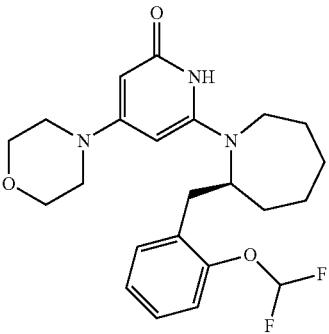 [SMILES: O=c1cc(N2CCOCC2)cc(N2CCCCC[C@H]2Cc2ccccc2OC(F)F)[nH]1] |
| 82 | 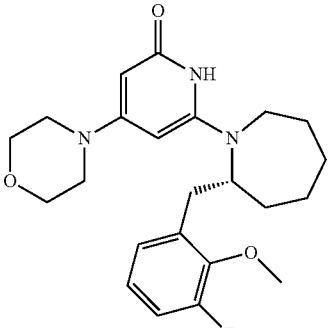 |
| 83 | 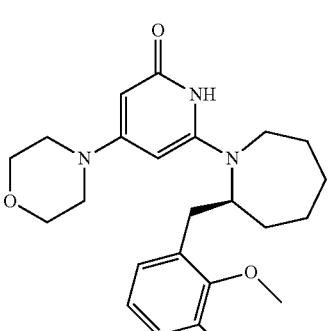 |
| 84 | 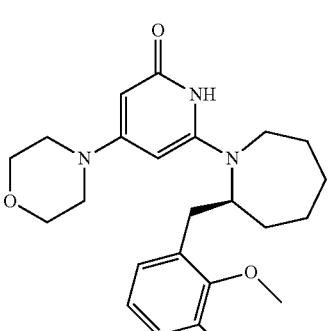 |
| 85 | 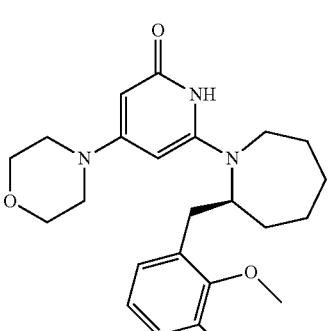 |

TABLE 1-continued
| Example | Structure |
|---|---|
| 86 | 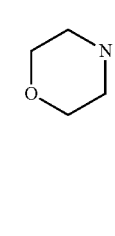 |
| 87 | 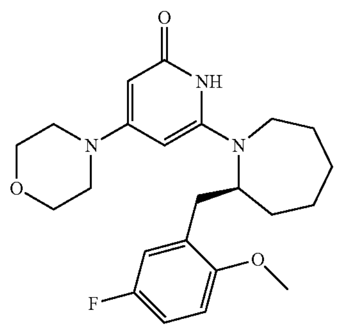 [SMILES: COc1ccc(F)cc1C[C@@H]1CCCCCN1c1cc(N2CCOCC2)cc(=O)[nH]1] |
| 88 | 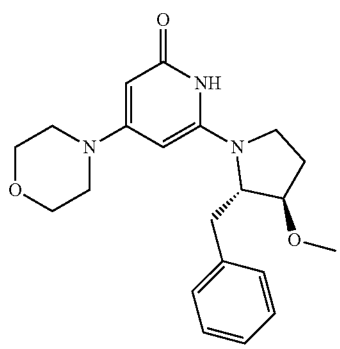 [SMILES: CO[C@@H]1CCN(c2cc(N3CCOCC3)cc(=O)[nH]2)[C@H]1Cc1ccccc1] |
| 89 | 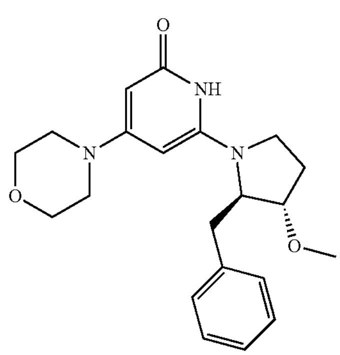 [SMILES: CO[C@H]1CCN(c2cc(N3CCOCC3)cc(=O)[nH]2)[C@@H]1Cc1ccccc1] |
| 90 | 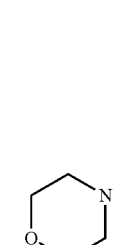 |
| 91 | |
| 92 | |
| 93 | |

TABLE 1-continued

| Example | Structure |
|---------|-----------|
| 94 | 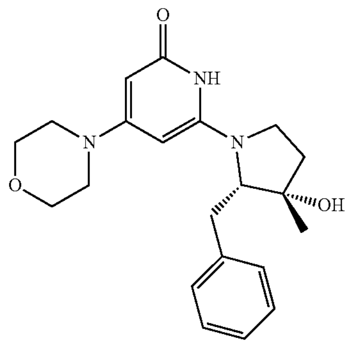 [SMILES: C[C@]1(O)CCN(c2cc(N3CCOCC3)cc(=O)[nH]2)[C@H]1Cc1ccccc1] |
| 95 | 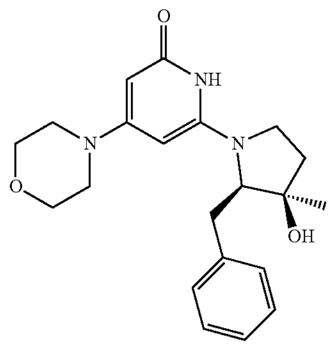 [SMILES: C[C@@]1(O)CCN(c2cc(N3CCOCC3)cc(=O)[nH]2)[C@@H]1Cc1ccccc1] |
| 96 | 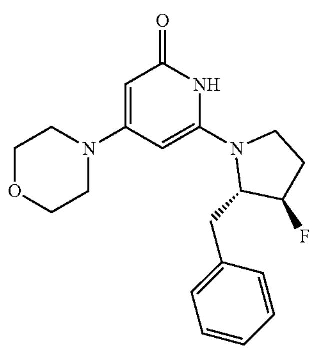 [SMILES: O=c1cc(N2CCOCC2)cc(N2CC[C@@H](F)[C@@H]2Cc2ccccc2)[nH]1] |
| 97 | 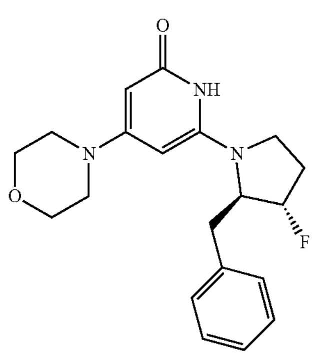 [SMILES: O=c1cc(N2CCOCC2)cc(N2CC[C@H](F)[C@H]2Cc2ccccc2)[nH]1] |
| 98 | |
| 99 | |
| 100 | stereoisomer 1 |
| 101 | stereoisomer 2 |

TABLE 1-continued

| Example | Structure |
|---------|-----------|
| 102 | 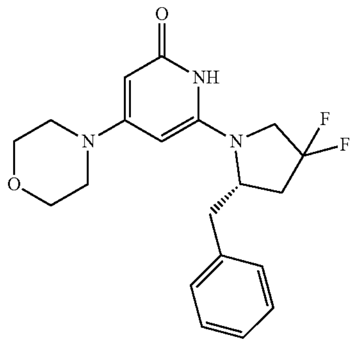 [SMILES: O=c1cc(N2CCOCC2)cc(N2CC(F)(F)C[C@@H]2Cc2ccccc2)[nH]1] |
| 103 | 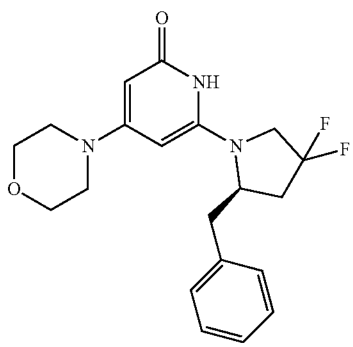 [SMILES: O=c1cc(N2CCOCC2)cc(N2CC(F)(F)C[C@H]2Cc2ccccc2)[nH]1] |
| 104 | 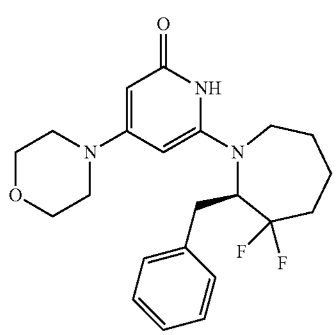 [SMILES: O=c1cc(N2CCOCC2)cc(N2CCCCC(F)(F)[C@H]2Cc2ccccc2)[nH]1] |
| 105 | 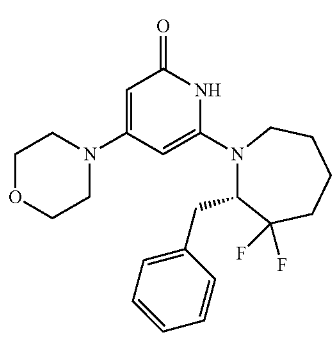 [SMILES: O=c1cc(N2CCOCC2)cc(N2CCCCC(F)(F)[C@@H]2Cc2ccccc2)[nH]1] |
| 106 | 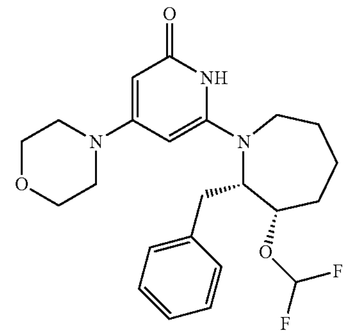 [SMILES: O=c1cc(N2CCOCC2)cc(N2CCCC[C@H](OC(F)F)[C@@H]2Cc2ccccc2)[nH]1] |
| 107 | 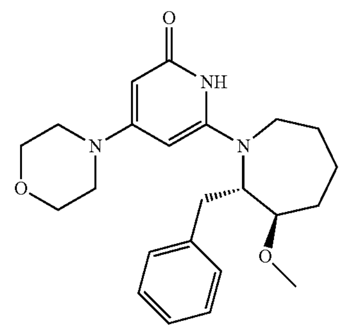 [SMILES: CO[C@@H]1CCCCN(c2cc(N3CCOCC3)cc(=O)[nH]2)[C@H]1Cc1ccccc1] |
| 108 | 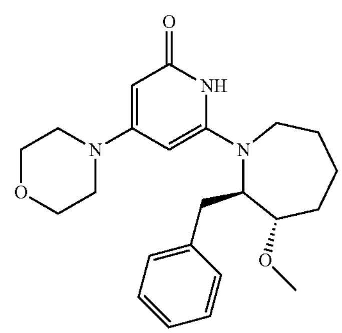 [SMILES: CO[C@H]1CCCCN(c2cc(N3CCOCC3)cc(=O)[nH]2)[C@@H]1Cc1ccccc1] |
| 109 | 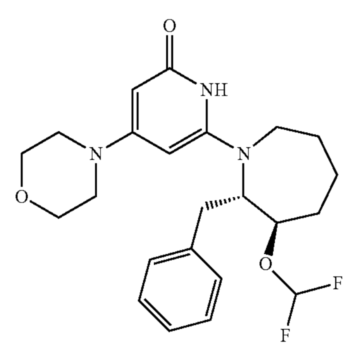 [SMILES: O=c1cc(N2CCOCC2)cc(N2CCCC[C@@H](OC(F)F)[C@@H]2Cc2ccccc2)[nH]1] |

TABLE 1-continued

| Example | Structure |
|---|---|
| 110 | 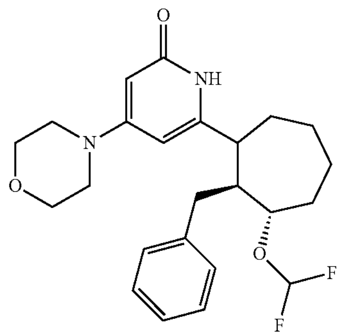 [SMILES: O=c1cc(N2CCOCC2)cc(C2CCCC[C@H](OC(F)F)[C@H]2Cc2ccccc2)[nH]1] |
| 111 | 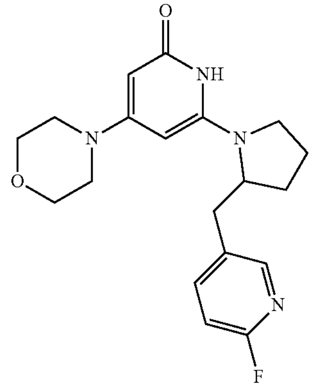 [SMILES: O=c1cc(N2CCOCC2)cc(N2CCCC2Cc2ccc(F)nc2)[nH]1] |
| 112 | 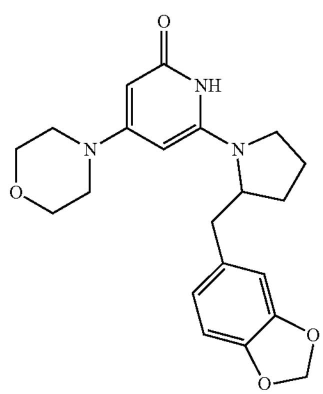 [SMILES: O=c1cc(N2CCOCC2)cc(N2CCCC2Cc2ccc3c(c2)OCO3)[nH]1] |
| 113 | 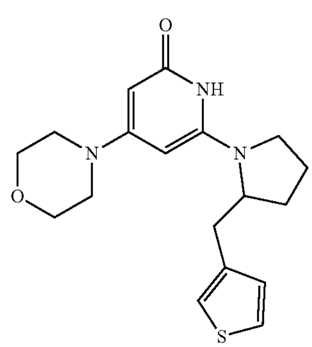 [SMILES: O=c1cc(N2CCOCC2)cc(N2CCCC2Cc2ccsc2)[nH]1] |
| 114 | 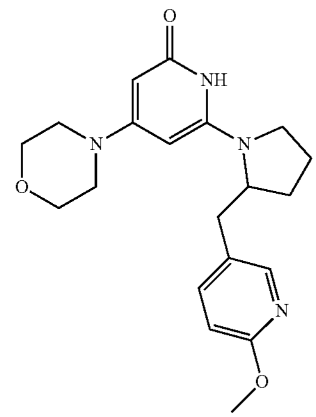 [SMILES: COc1ccc(CC2CCCN2c2cc(N3CCOCC3)cc(=O)[nH]2)cn1] |
| 115 | 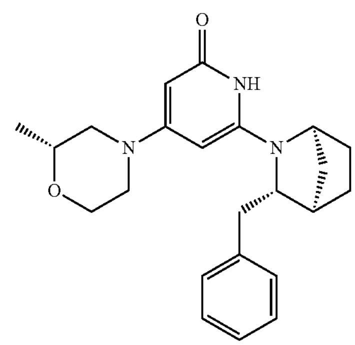 [SMILES: C[C@@H]1CN(c2cc(N3[C@H]4CC[C@H](C4)[C@@H]3Cc3ccccc3)[nH]c(=O)c2)CCO1] |
| 116 | 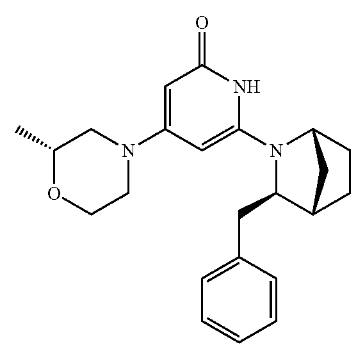 [SMILES: C[C@@H]1CN(c2cc(N3[C@@H]4CC[C@@H](C4)[C@H]3Cc3ccccc3)[nH]c(=O)c2)CCO1] |
| 117 | 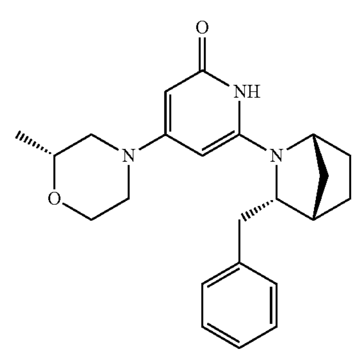 [SMILES: C[C@@H]1CN(c2cc(N3[C@@H]4CC[C@@H](C4)[C@@H]3Cc3ccccc3)[nH]c(=O)c2)CCO1] |

TABLE 1-continued

| Example | Structure |
|---|---|
| 118 | 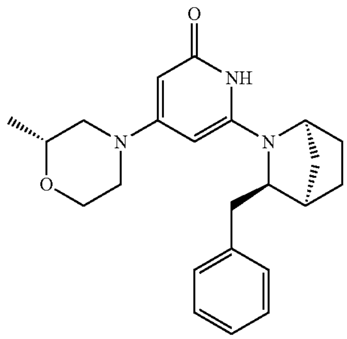 [SMILES: C[C@@H]1CN(c2cc(N3[C@H]4CC[C@H](C4)[C@H]3Cc3ccccc3)[nH]c(=O)c2)CCO1] |
| 119 | 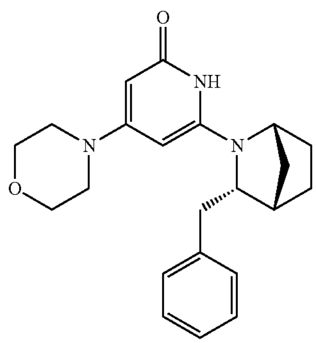 [SMILES: O=c1cc(N2CCOCC2)cc(N2[C@@H]3CC[C@@H](C3)[C@@H]2Cc2ccccc2)[nH]1] |
| 120 | 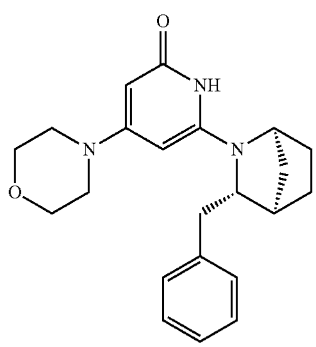 [SMILES: O=c1cc(N2CCOCC2)cc(N2[C@H]3CC[C@H](C3)[C@@H]2Cc2ccccc2)[nH]1] |
| 121 | 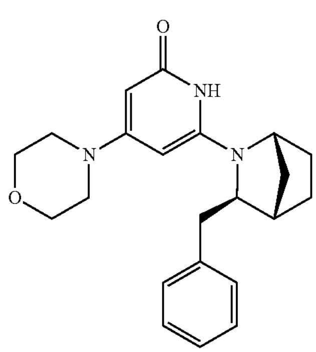 [SMILES: O=c1cc(N2CCOCC2)cc(N2[C@@H]3CC[C@@H](C3)[C@H]2Cc2ccccc2)[nH]1] |
| 122 | 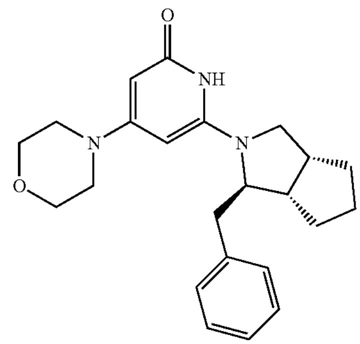 [SMILES: O=c1cc(N2CCOCC2)cc(N2C[C@@H]3CCC[C@@H]3[C@H]2Cc2ccccc2)[nH]1] |
| 123 | 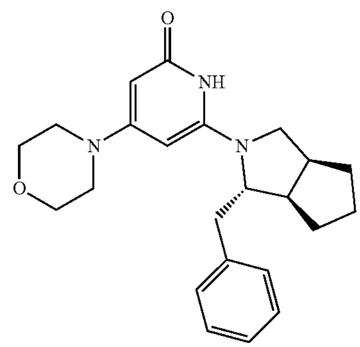 [SMILES: O=c1cc(N2CCOCC2)cc(N2C[C@H]3CCC[C@H]3[C@@H]2Cc2ccccc2)[nH]1] |
| 124 | 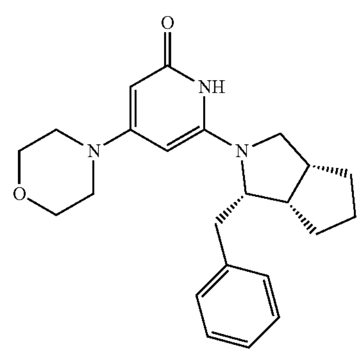 [SMILES: O=c1cc(N2CCOCC2)cc(N2C[C@@H]3CCC[C@@H]3[C@@H]2Cc2ccccc2)[nH]1] |
| 125 | 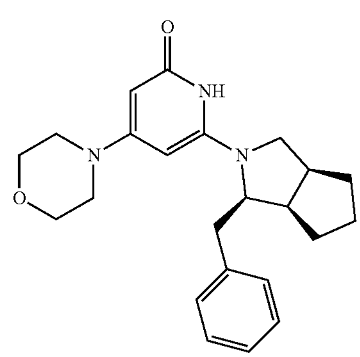 [SMILES: O=c1cc(N2CCOCC2)cc(N2C[C@H]3CCC[C@H]3[C@H]2Cc2ccccc2)[nH]1] |

TABLE 1-continued

| Example | Structure |
|---------|-----------|
| 126 | 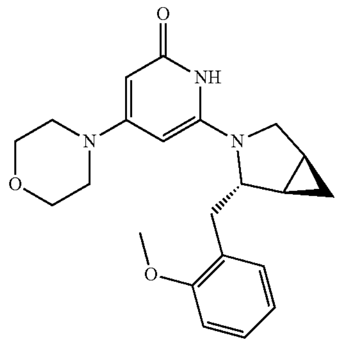 [SMILES: COc1ccccc1C[C@H]1[C@@H]2C[C@@H]2CN1c1cc(N2CCOCC2)cc(=O)[nH]1] |
| 127 | 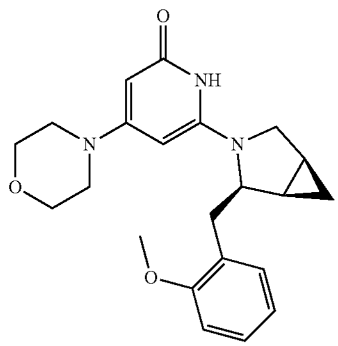 [SMILES: COc1ccccc1C[C@@H]1[C@@H]2C[C@@H]2CN1c1cc(N2CCOCC2)cc(=O)[nH]1] |
| 128 | 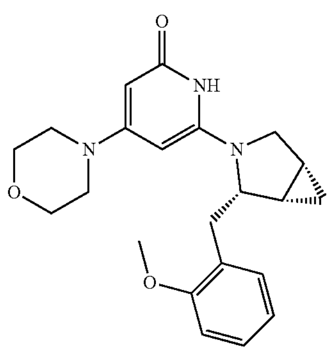 [SMILES: COc1ccccc1C[C@H]1[C@H]2C[C@H]2CN1c1cc(N2CCOCC2)cc(=O)[nH]1] |
| 129 | 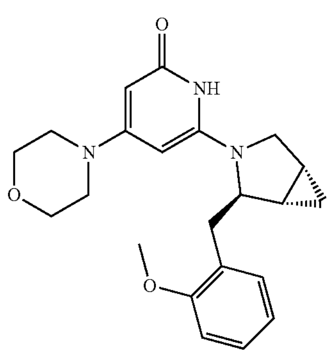 [SMILES: COc1ccccc1C[C@@H]1[C@H]2C[C@H]2CN1c1cc(N2CCOCC2)cc(=O)[nH]1] |
| 130 | 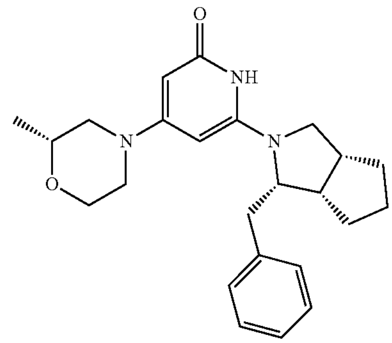 [SMILES: C[C@@H]1CN(c2cc(N3C[C@@H]4CCC[C@@H]4[C@@H]3Cc3ccccc3)[nH]c(=O)c2)CCO1] |
| 131 | 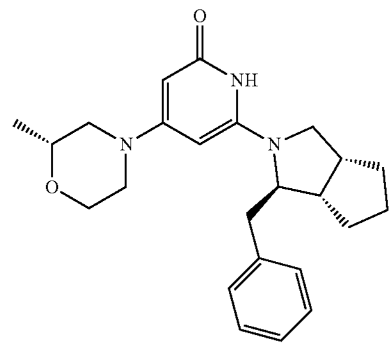 [SMILES: C[C@@H]1CN(c2cc(N3C[C@@H]4CCC[C@@H]4[C@H]3Cc3ccccc3)[nH]c(=O)c2)CCO1] |
| 132 | 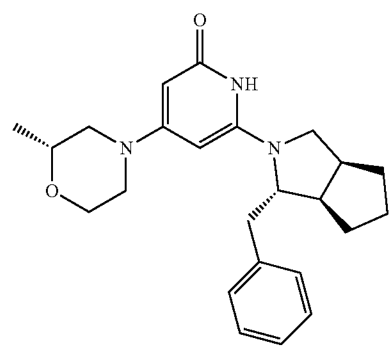 [SMILES: C[C@@H]1CN(c2cc(N3C[C@H]4CCC[C@H]4[C@@H]3Cc3ccccc3)[nH]c(=O)c2)CCO1] |
| 133 | 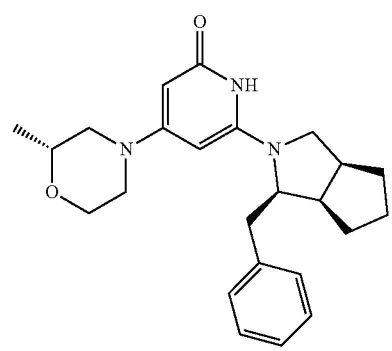 [SMILES: C[C@@H]1CN(c2cc(N3C[C@H]4CCC[C@H]4[C@H]3Cc3ccccc3)[nH]c(=O)c2)CCO1] |

TABLE 1-continued

| Example | Structure |
|---------|-----------|
| 134 | 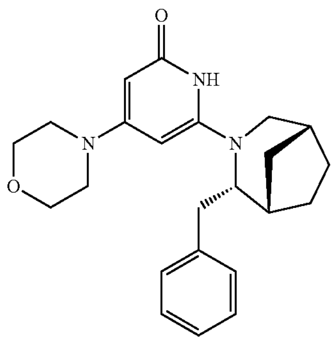 [SMILES: O=c1cc(N2CCOCC2)cc(N2C[C@@H]3CC[C@@H](C3)[C@@H]2Cc2ccccc2)[nH]1] |
| 135 | 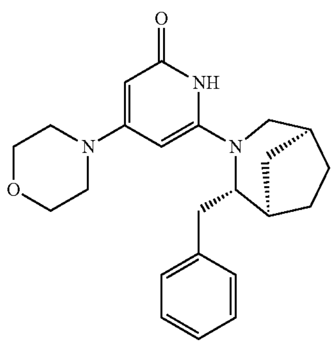 [SMILES: O=c1cc(N2CCOCC2)cc(N2C[C@H]3CC[C@H](C3)[C@@H]2Cc2ccccc2)[nH]1] |
| 136 | 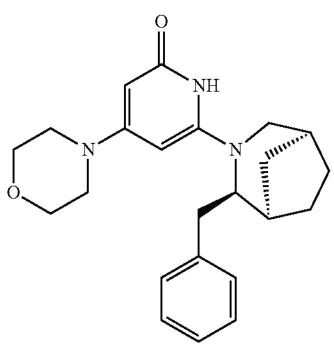 [SMILES: O=c1cc(N2CCOCC2)cc(N2C[C@H]3CC[C@H](C3)[C@H]2Cc2ccccc2)[nH]1] |
| 137 | 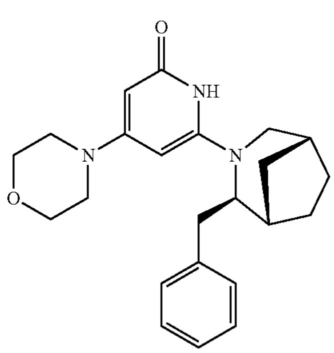 [SMILES: O=c1cc(N2CCOCC2)cc(N2C[C@@H]3CC[C@@H](C3)[C@H]2Cc2ccccc2)[nH]1] |
| 138 | |
| 139 | |
| 140 | |
| 141 | |

TABLE 1-continued

| Example | Structure |
|---------|-----------|
| 142 | 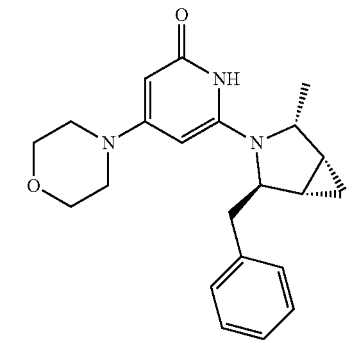 [SMILES: C[C@@H]1[C@@H]2C[C@@H]2[C@@H](Cc2ccccc2)N1c1cc(N2CCOCC2)cc(=O)[nH]1] |
| 143 | 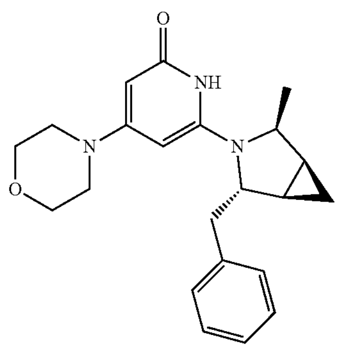 [SMILES: C[C@H]1[C@H]2C[C@H]2[C@H](Cc2ccccc2)N1c1cc(N2CCOCC2)cc(=O)[nH]1] |
| 144 | 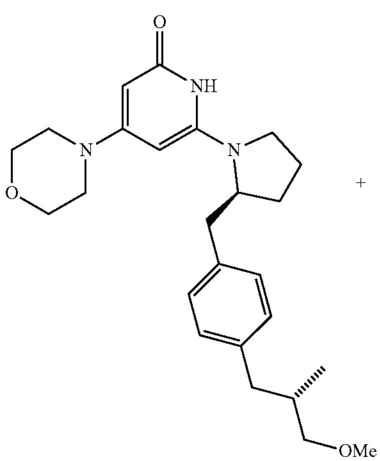 [SMILES: COC[C@@H](C)Cc1ccc(C[C@@H]2CCCN2c2cc(N3CCOCC3)cc(=O)[nH]2)cc1] |
| 145 | 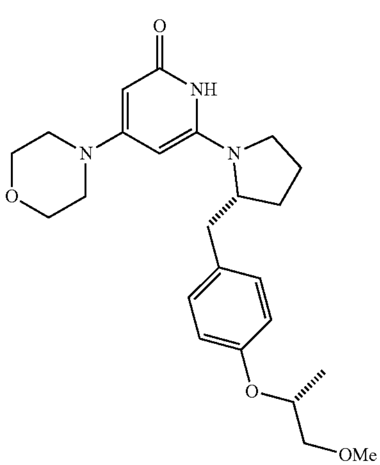 [SMILES: COC[C@@H](C)Oc1ccc(C[C@H]2CCCN2c2cc(N3CCOCC3)cc(=O)[nH]2)cc1] |
| 146 | |
| 147 | |
| 148 | |

TABLE 1-continued

| Example | Structure |
|---|---|
| 149 | |
| 150 | |
| 151 | |
| 152 | 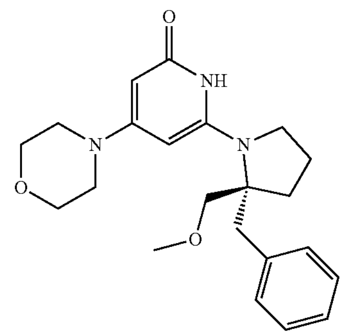 [SMILES: COC[C@]1(Cc2ccccc2)CCCN1c1cc(N2CCOCC2)cc(=O)[nH]1] |
| 153 | 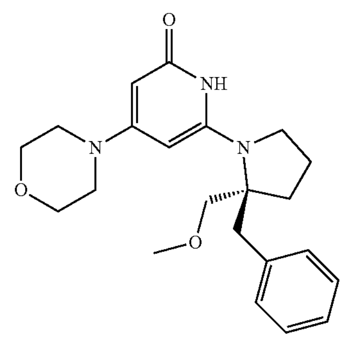 [SMILES: COC[C@@]1(Cc2ccccc2)CCCN1c1cc(N2CCOCC2)cc(=O)[nH]1] |
| 154 | 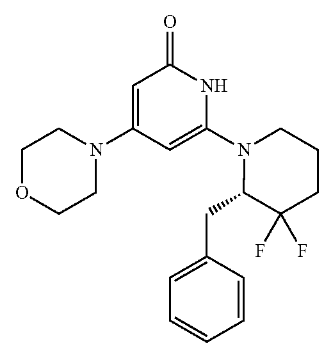 [SMILES: O=c1cc(N2CCOCC2)cc(N2CCCC(F)(F)[C@@H]2Cc2ccccc2)[nH]1] |
| 155 | 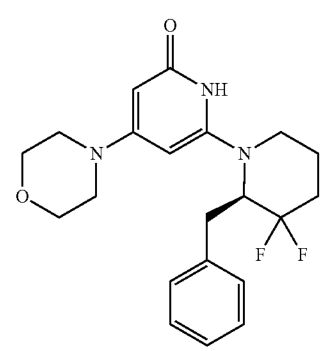 [SMILES: O=c1cc(N2CCOCC2)cc(N2CCCC(F)(F)[C@H]2Cc2ccccc2)[nH]1] |

TABLE 1-continued

| Example | Structure |
|---|---|
| 156 | (structure) |
| 157 | (structure) |
| 158 | (structure) |
| 159 | (structure) |
| 160 | (structure) |
| 161 | (structure) |
| 162 | (structure) |
| 163 | (structure) |

TABLE 1-continued

| Example | Structure |
|---------|-----------|
| 164 | 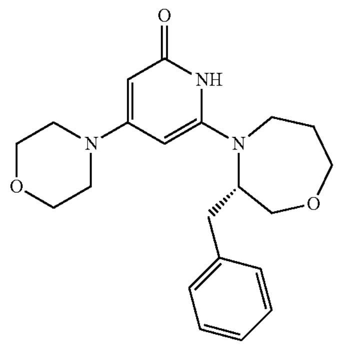 [SMILES: O=c1cc(N2CCOCC2)cc(N2CCCOC[C@@H]2Cc2ccccc2)[nH]1] |
| 165 | stereoisomer 1 |
| 166 | mixture of 2 isomers |
| 167 | 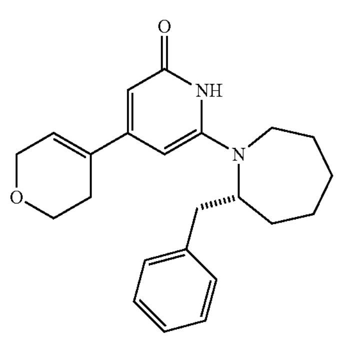 [SMILES: O=c1cc(C2=CCOCC2)cc(N2CCCCC[C@@H]2Cc2ccccc2)[nH]1] |
| 168 | |
| 169 | |
| 170 | |
| 171 | |

TABLE 1-continued
| Example | Structure |
|---|---|
| 172 | 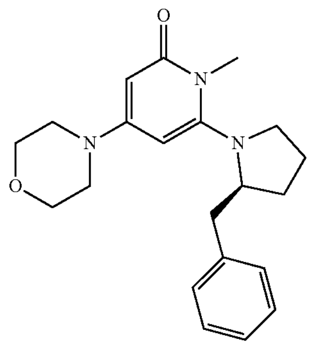 [SMILES: Cn1c(N2CCC[C@H]2Cc2ccccc2)cc(N2CCOCC2)cc1=O] |
| 173 | 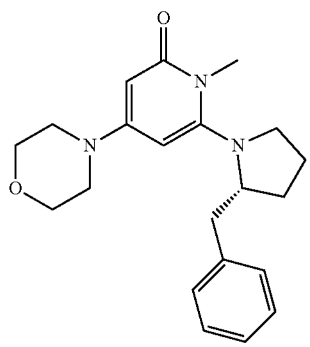 [SMILES: Cn1c(N2CCC[C@@H]2Cc2ccccc2)cc(N2CCOCC2)cc1=O] |
| 174 | 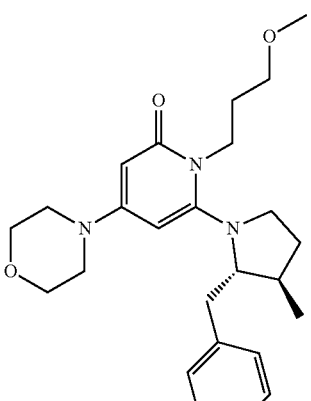 |
| 175 | 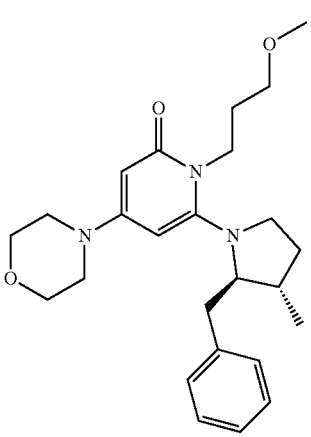 [SMILES: COCCCn1c(N2CC[C@H](C)[C@H]2Cc2ccccc2)cc(N2CCOCC2)cc1=O] |
| 176 | 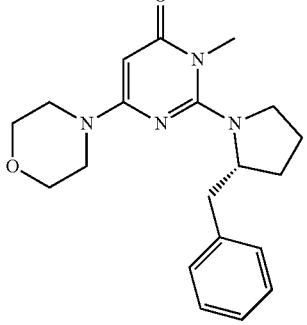 |
| 177 | 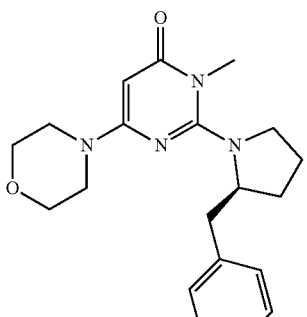 |
| 178 | 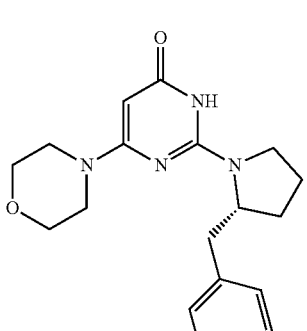 |
| 179 | 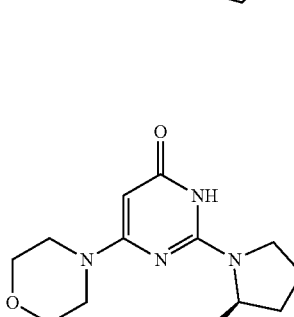 |

TABLE 1-continued

| Example | Structure |
|---------|-----------|
| 180 | 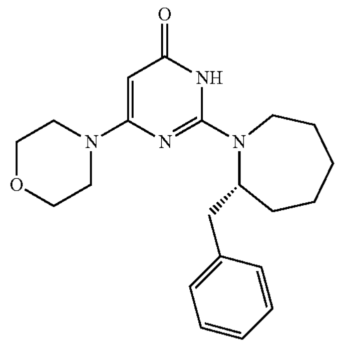 |
| 181 | 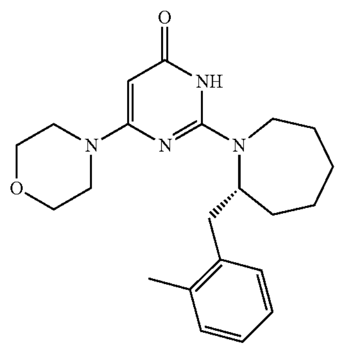 [SMILES: Cc1ccccc1C[C@H]1CCCCCN1c1nc(N2CCOCC2)cc(=O)[nH]1] |
| 182 | 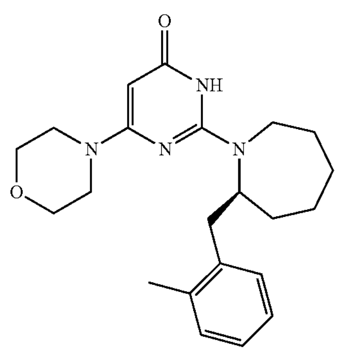 [SMILES: Cc1ccccc1C[C@@H]1CCCCCN1c1nc(N2CCOCC2)cc(=O)[nH]1] |
| 183 | 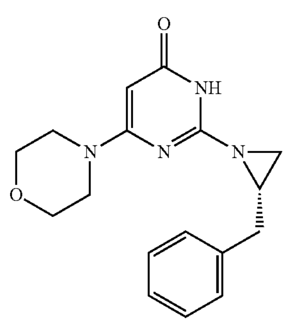 [SMILES: O=c1cc(N2CCOCC2)nc(N2C[C@@H]2Cc2ccccc2)[nH]1] |
| 184 | 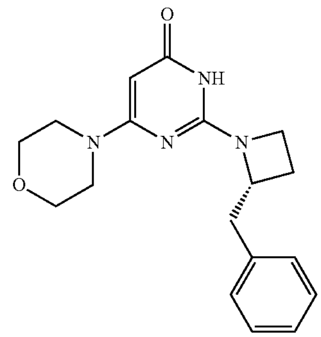 [SMILES: O=c1cc(N2CCOCC2)nc(N2CC[C@@H]2Cc2ccccc2)[nH]1] |
| 185 | 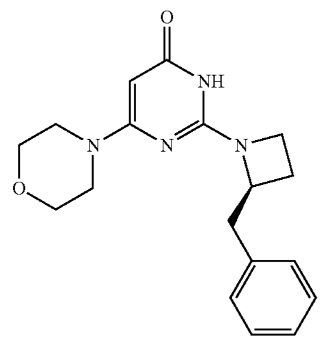 [SMILES: O=c1cc(N2CCOCC2)nc(N2CC[C@H]2Cc2ccccc2)[nH]1] |
| 186 | 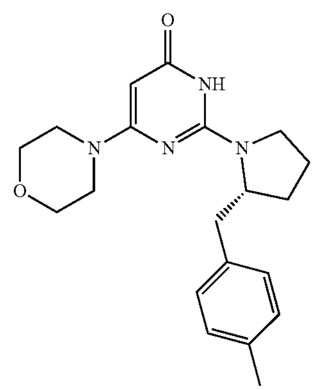 [SMILES: Cc1ccc(C[C@H]2CCCN2c2nc(N3CCOCC3)cc(=O)[nH]2)cc1] |
| 187 | 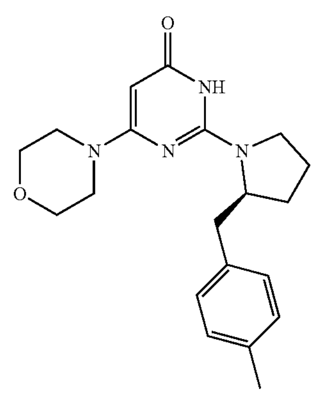 [SMILES: Cc1ccc(C[C@@H]2CCCN2c2nc(N3CCOCC3)cc(=O)[nH]2)cc1] |

TABLE 1-continued

| Example | Structure |
|---------|-----------|
| 188 | 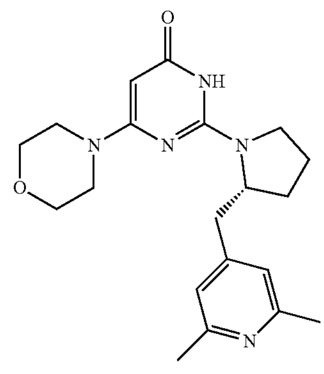 [SMILES: Cc1cc(C[C@H]2CCCN2c2nc(N3CCOCC3)cc(=O)[nH]2)cc(C)n1] |
| 189 | 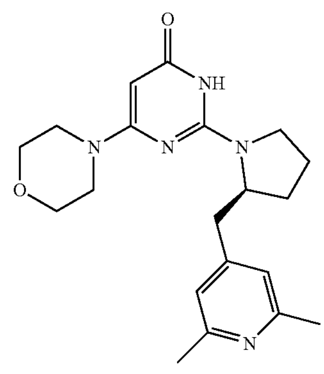 [SMILES: Cc1cc(C[C@@H]2CCCN2c2nc(N3CCOCC3)cc(=O)[nH]2)cc(C)n1] |
| 190 | 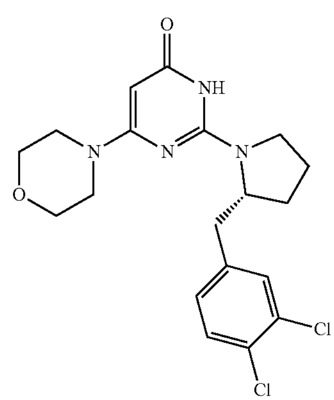 [SMILES: O=c1cc(N2CCOCC2)nc(N2CCC[C@@H]2Cc2ccc(Cl)c(Cl)c2)[nH]1] |
| 191 | 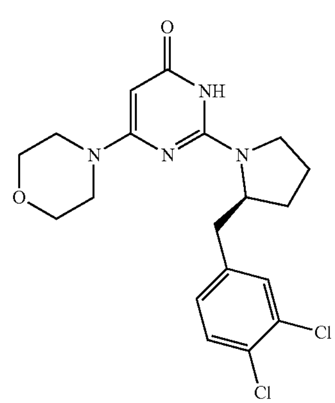 [SMILES: O=c1cc(N2CCOCC2)nc(N2CCC[C@H]2Cc2ccc(Cl)c(Cl)c2)[nH]1] |
| 192 | |
| 193 | |
| 194 | |
| 195 | |

TABLE 1-continued
| Example | Structure |
|---------|-----------|
| 196 | 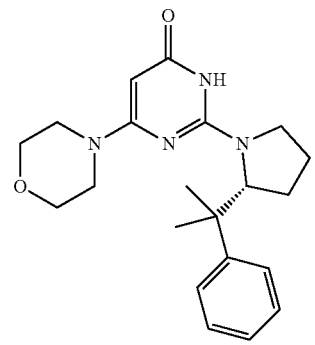 [SMILES: CC(C)(c1ccccc1)[C@H]1CCCN1c1nc(N2CCOCC2)cc(=O)[nH]1] |
| 197 | 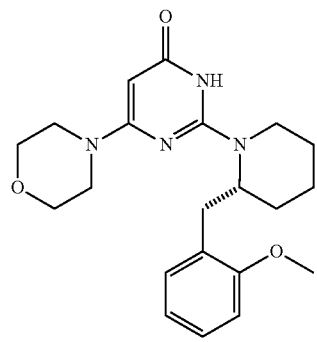 [SMILES: COc1ccccc1C[C@H]1CCCCN1c1nc(N2CCOCC2)cc(=O)[nH]1] |
| 198 | 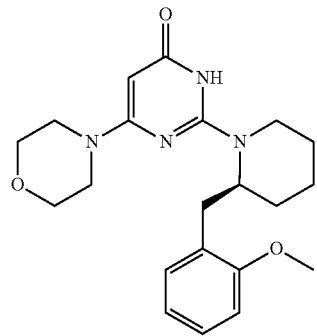 [SMILES: COc1ccccc1C[C@@H]1CCCCN1c1nc(N2CCOCC2)cc(=O)[nH]1] |
| 199 | 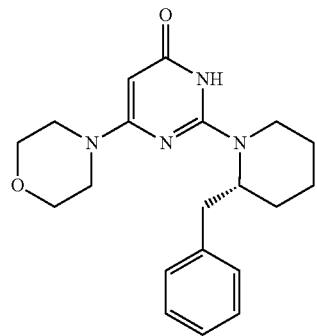 |
TABLE 1-continued
| Example | Structure |
|---------|-----------|
| 200 | 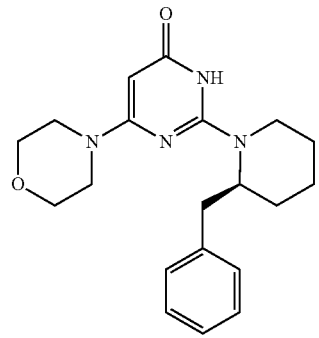 [SMILES: O=c1cc(N2CCOCC2)nc(N2CCCC[C@H]2Cc2ccccc2)[nH]1] |
| 201 | 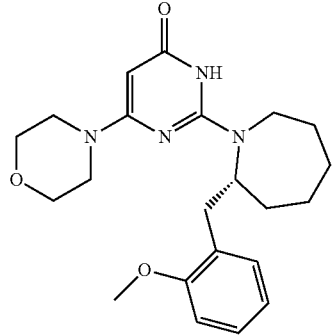 [SMILES: COc1ccccc1C[C@H]1CCCCCN1c1nc(N2CCOCC2)cc(=O)[nH]1] |
| 202 | 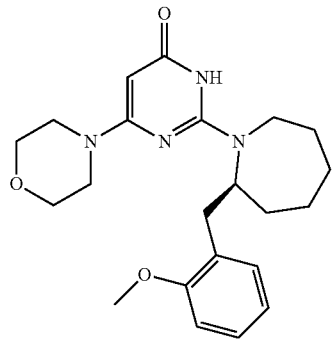 [SMILES: COc1ccccc1C[C@@H]1CCCCCN1c1nc(N2CCOCC2)cc(=O)[nH]1] |
| 203 | 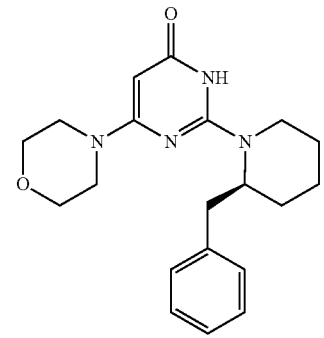 |

TABLE 1-continued
| Example | Structure |
|---------|-----------|
| 204 | 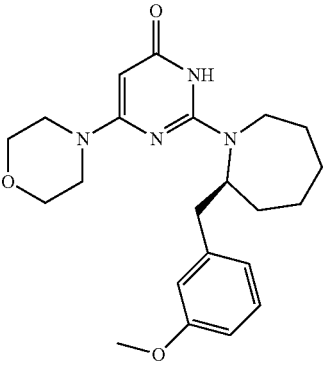 [SMILES: COc1cccc(C[C@@H]2CCCCCN2c2nc(N3CCOCC3)cc(=O)[nH]2)c1] |
| 205 | 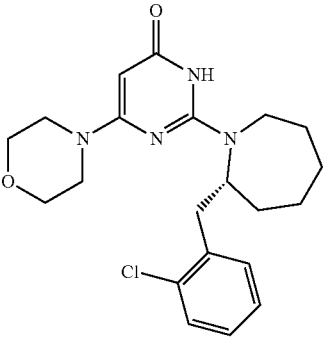 [SMILES: O=c1cc(N2CCOCC2)nc(N2CCCCC[C@@H]2Cc2ccccc2Cl)[nH]1] |
| 206 | 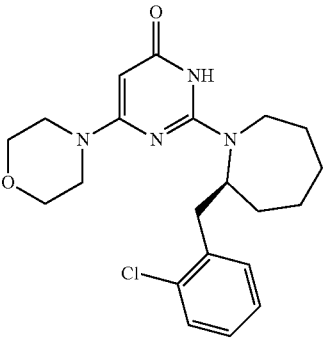 [SMILES: O=c1cc(N2CCOCC2)nc(N2CCCCC[C@H]2Cc2ccccc2Cl)[nH]1] |
| 207 | 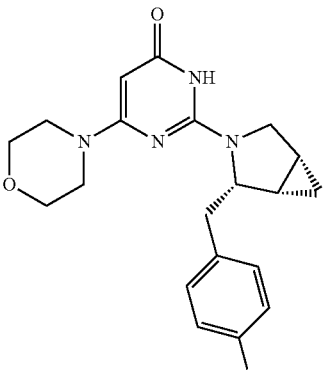 |
| 208 | 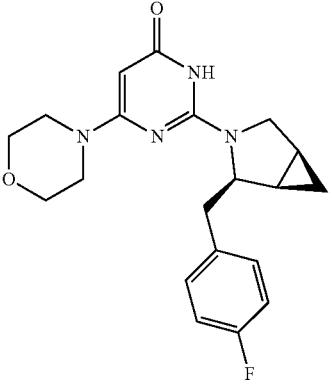 [SMILES: O=c1cc(N2CCOCC2)nc(N2C[C@H]3C[C@H]3[C@H]2Cc2ccc(F)cc2)[nH]1] |
| 209 | 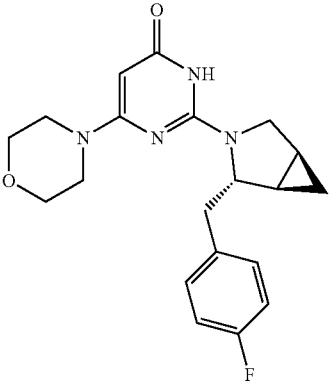 [SMILES: O=c1cc(N2CCOCC2)nc(N2C[C@H]3C[C@H]3[C@@H]2Cc2ccc(F)cc2)[nH]1] |
| 210 | 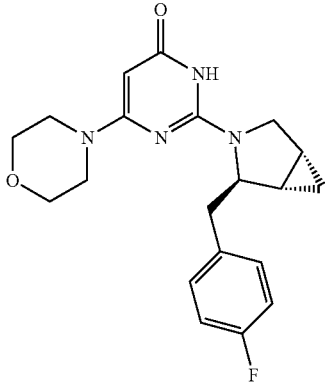 [SMILES: O=c1cc(N2CCOCC2)nc(N2C[C@@H]3C[C@@H]3[C@H]2Cc2ccc(F)cc2)[nH]1] |
| 211 | 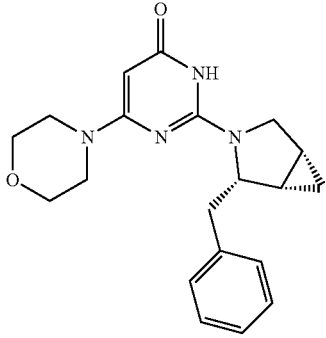 [SMILES: O=c1cc(N2CCOCC2)nc(N2C[C@@H]3C[C@@H]3[C@@H]2Cc2ccccc2)[nH]1] |

TABLE 1-continued
| Example | Structure |
|---|---|
| 212 | 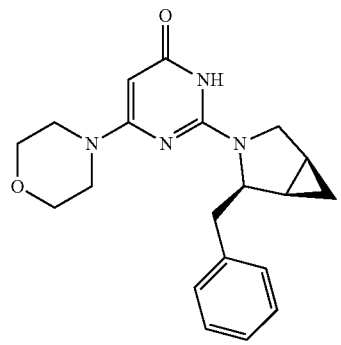 |
| 213 | 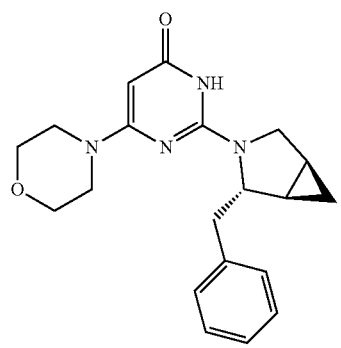 [SMILES: O=c1cc(N2CCOCC2)nc(N2C[C@H]3C[C@H]3[C@@H]2Cc2ccccc2)[nH]1] |
| 214 | 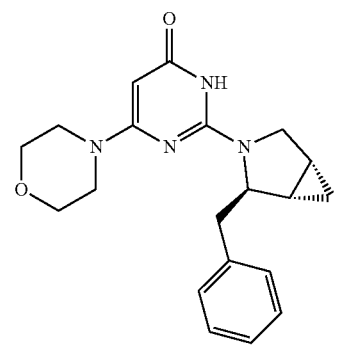 [SMILES: O=c1cc(N2CCOCC2)nc(N2C[C@@H]3C[C@@H]3[C@H]2Cc2ccccc2)[nH]1] |
| 215 | 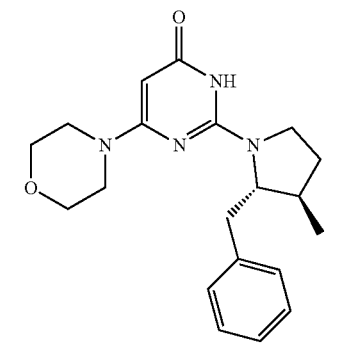 [SMILES: C[C@@H]1CCN(c2nc(N3CCOCC3)cc(=O)[nH]2)[C@H]1Cc1ccccc1] |ует
TABLE 1-continued
| Example | Structure |
|---|---|
| 216 | 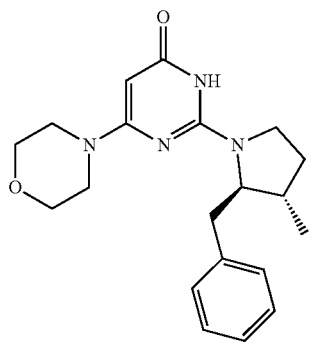 [SMILES: C[C@H]1CCN(c2nc(N3CCOCC3)cc(=O)[nH]2)[C@@H]1Cc1ccccc1] |
| 217 | 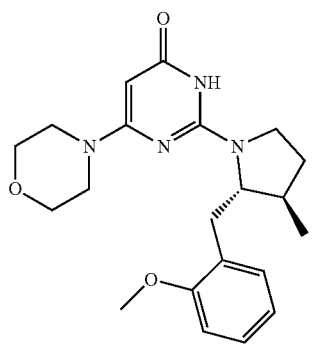 [SMILES: COc1ccccc1C[C@H]1[C@H](C)CCN1c1nc(N2CCOCC2)cc(=O)[nH]1] |
| 218 | 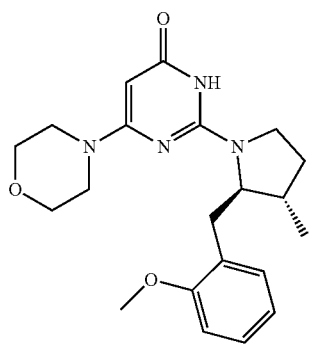 [SMILES: COc1ccccc1C[C@@H]1[C@@H](C)CCN1c1nc(N2CCOCC2)cc(=O)[nH]1] |
| 219 | 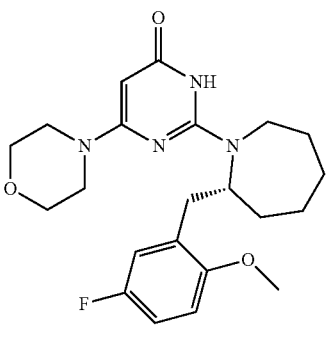 [SMILES: COc1ccc(F)cc1C[C@H]1CCCCCN1c1nc(N2CCOCC2)cc(=O)[nH]1] |

TABLE 1-continued

| Example | Structure |
|---|---|
| 220 | 6-morpholino-2-[(2S)-2-[(5-fluoro-2-methoxyphenyl)methyl]azepan-1-yl]-1H-pyrimidin-4-one |
| 221 | 6-morpholino-2-[(2S)-2-[(4-fluorophenyl)methyl]azepan-1-yl]-1H-pyrimidin-4-one |
| 222 | 6-morpholino-2-[(2R)-2-[(4-fluorophenyl)methyl]azepan-1-yl]-1H-pyrimidin-4-one |
| 223 | 6-morpholino-2-[(2S)-2-[(2,3-difluorophenyl)methyl]azepan-1-yl]-1H-pyrimidin-4-one |
| 224 | 6-morpholino-2-[(2S)-2-[(2,6-difluorophenyl)methyl]azepan-1-yl]-1H-pyrimidin-4-one |
| 225 | 6-morpholino-2-[(2S)-2-[(2,3-dihydrobenzofuran-7-yl)methyl]azepan-1-yl]-1H-pyrimidin-4-one |
| 226 | 6-morpholino-2-[(2R)-2-[(2,3-dihydrobenzofuran-7-yl)methyl]azepan-1-yl]-1H-pyrimidin-4-one |
| 227 | 6-morpholino-2-[(2S)-2-[(4-fluoro-2-methoxyphenyl)methyl]azepan-1-yl]-1H-pyrimidin-4-one |

TABLE 1-continued
| Example | Structure |
|---------|-----------|
| 228 | 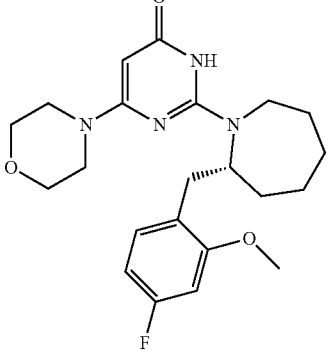 |
| 229 | 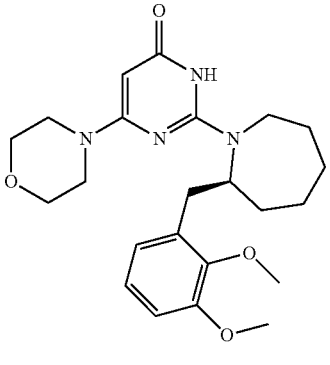 [SMILES: COc1cccc(C[C@@H]2CCCCCN2c2nc(N3CCOCC3)cc(=O)[nH]2)c1OC] |
| 230 | 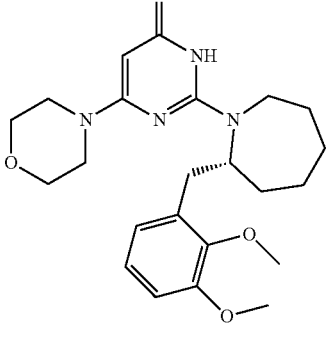 |
| 231 | 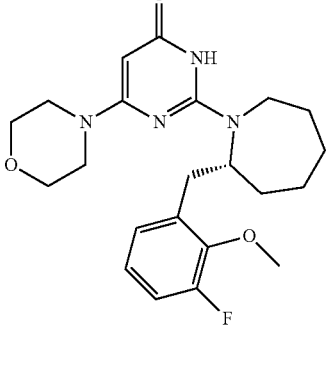 |
TABLE 1-continued
| Example | Structure |
|---------|-----------|
| 232 | 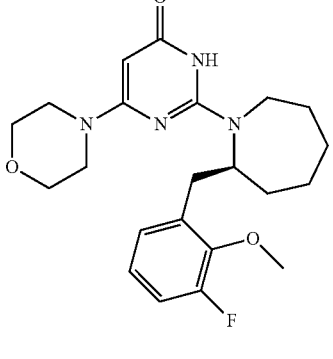 |
| 233 | 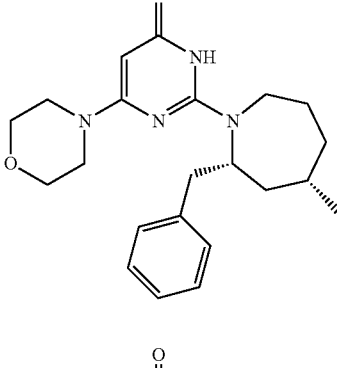 |
| 234 | 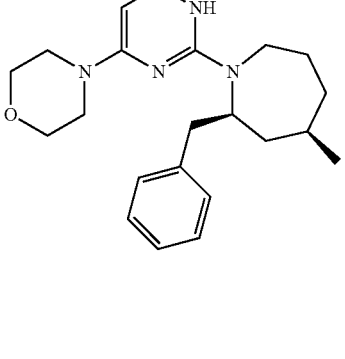 |
| 235 | 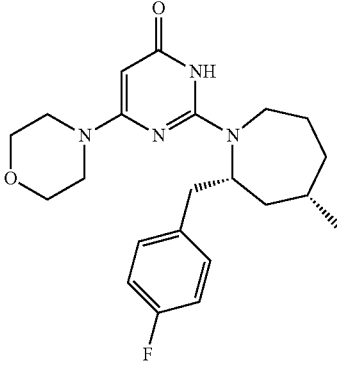 [SMILES: C[C@H]1CCCN(c2nc(N3CCOCC3)cc(=O)[nH]2)[C@@H](Cc2ccc(F)cc2)C1] |

TABLE 1-continued

| Example | Structure |
|---|---|
| 236 | (morpholine)-pyrimidinone-N-azepane with 4-fluorobenzyl and methyl substituents |
| 237 | (morpholine)-pyrimidinone-N-azepane with 2-methoxybenzyl and methyl substituents |
| 238 | (morpholine)-pyrimidinone-N-azepane with 2-methoxybenzyl and methyl substituents |
| 239 | (morpholine)-pyrimidinone-N-azepane with 2-methoxybenzyl and gem-difluoro substituents |
| 240 | (morpholine)-pyrimidinone-N-azepane with benzyl and isopropyl substituents |
| 241 | (morpholine)-pyrimidinone-N-azepane with benzyl and isopropyl substituents |
| 242 | (morpholine)-pyrimidinone-N-azepane with benzyl and gem-dimethyl substituents |
| 243 | (morpholine)-pyrimidinone-N-azepane with benzyl and gem-dimethyl substituents |

TABLE 1-continued

| Example | Structure |
|---|---|
| 244 | (morpholine)-pyrimidin-4(3H)-one-2-yl linked to azepane with benzyl and 4,4-difluoro substituents |
| 245 | (morpholine)-pyrimidin-4(3H)-one-2-yl linked to 5,5-dimethyl azepane with benzyl substituent |
| 246 | (morpholine)-pyrimidin-4(3H)-one-2-yl linked to methyl-substituted azepane with benzyl group, stereoisomer 2 |
| 247 | (morpholine)-pyrimidin-4(3H)-one-2-yl linked to methyl-substituted azepane with benzyl group, stereoisomer 1 |
| 248 | (morpholine)-pyrimidin-4(3H)-one-2-yl linked to azepane with thiophen-3-ylmethyl substituent |
| 249 | (morpholine)-pyrimidin-4(3H)-one-2-yl linked to azepane with thiophen-3-ylmethyl substituent |
| 250 | (morpholine)-pyrimidin-4(3H)-one-2-yl linked to pyrrolidine with 1-phenylethyl substituent |
| 251 | (morpholine)-pyrimidin-4(3H)-one-2-yl linked to pyrrolidine with 1-phenylethyl substituent |

TABLE 1-continued

| Example | Structure |
|---|---|
| 252 | (structure) enantiomeric mixture 1 & 2 |
| 253 | (structure) |
| 254 | (structure) |
| 255 | (structure) |
| 256 | (structure) |
| 257 | (structure) |
| 258 | (structure) |
| 259 | (structure) |

TABLE 1-continued
| Example | Structure |
|---|---|
| 260 | 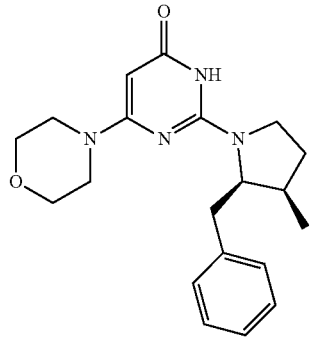 [SMILES: C[C@@H]1CCN(c2nc(N3CCOCC3)cc(=O)[nH]2)[C@@H]1Cc1ccccc1] |
| 261 | 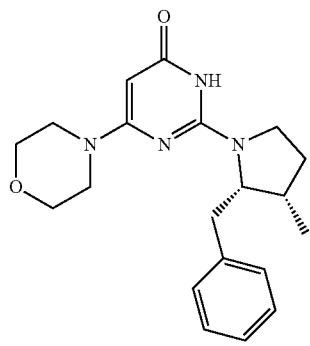 [SMILES: C[C@H]1CCN(c2nc(N3CCOCC3)cc(=O)[nH]2)[C@H]1Cc1ccccc1] |
| 262 | 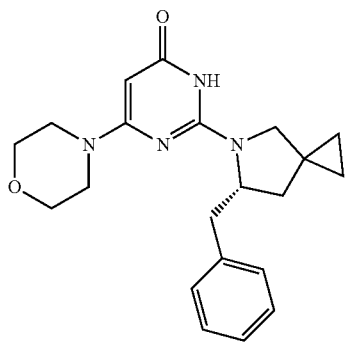 [SMILES: O=c1cc(N2CCOCC2)nc(N2CC3(CC3)C[C@@H]2Cc2ccccc2)[nH]1] |
| 263 | 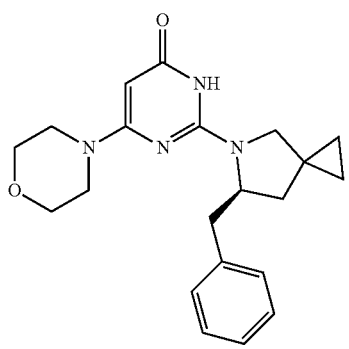 [SMILES: O=c1cc(N2CCOCC2)nc(N2CC3(CC3)C[C@H]2Cc2ccccc2)[nH]1] |
| 264 | 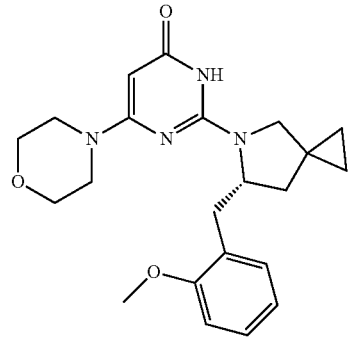 [SMILES: COc1ccccc1C[C@H]1CC2(CC2)CN1c1nc(N2CCOCC2)cc(=O)[nH]1] |
| 265 | 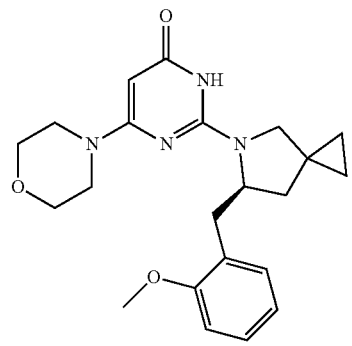 [SMILES: COc1ccccc1C[C@@H]1CC2(CC2)CN1c1nc(N2CCOCC2)cc(=O)[nH]1] |
| 266 | 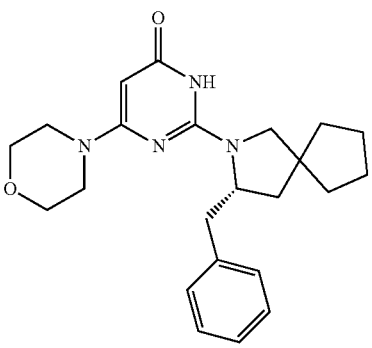 [SMILES: O=c1cc(N2CCOCC2)nc(N2CC3(CCCC3)C[C@@H]2Cc2ccccc2)[nH]1] |
| 267 | 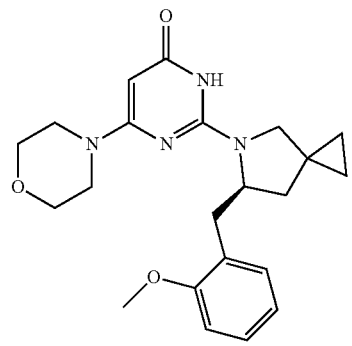 [SMILES: COc1ccccc1C[C@@H]1CC2(CC2)CN1c1nc(N2CCOCC2)cc(=O)[nH]1] |

TABLE 1-continued

| Example | Structure |
|---|---|
| 268 | (structure) |
| 269 | (structure) |
| 270 | (structure) |
| 271 | (structure) |
| 272 | (structure) |
| 273 | (structure) |
| 274 | (structure) |
| 275 | (structure) |

TABLE 1-continued
| Example | Structure |
|---|---|
| 276 | 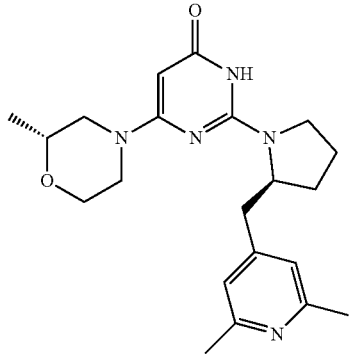 |
| 277 | 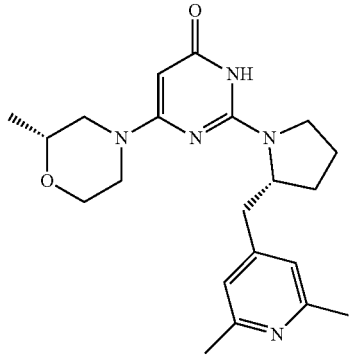 |
| 278 | 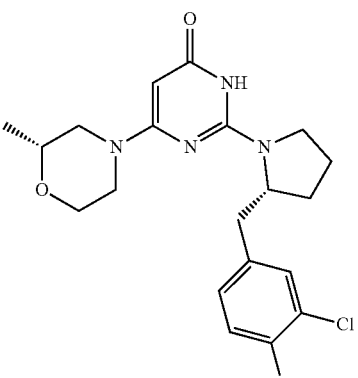 |
| 279 | 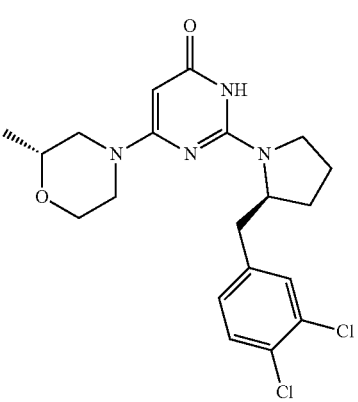 [SMILES: C[C@@H]1CN(c2cc(=O)[nH]c(N3CCC[C@H]3Cc3ccc(Cl)c(Cl)c3)n2)CCO1] |
| 280 | 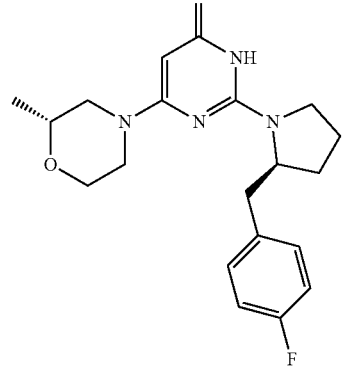 |
| 281 | 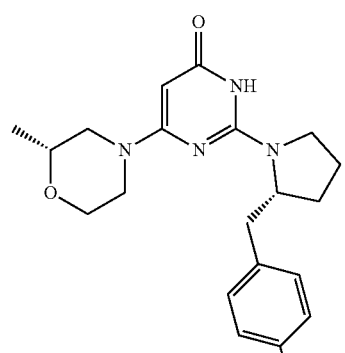 |
| 282 | 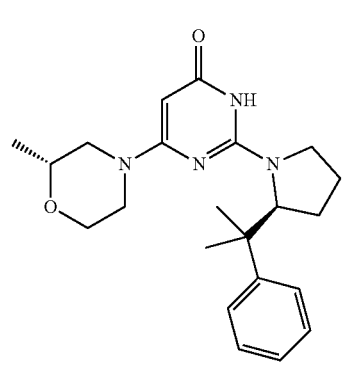 [SMILES: C[C@@H]1CN(c2cc(=O)[nH]c(N3CCC[C@H]3C(C)(C)c3ccccc3)n2)CCO1] |
| 283 | 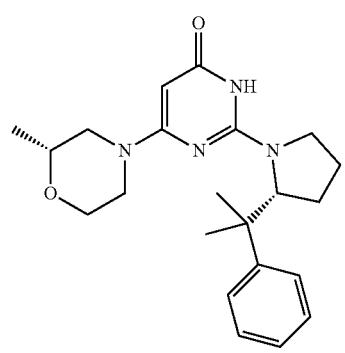 [SMILES: C[C@@H]1CN(c2cc(=O)[nH]c(N3CCC[C@@H]3C(C)(C)c3ccccc3)n2)CCO1] |

TABLE 1-continued

| Example | Structure |
|---|---|
| 284 | (structure) |
| 285 | (structure) |
| 286 | (structure) |
| 287 | (structure) |
| 288 | (structure) |
| 289 | (structure) |
| 290 | (structure) |
| 291 | (structure) |
| 292 | (structure) |

TABLE 1-continued
| Example | Structure |
|---|---|
| 293 | 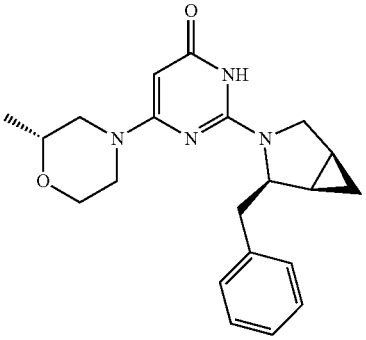 |
| 294 | 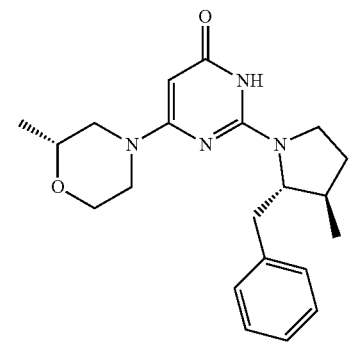 [SMILES: C[C@@H]1CN(c2cc(=O)[nH]c(N3CC[C@@H](C)[C@@H]3Cc3ccccc3)n2)CCO1] |
| 295 | 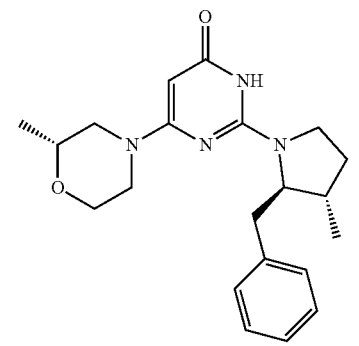 [SMILES: C[C@@H]1CN(c2cc(=O)[nH]c(N3CC[C@H](C)[C@H]3Cc3ccccc3)n2)CCO1] |
| 296 | 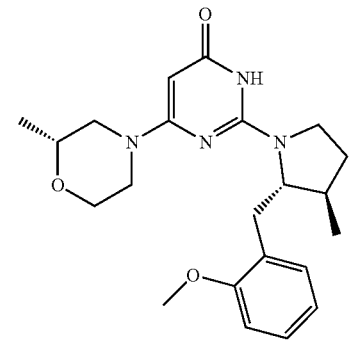 [SMILES: COc1ccccc1C[C@H]1[C@H](C)CCN1c1nc(N2CCO[C@H](C)C2)cc(=O)[nH]1] |
| 297 | 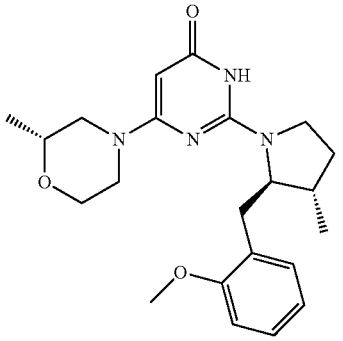 [SMILES: COc1ccccc1C[C@@H]1[C@@H](C)CCN1c1nc(N2CCO[C@H](C)C2)cc(=O)[nH]1] |
| 298 | 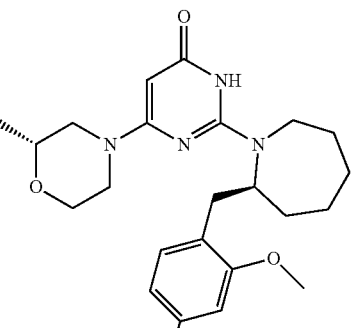 |
| 299 | 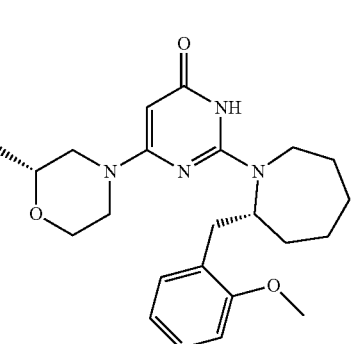 |
| 300 | 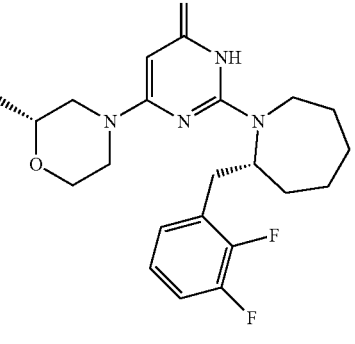 |

TABLE 1-continued
| Example | Structure |
|---|---|
| 301 | 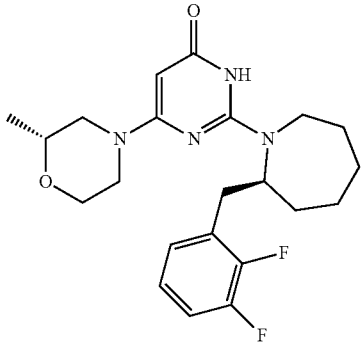 [SMILES: C[C@@H]1CN(c2cc(=O)[nH]c(N3CCCCC[C@H]3Cc3cccc(F)c3F)n2)CCO1] |
| 302 | 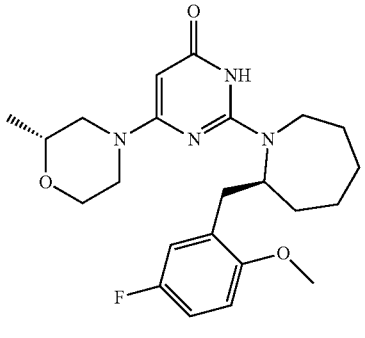 [SMILES: COc1ccc(F)cc1C[C@@H]1CCCCCN1c1nc(N2CCO[C@H](C)C2)cc(=O)[nH]1] |
| 303 | 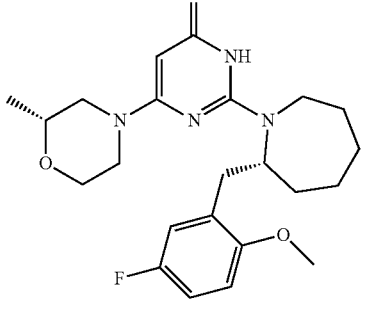 |
| 304 | 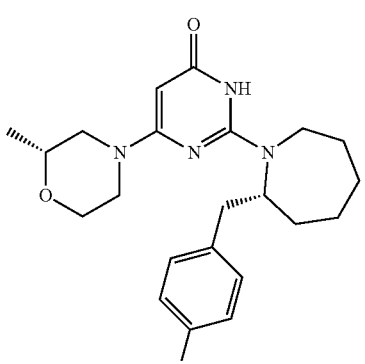 |
| 305 | 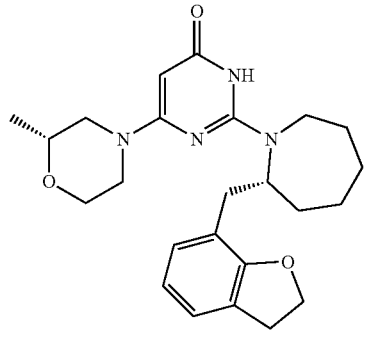 [SMILES: C[C@@H]1CN(c2cc(=O)[nH]c(N3CCCCC[C@@H]3Cc3cccc4c3OCC4)n2)CCO1] |
| 306 | 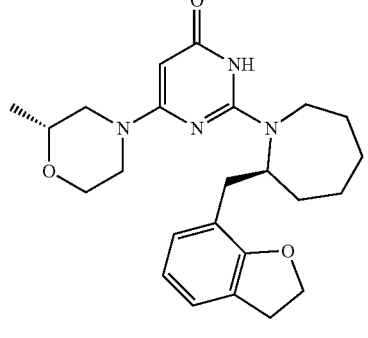 |
| 307 | 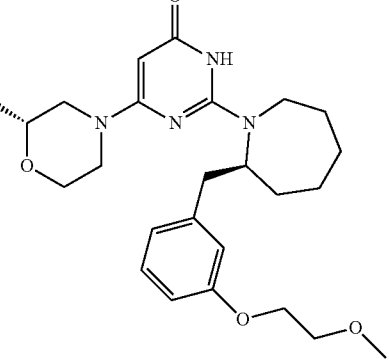 |
| 308 | 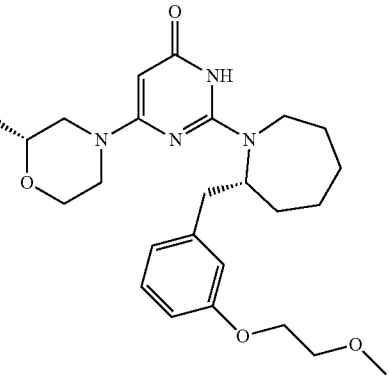 |

TABLE 1-continued

| Example | Structure |
|---|---|
| 309 | 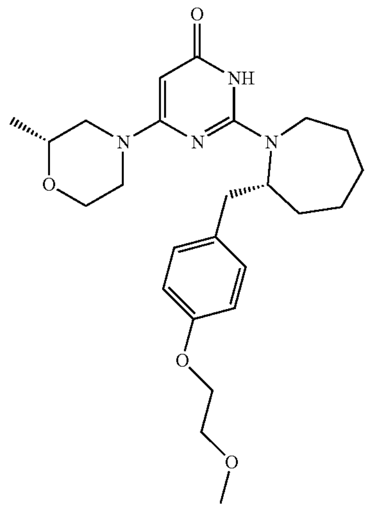 [SMILES: COCCOc1ccc(C[C@H]2CCCCCN2c2nc(N3CCO[C@H](C)C3)cc(=O)[nH]2)cc1] |
| 310 | 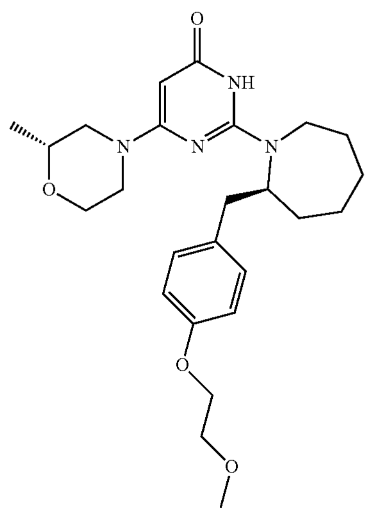 [SMILES: COCCOc1ccc(C[C@@H]2CCCCCN2c2nc(N3CCO[C@H](C)C3)cc(=O)[nH]2)cc1] |
| 311 | 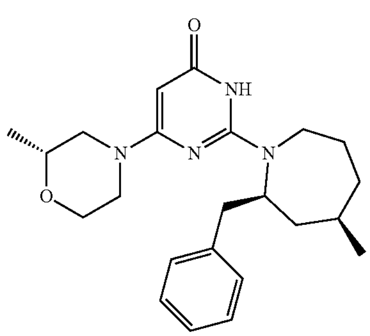 |
| 312 | 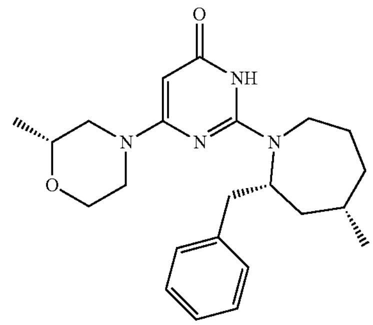 |
| 313 | 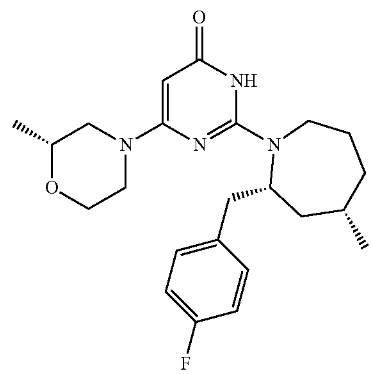 |
| 314 | 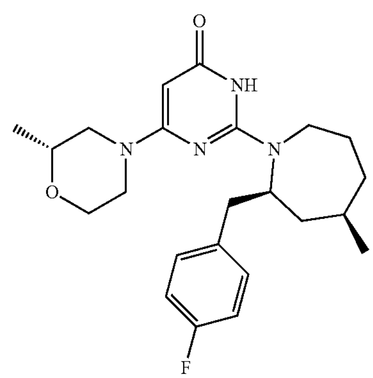 |
| 315 | 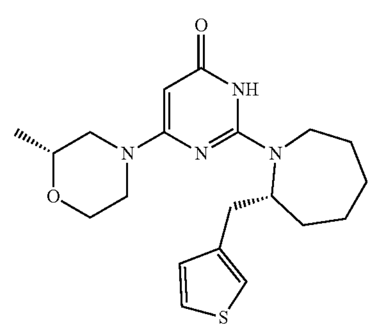 [SMILES: C[C@@H]1CN(c2cc(=O)[nH]c(N3CCCCC[C@@H]3Cc3ccsc3)n2)CCO1] |

TABLE 1-continued

| Example | Structure |
|---|---|
| 316 | (structure) |
| 317 | (structure) |
| 318 | (structure) |
| 319 | (structure) |
| 320 | (structure) stereoisomer 1 |
| 321 | (structure) stereoisomer 2 |
| 322 | (structure) |
| 323 | (structure) |

TABLE 1-continued

| Example | Structure |
|---|---|
| 324 | (structure) |
| 325 | (structure) |
| 326 | (structure) stereoisomer 1 |
| 327 | (structure) stereoisomer 2 |
| 328 | (structure) stereoisomer 3 |
| 329 | (structure) enantiomeric mixture 1 & 2 |
| 330 | (structure) enantiomeric mixture 3 & 4 |
| 331 | (structure) |

TABLE 1-continued
| Example | Structure |
|---|---|
| 332 | 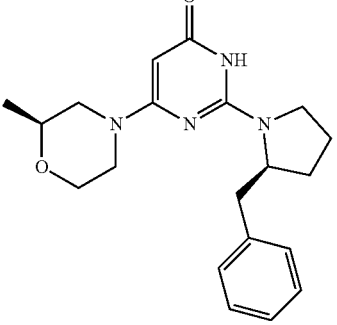 |
| 333 | 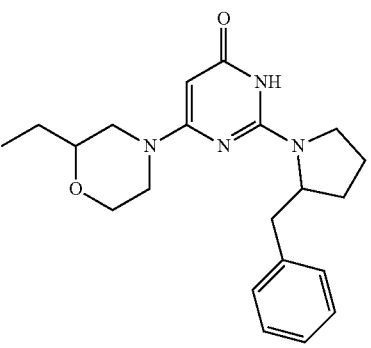 [SMILES: CCC1CN(c2cc(=O)[nH]c(N3CCCC3Cc3ccccc3)n2)CCO1]  stereoisomer 1 |
| 334 | 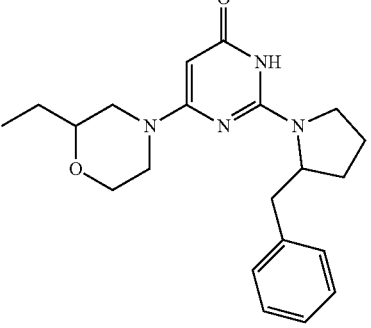  stereoisomer 2 |
| 335 | 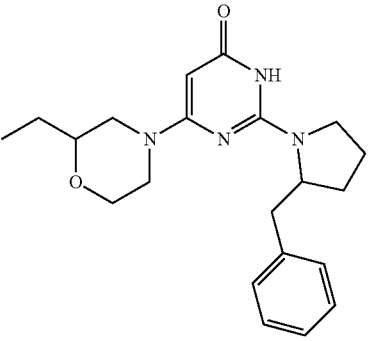 [SMILES: CCC1CN(c2cc(=O)[nH]c(N3CCCC3Cc3ccccc3)n2)CCO1]  stereoisomer 3 |
| 336 | 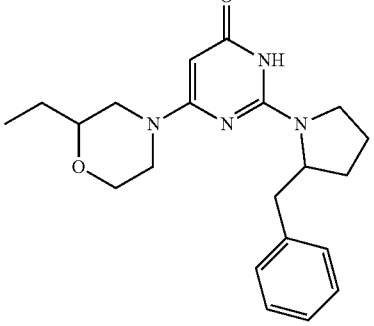  stereoisomer 4 |
| 337 | 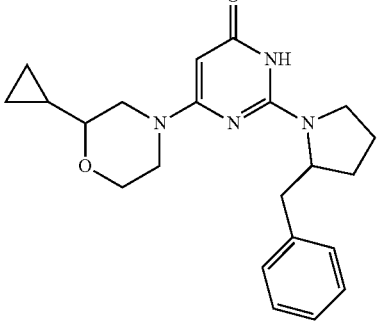  stereoisomer 1 |
| 338 | 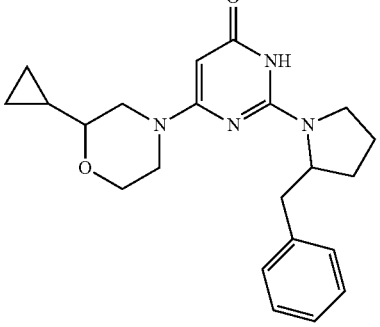  stereoisomer 2 |
| 339 | 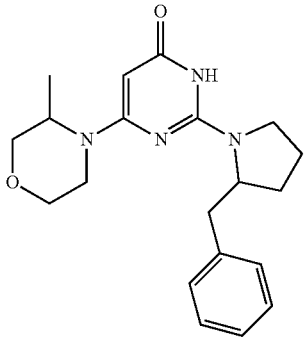 [SMILES: CC1COCCN1c1cc(=O)[nH]c(N2CCCC2Cc2ccccc2)n1]  stereoisomer 1 |

TABLE 1-continued
| Example | Structure |
|---|---|
| 340 | 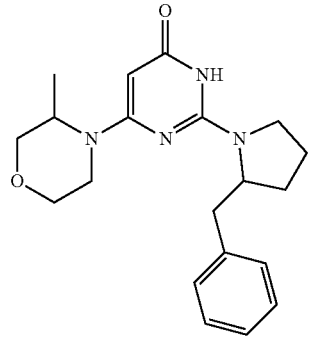 [SMILES: CC1COCCN1c1cc(=O)[nH]c(N2CCCC2Cc2ccccc2)n1]<br>stereoisomer 2 |
| 341 | 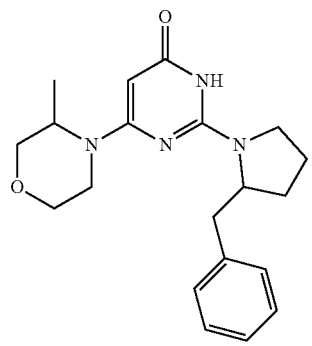 [SMILES: CC1COCCN1c1cc(=O)[nH]c(N2CCCC2Cc2ccccc2)n1]<br>stereoisomer 3 |
| 342 | 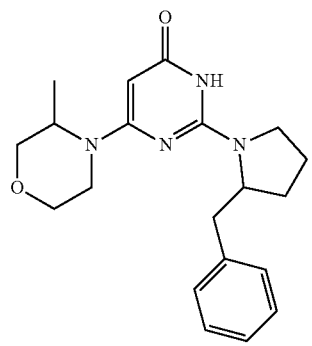 [SMILES: CC1COCCN1c1cc(=O)[nH]c(N2CCCC2Cc2ccccc2)n1]<br>stereoisomer 4 |
| 343 | 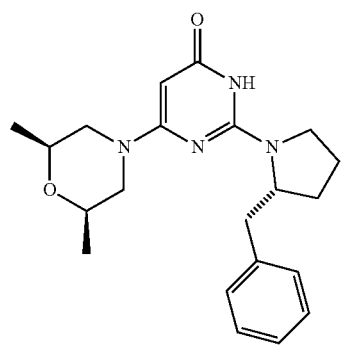 [SMILES: C[C@@H]1CN(c2cc(=O)[nH]c(N3CCC[C@@H]3Cc3ccccc3)n2)C[C@H](C)O1] |
| 344 | 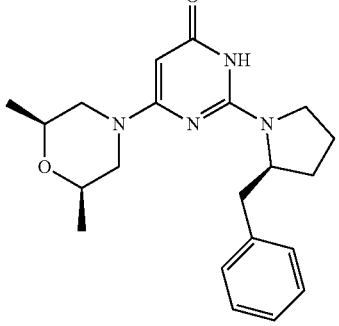 |
| 345 | 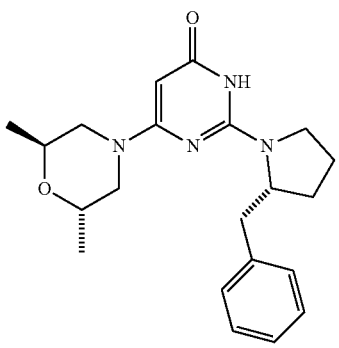 [SMILES: C[C@H]1CN(c2cc(=O)[nH]c(N3CCC[C@@H]3Cc3ccccc3)n2)C[C@H](C)O1] |
| 346 | 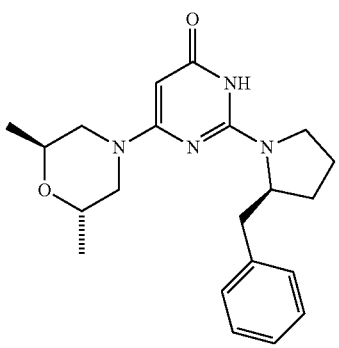 [SMILES: C[C@H]1CN(c2cc(=O)[nH]c(N3CCC[C@H]3Cc3ccccc3)n2)C[C@H](C)O1] |
| 347 | 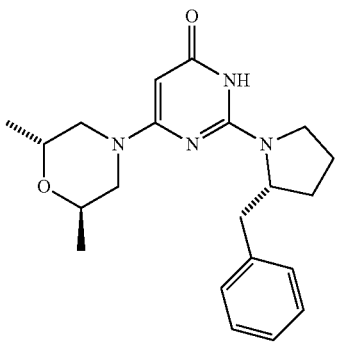 [SMILES: C[C@@H]1CN(c2cc(=O)[nH]c(N3CCC[C@@H]3Cc3ccccc3)n2)C[C@@H](C)O1] |

TABLE 1-continued
| Example | Structure |
|---|---|
| 348 | 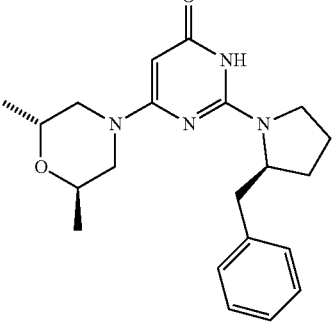 |
| 349 | 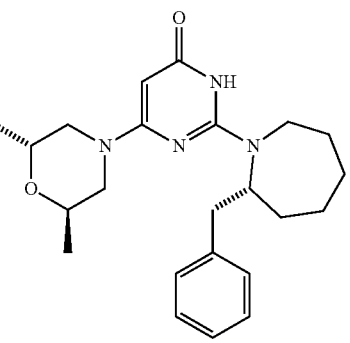 |
| 350 | 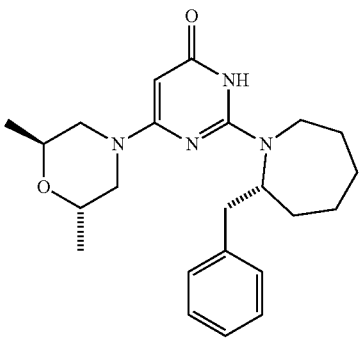 [SMILES: C[C@H]1CN(c2cc(=O)[nH]c(N3CCCCC[C@@H]3Cc3ccccc3)n2)C[C@H](C)O1] |
| 351 | 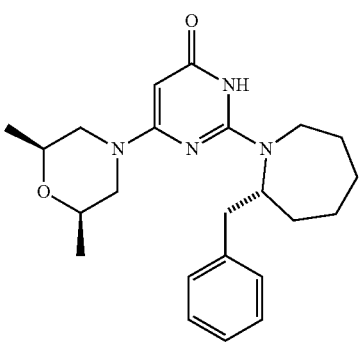 [SMILES: C[C@@H]1CN(c2cc(=O)[nH]c(N3CCCCC[C@@H]3Cc3ccccc3)n2)C[C@H](C)O1] |
| 352 | 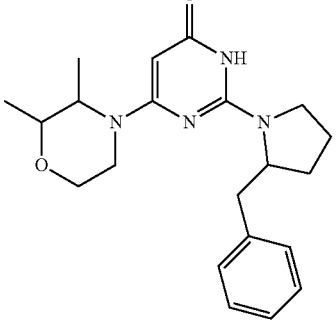<br>stereoisomer 1 |
| 353 | 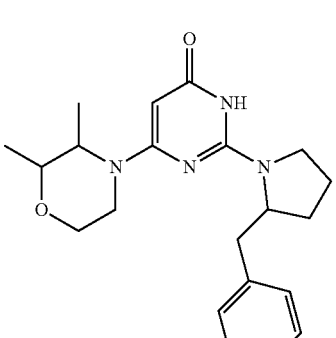<br>stereoisomer 2 |
| 354 | 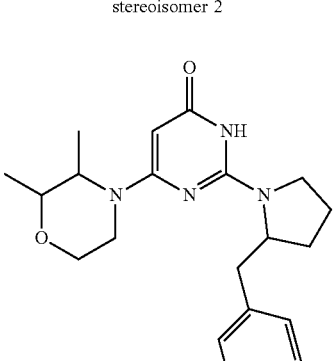<br>stereoisomer 3 |
| 355 | 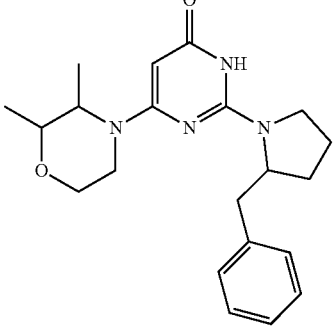<br>stereoisomer 4 |

TABLE 1-continued

| Example | Structure |
|---|---|
| 356 | 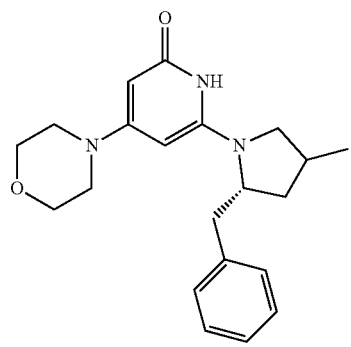 [SMILES: CC1C[C@H](Cc2ccccc2)N(c2cc(N3CCOCC3)cc(=O)[nH]2)C1] | or a deuterated analog, pharmaceutically acceptable salt, solvate, prodrug, stereoisomer, or mixture of stereoisomers thereof.

In some embodiments, a compound of formula

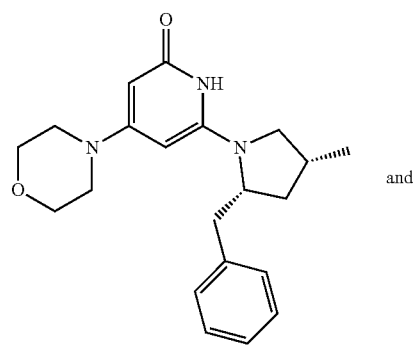

for example, Example 100 or Example 101, has a structure selected from

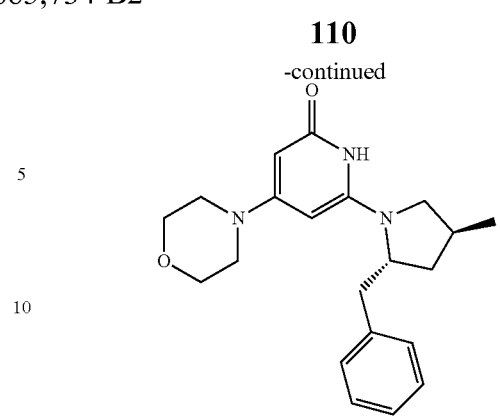

In some embodiments, a compound of formula

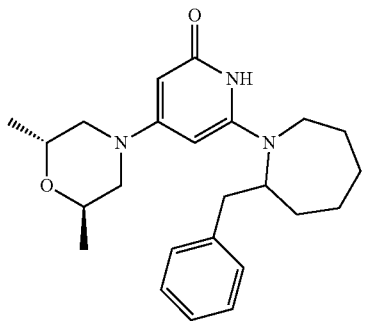 [SMILES: C[C@@H]1CN(c2cc(N3CCCCCC3Cc3ccccc3)[nH]c(=O)c2)C[C@@H](C)O1]

for example, Example 165, has a structure selected from

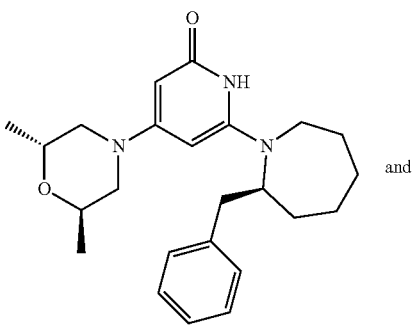

and

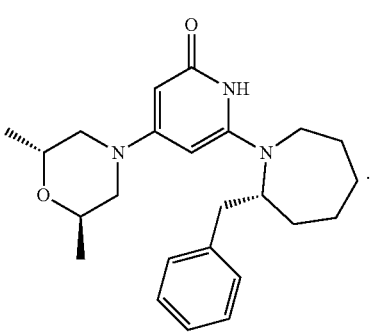

In some embodiments, a compound of formula
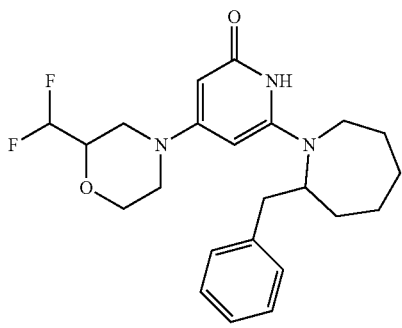 [SMILES: O=c1cc(N2CCOC(C(F)F)C2)cc(N2CCCCCC2Cc2ccccc2)[nH]1]
for example, Example 166, has a structure selected from
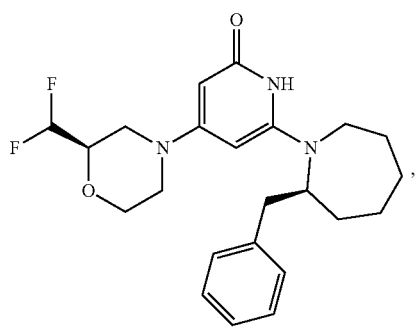
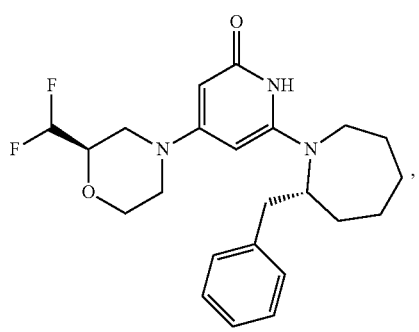
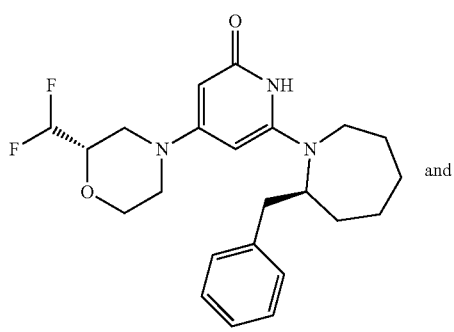 and
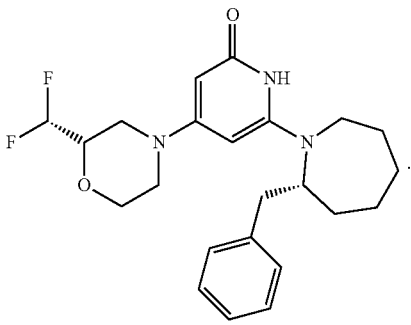
In some embodiments, a compound of formula
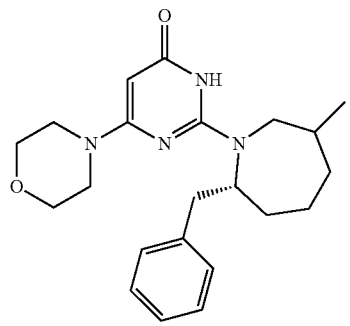 [SMILES: CC1CCC[C@H](Cc2ccccc2)N(c2nc(N3CCOCC3)cc(=O)[nH]2)C1]
for example, Example 246 or 247, has a structure selected from
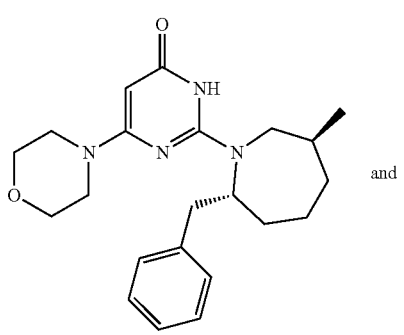 and
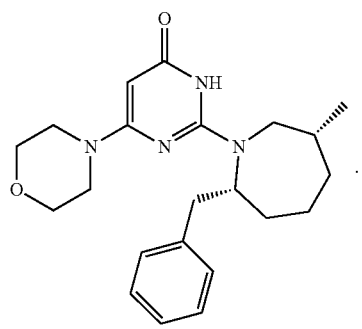

In some embodiments, a compound of formula
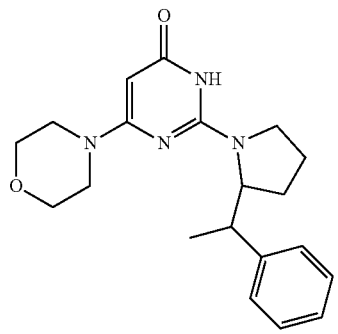 [SMILES: CC(c1ccccc1)C1CCCN1c1nc(N2CCOCC2)cc(=O)[nH]1]
for example, Example 252, has a structure selected from
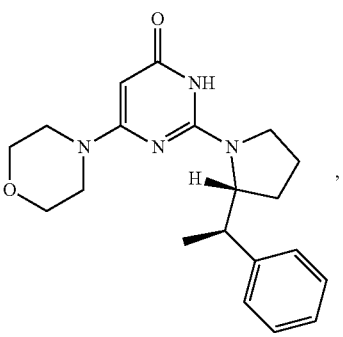
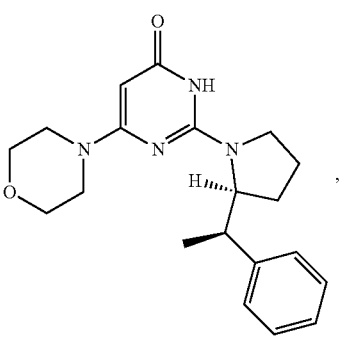
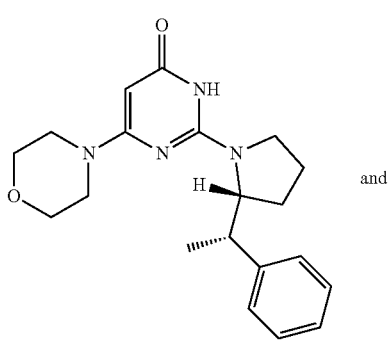
-continued
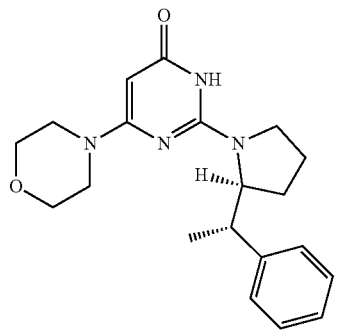
In some embodiments, a compound of formula
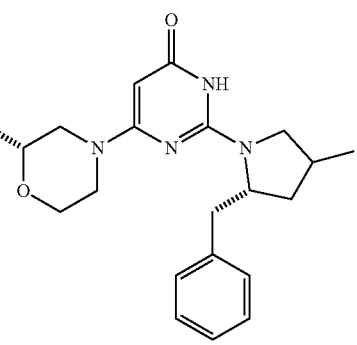
for example, Example 320 or 321, has a structure selected from
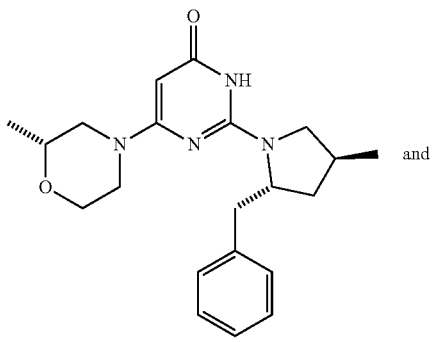
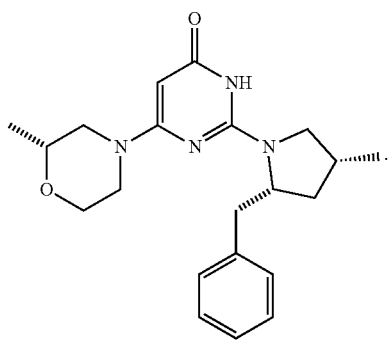

In some embodiments, a compound of formula
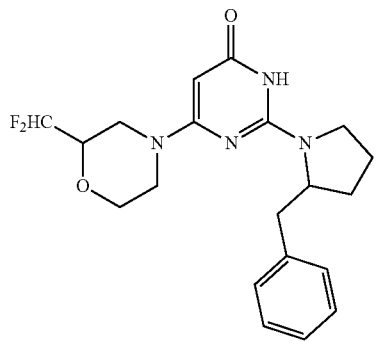 [SMILES: O=c1cc(N2CCOC(C(F)F)C2)nc(N2CCCC2Cc2ccccc2)[nH]1]
for example, Example 326, 327, or 328, has a structure selected from
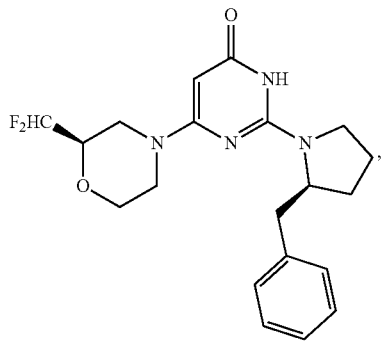
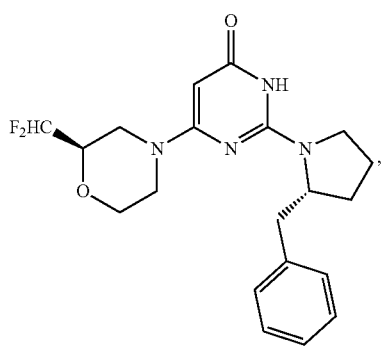
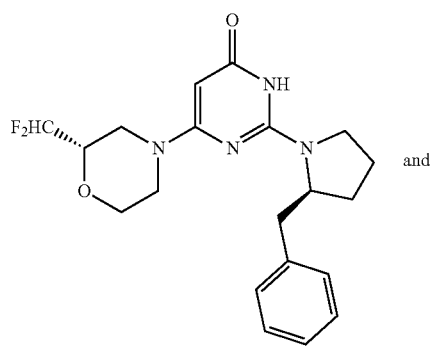
and
In some embodiments, a compound of formula
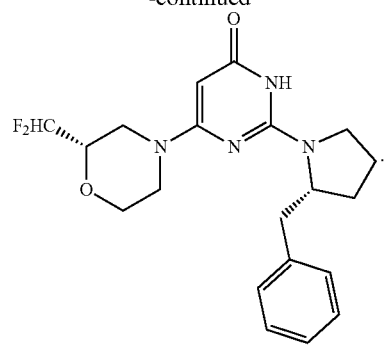
for example, Example 329 or 330, has a structure selected from
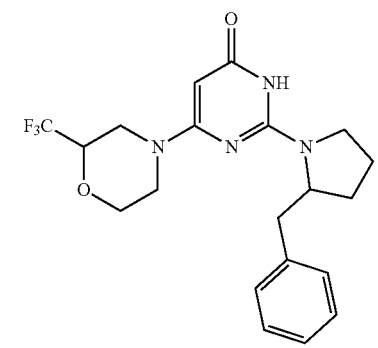 [SMILES: O=c1cc(N2CCOC(C(F)(F)F)C2)nc(N2CCCC2Cc2ccccc2)[nH]1]
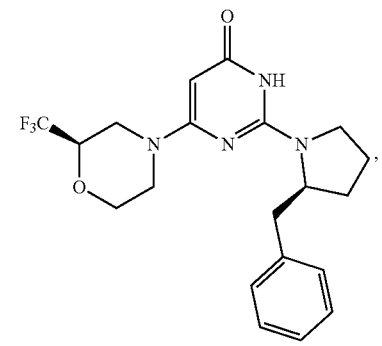
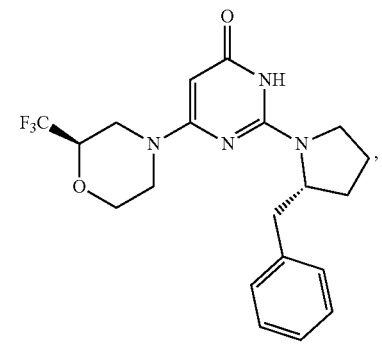

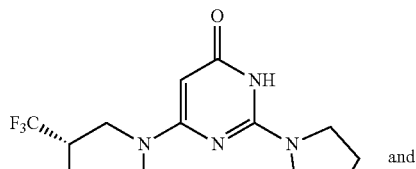
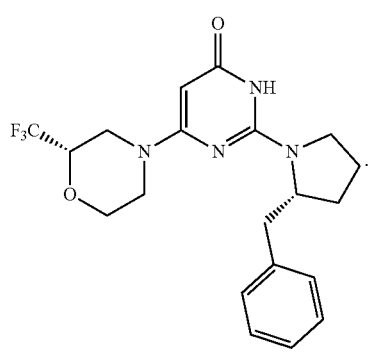
In some embodiments, a compound of formula
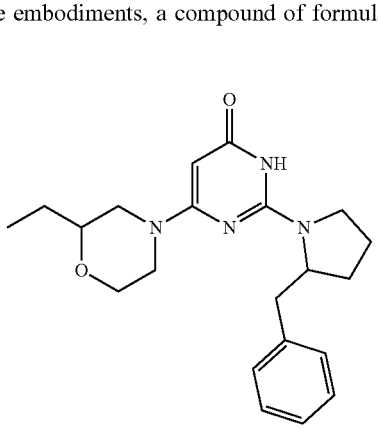
for example, Example 333, 334, 335 or 336 has a structure selected from
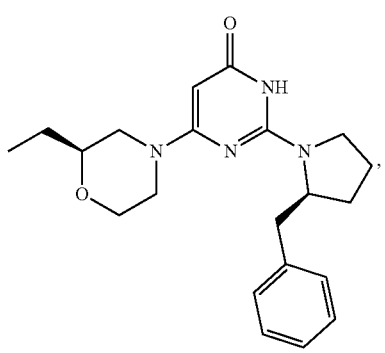
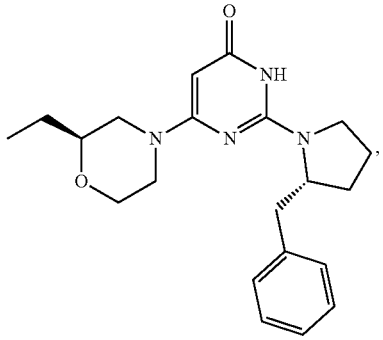
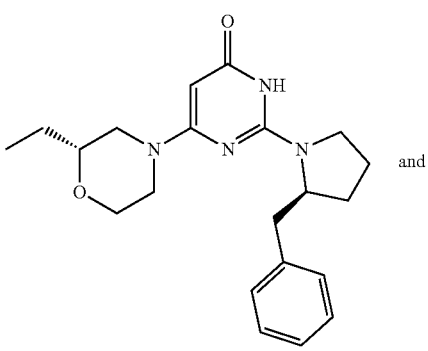
In some embodiments, a compound of formula
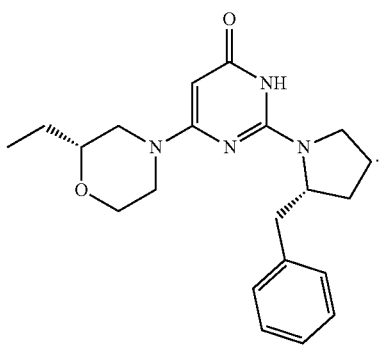
for example, Example 337 or 338, has a structure selected from

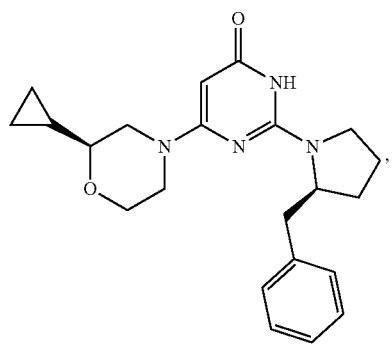
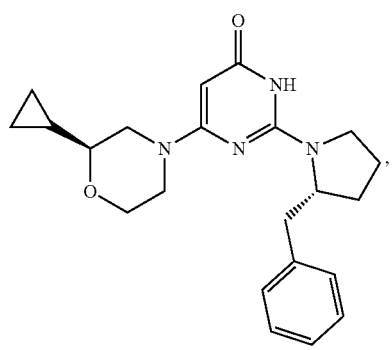
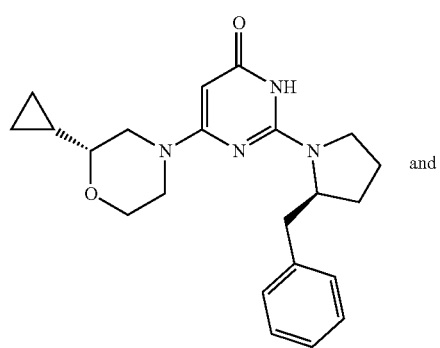
and
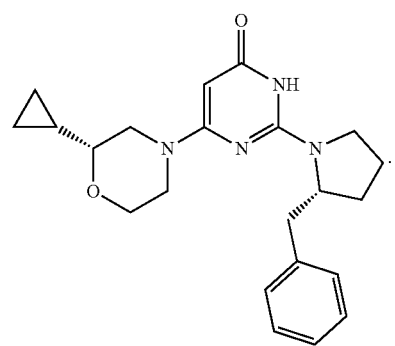
In some embodiments, a compound of formula
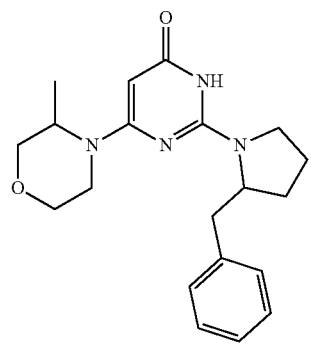
for example, Example 339, 340, 341, or 342, has a structure selected from
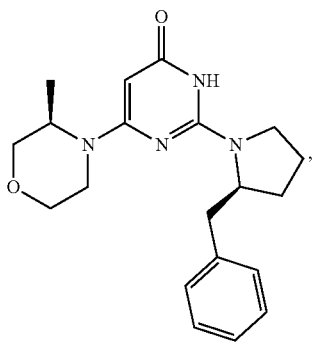
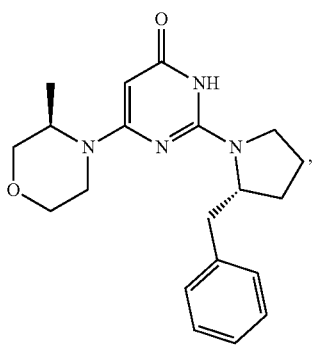
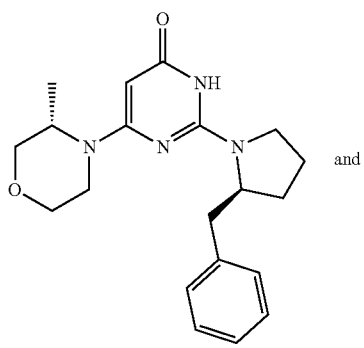
and

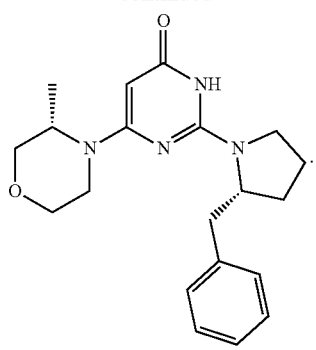
In some embodiments, a compound of formula
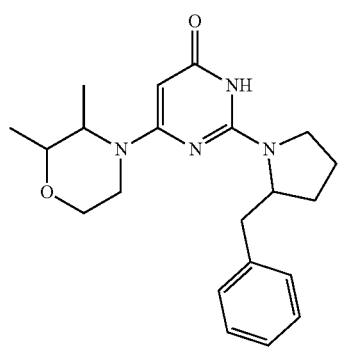 [SMILES: CC1OCCN(c2cc(=O)[nH]c(N3CCCC3Cc3ccccc3)n2)C1C]
for example, Example 352, 353, 354, or 355, has a structure selected from
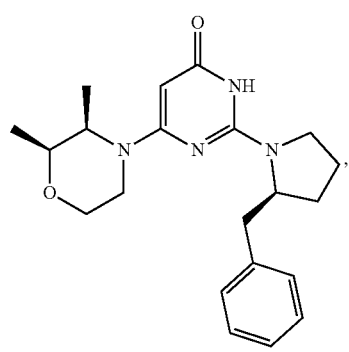
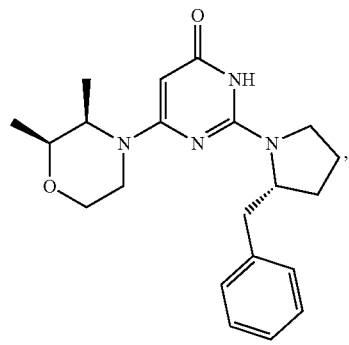
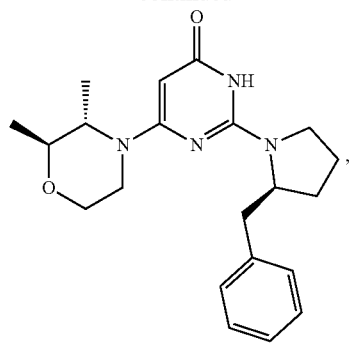
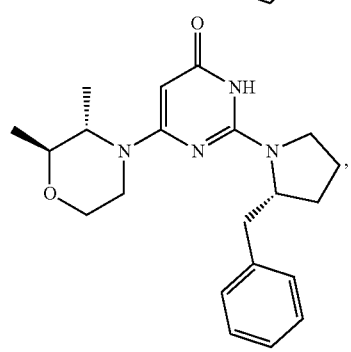
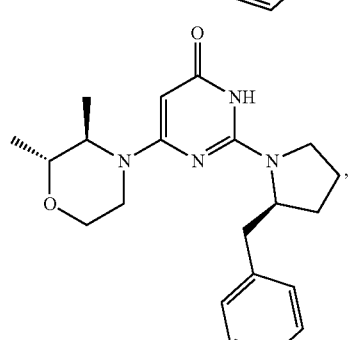
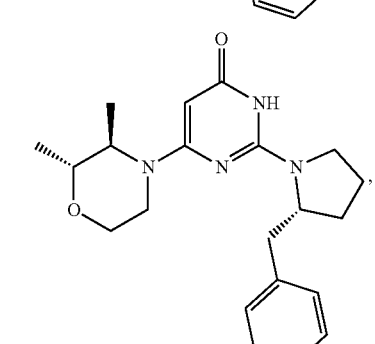
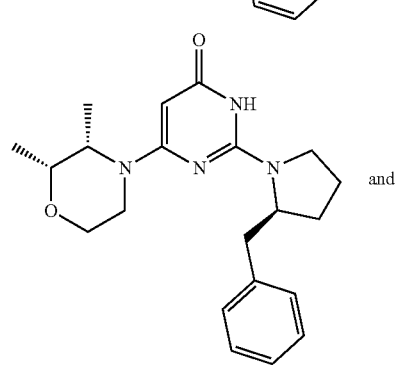
and

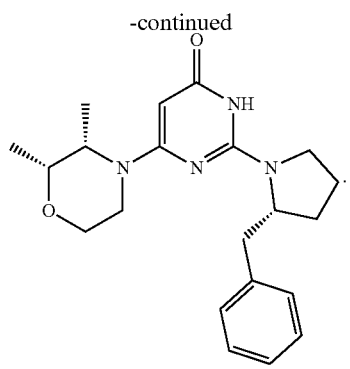

Treatment Methods and Uses

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting an ATM kinase. Also provided is a use of a compound, or pharmaceutically acceptable salt thereof, described herein in the manufacture of medicament for inhibiting an ATM kinase. Also provided is at least one compound, or pharmaceutically acceptable salt thereof, described herein for use in a method for inhibiting an ATM kinase. In some embodiments, the inhibition is in a cell.

Also provided is a method of treating a condition or disorder mediated by ATM in a subject in need of such a treatment, comprising administering to the subject a therapeutically effective amount of a compound, or pharmaceutically acceptable salt thereof, described herein. Also provided is a use of a compound, or pharmaceutically acceptable salt thereof, described herein in the manufacture of medicament for the treatment of a condition or disorder mediated by ATM.

Also provided is a method of treating a condition or disorder responsive to inhibition of an ATM kinase in a patient in need thereof comprising administering to the patient a therapeutically effective amount of a compound, or pharmaceutically acceptable salt thereof, described herein. In some embodiments, condition or disorder involves a neurodegenerative pathology. In some embodiments, the condition or disorder is Huntington's disease.

In some embodiments, the condition or disorder mediated by ATM comprises a neurodegenerative disease. Accordingly, also provided is a method of treating a neurodegenerative disease mediated by ATM in a subject in need of such a treatment, comprising administering to the subject a therapeutically effective amount of a compound, or pharmaceutically acceptable salt thereof, described herein.

In some embodiments, the neurodegenerative disease is Huntington's disease, Alzheimer's disease, Parkinson's disease, neuronal intranuclear inclusion disease (NIID), dentatorubral pallidolusyian atrophy (DRPLA), Friedreich's ataxia, Rubenstein-Taubi syndrome, a polyglutamine disease such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, or mixed connective tissue disease. In some embodiments, the neurodegenerative disease is Huntington's disease. In some embodiments, the neurodegenerative disease is Alzheimer's disease.

In some embodiments, the condition or disorder mediated by ATM comprises cancer. Accordingly, also provided is a method of treating cancer mediated by ATM in a subject in need of such a treatment, comprising administering to the subject a therapeutically effective amount of a compound, or pharmaceutically acceptable salt thereof, described herein. In some embodiments, the cancer is lymphoma, pancreatic cancer, colorectal cancer, hepatocellular carcinoma, Waldenstrom macroglobulinemia, hormone refractory cancer of the prostate, leukemia, acute myeloid leukemia, breast cancer, lung cancer, ovarian cancer, prostate cancer, head and neck cancer, renal cancer, gastric cancer, brain cancer, head and neck squamous cell carcinoma, B-cell lymphoma, diffuse large B-cell lymphoma, peripheral T-cell lymphoma, or cutaneous T-cell lymphoma. In some further embodiments, the cancer is selected from the following types: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, non-small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Also provided are methods of sensitization of tumors to radiotherapy by administering the compound according to the present disclosure before, during or after irradiation of the tumor for treating cancer.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

Pharmaceutical Compositions and Modes of Administration

In some embodiments, a compound, or a deuterated analog, pharmaceutically acceptable salt, solvate, prodrug, stereoisomer, or mixture of stereoisomers thereof, described herein, described herein are administered as a pharmaceutical composition. Accordingly, provided are pharmaceutical compositions comprising a compound, or a deuterated analog, pharmaceutically acceptable salt, solvate, prodrug, stereoisomer, or mixture of stereoisomers thereof, described herein together with a pharmaceutically acceptable vehicle chosen from carriers, adjuvants, and excipients. A compound of the present disclosure can be formulated into pharmaceutical compositions using techniques well known to those in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or a deuterated analog, pharmaceutically acceptable salt, solvate, prodrug, stereoisomer, or mixture of stereoisomers thereof, is sufficient to provide a practical quantity of material for administration per unit dose of the compound, or a deuterated analog, pharmaceutically acceptable salt, solvate, prodrug, stereoisomer, or mixture of stereoisomers thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or a deuterated analog, pharmaceutically acceptable salt, solvate, prodrug, stereoisomer, or mixture of stereoisomers thereof, described herein.

Effective concentrations of a compound, or a deuterated analog, pharmaceutically acceptable salt, solvate, prodrug, stereoisomer, or mixture of stereoisomers thereof, described herein are mixed with a suitable pharmaceutically acceptable vehicle. In instances in which the compound, or a deuterated analog, pharmaceutically acceptable salt, solvate, prodrug, stereoisomer, or mixture of stereoisomers thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of a compound, or a deuterated analog, pharmaceutically acceptable salt, solvate, prodrug, stereoisomer, or mixture of stereoisomers thereof, described herein, the resulting mixture may be a solution, suspension, emulsion or the like. The form of the resulting mixture depends upon a number of factors, including the intended mode of administration and the solubility of the compound, or a deuterated analog, pharmaceutically acceptable salt, solvate, prodrug, stereoisomer, or mixture of stereoisomers thereof, in the chosen vehicle. The effective concentration sufficient for ameliorating the symptoms of the disease treated may be empirically determined.

A compound, or a deuterated analog, pharmaceutically acceptable salt, solvate, prodrug, stereoisomer, or mixture of stereoisomers thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of a compound, a deuterated analog, pharmaceutically acceptable salt, solvate, prodrug, stereoisomer, or mixture of stereoisomers thereof, described herein. In some embodiments, oral pharmaceutical compositions contain at least 5% (weight %) of a compound, or a deuterated analog, pharmaceutically acceptable salt, solvate, prodrug, stereoisomer, or mixture of stereoisomers thereof, described herein. Some embodiments contain from 25% to 50% or from 5% to 75% of a compound, or a deuterated analog, pharmaceutically acceptable salt, solvate, prodrug, stereoisomer, or mixture of stereoisomers thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or a deuterated analog, pharmaceutically acceptable salt, solvate, prodrug, stereoisomer, or mixture of stereoisomers thereof, described herein can be incorporated into oral liquid preparations such as aqueous or oily suspensions, solutions, emulsions, syrups, or elixirs, for example. Furthermore, pharmaceutical compositions containing the compound, or a deuterated analog, pharmaceutically acceptable salt, solvate, prodrug, stereoisomer, or mixture of stereoisomers thereof, described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or a deuterated analog, pharmaceutically acceptable salt, solvate, prodrug, stereoisomer, or mixture of stereoisomers thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or a deuterated analog, pharmaceutically acceptable salt, solvate, prodrug, stereoisomer, or mixture of stereoisomers thereof, described herein may be administered parenterally in a sterile medium. Parenteral administration includes subcutaneous injections, intravenous, intramuscular, intrathecal injection or infusion techniques. The compound, or a deuterated analog, pharmaceutically acceptable salt, solvate, prodrug, stereoisomer, or mixture of stereoisomers thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or a deuterated analog, pharmaceutically acceptable salt, solvate, prodrug, stereoisomer, or mixture of stereoisomers thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or a deuterated analog, pharmaceutically acceptable salt, solvate, prodrug, stereoisomer, or mixture of stereoisomers thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or a deuterated analog, pharmaceutically acceptable salt, solvate, prodrug, stereoisomer, or mixture of stereoisomers thereof, described herein may also be formulated for transdermal administration as a transdermal patch.

Topical pharmaceutical compositions comprising a compound, or a deuterated analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or a deuterated analog, pharmaceutically acceptable salt, solvate, prodrug, stereoisomer, or mixture of stereoisomers thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or a deuterated analog, pharmaceutically acceptable salt, solvate, prodrug, stereoisomer, or mixture of stereoisomers thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or a deuterated analog, pharmaceutically acceptable salt, solvate, prodrug, stereoisomer, or mixture of stereoisomers thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of a compound, or a deuterated analog, pharmaceutically acceptable salt, solvate, prodrug, stereoisomer, or mixture of stereoisomers thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition. The additional active agent may be an agent described herein, e.g., with respect to combination therapy. or as known in the art.

Packages

Also provided are packaged pharmaceutical compositions. Such packaged compositions include a pharmaceutical composition comprising a compound, or a deuterated analog, pharmaceutically acceptable salt, solvate, prodrug, stereoisomer, or mixture of stereoisomers thereof, described herein, and instructions for using the composition to treat a subject (typically a human patient). In some embodiments, the instructions are for using the pharmaceutical composition to treat a subject suffering a condition or disorder mediated by ATM. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or a deuterated analog, pharmaceutically acceptable salt, solvate, prodrug, stereoisomer, or mixture of stereoisomers thereof, can be administered alone, as mixtures, or in combination with other active agents.

Combination Therapy

The methods described herein include methods for treating Huntington's disease, including treating memory and/or cognitive impairment associated with Huntington's disease, comprising administering to a subject, simultaneously or sequentially, a compound, or a deuterated analog, pharmaceutically acceptable salt, solvate, prodrug, stereoisomer, or mixture of stereoisomers thereof, described herein and one or more additional agents used in the treatment of Huntington's disease such as, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising a compound, or pharmaceutically acceptable salt thereof, described herein and one or more additional pharmaceutical agents used in the treatment of Huntington's disease such as, but not limited to, Amitriptyline, Imipramine, Desipramine, Nortriptyline, Paroxetine, Fluoxetine, Setraline, Terabenazine, Haloperidol, Chlorpromazine, Thioridazine, Sulpride, Quetiapine, Clozapine, and Risperidone. Similarly, also provided are packaged pharmaceutical compositions containing a pharmaceutical composition comprising a compound, or a deuterated analog, pharmaceutically acceptable salt, solvate, prodrug, stereoisomer, or mixture of stereoisomers thereof described herein, and another composition comprising one or more additional pharmaceutical agents used in the treatment of Huntington's disease such as, but not limited to, Amitriptyline, Imipramine, Desipramine, Nortriptyline, Par-oxetine, Fluoxetine, Setraline, Terabenazine, Haloperidol, Chlorpromazine, Thioridazine, Sulpride, Quetiapine, Clozapine, and Risperidone.

Also provided are methods for treating Alzheimer's disease, including treating memory and/or cognitive impairment associated with Alzheimer's disease, comprising administering to a subject, simultaneously or sequentially, a compound, or a deuterated analog, pharmaceutically acceptable salt, solvate, prodrug, stereoisomer, or mixture of stereoisomers thereof, described herein and one or more additional agents used in the treatment of Alzheimer's disease such as, but not limited to, Reminyl®, Cognex®, Aricept®, Exelon®, Akatinol®, Neotropin™, Eldepryl®, Estrogen and Clioquinol. In methods using simultaneous administration, the agents can be present in a combined composition or can be administered separately. Also provided are pharmaceutical compositions comprising a compound, or a deuterated analog, pharmaceutically acceptable salt, solvate, prodrug, stereoisomer, or mixture of stereoisomers thereof, described herein, and one or more additional pharmaceutical agents used in the treatment of Alzheimer's disease such as, but not limited to, Reminyl®, Cognex®, Aricept®, Exelon®, Akatinol®, Neotropin™, Eldepryl®, Estrogen and Clioquinol. Similarly, also provided are packaged pharmaceutical compositions containing a pharmaceutical composition comprising a compound, or a deuterated analog, pharmaceutically acceptable salt, solvate, prodrug, stereoisomer, or mixture of stereoisomers thereof, described herein, and another composition comprising one or more additional pharmaceutical agents used in the treatment of Alzheimer's disease such as, but not limited to Reminyl®, Cognex®, Aricept®, Exelon®, Akatinol®, Neotropin™, Eldepryl®, Estrogen and Clioquinol.

Also provided are methods for treating cancer comprising administering to a subject, simultaneously or sequentially, a compound, or a deuterated analog, pharmaceutically acceptable salt, solvate, prodrug, stereoisomer, or mixture of stereoisomers thereof, described herein and one or more additional active agents used in the treatment of cancer such as, but not limited to, the following categories of anti-tumor agents:

(i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin $\alpha_v\beta_3$ function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising a compound, or a deuterated analog, pharmaceutically acceptable salt, solvate, prodrug, stereoisomer, or mixture of stereoisomers thereof, described herein, and one or more anti-tumor agent as described herein. Similarly, also provided are packaged pharmaceutical compositions containing a pharmaceutical composition comprising a compound, or a deuterated analog, pharmaceutically acceptable salt, solvate, prodrug, stereoisomer, or mixture of stereoisomers thereof, described herein, and another composition comprising one or more one or more anti-tumor agent as described herein. When used in combination with one or more additional pharmaceutical agent or agents, the compounds described herein may be administered prior to, concurrently with, or following administration of the additional pharmaceutical agent or agents.

In some embodiments, the compounds, or a deuterated analog, pharmaceutically acceptable salt, solvate, prodrug, stereoisomer, or mixture of stereoisomers thereof, described herein, are administered in conjunction with surgery or radiotherapy, optionally in combination with one or more additional agents used in the treatment of cancer.

Dosing

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or a deuterated analog, pharmaceutically acceptable salt, solvate, prodrug, stereoisomer, or mixture of stereoisomers thereof, described herein is typically administered at dosage levels and in a manner customary for ATM inhibitors. For example, the compound, or a deuterated analog, pharmaceutically acceptable salt, solvate, prodrug, stereoisomer, or mixture of stereoisomers thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of a compound, or a deuterated analog, pharmaceutically acceptable salt, solvate, prodrug, stereoisomer, or mixture of stereoisomers thereof, described herein, for example, 0.1-50 mg of a compound, or a deuterated analog, pharmaceutically acceptable salt, solvate, prodrug, stereoisomer, or mixture of stereoisomers thereof, described herein. For intravenous administration, the compound or a deuterated analog, pharmaceutically acceptable salt, solvate, prodrug, stereoisomer, or mixture of stereoisomers thereof, can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of a compound, or a deuterated analog, pharmaceutically acceptable salt, solvate, prodrug, stereoisomer, or mixture of stereoisomers thereof, described herein.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromathography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

EXAMPLES

Compounds were named with the aid of the Cambridgesoft Chemistry Cartridge (v. 16.0.0.82) software.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

General Synthesis

Compounds of the present disclosure may be synthesized in accordance with the general reaction schemes and/or examples described below. The general schemes may be altered by substitution of the starting materials with other materials having similar structures to result in corresponding products. The structure of the desired product will generally make apparent to a person of skill in the art the required starting materials.

Scheme 1 provides exemplary synthetic routes for the synthesis of compounds provided herein (e.g., compounds of Formula I). The compounds of Formula I, or other formulas or compounds disclosed herein, are typically prepared by first providing the core Formula X(a) and then attaching the desired substituents using suitable conditions (e.g., coupling).

In some embodiments, synthesis of a compound of Formula I proceeds according to Scheme 1.

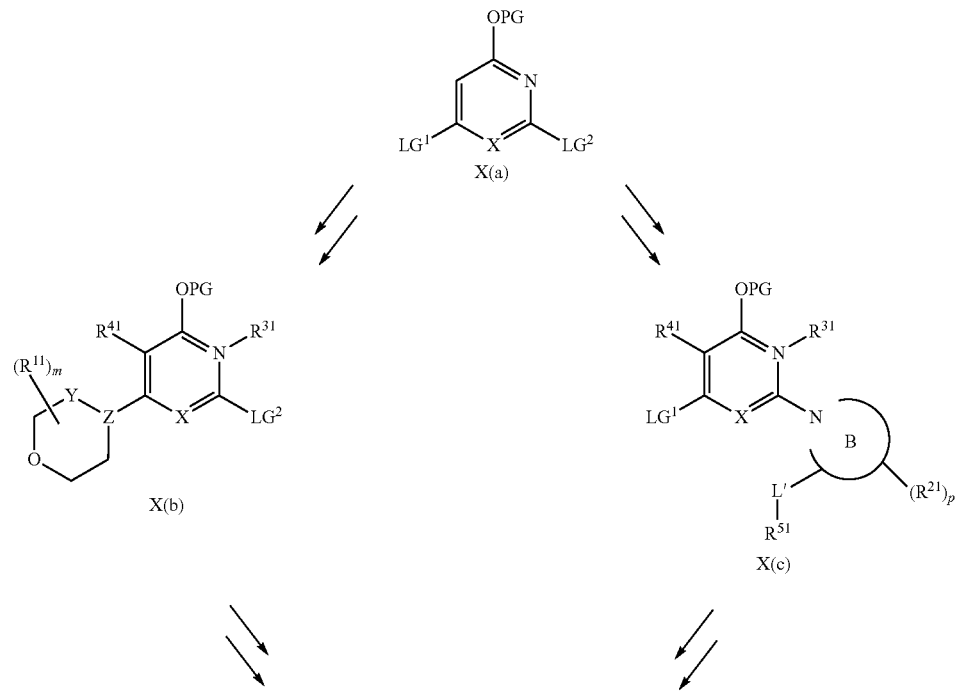

-continued

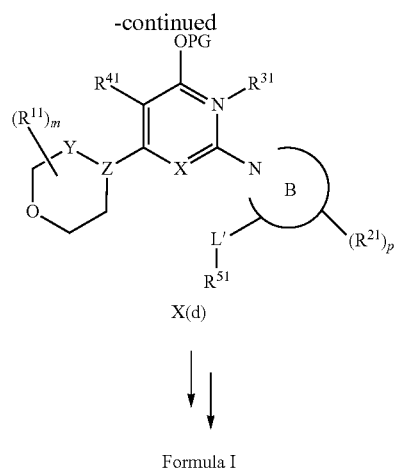

X(d)

↓↓

Formula I

In Scheme 1, a compound of Formula X(a) is transformed into a compound of Formula X(b) or of Formula X(c). The compound of Formula X(b) or Formula X(c), respectively, can then be transformed into a compound of Formula X(d), and subsequently into a compound of Formula I. Compound X(a) may be obtained by known methods or by methods described herein, specifically as described with respect to synthesis of any of Scaffold 1, Scaffold 2, Scaffold 3, Scaffold 4, Scaffold 5, Scaffold 6, or Scaffold 7. In Scheme 1, X, Y, Z, m, and p are as defined in Formula I.

In Scheme 1, Each of $LG^1$ and $LG^2$ is independently a suitable leaving group, e.g., a halide (e.g., chloro, bromo, iodo) or a sulfur derivative (e.g., $SCH_3$, $S(O)_2CH_3$). Where $LG^1$ or $LG^2$ is a sulfur derivative, the group may be activated by oxidation to a sulfone (e.g., by mCPBA). $LG^1$ or $LG^2$ may be displaced under nucleophilic aryl coupling conditions, for example, using a metal catalyst (e.g., $Pd_2(dba)_3$, RuPhos palladacycle G1 methyl tert-butyl ether adduct, RuPhos, $Pd(OAc)_2$) optionally in contact with a ligand (e.g., BINAP, 2,2'-bis(diphenylphosphino)-1,1'-binaphthyl) in an inert solvent (e.g., 1,4-dioxane, DMF, THF), in the presence of a base (e.g., $Cs_2CO_3$, NaOtBu, NaH, $Na_2CO_3$). When the reaction is substantially complete, the product is isolated by conventional means. Examples of displacement of $LG^1$ or $LG^2$ include, but are not limited to, Method C and Method D. Alternatively, $LG^1$ or $LG^2$ may be displaced under nucleophilic displacement conditions, for example, in the presence of a base (e.g., DIPEA, triethylamine) in an inert solvent (e.g., DMSO, DMF), optionally in the presence of a fluoride source (e.g., TBAF) at a temperature of rt to 100° C. for 1 to 72 hours. When the reaction is substantially complete, the product is isolated by conventional means. Examples of nucleophilic displacement of $LG^1$ or $LG^2$ include, but are not limited to, Method F and Method G.

PG is a hydroxyl protecting group, for example, a para-methoxybenzyl or a tert-butyl. PG can be removed under suitable hydroxyl deprotection conditions, including hydrogenation in contact with a catalyst, for example, palladium on carbon in the presence of a reducing agent, e.g., hydrogen or 1-methylcyclohexa-1,4-diene. The reaction may be conducted in an inert solvent, e.g., an alcohol such as ethanol, or an ether such as tetrahydrofuran, at a temperature of rt to 150° C. for 5 minutes to 24 hours. When the reaction is substantially complete, the product is isolated by conventional means. Alternatively, PG can be removed under suitable acidic conditions, for example, including an acid such as $TiCl_4$ in an inert solvent, for example, DCM, at a temperature of −78° C. to rt. When the reaction is substantially complete, the product is isolated by conventional means. Examples of deprotection of PG include, but are not limited to, Method E.

$R^{41}$ is hydrogen or $R^4$. Where $R^{41}$ is hydrogen, $R^4$ may be appended by a standard synthetic transformation, e.g., nucleophilic displacement. $R^{31}$ is hydrogen or $R^3$, or $R^{31}$ is absent. Where $R^{31}$ is hydrogen, $R^3$ may be appended by a standard synthetic transformation, e.g., nucleophilic displacement. Each $R^{11}$ is independently $R^1$ or a derivative of $R^1$. Where $R^{11}$ is a derivative, $R^1$ may be obtained by standard synthetic transformations. Each $R^{21}$ is independently $R^2$ or a derivative of $R^2$. Where $R^{21}$ is a derivative, $R^2$ may be obtained by standard synthetic transformations. $R^{51}$ is $R^5$ or a derivative of $R^5$. Where $R^{51}$ is a derivative, $R^5$ may be obtained by standard synthetic transformations. L' is L or a derivative of L. Where L' is a derivative, L may be obtained by standard synthetic transformations.

A person of skill in the art will appreciate that any of a compound of Formula X(a), X(b), X(c), or X(d) may be available from a commercial supplier for a particular embodiment. Alternative synthesis of a compound of Formula X(a), X(b), X(c), or X(d) may be as described herein or as known to those of skill in the art.

SYNTHETIC EXAMPLES

1. Analytical Methods

Purification Method:
Preparative HPLC purification was performed by reverse phase HPLC using a Waters Fractionlynx™ preparative HPLC system (2525 pump, 2996/2998 UV/VIS detector, 2767 liquid handler) or an equivalent HPLC system such as a Gilson Trilution® UV directed system. The Waters® 2767 liquid handler acted as both auto-sampler and fraction collector.

The columns used for the preparative purification of the compounds were a Waters Sunfire® OBD Phenomenex Luna® Phenyl Hexyl or Waters Xbridge® Phenyl at 10 μm 19×150 mm or Waters CSH™ Phenyl Hexyl, 19×150, 5 μm column.

Appropriate focused gradients were selected based on acetonitrile and methanol solvent systems under either acidic or basic conditions. The modifiers used under acidic/ basic conditions were formic acid or trifluoroacetic acid (0.1% V/V) and ammonium bicarbonate (10 mM) respectively.

The purification was controlled by Waters Fractionlynx™ software through monitoring at 210-400 nm, and triggered a threshold collection value at 260 nm and, when using the Fractionlynx™, the presence of target molecular ion as observed under APi conditions. Collected fractions were analysed by LCMS (Waters Acquity® systems with Waters® SQD).

Analytical Method A:

Analytical UPLC-MS was performed on a Waters Acquity I-Class UPLC with Waters Diode Array Detector (210-400 nm) coupled to a Waters SQD2 single quadrapole UPLC mass spectrometer using an HSS C18 column (1.8 um 100×2.1 mm plus guard). Method details are: 1) mobile phase: A: 0.1% formic acid (v/v) in water; B: 0.1% formic acid (v/v) in acetonitrile; 2) Gradient 0-1.2 min 95% A 5% B, 1.2-3.5 min linear gradient to 0% A 100% B, 3.5-4.9 min 0% A 100% B, 4.9-5.0 min gradient to 95% A 5% B, 5.0 min-6.0 min 95% A to 5% B. 3) Flow rate 0.5 mL/min.

Analytical Method B:

Analytical UPLC-MS was performed on a Waters Acquity I-Class UPLC with Waters Diode Array Detector (210-400 nm) coupled to a Waters SQD2 single quadrapole UPLC mass spectrometer using a BEH Shield RP18 column (1.7 um 100×2.1 mm. plus guard cartridge). Method details are: 1) mobile phase: A: 10 mM ammonium bicarbonate in water; B: acetonitrile; 2) Gradient 0-1.2 min 95% A 5% B, 1.2-3.5 min linear gradient to 0% A 100% B, 3.5-4.9 min 0% A 100% B, 4.9-5.0 min gradient to 95% A 5% B, 5.0 min-6.0 min 95% A to 5% B. 3) Flow rate 0.5 mL/min.

SFC Method:

All compounds purified using Supercritical Fluid Chromatography (SFC) used either Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module). Where the Waters 2767 liquid handler was used it acted as both auto-sampler and fraction collector.

The compounds were purified using an appropriate column from YMC Amylose-C, YMC Cellulose-C, Phenomenex LUX Cellulose-3 and Phenomenex LUX Cellulose-4. Appropriate isocratic methods were selected based on methanol, ethanol or isopropanol solvent systems under un-modified or basic conditions. The standard method used was modifier/$CO_2$, 100 ml/min (or as appropriate), 120 Bar backpressure, 40° C. column temperature were the specific modifier composition was as stated by the method development.

The modifier used under basic conditions was diethyl amine (0.1% V/V). The purification was controlled either by Waters Fractionlynx or Waters Chromscope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation.

Analytical Method SFC1

| Column | See Specific Method |
| --- | --- |
| Column Dimensions | 250 × 4.6 mm id 5 um |
| Mobile Phase | A-$CO_2$ |
| | B-Primary Solvents |
| | B-Secondary Solvents |

| Gradient | Time (min) | % B |
| --- | --- | --- |
| | 0 | 5 |
| | 0.5 | 5 |
| | 3 | 55 |
| | 4.5 | 55 |
| | 4.6 | 5 |
| | 5 | 5 |

| Temperature | 40° C. |
| --- | --- |
| Flow Rate | 5.0 ml/min |
| System Back Pressure | 120 bar |
| Detector | DAD 210-400 nm |
| Injection Volume | 5 µl, variable |
| MS | Electrospray +/−ve ionization |
| Cone voltage | 25 V |
| Source Temperature | 150° C. |
| Mass Range | 100-1000 amu |
| Solvents and reagents used are HPLC gradient grade or equivalent | |

| $CO_2$ Grade | 99.995% |
| --- | --- |
| B-Primary Solvents | Methanol/Ethanol/Isopropanol |
| B-Secondary Solvents | Methanol (+0.1% Diethylamine)/Ethanol (+0.1% Diethylamine)/Isopropanol (+0.1% Diethylamine) or as specified |

Analytical Method SFC4

| Column | See Specific Method |
| --- | --- |
| Column Dimensions | 150 × 2.1 mm id 5 um |
| | 100 × 3.0 mm id 1.7 um |
| Mobile Phase | A-$CO_2$ |
| | B-Primary Solvents |
| | B-Secondary Solvents |

| Gradient | Time (min) | % B |
| --- | --- | --- |
| | 0 | 5 |
| | 0.5 | 5 |
| | 3 | 55 |
| | 4.5 | 55 |
| | 4.6 | 5 |
| | 5 | 5 |

| Temperature | 40° C. |
| --- | --- |
| Flow Rate | 0.95 ml/min |
| System Back Pressure | 120 bar |
| Detector | DAD 210-400 nm |
| Injection Volume | 2 µl, variable |
| MS | Electrospray +/−ve ionization |
| Cone voltage | 25 V |
| Source Temperature | 150° C. |
| Mass Range | 100-1000 amu |
| Solvents and reagents used are HPLC gradient grade or equivalent | |

| $CO_2$ Grade | 99.995% |
| --- | --- |
| B-Primary Solvents | Methanol/Ethanol/Isopropanol |
| B-Secondary Solvents | Methanol (+0.1% Diethylamine)/Ethanol (+0.1% Diethylamine)/Isopropanol (+0.1% Diethylamine) or as specified |

Analytical Method HPLC:

All compounds were purified using Gilson AutoPrep system (Gilson 322 pump, Gilson 155 UV/VIS detector, GX-281 liquid handler). The Gilson GX-281 liquid handler acted as both auto-sampler and fraction collector.

The compounds were purified using the column stated in the specific example.

Appropriate isocratic methods were selected based on ethanol or isopropanol solvent systems under acidic or basic conditions. The standard method used was modifier/Heptane, 20 ml/min, room temperature where the specific modifier composition was as stated by the method development.

The modifier used under basic conditions was diethyl amine (0.1% V/V). The modifier used under acidic conditions was formic acid (0.1% V/V).

The purification was controlled by Gilson Trilution V2.1 through monitoring at a specified wavelength determined by method development and triggered a threshold collection value at an appropriate wavelength. Collected fractions were analysed by Agilent 1200 series HPLC system with DAD detector. The fractions that contained the desired product were concentrated by vacuum centrifugation.

2. Scaffolds

The following scaffolds were used in the synthesis of final compounds.

| Scaffold | Name |
|---|---|
| 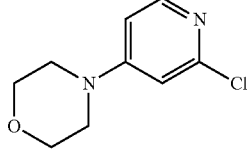 | Scaffold 1 |
| 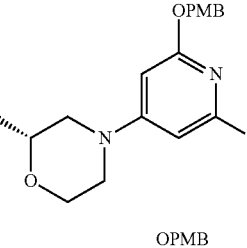 | Scaffold 2 |
| 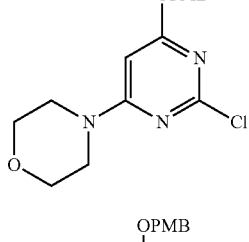 | Scaffold 3 |
| 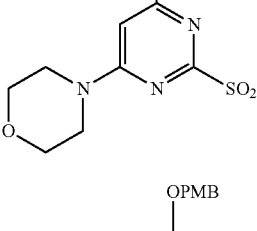 | Scaffold 4 |
| 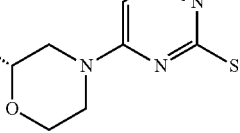 | Scaffold 5 |
| 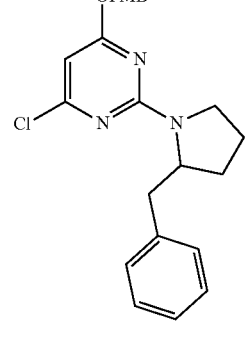 | Scaffold 6 |
| 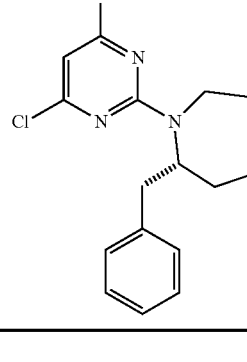 | Scaffold 7 |

General Methods for the Preparation of Scaffolds 1-4

Method A: To a mixture of (4-methoxyphenyl)methanol (1.1 eq.) in THF (0.4 M) at 0° C. was added portionwise NaH (2 eq., 60% mineral oil). The reaction was stirred for 15 minutes. 4-(2,6-dichloropyridin-4-yl)morpholine derivative (1 eq.) was added dropwise as a solution in THF (0.7 M). After complete addition the reaction was warmed to rt and heated at reflux for 19 h. The reaction mixture was cooled to 0° C. and cautiously quenched with water. The THF was removed under reduced pressure. The residue was dissolved in EtOAc and washed sequentially with water and brine. The organic extract was dried ($MgSO_4$), filtered and concentrated under reduced pressure. The crude product was either triturated or purified by silica gel column chromatography.

Method B: A mixture of amine (1.0 eq.), 2,6-dichloro-4-iodopyridine (1.0 eq.), NaOtBu (2 eq.), $PdCl_2$ ($tBu_2$Pferrocene)$_2$ (0.025 eq.) in toluene (0.3 M) was placed in a sealed reaction tube under nitrogen and heated at 50° C. for 20 h. The reaction mixture was cooled to rt and filtered through celite. The mixture was concentrated under reduced pressure and purified by silica gel chromatography.

Scaffold 1: 4-(2-chloro-6-((4-methoxybenzyl)oxy)pyridin-4-yl)morpholine

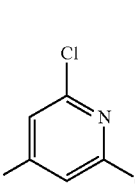 Step 1

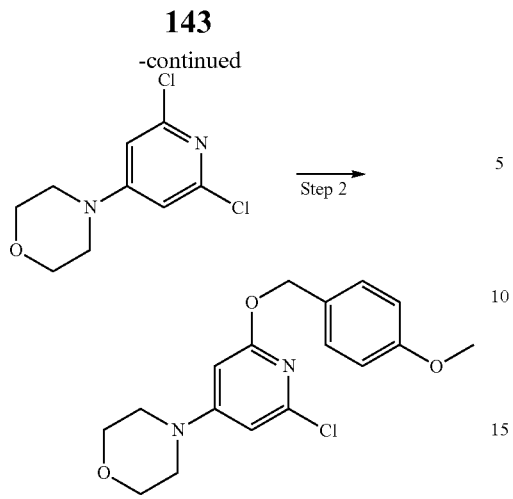

Step 1: 4-(2,6-dichloropyridin-4-yl)morpholine 2,6-dichloropyridin-4-amine (10 g, 61.3 mmol) was dissolved in DMF (200 mL) and cooled to 0° C. Sodium hydride (6.13 g, 153 mmol) was added portionwise over 20 min. After 15 minutes 1-chloro-2-(2-ethoxy)ethane (8.63 mL, 73.62 mmol) was added dropwise. The reaction mixture was warmed to rt and stirred for 21.5 h. After this time the reaction was cooled to 0° C. and cautiously quenched with water. The DMF was removed under reduced pressure. The resultant residue was dissolved in DCM and washed with water. The organic layers were dried (MgSO$_4$), filtered and concentrated under reduced pressure. The crude product was triturated with EtOAc and iso-hexane to afford the title compound.

Step 2: 4-(2-chloro-6-((4-methoxybenzyl)oxy)pyridin-4-yl)morpholine

Following Method A using 4-(2,6-dichloropyridin-4-yl)morpholine (9.27 g, 39.8 mmol). The crude product was triturated with EtOAc and iso-hexane to afford the title compound. $^1$H NMR (400 MHz, CDCl$_3$): δ 7.39-7.35 (2H, m), 6.91-6.88 (2H, m), 6.40 (1H, d, J=2.0 Hz), 5.99 (1H, d, J=2.0 Hz), 5.25 (2H, s), 3.81-3.77 (7H, m), 3.25-3.21 (4H, m).

Scaffold 2: (R)-4-(2-chloro-6-((4-methoxybenzyl)oxy)pyridin-4-yl)-2-methylmorpholine

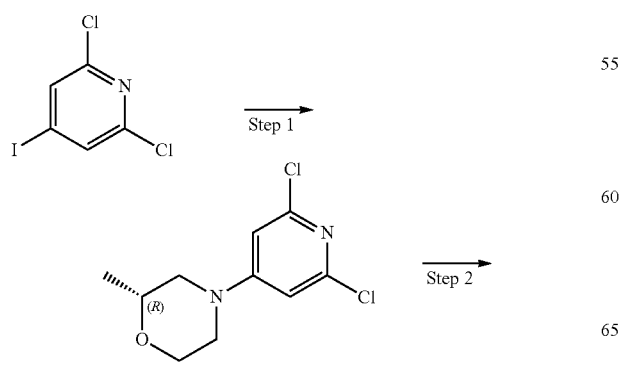

Step 1: (R)-4-(2,6-dichloropyridin-4-yl)-2-methylmorpholine

Following Method B using 2-R-methyl morpholine (0.5 g, 5 mmol). Purified by silica gel column chromatography (gradient elution, 10-50% EtOAc/iso-hexane) to afford the title compound.

Step 2: (R)-4-(2-chloro-6-((4-methoxybenzyl)oxy)pyridin-4-yl)-2-methylmorpholine Following Method A using (R)-4-(2,6-dichloropyridin-4-yl)-2-methylmorpholine (1.6 g, 6.4 mmol). Purified by silica gel column chromatography (gradient elution, 5-40% EtOAc/iso-hexane) to afford the title compound. $^1$H NMR (400 MHz, CDCl$_3$): δ 7.39-7.36 (2H, m), 6.91-6.88 (2H, m), 6.40 (1H, d, J=2.0 Hz), 5.98 (1H, d, J=2.0 Hz), 5.24 (2H, s), 4.00-3.95 (1H, m), 3.81 (3H, s), 3.71-3.61 (2H, m), 3.52-3.42 (2H, m), 2.96-2.88 (1H, m), 2.58 (1H, dd, J=10.4, 12.4 Hz), 1.24-1.21 (3H, m).

Scaffold 3: 4-(2-chloro-6-((4-methoxybenzyl)oxy)pyrimidin-4-yl)morpholine

Scaffold 3 was prepared according to the route described in *Bioorganic & Medicinal Chemistry Letters*, 2012, 22(21), 6665-6670.

Scaffold 4: 4-(6-((4-methoxybenzyl)oxy)-2-(methylthio)pyrimidin-4-yl)morpholine

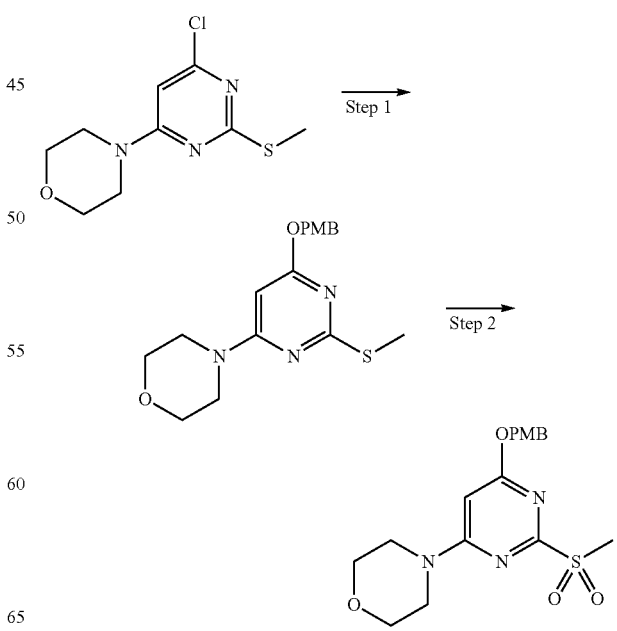

Step 1: 4-(6-((4-methoxybenzyl)oxy)-2-(methylthio) pyrimidin-4-yl)morpholine NaH (3.43 g, 85.8 mmol, 60% dispersion in mineral oil) was suspended in DMF (70 mL) and cooled to 0° C. 4-methoxy benzyl alcohol (6.52 g, 47.2 mmol) in DMF (30 mL) was added dropwise to the suspension over 15 minutes. After stirring at 0° C. for 15 minutes 4-(6-chloro-2-(methylthio)pyrimidin-4-yl)morpholine (10.54 g, 42.9 mmol, prepared according to WO 2008/125839) in DMF (90 mL). The reaction was allowed to warm to rt and stirred for 4.5 h. The reaction was cooled to 0° C. and cautiously quenched with water. The reaction mixture was concentrated under reduced pressure. The residue was dissolved in EtOAc and washed with brine and water. The organic extracts were dried (MgSO₄), filtered and concentrated under reduced pressure. Purified by silica gel column chromatography (gradient elution, 10-50% EtOAc/iso-hexane) to afford the title compound.

Step 2: 4-(6-((4-methoxybenzyl)oxy)-2-(methylsulfonyl)pyrimidin-4-yl)morpholine mCPBA (759 mg, 4.4 mmol, 50-55% wt in H₂O) was added portionwise to a solution of 4-(6-((4-methoxybenzyl)oxy)-2-(methylthio)pyrimidin-4-yl)morpholine (695 mg, 2.0 mmol) in DCM (20 mL) at r.t. After 2 h the reaction was filtered, washing the precipitate with DCM. The filtrate was washed successively with saturated NaHCO₃ (aqueous solution), brine, dried (phase separator) and concentrated under reduced pressure to afford the product, which was used without further purification in the next step. $^1$H NMR (400 MHz, CDCl₃): δ 7.38-7.35 (2H, m), 6.91-6.88 (2H, m), 5.88 (1H, s), 5.36 (2H, s), 3.81 (3H, s), 3.78-3.74 (4H, m), 3.63-3.57 (4H, m), 3.26 (3H, s).

Scaffold 5: (R)-4-(6-((4-methoxybenzyl)oxy)-2-(methylsulfonyl)pyrimidin-4-yl)-2-methylmorpholine

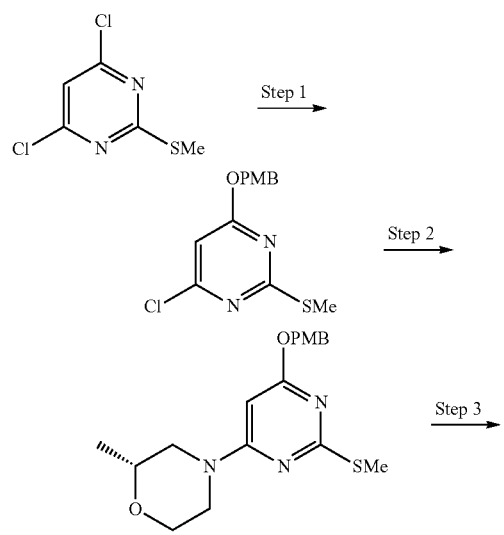

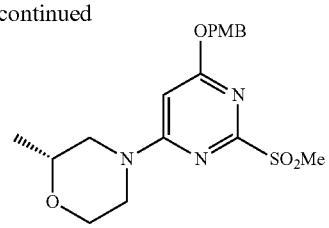

Step 1: 4-chloro-6-((4-methoxybenzyl)oxy)-2-(methylthio)pyrimidine

A solution of 4,6-dichloro-2-(methylthio)pyrimidine (15.0 g, 77.0 mmol) in dry DMF (205 mL) was treated at rt with para-methoxybenzyl alcohol (11.7 g, 84.6 mmol) and K₂CO₃ (42.6 g, 308 mmol). The reaction was stirred at 60° C. for 64 h. After cooling to r.t., the mixture was diluted with water (700 mL) and stirred vigorously at rt for 2 h. The solids that formed were collected by filtration, washing with water, to give the title compound. $^1$H NMR (400 MHz, CDCl₃): δ 7.35 (2H, d, J=8.8 Hz), 6.92-6.89 (2H, m), 6.42 (1H, s), 5.35 (2H, s), 3.81 (3H, s), 2.56 (3H, s).

Step 2: (R)-4-(6-((4-methoxybenzyl)oxy)-2-(methylthio)pyrimidin-4-yl)-2-methylmorpholine A solution of 4-chloro-6-((4-methoxybenzyl)oxy)-2-(methylthio)pyrimidine (11.3 g, 38.0 mmol) in dry THF (95 mL) was treated with DIPEA (20.0 mL, 114 mmol) and (2R)-methylmorpholine hydrochloride (5.75 g, 41.8 mmol). The mixture was stirred at 65° C. for 16 h. After cooling to r.t., the reaction mixture was poured into water. DCM was added and the layers were separated by passage through a hydrophobic frit. The DCM layer was concentrated and purified by silica gel column chromatography (gradient elution, 0-25% EtOAc/iso-hexane) to give the title compound. $^1$H NMR (400 MHz, CDCl₃): δ 7.36-7.33 (2H, m), 6.90-6.87 (2H, m), 5.53 (1H, s), 5.30 (2H, s), 4.09-3.91 (3H, m), 3.81 (3H, s), 3.64-3.54 (2H, m), 2.96 (1H, ddd, J=3.6, 11.9, 13.0 Hz), 2.61 (1H, dd, J=10.5, 13.0 Hz), 2.51 (3H, s), 1.22 (3H, d, J=6.5 Hz).

Step 3: (R)-4-(6-((4-methoxybenzyl)oxy)-2-(methylsulfonyl)pyrimidin-4-yl)-2-methylmorpholine A solution of (R)-4-(6-((4-methoxybenzyl)oxy)-2-(methylthio)pyrimidin-4-yl)-2-methylmorpholine (9.37 g, 25.9 mmol) in DCM (172 mL) was treated with mCPBA (19.7 g, 57.0 mmol, 50-55 wt % in H₂O) at rt and the mixture was stirred at rt for 4 h. The solid impurity was then filtered off and the organic filtrate was shaken with NaHCO₃ saturated solution (2×). The organic phase was dried (phase separator) and concentrated under reduced pressure. The residue was purified by silica gel column chromatography (gradient elution, 0-65% EtOAc/iso-hexane) to give the title compound. $^1$H NMR (400 MHz, CDCl₃): δ 7.36 (2H, d, J=8.7 Hz), 6.90 (2H, d, J=8.7 Hz), 5.88 (1H, s), 5.35 (2H, s), 4.14-4.02 (2H, m), 3.98 (1H, ddd, J=1.4, 3.7, 11.8 Hz), 3.81 (3H, s), 3.69-3.55 (2H, m), 3.26 (3H, s), 3.07 (1H, ddd, J=3.7, 11.9, 12.9 Hz), 2.71 (1H, dd, J=10.5, 13.1 Hz), 1.24 (3H, d, J=6.4 Hz).

Scaffold 6: 2-(2-Benzylpyrrolidin-1-yl)-4-chloro-6-((4-methoxybenzyl)oxy)pyrimidine Scaffold 7: (R)-2-Benzyl-1-(4-chloro-6-((4-methoxybenzyl)oxy)pyrimidin-2-yl)azepane

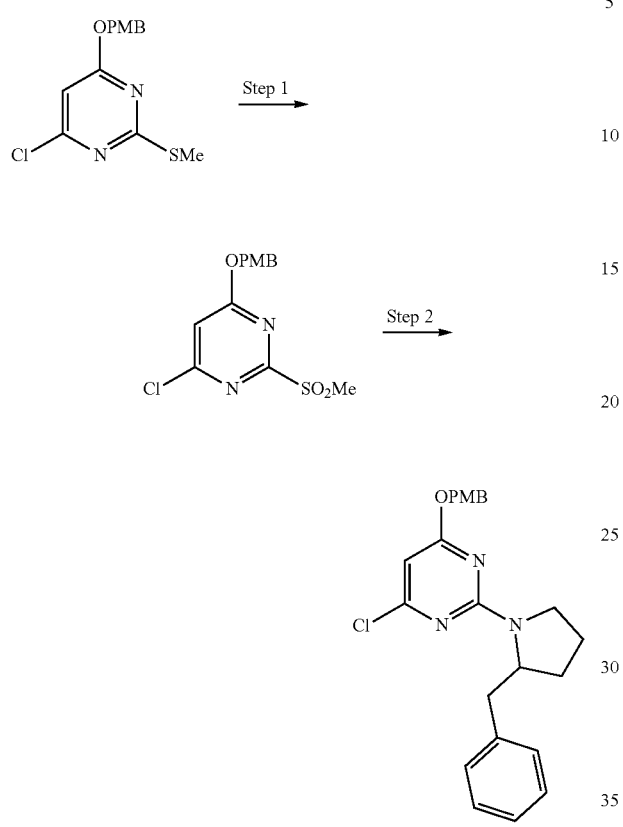

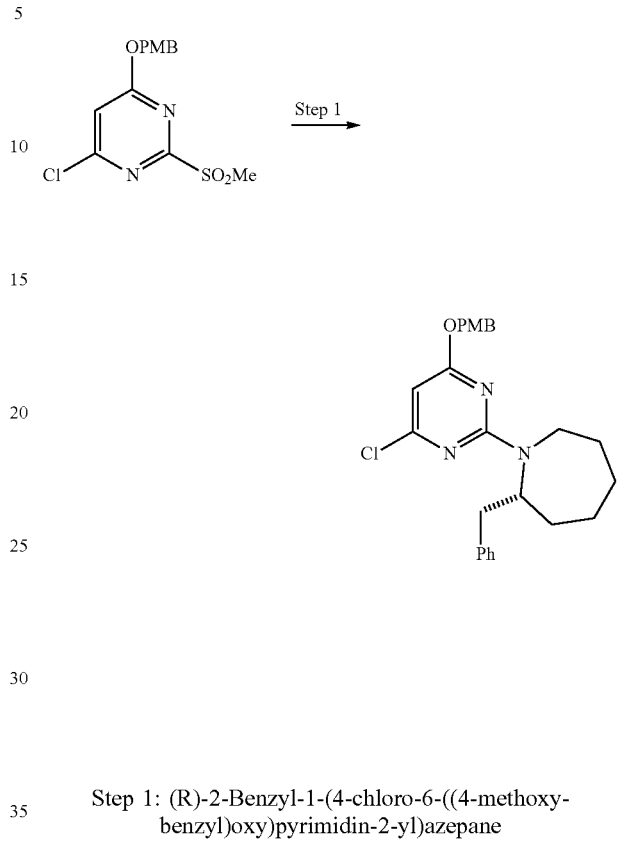

Step 1: (R)-2-Benzyl-1-(4-chloro-6-((4-methoxybenzyl)oxy)pyrimidin-2-yl)azepane

Step 1: 4-Chloro-6-((4-methoxybenzyl)oxy)-2-(methylsulfonyl)pyrimidine

A solution of 4-chloro-6-((4-methoxybenzyl)oxy)-2-(methylthio)pyrimidine (1.11 g, 3.75 mmo, Scaffold 5, step 1) in DCM (35 mL) was cooled at 0° C. and treated with mCPBA (2.75 g, 7.97 mmol, 50 wt % in water). The reaction mixture was warmed to rt and stirred for 21 h. The reaction mixture was washed with 2 M NaOH (20 mL) and the organic layer dried (phase separator). After concentration the title compound was obtained containing 9 wt % DCM. $^1$H NMR (400 MHz, CDCl$_3$): δ 7.41 (2H, d, J=8.6 Hz), 6.94-6.90 (3H, m), 5.48 (2H, s), 3.82 (3H, s), 3.34 (3H, s).

Step 2: 2-(2-Benzylpyrrolidin-1-yl)-4-chloro-6-((4-methoxybenzyl)oxy)pyrimidine

Following Method G from 4-chloro-6-((4-methoxybenzyl)oxy)-2-(methylsulfonyl)pyrimidine (1.14 g, 3.49 mmol) and 2-benzylpyrrolidine (602 mg, 3.73 mmol). The reaction was stirred at 80° C. for 17 h. Purification by silica gel column chromatography (gradient elution, 0-100% EtOAc/iso-hexane) gave the title compound. $^1$H NMR (400 MHz, CDCl$_3$): δ 7.41-7.17 (7H, m), 6.89 (2H, d, J=6.8 Hz), 6.04 (1H, s), 5.49-5.27 (2H, m), 4.39 (1H, br s), 3.80 (3H, s), 3.62-3.49 (2H, m), 3.27 (1H, d, J=13.6 Hz), 2.62 (1H, br s), 1.90-1.79 (4H, m).

Following Method G from 4-Chloro-6-((4-methoxybenzyl)oxy)-2-(methylsulfonyl)pyrimidine (1.72 g, 4.79 mmol, Scaffold 6, step 1) and (R)-2-benzylazepane (906 mg, 4.79 mmol, Example 3, step 2). The reaction was stirred at 80° C. for 4 days. Purification by silica gel column chromatography (gradient elution, 0-100% EtOAc/iso-hexane) gave the title compound. $^1$H NMR (400 MHz, CDCl$_3$): δ 7.33 (2H, dd, J=5.3, 8.3 Hz), 7.28-7.13 (5H, m), 6.90 (2H, d, J=7.3 Hz), 5.96 (1H, d, J=6.6 Hz), 5.33-5.17 (2H, m), 4.79-4.63 (1H, m), 4.25-4.17 (1H, m), 3.82 (3H, s), 2.95-2.81 (2H, m), 2.72-2.61 (1H, m), 2.02-1.91 (1H, m), 1.81-1.68 (3H, m), 1.59-1.52 (1H, m), 1.52-1.36 (1H, m), 1.23-1.09 (2H, m).

3. Intermediate Synthesis

Intermediate 1, (1S*,2S*,5R*)-2-benzyl-3-azabicyclo[3.1.0]hexane, and Intermediate 2, (1S*,2R*,5R*)-2-benzyl-3-azabicyclo[3.1.0]hexane

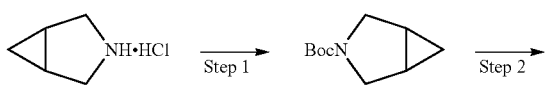

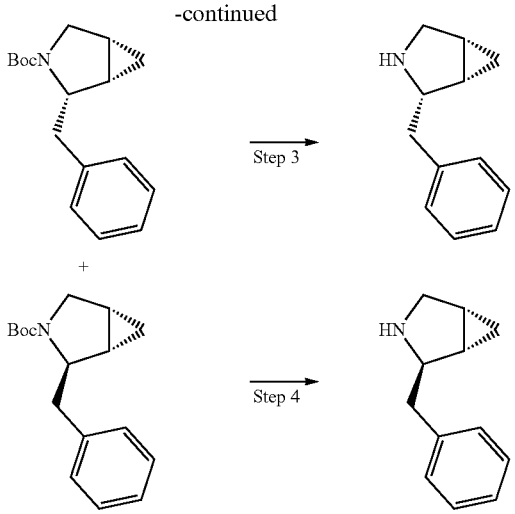

Step 1: tert-butyl 3-azabicyclo[3.1.0]hexane-3-carboxylate

Boc anhydride (2.6 g, 11.9 mmol) and a solution of NaHCO$_3$ (3.32 g, 39.5 mmol) in water (78 mL) was added to a suspension of the 3-azabicyclo[3.1.0]hexane hydrochloride (950 mg, 7.9 mmol) in THF (26 mL). The resulting biphasic mixture was stirred vigorously overnight at r.t. The reaction mixture was diluted with water and DCM. The layers were separated and the organic phase dried (phase separator) and concentrated under reduced pressure. The residue was purified by silica gel column chromatography (gradient elution, 0-10% EtOAc/iso-hexane) to afford the title compound.

Step 2: tert-butyl (1S*,2S*,5R*)-2-benzyl-3-azabicyclo[3.1.0]hexane-3-carboxylate and tert-butyl (1S*,2R*,5R*)-2-benzyl-3-azabicyclo[3.1.0]hexane-3-carboxylate To a solution of the tert-butyl 3-azabicyclo[3.1.0]hexane-3-carboxylate (1.50 g, <7.9 mmol) in diethyl ether (27 mL), under N$_2$ atmosphere, was added tetramethylethylenediamine (1.23 mL, 8.2 mmol) and the reaction mixture cooled to −78° C. sec-BuLi (11.8 mL, 10.6 mmol, 0.9 M in cyclohexane) was added and the mixture was stirred at −78° C. for 30 min. Benzyl bromide (1.95 mL, 16.4 mmol) was added dropwise at −78° C. After complete addition the reaction was allowed to slowly warm to rt overnight. The reaction was quenched with saturated aqueous NH$_4$Cl solution, the layers separated and the aqueous further extracted with Et$_2$O (×2). The combined organic extracts were dried (MgSO$_4$) and concentrated under reduced pressure. The crude material was purified by silica gel column chromatography (gradient elution, 0-10% EtOAc/iso-hexane) to afford the title compound as separate diastereomers tert-butyl (1S*,2R*,5R*)-2-benzyl-3-azabicyclo[3.1.0]hexane-3-carboxylate and tert-butyl (1S*,2S*,5R*)-2-benzyl-3-azabicyclo[3.1.0]hexane-3-carboxylate.

Step 3: (1S*,2S*,5R*)-2-benzyl-3-azabicyclo[3.1.0]hexane

To tert-butyl (1S*2S*,5R*)-2-benzyl-3-azabicyclo[3.1.0]hexane-3-carboxylate (570 mg, 2.09 mmol) was added DCM (5 mL) and TFA (5 mL) and the resulting mixture was stirred at rt for 1 h. The solvent was evaporated and purified by SCX cartridge eluting sequentially with DCM:MeOH, 1:1 then 3:1 DCM:7 N ammonia in methanol. The ammonia in methanol fractions were combined and concentrated under reduced pressure to afford the title compound. nOe experiments allowed determination of the stereochemistry of the benzyl group relative to the cyclopropyl group. $^1$H NMR (400 MHz, CDCl$_3$): δ 7.32-7.17 (5H, m), 3.41 (1H, ddd, J=3.0, 5.5, 8.1 Hz), 2.94 (2H, d, J=1.8 Hz), 2.82 (1H, dd, J=5.9, 13.0 Hz), 2.61 (1H, dd, J=7.8, 13.1 Hz), 1.38-1.32 (1H, m), 1.30-1.23 (1H, m), 0.40-0.34 (1H, m), 0.34-0.30 (1H, m). NH not observed.

Step 4: (1S*,2R*,5R*)-2-benzyl-3-azabicyclo[3.1.0]hexane)

To tert-butyl (1S*2R*5R*)-2-benzyl-3-azabicyclo[3.1.0]hexane-3-carboxylate (400 mg, 1.46 mmol) was added DCM (3.5 mL) and TFA (3.5 mL) and the resulting mixture was stirred at rt for 1 h. The solvent was evaporated and purified by SCX cartridge eluting sequentially with DCM:MeOH, 1:1 then 3:1 DCM:7 N ammonia in methanol. The ammonia in methanol fractions were combined and concentrated under reduced pressure to afford the title compound. nOe experiments allowed determination of the stereochemistry of the benzyl group relative to the cyclopropyl group. $^1$H NMR (400 MHz, CDCl$_3$): δ 7.32-7.17 (5H, m), 3.29 (1H, t, J=7.2 Hz), 3.00 (1H, dd, J=3.2, 11.2 Hz), 2.87 (1H, d, J=11.0 Hz), 2.69 (1H, dd, J=7.2, 13.5 Hz), 2.60 (1H, dd, J=7.5, 13.4 Hz), 1.43-1.36 (1H, m), 1.29 (1H, ddd, J=4.0, 6.2, 7.9 Hz), 0.45 (1H, dt, J=5.0, 7.7 Hz), 0.15 (1H, dd, J=4.0, 8.7 Hz). NH not observed.

Intermediate 3, (1R*, 2R*, 5S*)-2-(4-fluorobenzyl)-3-azabicyclo[3.1.0]hexane, and Intermediate 4, (1R*, 2S*, 5S*)-2-(4-fluorobenzyl)-3-azabicyclo[3.1.0]hexane

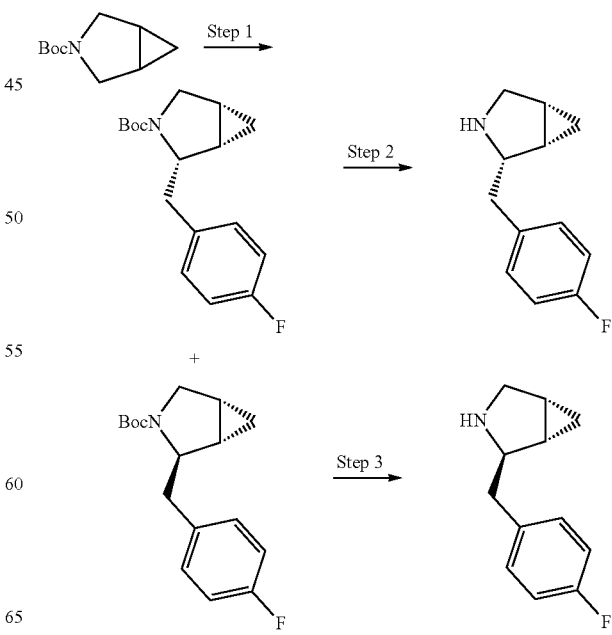

Step 1: tert-butyl (1R*, 2R*, 5S*)-2-(4-fluorobenzyl)-3-azabicyclo[3.1.0]hexane-3-carboxylate and tert-butyl (1R*, 2S*, 5S*)-2-(4-fluorobenzyl)-3-azabicyclo[3.1.0]hexane-3-carboxylate (−)-Sparteine was freshly distilled over KOH to give a colorless oil and the optical rotation was found to match that reported in the literature ($[\alpha]_D^{20}$—16.0 (c 10 g/100 mL, EtOH). To a solution of (−)-sparteine (1.0 mL, 4.35 mmol) in Et$_2$O (11 mL) at −78° C. was added sec-BuLi (3.1 mL of a 1.4 M solution in hexanes, 4.35 mmol) and the resulting mixture was stirred for 10 min at −78° C. and then transferred to a solution of tert-butyl 3-azabicyclo[3.1.0]hexane-3-carboxylate (613 mg, 3.35 mmol) in Et$_2$O (11 mL) at −78° C. The resulting reaction mixture was stirred at −78° C. for 5 h, and then 4-fluorobenzylbromide (0.63 mL, 5.02 mmol) was added. This mixture was then allowed to slowly warm to room temperature over 3 h. Water was then added, and the aqueous was extracted with Et$_2$O (×2). The organic phase was dried (MgSO$_4$) and evaporated to give the crude oil which was purified by silica chromatography (gradient elution, 0-25% iso-Hex/EtOAc) to afford tert-butyl (1R*,2R*, 5S*)-2-(4-fluorobenzyl)-3-azabicyclo[3.1.0]hexane-3-carboxylate and tert-butyl (1R*,2S*,5S*)-2-(4-fluorobenzyl)-3-azabicyclo[3.1.0]hexane-3-carboxylate.

Step 2: (1R*,2R*,5S*)-2-(4-fluorobenzyl)-3-azabicyclo[3.1.0]hexane

To tert-butyl (1R*,2R*,5S*)-2-(4-fluorobenzyl)-3-azabicyclo[3.1.0]hexane-3-carboxylate (176 mg, 0.603 mmol) was added DCM (1.5 mL) and TFA (1.5 mL) and the resulting mixture was stirred at rt for 3 h. The solvent was evaporated and the residue partitioned between DCM and saturated aqueous sodium bicarbonate. The combined organic phases were passed through a phase separator and evaporated to afford the title compound.

(1R*,2R*,5S*)-2-(4-fluorobenzyl)-3-azabicyclo[3.1.0]hexane $^1$H NMR δ (ppm) (400 MHz, CDCl$_3$) 7.23-7.16 (2H, m), 7.00-6.94 (2H, m), 3.44-3.38 (1H, m), 2.96 (2H, d, J=1.9 Hz), 2.80 (1H, dd, J=6.0, 13.2 Hz), 2.61 (1H, dd, J=7.9, 13.3 Hz), 1.43-1.36 (1H, m), 1.30-1.23 (1H, m), 0.42-0.31 (2H, m), NH not observed. nOe seen between cyclopropyl CH$_2$ and benzylic CH$_2$ consistent with cis relative stereochemistry.

Step 3: (1R*,2S*,5S*)-2-(4-fluorobenzyl)-3-azabicyclo[3.1.0]hexane

To tert-butyl (1R*,2S*,5S*)-2-(4-fluorobenzyl)-3-azabicyclo[3.1.0]hexane-3-carboxylate (320 mg, 1.10 mmol) were added DCM (1.5 mL) and TFA (1.5 mL) and the resulting mixture it was stirred at rt for 3 h. The solvent was evaporated and the residue partitioned between DCM and saturated aqueous sodium bicarbonate. The combined organic phases were passed through a phase separator and evaporated to afford the title compound.

(1R*,2S*,5S*)-2-(4-fluorobenzyl)-3-azabicyclo[3.1.0]hexane $^1$H NMR δ (ppm) (400 MHz, CDCl$_3$) 7.21-7.14 (2H, m), 7.00-6.95 (2H, m), 3.26 (1H, t, J=7.2 Hz), 2.98 (1H, dd, J=3.4, 11.2 Hz), 2.87 (1H, d, J=11.2 Hz), 2.69-2.55 (2H, m), 1.45-1.34 (1H, m), 1.31-1.26 (1H, m), 0.48 (1H, dt, J=5.0, 7.7 Hz), 0.16 (1H, q, J=4.4 Hz), NH not observed. nOe seen between cyclopropyl CH$_2$ and NCH consistent with trans relative stereochemistry.

Intermediate 5: (R)-5-benzylpyrrolidin-2-one

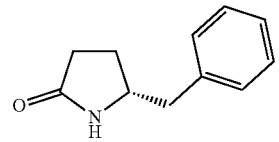 [SMILES: O=C1CC[C@H](Cc2ccccc2)N1]

Intermediate 5 was prepared according to the route described in *Journal of the American Chemical Society*, Volume 138, Issue 51, 16839-16848.

Intermediate 6: (2R*, 3S*)-2-benzyl-3-methylpyrrolidine

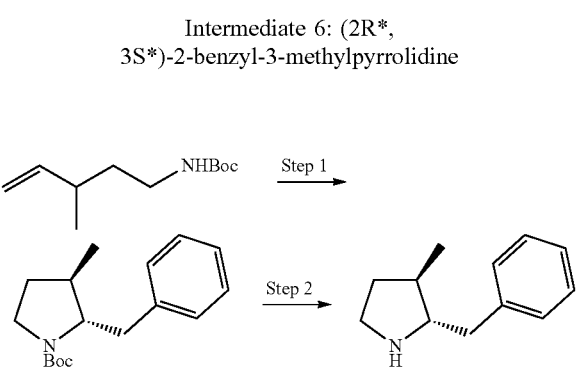

Step 1: tert-butyl (2R*,3S*)-2-benzyl-3-methylpyrrolidine-1-carboxylate

Palladium (II) acetate (18 mg, 0.08 mmol, Dpe-phos (86 mg, 0.16 mmol) and sodium tert-butoxide (884 mg, 9.2 mmol) were placed in a reaction tube sealed, evacuated and re-filled with nitrogen (×3). 3-Methylpent-4-en-1-yl)carbamate (798 mg, 4.0 mmol) was dissolved in dioxane (16 mL) and degassed. The solution was added to the reaction tube followed by bromobenzene (0.25 mL, 4.8 mmol) and the reaction heated at 100° C. for 17.5 h. The reaction mixture was cooled to r.t., diluted with NH$_4$Cl. The reaction mixture was extracted with EtOAc (×3). The organic extracts dried (phase separator) and concentrated under reduced pressure. The crude product was purified by silica gel column chromatography (gradient elution, 2-20% EtOAc/iso-hexane) to afford the title compound.

Step 2: (2R*,3S*)-2-benzyl-3-methylpyrrolidine tert-Butyl (2R*,3S*)-2-benzyl-3-methylpyrrolidine-1-carboxylate (785 mg, 2.85 mmol) was dissolved in 4 M HCl in dioxane (7.1 mL) at rt with stirring. After 2 h the reaction mixture was concentrated under reduced pressure. The residue was dissolved in DCM and washed with saturated NaHCO$_3$ solution. The organic extract was dried (phase separator) and concentrated under reduced pressure to afford the title compound. $^1$H NMR (400 MHz, CDCl$_3$): δ 7.32-7.16 (5H, m), 3.00-2.79 (3H, m), 2.77-2.68 (1H, m), 2.59 (1H, dd, J=8.5, 13.3 Hz), 2.08-1.96 (1H, m), 1.76-1.66 (1H, m), 1.42-1.31 (1H, m), 1.00 (3H, d, J=6.6 Hz), NH not observed.

Intermediate 7: (2R*,3S*)-2-(2-methoxybenzyl)-3-methylpyrrolidine

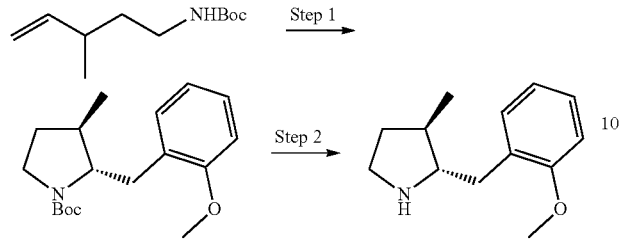

Step 1: tert-butyl(2R*,3S*)-2-(2-methoxybenzyl)-3-methylpyrrolidine-1-carboxylate Palladium (II) acetate (4.5 mg, 0.02 mmol), Dpe-phos (22 mg, 0.04 mmol) and sodium tert-butoxide (221 mg, 2.30 mmol) were placed in a reaction tube sealed, evacuated and re-filled with nitrogen (×3). 3-Methylpent-4-en-1-yl)carbamate (199 mg, 1.00 mmol) was dissolved in dioxane (4 mL) and degassed. The solution was added to the reaction tube followed by 2-bromoanisole (0.15 mL, 1.2 mmol) and the reaction heated at 100° C. for 17.25 h. The reaction mixture was cooled to r.t., diluted with NH$_4$Cl. The reaction mixture was extracted with EtOAc (×3). The organic extracts dried (phase separator) and concentrated under reduced pressure. The crude product was purified by silica gel column chromatography (gradient elution, 2-20% EtOAc/iso-hexane) to afford the title compound.

Step 2: (2R*,3S*)-2-(2-methoxybenzyl)-3-methylpyrrolidine tert-Butyl (2R*,3S*)-2-(2-methoxybenzyl)-3-methylpyrrolidine-1-carboxylate (216 mg, 0.71 mmol) was dissolved in 4 M HCl in dioxane (1.8 mL) at rt with stirring. After 2 h the reaction mixture was concentrated under reduced pressure. The residue was dissolved purified by SCX cartridge eluting with DCM (3 CV), Methanol (3 CV) followed by 4:1 DCM:7N methanolic ammonia (6 CV). The methanolic ammonia fractions were combined and concentrated under reduced pressure to afford the title compound. $^1$H NMR (400 MHz, CDCl$_3$): δ 7.21-7.16 (2H, m), 6.91-6.82 (2H, m), 3.81 (3H, s), 3.01-2.78 (4H, m), 2.73 (1H, br s), 2.64 (1H, dd, J=8.1, 13.4 Hz), 2.06-1.94 (1H, m), 1.78-1.68 (1H, m), 1.42-1.30 (1H, m), 0.98 (3H, d, J=7.8 Hz).

Intermediate 8: 2-(4-fluoro-2-methoxybenzyl)azepane

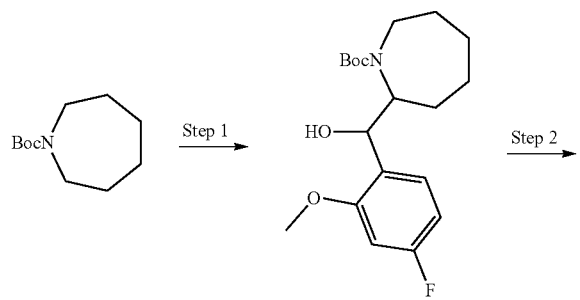

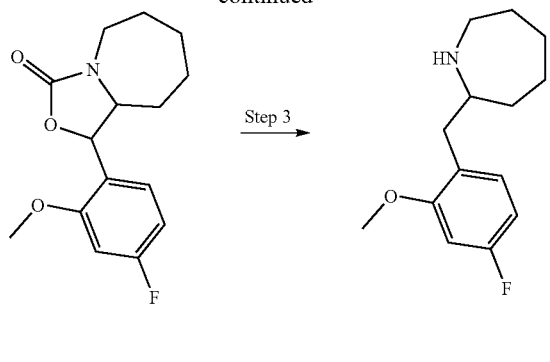

Step 1: tert-Butyl 2-((4-fluoro-2-methoxyphenyl)(hydroxy)methyl)azepane-1-carboxylate TMEDA (0.75 mL, 5.01 mmol) was added to a solution of tert-butyl azepane-1-carboxylate (1 g, 5.01 mmol) in Et$_2$O (10 mL). The mixture was cooled to −78° C. and sec-BuLi (4.66 mL, 6.52 mmol, 1.4 M in cyclohexane) was added dropwise. After 2 h 4-fluoro-2-methoxybenzaldehyde (0.85 g, 5.52 mmol) in Et$_2$O (5 mL) was added dropwise at −78° C. After 3 h, during which time the cooling bath temperature had risen to −20° C., the reaction was quenched with water. The ether was removed in vacuo and the remaining aqueous layer was extracted with DCM, separating the layers using a phase separator. The DCM was removed in vacuo to afford the title compound, which was used in the next step without further purification.

Step 2: 1-(4-Fluoro-2-methoxyphenyl)hexahydro-1H,3H-oxazolo[3,4-a]azepin-3-one KOtBu (56 mg, 0.50 mmol) was added to a solution of tert-butyl 2-((4-fluoro-2-methoxyphenyl)(hydroxy)methyl)azepane-1-carboxylate (1.22 g, 3.46 mmol) in i-PrOH (20 mL). The reaction mixture was heated at reflux for 4 h and then cooled to r.t. The solvent was removed in vacuo to give an oil residue, which was purified by silica gel column chromatography (gradient elution, 0-30% EtOAc/iso-hexane) to afford the title compound.

Step 3: 2-(4-fluoro-2-methoxybenzyl)azepane

To a solution of 1-(4-fluoro-2-methoxyphenyl)hexahydro-1H,3H-oxazolo[3,4-a]azepin-3-one (700 mg, 2.51 mmol) in MeOH (5 mL) was added NaOMe (0.48 mL, 2.63 mmol, 5.5 M solution in methanol) and Pd(OH)$_2$ (63 mg, 25 g/mol). The mixture was stirred under hydrogen (1 atmosphere) for 48 hours at r.t. The reaction was filtered through Celite, washing with MeOH, and the collected solution acidified to ~pH 2 with 1 M HCl. The solvent was removed in vacuo and the residue purified by SCX chromatography (eluting with 50% MeOH/DCM followed by 10% 7N methanolic ammonia in methanol/methanol). Concentration of the ammonical fractions in vacuo yielded the title compound. $^1$H NMR (400 MHz, CDCl$_3$): δ 7.07-7.04 (1H, m), 6.61-6.56 (2H, m), 3.79 (3H, s), 2.99-2.93 (1H, m), 2.91-2.84 (1H, m), 2.68-2.54 (3H, m), 1.80-1.44 (7H, m), 1.41-1.31 (1H, m), NH not observed.

The following examples were prepared using a procedure analogous to that described for Intermediate 8 starting from the reported aldehyde.

| Intermediate | Structure and Name | Aldehyde | NMR |
|---|---|---|---|
| Intermediate 9 | 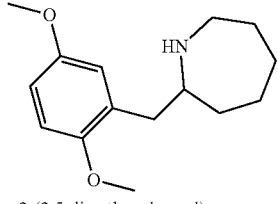<br>2-(2,5-dimethoxybenzyl)azepane | 2,5-dimethoxy-benzaldehyde | $^1$H NMR (400 MHz, CDCl$_3$): δ 6.79-6.70 (3H, m), 3.76 (6H, d, J = 4.5 Hz), 3.00-2.87 (2H, m), 2.71-2.51 (3H, m), 1.83-1.76 (1H, m), 1.73-1.34 (7H, m), NH not observed |
| Intermediate 10 | 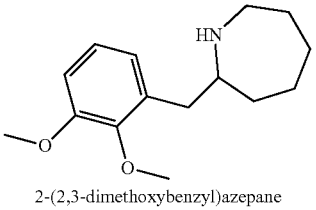<br>2-(2,3-dimethoxybenzyl)azepane | 2,3-dimethoxy-benzaldehyde | $^1$H NMR (400 MHz, CDCl$_3$): δ 6.98 (1H, t, J = 8 Hz), 6.81-6.77 (2H, m), 3.86 (3H, s), 3.82 (3H, s), 2.99-2.87 (2H, m), 2.73-2.52 (3H, m), 1.83-1.76 (1H, m), 1.73-1.35 (7H, m), NH not observed |
| Intermediate 11 | 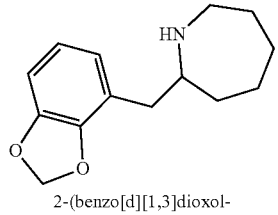<br>2-(benzo[d][1,3]dioxol-4-ylmethyl)azepane | benzo[d][1,3]dioxole-4-carbaldehyde | $^1$H NMR (400 MHz, CDCl$_3$): δ 6.78-6.66 (3H, m), 5.93 (2H, s), 3.00-2.92 (2H, m), 2.70-2.58 (3H, m), 1.85-1.78 (1H, m), 1.73-1.33 (7H, m), NH not observed |
| Intermediate 12 | 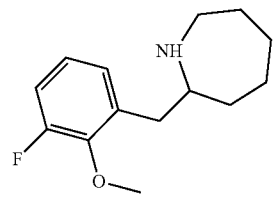 [SMILES: COc1c(F)cccc1CC1CCCCCN1]<br>2-(3-fluoro-2-methoxybenzyl)azepane | 3-fluoro-2-methoxy-benzaldehyde | $^1$H NMR (400 MHz, CDCl$_3$): δ 6.98-6.92 (3H, m), 3.91 (3H, d, J = 1.9 Hz), 3.02-2.90 (2H, m), 2.77-2.60 (3H, m), 1.81-1.35 (8H, m), NH not observed. |
| Intermediate 13 | 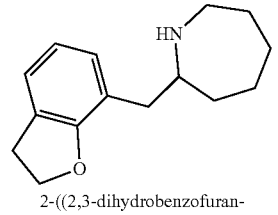<br>2-((2,3-dihydrobenzofuran-7-yl)methyl)azepane | benzofuran-7-carbaldehyde | $^1$H NMR (400 MHz, CDCl$_3$): δ 7.06 (1H, dd, J = 7.2 Hz), 6.94 (1H, d, J = 7.9 Hz), 6.77 (1H, t, J = 7.3 Hz), 4.54 (2H, t, J = 4.55 Hz), 3.20 (2H, t, J = 8.8 Hz), 2.99-2.91 (2H, m), 2.69-2.55 (3H, m), 1.84-1.77 (1H, m), 1.74-1.34 (7H, m), NH not observed |
| Intermediate 14 | 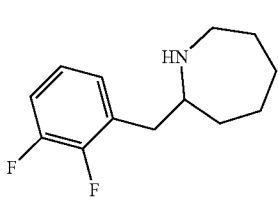 [SMILES: Fc1cccc(CC2CCCCCN2)c1F]<br>2-(2,3-difluorobenzyl)azepane | 2,3-difluoro-benzaldehyde | $^1$H NMR (400 MHz, CDCl$_3$): δ 7.04-6.93 (3H, m), 2.99-2.92 (2H, m), 2.79-2.62 (3H, m), 1.84-1.33 (8H, m), NH not observed |
| Intermediate 15 | 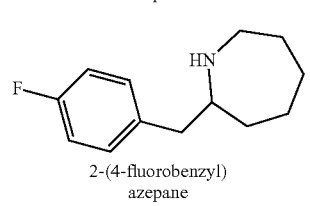<br>2-(4-fluorobenzyl)azepane | 4-fluoro-benzaldehyde | $^1$H NMR (400 MHz, CDCl$_3$): δ 7.17-7.13 (2H, m), 6.99-6.95 (2H, m), 2.97-2.92 (1H, m), 2.88-2.81 (1H, m), 2.68 (1H, dd, J = 5.5, 13.3 Hz), 2.62-2.55 (2H, m), 1.83-1.76 (1H, m), 1.73-1.45 (6H, m), 1.40-1.31 (1H, m), NH not observed |

| Intermediate | Structure and Name | Aldehyde | NMR |
|---|---|---|---|
| Intermediate 16 | 2-(3-(2-methoxyethoxy)benzyl)azepane | 3-(2-methoxyethoxy) benzaldehyde | $^1$H NMR (400 MHz, CDCl$_3$): δ 7.19 (1H, t, J = 7.7 Hz), 6.80 (3H, t, J = 6.0 Hz), 4.11 (2H, t, J = 4.5 Hz), 3.76 (2H, t, 4.7 Hz), 3.45 (3H, s), 2.96-2.83 (2H, m), 2.69 (1H, dd, J = 5.7, 13.4 Hz), 2.59-2.53 (2H, m), 1.83-1.32 (8H, m), NH not observed |
| Intermediate 17 | 2-(4-(2-methoxyethoxy) benzyl)azepane | 4-(2-methoxyethoxy) benzaldehyde | $^1$H NMR (400 MHz, CDCl$_3$): δ 7.10 (2H, d, J = 9.5 Hz), 6.87 (2H, d, J = 9.5 Hz), 4.11 (2H, t, J = 5.1 Hz), 3.74 (2H, t, J = 4.6 Hz), 3.45 (3H, s), 2.96-2.93 (1H, m), 2.85-2.78 (1H, m), 2.66 (1H, dd, J = 5.3, 14.0 Hz), 2.58-2.48 (2H, m), 1.82-1.31 (8H, m), NH not observed |
| Intermediate 18 | 2-(2-(difluoromethoxy) benzyl)azepane | 2-(difluoromethoxy) benzaldehyde | $^1$H NMR (400 MHz, CDCl$_3$): δ 7.24-7.08 (4H, m), 6.53 (1H, t, J = 74.2 Hz), 3.03-2.94 (2H, m), 2.80-2.62 (3H, m), 1.82-1.37 (8H, m), NH not observed. |
| Intermediate 19 | 2-(2-(difluoromethoxy) benzyl)azepane | 2-(difluoromethoxy) benzaldehyde | $^1$H NMR (400 MHz, CDCl$_3$): δ 7.22-7.18 (2H, m), 7.08-6.99 (2H, m), 2.99-2.91 (2H, m), 2.77-2.59 (3H, m), 1.84-1.77 (1H, m), 1.74-1.34 (7H, m), NH not observed. |

Intermediate 20: 2-benzyl-4,4-dimethylazepane

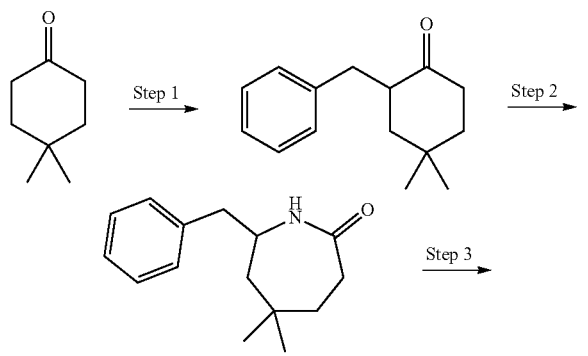

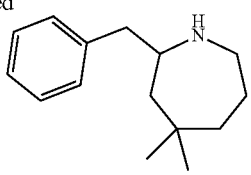

Step 1: 2-benzyl-4,4-dimethylcyclohexan-1-one 4,4-Dimethylcyclohexan-1-one (g, 7.93 mmol) in THF (15 mL) was added dropwise to a solution of LDA (4.36 mL, 8.73 mmol, 2 M in THF) at −40° C. After stirring for 1 h at 40° C., benzyl bromide (1.04 mL, 8.73 mmol) was added dropwise and the reaction allowed to warm to rt over 3 h. The reaction was quenched by addition of 1M HCl and the THF was removed in vacuo. The aqueous layer was extracted with DCM and the layers separated using a phase separator. The DCM layer was concentrated in vacuo to give a residual oil, which was purified by silica gel column chromatography (gradient elution, 0-20% EtOAc/iso-hexane) to afford the title compound.

Step 2: 7-benzyl-5,5-dimethylazepan-2-one

To a solution of 2-benzyl-4,4-dimethylcyclohexan-1-one (850 mg, 3.93 mmol) in methanesulfonic acid (2 mL) was added portionwise sodium azide (270 mg, 4.13 mmol), keeping the internal temperature below 30° C. After complete addition the reaction was stirred at rt for 2 h. The reaction mixture was added to water and the resultant white solid collected by filtration. The solid was purified by silica gel column chromatography (gradient elution, 0-100% EtOAc/iso-hexane) to afford the title compound.

Step 3: 2-benzyl-4,4-dimethylazepane

To a solution of 7-benzyl-5,5-dimethylazepan-2-one (430 mg, 1.86 mmol) in THF (10 mL) was added LiAlH$_4$ (3.7 mL, 3.72 mmol, 1M in THF). The reaction was heated at reflux for 3 h. The reaction was cooled to 0° C. and quenched by addition of water. The THF was removed in vacuo and the aqueous layer was extracted with EtOAc. The layers were separated and the EtOAc layer was dried (MgSO$_4$). The solvent was removed in vacuo to give a residue oil, which was purified by silica gel column chromatography (gradient elution, 0-10% DCM/MeOH) to afford the title compound.
$^1$H NMR (400 MHz, CDCl$_3$): δ 7.31-7.28 (2H, m), 7.22-7.19 (3H, m), 3.03-2.97 (1H, m), 2.94-2.87 (1H, m), 2.68-2.55 (3H, m), 1.61-1.39 (6H, m), 0.92 (3H, s), 0.89 (3H, s), NH not observed.

The following examples were prepared using a procedure analogous to that described for Intermediate 20 starting from the appropriate aldehyde and cyclohexanone:

| Intermediate | Structure and Name | Cyclohexanone | Aldehyde | NMR |
|---|---|---|---|---|
| Intermediate 21 | 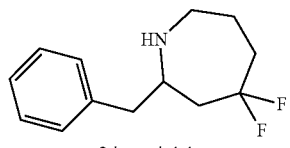<br>2-benzyl-4,4-difluoroazepane | 4,4-difluorocyclohexan-1-one | Benzaldehyde | $^1$H NMR (400 MHz, CDCl$_3$): δ 7.34-7.30 (2H, m), 7.25-7.19 (3H, m), 3.07-2.99 (2H, m), 2.76 (1H, dd, J = 5.4, 13.6 Hz), 2.71-2.65 (1H, m), 2.60 (1H, dd, J = 9.1, 14.1 Hz), 2.31-1.92 (4H, m), 1.73-1.67 (2H, m), NH not observed |
| Intermediate 22 | 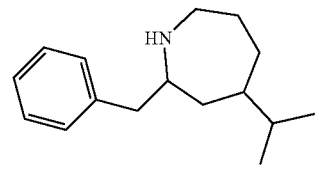 [SMILES: CC(C)C1CCCNC(Cc2ccccc2)C1]<br>2-benzyl-4-isopropylazepane | 4-isopropylcyclohexan-1-one | Benzaldehyde | $^1$H NMR (400 MHz, CDCl$_3$): δ 7.31-7.25 (2H, m), 7.22-7.19 (3H, m), 3.03-2.39 (5H, m), 1.82-1.18 (8H, m), 0.84-0.82 (6H, m), NH not observed |
| Intermediate 23 | 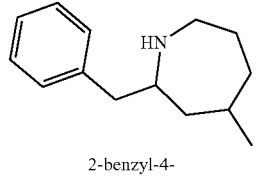<br>2-benzyl-4-methylazepane | 4-Methylcyclohexanone | Benzaldehyde | $^1$H NMR (400 MHz, CDCl$_3$): δ 7.31-7.27 (2H, m), 7.22-7.18 (3H, m), 3.04-2.86 (2H, m), 2.74-2.67 (2H, m), 2.63-2.44 (1H, m), 1.77-1.11 (8H, m), 0.98-0.91 (3H, m), NH not observed. |
| Intermediate 24 | 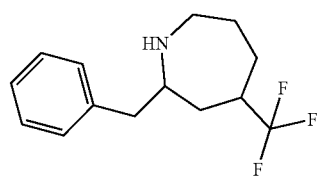 [SMILES: FC(F)(F)C1CCCNC(Cc2ccccc2)C1]<br>2-benzyl-4-(trifluoromethyl)azepane | 4-(trifluoromethyl)cyclohexan-1-one | Benzaldehyde | $^1$H NMR (400 MHz, CDCl$_3$): δ 7.33-7.19 (5H, m), 2.99-2.88 (2H, m), 2.82-2.75 (1H, m), 2.66-2.58 (2H, m), 2.33-2.24 (1H, m), 2.12-1.98 (2H, m), 1.88-1.79 (1H, m), 1.70-1.39 (3H, m), NH not observed |

| Intermediate | Structure and Name | Cyclohexanone | Aldehyde | NMR |
|---|---|---|---|---|
| Intermediate 25 | ![structure] 2-(4-fluorobenzyl)-4-methylazepane | 4-Methyl-cyclohexanone | 4-Fluoro-benzaldehyde | ¹H NMR (400 MHz, CDCl₃): δ 7.16-7.13 (2H, m), 7.00-6.95 (2H, m), 3.04-2.82 (2H, m), 2.74-2.64 (2H, m), 2.60-2.44 (1H, m), 1.77-1.27 (6H, m), 1.18-1.09 (1H, m), 0.92 (3H, d, J = 6.5 Hz), NH not observed |

Intermediate 26: 2-(Thiophen-3-ylmethyl)azepane

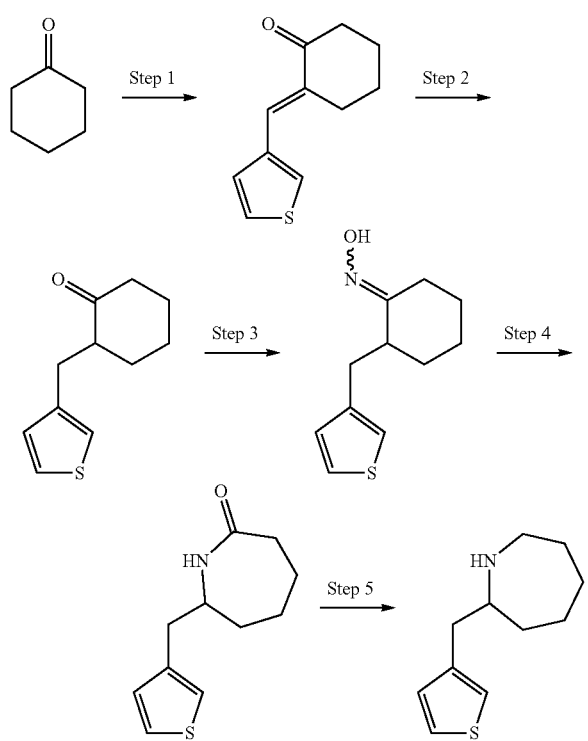

Step 1:
(E)-2-(Thiophen-3-ylmethylene)cyclohexan-1-one

Sodium hydroxide (1.6 g, 40.12 mmol) was added to cyclohexanone (7.88 g, 80.25 mmol) suspended in water (150 mL) at r.t. The reaction was stirred for 15 min before dropwise addition of 3-thiophenecarboxaldehyde (3 g, 26.75 mmol). After 18 h the resultant solid was collected by filtration and air dried to give a yellow solid, which was purified by silica gel column chromatography (gradient elution, 0-20% EtOAc/iso-hexane) to afford the title compound.

Step 2: 2-(Thiophen-3-ylmethyl)cyclohexan-1-one (E)-2-(Thiophen-3-ylmethylene)cyclohexan-1-one (800 mg, 4.17 mmol) was dissolved in MeOH (80 mL) and passed through an H-Cube reactor (1 mL/min, 50 bar, r.t.) fitted with a 10% palladium on carbon CatCart®. The collected elutant solvent was concentrated in vacuo to give a yellow solid, which was purified by silica gel column chromatography (gradient elution, 0-20% EtOAc/iso-hexane) to afford the title compound.

Step 3: 2-(Thiophen-3-ylmethyl)cyclohexan-1-one oxime 2-(Thiophen-3-ylmethyl)cyclohexan-1-one (800 mg, 4.12 mmol) was dissolved in MeOH (10 mL) and water (6 mL). Sodium carbonate (1.31 g, 12.35 mmol) was added followed by hydroxylamine hydrochloride (572 mg, 8.24 mmol) and the reaction stirred at r.t. overnight. The solvent was removed in vacuo and the residue suspended in DCM and water. The DCM layer was separated using a phase separator and concentrated in vacuo to give the title compound. Used without further purification in the next step.

Step 4: 7-(Thiophen-3-ylmethyl)azepan-2-one 2-(Thiophen-3-ylmethyl)cyclohexan-1-one oxime (857 mg, 4.09 mmol) was dissolved in acetone (50 mL) and water (50 mL). Sodium carbonate (1.74 g, 16.38 mmol) was added followed by tosyl chloride (1.56 g, 8.19 mmol) and the reaction stirred at rt overnight. The solvents were removed in vacuo and the residue dissolved in DCM and washed with water. The layers were separated using a phase separator and the DCM layer concentrated in vacuo to give a yellow solid residue. Purification by silica gel column chromatography (gradient elution, 0-30% EtOAc/iso-hexane) yielded the title compound.

Step 5: 2-(Thiophen-3-ylmethyl)azepane

To a solution of 7-(thiophen-3-ylmethyl)azepan-2-one (620 mg, 2.96 mmol) in THF (20 mL) was added lithium aluminium hydride (3 mL, 5.29 mmol, 2 M solution in THF) at r.t. The reaction was heated at reflux for 3 h. The reaction was cooled to r.t. followed by 0° C. and quenched by careful addition of water. The THF was removed in vacuo and the aqueous layer extracted with EtOAc. The layers were separated and the EtOAc layer dried (phase separator) and concentrated in vacuo to give a residue oil, which was purified by SCX chromatography (eluting with 50% MeOH/DCM followed by 10% 7N methanolic ammonia in methanol/methanol). Concentration of the ammonical fractions in vacuo yielded the title compound. ¹H NMR (400 MHz, CDCl₃): δ 7.27-7.25 (1H, m), 6.99 (1H, s), 6.96 (1H, d, J=5.1 Hz), 2.99-2.94 (1H, m), 2.90-2.83 (1H, m), 2.75-2.56 (3H, m), 1.84-1.78 (1H, m), 1.74-1.47 (6H, m), 1.41-1.31 (1H, m), NH not observed.

Intermediate 27:
4,4-Difluoro-2-(2-methoxybenzyl)azepane

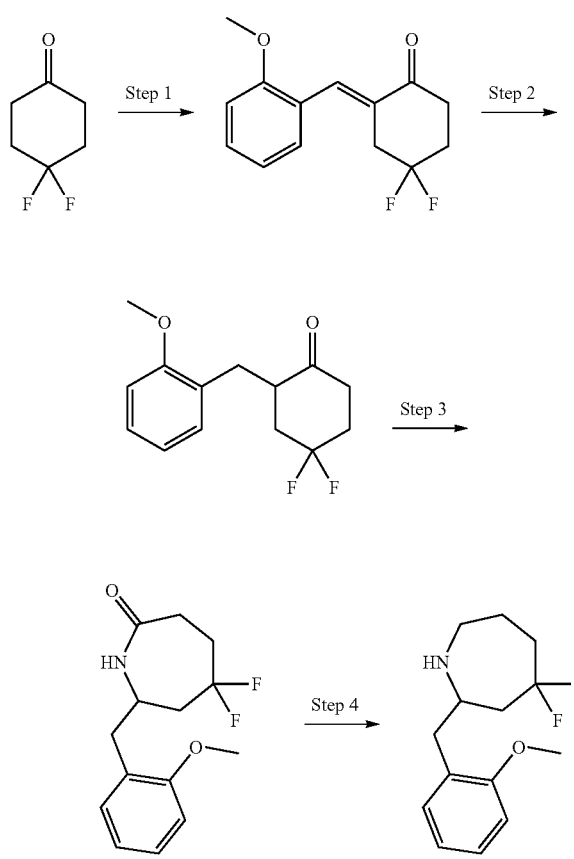

Step 1: (E)-4,4-Difluoro-2-(2-methoxybenzylidene) cyclohexan-1-one

Sodium hydroxide (0.75 g, 18.64 mmol) was added to a suspension of 4,4-difluorocyclohexan-1-one (5 g, 37.28 mmol) in water (100 mL) at r.t. After 15 min 2-methoxybenzaldehyde (1.69 g, 12.43 mmol) was added portionwise. After 72 h the reaction mixture was extracted with DCM and the DCM layer separated using a phase separator. The DCM layer was concentrated in vacuo to give a residue, which was purified by silica gel column chromatography (gradient elution, 0-20% EtOAc/iso-hexane) to yield the title compound.

Step 2: 4,4-Difluoro-2-(2-methoxybenzyl)cyclohexan-1-one (E)-4,4-Difluoro-2-(2-methoxybenzylidene)cyclohexan-1-one (1.8 g, 7.14 mmol) was dissolved in MeOH (180 mL) and passed through an H-Cube reactor (1 mL/min, 50 bar, r.t.) fitted with a 10% palladium on carbon CatCart®. The collected elutant was concentrated in vacuo to give a yellow solid, which was purified by silica gel column chromatography (gradient elution, 0-20% EtOAc/iso-hexane) to yield the title compound.

Step 3: 5,5-Difluoro-7-(2-methoxybenzyl)azepan-2-one

To a solution of 4,4-difluoro-2-(2-methoxybenzyl)cyclohexan-1-one (1.1 g, 4.33 mmol) in methanesulfonic acid (8 mL) was added sodium azide (0.3 g, 4.54 mmol) portionwise over 30 min at r.t. After 1 h the reaction was added to water. The aqueous layer was extracted with DCM and the layers separated using a phase separator. The DCM layer was concentrated in vacuo to give an oil, which was purified by silica gel column chromatography (gradient elution, 0-100% EtOAc/iso-hexane) to yield the title compound.

Step 4: 4,4-Difluoro-2-(2-methoxybenzyl)azepane

LiAlH$_4$ (2.5 mL, 4.93 mmol, 2M solution in THF) was added to a solution of 4,4-difluoro-2-(2-methoxybenzyl) azepane (664 mg, 2.47 mmol) in THF (10 mL) at r.t. The reaction was heated at reflux for 3 h. The reaction was cooled to r.t. followed by 0° C. and quenched by careful addition of water. The THF was removed in vacuo and the aqueous layer was extracted with EtOAc. The layers were separated and the EtOAc layer dried (phase separator) and concentrated in vacuo to give a residue oil, which was purified by SCX chromatography (eluting with 50% MeOH/DCM followed by 10% 7N methanolic ammonia in methanol/methanol). Concentration of the ammonical fractions in vacuo yielded the title compound. $^1$H NMR (400 MHz, CDCl$_3$): δ 7.22 (1H, t, J=7.8 Hz), 7.11 (1H, d, J=6.8 Hz), 6.92-6.86 (2H, m), 3.83 (3H, s), 3.09-3.00 (2H, m), 2.75-2.64 (3H, m), 2.30-1.92 (4H, m), 1.72-1.66 (2H, m), NH not observed.

The following example was prepared using a procedure analogous to that described for Intermediate 27 starting from the 4-methyl cyclohexanone and 2-methoxybenzaldehyde.

| Intermediate | Structure | Name | NMR |
|---|---|---|---|
| Intermediate 28 | 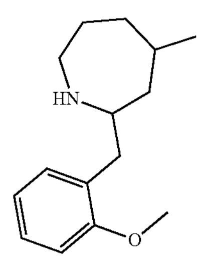 [SMILES: COc1ccccc1CC1CC(C)CCCN1] | 2-(2-methoxy benzyl)-4-methyl azepane | $^1$H NMR (400 MHz, CDCl$_3$): δ 7.19 (1H, t, J = 8.3 Hz), 7.13 (1H, d, J = 7.4 Hz), 6.91-6.84 (2H, m), 3.81 (3H, s), 3.05-2.89 (2H, m), 2.74-2.57 (3H, m), 1.74-1.12 (7H, m), 0.91 (3H, d, J = 6.6 Hz), NH not observed |

Intermediate 29: (R)-2-benzyl-6,6-dimethylazepane, Intermediate 30: (2R)-2-benzyl-6-methylazepane Diastereomer 1, and Intermediate 31: (2R)-2-benzyl-6-methylazepane Diastereomer 2

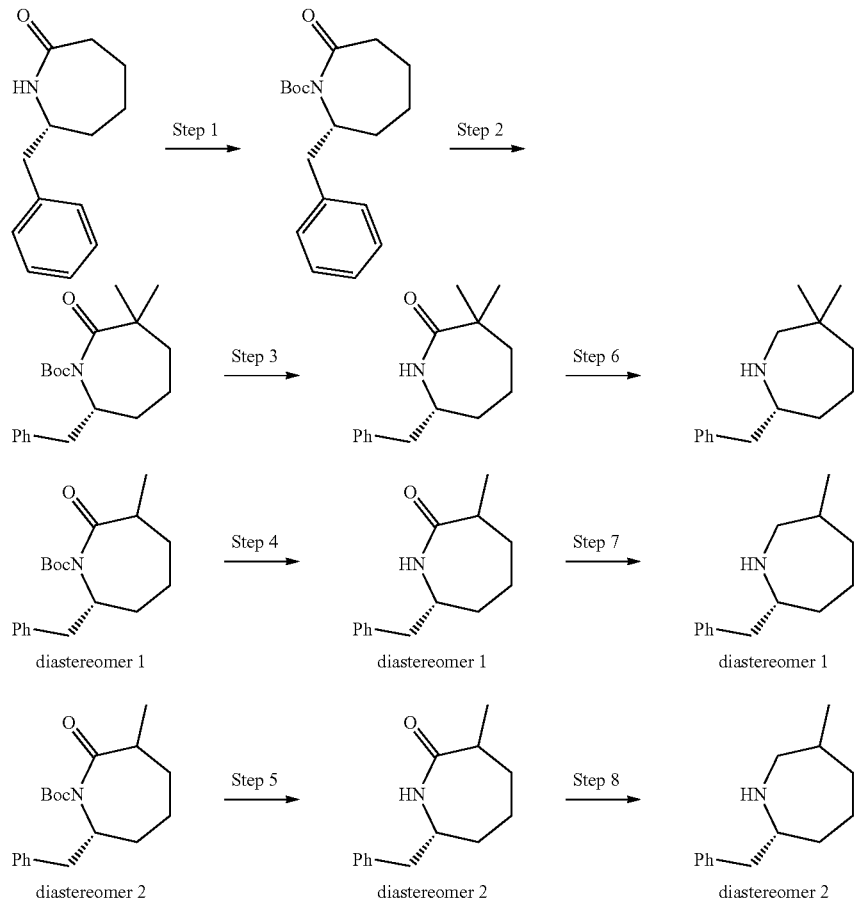

Step 1: tert-butyl (R)-2-benzyl-7-oxoazepane-1-carboxylate (R)-7-benzylazepan-2-one (3 g, 14.8 mmol, example 3, step 1) was dissolved in MeCN (25 mL) and di-tert-butyl dicarbonate (4.8 g, 22.2 mmol) and 4-(dimethylamino)pyridine (2.7 g, 22.2 mmol) were added and the mixture was heated to reflux for 18 h. The reaction mixture was cooled to rt and concentrated under reduced pressure. The crude product was purified by silica gel column chromatography (gradient elution, 0-20% EtOAc/iso-hexane) to afford the title compound.

Step 2: tert-butyl (R)-7-benzyl-3,3-dimethyl-2-oxoazepane-1-carboxylate, tert-butyl (7R)-7-benzyl-3-methyl-2-oxoazepane-1-carboxylate Diastereomer 1 and tert-butyl (7R)-7-benzyl-3-methy-2-oxoazepane-1-carboxylate Diastereomer 2 tert-Butyl (R)-2-benzyl-7-oxoazepane-1-carboxylate (960 mg, 3.17 mmol) was dissolved in THF, cooled to −78° C., and LHMDS (7.9 mL, 7.9 mmol, 1M in THF) was added and the resulting mixture was stirred for 1 h at −78° C. MeI (490 µL, 7.9 mmol) was added and the reaction allowed to warm to rt over 19 h. Water and Et$_2$O were added, the two phases separated and the aqueous phase was re-extracted with Et$_2$O (×1). The combined organic phases were dried (MgSO$_4$) and evaporated to afford a crude oil which was purified by silica gel column chromatography (gradient elution, 0-4% EtOAc/iso-hexane) to afford the title compounds. The first eluting component, tert-butyl (R)-7-benzyl-3,3-dimethyl-2-oxoazepane-1-carboxylate, was obtained. The second and third eluting compounds were tert-butyl (7R)-7-benzyl-3-methyl-2-oxoazepane-1-carboxylate diastereomer 1 and tert-butyl (7R)-7-benzyl-3-methyl-2-oxoazepane-1-carboxylate diastereomer 2 respectively.

Step 3: (R)-7-benzyl-3,3-dimethylazepan-2-one

DCM (1.5 mL) and TFA (1.5 mL) were added to tert-butyl (R)-7-benzyl-3,3-dimethyl-2-oxoazepane-1-carboxylate (200 mg, 0.60 mmol) and the resulting mixtures were stirred at r.t. After 3 h the solvent was evaporated and the residue was partitioned between DCM and saturated aqueous NaHCO$_3$ and re-extracted with DCM. The combined organic phases were dried (phase separator) and evaporated to afford the title compound.

Step 4: (7R)-7-benzyl-3-methylazepan-2-one Diastereomer 1

Following the method described for Intermediate 29 step 3 starting from tert-butyl (7R)-7-benzyl-3-methyl-2-oxoazepane-1-carboxylate diastereomer 1 (60 mg, 0.189 mmol) to afford the title compound.

Step 5: (7R)-7-benzyl-3-methylazepan-2-one Diastereomer 2

Following the method described for Intermediate 29 step 3 starting from tert-butyl (7R)-7-benzyl-3-methyl-2-oxoazepane-1-carboxylate diastereomer 2 (150 mg, 0.473 mmol) to afford the title compound.

Step 6: (R)-2-benzyl-6,6-dimethylazepane

Lithium aluminium hydride (1.2 mL, 1.2 mmol, 1M solution in THF) was added to a solution of (R)-2-benzyl-6,6-dimethylazepane (140 mg, 0.61 mmol) in THF (3 mL) and heated to 70° C. for 3 h. The mixtures were carefully quenched with aqueous NaOH (15% solution) and the THF evaporated. The aqueous phase was extracted with EtOAc (×2). The organic phases were dried (MgSO$_4$) and evaporated to give the title compound which used without purification in the next step. $^1$H NMR (400 MHz, CDCl$_3$): δ 7.32-7.26 (2H, m), 7.23-7.16 (3H, m), 2.87-2.77 (1H, m), 2.70 (1H, dd, J=5.1, 13.5 Hz), 2.64-2.53 (2H, m), 2.30 (1H, d, J=13.6 Hz). 1.77-1.26 (6H, m), 0.91 (3H, s), 0.79 (3H, s).

Step 7: (2R)-2-benzyl-6-methylazepane Diastereomer 1

Following the method described for Intermediate 29 step 6 starting from (7R)-7-benzyl-3-methylazepan-2-one diastereomer 1 (42 mg, 0.19 mmol) to afford the title compound. $^1$H NMR (400 MHz, CDCl$_3$): δ 7.32-7.25 (2H, m), 7.23-7.15 (3H, m), 2.96-2.87 (1H, m), 2.76-2.55 (4H, m), 1.87-1.56 (4H, m), 1.44-1.14 (3H, m), 0.88 (3H, d, J=6.6 Hz), NH not observed.

Step 8: (2R)-2-benzyl-6-methylazepane Diastereomer 2

Following the method described for Intermediate 29 step 6 starting from (7R)-7-benzyl-3-methylazepan-2-one diastereomer 2 (84 mg, 0.39 mmol) to afford the title compound. $^1$H NMR (400 MHz, CDCl$_3$): δ 7.32-7.25 (2H, m), 7.24-7.17 (3H, m), 2.95-2.84 (2H, m), 2.72 (1H, dd, J=5.2, 13.5 Hz), 2.57 (1H, dd, J=8.6, 13.4 Hz), 2.16 (1H, dd, J=10.5, 13.3 Hz), 1.82-1.71 (3H, m), 1.63-1.19 (4H, m), 0.80 (3H, d, J=6.6 Hz), NH not observed.

4. General Methods

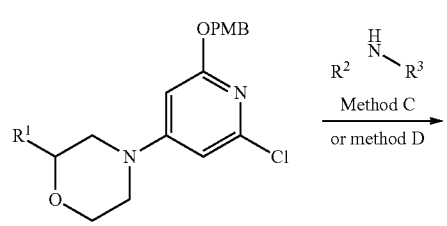

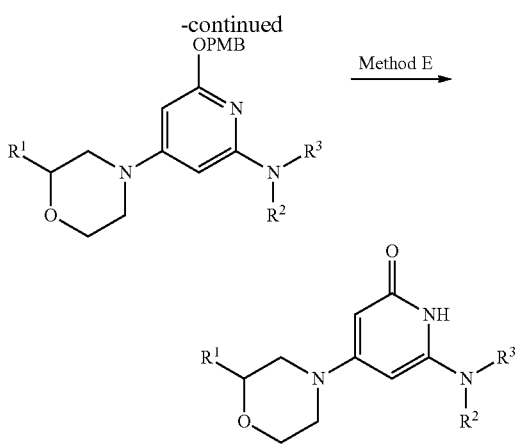

Method C

A suspension of aryl halide (1.0 eq.), amine (1.0 eq.), Cs$_2$CO$_3$ (1.5 eq.) in dry 1,4-dioxane (0.2 M) was sparged with N$_2$ for 15 min. Pd$_2$(dba)$_3$ (0.053 eq.) and 2,2'-bis(diphenylphosphino)-1,1'-binaphthyl (0.2 eq.) were then added, the reaction tube was sealed under N$_2$ and stirred at 100° C. for 16-40 h. After cooling to r.t., the mixture was filtered through Celite, washing thoroughly with CH$_2$Cl$_2$ and the filtrate was concentrated.

Method D

For solid amines the following method was followed: A mixture of amine (1.0-1.4 eq), aryl halide (1.0 eq), Cs$_2$CO$_3$ or NaOtBu (1.1 eq), RuPhos (0.05-0.1 eq), and RuPhos palladacycle G1 methyl tert-butyl ether adduct (0.05-0.1 eq) were placed in a stem block tube and sealed. The tube was evacuated and refilled with nitrogen (×3). 1,4-Dioxane (0.08-0.15 M) was added and the reaction heated at 85° C. for 16 h. The reaction mixture was cooled to rt and filtered through celite. The mixture was concentrated under reduced pressure.

In the case of the amine being an oil, it was introduced as a solution in dry 1,4-dioxane.

Method E

To a solution of the PMB protected compound (1.0 eq.) in ethanol (0.15 M) was added 5% palladium on carbon (100% by weight of PMB compound) and the reaction mixture purged with N$_2$ for 20 min. 1-Methylcyclohexa-1,4-diene (10 eq.) was added and the reaction heated at 75° C. for 1-18 h. The reaction was cooled to rt and filtered through celite, washing with methanol. The solution was concentrated under reduced pressure.

5. Syntheses of Example Compounds

Example 1: (R)-6-(2-benzylpyrrolidin-1-yl)-4-morpholinopyridin-2(1H)-one and Example 2: (S)-6-(2-benzylpyrrolidin-1-yl)-4-morpholinopyridin-2(1H)-one

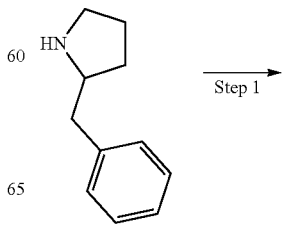

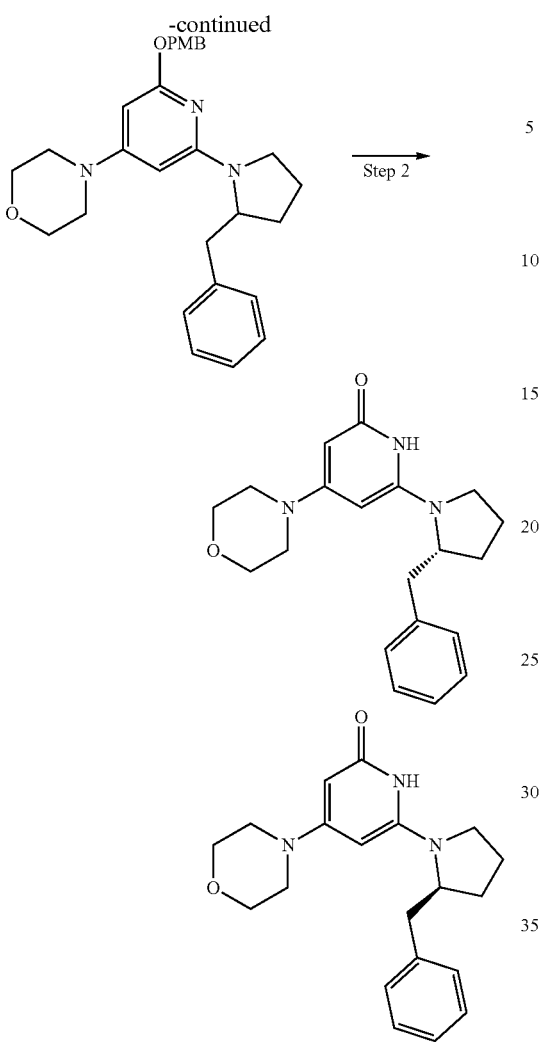

Step 1: 4-(2-(2-benzylpyrrolidin-1-yl)-6-((4-methoxybenzyl)oxy)pyridin-4-yl)morpholine Following Method C starting from 2-benzylpyrrolidine (53 mg, 0.30 mmol) and 4-(2-chloro-6-((4-methoxybenzyl)oxy)pyridin-4-yl)morpholine (101 mg, 0.30 mmol, Scaffold 1). After heating at 105° C. for 18.5 h, a further 0.5 eq pyrrolidine, 1.6 eq. cesium carbonate, 0.025 eq, $Pd_2(dba)_3$, and 0.1 eq. BINAP were added and the reaction heated at 105° C. for a further 23 h. The reaction was cooled to r.t. and filtered through celite, washing with DCM and the reaction concentrated under reduced pressure. The reaction was repeated on the same scale with 1,4-dioxane as the solvent. The crude mixtures of both reactions were combined and purified by silica gel column chromatography (gradient elution, 0-25% EtOAc/iso-hexane) to afford the title compound (170 mg, 61%).

Step 2: (S)-6-(2-benzylpyrrolidin-1-yl)-4-morpholinopyridin-2(1H)-one and (R)-6-(2-benzylpyrrolidin-1-yl)-4-morpholinopyridin-2(1H)-one Following Method E from 4-(2-(2-benzylpyrrolidin-1-yl)-6-((4-methoxybenzyl)oxy)pyridin-4-yl)morpholine (150 mg, 0.32 mmol). Purification by reverse phase preparative HPLC followed by SFC yielded the title compounds:

6-[(2S)-2-benzylpyrrolidin-1-yl]-4-morpholino-1H-pyridin-2-one; LCMS (ES+) 340 (M+H)+, RT 2.96 min (Analytical Method B); RT 5.78 min (Analytical Method SFC1, YMC CELLULOSE-SC, 45/55 IPA (0.1% DEA)/$CO_2$); $^1$H NMR (400 MHz, DMSO-$d_6$): δ 9.68 (1H, s), 7.32-7.29 (4H, m), 7.25-7.19 (1H, m), 5.15 (2H, s), 4.22-4.19 (1H, m), 3.71-3.67 (4H, m), 3.42-3.36 (1H, m), 3.21-3.14 (5H, m), 2.97 (1H, dd, J=3.5, 13.1 Hz), 2.56 (1H, dd, J=9.3, 13.2 Hz), 1.83-1.68 (4H, m).

6-[(2R)-2-benzylpyrrolidin-1-yl]-4-morpholino-1H-pyridin-2-one; LCMS (ES+) 340 (M+H)+, RT 2.97 min (Analytical Method B); RT 4.62 min (Analytical Method SFC1, YMC CELLULOSE-SC, 45/55 IPA (0.1% DEA)/$CO_2$); $^1$H NMR (400 MHz, DMSO-$d_6$): δ 9.68 (1H, s), 7.32-7.29 (4H, m), 7.25-7.19 (1H, m), 5.15 (2H, s), 4.22-4.19 (1H, m), 3.71-3.67 (4H, m), 3.42-3.36 (1H, m), 3.21-3.14 (5H, m), 2.97 (1H, dd, J=3.5, 13.1 Hz), 2.56 (1H, dd, J=9.3, 13.2 Hz), 1.83-1.68 (4H, m).

Example 2: (S)-6-(2-benzylpyrrolidin-1-yl)-4-morpholinopyridin-2(1H)-one

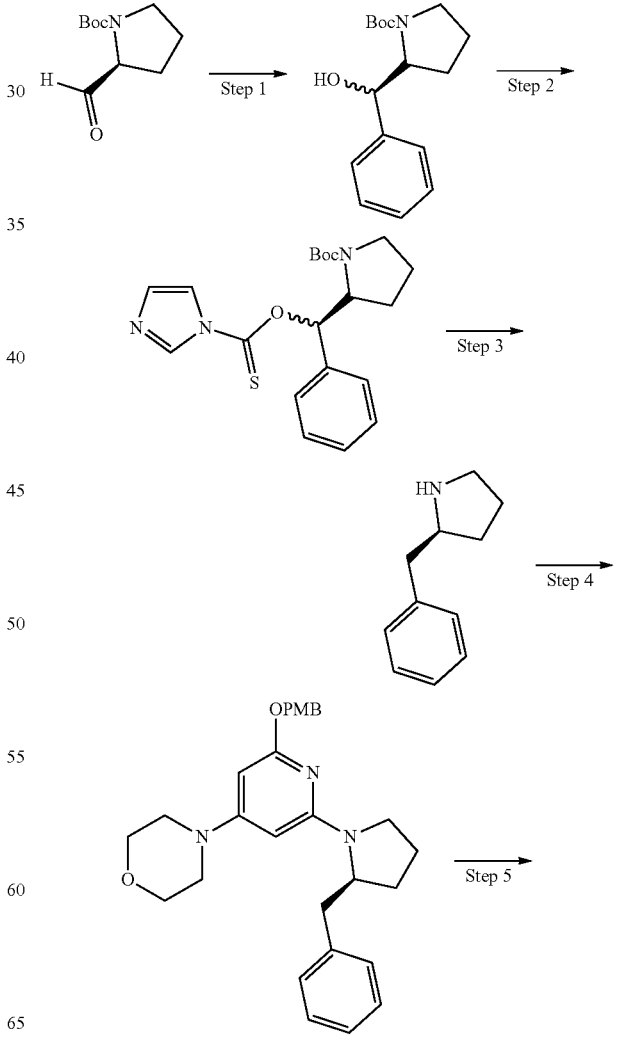

-continued

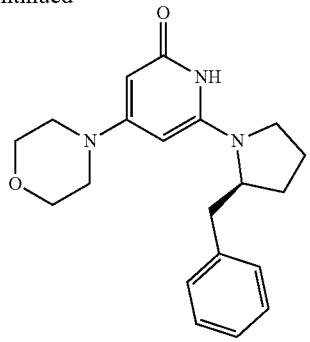

Step 1: tert-butyl (S)-2-(hydroxy(phenyl)methyl)pyrrolidine-1-carboxylate

Phenylmagnesium bromide (15 mL, 15 mmol, 1.0 M in THF) was added dropwise to a solution of tert-butyl (2S)-2-formylpyrrolidine-1-carboxylate (2.00 g, 10 mmol) in dry THF (20 mL) at −78° C. The reaction mixture was stirred at −78° C. for 2.5 h, before quenching with saturated aqueous NH$_4$Cl solution and diluted with water (10 mL). The mixture was extracted with EtOAc (×2), dried (MgSO$_4$), filtered and concentrated under reduced pressure. Purification by silica gel column chromatography (gradient elution, 0-25% EtOAc/iso-hexane) gave the title compound.

Step 2: tert-butyl (S)-2-(((1H-imidazole-1-carbonothioyl)oxy)(phenyl)methyl)pyrrolidine-1-carboxylate To a solution of tert-butyl (R)-2-(hydroxy(phenyl)methyl)pyrrolidine-1-carboxylate (242 mg, 0.87 mmol) in anhydrous THF (10 mL) was added DMAP (11 mg, 0.087 mmol) and diimidazole thiocarbonyl (233 mg, 1.31 mmol). The resultant solution was heated at reflux overnight. The solution was cooled to rt and the solvents removed in vacuo. The residue was dissolved in DCM, washed with water and the layers separated and dried (phase separator). The DCM was removed in vacuo and the resultant residue was purified by silica gel column chromatography (gradient 0-50% EtOAc/iso-hexane) to give the title compound.

Step 3: tert-butyl (S)-2-benzylpyrrolidine-1-carboxylate

To a solution of tert-butyl (R)-2-(((1H-imidazole-1-carbonothioyl)oxy)(phenyl)methyl)pyrrolidine-1-carboxylate (195 mg, 0.5 mmol) in anhydrous toluene (2 mL) was added tributyltin hydride (0.41 mL, 1.51 mmol) and AIBN (16 mg, 0.1 mmol). The solution was heated at reflux for 6 h and then cooled to r.t. The solvent was removed in vacuo and the residue purified by silica gel column chromatography (gradient 0-20% EtOAc/iso-hexane) to give the product.

Step 4: (S)-2-benzylpyrrolidine tert-Butyl (S)-2-benzylpyrrolidine-1-carboxylate (82 mg, 0.31 mmol) was dissolved in 4N HCl/dioxane (5 ml) and stirred at r.t. for 1 h. The solvent was removed in vacuo and the residue was purified by SCX chromatography (eluting with MeOH/DCM 1:1 and then collecting with 10% 7N NH$_3$ in MeOH/MeOH) to give the title compound.

Step 5: (S)-4-(2-(2-benzylpyrrolidin-1-yl)-6-((4-methoxybenzyl)oxy)pyridin-4-yl)morpholine Following Method C starting from (S)-2-benzylpyrrolidine (26 mg, 0.16 mmol) and 4-(2-chloro-6-((4-methoxybenzyl)oxy)pyridin-4-yl)morpholine (53 mg, 0.16 mmol, Scaffold 1). After heating at 105° C. for 115 h. The reaction mixture was cooled to r.t., filtered through celite and concentrated under reduced pressure. The crude mixture was purified by silica gel column chromatography (gradient elution, 0-20% EtOAc/iso-hexane) to give the title compound.

Step 6: (S)-6-(2-benzylpyrrolidin-1-yl)-4-morpholinopyridin-2(1H)-one

Following Method E starting from (S)-4-(2-(2-benzylpyrrolidin-1-yl)-6-((4-methoxybenzyl)oxy)pyridin-4-yl)morpholine (35 mg, 0.08 mmol). The crude material was purified by reverse phase preparative HPLC and freeze dried from MECN/H$_2$O to give the title compound. LCMS (ES+) 340 (M+H)$^+$, RT 2.74 min (Analytical Method A); RT 7.62 min (Analytical Method SFC1, YMC CELLULOSE-SC, 45/55 IPA (0.1% DEA)/CO$_2$); $^1$H NMR (400 MHz, DMSO-d$_6$): δ 9.68 (1H, s), 7.32-7.29 (4H, m), 7.25-7.19 (1H, m), 5.15 (2H, s), 4.22-4.19 (1H, m), 3.71-3.67 (4H, m), 3.42-3.36 (1H, m), 3.21-3.14 (5H, m), 2.97 (1H, dd, J=3.5, 13.1 Hz), 2.56 (1H, dd, J=9.3, 13.2 Hz), 1.83-1.68 (4H, m).

Example 3: (R)-6-(2-benzylazepan-1-yl)-4-morpholinopyridin-2(1H)-one

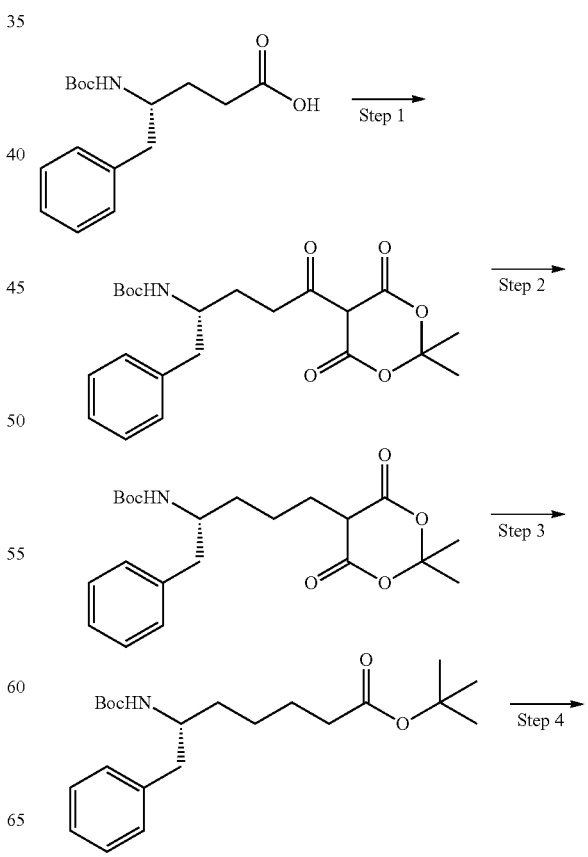

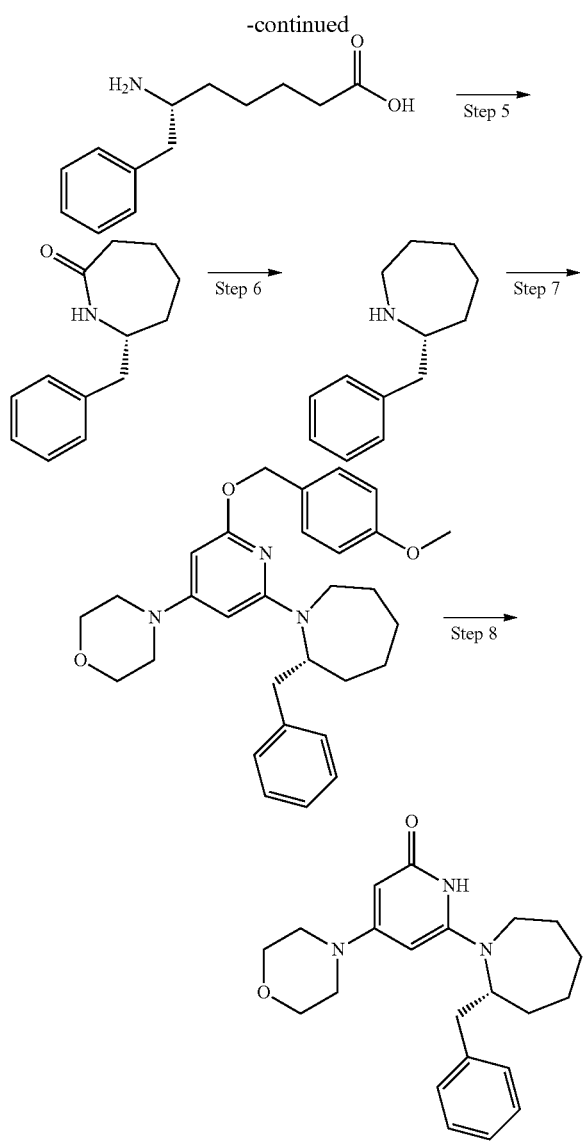

Step 1: tert-butyl(R)-(5-(2,2-dimethyl-4,6-dioxo-1,3-dioxan-5-yl)-5-oxo-1-phenylpentan-2-yl)carbamate (R)-4-((tert-Butoxycarbonyl)amino)-5-phenylpentanoic acid (3.0 g, 10.2 mmol) was dissolved in DCM (50 mL) and cooled to 0° C. Meldrum's acid (1.47 g, 10.2 mmol), EDC hydrochloride (2.94 g, 15.3 mmol) and DMAP (1.87 g, 15.3 mmol) were added sequentially to the reaction. The reaction mixture was stirred for 19 hours, removing the ice-bath after 1 hour. The reaction was transferred to a separating funnel and washed with 1 M potassium bisulfate aqueous solution. The organic extracts were dried (phase separator) and concentrated under reduced pressure to afford the title compound. Used without further purification in the next step.

Step 2: tert-butyl (R)-(5-(2,2-dimethyl-4,6-dioxo-1,3-dioxan-5-yl)-1-phenylpentan-2-yl)carbamate tert-Butyl (R)-(5-(2,2-dimethyl-4,6-dioxo-1,3-dioxan-5-yl)-5-oxo-1-phenylpentan-2-yl)carbamate (2.1 g, 5.01 mmol) was dissolved in DCM (50 mL) and cooled to 0° C. Acetic acid (3.16 mL, 55.1 mmol) was added followed by portionwise addition of NaBH$_4$ (759 mg, 20.05 mmol). The reaction was stirred at 0° C. for 3.5 h. The reaction mixture was cautiously quenched by dropwise addition of water (5 mL) followed by brine (~100 mL). The layers were separated and the aqueous layer extracted with DCM. The combined layers were washed with brine, dried (MgSO$_4$), filtered and concentrated under reduced pressure to afford the title compound. Used without further purification in the next step.

Step 3: tert-butyl (R)-6-((tert-butoxycarbonyl)amino)-7-phenylheptanoate tert-Butyl (R)-(5-(2,2-dimethyl-4,6-dioxo-1,3-dioxan-5-yl)-1-phenylpentan-2-yl)carbamate (1.86 g, 4.59 mmol) was dissolved in toluene (5 mL) and t-BuOH (5 mL). The reaction mixture was refluxed for 6 h. After this time the solvents were removed under reduced pressure. The resultant oil was dissolved in toluene and heated at reflux for 25 h. The reaction mixture was concentrated under reduced pressure. The oil was dissolved in DCM and NaHCO$_3$ (saturated aqueous solution) added. The layers were inseparable. A small quantity of brine was added to separate the layers. The aqueous layer was extracted with EtOAc. The combined organic layers were dried (phase separator) and concentrated under reduced pressure. The crude oil was purified by silica gel column chromatography (gradient elution 0-30% EtOAc/iso-hexane) to afford the title compound.

Step 4: (R)-6-amino-7-phenylheptanoic acid

TFA (2 mL) was added to tert-butyl (R)-6-((tert-butoxycarbonyl)amino)-7-phenylheptanoate (457 mg, 1.21 mmol) in DCM (2 mL) at r.t. with stirring. After 1.5 h the reaction mixture was concentrated under reduced pressure to afford a yellow oil. The oil was dissolved in 4M HCl in dioxane (10 mL) and stirred at r.t. for 4 h. The reaction mixture was concentrated under reduced pressure and dissolved in 4M HCl in dioxane (10 mL). After 6 h the reaction mixture was concentrated under reduced pressure and used without further purification in the next step.

Step 5: (R)-7-benzylazepan-2-one

EDC (348 mg, 1.82 mmol) and HOPO (201 mg, 1.82 mmol) were added to a solution of (R)-6-amino-7-phenylheptanoic acid (1.21 mmol) and triethylamine (1.01 mL, 7.26 mmol) in DMF (13 mL) at r.t. with stirring. After 54.5 h the reaction mixture was transferred to a separating funnel and diluted with DCM. The reaction mixture was washed sequentially with 1 M HCl (aq), NaHCO$_3$ (saturated aqueous solution) and brine. The organics were dried (MgSO$_4$), filtered and concentrated under reduced pressure. The residue was purified by silica gel column chromatography (gradient elution 50-70% EtOAc/iso-hexane) to afford the title compound.

Step 6: (R)-2-benzylazepane

Lithium aluminium hydride (0.59 mL, 0.59 mmol, 1 M solution in THF) was added dropwise to an ice-cooled solution of (R)-7-benzylazepan-2-one (60 mg, 0.30 mmol) in THF (2 mL). The reaction mixture was warmed to rt and heated at reflux for 3 h. The reaction mixture was cooled to r.t., followed by 0° C. and cautiously quenched with water. The THF was removed under reduced pressure. The mixture was diluted with water and EtOAc. The layers were separated and the organic extract dried (MgSO₄), filtered and concentrated under reduced pressure. The resultant oil was purified by SCX cartridge. The sample was loaded in DCM and eluted with 3 column volumes of DCM, 3 column volumes of methanol and 3 column volumes 7N NH₃ in MeOH/DCM (1:9). The basic fractions were combined and concentrated under reduced pressure to afford the title compound. Used without further purification in the next step.

Step 7: (R)-4-(2-(2-benzylazepan-1-yl)-6-((4-methoxybenzyl)oxy)pyridin-4-yl) morpholine Following Method D starting from 2-(R)-benzylazepane (64 mg, 0.19 mmol) and 4-(2-chloro-6-((4-methoxybenzyl)oxy)pyridin-4-yl)morpholine (40 mg, 0.21 mmol, Scaffold 1). The residue was purified by silica gel column chromatography (gradient elution 0-100% Et₂O/iso-hexane) to afford the title compound.

Step 8: (R)-6-(2-benzylazepan-1-yl)-4-morpholino-pyridin-2(1H)-one

Following Method E starting from (R)-4-(2-(2-benzylazepan-1-yl)-6-((4-methoxybenzyl)oxy)pyridin-4-yl)morpholine (31 mg, 0.064 mmol). The reaction was filtered through Celite and washed through with MeOH. The solvent was removed in vacuo and the residue purified by silica gel column chromatography (gradient elution 0-20% MeOH/EtOAc) to afford the title compound. LCMS (ES+) 368 (M+H)+, RT 2.91 min (Analytical Method A); RT 2.02 min (85.8% ee) (Analytical Method SFC1, YMC AMYLOSE-C, 35/65 IPA+0.1% DEAISO/CO₂); ¹H NMR (400 MHz, CDCl₃): δ 7.31-7.21 (3H, m), 7.16-7.12 (2H, m), 5.17 (1H, d, J=2.0 Hz), 4.89 (1H, d, J=2.0 Hz), 3.80-3.75 (6H, m), 3.40-3.35 (1H, m), 3.22-3.18 (4H, m), 2.99 (1H, dd, J=11.7, 16.0 Hz), 2.87-2.76 (2H, m), 2.15-2.05 (1H, m), 1.84-1.70 (2H, m), 1.57-1.45 (2H, m), 1.31-1.13 (2H, m).

Chiral Compounds: For all subsequent chiral compounds where the enantiomers were separated by Chiral SFC purification, the stereochemical assignments were made based on the biological activity of each enantiomer in the biochemical assay: all R enantiomers were assigned as the bioactive conformation based on the biological activity results obtained by the chirally pure synthesized (R)-6-(2-benzylazepan-1-yl)-4-morpholinopyridin-2(1H)-one (Example 3) and the lack of biological activity shown by (S)-6-(2-benzylpyrrolidin-1-yl)-4-morpholinopyridin-2(1H)-one (Example 2).

Example 3: (R)-6-(2-benzylazepan-1-yl)-4-morpholinopyridin-2(1H)-one and Example 4: (S)-6-(2-benzylazepan-1-yl)-4-morpholinopyridin-2(1H)-one

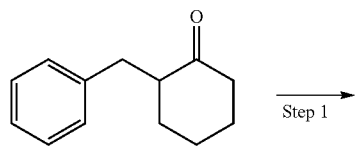

Step 1: 7-benzylazepan-2-one

Sodium azide (1.05 g, 16.17 mmol) was added to a solution of 2-benzylcyclohexan-1-one (2.9 g, 15.4 mmol) in methanesulfonic acid (12 mL), maintaining the reaction temperature below 25° C. After 2 hours the reaction was diluted with water (100 mL) to give a white solid suspension. The solid was collected by filtration, washing with water and air dried overnight to give the title compound.

A reference sample of chiral material from Example 3, step 5 was used to compare with the racemate and allow for

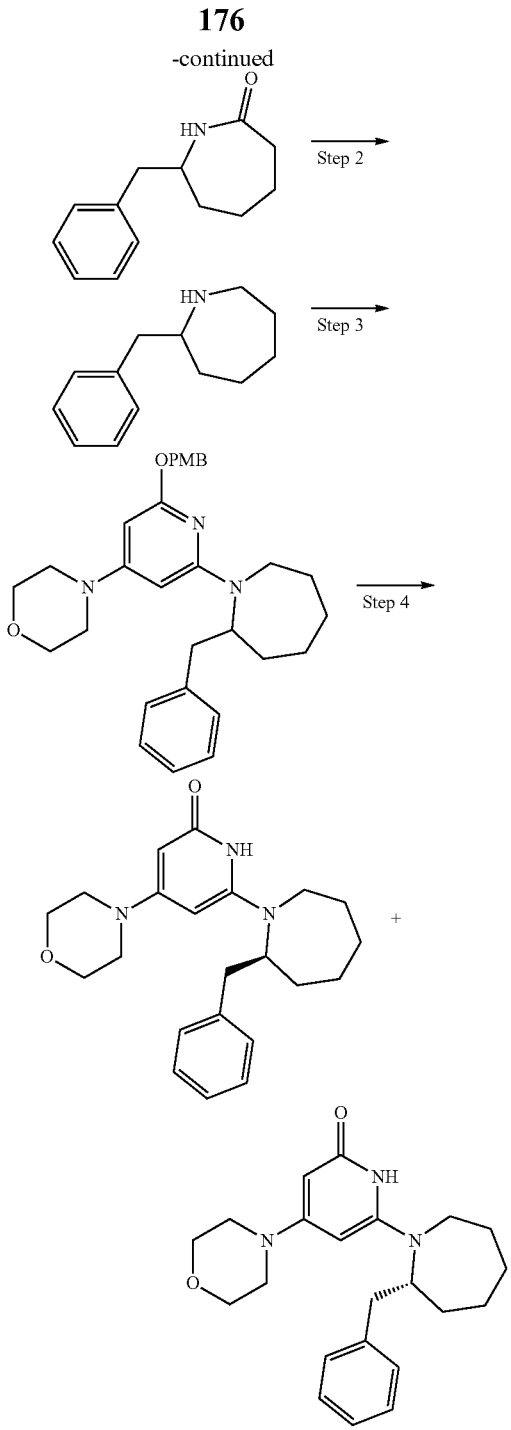

chiral separation of the enantiomers by SFC and subsequently to provide enantiomerically pure 2-(R)-benzyl azepane.

Step 2: 2-benzylazepane

Lithium aluminium hydride (23.2 mL, 23.2 mmol, 1 M in THF) was added dropwise to a solution of 7-benzylazepan-2-one (2.36 g, 11.61 mmol) in anhydrous THF (85 mL) at 0° C. After complete addition the reaction was allowed to warm to r.t. The reaction was heated at reflux for 2 h and then cooled to r.t. The reaction was cooled to 0° C. and quenched by dropwise addition of water (care!). After effervescence had subsided, the THF was removed in vacuo. The mixture was dissolved in EtOAc/water and the layers separated. The organic layer was dried (MgSO$_4$) and the solvent removed in vacuo. The residue was purified by silica gel column chromatography (gradient 0-10% 7N ammonia in methanol/DCM) to give the title compound.

Step 3: 4-(3-(2-benzylazepan-1-yl)-5-((4-methoxybenzyl)oxy)phenyl)morpholine A flask containing 4-(2-chloro-6-((4-methoxybenzyl)oxy)pyridin-4-yl)morpholine (2.67 g, 7.97 mmol, Scaffold 1), 2-benzylazepane (1.48 g, 7.82 mmol), NaOtBu (834 mg, 8.68 mmol), RuPhos (192 mg, 0.41 mmol) and RuPhos Pd G3 (330 mg, 0.39 mmol) in dioxane (50 mL) was evacuated and backfilled three times with N$_2$. The mixture was stirred at 85° C. for 20 h. After cooling to rt, the mixture was filtered through Celite, washing with MeOH. The filtrate was concentrated and purified by silica gel column chromatography (gradient elution, 0-50% EtOAc/iso-hexane) to give the title compound.

Step 4: (R)-6-(2-benzylazepan-1-yl)-4-morpholinopyridin-2(1H)-one and (S)-6-(2-benzylazepan-1-yl)-4-morpholinopyridin-2(1H)-one Following Method E from 4-(3-(2-benzylazepan-1-yl)-5-((4-methoxybenzyl)oxy)phenyl)morpholine (200 mg, 0.41 mmol). The reaction was filtered through Celite and washed through with MeOH. The solvent was removed in vacuo and the residue purified by reverse phase preparative HPLC. The resulting sample was further purified by SFC to afford the title compounds.

(R)-6-(2-benzylazepan-1-yl)-4-morpholinopyridin-2(1H)-one. LCMS (ES+) 368 (M+H)$^+$, RT 2.86 min (Analytical Method A); RT 2.88 min (Analytical Method SFC1, YMC AMYLOSE-C, 35/65 IPA+0.1% DEA/CO$_2$); $^1$H NMR (400 MHz, CDCl$_3$): δ 7.32-7.21 (3H, m), 7.16-7.11 (2H, m), 5.17 (1H, d, J=2.0 Hz), 4.89 (1H, d, J=1.9 Hz), 3.81-3.75 (5H, m), 3.41-3.33 (1H, m), 3.20 (4H, t, 5.0 Hz), 2.99 (1H, dd, J=12.2, 15.9 Hz), 2.86-2.76 (2H, m), 2.14-2.05 (1H, m), 1.87-1.67 (3H, m), 1.60-1.45 (2H, m), 1.31-1.12 (3H, m).

(S)-6-(2-benzylazepan-1-yl)-4-morpholinopyridin-2(1H)-one. LCMS (ES+) 368 (M+H)$^+$, RT 2.86 min (Analytical Method A); RT 2.06 min (Analytical Method SFC1, YMC AMYLOSE-C, 35/65 IPA+0.1% DEAISO)/CO$_2$) $^1$H NMR (400 MHz, CDCl$_3$): δ 7.32-7.21 (3H, m), 7.16-7.11 (2H, m), 5.17 (1H, d, J=2.0 Hz), 4.89 (1H, d, J=1.9 Hz), 3.81-3.75 (5H, m), 3.41-3.33 (1H, m), 3.20 (4H, t, 5.0 Hz), 2.99 (1H, dd, J=12.2, 15.9 Hz), 2.86-2.76 (2H, m), 2.14-2.05 (1H, m), 1.87-1.67 (3H, m), 1.60-1.45 (2H, m), 1.31-1.12 (3H, m).

Example 5: (S)-7-benzyl-1-(4-morpholino-6-oxo-1,6-dihydropyridin-2-yl)azepan-2-one and Example 6: (R)-7-benzyl-1-(4-morpholino-6-oxo-1,6-dihydropyridin-2-yl)azepan-2-one

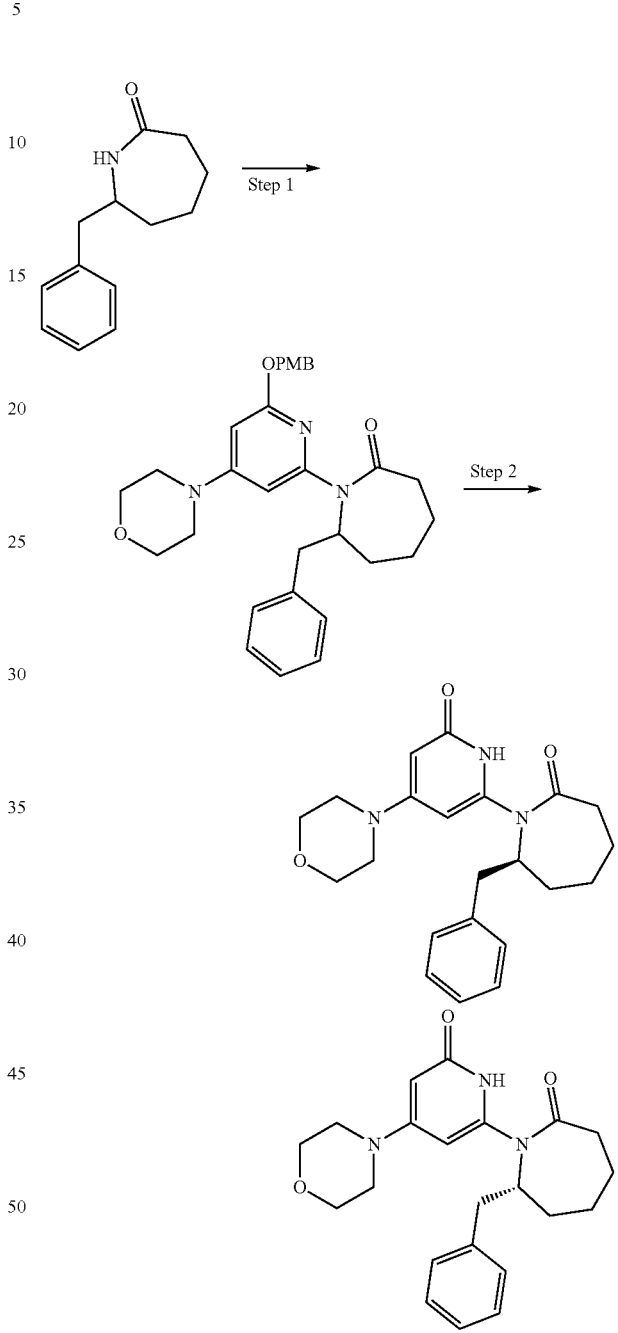

Step 1: 7-benzyl-1-(6-((4-methoxybenzyl)oxy)-4-morpholinopyridin-2-yl)azepan-2-one A suspension of 4-(2-chloro-6-((4-methoxybenzyl)oxy)pyridin-4-yl)morpholine (163 mg, 0.49 mmol, Scaffold 1), 7-benzylazepan-2-one (100 mg, 0.49 mmol, Example 3, step 1), Cs$_2$CO$_3$ (0.98 mmol) in dry 1,4-dioxane (3.3 mL) was purged with N$_2$ for 15 minutes. Pd(OAc)$_2$ (0.024 mmol) and 2,2'-bis(diphenylphosphino)-1,1'-binaphthyl (0.10 mmol) were then added, the reaction tube was sealed under N$_2$ and stirred at 100° C. for 16 h. After cooling to r.t., the mixture was filtered through Celite, washing thoroughly with CH₂Cl₂. The filtrate was concentrated and the residue purified by silica gel column chromatography (gradient elution, 0-100% EtOAc/iso-hexane) to afford the impure title compound.

Step 2: (S)-7-benzyl-1-(4-morpholino-6-oxo-1,6-dihydropyridin-2-yl)azepan-2-one and (R)-7-benzyl-1-(4-morpholino-6-oxo-1,6-dihydropyridin-2-yl)azepan-2-one Following Method E starting from 7-benzyl-1-(6-((4-methoxybenzyl)oxy)-4-morpholinopyridin-2-yl)azepan-2-one (168 mg, <0.33 mmol). Purification by reverse phase preparative HPLC followed by SFC and the enantiomers were freeze dried from MECN/H₂O to afford the title compounds.

(S)-7-benzyl-1-(4-morpholino-6-oxo-1,6-dihydropyridin-2-yl)azepan-2-one. LCMS (ES+) 382 (M+H)⁺, RT 2.82 min (Analytical Method B), RT 2.11 min (Analytical Method SFC1, YMC CELLULOSE-C+0.1% DEAISO 30% MeOH SOL3); ¹H NMR (400 MHz, CDCl₃): δ 9.89 (1H, br s), 7.32 (2H, dd, J=7.3, 7.3 Hz), 7.27-7.21 (1H, m), 7.18-7.14 (2H, m), 5.49 (1H, d, J=2.3 Hz), 5.11 (1H, d, J=1.8 Hz), 4.00-3.92 (1H, m), 3.73-3.69 (4H, m), 3.29 (1H, dd, J=8.8, 13.9 Hz), 3.08-3.03 (4H, m), 2.90-2.79 (3H, m), 2.06-1.89 (4H, m), 1.87-1.78 (2H, m).

(R)-7-benzyl-1-(4-morpholino-6-oxo-1,6-dihydropyridin-2-yl)azepan-2-one. LCMS (ES+) 382 (M+H)⁺, RT 2.82 min (Analytical Method B), RT 1.56 min (Analytical Method SFC1, YMC CELLULOSE-C+0.1% DEAISO 30% MeOH SOL3); ¹H NMR (400 MHz, CDCl₃): δ 9.74 (1H, br s), 7.35-7.29 (2H, m), 7.26-7.22 (1H, m), 7.18-7.14 (2H, m), 5.49 (1H, d, J=2.3 Hz), 5.12 (1H, d, J=1.8 Hz), 4.00-3.93 (1H, m), 3.73-3.69 (4H, m), 3.29 (1H, dd, J=9.0, 13.8 Hz), 3.05 (4H, dd, J=3.8, 5.8 Hz), 2.90-2.79 (3H, m), 2.04-1.90 (4H, m), 1.85-1.78 (2H, m).

The following examples were prepared using a procedure analogous to that described for Example 1 starting from the commercial amine and Scaffold 1 or Scaffold 2 as appropriate. Buchwald conditions Method C or Method D were used to couple the amine. The isomers were isolated after purification by Chiral SFC unless otherwise stated (*), in these cases the amine was purchased chirally pure.

| Example | Structure and Name | Amine | Buchwald conditions | Analytical data |
|---|---|---|---|---|
| Example 7 | 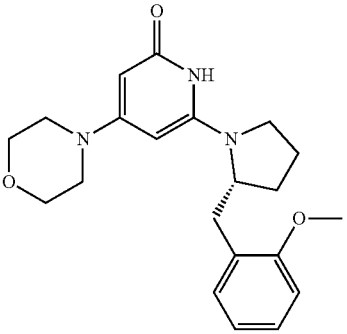 [SMILES: COc1ccccc1C[C@H]1CCCN1c1cc(N2CCOCC2)cc(=O)[nH]1]<br>(R)-6-(2-(2-methoxybenzyl)pyrrolidin-1-yl)-4-morpholinopyridin-2(1H)-one | 2-(2-methoxybenzyl)pyrrolidine | Method D | LCMS (ES+) 370 (M + H)⁺, RT 2.86 min (Analytical Method A), RT 2.45 min (Analytical Method SFC1, YMC CELLULOSE-C 30/70 IPA (0.1% DEA)/CO₂); ¹H NMR (400 MHz, CDCl₃): δ 8.99 (1H, s), 7.29 (1H, dd, J = 1.5, 7.9 Hz), 7.08 (1H, dd, J = 1.7, 7.3 Hz), 6.98 (1H, d, J = 7.9 Hz), 6.92 (1H, dd, J = 7.3, 7.3 Hz), 5.23 (1H, d, J = 2.1 Hz), 4.81 (1H, d, J = 2.3 Hz), 4.22 (3H, s), 3.91 (1H, dd, J = 7.4, 10.8 Hz), 3.81-3.77 (4H, m), 3.42 (1H, t, J = 8.3 Hz), 3.28-3.15 (6H, m), 2.27 (1H, dd, J = 11.2, 13.3 Hz), 2.21-2.02 (2H, m), 1.93-1.75 (2H, m). |
| Example 8 | 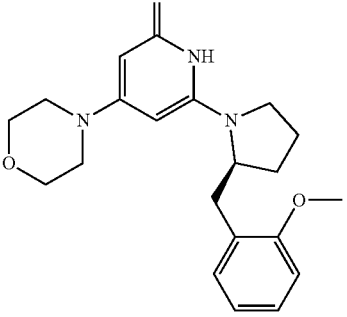<br>(S)-6-(2-(2-methoxybenzyl)pyrrolidin-1-yl)-4-morpholinopyridin-2(1H)-one | 2-(2-methoxybenzyl)pyrrolidine | Method D | LCMS (ES+) 370 (M + H)⁺, RT 2.87 min (Analytical Method A), RT 3.57 min (Analytical Method SFC1, YMC CELLULOSE-C 30/70 IPA (0.1% DEA)/CO₂); ¹H NMR (400 MHz, CDCl₃): δ 8.99 (1H, s), 7.29 (1H, dd, J = 1.5, 7.9 Hz), 7.08 (1H, dd, J = 1.7, 7.3 Hz), 6.98 (1H, d, J = 7.9 Hz), 6.92 (1H, dd, J = 7.3, 7.3 Hz), 5.23 (1H, d, J = 2.1 Hz), 4.81 (1H, d, J = 2.3 Hz), 4.22 (3H, s), 3.91 (1H, dd, J = 7.4, 10.8 Hz), 3.81-3.77 (4H, m), 3.42 (1H, t, J = 8.3 Hz), 3.28-3.15 (6H, m), 2.27 (1H, dd, J = 11.2, 13.3 Hz), 2.21-2.02 (2H, m), 1.93-1.75 (2H, m). |

| Example | Structure and Name | Amine | Buchwald conditions | Analytical data |
|---|---|---|---|---|
| Example 9 | 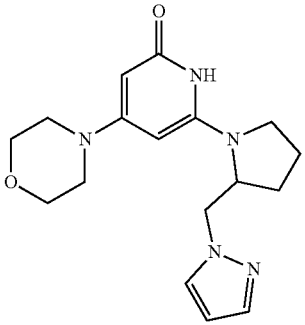<br>6-(2-((1H-pyrazol-1-yl)methyl)pyrrolidin-1-yl)-4-morpholinopyridin-2(1H)-one | 1-(pyrrolidin-2-ylmethyl)-1H-pyrazole | Method C | LCMS (ES+) 330 (M + H)+, RT 2.54 min (Analytical Method A); $^1$H NMR (400 MHz, CDCl$_3$): δ 7.53 (1H, d, J = 1.7 Hz), 7.40 (1H, d, J = 2.3 Hz), 6.23 (1H, t, J = 2.1 Hz), 5.23 (1H, d, J = 2.0 Hz), 4.98 (1H, d, J = 2.1 Hz), 4.42-4.38 (1H, m), 4.31 (1H, dd, J = 4.1, 13.6 Hz), 4.12 (1H, dd, J = 6.6, 14.0 Hz), 3.79 (4H, t, J = 4.9 Hz), 3.53-3.48 (1H, m), 3.31-3.24 (5H, m), 2.02-1.93 (3H, m), 1.78-1.63 (1H, m). NH not observed. |
| Example 10 | 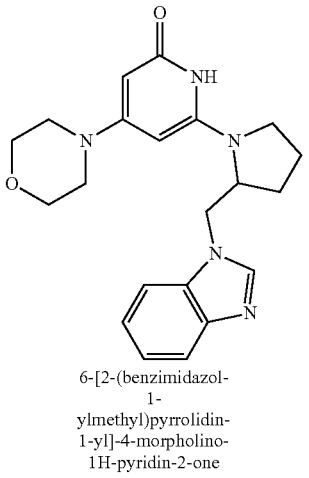<br>6-[2-(benzimidazol-1-ylmethyl)pyrrolidin-1-yl]-4-morpholino-1H-pyridin-2-one | 1-(pyrrolidin-2-ylmethyl)-1H-benzo[d]imidazole | Method C | LCMS (ES+) 380 (M + H)+, RT 2.38 min (Analytical Method A); $^1$H NMR (400 MHz, CDCl$_3$): δ 8.10 (1H, s), 7.80-7.77 (1H, m), 7.40-7.36 (1H, m), 7.30-7.27 (1H, m), 7.27-7.26 (2H, m), 5.27 (1H, d, J = 2.0 Hz), 4.79-4.75 (2H, m), 4.40 (1H, m), 4.30 (1H, dd, J = 4.6, 14.7 Hz), 4.30 (1H, dd, J = 6.0, 14.7 Hz), 3.77-3.73 (4H, m), 3.43 (1H, dt, J = 2.4, 9.0 Hz), 3.30-3.17 (1H, m), 3.17-3.11 (4H, m), 2.09-1.98 (1H, m), 1.94-1.81 (2H, m), 1.58-1.45 (1H, m). |
| Example 11 | 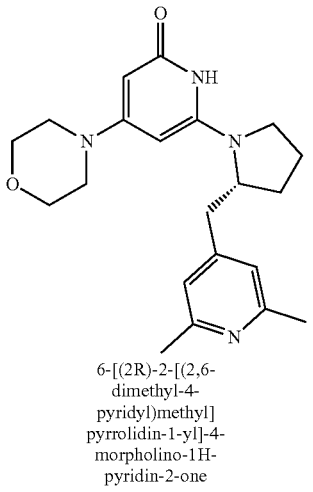<br>6-[(2R)-2-[(2,6-dimethyl-4-pyridyl)methyl]pyrrolidin-1-yl]-4-morpholino-1H-pyridin-2-one | 2,6-dimethyl-4-(pyrrolidin-2-ylmethyl)pyridine | Method C | LCMS (ES+) 369 (M + H)+, RT 2.17 min (Analytical Method A); RT 3.51 min (Analytical Method SFC1, YMC AMYLOSE-C, 30/70 MeOH + 0.1% DEAISO/CO2): $^1$H NMR (400 MHz, CDCl3): δ 6.83 (2H, s), 5.23 (1H, d, J = 2.0 Hz), 4.87 (1H, d, J = 2.0 Hz), 4.33-4.29 (1H, m), 3.81-3.77 (4H, m), 3.53-3.46 (1H, m), 3.36-3.28 (1H, m), 3.27-3.22 (4H, m), 2.98 (1H, dd, J = 3.7, 13.5 Hz), 2.53-2.46 (7H, m), 1.98-1.76 (4H, m). NH not observed. |

| Example | Structure and Name | Amine | Buchwald conditions | Analytical data |
|---|---|---|---|---|
| Example 12 | 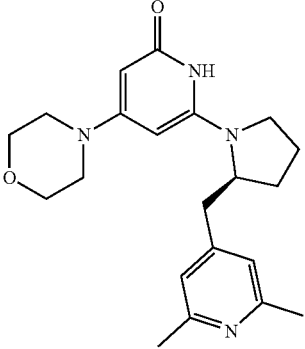 [SMILES: Cc1cc(C[C@@H]2CCCN2c2cc(N3CCOCC3)cc(=O)[nH]2)cc(C)n1]<br>(6-[(2S)-2-[(2,6-dimethyl-4-pyridyl)methyl]pyrrolidin-1-yl]-4-morpholino-1H-pyridin-2-one | 2,6-dimethyl-4-(pyrrolidin-2-ylmethyl)pyridine | Method C | LCMS (ES+) 369 (M + H)+, RT 2.17 min (Analytical Method A); RT 2.01 min (Analytical Method SFC1, YMC AMYLOSE-C, 30/70 MeOH + 0.1% DEAISO/CO$_2$); $^1$H NMR (400 MHz, CDCl$_3$): δ 6.83 (2H, s), 5.23 (1H, d, J = 2.0 Hz), 4.87 (1H, d, J = 2.0 Hz), 4.33-4.29 (1H, m), 3.81-3.77 (4H, m), 3.53-3.46 (1H, m), 3.36-3.28 (1H, m), 3.27-3.22 (4H, m), 2.98 (1H, dd, J = 3.7, 13.5 Hz), 2.53-2.46 (7H, m), 1.98-1.76 (4H, m). NH not observed. |
| Example 13 | 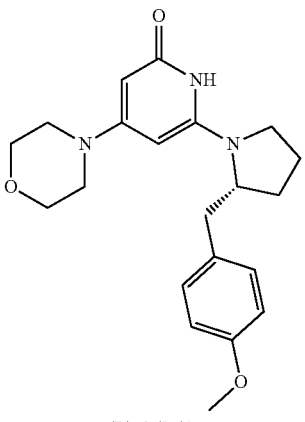<br>(R)-6-(2-(4-methoxybenzyl)pyrrolidin-1-yl)-4-morpholino pyridin-2(1H)-one | 2-(4-methoxybenzyl)pyrrolidine | Method C | LCMS (ES+) 370 (M + H)+, RT 2.72 min (Analytical Method A); RT 1.48 min (Analytical Method SFC4, YMC AMYLOSE-C + 0.1% DEAISO 50% IPA SOL4); $^1$H NMR (400 MHz, CDCl3): δ 7.08-7.05 (2H, m), 6.85-6.82 (2H, m), 5.21 (1H, d, J = 2.0 Hz), 4.87 (1H, d, J = 2.3 Hz), 4.03-3.96 (1H, m), 3.79 (7H, m), 3.38 (1H, dt, J = 2.2, 8.6 Hz), 3.27-3.23 (5H, m), 2.88 (1H, dd, J = 3.8, 13.9 Hz), 2.68 (1H, dd, J = 8.1, 13.9 Hz), 1.94-1.89 (3H, m), 1.83-1.75 (1H, m). NH not observed. |
| Example 14 | 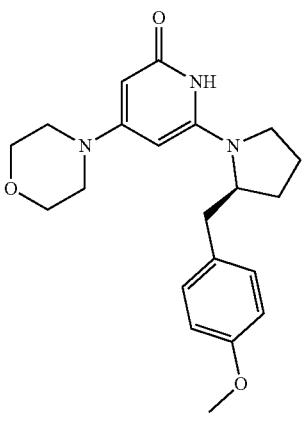 [SMILES: COc1ccc(C[C@@H]2CCCN2c2cc(N3CCOCC3)cc(=O)[nH]2)cc1]<br>(S)-6-(2-(4-methoxybenzyl)pyrrolidin-1-yl)-4-morpholino pyridin-2(1H)-one | 2-(4-methoxybenzyl)pyrrolidine | Method C | LCMS (ES+) 370 (M + H)+, RT 2.72 min (Analytical Method A); RT 1.01 min (Analytical method SFC4, YMC AMYLOSE-C + 0.1% DEAISO 50% IPA SOL4); $^1$H NMR (400 MHz, CDCl$_3$): δ 7.08-7.04 (2H, m), 6.85-6.82 (2H, m), 5.21 (1H, d, J = 2.0 Hz), 4.87 (1H, d, J = 2.0 Hz), 4.00-3.97 (1H, m), 3.80-3.77 (7H, m), 3.37 (1H, dt, J = 2.0, 8.7 Hz), 3.27-3.22 (5H, m), 2.87 (1H, dd, J = 3.8, 13.9 Hz), 2.68 (1H, dd, J = 8.1, 13.9 Hz), 1.95-1.89 (3H, m), 1.83-1.74 (1H, m). NH not observed. |

-continued

| Example | Structure and Name | Amine | Buchwald conditions | Analytical data |
|---|---|---|---|---|
| Example 15 | 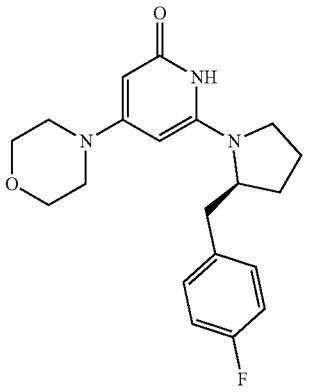 [SMILES: O=c1cc(N2CCOCC2)cc(N2CCC[C@H]2Cc2ccc(F)cc2)[nH]1]<br>(S)-6-(2-(4-fluorobenzyl)pyrrolidin-1-yl)-4-morpholino pyridin-2(1H)-one | 2-(4-fluorobenzyl)pyrrolidine | Method C | LCMS (ES+) 358 (M + H)$^+$, RT 2.76 min (Analytical Method A); RT 1.70 min (Analytical Method SFC4, YMC AMYLOSE-C + 0.1% DEAISO 35% IPA SOL4); $^1$H NMR (400 MHz, CDCl$_3$): δ 7.15-7.10(2H, m), 7.00-6.95 (2H, m), 5.21 (1H, d, J = 2.3 Hz), 4.86 (1H, d, J = 2.0 Hz), 4.16-4.11 (1H, m), 3.81-3.77 (4H, m), 3.41 (1H, dt, J = 2.4, 8.7 Hz), 3.29-3.22 (5H, m), 2.93 (1H, dd, J = 3.9, 13.8 Hz), 2.69 (1H, dd, J = 8.1, 13.9 Hz), 1.91-1.82 (4H, m). NH not observed. |
| Example 16 | 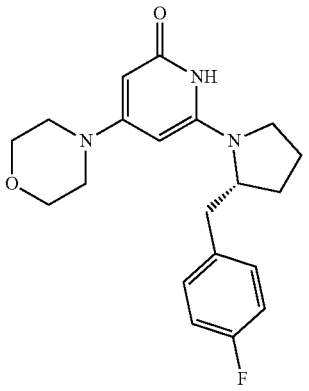 [SMILES: O=c1cc(N2CCOCC2)cc(N2CCC[C@@H]2Cc2ccc(F)cc2)[nH]1]<br>(R)-6-(2-(4-fluorobenzyl)pyrrolidin-1-yl)-4-morpholino pyridin-2(1H)-one | 2-(4-fluorobenzyl)pyrrolidine | Method C | LCMS (ES+) 358 (M + H)$^+$, RT 2.76 min (Analytical Method A); RT 2.24 min (Analytical Method SFC4, YMC AMYLOSE-C + 0.1% DEAISO 35% IPA SOL4); $^1$H NMR (400 MHz, CDCl$_3$): δ 7.15-7.10 (2H, m), 7.00-6.94 (2H, m), 5.21 (1H, d, J = 2.3 Hz), 4.86 (1H, d, J = 2.0 Hz), 4.18-4.13 (1H, m), 3.82-3.77 (4H, m), 3.42 (1H, dt, J = 2.4, 8.5 Hz), 3.30-3.22 (5H, m), 2.93 (1H, dd, J = 3.7, 13.8 Hz), 2.69 (1H, dd, J = 8.2, 13.8 Hz), 1.92-1.75 (4H, m). NH not observed. |
| Example 17 | 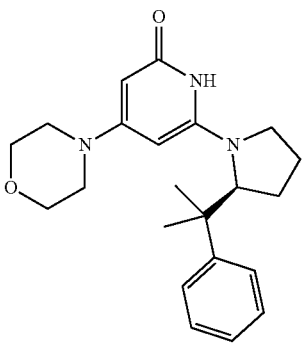 [SMILES: CC(C)(c1ccccc1)[C@@H]1CCCN1c1cc(N2CCOCC2)cc(=O)[nH]1]<br>(S)-4-morpholino-6-(2-(2-phenylpropan-2-yl)pyrrolidin-1-yl)pyridin-2(1H)-one | 2-(2-phenyl propan-2-yl)pyrrolidine | Method D | LCMS (ES+) 368 (M + H)$^+$, RT 2.93 min (Analytical Method A); RT 2.12 min (Analytical Method SFC4, YMC AMYLOSE-C + 0.1% DEAISO 25% MeOH SOL3); $^1$H NMR (400 MHz, CDCl$_3$): δ 7.40-7.36 (2H, m), 7.32-7.27 (2H, m), 7.24-7.20 (1H, m), 5.22 (1H, d, J = 2.0 Hz), 4.94 (1H, d, J = 2.0 Hz), 4.21 (1H, dd, J = 5.1, 5.1 Hz), 3.82-3.77 (4H, m), 3.30-3.19 (6H, m), 1.81 (2H, dd, J = 5.4, 9.5 Hz), 1.68-1.59 (1H, m), 1.39 (6H, s), 1.15-1.02 (1H, m). NH not observed. |

| Example | Structure and Name | Amine | Buchwald conditions | Analytical data |
|---|---|---|---|---|
| Example 18 | 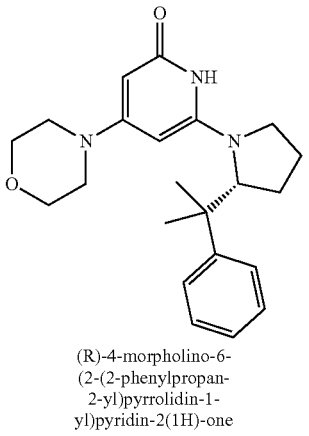<br>(R)-4-morpholino-6-(2-(2-phenylpropan-2-yl)pyrrolidin-1-yl)pyridin-2(1H)-one | 2-(2-phenyl propan-2-yl)pyrrolidine | Method D | LCMS (ES+) 368 (M + H)+, RT 2.92 min (Analytical Method A); RT 1.60 min (Analytical Method SFC4, YMC AMYLOSE-C + 0.1% DEAISO 25% MeOH SOL3); $^1$H NMR (400 MHz, CDCl3): δ 7.40-7.36 (2H, m), 7.32-7.27 (2H, m), 7.25-7.20 (1H, m), 5.22 (1H, d, J = 2.0 Hz), 4.94 (1H, d, J = 2.3 Hz), 4.19 (1H, dd, J = 5.1, 5.1 Hz), 3.82-3.77 (4H, m), 3.29-3.19 (6H, m), 1.86-1.79 (2H, m), 1.66-1.66 (1H, m), 1.39 (6H, s), 1.15-1.02 (1H, m). NH not observed. |
| Example 19 | 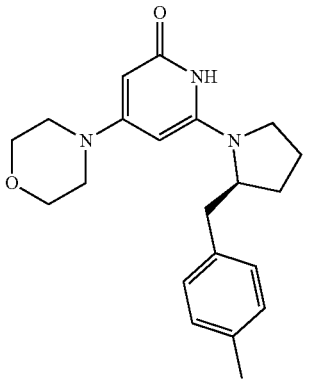<br>(S)-6-(2-(4-methylbenzyl)pyrrolidin-1-yl)-4-morpholinopyridin-2(1H)-one | 2-(4-methylbenzyl)pyrrolidine | Method C | LCMS (ES+) 354 (M + H)$^+$, RT 2.84 min (Analytical Method A); RT 3.64 min (Analytical Method SFC4, YMC AMYLOSE-C + 0.1% DEAISO 25% IPA SOL4); $^1$H NMR (400 MHz, CDCl$_3$): δ 7.11 (2H, d, J = 7.8 Hz), 7.06-7.02 (2H, m), 5.21 (1H, d, J = 2.0 Hz), 4.88 (1H, d, J = 2.0 Hz), 4.04-3.99 (1H, m), 3.81-3.77 (4H, m), 3.45-3.40 (1H, m), 3.27-3.22 (5H, m), 2.92 (1H, dd, J = 3.5, 13.6 Hz), 2.65 (1H, dd, J = 8.6, 13.9 Hz), 2.33 (3H, s), 1.96-1.78 (4H, m). NH not observed |
| Example 20 | 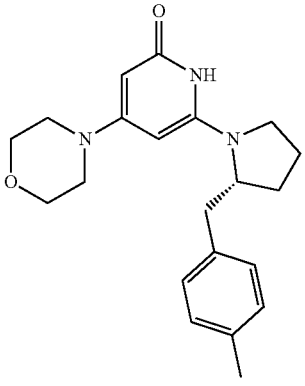<br>(R)-6-(2-(4-methylbenzyl)pyrrolidin-1-yl)-4-morpholinopyridin-2(1H)-one | 2-(4-methylbenzyl)pyrrolidine | Method C | LCMS (ES+) 354 (M + H)$^+$, RT 2.84 min (Analytical Method A); RT 4.33 min (Analytical Method SFC1, YMC AMYLOSE-C + 0.1% DEAISO 25% IPA SOL4); $^1$H NMR (400 MHz, CDCl$_3$): δ 7.11 (2H, d, J = 7.6 Hz), 7.06-7.02 (2H, m), 5.21 (1H, d, J = 2.3 Hz), 4.88 (1H, d, J = 2.0 Hz), 4.04-3.97 (1H, m), 3.81-3.77 (4H, m), 3.44-3.37 (1H, m), 3.27-3.22 (5H, m), 2.92 (1H, dd, J = 3.5, 13.9 Hz), 2.66 (1H, dd, J = 8.5, 13.8 Hz), 2.33 (3H, s), 1.94-1.89 (4H, m). NH not observed. |

| Example | Structure and Name | Amine | Buchwald conditions | Analytical data |
|---|---|---|---|---|
| Example 21 | 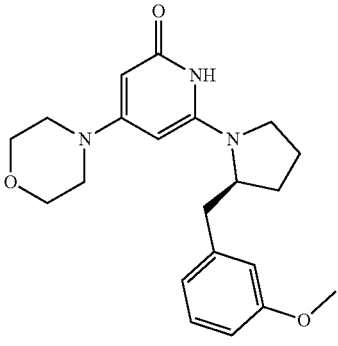 [SMILES: COc1cccc(C[C@@H]2CCCN2c2cc(N3CCOCC3)cc(=O)[nH]2)c1]<br>(S)-6-(2-(3-methoxybenzyl)pyrrolidin-1-yl)-4-morpholinopyridin-2(1H)-one | 2-(3-methoxybenzyl)pyrrolidine | Method C | LCMS (ES+) 370 (M + H)$^+$, RT 2.73 min (Analytical Method A); RT 1.86 min (Analytical Method SFC1, YMC AMYLOSE-C, 40/60 IPA + 0.1% DEAISO/CO$_2$); $^1$H NMR (400 MHz, CDCl$_3$): δ 7.21 (1H, dd, J = 7.8, 7.8 Hz), 6.79-6.73 (3H, m), 5.21 (1H, d, J = 1.4 Hz), 4.88 (1H, d, J = 1.5 Hz), 4.12-4.09 (1H, m), 3.82-3.77 (7H, m), 3.52-3.45 (1H, m), 3.30 (1H, d, J = 7.3 Hz), 3.28-3.21 (4H, m), 2.97 (1H, dd, J = 3.7, 13.8 Hz), 2.64 (1H, dd, J = 8.6, 13.6 Hz), 1.94-1.86 (4H, m), NH not observed. |
| Example 22 | 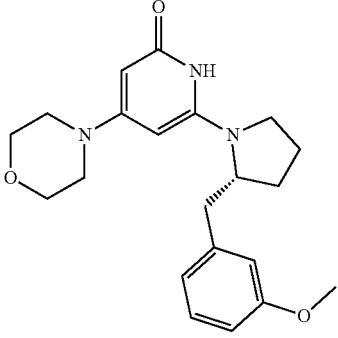 [SMILES: COc1cccc(C[C@H]2CCCN2c2cc(N3CCOCC3)cc(=O)[nH]2)c1]<br>(R)-6-(2-(3-methoxybenzyl)pyrrolidin-1-yl)-4-morpholinopyridin-2(1H)-one | 2-(3-methoxybenzyl)pyrrolidine | Method C | LCMS (ES+) 370 (M + H)$^+$, RT 2.73 min (Analytical Method A); RT 2.99 min (Analytical Method SFC1, YMC AMYLOSE-C, 40/60 IPA + 0.1% DEAISO/CO$_2$); $^1$H NMR (400 MHz, CDCl$_3$): δ 7.21 (1H, dd, J = 7.7, 7.7 Hz), 6.79-6.74 (3H, m), 5.22 (1H, d, J = 1.8 Hz), 4.89 (1H, d, J = 1.8 Hz), 4.77 (1H, br s), 4.16-4.08 (1H, m), 3.81-3.77 (7H, m), 3.55-3.47 (1H, m), 3.33-3.27 (1H, m), 3.27-3.20 (4H, m), 2.97 (1H, dd, J = 3.8, 13.6 Hz), 2.62 (1H, dd, J = 8.6, 13.6 Hz), 1.92-1.86 (4H, m). |
| Example 23 | 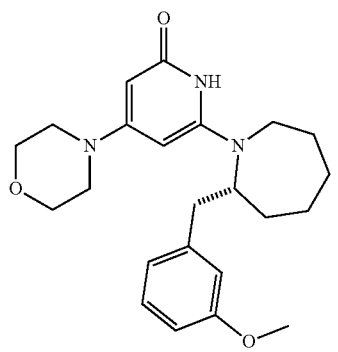 [SMILES: COc1cccc(C[C@H]2CCCCCN2c2cc(N3CCOCC3)cc(=O)[nH]2)c1]<br>(R)-6-(2-(3-methoxybenzyl)azepan-1-yl)-4-morpholinopyridin-2(1H)-one | 2-(3-methoxybenzyl)azepane | Method D | LCMS (ES+) 398 (M + H)$^+$, RT 2.90 min (Analytical Method A), 2.17 min (Analytical Method SFC4, YMC AMYLOSE-C + 0.1% DEAISO 35% IPA SOL4); $^1$H NMR (400 MHz, CDCl$_3$): δ 7.20 (1H, t, J = 8.0 Hz), 6.79-6.69 (3H, m), 5.17 (1H, d, J = 2.0 Hz), 4.90 (1H, d, J = 2.0 Hz), 3.82-3.77 (8H, m), 3.43 (1H, d, J = 16.3 Hz), 3.22-3.18 (4H, m), 3.03 (1H, dd, J = 11.9, 15.7 Hz), 2.82 (1H, dd, J = 5.3, 13.1 Hz), 2.74 (1H, dd, J = 7.1, 13.4 Hz), 2.16-2.06 (1H, m), 1.86-1.70 (3H, m), 1.59-1.44 (2H, m), 1.31-1.13 (2H, m). NH not observed. |

-continued

| Example | Structure and Name | Amine | Buchwald conditions | Analytical data |
|---|---|---|---|---|
| Example 24 | 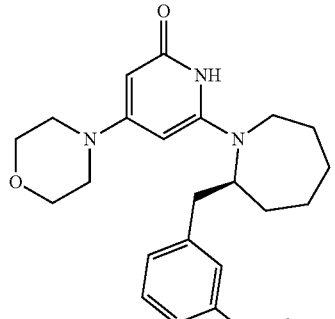<br>(S)-6-(2-(3-methoxybenzyl)azepan-1-yl)-4-morpholinopyridin-2(1H)-one | 2-(3-methoxybenzyl)azepane | Method D | LCMS (ES+) 398 (M + H)+, RT 2.91 min (Analytical Method A), 1.51 min (Analytical Method SFC4, YMC AMYLOSE-C + 0.1% DEAISO 35% IPA SOL4); $^1$H NMR (400 MHz, CDCl$_3$): δ 7.20 (1H, t, J = 7.8 Hz), 6.79-6.69 (3H, m), 5.17 (1H, d, J = 2.0 Hz), 4.89 (1H, d, J = 2.0 Hz), 3.84-3.74 (8H, m), 3.43 (1H, d, J = 16.5 Hz), 3.22-3.17 (4H, m), 3.03 (1H, dd, J = 11.9, 15.7 Hz), 2.82 (1H, dd, J = 5.5, 13.7 Hz), 2.74 (1H, dd, J = 7.4, 13.4 Hz), 2.15-2.05 (1H, m), 1.84-1.69 (3H, m), 1.59-1.44 (2H, m), 1.31-1.12 (2H, m). NH not observed. |
| Example 25 | 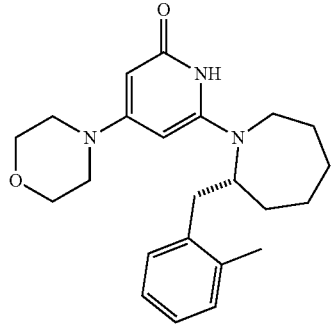 [SMILES: Cc1ccccc1C[C@H]1CCCCCN1c1cc(N2CCOCC2)cc(=O)[nH]1]<br>(R)-6-(2-(2-methylbenzyl)azepan-1-yl)-4-morpholinopyridin-2(1H)-one | 2-(2-methylbenzyl)azepane | Method D | LCMS (ES+) 382 (M + H)+, RT 3.04 min (Analytical Method A), 2.39 min (Analytical Method SFC4, LUX CELLULOSE-4 + 0.1% DEAISO 55% IPA SOL4); $^1$H NMR (400 MHz, CDCl$_3$): δ 7.17 (1H, t, J = 7.6 Hz), 7.04 (1H, d, J = 7.6 Hz), 6.97-6.91 (2H, m), 5.18 (1H, d, J = 2.0 Hz), 4.91 (1H, d, J = 2.0 Hz), 3.80-3.75 (5H, m), 3.41 (1H, d, J = 15.7 Hz), 3.22-3.18 (4H, m), 3.03 (1H, dd, J = 11.6, 16.2 Hz), 2.81 (1H, dd, J = 3.9, 13.4 Hz), 2.73 (1H, dd, J = 6.7, 13.0 Hz), 2.31 (3H, s), 2.14-2.03 (1H, m), 1.87-1.70 (3H, m), 1.59-1.44 (2H, m), 1.28-1.16 (2H, m). NH not observed. |
| Example 26 | 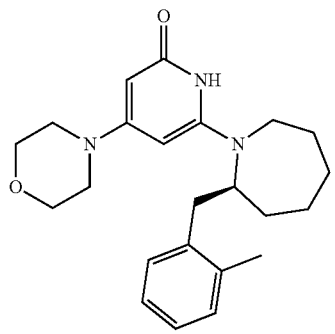 [SMILES: Cc1ccccc1C[C@@H]1CCCCCN1c1cc(N2CCOCC2)cc(=O)[nH]1]<br>(S)-6-(2-(2-methylbenzyl)azepan-1-yl)-4-morpholinopyridin-2(1H)-one | 2-(2-methylbenzyl)azepane | Method D | LCMS (ES+) 382 (M + H)+, RT 3.04 min (Analytical Method A), 1.73 min (Analytical Method SFC4, LUX CELLULOSE-4 + 0.1% DEAISO 55% IPA SOL4); $^1$H NMR (400 MHz, CDCl$_3$): δ 7.17 (1H, t, J = 7.6 Hz), 7.04 (1H, d, J = 7.6 Hz), 6.97-6.91 (2H, m), 5.18 (1H, d, J = 2.0 Hz), 4.90 (1H, d, J = 2.0 Hz), 3.80-3.75 (5H, m), 3.40 (1H, d, J = 16.5 Hz), 3.22-3.19 (4H, m), 3.08-2.98 (1H, m), 2.81 (1H, dd, J = 5.5, 13.4 Hz), 2.73 (1H, dd, J = 7.3, 13.6 Hz), 2.31 (3H, s), 2.16-2.05 (1H, m), 1.87-1.70 (3H, m), 1.60-1.44 (2H, m), 1.37-1.12 (2H, m). NH not observed. |

| Example | Structure and Name | Amine | Buchwald conditions | Analytical data |
|---|---|---|---|---|
| Example 27 | 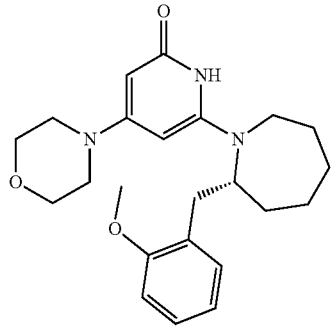 [SMILES: COc1ccccc1C[C@H]1CCCCCN1c1cc(N2CCOCC2)cc(=O)[nH]1]<br>(R)-6-(2-(2-methoxybenzyl)azepan-1-yl)-4-morpholinopyridin-2(1H)-one | 2-(2-methoxybenzyl)azepane | Method D | LCMS (ES+) 398 (M + H)+, RT 3.03 min (Analytical Method A); RT 2.40 min (Analytical Method SFC4, YMC AMYLOSE-C + 0.1% DEAISO 30% MeOH SOL3); $^1$H NMR (400 MHz, CDCl$_3$): δ 7.28-7.22 (1H, m), 7.07 (1H, dd, J = 1.6, 7.3 Hz), 6.95 (1H, d, J = 7.9 Hz), 6.89 (1H, dd, J = 7.3, 7.3 Hz), 5.23 (1H, d, J = 2.1 Hz), 4.95 (1H, d, J = 2.1 Hz), 4.18 (3H, s), 3.81-3.77 (6H, m), 3.44 (1H, d, J = 16.0 Hz), 3.31 (1H, dd, J = 11.7, 15.2 Hz), 3.25 (4H, dd, J = 4.0, 5.9 Hz), 3.14 (1H, dd, J = 3.1, 13.1 Hz), 2.45 (1H, dd, J = 10.9, 13.1 Hz), 2.02-1.93 (1H, m), 1.89-1.72 (2H, m), 1.69-1.58 (1H, m), 1.46-1.25 (2H, m), 1.19-1.08 (1H, m). NH not observed. |
| Example 28 | 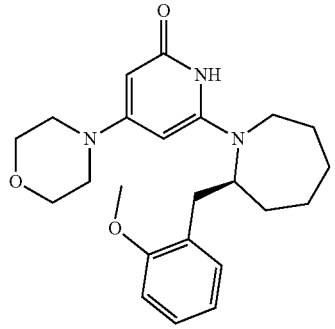 [SMILES: COc1ccccc1C[C@@H]1CCCCCN1c1cc(N2CCOCC2)cc(=O)[nH]1]<br>(S)-6-(2-(2-methoxybenzyl)azepan-1-yl)-4-morpholinopyridin-2(1H)-one | 2-(2-methoxybenzyl)azepane | Method D | LCMS (ES+) 398 (M + H)+, RT 3.03 min (Analytical Method A); RT 1.85 min (100% ee) (Analytical Method SFC4, YMC AMYLOSE-C + 0.1% DEAISO 30% MeOH SOL3); $^1$H NMR (400 MHz, CDCl$_3$): δ 7.28-7.23 (1H, m), 7.07 (1H, dd, J = 1.6, 7.3 Hz), 6.96 (1H, d, J = 7.9 Hz), 6.89 (1H, dd, J = 7.3, 7.3 Hz), 5.22 (1H, d, J = 2.0 Hz), 4.94 (1H, d, J = 2.0 Hz), 4.20 (3H, s), 3.81-3.77 (6H, m), 3.45-3.39 (1H, m), 3.35-3.27 (1H, m), 3.25 (4H, dd, J = 3.9, 5.9 Hz), 3.15 (1H, dd, J = 2.9, 13.1 Hz), 2.44 (1H, dd, J = 11.2, 13.0 Hz), 2.02-1.93 (1H, m), 1.87-1.70 (2H, m), 1.68-1.60 (1H, m), 1.46-1.25 (2H, m), 1.18-1.08 (1H, m). NH not observed. |
| Example 29 | 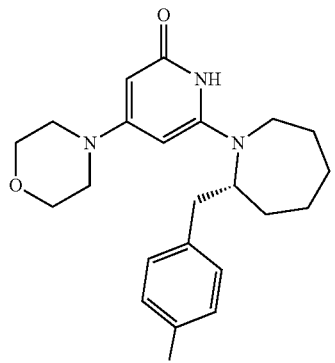<br>6-[(2R)-2-[(4-methoxyphenyl)methyl]azepan-1-yl]-4-morpholino-1H-pyridin-2-one | 2-(4-methoxybenzyl)azepane | Method D | LCMS (ES+) 398 (M + H)+, RT 2.96 min (Analytical Method A); RT 3.45 min (Analytical Method SFC1, YMC AMYLOSE-C + 0.1% DEAISO 35% IPA SOL6); $^1$H NMR (400 MHz, CDCl3): δ 7.06-7.02 (2H, m), 6.84-6.80 (2H, m), 5.18 (1H, d, J = 1.9 Hz), 4.89 (1H, d, J = 1.9 Hz), 3.78-3.70 (8H, m), 3.36 (1H, d, J = 16.0 Hz), 3.23-3.19 (4H, m), 2.94 (1H, dd, J = 12.0, 15.9 Hz), 2.77-2.74 (2H, m), 2.12-2.00 (1H, m), 1.84-1.69 (3H, m), 1.55-1.44 (2H, m), 1.29-1.12 (2H, m). NH not observed. |

-continued

| Example | Structure and Name | Amine | Buchwald conditions | Analytical data |
|---|---|---|---|---|
| Example 30 | 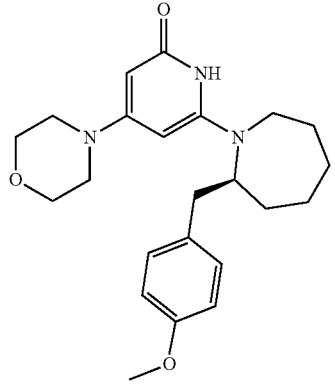 [SMILES: COc1ccc(C[C@@H]2CCCCCN2c2cc(N3CCOCC3)cc(=O)[nH]2)cc1]<br>6-[(2S)-2-[(4-methoxyphenyl)methyl]azepan-1-yl]-4-morpholino-1H-pyridin-2-one | 2-(4-methoxybenzyl)azepane | Method D | LCMS (ES+) 398 (M + H)+, RT 2.96 min (Analytical Method A); RT 2.55 min (Analytical Method SFC1, YMC AMYLOSE-C + 0.1% DEAISO 35% IPA SOL6); $^1$H NMR (400 MHz, CDCl3): δ 7.04 (2H, d, J = 8.7 Hz), 6.82 (2H, d, J = 8.5 Hz), 5.17 (1H, d, J = 2.0 Hz), 4.88 (1H, d, J = 1.9 Hz), 3.79-3.75 (8H, m), 3.37 (1H, d, J = 15.2 Hz), 3.22-3.18 (4H, m), 2.94 (1H, dd, J = 12.2, 15.8 Hz), 2.77-2.74 (2H, m), 2.11-2.00 (1H, m), 1.84-1.69 (3H, m), 1.56-1.44 (2H, m), 1.27-1.13 (2H, m). NH not observed. |
| Example 31 | 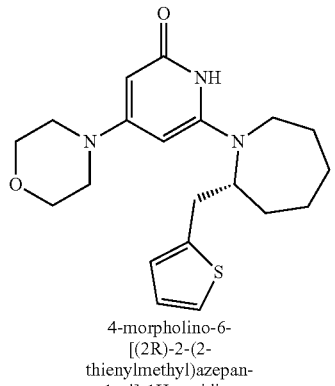<br>4-morpholino-6-[(2R)-2-(2-thienylmethyl)azepan-1-yl]-1H-pyridin-2-one | 2-(thiophen-2-ylmethyl)azepane | Method D | LCMS (ES+) 374 (M + H)+, RT 2.98 min (Analytical Method A); RT 2.27 min (Analytical Method SFC1, YMC AMYLOSE-C + 0.1% DEAISO 40% IPA SOL6); $^1$H NMR (400 MHz, CDCl3): δ 7.17 (1H, dd, J = 1.0, 5.1 Hz), 6.94 (1H, dd, J = 3.4, 5.2 Hz), 6.81 (1H, d, J = 2.8 Hz), 5.19 (1H, d, J = 2.0 Hz), 4.93 (1H, d, J = 2.0 Hz), 3.80-3.76 (5H, m), 3.44 (1H, d, J = 16.7 Hz), 3.25-3.22 (4H, m), 3.07-3.00 (3H, m), 2.24-2.15 (1H, m), 1.86-1.75 (3H, m), 1.59-1.47 (2H, m), 1.33-1.15 (2H, m). NH not observed. |
| Example 32 | 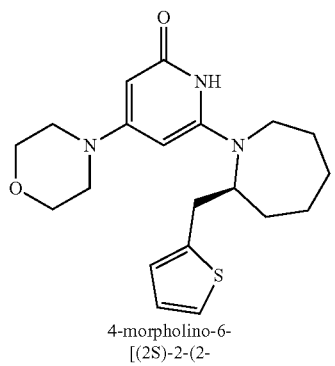<br>4-morpholino-6-[(2S)-2-(2-thienylmethyl)azepan-1-yl]-1H-pyridin-2-one | 2-(thiophen-2-ylmethyl)azepane | Method D | LCMS (ES+) 374 (M + H)+, RT 2.98 min (Analytical Method A); RT 1.69 min (Analytical Method SFC1, YMC AMYLOSE-C + 0.1% DEAISO 40% IPA SOL6); $^1$H NMR (400 MHz, CDCl3): δ 7.17 (1H, dd, J = 1.0, 5.1 Hz), 6.94 (1H, dd, J = 3.4, 5.2 Hz), 6.81 (1H, d, J = 2.8 Hz), 5.19 (1H, d, J = 2.0 Hz), 4.93 (1H, d, J = 2.0 Hz), 3.80-3.76 (5H, m), 3.44 (1H, d, J = 16.7 Hz), 3.25-3.22 (4H, m), 3.07-3.00 (3H, m), 2.24-2.15 (1H, m), 1.86-1.75 (3H, m), 1.59-1.47 (2H, m), 1.33-1.15 (2H, m). NH not observed. |

| Example | Structure and Name | Amine | Buchwald conditions | Analytical data |
|---|---|---|---|---|
| Example 33 | 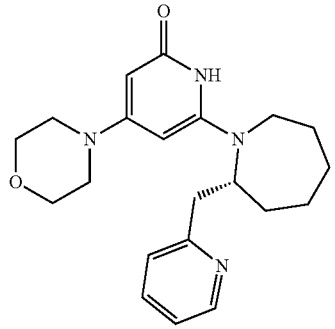 [SMILES: O=c1cc(N2CCOCC2)cc(N2CCCCC[C@@H]2Cc2ccccn2)[nH]1]<br>(R)-4-morpholino-6-(2-(pyridin-2-ylmethyl)azepan-1-yl)pyridin-2(1H)-one | 2-(pyridin-2-ylmethyl)azepane | Method D | LCMS (ES+) 369 (M + H)+, RT 2.57 min (Analytical Method A); RT 6.78 min (Analytical Method SFC4, YMC CELLULOSE-SC + 0.1% DEAISO 45% IPA SOL4); $^1$H NMR (400 MHz, CDCl$_3$): δ 8.66 (1H, d, J = 4.0 Hz), 7.61-7.55 (1H, m), 7.16 (1H, dd, J = 4.9, 6.7 Hz), 7.07 (1H, d, J = 7.6 Hz), 5.15 (2H, dd, J = 2.0, 22.0 Hz), 4.28-4.19 (1H, m), 3.79-3.76 (4H, m), 3.45 (1H, d, J = 16.2 Hz), 3.27-3.22 (5H, m), 3.06 (1H, dd, J = 5.3, 14.4 Hz), 2.87 (1H, dd, J = 6.4, 14.5 Hz), 2.20-2.10 (1H, m), 1.90-1.50 (5H, m), 1.38-1.17 (2H, m). NH not observed. |
| Example 34 | 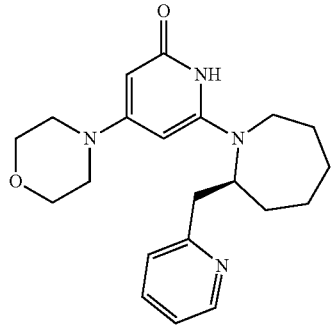 [SMILES: O=c1cc(N2CCOCC2)cc(N2CCCCC[C@H]2Cc2ccccn2)[nH]1]<br>(S)-4-morpholino-6-(2-(pyridin-2-ylmethyl)azepan-1-yl)pyridin-2(1H)-one | 2-(pyridin-2-ylmethyl)azepane | Method D | LCMS (ES+) 369 (M + H)+, RT 2.57 min (Analytical Method A); RT 5.78 min (Analytical Method SFC4, YMC CELLULOSE-SC + 0.1% DEAISO 45% IPA SOL4); $^1$H NMR (400 MHz, CDCl3): δ 8.67 (1H, ddt, J = 0.8, 2.2, 2.5 Hz), 7.58 (1H, ddd, J = 7.6, 7.6, 1.8 Hz), 7.16 (1H, ddt, J = 1.0, 4.1, 3.8 Hz), 7.07 (1H, d, J = 7.6 Hz), 5.18 (1H, d, J = 2.3 Hz), 5.12 (1H, d, J = 2.0 Hz), 4.23 (1H, td, J = 5.9, 17.1 Hz), 3.79-3.75 (4H, m), 3.45 (1H, d, J = 15.7 Hz), 3.27-3.19 (5H, m), 3.06 (1H, dd, J = 5.3, 14.4 Hz), 2.87 (1H, dd, J = 6.3, 14.4 Hz), 2.20-2.11 (1H, m), 1.91-1.51 (5H, m), 1.38-1.17 (2H, m). NH not observed. |
| Example 35 | 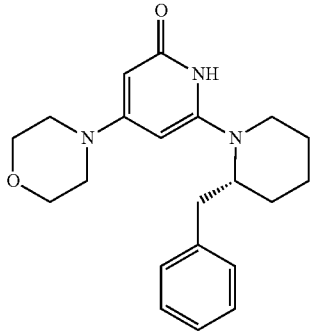 [SMILES: O=c1cc(N2CCOCC2)cc(N2CCCC[C@@H]2Cc2ccccc2)[nH]1]<br>(R)-6-(2-benzylpiperidin-1-yl)-4-morpholinopyridin-2(1H)-one | 2-benzylpiperidine | Method D | LCMS (ES+) 354 (M + H)+, RT 2.84 min (Analytical Method A); RT 2.68 min (Analytical Method SFC4, YMC CELLULOSE-C + 0.1% DEAISO 25% IPA SOL4) $^1$H NMR (400 MHz, CDCl$_3$): δ 7.28-7.21 (2H, m), 7.20-7.12 (3H, m), 5.23 (1H, d, J = 2.1 Hz), 5.04 (1H, d, J = 2.2 Hz), 4.14-4.07 (1H, m), 3.77 (4H, t, J = 4.9 Hz), 3.45-3.39 (1H, m), 3.25-3.09 (5H, m), 2.92-2.81 (2H, m), 1.81-1.60 (6H, m). NH not observed |

| Example | Structure and Name | Amine | Buchwald conditions | Analytical data |
|---|---|---|---|---|
| Example 36 | 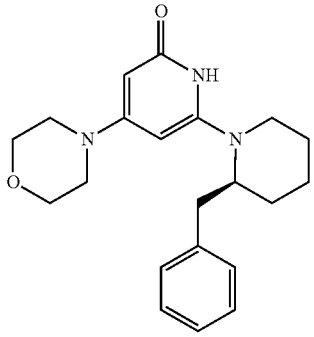 [SMILES: O=c1cc(N2CCOCC2)cc(N2CCCC[C@H]2Cc2ccccc2)[nH]1]<br>(S)-6-(2-benzylpiperidin-1-yl)-4-morpholinopyridin-2(1H)-one | 2-benzylpiperidine | Method D | LCMS (ES+) 354 (M + H)+, RT 2.84 min (Analytical Method A); RT 3.34 min (Analytical Method SFC4, YMC CELLULOSE-C + 0.1% DEAIS0 25% IPA SOL4); $^1$H NMR (400 MHz, CDCl$_3$): δ 7.28-7.21 (2H, m), 7.20-7.12 (3H, m), 5.23 (1H, d, J = 2.1 Hz), 5.04 (1H, d, J = 2.2 Hz), 4.14-4.07 (1H, m), 3.77 (4H, t, J = 4.9 Hz), 3.45-3.39 (1H, m), 3.25-3.09 (5H, m), 2.92-2.81 (2H, m), 1.81-1.60 (6H, m). NH not observed. |
| Example 37 | 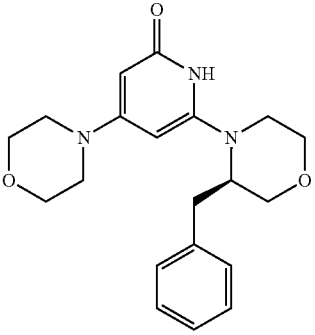 [SMILES: O=c1cc(N2CCOCC2)cc(N2CCOC[C@H]2Cc2ccccc2)[nH]1]<br>(R)-6-(3-benzylmorpholino)-4-morpholinopyridin-2(1H)-one | 3-benzylmorpholine | Method C | LCMS (ES+) 356 (M + H)+, RT 2.67 min (Analytical Method A); RT 0.84 min (Analytical Method SFC1, YMC AMYLOSE-C, 50/50 MeOH + 0.1% DEAISO/CO$_2$); $^1$H NMR (400 MHz, CDCl$_3$): δ 7.22-7.15 (5H, m), 5.26 (1H, d, J = 2.0 Hz), 5.10 (1H, d, J = 1.8 Hz), 4.13 (1H, d, J = 10.6 Hz), 4.03 (1H, dd, J = 3.0, 11.4 Hz), 3.81-3.76 (4H, m), 3.75-3.63 (3H, m), 3.38 (1H, dt, J = 3.7, 11.9 Hz), 3.28-3.22 (5H, m), 3.12 (1H, dd, J = 10.8, 13.0 Hz), 2.74 (1H, dd, J = 4.0, 13.1 Hz). NH not observed. |
| Example 38 | 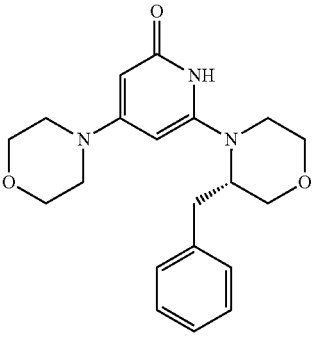 [SMILES: O=c1cc(N2CCOCC2)cc(N2CCOC[C@@H]2Cc2ccccc2)[nH]1]<br>(S)-6-(3-benzylmorpholino)-4-morpholinopyridin-2(1H)-one | 3-benzylmorpholine | Method C | LCMS (ES+) 356 (M + H)+, RT 2.67 min (Analytical Method A); RT 1.85 min (Analytical Method SFC1, YMC AMYLOSE-C, 50/50 MeOH + 0.1% DEA/CO2); $^1$H NMR (400 MHz, CDCl3): δ 7.24-7.15 (5H, m), 5.27 (1H, d, J = 2.0 Hz), 5.11 (1H, d, J = 2.0 Hz), 4.09-4.00 (2H, m), 3.81-3.77 (4H, m), 3.76-3.63 (3H, m), 3.37 (1H, dt, J = 3.7, 12.0 Hz), 3.28-3.20 (5H, m), 3.12 (1H, dd, J = 11.0, 13.2 Hz), 2.74 (1H, dd, J = 3.8, 12.9 Hz). NH not observed. |

| Example | Structure and Name | Amine | Buchwald conditions | Analytical data |
|---|---|---|---|---|
| Example 39 | 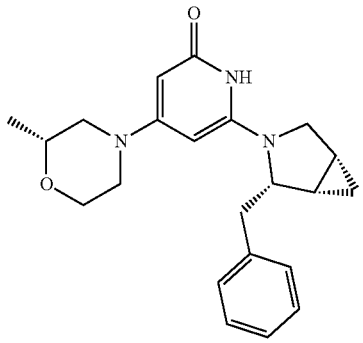 [SMILES: C[C@@H]1CN(c2cc(N3C[C@@H]4C[C@@H]4[C@@H]3Cc3ccccc3)[nH]c(=O)c2)CCO1]<br>6-((1S,2S,5R)-2-benzyl-3-azabicyclo[3.1.0]hexan-3-yl)-4-((R)-2-methylmorpholino)pyridin-2(1H)-one | Intermediate 1 | Method D | LCMS (ES+) 366 (M + H)+, RT 3.05 min (Analytical Method A); RT 2.43 min (Analytical Method SFC4, YMC AMYLOSE-C, 20/80 MeOH + 0.1% DEAISO/CO$_2$); $^1$H NMR (400 MHz, CDCl$_3$): δ 7.35-7.23 (5H, m), 5.28 (1H, d, J = 2.3 Hz), 5.02 (1H, d, J = 2.0 Hz), 4.00-3.92 (2H, m), 3.88 (1H, d, J = 9.1 Hz), 3.73-3.63 (2H, m), 3.54-3.42 (3H, m), 3.25 (1H, dd, J = 2.8, 13.6 Hz), 2.97 (1H, dt, J = 3.6, 12.3 Hz), 2.65-2.51 (2H, m), 1.73-1.67 (2H, m), 1.23 (3H, d, J = 6.1 Hz), 0.78 (1H, dt, J = 5.1, 8.0 Hz), 0.62 (1H, q, J = 4.4 Hz), NH not observed. |
| Example 40 | 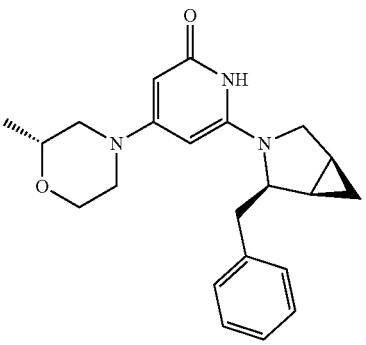 [SMILES: C[C@@H]1CN(c2cc(N3C[C@H]4C[C@H]4[C@H]3Cc3ccccc3)[nH]c(=O)c2)CCO1]<br>6-((1R,2R,5S)-2-benzyl-3-azabicyclo[3.1.0]hexan-3-yl)-4-((R)-2-methylmorpholino)pyridin-2(1H)-one | Intermediate 1 | Method D | LCMS (ES+) 366 (M + H)+, RT 3.05 min (Analytical Method A); RT 3.60 min (Analytical Method SFC4, YMC AMYLOSE-C, 20/80 MeOH + 0.1% DEAISO/CO$_2$); $^1$H NMR (400 MHz, CDCl$_3$): δ 7.36-7.24 (5H, m), 5.28 (1H, d, J = 2.0 Hz), 5.01 (1H, d, J = 2.3 Hz), 3.99-3.92 (2H, m), 3.85 (1H, d, J = 8.8 Hz), 3.72-3.63 (2H, m), 3.55 (1H, dd, J = 2.3, 10.6 Hz), 3.48-3.42 (2H, m), 3.25 (1H, dd, J = 2.7, 13.5 Hz), 2.96 (1H, dt, J = 3.7, 12.2 Hz), 2.67-2.52 (2H, m), 1.73-1.67 (2H, m), 1.23 (3H, d, J = 6.1 Hz), 0.78 (1H, dt, J = 5.1, 8.0 Hz), 0.62 (1H, q, J = 4.5 Hz), NH not observed. |
| Example 41 | 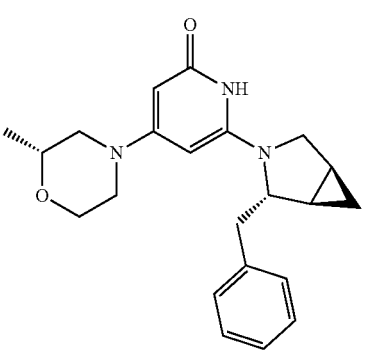 [SMILES: C[C@@H]1CN(c2cc(N3C[C@H]4C[C@H]4[C@@H]3Cc3ccccc3)[nH]c(=O)c2)CCO1]<br>6-((1R,2S,5S)-2-benzyl-3-azabicyclo[3.1.0]hexan-3-yl)-4-((R)-2-methylmorpholino)pyridin-2(1H)-one | Intermediate 2 | Method D | LCMS (ES+) 366 (M + H)+, RT 2.91 min (Analytical Method A); RT 2.43 min (Analytical Method SFC4, YMC AMYLOSE-C, 30/70 IPA + 0.1% DEAISO/CO$_2$); $^1$H NMR (400 MHz, CDCl$_3$): δ 7.30-7.16 (5H, m), 5.22 (1H, d, J = 2.0 Hz), 4.81 (1H, d, J = 2.0 Hz), 4.26 (1H, dd, J = 3.4, 8.0 Hz), 3.97 (1H, dd, J = 2.3, 11.6 Hz), 3.73-3.62 (2H, m), 3.54-3.46 (2H, m), 3.35 (1H, d, J = 9.1 Hz), 3.14 (1H, dd, J = 4.0, 9.1 Hz), 3.02-2.90 (2H, m), 2.79 (1H, dd, J = 8.0, 13.5 Hz), 2.60 (1H, dd, J = 10.4, 12.6 Hz), 1.55-1.43 (2H, m), 1.23 (3H, d, J = 6.3 Hz), 0.65 (1H, dt, J = 5.1, 7.7 Hz), 0.20 (1H, q, J = 4.4 Hz), NH not observed. |

| Example | Structure and Name | Amine | Buchwald conditions | Analytical data |
|---|---|---|---|---|
| Example 42 | 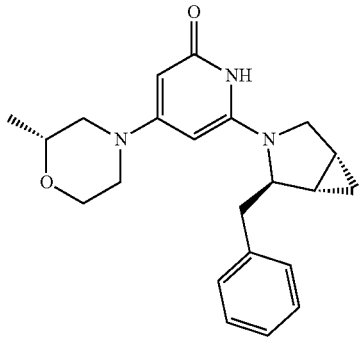 [SMILES: C[C@@H]1CN(c2cc(N3C[C@@H]4C[C@@H]4[C@H]3Cc3ccccc3)[nH]c(=O)c2)CCO1]<br>6-((1S,2R,5R)-2-benzyl-3-azabicyclo[3.1.0]hexan-3-yl)-4-((R)-2-methylmorpholino)pyridin-2(1H)-one | Intermediate 2 | Method D | LCMS (ES+) 366 (M + H)+, RT 2.91 min (Analytical Method A); RT 2.23 min (Analytical Method SFC4, YMC AMYLOSE-C, 30/70 IPA + 0.1% DEAISO/CO$_2$); $^1$H NMR (400 MHz, CDCl$_3$): δ 7.29-7.15 (5H, m), 5.21 (1H, d, J = 2.0 Hz), 4.80 (1H, d, J = 2.0 Hz), 4.23 (1H, dd, J = 3.4, 7.7 Hz), 3.96 (1H, ddd, J = 1.3, 3.4, 11.5 Hz), 3.72-3.63 (2H, m), 3.55-3.43 (2H, m), 3.33 (1H, d, J = 9.3 Hz), 3.13 (1H, dd, J = 4.0, 9.1 Hz), 3.02-2.90 (2H, m), 2.80 (1H, dd, J = 7.8, 13.6 Hz), 2.59 (1H, dd, J = 10.5, 12.5 Hz), 1.56-1.43 (2H, m), 1.23 (3H, d, J = 6.1 Hz), 0.65 (1H, dt, J = 5.1, 7.7 Hz), 0.20 (1H, q, J = 4.4 Hz), NH not observed. |
| Example 43 | 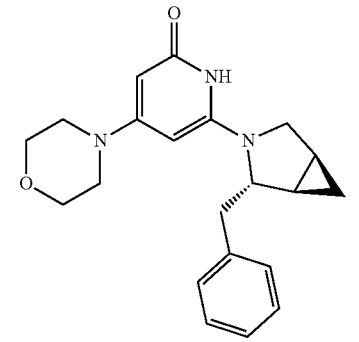 [SMILES: O=c1cc(N2CCOCC2)cc(N2C[C@H]3C[C@H]3[C@@H]2Cc2ccccc2)[nH]1]<br>6-((1R,2S,5S)-2-benzyl-3-azabicyclo[3.1.0]hexan-3-yl)-4-morpholinopyridin-2(1H)-one | Intermediate 2 | Method D | LCMS (ES+) 352 (M + H)+, RT 2.83 min (Analytical Method A); RT 1.65 min (Analytical Method SFC4, YMC AMYLOSE-C, 40/60 IPA + 0.1% DEAISO/CO$_2$); $^1$H NMR (400 MHz, CDCl$_3$): δ 7.27-7.26 (3H, m), 7.19-7.15 (2H, m), 5.22 (1H, d, J = 2.0 Hz), 4.82 (1H, d, J = 2.0 Hz), 4.22 (1H, dd, J = 3.4, 7.7 Hz), 3.81-3.77 (4H, m), 3.33 (1H, d, J = 9.3 Hz), 3.27-3.23 (4H, m), 3.12 (1H, dd, J = 4.0, 9.1 Hz), 2.99 (1H, dd, J = 3.3, 13.6 Hz), 2.81 (1H, dd, J = 8.0, 13.5 Hz), 1.56-1.39 (2H, m), 0.66 (1H, dt, J = 5.2, 7.8 Hz), 0.19 (1H, q, J = 4.3 Hz), NH not observed. |
| Example 44: | 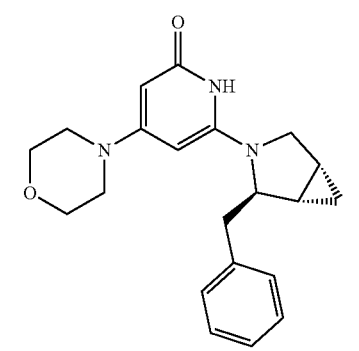 [SMILES: O=c1cc(N2CCOCC2)cc(N2C[C@@H]3C[C@@H]3[C@H]2Cc2ccccc2)[nH]1]<br>6-((1S,2R,5R)-2-benzyl-3-azabicyclo[3.1.0]hexan-3-yl)-4-morpholinopyridin-2(1H)-one | Intermediate 2 | Method D | LCMS (ES+) 352 (M + H)+, RT 2.83 min (Analytical Method A); RT 1.06 min (Analytical Method SFC4, YMC AMYLOSE-C, 40/60 IPA + 0.1% DEAISO/CO$_2$); $^1$H NMR (400 MHz, CDCl$_3$): δ 7.30-7.20 (3H, m), 7.20-7.16 (2H, m), 5.22 (1H, d, J = 2.3 Hz), 4.81 (1H, d, J = 2.3 Hz), 4.27 (1H, dd, J = 3.3, 7.8 Hz), 3.82-3.77 (4H, m), 3.34 (1H, d, J = 9.1 Hz), 3.27-3.22 (4H, m), 3.13 (1H, dd, J = 4.0, 9.1 Hz), 2.99 (1H, dd, J = 3.3, 13.6 Hz), 2.79 (1H, dd, J = 8.0, 13.5 Hz), 1.55-1.42 (2H, m), 0.65 (1H, dt, J = 5.2, 7.8 Hz), 0.20 (1H, q, J = 4.4 Hz); NH not observed. |

| Example | Structure and Name | Amine | Buchwald conditions | Analytical data |
|---|---|---|---|---|
| Example 45 | 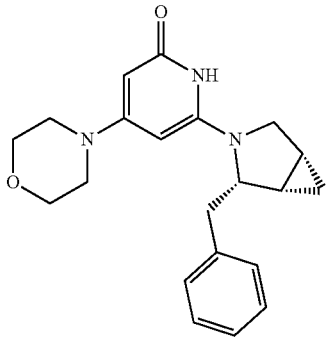 [SMILES: O=c1cc(N2CCOCC2)cc(N2C[C@@H]3C[C@@H]3[C@@H]2Cc2ccccc2)[nH]1]<br>6-((1S,2S,5R)-2-benzyl-3-azabicyclo[3.1.0]hexan-3-yl)-4-morpholinopyridin-2(1H)-one | Intermediate 1 | Method D | LCMS (ES+) 352 (M + H)+, RT 2.95 min (Analytical Method A); RT 1.58 min (Analytical Method SFC4, YMC AMYLOSE-C, 30/70 MeOH + 0.1% DEAISO/CO$_2$); $^1$H NMR (400 MHz, CDCl$_3$): δ 7.35-7.24 (5H, m), 5.29 (1H, d, J = 2.0 Hz), 5.02 (1H, d, J = 2.0 Hz), 4.00-3.94 (1H, m), 3.91 (1H, d, J = 8.4 Hz), 3.82-3.78 (4H, m), 3.45 (1H, dd, J = 3.8, 9.1 Hz), 3.30-3.23 (5H, m), 2.54 (1H, dd, J = 9.9, 13.6 Hz), 1.71-1.65 (2H, m), 0.77 (1H, dt, J = 5.1, 8.0 Hz), 0.62 (1H, q, J = 4.5 Hz), NH not observed. |
| Example 46 | 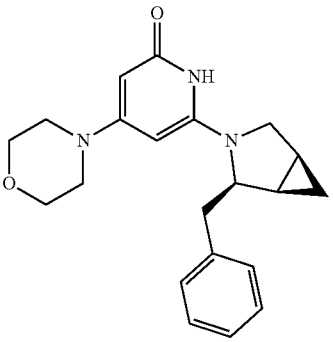 [SMILES: O=c1cc(N2CCOCC2)cc(N2C[C@H]3C[C@H]3[C@H]2Cc2ccccc2)[nH]1]<br>6-((1R,2R,5S)-2-benzyl-3-azabicyclo[3.1.0]hexan-3-yl)-4-morpholinopyridin-2(1H)-one | Intermediate 1 | Method D | LCMS (ES+) 352 (M + H)+, RT 3.09 min (Analytical Method B); RT 2.13 min (Analytical Method SFC4, YMC AMYLOSE-C, 15/85 MeOH + 0.1% DEAISO/CO$_2$); $^1$H NMR δ (ppm) (400 MHz, CDCl$_3$) 7.35-7.22 (5H, m), 5.29 (1H, d, J = 2.0 Hz), 5.02 (1H, d, J = 2.0 Hz), 4.00-3.92 (2H, m), 3.82-3.78 (4H, m), 3.45 (1H, dd, J = 3.9, 9.0 Hz), 3.30-3.24 (5H, m), 2.53 (1H, dd, J = 10.0, 13.5 Hz), 1.72-1.63 (2H, m), 0.77 (1H, dt, J = 5.1, 7.9 Hz), 0.62 (1H, q, J = 4.5 Hz). NH not observed. |
| Example 47 | 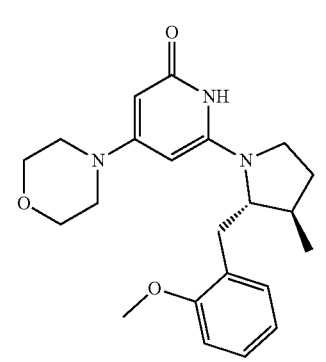 [SMILES: COc1ccccc1C[C@H]1[C@H](C)CCN1c1cc(N2CCOCC2)cc(=O)[nH]1]<br>6-((2S,3R)-2-(2-methoxybenzyl)-3-methylpyrrolidin-1-yl)-4-morpholinopyridin-2(1H)-one | Intermediate 7 | Method D | LCMS (ES+) 384 (M + H)+, RT 3.32 min (Analytical Method B); RT 2.08 min (Analytical Method SFC4, YMC CELLULOSE-C + 0.1% DEAISO 35% IPA SOL4); $^1$H NMR (400 MHz, CDCl$_3$): δ 8.95 (1H, br s), 7.30-7.27 (1H, m), 7.07 (1H, d, J = 7.1 Hz), 6.97 (1H, d, J = 8.1 Hz), 6.91 (1H, dd, J = 7.3, 7.3 Hz), 5.23 (1H, s), 4.82 (1H, s), 4.22 (3H, s), 3.82-3.75 (4H, m), 3.50 (1H, d, J = 10.9 Hz), 3.41-3.31 (2H, m), 3.28-3.24 (4H, m), 3.20 (1H, d, J = 13.2 Hz), 2.39-2.21 (3H, m), 1.74-1.67 (1H, m), 0.82 (3H, d, J = 6.8 Hz). |

| Example | Structure and Name | Amine | Buchwald conditions | Analytical data |
|---|---|---|---|---|
| Example 48 | 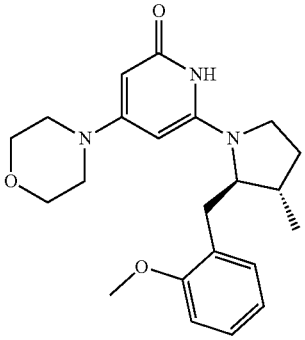 [SMILES: COc1ccccc1C[C@@H]1[C@@H](C)CCN1c1cc(N2CCOCC2)cc(=O)[nH]1]<br>6-((2R,3S)-2-(2-methoxybenzyl)-3-methylpyrrolidin-1-yl)-4-morpholinopyridin-2(1H)-one | Intermediate 7 | Method D | LCMS (ES+) 384 (M + H)+, RT 2.95 min (Analytical Method A); RT 1.41 min (Analytical Method SFC4, YMC CELLULOSE-C + 0.1% DEAISO 35% IPA SOL4); $^1$H NMR (400 MHz, CDCl$_3$): δ 8.99 (1H, s), 7.28 (1H, d, J = 10.6 Hz), 7.07 (1H, d, J = 7.3 Hz), 6.97 (1H, d, J = 8.1 Hz), 6.91 (1H, dd, J = 7.5, 7.5 Hz), 5.23 (1H, s), 4.82 (1H, s), 4.21 (3H, s), 3.79 (4H, dd, J = 4.8, 4.8 Hz), 3.50 (1H, d, J = 10.9 Hz), 3.39-3.32 (2H, m), 3.29-3.24 (4H, m), 3.20 (1H, d, J = 13.2 Hz), 2.36-2.23 (3H, m), 1.74-1.69 (1H, m), 0.82 (3H, d, J = 6.8 Hz). |
| Example 49 | 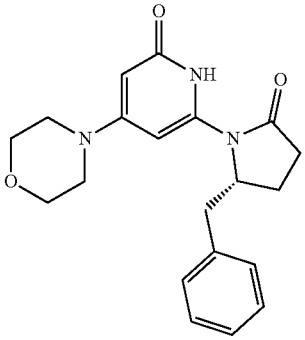 [SMILES: O=C1CC[C@H](Cc2ccccc2)N1c1cc(N2CCOCC2)cc(=O)[nH]1]<br>(R)-6-(2-benzyl-5-oxopyrrolidin-1-yl)-4-morpholino pyridin-2(1H)-one | Intermediate 5 | Method D | LCMS (ES+) 354 (M + H)$^+$, RT 2.79 min (Analytical Method A); RT 1.96 min (Analytical Method SFC1, YMC AMYLOSE-C, 40/60 MeOH (0.1% DEAISO)/CO$_2$); $^1$H NMR (400 MHz, CDCl$_3$): δ 7.35-7.27 (3H, m), 7.14-7.12 (2H, m), 5.61 (1H, d, J = 2.3 Hz), 5.58 (1H, d, J = 1.9 Hz), 4.52-4.48 (1H, m), 3.81 (4H, t, J = 4.9 Hz), 3.26 (4H, t, J = 5.0 Hz), 3.04-2.95 (2H, m), 2.42-2.30 (1H, m), 2.24-2.10 (2H, m), 2.04-1.96 (1H, m), NH not observed |
| Example 50 | 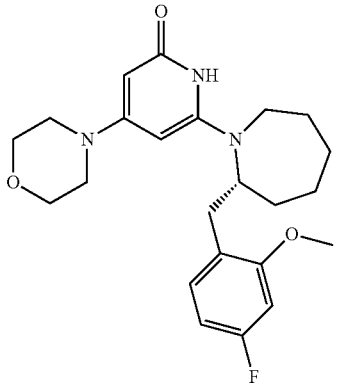 [SMILES: COc1cc(F)ccc1C[C@H]1CCCCCN1c1cc(N2CCOCC2)cc(=O)[nH]1]<br>(R)-6-(2-(4-fluoro-2-methoxybenzyl)azepan-1-yl)-4-morpholinopyridin-2(1H)-one | Intermediate 8 | Method D | LCMS (ES+) 416 (M + H)$^+$, RT 3.35 min (Analytical Method B); RT 3.03 min (Analytical Method SFC4, YMC AMYLOSE-C, 25/75 MeOH (0.1% DEAISO)/CO$_2$); $^1$H NMR (400 MHz, CDCl$_3$): δ 8.86 (1H, brs), 6.99 (1H, dd, J = 6.7, 8.0 Hz), 6.69 (1H, dd, J = 2.4, 10.7 Hz), 6.59 (1H, ddd, J = 8.2, 8.2, 2.6 Hz), 5.22 (1H, d, J = 2.3 Hz), 4.19 (3H, s), 4.93 (1H, d, J = 2.0 Hz), 4.19 (3H, s), 3.79 (4H, t, J = 4.8 Hz), 3.75-3.67 (1H, m), 3.44-3.40 (1H, m), 3.32-3.23 (1H, m), 3.07 (1H, dd, J = 2.7, 13.6 Hz), 2.43 (1H, dd, J = 10.9, 13.0 Hz), 2.01-1.93 (1H, m), 1.87-1.59 (3H, m), 1.43-1.26 (3H, m), 1.18-1.09 (1H, m) |

| Example | Structure and Name | Amine | Buchwald conditions | Analytical data |
|---|---|---|---|---|
| Example 51 | 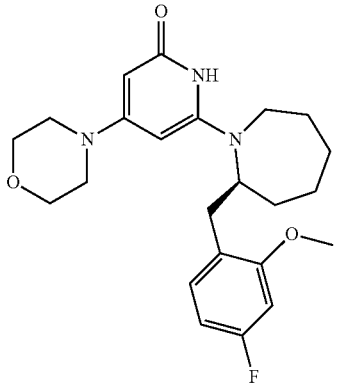 [SMILES: COc1cc(F)ccc1C[C@@H]1CCCCCN1c1cc(N2CCOCC2)cc(=O)[nH]1]<br>(S)-6-(2-(4-fluoro-2-methoxybenzyl)azepan-1-yl)-4-morpholinopyridin-2(1H)-one | Intermediate 8 | Method D | LCMS (ES+) 416 (M + H)+, RT 3.35 min (Analytical Method B); RT 2.35 min (Analytical Method SFC4, YMC AMYLOSE-C + 0.1% DEAISO 25% MeOH SOL3); $^1$H NMR (400 MHz, CDCl$_3$): δ 8.86 (1H, br s), 6.99 (1H, dd, J = 6.7, 8.0 Hz), 6.69 (1H, dd, J = 2.4, 10.7 Hz), 6.59 (1H, ddd, J = 8.2, 8.2, 2.6 Hz), 5.22 (1H, d, J = 2.3 Hz), 4.19 (3H, s), 4.93 (1H, d, J = 2.0 Hz), 4.19 (3H, s), 3.79 (4H, t, J = 4.8 Hz), 3.75-3.67 (1H, m), 3.44-3.40 (1H, m), 3.32-3.23 (1H, m), 3.07 (1H, dd, J = 2.7, 13.6 Hz), 2.43 (1H, dd, J = 10.9, 13.0 Hz), 2.01-1.93 (1H, m), 1.87-1.59 (3H, m), 1.43-1.26 (3H, m), 1.18-1.09 (1H, m). |
| Example 52 | 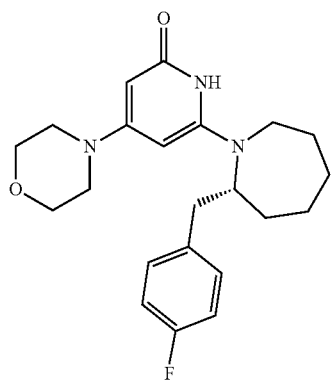 [SMILES: O=c1cc(N2CCOCC2)cc(N2CCCCC[C@@H]2Cc2ccc(F)cc2)[nH]1]<br>(R)-6-(2-(4-fluorobenzyl)azepan-1-yl)-4-morpholino pyridin-2(1H)-one | Intermediate 15 | Method D | LCMS (ES+) 386 (M + H)+, RT 3.04 min (Analytical Method A); RT 4.09 min (Analytical Method SFC4, LUX CELLULOSE-4, 40/60 IPA (0.1% DEAISO)/CO$_2$); $^1$H NMR (400 MHz, CDCl$_3$): δ 7.10-7.07 (2H, m), 6.99-6.95 (2H, m), 5.18 (1H, d, J = 2.2 Hz), 4.87 (1H, d, J = 2.2 Hz), 3.85-3.76 (5H, m), 3.40 (1H, d, J = 16.8 Hz), 3.21 (4H, t, J = 4.5 Hz), 2.93 (1H, dd, J = 12.3, 15.5 Hz), 2.79 (2H, d, J = 6.5 Hz), 2.11-2.04 (1H, m), 1.83-1.70 (3H, m), 1.57-1.44 (2H, m), 1.31-1.14 (2H, m), NH not observed |
| Example 53 | 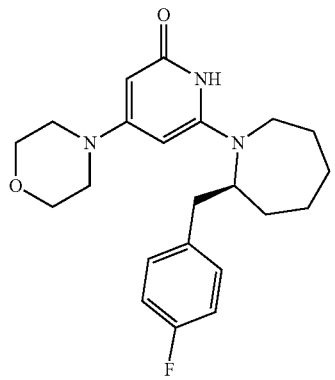 [SMILES: O=c1cc(N2CCOCC2)cc(N2CCCCC[C@H]2Cc2ccc(F)cc2)[nH]1]<br>(S)-6-(2-(4-fluorobenzyl)azepan-1-yl)-4-morpholino pyridin-2(1H)-one | Intermediate 15 | Method D | LCMS (ES+) 386 (M + H)+, RT 3.03 min (Analytical Method A); RT 3.42 min (Analytical Method SFC4, LUX CELLULOSE-4, 40/60 IPA (0.1% DEAISO)/CO$_2$); $^1$H NMR (400 MHz, CDCl$_3$): δ 7.10-7.07 (2H, m), 6.99-6.95 (2H, m), 5.18 (1H, d, J = 2.2 Hz), 4.87 (1H, d, J = 2.2 Hz), 3.85-3.76 (5H, m), 3.40 (1H, d, J = 16.8 Hz), 3.21 (4H, t, J = 4.5 Hz), 2.93 (1H, dd, J = 12.3, 15.5 Hz), 2.79 (2H, d, J = 6.5 Hz), 2.11-2.04 (1H, m), 1.83-1.70 (3H, m), 1.57-1.44 (2H, m), 1.31-1.14 (2H, m), NH not observed |

| Example | Structure and Name | Amine | Buchwald conditions | Analytical data |
|---------|--------------------|-------|---------------------|-----------------|
| Example 54 | 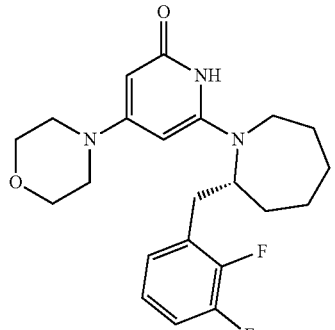<br>(R)-6-(2-(2,3-difluorobenzyl)azepan-1-yl)-4-morpholinopyridin-2(1H)-one | Intermediate 14 | Method D | LCMS (ES+) 404 (M + H)+, RT 3.16 min (Analytical Method B); RT 1.96 min (Analytical Method SFC4, LUX CELLULOSE-4, 40/60 IPA (0.1% DEAISO)/CO$_2$); $^1$H NMR (400 MHz, CDCl$_3$): δ 7.09-6.97 (2H, m), 6.92-6.89 (1H, m), 5.18 (1H, d, J = 1.2 Hz), 5.06 (1H, d, J = 1.9 Hz), 3.95-3.87 (1H, m), 3.79 (4H, t, J = 5.0 Hz), 3.49 (1H, d, J = 17.0 Hz), 3.24 (4H, t, J = 4.8 Hz), 3.14 (1H, dd, J = 12.3, 16.3 Hz), 3.05 (1H, dd, J = 5.7, 13.3 Hz), 2.70 (1H, dd, J = 8.2, 13.0 Hz), 2.07-2.00 (1H, m), 1.87-1.77 (3H, m), 1.60-1.40 (2H, m), 1.33-1.14 (2H, m), NH not observed |
| Example 55 | 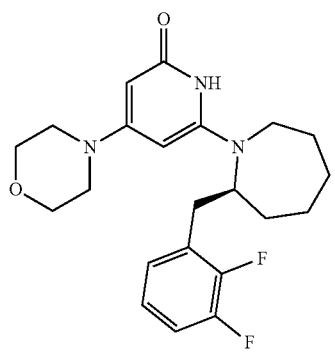 [SMILES: O=c1cc(N2CCOCC2)cc(N2CCCCC[C@H]2Cc2cccc(F)c2F)[nH]1]<br>(S)-6-(2-(2,3-difluorobenzyl)azepan-1-yl)-4-morpholinopyridin-2(1H)-one | Intermediate 14 | Method D | LCMS (ES+) 404 (M + H)+, RT 3.16 min (Analytical Method B); RT 2.41 min (Analytical Method SFC4, LUX CELLULOSE-4, 40/60 IPA (0.1% DEAISO)/CO$_2$); $^1$H NMR (400 MHz, CDCl$_3$): δ 7.09-6.97 (2H, m), 6.92-6.89 (1H, m), 5.18 (1H, d, J = 1.2 Hz), 5.06 (1H, d, J = 1.9 Hz), 3.95-3.87 (1H, m), 3.79 (4H, t, J = 5.0 Hz), 3.49 (1H, d, J = 17.0 Hz), 3.24 (4H, t, J = 4.8 Hz), 3.14 (1H, dd, J = 12.3, 16.3 Hz), 3.05 (1H, dd, J = 5.7, 13.3 Hz), 2.70 (1H, dd, J = 8.2, 13.0 Hz), 2.07-2.00 (1H, m), 1.87-1.77 (3H, m), 1.60-1.40 (2H, m), 1.33-1.14 (2H, m), NH not observed |
| Example 56 | 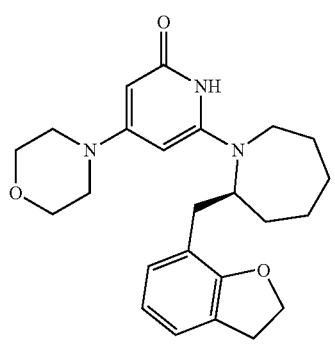 [SMILES: O=c1cc(N2CCOCC2)cc(N2CCCCC[C@H]2Cc2cccc3c2OCC3)[nH]1]<br>(S)-6-(2-((2,3-dihydrobenzofuran-7-yl)methyl)azepan-1-yl)-4-morpholinopyridin-2(1H)-one | Intermediate 13 | Method D | LCMS (ES+) 410 (M + H)+, RT 3.25 min (Analytical Method B); RT 10.76 min (Analytical Method SFC4, YMC CELLULOSE-C, 10/90 MeOH (0.1% DEAISO)/CO$_2$); $^1$H NMR (400 MHz, CDCl$_3$): δ 7.10 (1H, d, J = 7.4 Hz), 6.87 (1H, d, J = 7.4 Hz), 6.78 (1H, t, J = 7.2 Hz), 5.20 (1H, d, J = 1.5 Hz), 5.09 (1H, s), 4.81-4.67 (2H, m), 3.86-3.78 (5H, m), 3.44 (1H, d, J = 15.1 Hz), 3.31-3.23 (7H, m), 3.03 (1H, dd, J = 3.8, 13.4 Hz), 2.49 (1H, dd, J = 10.3, 13.4 Hz), 2.08-2.00 (1H, m), 1.87-1.56 (4H, m), 1.44-1.27 (2H, m), 1.20-1.10 (1H, m) NH not observed |

| Example | Structure and Name | Amine | Buchwald conditions | Analytical data |
|---|---|---|---|---|
| Example 57 | 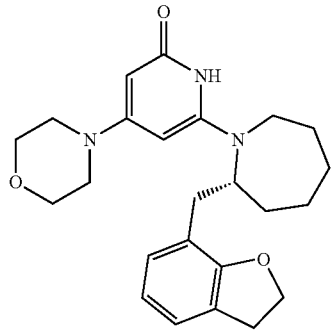 [SMILES: O=c1cc(N2CCOCC2)cc(N2CCCCC[C@@H]2Cc2cccc3c2OCC3)[nH]1]<br>(R)-6-(2-((2,3-dihydrobenzofuran-7-yl)methyl)azepan-1-yl)-4-morpholinopyridin-2(1H)-one | Intermediate 13 | Method D | LCMS (ES+) 410 (M + H)+, RT 3.25 min (Analytical Method B); RT 9.87 min (Analytical Method SFC4, YMC CELLULOSE-C, 10/90 MeOH (0.1% DEAISO)/CO$_2$); $^1$H NMR (400 MHz, CDCl$_3$): δ 7.10 (1H, d, J = 7.4 Hz), 6.87 (1H, d, J = 7.4 Hz), 6.78 (1H, t, J = 7.2 Hz), 5.20 (1H, d, J = 1.5 Hz), 5.09 (1H, s), 4.81-4.67 (2H, m), 3.86-3.78 (5H, m), 3.44 (1H, d, J = 15.1 Hz), 3.31-3.23 (7H, m), 3.03 (1H, dd, J = 3.8, 13.4 Hz), 2.49 (1H, dd, J = 10.3, 13.4 Hz), 2.08-2.00 (1H, m), 1.87-1.56 (4H, m), 1.44-1.27 (2H, m), 1.20-1.10 (1H, m) NH not observed |
| Example 58 | 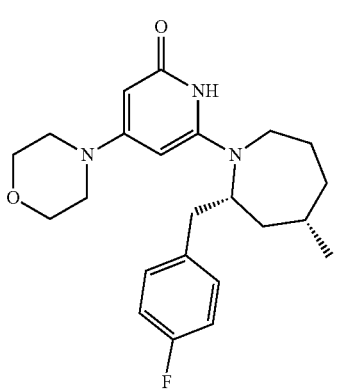 [SMILES: C[C@H]1CCCN(c2cc(N3CCOCC3)cc(=O)[nH]2)[C@@H](Cc2ccc(F)cc2)C1]<br>6-((2R,4S)-2-(4-fluorobenzyl)-4-methylazepan-1-yl)-4-morpholinopyridin-2(1H)-one | Intermediate 25 | Method D | LCMS (ES+) 400 (M + H)+, RT 3.02 min (Analytical Method A); RT 2.60 min (Analytical Method SFC4, YMC AMYLOSE-C, 20/80 MeOH (0.1% DEAISO)/CO$_2$); $^1$H NMR (400 MHz, CDCl$_3$): δ 7.08 (2H, dd, J = 6.0, 8.6 Hz), 6.97 (2H, t, J = 8.3 Hz), 5.18 (1H, d, J = 1.8 Hz), 4.85 (1H, d, J = 2.1 Hz), 3.88-3.76 (5H, m), 3.39-3.34 (1H, m), 3.20 (4H, t, J = 5.0 Hz), 2.95-2.88 (1H, m), 2.83-2.72 (2H, m), 1.79-1.47 (6H, m), 1.11-1.01 (1H, m), 0.93 (3H, d, J = 6.4 Hz), NH not observed. |
| Example 59 | 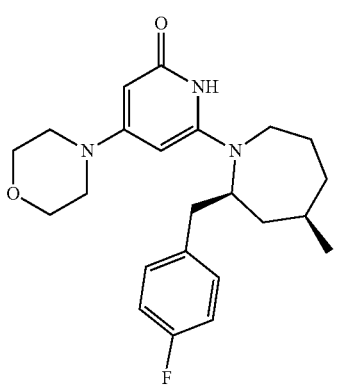 [SMILES: C[C@@H]1CCCN(c2cc(N3CCOCC3)cc(=O)[nH]2)[C@H](Cc2ccc(F)cc2)C1]<br>6-((2S,4R)-2-(4-fluorobenzyl)-4-methylazepan-1-yl)-4-morpholinopyridin-2(1H)-one | Intermediate 25 | Method D | LCMS (ES+) 400 (M + H)+, RT 3.01 min (Analytical Method A);); RT 2.80 min (Analytical Method SFC4, LUX CELLULOSE-4, 40/60 IPA (0.1% DEAISO)/CO$_2$); $^1$H NMR (400 MHz, CDCl$_3$): δ 7.08 (2H, dd, J = 6.0, 8.6 Hz), 6.97 (2H, t, J = 8.3 Hz), 5.18 (1H, d, J = 1.8 Hz), 4.85 (1H, d, J = 2.1 Hz), 3.88-3.76 (5H, m), 3.39-3.34 (1H, m), 3.20 (4H, t, J = 5.0 Hz), 2.95-2.88 (1H, m), 2.83-2.72 (2H, m), 1.79-1.47 (6H, m), 1.11-1.01 (1H, m), 0.93 (3H, d, J = 6.4 Hz), NH not observed |

| Example | Structure and Name | Amine | Buchwald conditions | Analytical data |
|---|---|---|---|---|
| Example 60 | 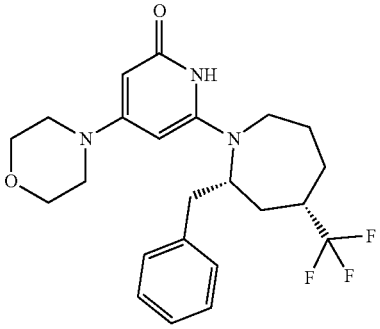 [SMILES: O=c1cc(N2CCOCC2)cc(N2CCC[C@H](C(F)(F)F)C[C@@H]2Cc2ccccc2)[nH]1]<br>6-((2R,4S)-2-benzyl-4-(trifluoromethyl)azepan-1-yl)-4-morpholinopyridin-2(1H)-one | Intermediate 24 | Method D | LCMS (ES+) 436 (M + H)+, RT 3.05 min (Analytical Method A); RT 1.85 min (Analytical Method SFC4, YMC AMYLOSE-C, 15/85 MeOH (0.1% DEAISO)/CO$_2$); $^1$H NMR (400 MHz, CDCl$_3$): δ 7.32-7.22 (3H, m), 7.15-7.13 (2H, m), 5.20 (1H, d, J = 1.8 Hz), 4.91 (1H, d, J = 1.8 Hz), 4.04-3.97 (1H, m), 3.77 (4H, t, J = 4.7 Hz), 3.60-3.55 (1H, m), 3.19 (4H, dd, J = 4.2, 5.8 Hz), 2.96-2.81 (3H, m), 2.29 (1H, dd, J = 5.8, 15.0 Hz), 2.09-1.99 (2H, m), 1.85-1.79 (1H, m), 1.68-1.57 (2H, m), 1.41-1.30 (1H, m), NH not observed |
| Example 61 | 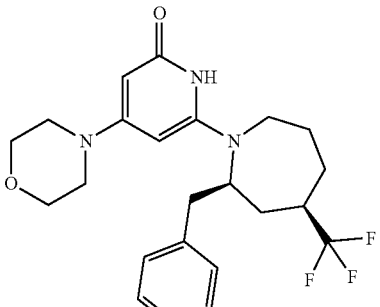<br>6-((2S,4R)-2-benzyl-4-(trifluoromethyl)azepan-1-yl)-4-morpholinopyridin-2(1H)-one | Intermediate 24 | Method D | LCMS (ES+) 436 (M + H)+, RT 3.05 min (Analytical Method A); RT 2.75 min (Analytical Method SFC4, LUX CELLULOSE-4, 30/70 IPA (0.1% DEAISO)/CO$_2$); $^1$H NMR (400 MHz, CDCl$_3$): δ 7.32-7.22 (3H, m), 7.15-7.13 (2H, m), 5.20 (1H, d, J = 1.8 Hz), 4.91 (1H, d, J = 1.8 Hz), 4.04-3.97 (1H, m), 3.77 (4H, t, J = 4.7 Hz), 3.60-3.55 (1H, m), 3.19 (4H, dd, J = 4.2, 5.8 Hz), 2.96-2.81 (3H, m), 2.29 (1H, dd, J = 5.8, 15.0 Hz), 2.09-1.99 (2H, m), 1.85-1.79 (1H, m), 1.68-1.57 (2H, m), 1.41-1.30 (1H, m), NH not observed |
| Example 62 | 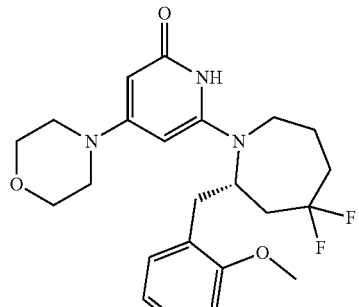<br>(S)-6-(4,4-difluoro-2-(2-methoxybenzyl)azepan-1-yl)-4-morpholinopyridin-2(1H)-one | Intermediate 27 | Method D | LCMS (ES+) 434 (M + H)+, RT 3.22 min (Analytical Method B); RT 2.46 min (Analytical Method SFC4, YMC AMYLOSE-C, 30/70 IPA (0.1% DEAISO)/CO$_2$); $^1$H NMR δ (ppm) (400 MHz, CDCl$_3$) 7.31-7.29 (1H, m), 7.05-7.03 (1H, m), 6.98 (1H, d, J = 8.6 Hz), 6.91 (1H, t, J = 6.9 Hz), 5.25 (1H, d, J = 1.9 Hz), 4.91 (1H, d, J = 2.4 Hz), 4.21 (3H, s), 4.05 (1H, m), 3.79 (4H, t, J = 4.8 Hz), 3.60-3.55 (1H, m), 3.43-3.36 (1H, m), 3.27-3.17 (5H, m), 2.49 (1H, t, J = 12.0 Hz), 2.38-2.28 (1H, m), 2.21-2.07 (2H, m), 1.98-1.82 (2H, m), NH not observed |

| Example | Structure and Name | Amine | Buchwald conditions | Analytical data |
|---|---|---|---|---|
| Example 63 | 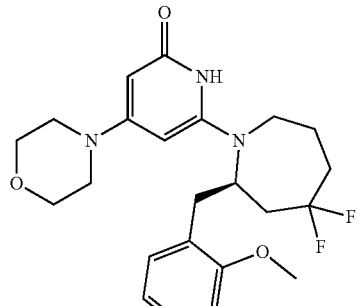<br>(R)-6-(4,4-difluoro-2-(2-methoxybenzyl)azepan-1-yl)-4-morpholinopyridin-2(1H)-one | Intermediate 27 | Method D | LCMS (ES+) 434 (M + H)+, RT 3.22 min (Analytical Method B); RT 3.37 min (Analytical Method SFC4, YMC AMYLOSE-C, 30/70 IPA (0.1% DEAISO)/CO$_2$); $^1$H NMR δ (ppm) (400 MHz, CDCl$_3$) 7.31-7.29 (1H, m), 7.05-7.03 (1H, m), 6.98 (1H, d, J = 8.6 Hz), 6.91 (1H, t, J = 6.9 Hz), 5.25 (1H, d, J = 1.9 Hz), 4.91 (1H, d, J = 2.4 Hz), 4.21 (3H, s), 4.05 (1H, m), 3.79 (4H, t, J = 4.8 Hz), 3.60-3.55 (1H, m), 3.43-3.36 (1H, m), 3.27-3.17 (5H, m), 2.49 (1H, t, J = 12.0 Hz), 2.38-2.28 (1H, m), 2.21-2.07 (2H, m), 1.98-1.82 (2H, m), NH not observed |
| Example 64 | 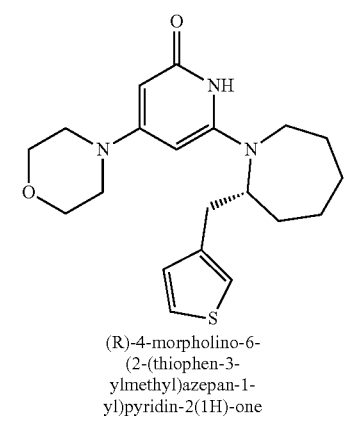<br>(R)-4-morpholino-6-(2-(thiophen-3-ylmethyl)azepan-1-yl)pyridin-2(1H)-one | Intermediate 26 | Method D | LCMS (ES+) 374 (M + H)+, RT 2.85 min (Analytical Method A); RT 1.82 min (Analytical Method SFC4, YMC AMYLOSE-C, 40/60 IPA (0.1% DEAISO)/CO$_2$); $^1$H NMR δ (ppm) (400 MHz, CDCl$_3$) 7.28-7.26 (1H, m), 6.98-6.97 (1H, m), 6.89 (1H, dd, J = 1.1, 4.8 Hz), 5.18 (1H, J = 2.0 Hz), 4.89 (1H, d, J = 2.2 Hz), 3.80-3.75 (5H, m), 3.42-3.37 (1H, m), 3.22-3.20 (4H, m), 2.98 (1H, dd, J = 11.8, 16.0), 2.90-2.80 (2H, m), 2.17-2.09 (1H, m),, 1.84-1.70 (3H, m), 1.59-1.47 (2H, m), 1.31-1.16 (2H, m), NH not observed. |
| Example 65 | 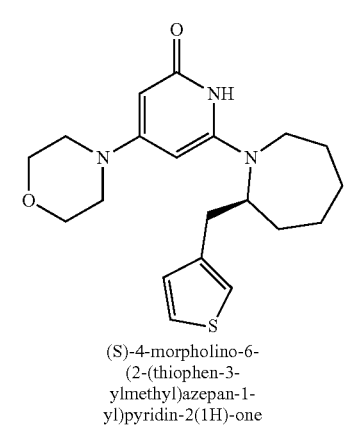<br>(S)-4-morpholino-6-(2-(thiophen-3-ylmethyl)azepan-1-yl)pyridin-2(1H)-one | Intermediate 26 | Method D | LCMS (ES+) 374 (M + H)+, RT 2.85 min (Analytical Method A); RT 1.30 min (Analytical Method SFC4, YMC AMYLOSE-C, 40/60 IPA (0.1% DEAISO)/CO$_2$); $^1$H NMR δ (ppm) (400 MHz, CDCl$_3$) 7.28-7.26 (1H, m), 6.98-6.97 (1H, m), 6.89 (1H, dd, J = 1.1, 4.8 Hz), 5.18 (1H, J = 2.0 Hz), 4.89 (1H, d, J = 2.2 Hz), 3.80-3.75 (5H, m), 3.42-3.37 (1H, m), 3.22-3.20 (4H, m), 2.98 (1H, dd, J = 11.8, 16.0), 2.90-2.80 (2H, m), 2.17-2.09 (1H, m),, 1.84-1.70 (3H, m), 1.59-1.47 (2H, m), 1.31-1.16 (2H, m), NH not observed. |

| Example | Structure and Name | Amine | Buchwald conditions | Analytical data |
|---|---|---|---|---|
| Example 66 | 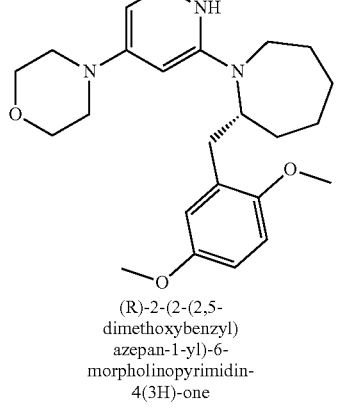<br>(R)-2-(2-(2,5-dimethoxybenzyl)azepan-1-yl)-6-morpholinopyrimidin-4(3H)-one | Intermediate 9 | Method D | LCMS (ES+) 428 (M + H)+, RT 3.07 min (Analytical Method A); RT 2.11 min (Analytical Method SFC4, YMC AMYLOSE-C, 35/65 MeOH (0.1% DEAISO)/$CO_2$); $^1$H NMR (400 MHz, $CDCl_3$): δ 9.00 (1H, br s), 6.87 (1H, d, J = 9.1 Hz), 6.76 (1H, dd, J = 3.5, 8.7 Hz), 6.66 (1H, d, J = 2.9 Hz), 5.21 (1H, d, J = 1.8 Hz), 4.93 (1H, d, J = 1.6 Hz), 4.15 (3H, s), 3.80-3.72 (8H, m), 3.44-3.40 (1H, m), 3.34-3.23 (5H, m), 3.12 (1H, dd, J = 2.7, 13.1 Hz), 2.38 (1H, dd, J = 11.4, 12.8 Hz), 2.04-1.97 (1H, m), 1.87-1.57 (4H, m), 1.44-1.26 (2H, m), 1.18-1.08 (1H, m) |
| Example 67 | 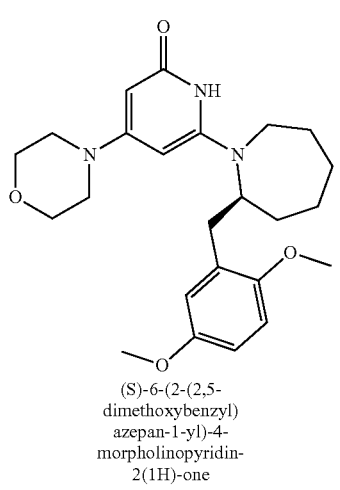<br>(S)-6-(2-(2,5-dimethoxybenzyl)azepan-1-yl)-4-morpholinopyridin-2(1H)-one | Intermediate 9 | Method D | LCMS (ES+) 428 (M + H)+, RT 3.06 min (Analytical Method A); RT 1.47 min (Analytical Method SFC4, YMC AMYLOSE-C, 35/65 MeOH (0.1% DEAISO)/$CO_2$); $^1$H NMR (400 MHz, $CDCl_3$): δ 9.00 (1H, brs), 6.87 (1H, d, J = 9.1 Hz), 6.76 (1H, dd, J = 3.5, 8.7 Hz), 6.66 (1H, d, J = 2.9 Hz), 5.21 (1H, d, J = 1.8 Hz), 4.93 (1H, d, J = 1.6 Hz), 4.15 (3H, s), 3.80-3.72 (8H, m), 3.44-3.40 (1H, m), 3.34-3.23 (5H, m), 3.12 (1H, dd, J = 2.7, 13.1 Hz), 2.38 (1H, dd, J = 11.4, 12.8 Hz), 2.04-1.97 (1H, m), 1.87-1.57 (4H, m), 1.44-1.26 (2H, m), 1.18-1.08 (1H, m). |
| Example 68 | <br>(R)-6-(2-(2,3-dimethoxybenzyl)azepan-1-yl)-4-morpholinopyridin-2(1H)-one | Intermediate 10 | Method D | LCMS (ES+) 428 (M + H)+, RT 3.21 min (Analytical Method B); RT 2.18 min (Analytical Method SFC4, YMC AMYLOSE-C, 30/70 IPA (0.1% DEAISO)/$CO_2$); $^1$H NMR (400 MHz, $CDCl_3$): δ 6.94 (1H, t, J = 7.9 Hz), 6.84 (1H, dd, J = 1.6, 8.1 Hz), 6.70 (1H, dd, J = 1.6, 7.4 Hz), 5.21 (1H, d, J = 2.3 Hz), 5.01 (1H, d, J = 2.3 Hz), 4.05 (3H, s), 3.87 (3H, s), 3.80-3.68 (5H, m), 3.45-3.41 (1H, m), 3.30-3.20 (5H, m), 3.03 (1H, dd, J = 3.8, 12.9 Hz), 2.46 (1H, dd, J = 10.3, 13.0 Hz), 1.97-1.55 (5H, m), 1.42-1.23 (3H, m), 1.15-1.06 (1H, m) |

| Example | Structure and Name | Amine | Buchwald conditions | Analytical data |
|---|---|---|---|---|
| Example 69 | 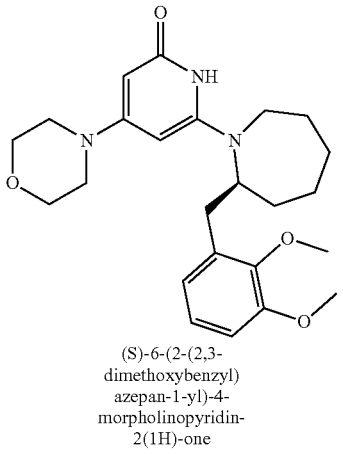<br>(S)-6-(2-(2,3-dimethoxybenzyl)azepan-1-yl)-4-morpholinopyridin-2(1H)-one | Intermediate 10 | Method D | LCMS (ES+) 428 (M + H)$^+$, RT 3.21 min (Analytical Method B); RT 2.64 min (Analytical Method SFC4, YMC AMYLOSE-C, 30/70 IPA (0.1% DEAISO)/CO$_2$); $^1$H NMR (400 MHz, CDCl$_3$): δ 6.94 (1H, t, J = 7.9 Hz), 6.84 (1H, dd, J = 1.6, 8.1 Hz), 6.70 (1H, dd, J = 1.6, 7.4 Hz), 5.21 (1H, d, J = 2.3 Hz), 5.01 (1H, d, J = 2.3 Hz), 4.05 (3H, s), 3.87 (3H, s), 3.80-3.68 (5H, m), 3.45-3.41 (1H, m), 3.30-3.20 (5H, m), 3.03 (1H, dd, J = 3.8, 12.9 Hz), 2.46 (1H, dd, J = 10.3, 13.0 Hz), 1.97-1.55 (5H, m), 1.42-1.23 (3H, m), 1.15-1.06 (1H, m). |
| Example 70 | 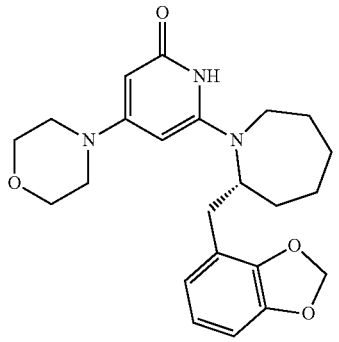 [SMILES: O=c1cc(N2CCOCC2)cc(N2CCCCC[C@@H]2Cc2cccc3c2OCO3)[nH]1]<br>(R)-6-(2-(benzo[d][1,3]dioxol-4-ylmethyl)azepan-1-yl)-4-morpholinopyridin-2(1H)-one | Intermediate 11 | Method D | LCMS (ES+) 412 (M + H)$^+$, RT 3.01 min (Analytical Method A); RT 2.84 min (Analytical Method SFC4, YMC CELLULOSE-C, 25/75 IPA (0.1% DEAISO)/CO$_2$); $^1$H NMR δ (ppm) (400 MHz, CDCl$_3$) 6.78-6.72 (2H, m), 6.61 (1H, dd, J = 1.8, 7.2 Hz), 6.02 (1H, d, J = 1.4 Hz), 5.99 (1H, d, J = 1.4 Hz), 5.19 (1H, d, J = 2.3 Hz), 5.03 (1H, d, J = 2.3 Hz), 3.87-3.77 (5H, m), 3.47-3.43 (1H, m), 3.25-3.18 (5H, m), 2.99 (1H, dd, J = 4.3, 13.3 Hz), 2.59 (1H, dd, J = 9.4, 13.6 Hz), 2.12-2.05 (1H, m), 1.88-1.74 (3H, m), 1.64-1.52 (1H, m), 1.49-1.40 (1H, m), 1.36-1.12 (2H, m), NH not observed |
| Example 71 | 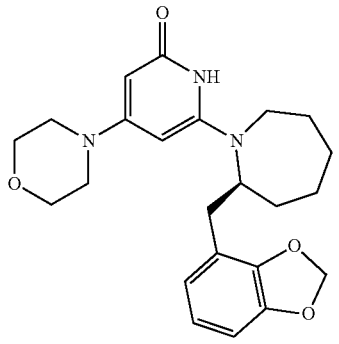 [SMILES: O=c1cc(N2CCOCC2)cc(N2CCCCC[C@H]2Cc2cccc3c2OCO3)[nH]1]<br>(S)-6-(2-(benzo[d][1,3]dioxol-4-ylmethyl)azepan-1-yl)-4-morpholinopyridin-2(1H)-one | Intermediate 11 | Method D | LCMS (ES+) 412 (M + H)$^+$, RT 3.01 min (Analytical Method A); RT 3.53 min (Analytical Method SFC4, YMC CELLULOSE-C, 25/75 IPA (0.1% DEAISO)/CO$_2$); $^1$H NMR δ (ppm) (400 MHz, CDCl$_3$) 6.78-6.72 (2H, m), 6.61 (1H, dd, J = 1.8, 7.2 Hz), 6.02 (1H, d, J = 1.4 Hz), 5.99 (1H, d, J = 1.4 Hz), 5.19 (1H, d, J = 2.3 Hz), 5.03 (1H, d, J = 2.3 Hz), 3.87-3.77 (5H, m), 3.47-3.43 (1H, m), 3.25-3.18 (5H, m), 2.99 (1H, dd, J = 4.3, 13.3 Hz), 2.59 (1H, dd, J = 9.4, 13.6 Hz), 2.12-2.05 (1H, m), 1.88-1.74 (3H, m), 1.64-1.52 (1H, m), 1.49-1.40 (1H, m), 1.36-1.12 (2H, m), NH not observed |

| Example | Structure and Name | Amine | Buchwald conditions | Analytical data |
|---|---|---|---|---|
| Example 72 | 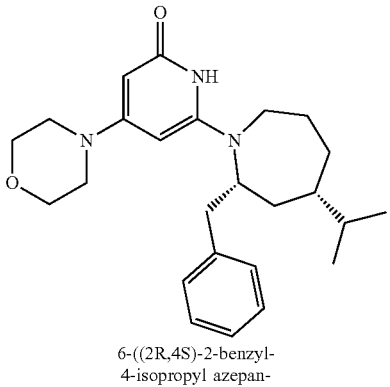<br>6-((2R,4S)-2-benzyl-4-isopropyl azepan-1-yl)-4-morpholinopyridin-2(1H)-one | Intermediate 22 | Method D | LCMS (ES+) 410 (M + H)+, RT 3.19 min (Analytical Method A); RT 3.22 min (Analytical Method SFC4, YMC CELLULOSE-C, 35/65 IPA (0.1% DEAISO)/CO$_2$); $^1$H NMR (400 MHz, CDCl$_3$): δ 7.31-7.22 (3H, m), 7.14-7.12 (2H, m), 5.15 (1H, d, J = 2.1 Hz), 4.83 (1H, d, J = 1.9 Hz), 3.78-3.69 (5H, m), 3.39-3.35 (1H, m), 3.18 (4H, dd, J = 3.9, 5.5 Hz), 2.96 (1H, dd, J = 12.2, 16.2 Hz), 2.87-2.77 (2H, m), 1.88 (1H, dd, J = 5.8, 14.5 Hz), 1.77-1.36 (5H, m), 1.21-1.10 (2H, m), 0.81 (3H, d, J = 2.1 Hz), 0.79 (3H, d, J = 1.9 Hz), NH not observed |
| Example 73 | 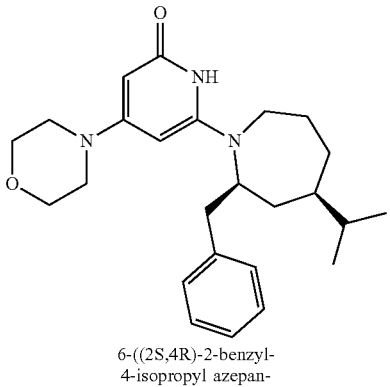<br>6-((2S,4R)-2-benzyl-4-isopropyl azepan-1-yl)-4-morpholinopyridin-2(1H)-one | Intermediate 22 | Method D | LCMS (ES+) 410 (M + H)+, RT 3.46 min (Analytical Method B); RT 7.21 min (Analytical Method SFC4, YMC AMYLOSE-C, 10/90 MeOH (0.1% DEAISO)/CO$_2$); $^1$H NMR (400 MHz, CDCl$_3$): δ 7.31-7.22 (3H, m), 7.14-7.12 (2H, m), 5.15 (1H, d, J = 2.1 Hz), 4.83 (1H, d, J = 1.9 Hz), 3.78-3.69 (5H, m), 3.39-3.35 (1H, m), 3.18 (4H, dd, J = 3.9, 5.5 Hz), 2.96 (1H, dd, J = 12.2, 16.2 Hz), 2.87-2.77 (2H, m), 1.88 (1H, dd, J = 5.8, 14.5 Hz), 1.77-1.36 (5H, m), 1.21-1.10 (2H, m), 0.81 (3H, d, J = 2.1 Hz), 0.79 (3H, d, J = 1.9 Hz), NH not observed |
| Example 74 | 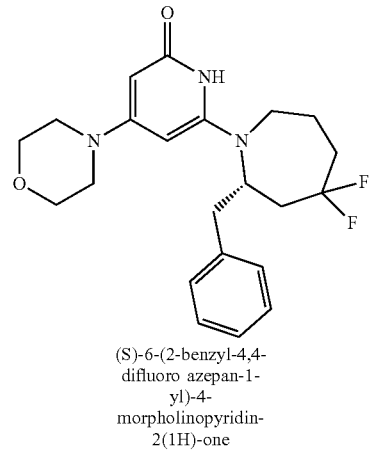<br>(S)-6-(2-benzyl-4,4-difluoro azepan-1-yl)-4-morpholinopyridin-2(1H)-one | Intermediate 21 | Method D | LCMS (ES+) 404 (M + H)+, RT 2.93 min (Analytical Method A); RT 6.80 min (Analytical Method SFC1, LUX CELLULOSE-4, 35/65 IPA (0.1% DEAISO)/CO$_2$); $^1$H NMR (400 MHz, CDCl$_3$): δ 7.32-7.23 (3H, m), 7.15-7.13 (2H, m), 5.24 (1H, d, J = 1.9 Hz), 5.01 (1H, d, J = 2.2 Hz), 4.19-4.12 (1H, m), 3.80-3.71 (5H, m), 3.22 (4H, t, J = 4.8 Hz), 2.97-2.83 (3H, m), 2.46-2.05 (3H, m), 1.90-1.71 (3H, m), NH not observed |

| Example | Structure and Name | Amine | Buchwald conditions | Analytical data |
|---|---|---|---|---|
| Example 75 | 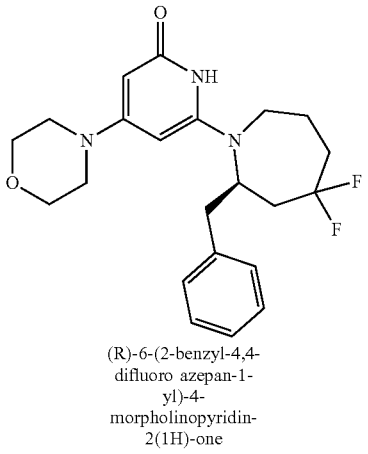<br>(R)-6-(2-benzyl-4,4-difluoro azepan-1-yl)-4-morpholinopyridin-2(1H)-one | Intermediate 21 | Method D | LCMS (ES+) 404 (M + H)$^+$, RT 2.93 min (Analytical Method A); RT 5.24 min (Analytical Method SFC1, LUX CELLULOSE-4, 35/65 IPA (0.1% DEAISO)/CO$_2$); $^1$H NMR (400 MHz, CDCl$_3$): δ 7.32-7.23 (3H, m), 7.15-7.13 (2H, m), 5.24 (1H, d, J = 1.9 Hz), 5.01 (1H, d, J = 2.2 Hz), 4.19-4.12 (1H, m), 3.80-3.71 (5H, m), 3.22 (4H, t, J = 4.8 Hz), 2.97-2.83 (3H, m), 2.46-2.05 (3H, m), 1.90-1.71 (3H, m), NH not observed |
| Example 76 | 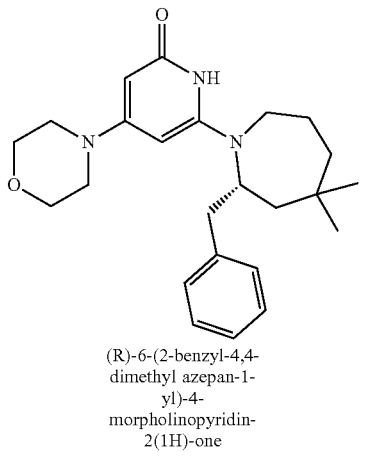<br>(R)-6-(2-benzyl-4,4-dimethyl azepan-1-yl)-4-morpholinopyridin-2(1H)-one | Intermediate 20 | Method D | LCMS (ES+) 396 (M + H)$^+$, RT 3.07 min (Analytical Method A); RT 4.48 min (Analytical Method SFC1, YMC AMYLOSE-C, 20/80 IPA (0.1% DEAISO)/CO$_2$); $^1$H NMR (400 MHz, CDCl$_3$): δ 7.31-7.22 (3H, m), 7.14-7.12 (2H, m), 5.17 (1H, d, J = 1.7 Hz), 4.85 (1H, d, J = 2.3 Hz), 3.79-3.70 (5H, m), 3.38-3.33 (1H, m), 3.19 (4H, t, J = 5.0 Hz), 2.95-2.73 (3H, m), 1.73-1.57 (3H, m), 1.47-1.41 (1H, m), 1.25-1.18 (2H, m), 0.93 (3H, s), 0.78 (3H, s), NH not observed |
| Example 77 | 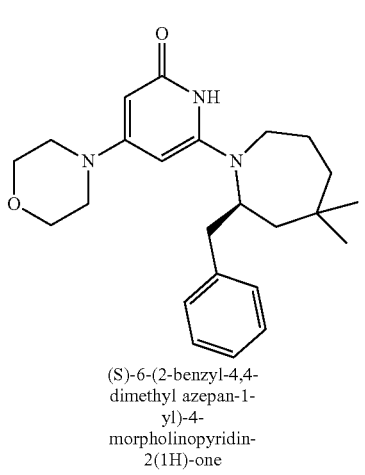<br>(S)-6-(2-benzyl-4,4-dimethyl azepan-1-yl)-4-morpholinopyridin-2(1H)-one | Intermediate 20 | Method D | LCMS (ES+) 396 (M + H)$^+$, RT 3.06 min (Analytical Method A); RT 5.75 min (Analytical Method SFC1, YMC AMYLOSE-C, 20/80 IPA (0.1% DEAISO)/CO$_2$); $^1$H NMR (400 MHz, CDCl$_3$): δ 7.31-7.22 (3H, m), 7.14-7.12 (2H, m), 5.17 (1H, d, J = 1.7 Hz), 4.85 (1H, d, J = 2.3 Hz), 3.79-3.70 (5H, m), 3.38-3.33 (1H, m), 3.19 (4H, t, J = 5.0 Hz), 2.95-2.73 (3H, m), 1.73-1.57 (3H, m), 1.47-1.41 (1H, m), 1.25-1.18 (2H, m), 0.93 (3H, s), 0.78 (3H, s), NH not observed |

| Example | Structure and Name | Amine | Buchwald conditions | Analytical data |
|---|---|---|---|---|
| Example 78 | 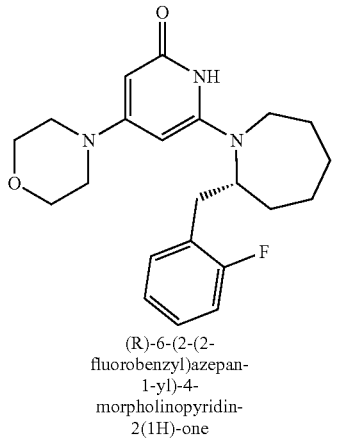<br>(R)-6-(2-(2-fluorobenzyl)azepan-1-yl)-4-morpholinopyridin-2(1H)-one | Intermediate 19 | Method D | LCMS (ES+) 386 (M + H)+, RT 3.24 min (Analytical Method B); RT 3.90 min (Analytical Method SFC4, LUX CELLULOSE-4, 55/45 IPA (0.1% DEAISO)/CO$_2$); $^1$H NMR (400 MHz, CDCl$_3$): δ 7.25-7.20 (1H, m), 7.17-7.12 (1H, m), 7.09-7.01 (2H, m), 5.19 (1H, d, J = 1.8 Hz), 5.09 (1H, d, J = 1.9 Hz), 3.90-3.82 (1H, m), 3.79 (4H, t, J = 5.0 Hz), 3.48 (1H, d, J = 15.7 Hz), 3.24 (4H, t, J = 5.0 Hz), 3.17 (1H, dd, J = 11.9, 15.9 Hz), 3.08 (1H, dd, J = 5.3, 13.6 Hz), 2.62 (1H, dd, J = 8.7, 13.4 Hz), 2.04-1.97 (1H, m), 1.87-1.74 (3H, m), 1.60-1.39 (2H, m), 1.34-1.13 (2H, m), NH not observed |
| Example 79 | 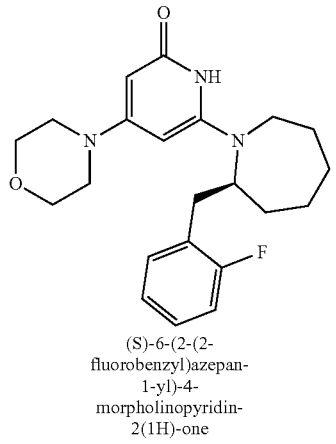<br>(S)-6-(2-(2-fluorobenzyl)azepan-1-yl)-4-morpholinopyridin-2(1H)-one | Intermediate 19 | Method D | LCMS (ES+) 386 (M + H)+, RT 3.24 min (Analytical Method B); RT 1.80 min (Analytical Method SFC4, LUX CELLULOSE-4, 5/95 IPA (0.1% DEAISO)/CO$_2$); $^1$H NMR (400 MHz, CDCl$_3$): δ 7.25-7.20 (1H, m), 7.17-7.12 (1H, m), 7.09-7.01 (2H, m), 5.19 (1H, d, J = 1.8 Hz), 5.09 (1H, d, J = 1.9 Hz), 3.90-3.82 (1H, m), 3.79 (4H, t, J = 5.0 Hz), 3.48 (1H, d, J = 15.7 Hz), 3.24 (4H, t, J = 5.0 Hz), 3.17 (1H, dd, J = 11.9, 15.9 Hz), 3.08 (1H, dd, J = 5.3, 13.6 Hz), 2.62 (1H, dd, J = 8.7, 13.4 Hz), 2.04-1.97 (1H, m), 1.87-1.74 (3H, m), 1.60-1.39 (2H, m), 1.34-1.13 (2H, m), NH not observed |
| Example 80 | 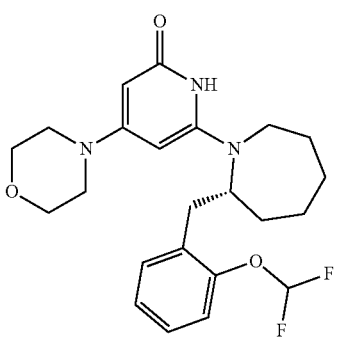 [SMILES: O=c1cc(N2CCOCC2)cc(N2CCCCC[C@@H]2Cc2ccccc2OC(F)F)[nH]1]<br>(R)-6-(2-(2-(difluoromethoxy)benzyl)azepan-1-yl)-4-morpholinopyridin-2(1H)-one | Intermediate 18 | Method D | LCMS (ES+) 434 (M + H)+, RT 3.01 min (Analytical Method A); RT 3.67 min (Analytical Method SFC4, LUX CELLULOSE-4, 30/70 MeOH (0.1% DEAISO)/CO$_2$); $^1$H NMR (400 MHz, CDCl$_3$): δ 7.28-6.84 (5H, m), 5.16 (1H, d, J = 2.4 Hz), 4.94 (1H, d, J = 2.4 Hz), 3.84-3.76 (5H, m), 3.45 (1H, d, J = 15.7 Hz), 3.27-3.20 (5H, m), 3.06 (1H, dd, J = 5.2, 13.1 Hz), 2.62 (1H, dd, J = 8.8, 13.3 Hz), 2.04-1.97 (1H, m), 1.87-1.76 (3H, m), 1.65-1.53 (1H, m), 1.48-1.39 (1H, m), 1.36-1.24 (1H, m), 1.21-1.12 (1H, m) |

| Example | Structure and Name | Amine | Buchwald conditions | Analytical data |
|---|---|---|---|---|
| Example 81 | 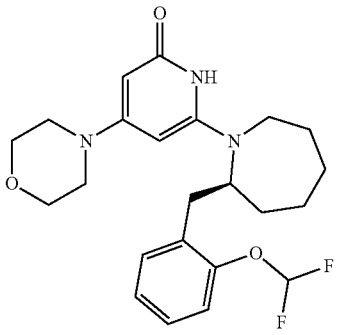 [SMILES: O=c1cc(N2CCOCC2)cc(N2CCCCC[C@H]2Cc2ccccc2OC(F)F)[nH]1]<br>(S)-6-(2-(2-(difluoromethoxy)benzyl)azepan-1-yl)-4-morpholinopyridin-2(1H)-one | Intermediate 18 | Method D | LCMS (ES+) 434 (M + H)+, RT 3.01 min (Analytical Method A); RT 3.11 min (Analytical Method SFC4, LUX CELLULOSE-4, 30/70 MeOH (0.1% DEAISO)/$CO_2$); $^1$H NMR (400 MHz, $CDCl_3$): δ 7.28-6.84 (5H, m), 5.16 (1H, d, J = 2.4 Hz), 4.94 (1H, d, J = 2.4 Hz), 3.84-3.76 (5H, m), 3.45 (1H, d, J = 15.7 Hz), 3.27-3.20 (5H, m), 3.06 (1H, dd, J = 5.2, 13.1 Hz), 2.62 (1H, dd, J = 8.8, 13.3 Hz), 2.04-1.97 (1H, m), 1.87-1.76 (3H, m), 1.65-1.53 (1H, m), 1.48-1.39 (1H, m), 1.36-1.24 (1H, m), 1.21-1.12 (1H, m) |
| Example 82 | 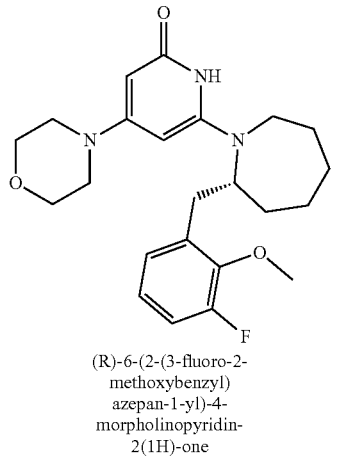<br>(R)-6-(2-(3-fluoro-2-methoxybenzyl)azepan-1-yl)-4-morpholinopyridin-2(1H)-one | Intermediate 12 | Method D | LCMS (ES+) 416 (M + H)+, RT 3.31 min (Analytical Method B); RT 4.96 min (Analytical Method SF4, LUX CELLULOSE-4, 30/70 MeOH (0.1% DEAISO)/$CO_2$); $^1$H NMR (400 MHz, $CDCl_3$): δ 7.02-6.97 (1H, m), 6.91 (1H, dt, J = 4.7, 7.7 Hz), 6.86-6.84 (1H, m), 5.21 (1H, d, J = 2.1 Hz), 4.98 (1H, d, J = 2.3 Hz), 4.20 (3H, d, J = 3 Hz), 3.79 (4H, t, J = 4.9 Hz), 3.76-3.68 (1H, m), 3.43 (1H, d, J = 15.8 Hz), 3.30-3.23 (5H, m), 3.05 (1H, dd, J = 3.8, 13.0 Hz), 2.50 (1H, dd, J = 10.4, 12.5 Hz), 1.98-1.91 (1H, m), 1.87-1.75 (3H, m), 1.68-1.56 (1H, m), 1.43-1.25 (2H, m), 1.18-1.08 (1H, m), NH not observed |
| Example 83 | 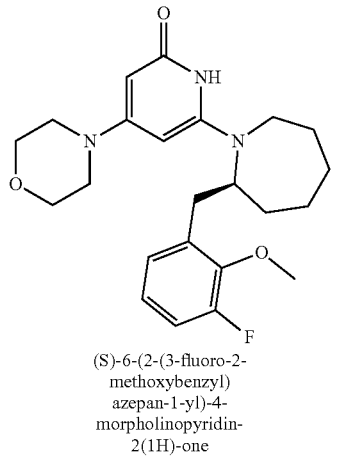<br>(S)-6-(2-(3-fluoro-2-methoxybenzyl)azepan-1-yl)-4-morpholinopyridin-2(1H)-one | Intermediate 12 | Method D | LCMS (ES+) 416 (M + H)+, RT 3.04 min (Analytical Method A); RT 4.34 min (Analytical Method SFC4, LUX CELLULOSE-4, 30/70 MeOH (0.1% DEAISO)/$CO_2$); $^1$H NMR (400 MHz, $CDCl_3$): δ 7.02-6.97 (1H, m), 6.91 (1H, dt, J = 4.7, 7.7 Hz), 6.86-6.84 (1H, m), 5.21 (1H, d, J = 2.1 Hz), 4.98 (1H, d, J = 2.3 Hz), 4.20 (3H, d, J = 3 Hz), 3.79 (4H, t, J = 4.9 Hz), 3.76-3.68 (1H, m), 3.43 (1H, d, J = 15.8 Hz), 3.30-3.23 (5H, m), 3.05 (1H, dd, J = 3.8, 13.0 Hz), 2.50 (1H, dd, J = 10.4, 12.5 Hz), 1.98-1.91 (1H, m), 1.87-1.75 (3H, m), 1.68-1.56 (1H, m), 1.43-1.25 (2H, m), 1.18-1.08 (1H, m), NH not observed |

| Example | Structure and Name | Amine | Buchwald conditions | Analytical data |
|---|---|---|---|---|
| Example 84 | 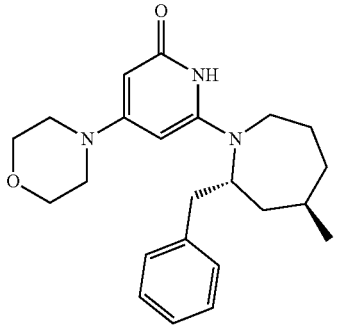 [SMILES: C[C@@H]1CCCN(c2cc(N3CCOCC3)cc(=O)[nH]2)[C@@H](Cc2ccccc2)C1]<br>6-((2R,4R)-2-benzyl-4-methylazepan-1-yl)-4-morpholinopyridin-2(1H)-one | Intermediate 23 | Method D | LCMS (ES+) 382 (M + H)+, RT 3.22 min (Analytical Method B); RT 2.11 min (Analytical Method SFC4, LUX CELLULOSE-4, 45/55 IPA (0.1% DEAISO)/CO$_2$); $^1$H NMR (400 MHz, CDCl$_3$): δ 7.31-7.21 (3H, m), 7.14-7.12 (2H, m), 5.16 (1H, d, J = 2.3 Hz), 4.86 (1H, d, J = 2.3 Hz), 3.86-3.80 (1H, m), 3.77 (4H, t, J = 5.1 Hz), 3.36 (1H, d, J = 15.2 Hz), 3.19 (4H, t, J = 5.1 Hz), 3.01-2.94 (1H, m), 2.79 (2H, d, J = 5.7 Hz), 1.82-1.45 (6H, m), 1.13-1.02 (1H, m), 0.93 (3H, d, J = 6.1 Hz), NH not observed |
| Example 85 | 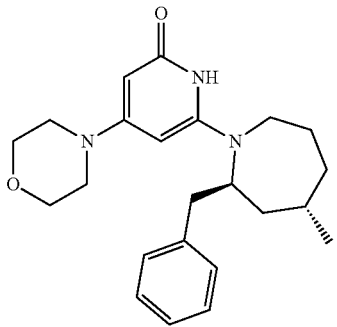 [SMILES: C[C@H]1CCCN(c2cc(N3CCOCC3)cc(=O)[nH]2)[C@H](Cc2ccccc2)C1]<br>6-((2S,4S)-2-benzyl-4-methylazepan-1-yl)-4-morpholinopyridin-2(1H)-one as an off-white solid | Intermediate 23 | Method D | LCMS (ES+) 382 (M + H)+, RT 3.22 min (Analytical Method B); RT 1.73 min (Analytical Method SFC1, LUX CELLULOSE-4, 45/55 IPA (0.1% DEAISO)/CO$_2$); $^1$H NMR (400 MHz, CDCl$_3$): δ 7.31-7.21 (3H, m), 7.14-7.12 (2H, m), 5.16 (1H, d, J = 2.3 Hz), 4.86 (1H, d, J = 2.3 Hz), 3.86-3.80 (1H, m), 3.77 (4H, t, J = 5.1 Hz), 3.36 (1H, d, J = 15.2 Hz), 3.19 (4H, t, J = 5.1 Hz), 3.01-2.94 (1H, m), 2.79 (2H, d, J = 5.7 Hz), 1.82-1.45 (6H, m), 1.13-1.02 (1H, m), 0.93 (3H, d, J = 6.1 Hz), NH not observed |

Intermediates for the following compounds were prepared in the same manner as before, the amines were used without purification in the Buchwald coupling.

| Example | Structure and Name | Amine | Buchwald conditions | Analytical data |
|---|---|---|---|---|
| Example 86 | 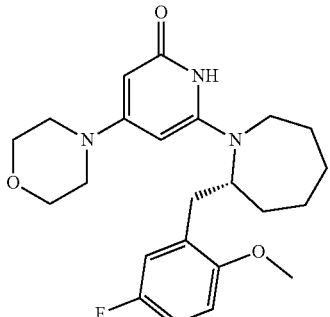<br>(R)-6-(2-(5-fluoro-2-methoxybenzyl)-azepan-1-yl)-4-morpholinopyridin-2(1H)-one | 2-(5-fluoro-2-methoxy benzyl) azepane | Method D | LCMS (ES+) 416 (M + H)+, RT 3.17 min (Analytical Method A); RT 2.55 min (Analytical Method SFC4, YMC AMYLOSE-C, 30/70 MeOH (0.1% DEAISO)/CO$_2$); $^1$H NMR (400 MHz, CDCl$_3$): δ 8.90 (1H, br s), 6.96-6.85 (2H, m), 6.82-6.79 (1H, m), 5.22 (1H, s), 5.22 (1H, d, J = 1.9 Hz), 4.93 (1H, d, J = 1.7 Hz), 4.18 (3H, s), 3.80-3.72 (5H, m), 3.45-3.41 (1H, m), 3.33-3.24 (5H, m), 3.13 (1H, dd, J = 2.2, 12.9 Hz), 2.43-2.37 (1H, m), 2.03-1.95 (1H, m), 1.87-1.65 (3H, m), 1.45-1.26 (2H, m), 1.19-1.10 (1H, m) |

| Example | Structure and Name | Amine | Buchwald conditions | Analytical data |
|---|---|---|---|---|
| Example 87 | (S)-6-(2-(5-fluoro-2-methoxybenzyl)-azepan-1-yl)-4-morpholinopyridin-2(1H)-one | 2-(5-fluoro-2-methoxy benzyl) azepane | Method D | LCMS (ES+) 416 (M + H)+, RT 3.13 min (Analytical Method A); RT 1.67 min (Analytical Method SFC4, YMC AMYLOSE-C, 30/70 MeOH (0.1% DEAISO)/$CO_2$); $^1$H NMR (400 MHz, $CDCl_3$): δ 8.90 (1H, br s), 6.96-6.85 (2H, m), 6.82-6.79 (1H, m), 5.22 (1H, s), 5.22 (1H, d, J = 1.9 Hz), 4.93 (1H, d, J = 1.7 Hz), 4.18 (3H, s), 3.80-3.72 (5H, m), 3.45-3.41 (1H, m), 3.33-3.24 (5H, m), 3.13 (1H, dd, J = 2.2, 12.9 Hz), 2.43-2.37 (1H, m), 2.03-1.95 (1H, m), 1.87-1.65 (3H, m), 1.45-1.26 (2H, m), 1.19-1.10 (1H, m) |

Example 88: 6-((2S,3R)-2-benzyl-3-methoxypyrrolidin-1-yl)-4-morpholinopyridin-2(1H)-one and Example 89: 6-((2R,3S)-2-benzyl-3-methoxypyrrolidin-1-yl)-4-morpholinopyridin-2(1H)-one

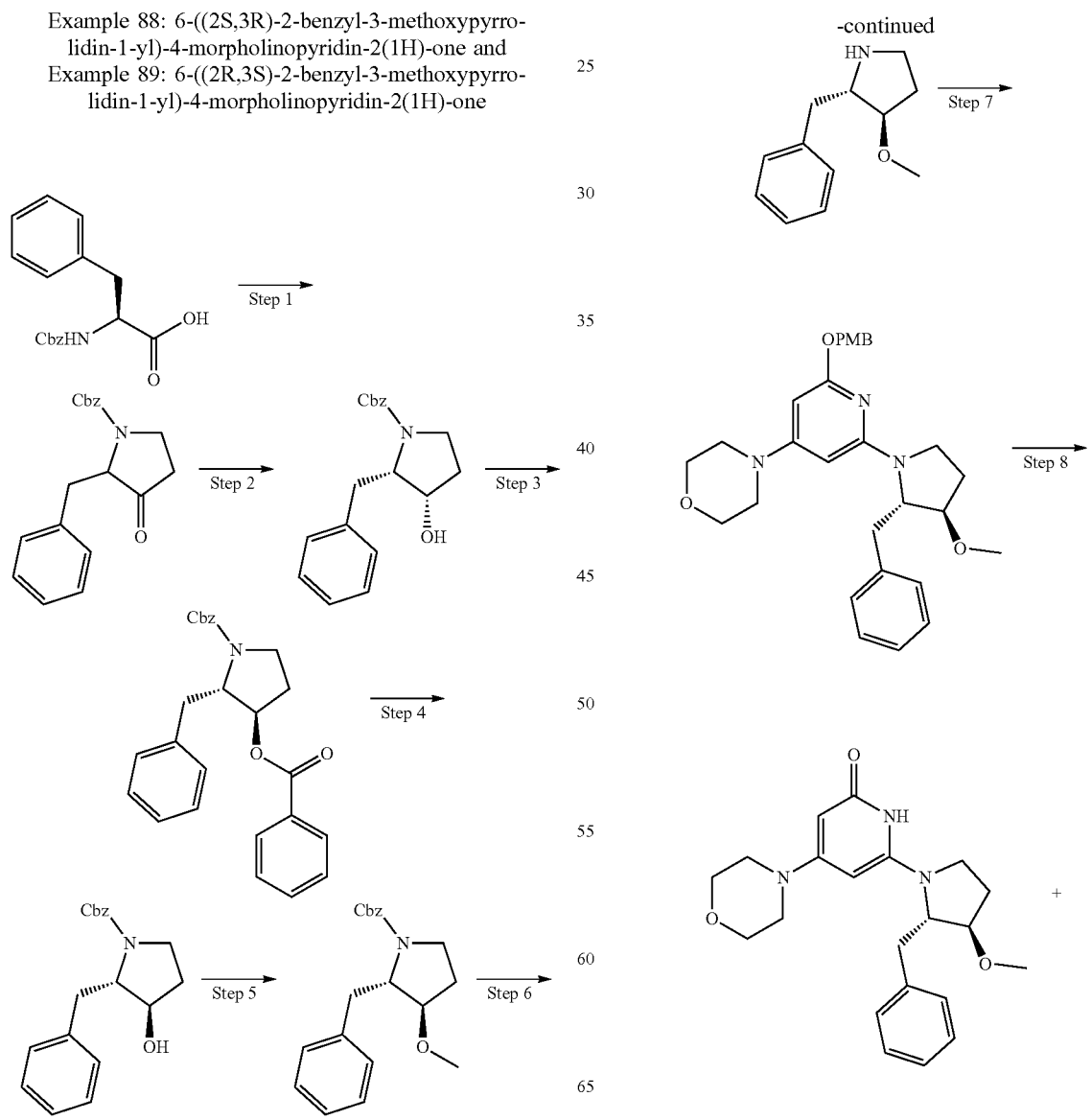

-continued

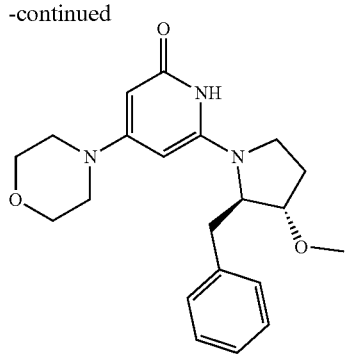

Step 1: Benzyl 2-benzyl-3-oxopyrrolidine-1-carboxylate

KOtBu (1.58 g, 14.04 mmol) was added to a solution of ((benzyloxy)carbonyl)-L-phenylalanine (4.0 g, 12.7 mmol) in anhydrous THF (30 mL) at r.t. After 15 min a solution of methyl acrylate (1.16 mL, 12.76 mmol) in anhydrous THF (5 mL) was added dropwise and the resultant solution heated at reflux for 2.5 h. The reaction mixture was cooled to rt and diluted with 1M aqueous HCl. The solvent was removed under reduced pressure and the aqueous extracted with EtOAc. The organic extracts were washed with brine and dried (MgSO$_4$). The solvent was removed in vacuo to give an oil which was stirred vigorously with 0.3M HCl at reflux for 4 days. The mixture was cooled to rt and the aqueous layer extracted with EtOAc. The organic layer was washed with NaHCO$_3$ (saturated aqueous solution), brine and dried (MgSO$_4$) and concentrated under reduced pressure. The resultant residue was purified by silica gel column chromatography (gradient elution 0-50% EtOAc/iso-hexane) to give the title compound.

Step 2: benzyl (2S*,3S*)-2-benzyl-3-hydroxypyrrolidine-1-carboxylate

Benzyl 2-benzyl-3-oxopyrrolidine-1-carboxylate (613 mg, 1.98 mmol) was dissolved in MeOH (0.2 M) and the resultant mixture cooled in an ice-bath. NaBH$_4$ (1.1 eg.) was added in one portion and the reaction allowed to warm to rt over 1 h. The reaction was quenched by careful addition of water and the MeOH was removed under reduced pressure. The aqueous layer was extracted with DCM and the layers separated. The organic extracts were dried (phase separator) and concentrated under reduced pressure. The mixture was purified by silica gel column chromatography eluting with gradient 0-50% EtOAc/iso-hexane to afford the title compound.

Step 3: benzyl (2S*,3R*)-3-(benzoyloxy)-2-benzylpyrrolidine-1-carboxylate

Benzoic acid (1.92 mmol) and triphenylphophine (1.92 mmol) were added to a solution of the benzyl (2S*,3S*)-2-benzyl-3-hydroxypyrrolidine-1-carboxylate (498 mg, 1.60 mmol) in THF (10 mL) and cooled to 0° C. DIAD (1.92 mmol) was added dropwise and the reaction allowed to warm to rt over 5 h. The reaction mixture was concentrated in vacuo and purified by silica gel column chromatography (gradient elution, 0-50% EtOAc/iso-hexane) to afford the title compound.

Step 4: benzyl (2S*,3R*)-2-benzyl-3-hydroxypyrrolidine-1-carboxylate

Benzyl (2S*,3R*)-3-(benzoyloxy)-2-benzylpyrrolidine-1-carboxylate (465 mg, 1.12 mmol) was dissolved in MeOH (10 mL) and water (5 mL). Lithium hydroxide monohydrate (70.5 mg, 1.68 mmol) was added in one portion and the reaction heated at 50° C. for 3 h. The methanol was removed in vacuo and the aqueous layer was extracted with DCM. The layers were separated, dried (phase separator) and concentrated in vacuo. Purification by silica gel chromatography (gradient elution, 0-30% EtOAc/iso-hexane) yielded the title compound.

Step 5: benzyl (2S*,3R*)-2-benzyl-3-methoxypyrrolidine-1-carboxylate

NaH (77 mg, 1.93 mmol, 60% dispersion in mineral oil) was added in one portion to benzyl (2S*,3R*)-2-benzyl-3-hydroxypyrrolidine-1-carboxylate (300 mg, 0.96 mmol) in anhydrous DMF (5 mL) at 0° C. After 20 min methyl iodide (0.09 mL, 1.45 mmol) was added and the reaction allowed to warm to rt over 2 h. The reaction was cooled in an ice-bath and quenched by addition of water. The DMF was removed in vacuo and the residue dissolved in DCM. The DCM was washed with water and the layers separated. The organic extract was dried (phase separator) and concentrated in vacuo. The residue was purified by silica gel column chromatography (gradient 0-30% EtOAc/iso-hexane) to give the title compound.

Step 6: (2S*,3R*)-2-benzyl-3-methoxypyrrolidine

Following Method E starting from rac-benzyl (2R,3S)-2-benzyl-3-methoxypyrrolidine-1-carboxylate (250 mg, 0.77 mmol). After filtering the reaction mixture through celite the solvent was removed in vacuo to give the title compound. Used without further purification.

Step 7: 4-(2-((2S*,3R*)-2-benzyl-3-methoxypyrrolidin-1-yl)-6-((4-methoxybenzyl)oxy)pyridin-4-yl)morpholine Following Method D starting from (2S*,3R*)-2-benzyl-3-methoxypyrrolidine (94 mg, 0.49 mmol) and 4-(2-chloro-6-((4-methoxybenzyl)oxy)pyridin-4-yl)morpholine (150 mg, 0.45 mmol, scaffold 1). The residue was purified by silica gel column chromatography (gradient 0-50% EtOAc/iso-hexane) to give the title compound.

Step 8: 6-((2S,3R)-2-benzyl-3-methoxypyrrolidin-1-yl)-4-morpholinopyridin-2(1H)-one and 6-((2R,3S)-2-benzyl-3-methoxypyrrolidin-1-yl)-4-morpholinopyridin-2(1H)-one Following Method E starting from 4-(2-((2S*,3R*)-2-benzyl-3-methoxypyrrolidin-1-yl)-6-((4-methoxybenzyl)oxy)pyridin-4-yl)morpholine (190 mg, 0.39 mmol). The residue was purified by reverse phase preparative HPLC. The sample was further purified by SFC chiral chromatography to give the title compounds.

6-((2S,3R)-2-benzyl-3-methoxypyrrolidin-1-yl)-4-morpholinopyridin-2(1H)-one; LCMS (ES+) 370 (M+H)$^+$, RT 2.85 min (Analytical Method A); RT 3.37 min (Analytical Method SFC4, YMC AMYLOSE-C, 30/70 IPA (0.1% DEAISO)/CO$_2$); $^1$H NMR (400 MHz, CDCl$_3$): δ 7.36-7.17 (5H, m), 5.21 (1H, d, J=2.1 Hz), 4.88 (1H, d, J=2.1 Hz), 4.07

(1H, dd, J=4.1, 8.5 Hz), 3.78 (4H, t, J=4.9 Hz), 3.74 (1H, d, J=4.0 Hz), 3.51-3.39 (2H, m), 3.23 (4H, dd, J=3.7, 6.0 Hz), 3.16 (3H, s), 2.99 (1H, dd, J=4.2, 14.2 Hz), 2.66 (1H, dd, J=8.5, 14.2 Hz), 2.10-2.05 (1H, m), 1.89-1.80 (1H, m), NH not observed.

6-((2R,3S)-2-benzyl-3-methoxypyrrolidin-1-yl)-4-morpholinopyridin-2(1H)-one; LCMS (ES+) 370 (M+H)⁺, RT 2.85 min (Analytical Method A); RT 2.52 min (Analytical Method SFC4, YMC AMYLOSE-C, 30/70 IPA (0.1% DEAISO)/CO₂); ¹H NMR (400 MHz, CDCl₃): δ 7.36-7.17 (5H, m), 5.21 (1H, d, J=2.1 Hz), 4.88 (1H, d, J=2.1 Hz), 4.07 (1H, dd, J=4.1, 8.5 Hz), 3.78 (4H, t, J=4.9 Hz), 3.74 (1H, d, J=4.0 Hz), 3.51-3.39 (2H, m), 3.23 (4H, dd, J=3.7, 6.0 Hz), 3.16 (3H, s), 2.99 (1H, dd, J=4.2, 14.2 Hz), 2.66 (1H, dd, J=8.5, 14.2 Hz), 2.10-2.05 (1H, m), 1.89-1.80 (1H, m), NH not observed.

Example 90: 6-((2S,3R)-2-benzyl-3-(difluoromethoxy)pyrrolidin-1-yl)-4-morpholinopyridin-2(1H)-one and Example 91: 6-((2R,3S)-2-benzyl-3-(difluoromethoxy)pyrrolidin-1-yl)-4-morpholinopyridin-2(1H)-one

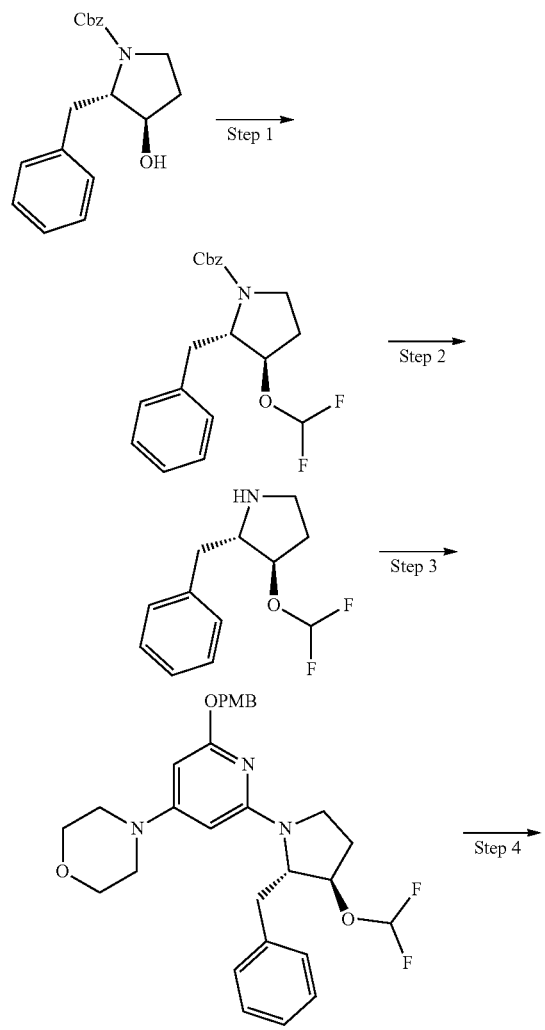

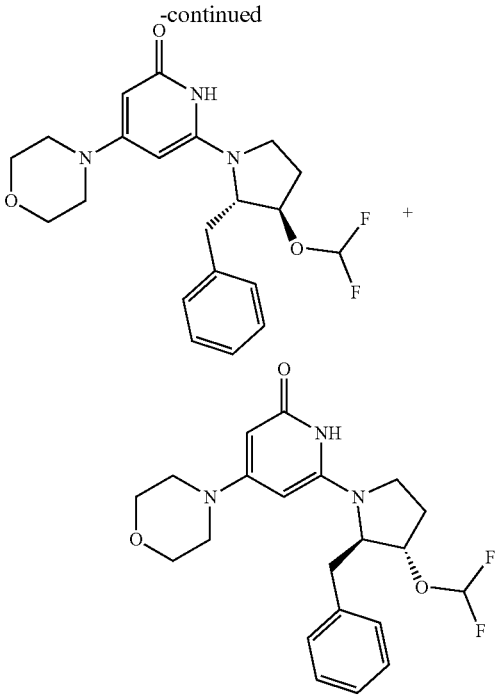

Step 1: benzyl (2S*,3R*)-2-benzyl-3-(difluoromethoxy)pyrrolidine-1-carboxylate Benzyl (2S*,3R*)-2-benzyl-3-hydroxypyrrolidine-1-carboxylate (227 mg, 0.73 mmol, Example 88 step 4) was dissolved in MeCN (6 mL) and copper(I) iodide (0.14 mmol) was added. The resulting mixture was heated to 50° C. and 2,2-difluoro-2-(fluorosulfyl) acetic acid (1.1 mmol) in MeCN (4 mL) was added dropwise over 20 min. The resulting mixture was stirred at 50° C. for a further 1 h. The reaction was cooled to rt and the solvent removed in vacuo to give a residue which was dissolved in DCM and washed with water, separating the layers using a phase separator. The DCM layer was concentrated in vacuo and the resultant residue purified by silica gel column chromatography (gradient elution, 0-30% EtOAc/iso-hexane) yielded the title compound/

Step 2: (2S*,3R*)-2-benzyl-3-(difluoromethoxy)pyrrolidine

Following Method E using rac-benzyl (2S*,3R*)-2-benzyl-3-(difluoromethoxy)pyrrolidine-1-carboxylate (110 mg, 0.3 mmol). After filtering through celite the solvent was removed in vacuo to give the title compound. Used without further purification.

Step 3: 4-(2-((2S*,3R*)-2-benzyl-3-(difluoromethoxy)pyrrolidin-1-yl)-6-((4-methoxybenzyl)oxy) pyridin-4-yl)morpholine Following Method D starting from (2S*,3R*)-2-benzyl-3-(difluoromethoxy)pyrrolidine (50 mg, 0.2 mmol) and 4-(2-chloro-6-((4-methoxybenzyl)oxy)pyridin-4-yl)morpholine (65 mg, 0.2 mmol, Scaffold 1). The residue was dissolved in DCM and washed with water. The organic extracts dried (phase separator) and concentrated in vacuo.

The residue was purified by silica gel column chromatography (gradient elution, 0-30% EtOAc/iso-hexane) to afford the title compound.

Step 4: 6-((2S,3R)-2-benzyl-3-(difluoromethoxy) pyrrolidin-1-yl)-4-morpholinopyridin-2(1H)-one and 6-((2R,3S)-2-benzyl-3-(difluoromethoxy)pyrrolidin-1-yl)-4-morpholinopyridin-2(1H)-one Following Method E starting from 4-(2-((2S*,3R*)-2-benzyl-3-(difluoromethoxy)pyrrolidin-1-yl)-6-((4-methoxybenzyl)oxy)pyridin-4-yl)morpholine (50 mg, 0.1 mmol). The residue was purified by reverse phase preparative HPLC followed by SFC to afford the title compounds.

6-((2S,3R)-2-benzyl-3-(difluoromethoxy)pyrrolidin-1-yl)-4-morpholinopyridin-2(1H)-one; LCMS (ES+) 406 (M+H)$^+$, RT 3.01 min (Analytical Method B); RT 1.43 min (Analytical Method SFC4, YMC AMYLOSE-C, 30/70 EtOH (0.1% DEAISO)/CO$_2$); $^1$H NMR (400 MHz, CDCl$_3$): δ 7.34-7.29 (3H, m), 7.18-7.16 (2H, m), 6.13 (1H, t, J=73.6 Hz), 5.24 (1H, d, J=2.1 Hz), 4.88 (1H, d, J=2.0 Hz), 4.67 (1H, d, J=4.0 Hz), 4.18 (1H, dd, J=4.5, 7.8 Hz), 3.78 (4H, t, J=4.8 Hz), 3.54-3.44 (2H, m), 3.24-3.21 (4H, m), 2.99 (1H, dd, J=4.5, 14.7 Hz), 2.78 (1H, dd, J=8.1, 14.4 Hz), 2.15-2.09 (1H, m), 1.97-1.87 (2H, m).

6-((2R,3S)-2-benzyl-3-(difluoromethoxy)pyrrolidin-1-yl)-4-morpholinopyridin-2(1H)-one; LCMS (ES+) 406 (M+H)$^+$, RT 2.87 min (Analytical Method A); RT 1.79 min (Analytical Method SFC4, YMC AMYLOSE-C, 30/70 EtOH (0.1% DEAISO)/CO$_2$); $^1$H NMR (400 MHz, CDCl$_3$): δ 7.34-7.29 (3H, m), 7.18-7.16 (2H, m), 6.13 (1H, t, J=73.6 Hz), 5.24 (1H, d, J=2.1 Hz), 4.88 (1H, d, J=2.0 Hz), 4.67 (1H, d, J=4.0 Hz), 4.18 (1H, dd, J=4.5, 7.8 Hz), 3.78 (4H, t, J=4.8 Hz), 3.54-3.44 (2H, m), 3.24-3.21 (4H, m), 2.99 (1H, dd, J=4.5, 14.7 Hz), 2.78 (1H, dd, J=8.1, 14.4 Hz), 2.15-2.09 (1H, m), 1.97-1.87 (2H, m).

Example 92: 6-((2S,3S)-2-benzyl-3-methoxypyrrolidin-1-yl)-4-morpholinopyridin-2(1H)-one and
Example 93: 6-((2R,3R)-2-benzyl-3-methoxypyrrolidin-1-yl)-4-morpholinopyridin-2(1H)-one

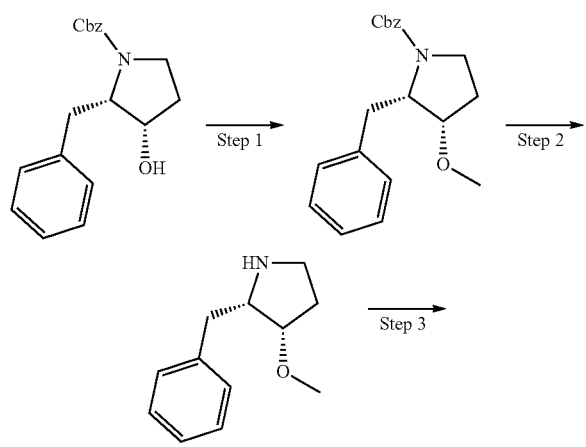

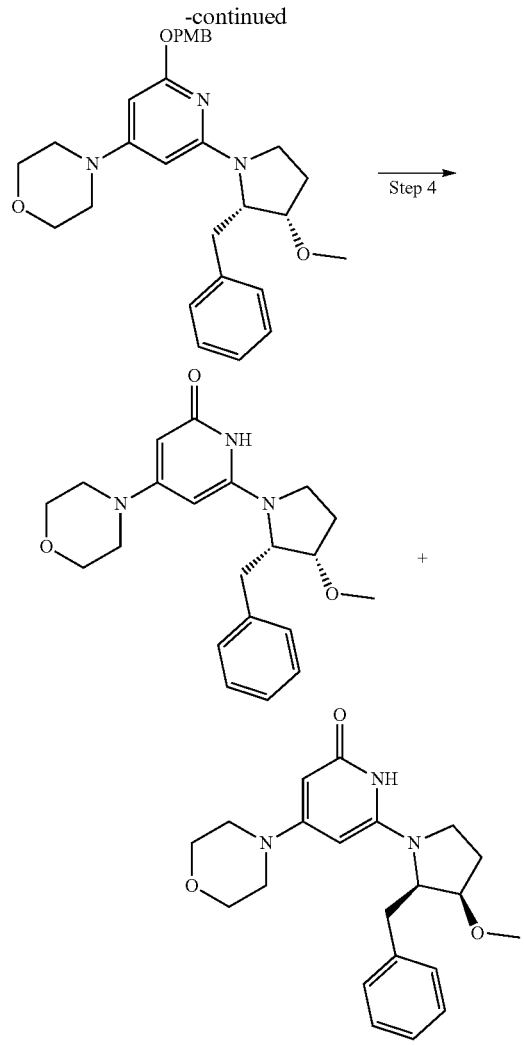

Step 1: benzyl (2S*,3S*)-2-benzyl-3-methoxypyrrolidine-1-carboxylate

Following the method described for the preparation of Example 88 step 4 from benzyl (2S*,3S*)-2-benzyl-3-hydroxypyrrolidine-1-carboxylate (338 mg, 1.09 mmol, Example 88 step 2). The mixture was purified by silica gel column chromatography (gradient 0-50% EtOAc/iso-hexane) to give the title compound.

Step 2: (2S*,3S*)-2-benzyl-3-methoxypyrrolidine

Following Method E starting from benzyl (2S*,3S*)-2-benzyl-3-methoxypyrrolidine-1-carboxylate (300 mg, 0.92 mmol). The mixture was purified by SCX chromatography (eluting with MeOH/DCM 1:1 and then collecting with 10% 7N NH$_3$ in MeOH/methanol) to give title compound.

Step 3: 4-(2-((2S*,3S*)-2-benzyl-3-methoxypyrrolidin-1-yl)-6-((4-methoxybenzyl)oxy)pyridin-4-yl)morpholine Following Method D starting from (2S*,3S*)-2-benzyl-3-methoxypyrrolidine (146 mg, 0.76 mmol) and 4-(2-chloro-6-((4-methoxybenzyl)oxy)pyridin-4-yl)morpholine (255 mg, 0.76 mmol, scaffold 1). The residue was dissolved in DCM and washed with water. The organic extracts were dried (phase separator) and the DCM layer concentrated in vacuo. The residue was purified by silica gel column chromatography (gradient 0-50% EtOAc/iso-hexane) to give the title compound.

Step 4: 6-((2S,3S)-2-benzyl-3-methoxypyrrolidin-1-yl)-4-morpholinopyridin-2(1H)-one and 6-((2R,3R)-2-benzyl-3-methoxypyrrolidin-1-yl)-4-morpholino-pyridin-2(1H)-one Following Method E starting from 4-(2-((2S*,3S*)-2-benzyl-3-methoxypyrrolidin-1-yl)-6-((4-methoxybenzyl)oxy)pyridin-4-yl)morpholine (130 mg, 0.26 mmol). The residue was purified by reverse phase preparative HPLC followed by SFC to afford the title compounds.

6-((2S,3S)-2-benzyl-3-methoxypyrrolidin-1-yl)-4-morpholinopyridin-2(1H)-one; LCMS (ES+) 370 (M+H)$^+$, RT 2.84 min (Analytical Method A); RT 2.23 min (Analytical Method SFC1, YMC AMYLOSE-C, 30/70 MeOH (0.1% DEAISO)/CO$_2$); $^1$H NMR (400 MHz, CDCl$_3$): δ 7.29-7.16 (5H, m), 5.15 (1H, d, J=1.9 Hz), 4.68 (1H, d, J=2.1 Hz), 4.12 (1H, q, J=5.8 Hz), 3.91-3.85 (1H, m), 3.73 (4H, t, 5 Hz), 3.53-3.47 (1H, m), 3.38 (3H, s), 3.30 (1H, q, J=8.5 Hz), 3.18-3.06 (5H, m), 2.77 (1H, dd, J=5.6, 14 Hz), 2.18-2.09 (1H, m), 1.90-1.79 (2H, m).

6-((2R,3R)-2-benzyl-3-methoxypyrrolidin-1-yl)-4-morpholinopyridin-2(1H)-one; LCMS (ES+) 370 (M+H)$^+$, RT 2.84 min (Analytical Method A); RT 2.96 min (Analytical Method SFC1, YMC AMYLOSE-C, 30/70 MeOH (0.1% DEAISO)/CO$_2$); $^1$H NMR (400 MHz, CDCl$_3$): δ 7.29-7.16 (5H, m), 5.15 (1H, d, J=1.9 Hz), 4.68 (1H, d, J=2.1 Hz), 4.12 (1H, q, J=5.8 Hz), 3.91-3.85 (1H, m), 3.73 (4H, t, 5 Hz), 3.53-3.47 (1H, m), 3.38 (3H, s), 3.30 (1H, q, J=8.5 Hz), 3.18-3.06 (5H, m), 2.77 (1H, dd, J=5.6, 14 Hz), 2.18-2.09 (1H, m), 1.90-1.79 (2H, m).

Example 94: 6-((2S,3S)-2-benzyl-3-hydroxy-3-methylpyrrolidin-1-yl)-4-morpholinopyridin-2(1H)-one and Example 95: 6-((2R,3R)-2-benzyl-3-hydroxy-3-methylpyrrolidin-1-yl)-4-morpholinopyridin-2(1H)-one

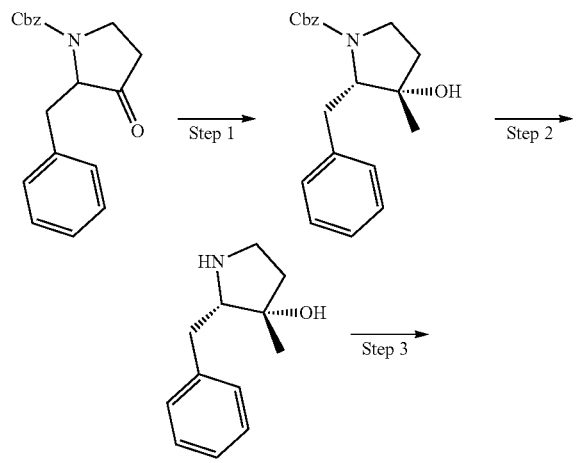

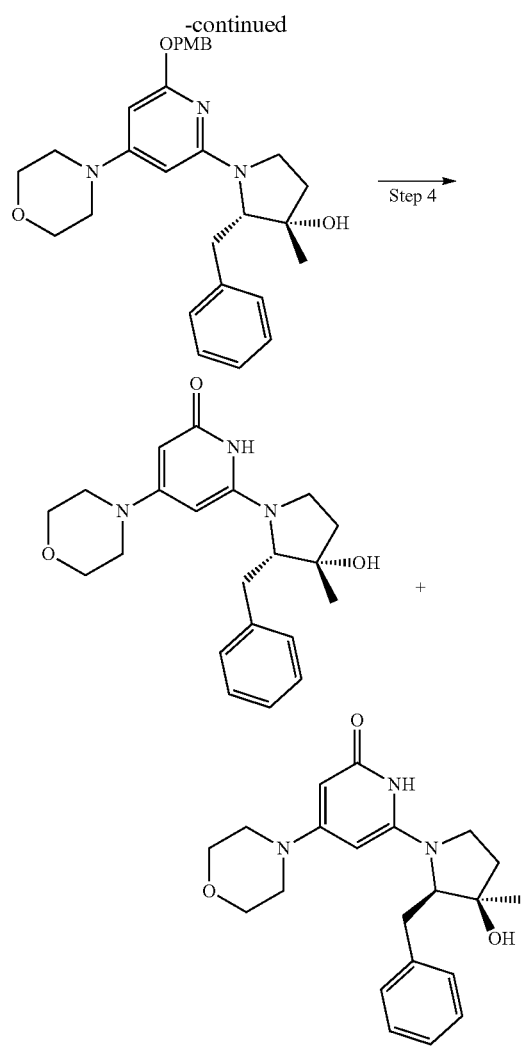

Step 1: benzyl (2S*,3S*)-2-benzyl-3-hydroxy-3-methylpyrrolidin-1-carboxylate

Methyl magnesium bromide (1.18 mL, 1.18 mmol, 3 M in diethyl ether) was added dropwise to a suspension of cerium (III) chloride (960 mg, 3.91 mmol) in dry THF (10 mL) at −78° C.; ensuring the temperature did not raise above −70° C. After 30 min a solution of benzyl 2-benzyl-3-oxopyrrolidine-1-carboxylate (500 mg, 1.62 mmol, Example 88, step 1) in dry THF (10 mL) was added dropwise, keeping the temperature below −70° C. After complete addition the reaction was stirred for a further 2 h, allowing the reaction to warm to 0° C. EtOAc was added and the insoluble material filtered through celite. The THF was removed in vacuo and the residue dissolved in EtOAc and washed with water and brine. The organic layer was dried (MgSO$_4$) and concentrated under reduced pressure. The resultant residue was purified by silica gel column chromatography (gradient 0-50% EtOAc/iso-hexane) to give the title compound.

Step 3: (2S*,3S*)-2-benzyl-3-methylpyrrolidin-3-ol

Following Method E starting from benzyl (2S,*3S*)-2-benzyl-3-hydroxy-3-methylpyrrolidine-1-carboxylate (284 mg, 0.97 mmol) to afford the title compound.

Step 4: (2S*,3S*)-2-benzyl-1-(6-((4-methoxybenzyl)oxy)-4-morpholinopyridin-2-yl)-3-methyl pyrrolidin-3-ol Following Method D starting from (2S*,3S*)-2-benzyl-3-methylpyrrolidin-3-ol (94 mg, 0.49 mmol) and 4-(2-chloro-6-((4-methoxybenzyl)oxy)pyridin-4-yl)morpholine (150 mg, 0.45 mmol, scaffold 1). The crude material was purified by silica gel column chromatography (gradient 0-50% EtOAc/iso-hexane) to give the title compound.

Step 5: 6-((2S,3S)-2-benzyl-3-hydroxy-3-methylpyrrolidin-1-yl)-4-morpholinopyridin-2(1H)-one and 6-((2R,3R)-2-benzyl-3-hydroxy-3-methylpyrrolidin-1-yl)-4-morpholinopyridin-2(1H)-one Following Method E starting from (2S*,3S*)-2-benzyl-1-(6-((4-methoxybenzyl)oxy)-4-morpholinopyridin-2-yl)-3-methylpyrrolidin-3-ol (200 mg, 0.4 mmol). The crude material was purified by reverse phase preparative HPLC followed by SFC to give the title compounds.

6-((2S,3S)-2-benzyl-3-hydroxy-3-methylpyrrolidin-1-yl)-4-morpholinopyridin-2(1H)-one; LCMS (ES+) 370 (M+H)$^+$, RT 2.51 min (Analytical Method A); RT 1.36 min (Analytical Method SFC4, YMC AMYLOSE-C, 25/75 MeOH (0.1% DEAISO)/CO$_2$); $^1$H NMR (400 MHz, CDCl$_3$): δ 7.29-7.17 (5H, m), 5.17 (1H, d, J=2.2 Hz), 4.67 (1H, d, J=2.2 Hz), 3.77 (1H, t, J=5.6 Hz), 3.72 (4H, t, J=4.8 Hz), 3.53 (1H, dt, J=4, 9.3 Hz), 3.29-3.05 (6H, m), 2.84 (1H, dd, J=5.2, 14.3 Hz), 2.01-1.85 (2H, m), 1.30 (3H, s), NH and OH not observed.

6-((2R,3R)-2-benzyl-3-hydroxy-3-methylpyrrolidin-1-yl)-4-morpholinopyridin-2(1H)-one; LCMS (ES+) 370 (M+H)$^+$, RT 2.51 min (Analytical Method A); RT 1.98 min (Analytical Method SFC4, YMC AMYLOSE-C, 25/75 MeOH (0.1% DEAISO)/CO$_2$); $^1$H NMR δ (ppm) (400 MHz, CDCl$_3$) 7.29-7.17 (5H, m), 5.17 (1H, d, J=2.2 Hz), 4.67 (1H, d, J=2.2 Hz), 3.77 (1H, t, J=5.6 Hz), 3.72 (4H, t, J=4.8 Hz), 3.53 (1H, dt, J=4, 9.3 Hz), 3.29-3.05 (6H, m), 2.84 (1H, dd, J=5.2, 14.3 Hz), 2.01-1.85 (2H, m), 1.30 (3H, s), NH and OH not observed.

Example 96: 6-((2S,3R)-2-benzyl-3-fluoropyrrolidin-1-yl)-4-morpholinopyridin-2(1H)-one and Example 97: 6-((2R,3S)-2-benzyl-3-fluoropyrrolidin-1-yl)-4-morpholinopyridin-2(1H)-one

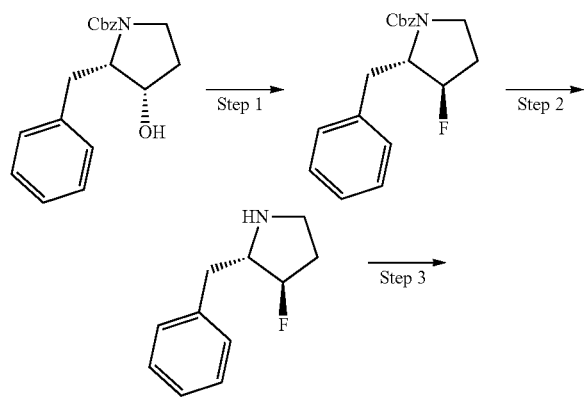

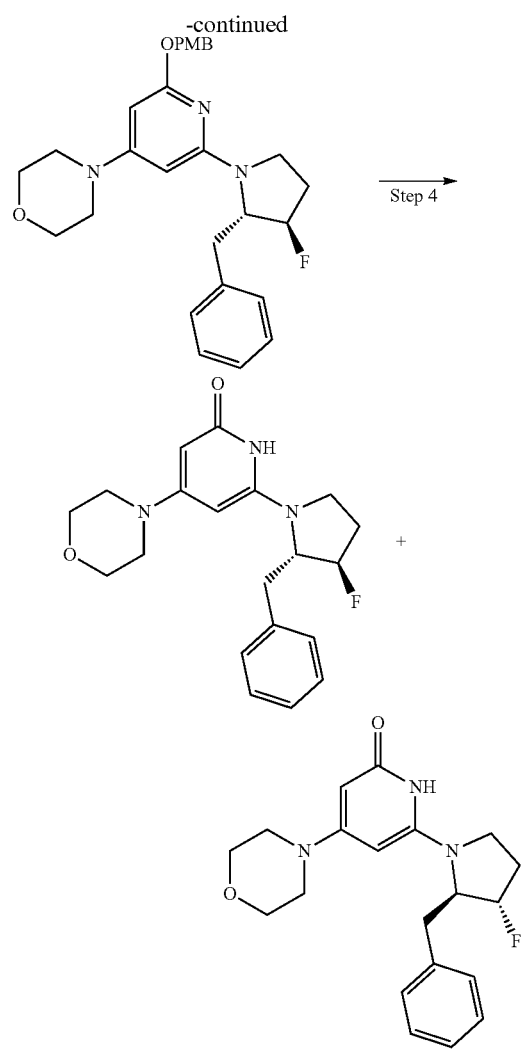

Step 1: benzyl (2S*,3R*)-2-benzyl-3-fluoropyrrolidine-1-carboxylate

DAST (2.28 mmol) was added dropwise to a solution of the benzyl (2S*,3S*)-2-benzyl-3-hydroxypyrrolidine-1-carboxylate (203 mg, 0.65 mmol, Example 88 step 2) in anhydrous DCM at −78° C. and the reaction allowed to warm to rt overnight. The reaction was cooled in an ice bath and quenched by the addition of NaHCO$_3$ (saturated aqueous solution). The phases were separated and the organic extracts dried (phase separator). The DCM layer was concentrated in vacuo. The mixture was purified by silica gel column chromatography (gradient elution with gradient 0-50% EtOAc/iso-hexane) to afford the title compound.

Step 2: (2S*,3R*)-2-benzyl-3-fluoropyrrolidine

Following Method E starting from benzyl (2S,*3R*)-2-benzyl-3-fluoropyrrolidine-1-carboxylate (120 mg, 0.38 mmol) to afford the title compound.

Step 3: 4-(2-((2S*,3R*)-2-benzyl-3-fluoropyrrolidin-1-yl)-6-((4-methoxybenzyl)oxy)pyridin-4-yl)morpholine Following Method D starting from (2S*,3R*)-2-benzyl-3-fluoropyrrolidine (43 mg, 0.24 mmol) and 4-(2-chloro-6-

((4-methoxybenzyl)oxy)pyridin-4-yl)morpholine (73 mg, 0.22 mmol, scaffold 1). The residue was purified by silica gel column chromatography (gradient 0-50% EtOAc/isohexane) to give the title compound.

Step 4: 6-((2S,3R)-2-benzyl-3-fluoropyrrolidin-1-yl)-4-morpholinopyridin-2(1H)-one and 6-((2R,3S)-2-benzyl-3-fluoropyrrolidin-1-yl)-4-morpholinopyridin-2(1H)-one Following Method E starting from 6-((2S*,3R*)-2-benzyl-3-fluoropyrrolidin-1-yl)-4-morpholinopyridin-2(1H)-one (100 mg, 0.21 mmol). The residue was purified by reverse phase preparative HPLC followed by SFC to afford the title compounds.

6-((2S,3R)-2-benzyl-3-fluoropyrrolidin-1-yl)-4-morpholinopyridin-2(1H)-one; LCMS (ES+) 358 (M+H)$^+$, RT 2.77 min (Analytical Method A); RT 1.75 min (Analytical Method SFC4, YMC AMYLOSE-C, 30/70 MeOH (0.1% DEAISO)/CO$_2$); $^1$H NMR (400 MHz, CDCl$_3$): δ 7.34-7.24 (3H, m), 7.18-7.16 (2H, m), 5.25 (1H, d, J=2.2 Hz), 5.02 (1H, dd, J=51.6, 2.9 Hz), 4.91 (1H, d, J=2.2 Hz), 4.32 (1H, dq, J=4.1, 10.4 Hz), 3.79 (4H, t, J=5.2 Hz), 3.63 (1H, t, J=9.2 Hz), 3.51 (1H, dt, J=7.0, 9.7 Hz), 3.24 (4H, dd, J=4.1, 5.9 Hz), 3.05-2.99 (1H, m), 2.70 (1H, dd, J=8.1, 14.0 Hz), 2.26-2.16 (1H, m), 1.95-1.75 (1H, m), NH not observed.

6-((2R,3S)-2-benzyl-3-fluoropyrrolidin-1-yl)-4-morpholinopyridin-2(1H)-one; LCMS (ES+) 358 (M+H)$^+$, RT 2.76 min (Analytical Method A); RT 2.23 min (Analytical Method SFC4, YMC AMYLOSE-C, 30/70 MeOH (0.1% DEAISO)/CO$_2$); $^1$H NMR (400 MHz, CDCl$_3$): δ 7.34-7.24 (3H, m), 7.18-7.16 (2H, m), 5.25 (1H, d, J=2.2 Hz), 5.02 (1H, dd, J=51.6, 2.9 Hz), 4.91 (1H, d, J=2.2 Hz), 4.32 (1H, dq, J=4.1, 10.4 Hz), 3.79 (4H, t, J=5.2 Hz), 3.63 (1H, t, J=9.2 Hz), 3.51 (1H, dt, J=7.0, 9.7 Hz), 3.24 (4H, dd, J=4.1, 5.9 Hz), 3.05-2.99 (1H, m), 2.70 (1H, dd, J=8.1, 14.0 Hz), 2.26-2.16 (1H, m), 1.95-1.75 (1H, m), NH not observed.

Example 98: (S)-6-(2-benzyl-3,3-difluoropyrrolidin-1-yl)-4-morpholinopyridin-2(1H)-one and Example 99: (R)-6-(2-benzyl-3,3-difluoropyrrolidin-1-yl)-4-morpholinopyridin-2(1H)-one

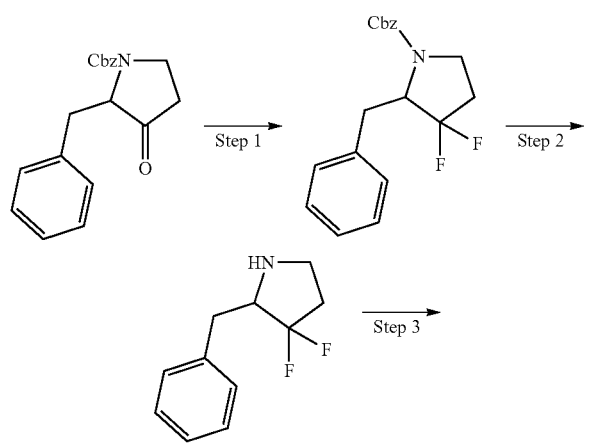

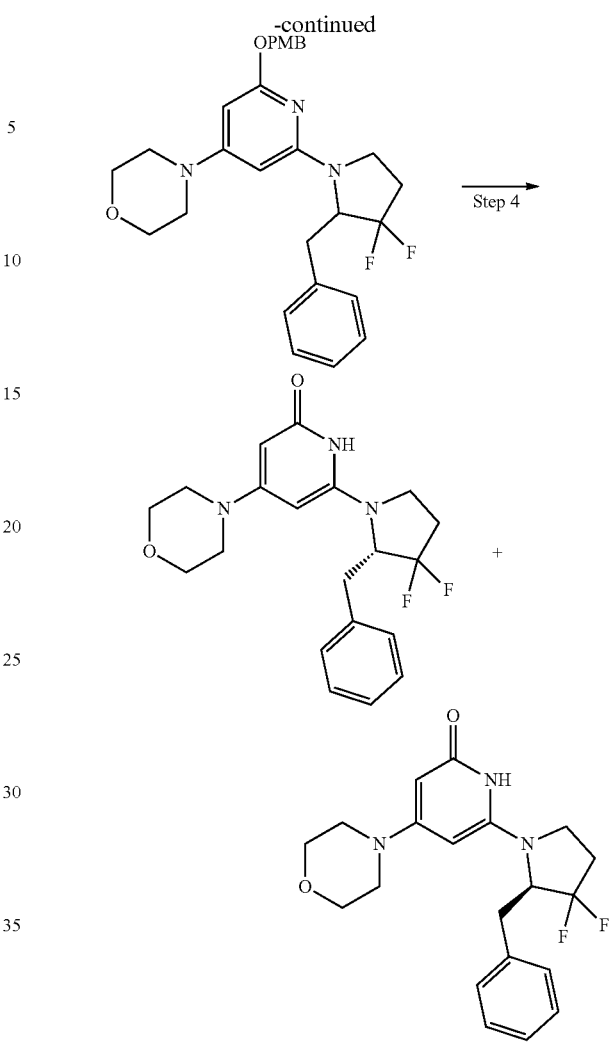

Step 1: benzyl 2-benzyl-3,3-difluoropyrrolidine-1-carboxylate

DAST (3.55 mmol) was added dropwise to a solution of benzyl 2-benzyl-3-oxopyrrolidine-1-carboxylate (500 mg, 1.62 mmol, Example 88 step 1) in anhydrous DCM at −78° C. and the reaction allowed to warm to rt overnight. The reaction was cooled to 0° C. and quenched with NaHCO$_3$ (saturated aqueous solution). The phases were separated and the organic extracts dried (phase separator). The DCM layer was concentrated in vacuo. The crude was purified by silica gel column chromatography (gradient 0-50% EtOAc/isohexane) to give the title compound.

Step 2: 2-benzyl-3,3-difluoropyrrolidine

Following Method E starting from benzyl 2-benzyl-3,3-difluoropyrrolidine-1-carboxylate (515 mg, 1.55 mmol). The reaction mixture was filtered through Celite and the solvent removed in vacuo to give the title compound. Used without further purification.

Step 3: 4-(2-(2-benzyl-3,3-difluoropyrrolidin-1-yl)-6-((4-methoxybenzyl)oxy)pyridin-4-yl)morpholine Following Method D starting from 2-benzyl-3,3-difluoropyrrolidine (97 mg, 0.49 mmol) and 4-(2-chloro-6-((4- methoxybenzyl)oxy)pyridin-4-yl)morpholine (150 mg, 0.45 mmol, scaffold 1). The residue was dissolved in DCM and washed with water. The organic extracts were dried (phase separator) and concentrated in vacuo. The residue was purified by silica gel column chromatography (gradient 0-50% EtOAc/iso-hexane) to give the title compound.

Step 4: (S)-6-(2-benzyl-3,3-difluoropyrrolidin-1-yl)-4-morpholinopyridin-2(1H)-one and (R)-6-(2-benzyl-3,3-difluoropyrrolidin-1-yl)-4-morpholinopyridin-2(1H)-one Following Method E starting from 4-(2-(2-benzyl-3,3-difluoropyrrolidin-1-yl)-6-((4-methoxybenzyl)oxy)pyridin-4-yl)morpholine (208 mg, 0.42 mmol). The residue was purified by reverse phase preparative HPLC followed by separation of the enantiomers by SFC to afford the title compounds.

(S)-6-(2-benzyl-3,3-difluoropyrrolidin-1-yl)-4-morpholinopyridin-2(1H)-one; LCMS (ES+) 376 (M+H)+, RT 2.84 min (Analytical Method A); RT 2.09 min (Analytical Method SFC1, YMC AMYLOSE-C, 25/75 MeOH (0.1% DEA)/CO$_2$); $^1$H NMR (400 MHz, CDCl$_3$): δ 7.29-7.20 (3H, m), 7.17-7.15 (2H, m), 5.27 (1H, d, J=2.2 Hz), 4.80 (1H, d, J=1.8 Hz), 4.35 (1H, dt, J=4.6, 18.2 Hz), 3.76 (4H, t, J=5.1 Hz), 3.51 (1H, dt, J=2.2, 9.8 Hz), 3.42-3.35 (1H, m), 3.28-3.13 (5H, m), 2.88 (1H, td, J=3, 14.3 Hz), 2.32-2.22 (1H, m), 1.92-1.74 (2H, m).

(R)-6-(2-benzyl-3,3-difluoropyrrolidin-1-yl)-4-morpholinopyridin-2(1H)-one; LCMS (ES+) 376 (M+H)+, RT 2.84 min (Analytical Method A); RT 2.99 min (Analytical Method SFC1, YMC AMYLOSE-C, 25/75 MeOH (0.1% DEA)/CO$_2$); $^1$H NMR (400 MHz, CDCl$_3$): δ 7.29-7.20 (3H, m), 7.17-7.15 (2H, m), 5.27 (1H, d, J=2.2 Hz), 4.80 (1H, d, J=1.8 Hz), 4.35 (1H, dt, J=4.6, 18.2 Hz), 3.76 (4H, t, J=5.1 Hz), 3.51 (1H, dt, J=2.2, 9.8 Hz), 3.42-3.35 (1H, m), 3.28-3.13 (5H, m), 2.88 (1H, td, J=3, 14.3 Hz), 2.32-2.22 (1H, m), 1.92-1.74 (2H, m).

Example 100: 6-((2R,4R*)-2-benzyl-4-methylpyrrolidin-1-yl)-4-morpholinopyridin-2(1H)-one Stereoisomer 1 and Example 101: 6-((2R,4R*)-2-benzyl-4-methylpyrrolidin-1-yl)-4-morpholinopyridin-2(1H)-one Stereoisomer 2

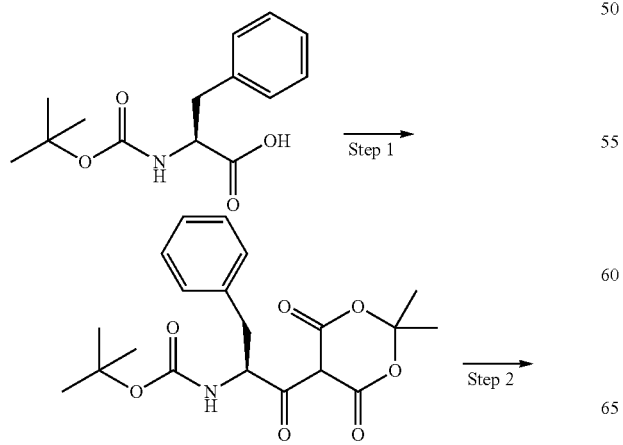

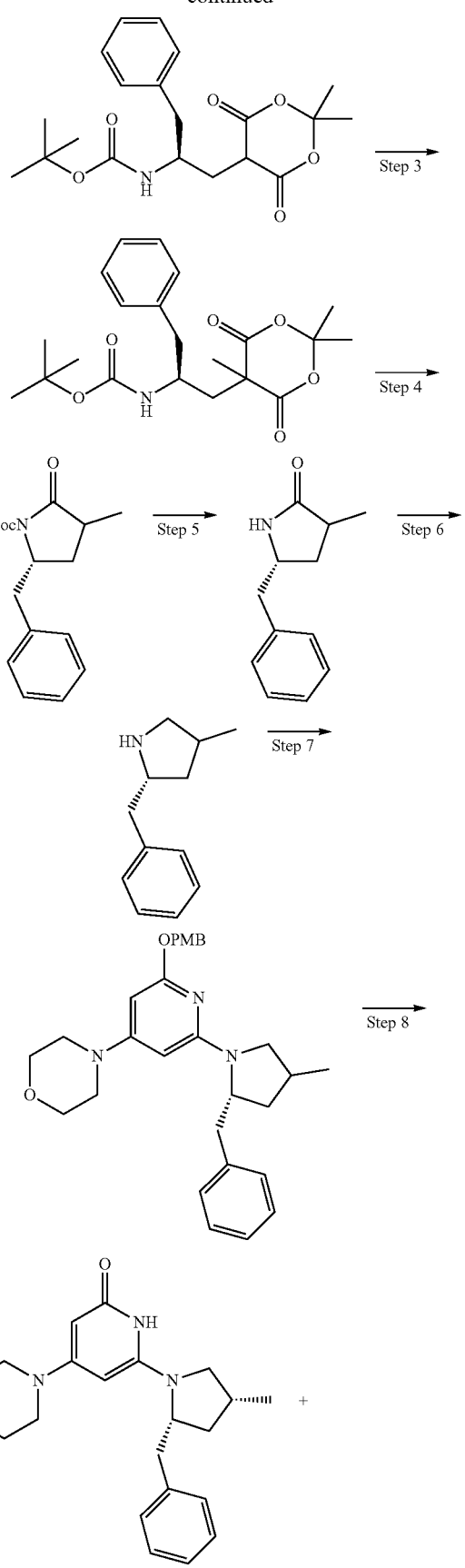

-continued

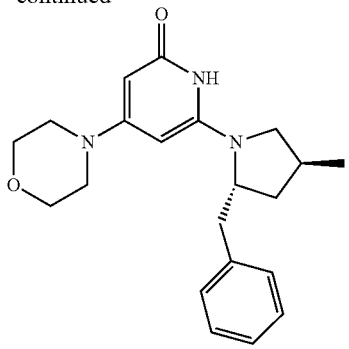

Step 1: tert-butyl (S)-(1-(2,2-dimethyl-4,6-dioxo-1,3-dioxan-5-yl)-1-oxo-3-phenylpropan-2-yl)carbamate EDC.HCl (3.25 g, 16.96 mmol) and DMAP (2.07 g, 19.96 mmol) were added to a solution of (tert-butoxycarbonyl)-L-phenylalanine (3 g, 11.3 mmol) in DCM (50 mL). Meldrum's acid (1.63 g, 11.3 mmol) was added and the resulting mixture stirred at rt overnight. The reaction was washed with 1 M potassium hydrogensulfate, water and brine. The DCM layer was concentrated in vacuo to give the title compound.

Step 2: tert-butyl (R)-(1-(2,2-dimethyl-4,6-dioxo-1,3-dioxan-5-yl)-3-phenylpropan-2-yl)carbamate NaBH$_4$ (1.55 g, 40.92 mmol) was added potionwise over 20 min to a solution of tert-butyl (S)-(1-(2,2-dimethyl-4,6-dioxo-1,3-dioxan-5-yl)-1-oxo-3-phenylpropan-2-yl)carbamate (4 g, 10.23 mmol) in DCM (100 mL) and acetic acid (6.4 mL, 112 mmol) at 0° C. After 3 h the reaction was quenched with water and the layers were separated. The DCM layer was washed with saturated sodium hydrogencarbonate and the layered separated. The DCM layer dried (phase separator) and concentrated in vacuo to give the title compound.

Step 3: tert-butyl (S)-(1-phenyl-3-(2,2,5-trimethyl-4,6-dioxo-1,3-dioxan-5-yl)propan-2-yl)carbamate K$_2$CO$_3$ (0.44 g, 3.18 mmol) was added to a solution of tert-Butyl (R)-(1-(2,2-dimethyl-4,6-dioxo-1,3-dioxan-5-yl)-3-phenylpropan-2-yl)carbamate (1 g, 2.65 mmol) in DMF (10 mL). The reaction mixture was cooled to 0° C. and methyl iodide (0.49 mL, 7.95 mmol) added. The reaction was allowed to warm to rt overnight. The DMF was removed in vacuo and the residue dissolved in DCM, washed with water and the layers separated. The organic extracts were dried (phase separator) and concentrated in vacuo. The residue was purified by silica gel column chromatography (gradient elution, 0-40% EtOAc/iso-hexane) to afford the title compound.

Step 4: tert-butyl (5R)-5-benzyl-3-methyl-2-oxopyrrolidine-1-carboxylate tert-Butyl (S)-(1-phenyl-3-(2,2,5-trimethyl-4,6-dioxo-1,3-dioxan-5-yl)propan-2-yl)carbamate (750 mg, 1.92 mmol) was dissolved in toluene (10 mL) and the reaction heated at reflux for 48 h. The solvent was removed in vacuo. The residue was purified by silica gel column chromatography (gradient elution, 0-10% EtOAc/iso-hexane) to afford the title compound.

Step 5: (5R)-5-benzyl-3-methylpyrrolidin-2-one tert-Butyl (5R)-5-benzyl-3-methyl-2-oxopyrrolidine-1-carboxylate (530 mg, 1.83 mmol) was dissolved in 4 M HCl in dioxane (5 mL) and the reaction was stirred at rt for 1 h. The solvent was removed in vacuo and the residue dissolved in DCM and washed with saturated NaHCO$_3$. The layers were separated and the organic extracts dried (phase separator) and concentrated under reduced pressure. The resultant oil was purified by silica gel column chromatography (gradient elution, 0-100% EtOAc/iso-hexane) to afford the title compound.

Step 6: (2R)-2-benzyl-4-methylpyrrolidine

LiAlH$_4$ (3.28 mL, 3.27 mmol, 1 M in THF) was added dropwise to a solution of (5R)-5-benzyl-3-methylpyrrolidin-2-one (310 mg, 1.64 mmol) in THF (10 mL). The reaction was heated at reflux for 5 h and then cooled to r.t. The reaction was cooled to 0° C. and quenched by addition of water. The THF was removed in vacuo and the aqueous layer extracted with EtOAc. The organic extracts were dried (MgSO$_4$) and concentrated under reduced pressure to give the title compound. Used without further purification.

Step 7: 4-(2-((2R)-2-benzyl-4-methylpyrrolidin-1-yl)-6-((4-methoxybenzyl)oxy)pyridin-4-yl)morpholine Following Method D starting from (2R)-2-benzyl-4-methylpyrrolidine (86 mg, 0.49 mmol) and 4-(2-chloro-6-((4-methoxybenzyl)oxy)pyridin-4-yl)morpholine (150 mg, 0.48 mmol, scaffold 1). The reaction was cooled to rt. and the solvent removed in vacuo. The residue was dissolved/suspended in DCM and washed with water and the layers separated. The organic extracts were dried (phase separator) and concentrated in vacuo. The residue was purified by silica gel column chromatography (gradient elution, 0-50% EtOAc/iso-hexane) to afford the title compound.

Step 8: 6-((2R,4R*)-2-benzyl-4-methylpyrrolidin-1-yl)-4-morpholinopyridin-2(1H)-one Stereoisomer 1 and 6-((2R,4R*)-2-benzyl-4-methylpyrrolidin-1-yl)-4-morpholinopyridin-2(1H)-one Stereoisomer 2

Following Method E starting from 4-(2-((2R)-2-benzyl-4-methylpyrrolidin-1-yl)-6-((4-methoxybenzyl)oxy)pyridin-4-yl)morpholine (200 mg, 0.42 mmol). Purification by SFC gave the title compounds.

6-((2R,4R*)-2-benzyl-4-methylpyrrolidin-1-yl)-4-morpholinopyridin-2(1H)-one diastereomer 1; LCMS (ES+) 354 (M+H)$^+$, RT 3.09 min (Analytical Method B); RT 2.19 min (Analytical Method SFC4, YMC AMYLOSE-C, 30% (IPA/ACN, 1:1)/(0.1% DEAISO)/CO$_2$); $^1$H NMR (400 MHz, CDCl3): δ 7.32-7.23 (3H, m), 7.18-7.16 (2H, m), 5.20 (1H, d, J=2.0 Hz), 4.85 (1H, d, J=2.2 Hz), 4.11-4.05 (1H, m), 3.79 (4H, t, J=4.8 Hz), 3.54 (1H, J=8.4 Hz), 3.25-3.23 (4H, m), 2.98 (1H, dd, J=3.9, 13.8 Hz), 2.82 (1H, t, J=8.9 Hz), 2.71 (1H, dd, J=8.4, 13.8 Hz), 2.35-2.25 (1H, m), 1.97 (1H, dd, J=6.1, 12.4 Hz), 1.64-1.56 (1H, m), 1.06 (3H, d, J=6.8 Hz), NH not observed.

6-((2R,4R*)-2-benzyl-4-methylpyrrolidin-1-yl)-4-morpholinopyridin-2(1H)-one diastereomer 2; LCMS (ES+) 354

(M+H)⁺, RT 3.09 min (Analytical Method B); RT 3.14 min (Analytical Method SFC1, YMC AMYLOSE-C, 30% (IPA/ACN, 1:1)/(0.1% DEAISO)/CO₂); ¹H NMR (400 MHz, CDCl₃): δ 7.30-7.20 (3H, m), 7.16-7.14 (2H, m), 5.24 (1H, d, J=2.2 Hz), 4.91 (1H, d, J=2.2 Hz), 4.17-4.10 (1H, m), 3.77 (4H, t, J=5.1 Hz), 3.54-3.49 (1H, m), 3.27-3.25 (4H, m), 3.19 (1H, dd, J=3.4, 13.9 Hz), 2.90 (1H, t, J=9.6 Hz), 2.64 (1H, dd, J=8.9, 13.6 Hz), 2.22-2.11 (2H, m), 1.47-1.38 (1H, m), 1.03 (3H, d, J=6.6 Hz), NH not observed.

Example 102: (S)-6-(2-benzyl-4,4-difluoropyrrolidin-1-yl)-4-morpholinopyridin-2(1H)-one and
Example 103: (R)-6-(2-benzyl-4,4-difluoropyrrolidin-1-yl)-4-morpholinopyridin-2(1H)-one

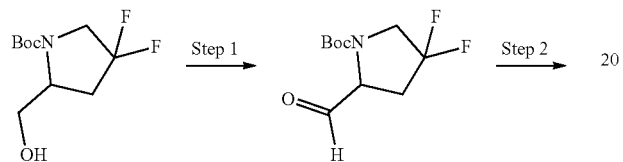

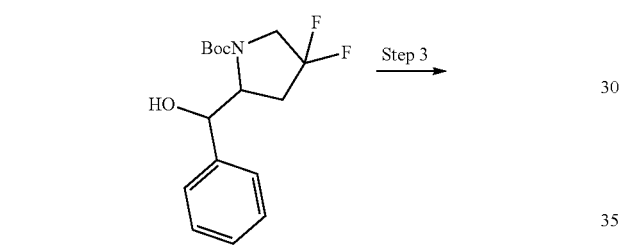

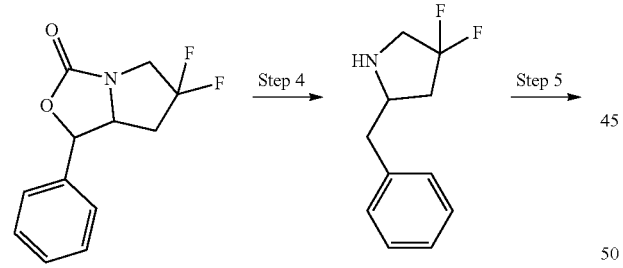

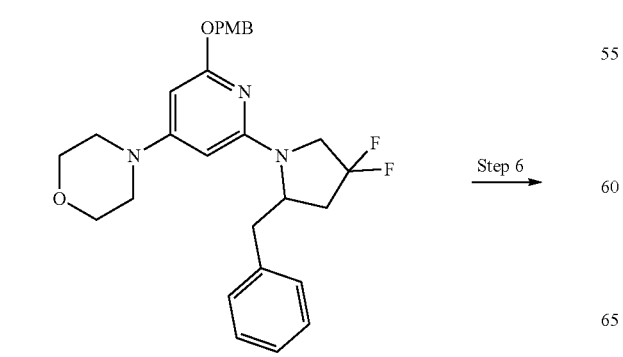

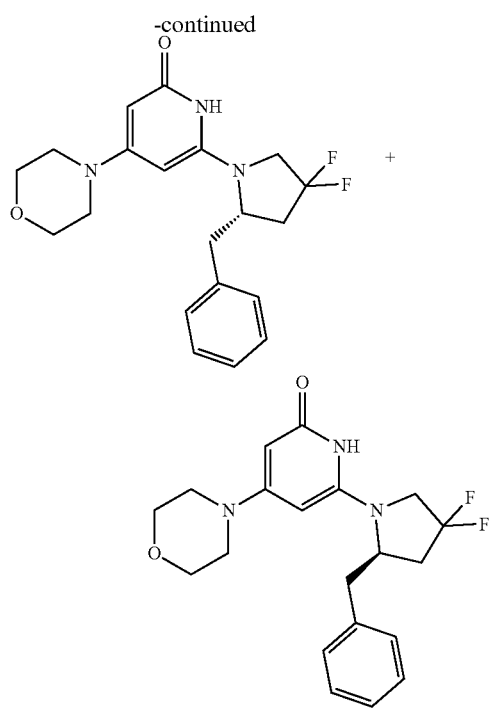

Step 1: tert-butyl 4,4-difluoro-2-formylpyrrolidine-1-carboxylate

Dess-Martin periodinane (4.92 g, 11.60 mmol) was added portionwise to a solution of tert-butyl 4,4-difluoro-2-(hydroxymethyl)pyrrolidine-1-carboxylate (2.5 g, 10.55 mmol) in DCM (30 mL) at 0° C. After complete addition the reaction was warmed to rt and stirred for 2 h. Saturated NaHCO₃ was added and the layers separated using a phase separator. The DCM was removed in vacuo to give a clear oil which was used to the next step without further purification.

Step 2: tert-butyl 4,4-difluoro-2-(hydroxy(phenyl)methyl)pyrrolidine-1-carboxylate Phenylmagnesium bromide (9.4 mL, 9.40 mmol, 1M in THF) was added dropwise to a solution of tert-butyl 4,4-difluoro-2-formylpyrrolidine-1-carboxylate (1.7 g, 7.23 mmol) in THF (15 mL) at −78° C. After 3 h the reaction was warmed to rt and quenched with water. The THF was removed in vacuo. The aqueous layer was extracted with EtOAc and the organic layer dried (MgSO₄). The solvent was removed in vacuo to give a residue, which was purified by silica gel column chromatography (gradient elution, 0-30% EtOAc/iso-hexane) yielded of the title compound.

Step 3: 6,6-difluoro-1-phenyltetrahydro-1H,3H-pyrrolo[1,2-c]oxazol-3-one

To a solution of tert-butyl 4,4-difluoro-2-(hydroxy(phenyl)methyl)pyrrolidine-1-carboxylate (1.23 g, 3.93 mmol) in isopropanol (20 mL) was added KOtBu (44 mg, 0.39 mmol). The reaction was heated at reflux for 3 h. Additional KOtBu (440 mg, 3.93 mmol) was added and the reaction heated at reflux for an additional 2 h. The reaction was cooled to rt and the solvent removed to give a residue oil, which was purified by silica gel column chromatography (gradient elution, 0-30% EtOAc/iso-hexane) to afford the title compound.

Step 4: 2-benzyl-4,4-difluoropyrrolidine

To a solution of 6,6-difluoro-1-phenyltetrahydro-1H,3H-pyrrolo[1,2-c]oxazol-3-one (310 mg, 1.29 mmol) in MeOH (5 mL) was added NaOMe (0.25 mL, 1.36 mmol, 5.5 M in methanol) and 20% palladium hydroxide on carbon. The reaction was stirred under an atmosphere of hydrogen (1 atmosphere) for 48 h. The reaction was filtered through Celite, washing the Celite with further MeOH. The collected filtrate was acidified (~pH 3) with 1M HCl and the solvent removed to give a residue, which was purified by SCX chromatography (eluting with 50% MeOH/DCM followed by 10% 7N methanolic ammonia in methanol/methanol). Concentration of the ammonical fractions in vacuo yielded the title compound.

Step 5: 4-(2-(2-benzyl-4,4-difluoropyrrolidin-1-yl)-6-((4-methoxybenzyl)oxy)pyridin-4-yl)morpholine Following Method D starting from 2-benzyl-4,4-difluoropyrrolidine and 4-(2-chloro-6-((4-methoxybenzyl)oxy)pyridin-4-yl)morpholine (scaffold 1). The reaction was cooled to rt. and the solvent removed in vacuo. The residue was dissolved/suspended in DCM and washed with water and the layers separated. The organic extracts were dried (phase separator) and concentrated in vacuo. The residue was purified by silica gel column chromatography (gradient elution, 0-50% EtOAc/iso-hexane) to afford the title compound.

Step 6: (S)-6-(2-benzyl-4,4-difluoropyrrolidin-1-yl)-4-morpholinopyridin-2(1H)-one and (R)-6-(2-benzyl-4,4-difluoropyrrolidin-1-yl)-4-morpholinopyridin-2(1H)-one Following Method E starting from 4-(2-(2-benzyl-4,4-difluoropyrrolidin-1-yl)-6-((4-methoxybenzyl)oxy)pyridin-4-yl)morpholine (S)-6-(2-benzyl-4,4-difluoropyrrolidin-1-yl)-4-morpholinopyridin-2(1H)-one; LCMS (ES+) 376 (M+H)+, RT 3.03 min (Analytical Method B); RT 4.65 min (Analytical Method SFC4, YMC CELLULOSE-C, 15/85 IPA (0.1% DEAISO)/CO2); $^1$H NMR (400 MHz, CDCl$_3$): δ 7.30-7.22 (5H, m), 5.32 (1H, d, J=2.0 Hz), 4.91 (1H, d, J=1.2 Hz), 4.73-4.66 (1H, m), 3.90-3.74 (6H, m), 3.29-3.26 (4H, m), 3.19 (1H, dd, J=4.3, 14.2 Hz), 2.50-2.25 (2H, m).

(R)-6-(2-benzyl-4,4-difluoropyrrolidin-1-yl)-4-morpholinopyridin-2(1H)-one; LCMS (ES+) 376 (M+H)+, RT 3.03 min (Analytical Method B); RT 5.53 min (Analytical Method SFC4, YMC CELLULOSE-C, 15/85 IPA (0.1% DEAISO)/CO2); $^1$H NMR (400 MHz, CDCl$_3$): δ 7.30-7.22 (5H, m), 5.32 (1H, d, J=2.0 Hz), 4.91 (1H, d, J=1.2 Hz), 4.73-4.66 (1H, m), 3.90-3.74 (6H, m), 3.29-3.26 (4H, m), 3.19 (1H, dd, J=4.3, 14.2 Hz), 2.50-2.25 (2H, m).

Example 104: (R)-6-(2-benzyl-3,3-difluoroazepan-1-yl)-4-morpholinopyridin-2(1H)-one and Example 105: (S)-6-(2-benzyl-3,3-difluoroazepan-1-yl)-4-morpholinopyridin-2(1H)-one

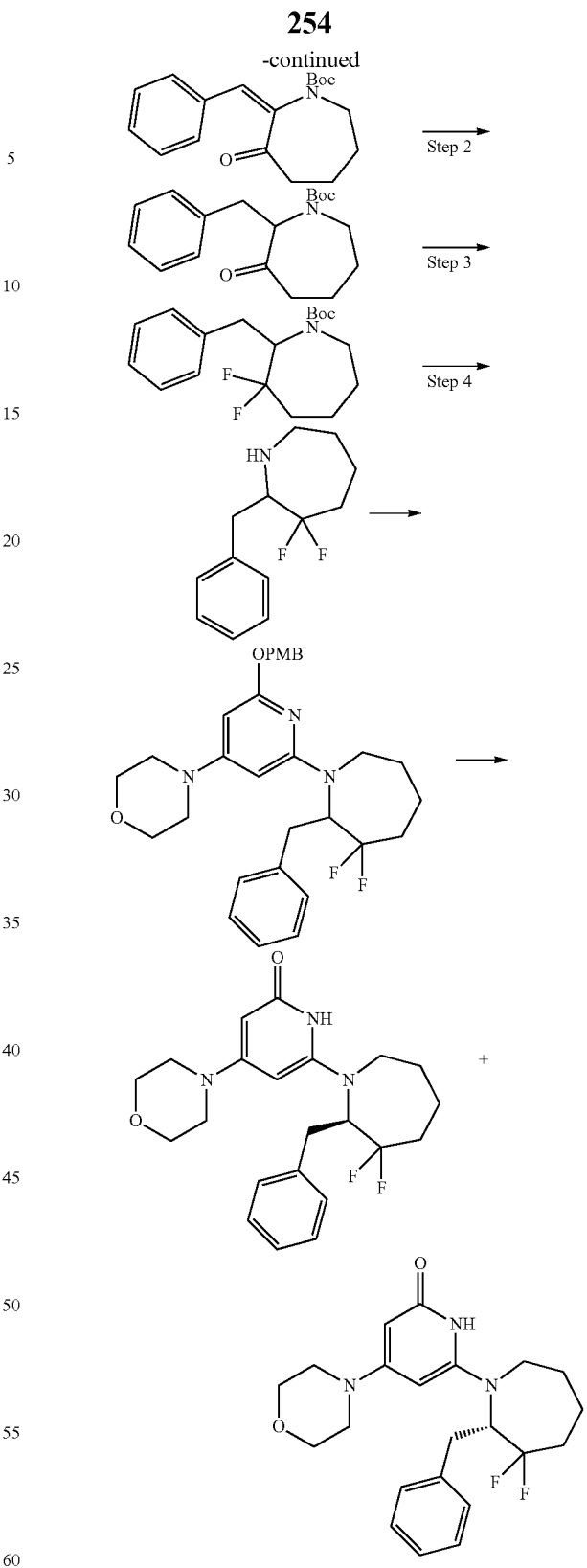

Step 1: tert-butyl (E)-2-benzylidene-3-oxoazepane-1-carboxylate

LDA (2.58 mL, 5.16 mmol, 2 M in THF) was added dropwise to a solution of tert-butyl 3-oxoazepane-1-carboxylate (g, 4.69 mmol) in dry THF (15 mL) at −40° C. The reaction was stirred for 1 h at −40° C. before benzaldehyde (1.43 mL, 14.08 mmol) was added dropwise. The reaction was allowed to warm to rt over 3 h. The reaction was quenched by addition of water and the THF removed under reduced pressure. The aqueous layer was extracted with DCM and the layers separated. The organic extracts were dried (phase separator) and concentrated under reduced pressure. The resultant oil was purified by silica gel column chromatography (gradient elution, 0-20% EtOAc/iso-hexane) to afford the title compound.

Step 2: tert-butyl 2-benzyl-3-oxoazepane-1-carboxylate tert-Butyl (E)-2-benzylidene-3-oxoazepane-1-carboxylate (300 mg, 1 mmol) was dissolved in MeOH (100 mL) and the resultant solution passed through an H-Cube (30 bar, r.t., 1 mL/min) using a Pd/C (10%) cartridge. The collected solvent was concentrated under reduced pressure. The residue was purified by silica gel column chromatography (gradient elution, 0-20% EtOAc/iso-hexane) to give the title compound.

Step 3: tert-butyl 2-benzyl-3,3-difluoroazepane-1-carboxylate tert-Butyl 2-benzyl-3-oxoazepane-1-carboxylate (1.95 g, 6.4 mmol) was dissolved in deoxofluor (21 mL, 50% in THF) and the reaction stirred at rt for 4 days. The reaction was cooled in an ice-bath and quenched by the careful addition of saturated NaHCO₃. The resulting aqueous layer was extracted with DCM, and the organic extracts dried (phase separator) and concentrated in vacuo. The crude mixture was purified by silica gel column chromatography (gradient elution, 0-20% EtOAc/iso-hexane) to give the title compound.

Step 4: 2-benzyl-3,3-difluoroazepane

Following the method described for the preparation of example 5 step 2 starting from tert-butyl 2-benzyl-3,3-difluoroazepane-1-carboxylate (15 mg, 0.046 mmol) to give the title compound. Used without further purification.

Step 5: 4-(2-(2-benzyl-3,3-difluoroazepan-1-yl)-6-((4-methoxybenzyl)oxy)pyridin-4-yl)morpholine Following Method D starting from 2-benzyl-3,3-difluoroazepane (270 mg, 1.2 mmol) and 4-(2-chloro-6-((4-methoxybenzyl)oxy)pyridin-4-yl)morpholine (401 mg, 1.2 mmol, scaffold 1). The crude material was purified by silica gel column chromatography (gradient elution 0-50% EtOAc/iso-hexane) to give the title compound.

Step 6: (S)-6-(2-benzyl-3,3-difluoroazepan-1-yl)-4-morpholinopyridin-2(1H)-one and (R)-6-(2-benzyl-3,3-difluoroazepan-1-yl)-4-morpholinopyridin-2(1H)-one Following Method E starting from 4-(2-(2-benzyl-3,3-difluoroazepan-1-yl)-6-((4-methoxybenzyl)oxy)pyridin-4-yl)morpholine (264 mg, 0.5 mmol). The crude material was purified by reverse phase preparative HPLC followed by SFC to give the title compounds.

(R)-6-(2-benzyl-3,3-difluoroazepan-1-yl)-4-morpholinopyridin-2(1H)-one; LCMS (ES+) 404 (M+H)⁺, RT 3.02 min (Analytical Method A); RT 2.27 min (Analytical Method SFC4, LUX CELLULOSE-4, 35/65 IPA (0.1% DEAISO)/CO₂); ¹H NMR (400 MHz, CDCl₃): δ 7.27-7.12 (5H, m), 5.17 (1H, d, J=1.9 Hz), 4.75 (1H, d, J=1.8 Hz), 4.35-4.20 (1H, m), 3.71 (4H, t, J=5.1 Hz), 3.60-3.51 (1H, m), 3.34-3.25 (1H, m), 3.19 (1H, dd, J=3.6, 13.5 Hz), 3.11-3.00 (4H, m), 2.93 (1H, dd, J=10.2, 14.6 Hz), 2.24-1.98 (2H, m), 1.82-1.65 (4H, m), NH not observed.

(S)-6-(2-benzyl-3,3-difluoroazepan-1-yl)-4-morpholinopyridin-2(1H)-one; LCMS (ES+) 404 (M+H)⁺, RT 3.02 min (Analytical Method A); RT 2.74 min (Analytical Method SFC4, LUX CELLULOSE-4, 35/65 IPA (0.1% DEAISO)/CO₂); ¹H NMR (400 MHz, CDCl₃): δ 7.27-7.12 (5H, m), 5.17 (1H, d, J=1.9 Hz), 4.75 (1H, d, J=1.8 Hz), 4.35-4.20 (1H, m), 3.71 (4H, t, J=5.1 Hz), 3.60-3.51 (1H, m), 3.34-3.25 (1H, m), 3.19 (1H, dd, J=3.6, 13.5 Hz), 3.11-3.00 (4H, m), 2.93 (1H, dd, J=10.2, 14.6 Hz), 2.24-1.98 (2H, m), 1.82-1.65 (4H, m), NH not observed.

Example 106: 6-((2S*,3S*)-2-benzyl-3-(difluoromethoxy)azepan-1-yl)-4-morpholinopyridin-2(1H)-one

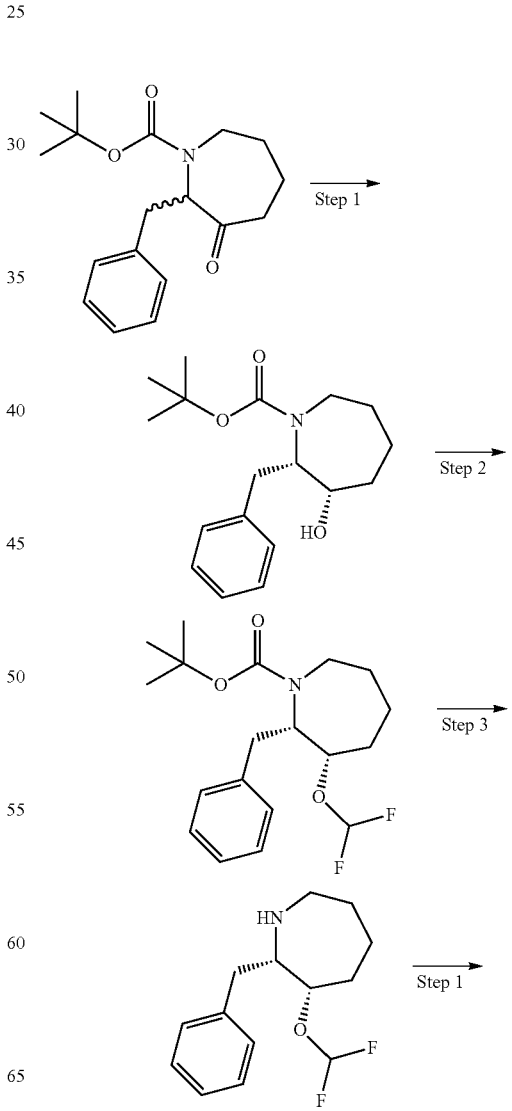

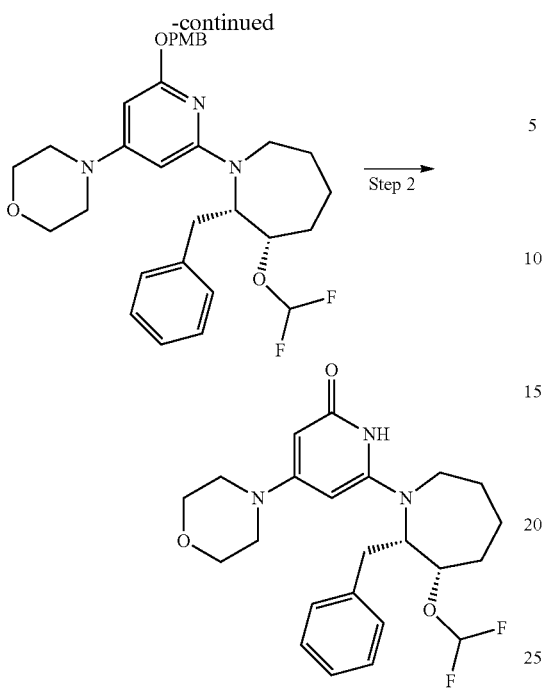

Step 1: tert-butyl-(2S*,3S*)-2-benzyl-3-hydroxyazepane-1-carboxylate

Following the method described for the preparation of Example 88 step 2 starting from tert-butyl-2-Benzyl-3-oxoazepane-1-carboxylate (118 mg, 0.39 mmol, example 104, step 2). The residue was purified by silica gel column chromatography (gradient elution, 0-20% EtOAc/iso-hexane) to afford the title compound.

Step 2: tert-butyl-(2S*,3S*)-2-benzyl-3-(difluoromethoxy)azepane-1-carboxylate Following the method described for the preparation of Example 90 step 1 starting from tert-butyl-(2S*,3S*)-2-benzyl-3-hydroxyazepane-1-carboxylate (100 mg, 0.33 mmol). The mixture was purified by silica gel column chromatography (gradient elution, 0-20% EtOAc/iso-hexane) to afford the title compound.

Step 3: (2S*,3S*)-2-benzyl-3-(difluoromethoxy)azepane

Following the method described for the preparation of example 73 step 5 starting using tert-butyl-(2S,3S)-2-benzyl-3-(difluoromethoxy)azepane-1-carboxylate (60 mg, 0.17 mmol). The title compound was obtained after free basing with saturated aqueous sodium hydrogen carbonate.

Step 4: 4-(2-((2S*,3S*)-2-benzyl-3-(difluoromethoxy)azepan-1-yl)-6-((4-methoxybenzyl)oxy)pyridin-4-yl)morpholine Following Method D starting from (2S*,3S*)-2-benzyl-3-(difluoromethoxy)azepane (30 mg, 0.18 mmol) and 4-(2-chloro-6-((4-methoxybenzyl)oxy)pyridin-4-yl)morpholine (36 mg, 0.11 mmol, scaffold 1). The residue was purified by silica gel column chromatography (gradient elution, 0-50% EtOAc/iso-hexane) to afford the title compound.

Step 5: 6-((2S*,3S*)-2-benzyl-3-(difluoromethoxy)azepan-1-yl)-4-morpholinopyridin-2(1H)-one Following Method E starting from 4-(2-((2S*,3S*)-2-benzyl-3-(difluoromethoxy)azepan-1-yl)-6-((4-methoxybenzyl)oxy)pyridin-4-yl)morpholine (35 mg, 0.06 mmol). The residue was purified by reverse phase preparative HPLC to afford the title compound (1.33 mg, 5%). LCMS (ES+) 434 (M+H)+, RT 2.99 min (Analytical Method A); $^1$H NMR (400 MHz, CDCl$_3$): δ 7.28-7.16 (5H, m), 6.16 (1H, dd, J=72.9, 76.9 Hz), 5.20 (1H, d, J=2.0 Hz), 4.91 (1H, d, J=2 Hz), 4.54-4.50 (1H, m), 4.16-4.11 (1H, m), 3.76 (4H, t, J=5 Hz), 3.5-3.36 (2H, m), 3.16 (4H, dd, J=3.7, 6.1 Hz), 3.01-2.99 (2H, m), 2.07-1.99 (1H, m), 1.94-1.83 (1H, m), 1.78-1.66 (3H, m), 1.59-1.52 (1H, m), NH not observed.

Example 107: 6-((2S,*3R*)-2-benzyl-3-methoxyazepan-1-yl)-4-morpholinopyridin-2(1H)-one, Stereoisomer 1 and Example 108: 6-((2S*,3R*)-2-benzyl-3-methoxyazepan-1-yl)-4-morpholinopyridin-2(1H)-one, Stereoisomer 2

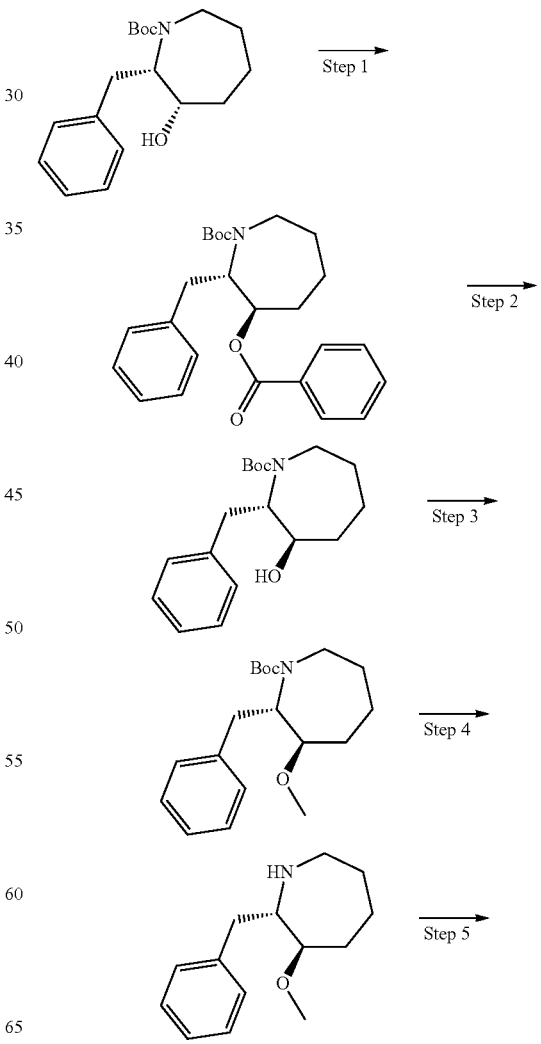

259

-continued

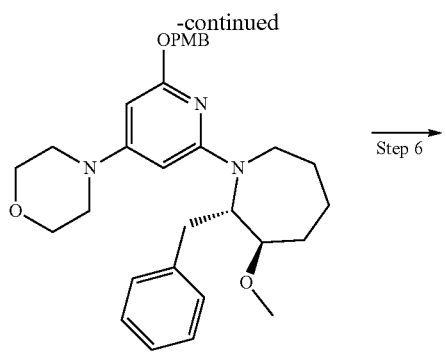

Step 6 →

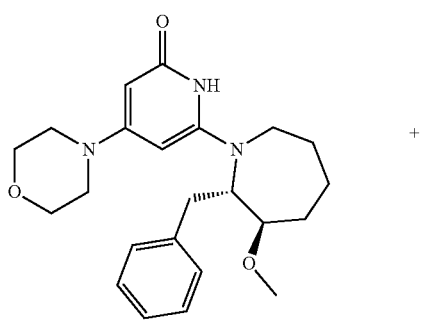

+

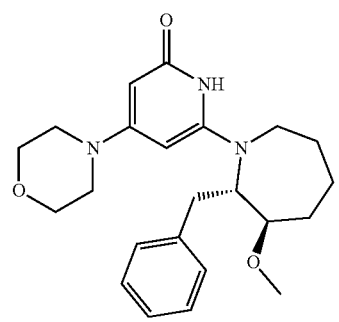 [SMILES: CO[C@@H]1CCCCN(c2cc(N3CCOCC3)cc(=O)[nH]2)[C@H]1Cc1ccccc1]

Step 1: tert-butyl-(2S*,3R*)-3-(benzoyloxy)-2-benzylazepane-1-carboxylate

Following the method described for the preparation of Example 88 step 3 starting from tert-butyl-(2S*,3S*)-2-benzyl-3-hydroxyazepane-1-carboxylate (1.19 g, 3.9 mmol, Example 106 step 1). Purification by silica gel column chromatography (gradient elution, 0-20% EtOAc/iso-hexane) yielded the title compound.

Step 2: tert-butyl-(2S*,3R*)-2-benzyl-3-hydroxyazepane-1-carboxylate

Following the method described for the preparation of Example 88 step 4 starting from tert-butyl-(2S*,3R*)-3-(benzoyloxy)-2-benzylazepane-1-carboxylate (1.09 g, 2.66 mmol). Purification by silica gel column chromatography (gradient elution, 0-30% EtOAc/iso-hexane) yielded the title compound.

260

Step 3: tert-butyl-(2S*,3R*)-2-benzyl-3-methoxyazepane-1-carboxylate

Following the method described for the preparation of Example 88 step 5 starting from tert-butyl-(2S,3R)-2-Benzyl-3-hydroxyazepane-1-carboxylate (200 mg, 0.65 mmol). Purification by silica gel chromatography (gradient elution, 0-30% EtOAc/iso-hexane) yielded the title compound.

Step 4: (2S*,3R*)-2-benzyl-3-methoxyazepane

Following the method described for the preparation of example 73 step 5 starting from tert-butyl-(2S*,3R*)-2-benzyl-3-methoxyazepane-1-carboxylate (102 mg, 0.38 mmol). The residue was partitioned between DCM and saturated aqueous NaHCO$_3$, dried (phase separator) and concentrated under reduced pressure to afford the title compound.

Step 5: 4-(2-((2S*,3R*)-2-benzyl-3-methoxyazepan-1-yl)-6-((4-methoxybenzyl)oxy)pyridin-4-yl)morpholine Following Method D starting from (2S*,3R*)-2-benzyl-3-methoxyazepane (98 mg, 0.48 mmol) and 4-(2-chloro-6-((4-methoxybenzyl)oxy)pyridin-4-yl)morpholine (150 mg, 0.48 mmol, scaffold 1). The residue was purified by silica gel column chromatography (gradient elution, 0-50% EtOAc/iso-hexane) to afford the title compound.

Step 6: 6-((2S*,3R*)-2-benzyl-3-methoxyazepan-1-yl)-4-morpholinopyridin-2(1H)-one, Stereoisomer 1 and 6-((2S*,3R*)-2-benzyl-3-methoxyazepan-1-yl)-4-morpholinopyridin-2(1H)-one, Stereoisomer 2

Following Method E starting from 4-(2-((2S*,3R*)-2-benzyl-3-methoxyazepan-1-yl)-6-((4-methoxybenzyl)oxy)pyridin-4-yl)morpholine (52 mg, 0.1 mmol). The crude material was purified by reverse phase preparative HPLC followed by SFC to afford the title compounds.

6-((2S*,3R*)-2-benzyl-3-methoxyazepan-1-yl)-4-morpholinopyridin-2(1H)-one, diastereomer 1; LCMS (ES+) 398 (M+H)$^+$, RT 2.98 min (Analytical Method A); RT 0.99 min (Analytical Method SFC4, YMC CELLULOSE-C, 30/70 MeOH (0.1% DEAISO)/CO$_2$); $^1$H NMR (400 MHz, CDCl$_3$): δ 7.27-7.18 (3H, m), 7.13-7.11 (2H, m), 5.14 (1H, d, J=2.2 Hz), 4.75 (1H, d, J=2.2 Hz), 3.76-3.71 (5H, m), 3.41 (3H, s), 3.39-3.33 (1H, m), 3.22 (1H, t, J=8.1 Hz), 3.15-3.06 (5H, m), 2.90 (1H, dd, J=7.6, 14.2 Hz), 2.79-2.72 (1H, m), 1.96-1.80 (2H, m), 1.68-1.52 (3H, m), 1.39-1.28 (1H, m), NH not observed.

6-((2S*,3R*)-2-benzyl-3-methoxyazepan-1-yl)-4-morpholinopyridin-2(1H)-one, diastereomer 2; LCMS (ES+) 398 (M+H)$^+$, RT 2.98 min (Analytical Method A); RT 1.47 min (Analytical Method SFC4, YMC CELLULOSE-C, 30/70 MeOH (0.1% DEAISO)/CO$_2$); $^1$H NMR (400 MHz, CDCl$_3$): δ 7.27-7.18 (3H, m), 7.13-7.11 (2H, m), 5.14 (1H, d, J=2.2 Hz), 4.75 (1H, d, J=2.2 Hz), 3.76-3.71 (5H, m), 3.41 (3H, s), 3.39-3.33 (1H, m), 3.22 (1H, t, J=8.1 Hz), 3.15-3.06 (5H, m), 2.90 (1H, dd, J=7.6, 14.2 Hz), 2.79-2.72 (1H, m), 1.96-1.80 (2H, m), 1.68-1.52 (3H, m), 1.39-1.28 (1H, m), NH not observed.

Example 109: 6-((2S*,3R*)-2-benzyl-3-(difluoromethoxy)azepan-1-yl)-4-morpholinopyridin-2(1H)-one, Stereoisomer 1 and Example 110: 6-((2S*,3R*)-2-benzyl-3-(difluoromethoxy)azepan-1-yl)-4-morpholinopyridin-2(1H)-one, Stereoisomer 2

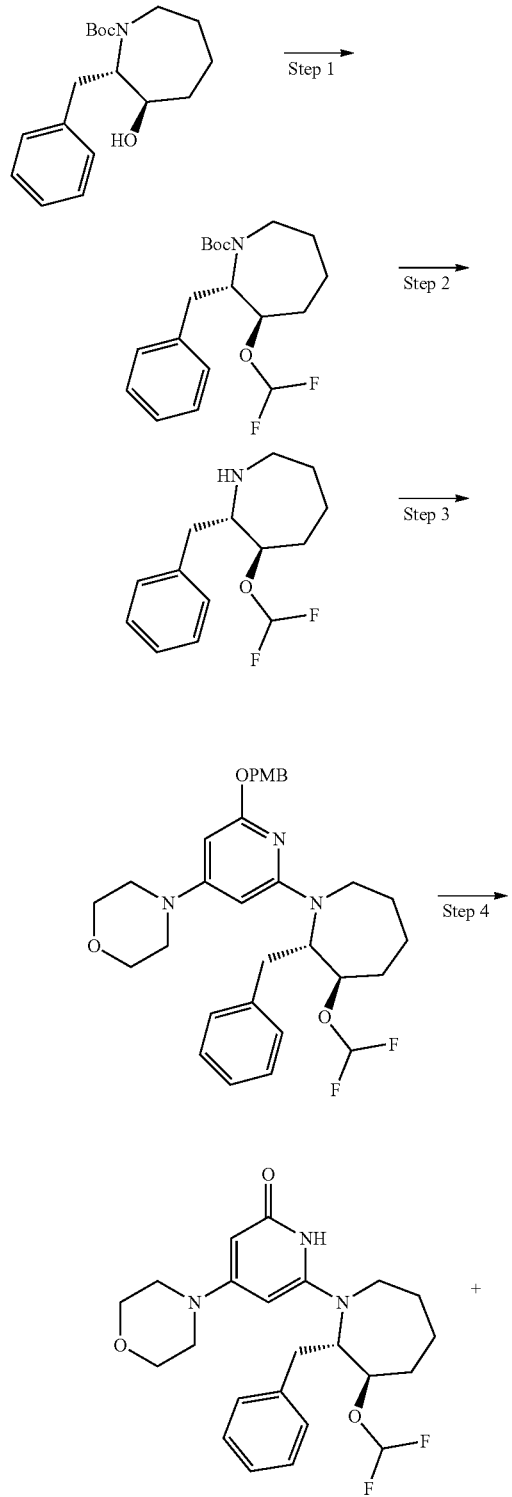

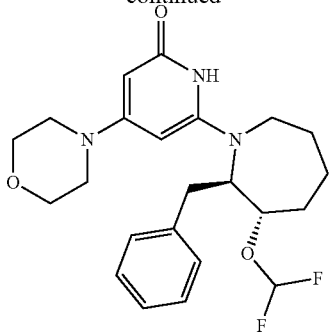

Step 1: tert-butyl-(2S*,3R*)-2-benzyl-3-(difluoromethoxy)azepane-1-carboxylate

Following the method described for the preparation of Example 90 step 1 starting from using tert-butyl-(2S*,3R*)-2-benzyl-3-hydroxyazepane-1-carboxylate (250 mg, 0.82 mmol, Example 107 step 2). Purification by silica gel column chromatography (gradient elution, 0-30% EtOAc/iso-hexane) yielded the title compound.

Step 2: (2S*,3R*)-2-benzyl-3-(difluoromethoxy)azepane

Following the method described for the preparation of example 73 step 5 starting from tert-butyl-(2S*,3R*)-2-benzyl-3-(difluoromethoxy)azepane-1-carboxylate (210 mg, 0.59 mmol). The residue was partitioned between DCM and saturated aqueous NaHCO₃, dried (phase separator) and concentrated under reduced pressure to afford the title compound.

Step 3: 4-(2-((2S*,3R*)-2-benzyl-3-(difluoromethoxy)azepan-1-yl)-6-((4-methoxybenzyl)oxy)pyridin-4-yl)morpholine Following Method D starting from rac-(2S,3R)-2-benzyl-3-(difluoromethoxy)azepane (70 mg, 0.27 mmol) and 4-(2-chloro-6-((4-methoxybenzyl)oxy)pyridin-4-yl)morpholine (92 mg, 0.27 mmol, scaffold 1). The residue was purified by silica gel column chromatography (gradient elution, 0-30% EtOAc/iso-hexane) yielded a mixture (75 mg) of rac-(2S,3R)-2-benzyl-3-(difluoromethoxy)azepane ~70% and title compound ~20%. as a clear oil. The reaction was repeated on this mixture using Method D using Cs₂CO₃ as the base. The residue was purified by silica gel column chromatography (gradient elution, 0-30% EtOAc/iso-hexane) to afford the title compound.

Step 4: 6-((2S*,3R*)-2-benzyl-3-(difluoromethoxy)azepan-1-yl)-4-morpholinopyridin-2(1H)-one, Stereoisomer 1 and 6-((2S*,3R*)-2-benzyl-3-(difluoromethoxy)azepan-1-yl)-4-morpholinopyridin-2(1H)-one, Stereoisomer 2

Following Method E starting from 4-(2-((2S*,3R*)-2-benzyl-3-(difluoromethoxy)azepan-1-yl)-6-((4-methoxybenzyl)oxy)pyridin-4-yl)morpholine (60 mg, 0.11 mmol). The residue was purified by reverse phase preparative HPLC followed by SFC to afford the title compounds.

6-((2S*,3R*)-2-benzyl-3-(difluoromethoxy)azepan-1-yl)-4-morpholinopyridin-2(1H)-one, diastereomer 1; LCMS (ES+) 434 (M+H)+, RT 3.11 min (Analytical Method B); RT 3.64 min (Analytical Method SFC1, YMC AMYLOSE-C, 20/80 IPA (0.1% DEAISO)/CO$_2$); $^1$H NMR (400 MHz, CDCl$_3$): δ 7.25-7.18 (3H, m), 7.13-7.11 (2H, m), 6.34 (1H, t, J=73.9 Hz), 5.14 (1H, d, J=2.0 Hz). 4.76 (1H, d, J=2.1 Hz), 4.21 (1H, t, J=8.9 Hz), 3.88-3.83 (1H, m), 3.73 (4H, t, J=4.5 Hz), 3.46-3.42 (1H, m), 3.16-3.05 (5H, m), 2.88 (1H, d, J=8.1, 13.8 Hz), 2.76-2.69 (1H, m), 2.04-1.99 (1H, m), 1.88-1.72 (2H, m), 1.65-1.60 (2H, m), 1.49-1.38 (1H, m), NH not observed 6-((2S*,3R*)-2-benzyl-3-(difluoromethoxy)azepan-1-yl)-4-morpholinopyridin-2(1H)-one, diastereomer 2; LCMS (ES+) 434 (M+H)+, RT 3.03 min (Analytical Method A); RT 3.14 min (Analytical Method SFC1, YMC AMYLOSE-C, 20/80 IPA (0.1% DEAISO)/CO$_2$); $^1$H NMR (400 MHz, CDCl$_3$): δ 7.25-7.18 (3H, m), 7.13-7.11 (2H, m), 6.34 (1H, t, J=73.9 Hz), 5.14 (1H, d, J=2.0 Hz). 4.76 (1H, d, J=2.1 Hz), 4.21 (1H, t, J=8.9 Hz), 3.88-3.83 (1H, m), 3.73 (4H, t, J=4.5 Hz), 3.46-3.42 (1H, m), 3.16-3.05 (5H, m), 2.88 (1H, d, J=8.1, 13.8 Hz), 2.76-2.69 (1H, m), 2.04-1.99 (1H, m), 1.88-1.72 (2H, m), 1.65-1.60 (2H, m), 1.49-1.38 (1H, m), NH not observed Example 111: 6-(2-((6-fluoropyridin-3-yl)methyl)pyrrolidin-1-yl)-4-morpholinopyridin-2(1H)-one

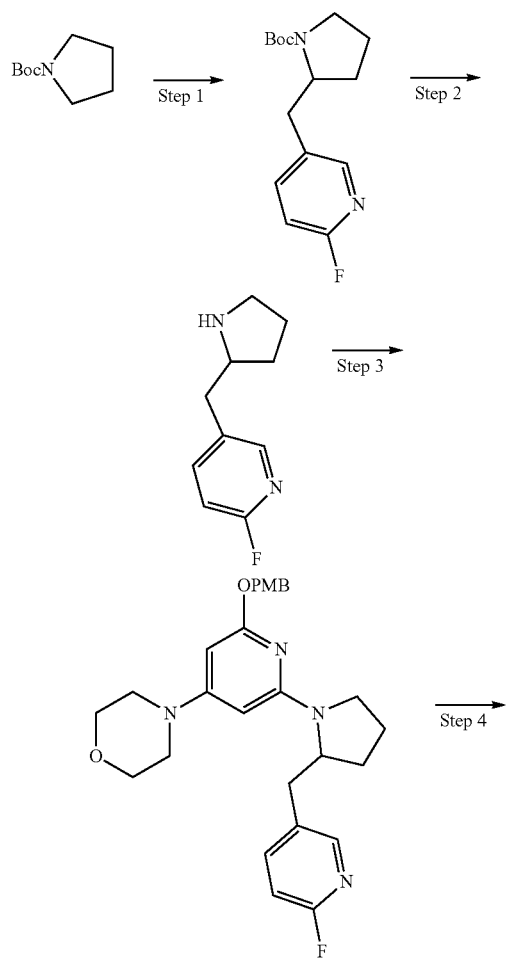

-continued

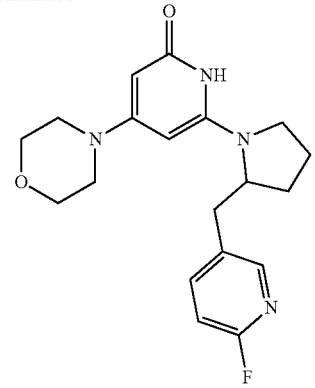

Step 1: tert-butyl 2-((6-fluoropyridin-3-yl)methyl)pyrrolidine-1-carboxylate

To a solution of N-Boc-pyrrolidine (751 mg, 4.4 mmol) in diethyl ether (0.3 M), under N$_2$ atmosphere, at −78° C. was added sec-BuLi (1.3 eq., 0.86 M solution in cyclohexane) and the mixture was stirred at −78° C. for 30 minutes. 5-(Bromomethyl)-2-fluoropyridine (1.00 g, 5.2 mmol) was added dropwise at −78° C. After complete addition the reaction was allowed to slowly warm to rt overnight. The reaction was quenched with saturated aqueous NH$_4$Cl solution, the layers separated and the aqueous further extracted with Et$_2$O (×2). The combined organic extracts were dried (MgSO$_4$) and concentrated under reduced pressure. The mixture was purified by silica gel column chromatography (gradient elution, 0-100% EtOAc/iso-hexane) to give the title compound.

Step 2: 2-fluoro-5-(pyrrolidin-2-ylmethyl)pyridine

To a solution of tert-butyl 2-((6-fluoropyridin-3-yl)methyl)pyrrolidine-1-carboxylate (150 mg, 0.53 mmol) in DCM (0.42 M) was added TFA (0.42 M) and the mixture stirred at rt for 1 h. The reaction was evaporated to dryness. Purified by SCX cartridge eluting sequentially with DCM: MeOH, 1:1 then 3:1 DCM:7 N ammonia in methanol. The ammonia in methanol fractions were combined and concentrated under reduced pressure to afford the title compound.

Step 3: 4-(2-(2-((6-fluoropyridin-3-yl)methyl)pyrrolidin-1-yl)-6-((4-methoxybenzyl)oxy)pyridin-4-yl)morpholine Following Method C starting from 2-fluoro-5-(pyrrolidin-2-ylmethyl)pyridine (60 mg, 0.33 mmol) and 4-(2-chloro-6-((4-methoxybenzyl)oxy)pyridin-4-yl)morpholine (110 mg, 0.33 mmol, Scaffold 1). Purification by silica gel column chromatography (gradient elution, 0-30% EtOAc/iso-hexane) yielded the title compound.

Step 4: 6-(2-((6-fluoropyridin-3-yl)methyl)pyrrolidin-1-yl)-4-morpholinopyridin-2(1H)-one Following Method E starting from 4-(2-(2-((6-fluoropyridin-3-yl)methyl)pyrrolidin-1-yl)-6-((4-methoxybenzyl)oxy)pyridin-4-yl)morpholine (119 mg, 0.25 mmol). Purification by reverse phase preparative HPLC followed by freeze drying from MeCN/H$_2$O yielded the title compound. LCMS (ES+) 359 (M+H)+, RT 2.57 min (Analytical Method A); $^1$H NMR (400 MHz, CDCl$_3$): δ 8.05 (1H, d, J=2.3 Hz), 7.73 (1H, dt, J=2.5, 8.1 Hz), 6.85 (1H, dd, J=2.9, 8.5 Hz), 5.21 (1H, d, J=2.0 Hz), 4.86 (1H, d, J=2.0 Hz), 4.42-4.38 (1H, m), 3.82-3.78 (4H, m), 3.46-3.39 (1H, m), 3.28-3.23 (5H, m), 3.00 (1H, dd, J=3.9, 14.0 Hz), 2.69 (1H, dd, J=8.5, 14.0 Hz), 2.02-1.91 (2H, m), 1.82-1.75 (2H, m), NH not observed.

The following examples were prepared using a procedure analogous to that described for Example 111 using the alkyl halide listed below. Buchwald conditions Method C or Method D were used to couple the amine to Scaffold 1. Purification by reverse phase preparative HPLC afforded the title compounds.

| Example | Structure and name | Alkyl halide | Buchwald conditions | Analytical data |
|---|---|---|---|---|
| Example 112 | 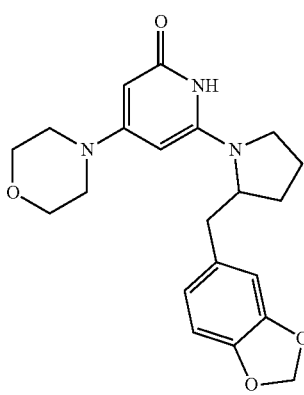<br>6-[2-(1,3-benzodioxol-5-ylmethyl)-pyrrolidin-1-yl]-4-morpholino-1H-pyridin-2-one | 5-(bromomethyl)-1,3-benzodioxole | Method D | LCMS (ES+) 384 (M + H)$^+$, RT 2.70 min (Analytical Method A); $^1$H NMR (400 MHz, CDCl$_3$): δ 6.75-6.70 (2H, m), 6.60 (1H, dd, J = 1.5, 7.8 Hz), 5.95-5.92 (2H, m), 5.22 (1H, d, J = 2.3 Hz), 4.86 (1H, d, J = 2.0 Hz), 4.07-4.02 (1H, m), 3.81-3.77 (4H, m), 3.45-3.39 (1H, m), 3.29-3.23 (5H, m), 2.91-2.85 (1H, m), 2.60 (1H, dd, J = 8.4, 14.2 Hz), 1.96-1.80 (4H, m), NH not observed. |
| Example 113 | 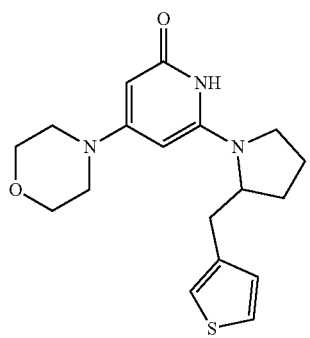<br>4-morpholino-6-[2-(3-thienylmethyl)-pyrrolidin-1-yl]-1H-pyridin-2-one | 3-(bromomethyl) thiophene | Method C | LCMS (ES+) 346 (M + H)$^+$, RT 2.76 min (Analytical Method A); $^1$H NMR δ (400 MHz, CDCl$_3$): δ 7.29-7.27 (1H, m), 7.02-6.99 (1H, m), 6.93 (1H, dd, J = 1.3, 5.1 Hz), 5.21 (1H, d, J = 2.3 Hz), 4.86 (1H, d, J = 2.0 Hz), 4.17-4.11 (1H, m), 3.81-3.77 (4H, m), 3.44 (1H, dt, J = 2.6, 8.7 Hz), 3.33-3.27 (1H, m), 3.27-3.22 (4H, m), 2.96 (1H, dd, J = 3.7, 14.3 Hz), 2.78 (1H, dd, J = 8.2, 14.3 Hz), 2.03-1.83 (4H, m), NH not observed. |
| Example 114 | 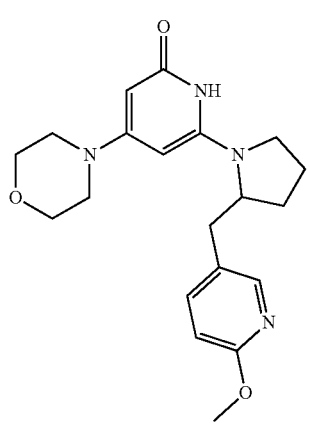<br>6-(2-((6-methoxypyridin-3-yl)-methyl)pyrrolidin-1-yl)-4-morpholinopyridin-2(1H)-one | 5-(bromomethyl)-2-methoxypyridine | Method C | LCMS (ES+) 371 (M + H)$^+$, RT 2.55 min (Analytical Method A); $^1$H NMR δ (400 MHz, CDCl$_3$): δ 7.96 (1H, d, J = 2.5 Hz), 7.42 (1H, dd, J = 2.4, 8.5 Hz), 6.68 (1H, d, J = 8.3 Hz), 5.22 (1H, d, J = 2.0 Hz), 4.87 (1H, d, J = 2.0 Hz), 4.17-4.13 (1H, m), 3.91 (3H, s), 3.79 (4H, dd, J = 4.9, 4.9 Hz), 3.44-3.38 (1H, m), 3.30-3.22 (5H, m), 2.88 (1H, dd, J = 3.7, 14.0 Hz), 2.69-2.61 (1H, m), 1.96-1.78 (4H, m), NH not observed. |

Intermediate 32: (R)-4-(2-((1S,3S,4R)-3-benzyl-2-azabicyclo[2.2.1]heptan-2-yl)-6-((4-methoxybenzyl)oxy)pyridin-4-yl)-2-methylmorpholine Intermediate 33: (R)-4-(2-((1R,3R,4S)-3-benzyl-2-azabicyclo[2.2.1]heptan-2-yl)-6-((4-methoxybenzyl)oxy)pyridin-4-yl)-2-methylmorpholine Intermediate 34: (R)-4-(2-((1R,3S,4S)-3-benzyl-2-azabicyclo[2.2.1]heptan-2-yl)-6-((4-methoxybenzyl)oxy)pyridin-4-yl)-2-methylmorpholine Intermediate 35: (R)-4-(2-((1S,3R,4R)-3-benzyl-2-azabicyclo[2.2.1]heptan-2-yl)-6-((4-methoxybenzyl)oxy)pyridin-4-yl)-2-methylmorpholine

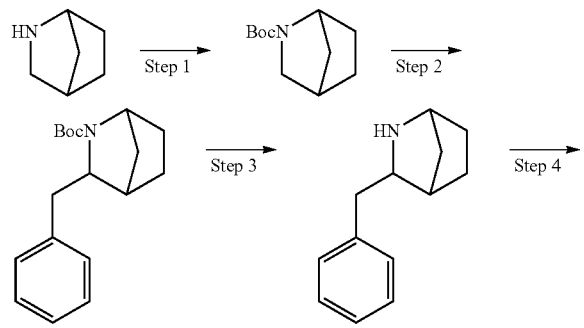

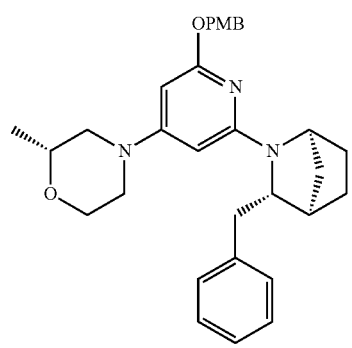

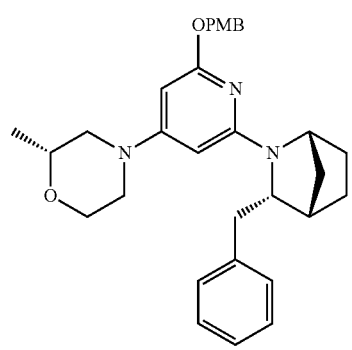

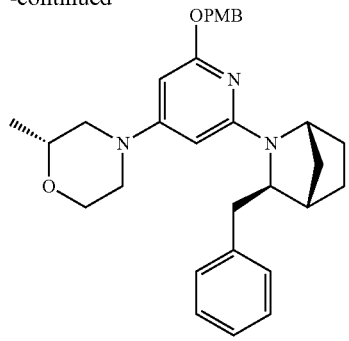

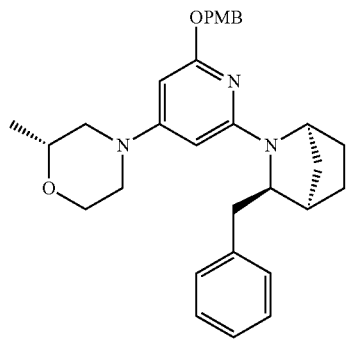

Step 1: tert-butyl 3-azabicyclo[2.2.1]heptane-3-carboxylate

Boc anhydride (1.05 eq.) and a solution of NaHCO₃ (5 eq.) in water (0.2 M) was added to a suspension of the 3-azabicyclo[2.2.1]heptane hydrochloride (2.0 g, 15.0 mmol) in THF (0.6 M). The resulting biphasic mixture was stirred vigorously overnight at r.t. The reaction mixture was diluted with water and DCM. The layers were separated and the organic phase dried (phase separator) and concentrated under reduced pressure to afford the title compound. Used without further purification in the next step.

Step 2: tert-butyl 2-benzyl-3-azabicyclo[2.2.1]heptane-3-carboxylate

Following the method described for the preparation of Intermediate 1 step 2 starting from tert-butyl 3-azabicyclo[2.2.1]heptane-3-carboxylate (3.0 g, 15 mmol) and benzyl bromide (3.6 mL, 30.4 mmol). Purification by silica gel column chromatography (gradient elution, 0-5% EtOAc/isohexane) afforded the title compound.

Step 3: 2-benzyl-3-azabicyclo[2.2.1]heptane

Following the method described for the preparation of Intermediate 1 step 3 starting from tert-butyl 2-benzyl-3-azabicyclo[2.2.1]heptane-3-carboxylate (615 mg, 2.14 mmol) to afford the title compound.

269

Step 4: (R)-4-(2-((1R,3R,4S)-3-benzyl-2-azabicyclo[2.2.1]heptan-2-yl)-6-((4-methoxybenzyl)oxy)pyridin-4-yl)-2-methylmorpholine, (R)-4-(2-((1R,3S,4S)-3-benzyl-2-azabicyclo[2.2.1]heptan-2-yl)-6-((4-methoxybenzyl)oxy)pyridin-4-yl)-2-methylmorpholine, (R)-4-(2-((1S,3R,4R)-3-benzyl-2-azabicyclo[2.2.1]heptan-2-yl)-6-((4-methoxybenzyl)oxy)pyridin-4-yl)-2-methylmorpholine, (R)-4-(2-((1S,3S,4R)-3-benzyl-2-azabicyclo[2.2.1]heptan-2-yl)-6-((4-methoxybenzyl)oxy)pyridin-4-yl)-2-methylmorpholine Following Method D starting from 3-benzyl-2-azabicyclo[2.2.1]heptane (430 mg, <2.14 mmol, Example 62 step 3) and (R)-4-(2-chloro-6-((4-methoxybenzyl)oxy)pyridin-4-yl)-2-methylmorpholine (746 mg, 2.14 mmol, Scaffold 1). Purification by reverse phase preparative HPLC followed by SFC yielded respectively Intermediate 32 (192 mg, 18%), Intermediate 33 (185 mg, 17%), Intermediate 34 (105 mg, 10%) and Intermediate 35 (137 mg, 13%).

Example 115: 6-((1S,3S,4R)-3-benzyl-2-azabicyclo[2.2.1]heptan-2-yl)-4-((R)-2-methylmorpholino)pyridin-2(1H)-one

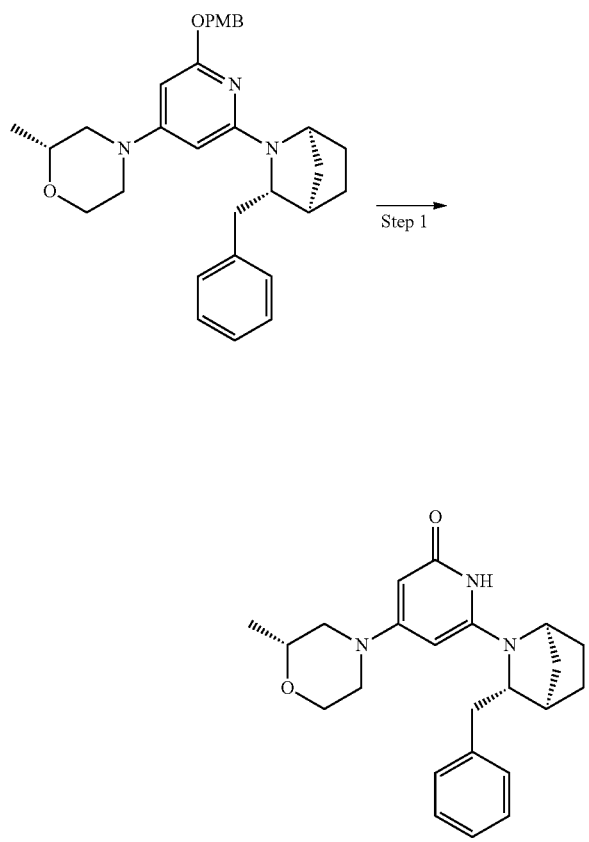

Following Method E starting from Intermediate 32 (192 mg, 0.38 mmol). Purification by reverse phase preparative HPLC followed by freeze drying from MeCN/H$_2$O afforded the title compound (relative stereochemistry between the benzyl group and bridgehead protons assigned by NMR nOe experiments). LCMS (ES+) 380 (M+H)$^+$, RT 3.19 min (Analytical Method B), RT 2.23 min (Analytical Method SFC1, YMC CELLULOSE-C 25/75 IPA (0.1% DEAISO)/CO$_2$); $^1$H NMR (400 MHz, CDCl$_3$) δ 7.34-7.30 (2H, m), 7.27-7.19 (3H, m), 5.21 (1H, d, J=2.1 Hz), 4.88 (1H, d, J=2.1 Hz), 4.53 (1H, s), 3.94 (1H, dd, J=2.3, 11.5 Hz), 3.71-3.60 (2H, m), 3.42 (2H, dd, J=14.5, 14.5 Hz), 3.20 (1H, dd, J=3.8, 9.2 Hz), 2.99-2.84 (2H, m), 2.65-2.54 (2H, m), 2.45-2.42 (1H, m), 2.02 (1H, d, J=10.8 Hz), 1.72-1.59 (3H, m), 1.45 (1H, d, J=10.2 Hz), 1.26-1.21 (4H, m), NH not observed.

Example 116: 6-((1R,3R,4S)-3-benzyl-2-azabicyclo[2.2.1]heptan-2-yl)-4-((R)-2-methylmorpholino)pyridin-2(1H)-one

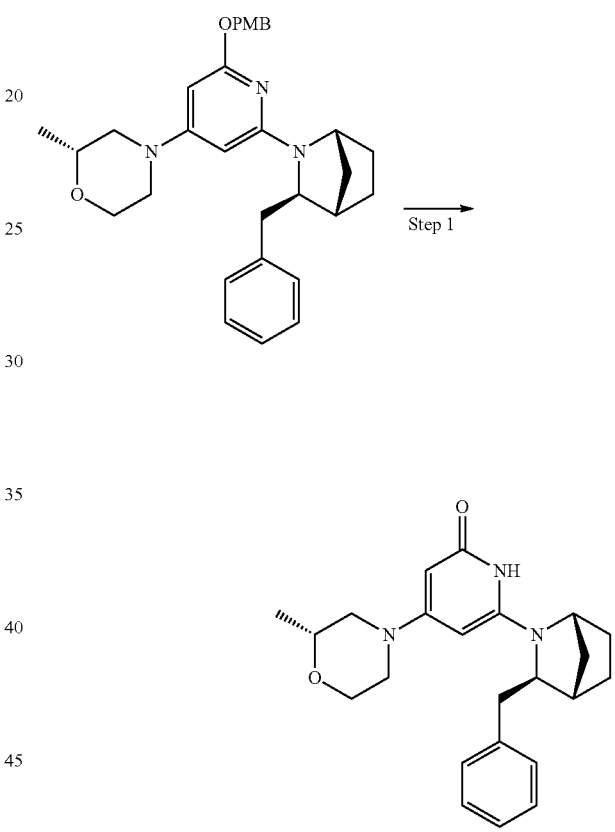

Following Method E starting from Intermediate 33 (185 mg, 0.37 mmol). The crude material was treated with DMSO/water and the resultant solid collected by filtration. The solid was purified by silica gel column chromatography (gradient elution, 0-5% MeOH/DCM) to afford the title compound (relative stereochemistry between the benzyl group and bridgehead protons assigned by NMR nOe experiments) LCMS (ES+) 380 (M+H)$^+$, RT 3.04 min (Analytical Method A), RT 2.52 min (Analytical Method SFC1, YMC CELLULOSE-C 25/75 IPA (0.1% DEAISO)/CO$_2$); $^1$H NMR (400 MHz, CDCl$_3$): δ 7.32 (2H, dd, J=7.2, 7.2 Hz), 7.28-7.18 (3H, m), 5.20 (1H, d, J=2.0 Hz), 4.86 (1H, d, J=2.0 Hz), 4.42 (1H, s), 3.94 (1H, dd, J=2.1, 11.5 Hz), 3.68-3.60 (2H, m), 3.41 (2H, dd, J=12.5, 28.4 Hz), 3.20 (1H, dd, J=3.9, 9.0 Hz), 2.98-2.87 (2H, m), 2.67-2.52 (2H, m), 2.45-2.45 (1H, m), 2.03 (1H, d, J=10.5 Hz), 1.71-1.60 (3H, m), 1.45 (1H, d, J=10.1 Hz), 1.30-1.24 (1H, m), 1.22 (3H, d, J=6.3 Hz), NH not observed.

Example 117: 6-((1R,3S,4S)-3-benzyl-2-azabicyclo[2.2.1]heptan-2-yl)-4-((R)-2-methylmorpholino)pyridin-2(1H)-one

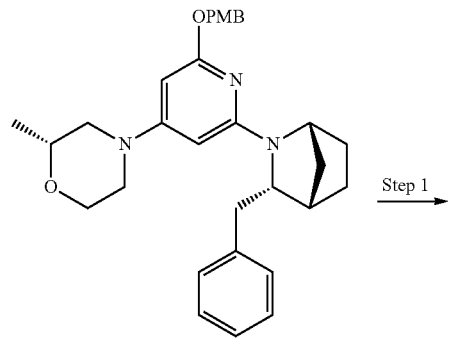

Example 118: 6-((1S,3R,4R)-3-benzyl-2-azabicyclo[2.2.1]heptan-2-yl)-4-((R)-2-methylmorpholino)pyridin-2(1H)-one

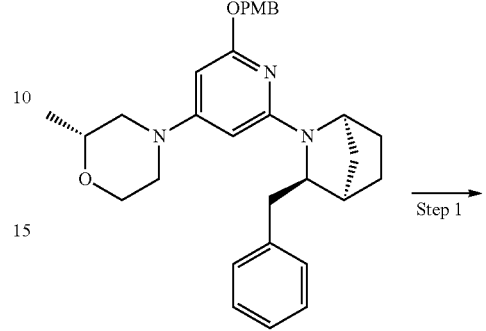

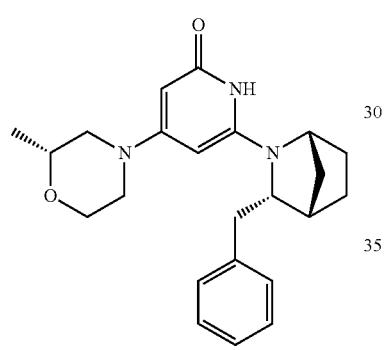

Following Method E starting from Intermediate 34 (105 mg, 0.21 mmol). Purification by reverse phase preparative HPLC followed by freeze drying from MeCN/H$_2$O yielded the title compound (relative stereochemistry between the benzyl group and bridgehead protons assigned by NMR nOe experiments). LCMS (ES+) 380 (M+H)$^+$, RT 3.20 min (Analytical Method B), RT 2.59 min (Analytical Method SFC1, YMC CELLULOSE-C 25/75 IPA (0.1% DEAISO)/CO$_2$); $^1$H NMR (400 MHz, CDCl$_3$): δ 10.39 (1H, br s), 7.33-7.28 (2H, m), 7.25-7.21 (3H, m), 5.19 (1H, d, J=2.1 Hz), 4.80 (1H, d, J=2.0 Hz), 4.31 (1H, s), 3.95 (1H, dd, J=2.3, 11.5 Hz), 3.86-3.79 (1H, m), 3.72-3.60 (2H, m), 3.44 (2H, d, J=12.4 Hz), 3.19 (1H, dd, J=4.1, 14.1 Hz), 2.94-2.86 (1H, m), 2.65-2.53 (2H, m), 2.44 (1H, s), 2.04-1.98 (1H, m), 1.86-1.80 (2H, m), 1.63-1.55 (2H, m), 1.47 (1H, d, J=9.7 Hz), 1.22 (3H, d, J=6.1 Hz).

Following Method E starting from Intermediate 35 (137 mg, 0.27 mmol). Purification by silica gel column chromatography (gradient elution, 0-15% MeOH/EtOAc), followed by a second silica gel column chromatography (gradient elution, 0-6% MeOH/DCM) and freeze drying from MeCN/H$_2$O afforded the title compound (relative stereochemistry between the benzyl group and bridgehead protons assigned by NMR nOe experiments). LCMS (ES+) 380 (M+H)$^+$, RT 3.03 min (Analytical Method A), RT 3.04 min (Analytical Method SFC1, YMC CELLULOSE-C25/75 IPA (0.1% DEAISO)/CO$_2$); $^1$H NMR (400 MHz, CDCl$_3$): δ7.31 (2H, dd, J=7.2, 7.2 Hz), 7.25-7.19 (3H, m), 5.20 (1H, d, J=2.3 Hz), 4.81 (1H, d, J=2.0 Hz), 4.23 (1H, s), 3.94 (1H, ddd, J=1.3, 3.4, 11.6 Hz), 3.83-3.77 (1H, m), 3.68-3.61 (2H, m), 3.48 (1H, td, J=2.0, 12.7 Hz), 3.39-3.33 (1H, m), 3.16 (1H, dd, J=4.2, 14.3 Hz), 2.91 (1H, dt, J=3.6, 12.1 Hz), 2.64 (1H, dd, J=9.9, 14.1 Hz), 2.57 (1H, dd, J=10.5, 12.6 Hz), 2.47 (1H, s), 2.06-1.98 (1H, m), 1.84-1.77 (2H, m), 1.65-1.56 (2H, m), 1.48 (1H, d, J=9.9 Hz), 122 (3H, d, J=6.3 Hz), NH not observed.

The following examples were prepared using a procedure analogous to that described for Example 115 starting 2-benzyl-3-azabicyclo[2.2.1]heptane and Scaffold 1. The relative cis/trans stereochemistry was determined by NMR nOe experiments.

| Example | Structure and Name | Analytical data |
|---|---|---|
| Example 119 | 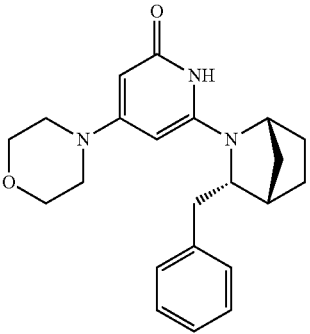<br>6-((1R,3S,4S)-3-benzyl-2-azabicyclo-[2.2.1]heptan-2-yl)-4-morpholino-pyridin-2(1H)-one | LCMS (ES+) 366 (M + H)+, RT 2.92 min (Analytical Method A); RT 1.67 min (Analytical Method SFC1, YMC CELLULOSE-C, 30/70 MeOH + 0.1% DEAISO/CO$_2$); $^1$H NMR (400 MHz, CDCl$_3$): δ 7.31 (2H, dd, J = 7.3, 7.3 Hz), 7.25-7.19 (3H, m), 5.20 (1H, d, J = 2.0 Hz), 4.81 (1H, d, J = 2.0 Hz), 4.23 (1H, s), 3.84-3.79 (1H, m), 3.79-3.74 (4H, m), 3.23-3.14 (5H, m), 2.62 (1H, dd, J = 9.9, 14.1 Hz), 2.45 (1H, s), 2.06-1.95 (1H, m), 1.84-1.76 (3H, m), 1.64-1.46 (2H, m), NH not observed. |
| Example 120 | 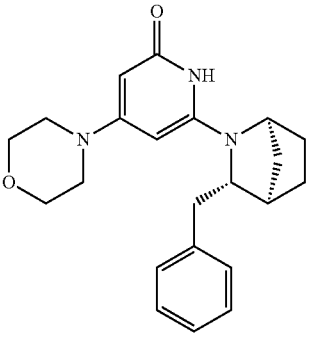<br>6-((1S,3S,4R)-3-benzyl-2-azabicyclo-[2.2.1]heptan-2-yl)-4-morpholino-pyridin-2(1H)-one | LCMS (ES+) 366 (M + H)+, RT 2.94 min (Analytical Method A); RT 1.61 min (Analytical Method SFC1, YMC CELLULOSE-C, 30/70 MeOH + 0.1% DEAISO/CO$_2$); $^1$H NMR (400 MHz, CDCl$_3$): δ 7.34-7.30 (2H, m), 7.26-7.22 (1H, m), 7.22-7.18 (2H, m), 5.21 (1H, d, J = 2.3 Hz), 4.87 (1H, d, J = 2.0 Hz), 4.41 (1H, s), 3.79-3.74 (4H, m), 3.24-3.15 (5H, m), 2.97 (1H, dd, J = 3.9, 14.3 Hz), 2.63 (1H, dd, J = 9.0, 14.3 Hz), 2.45-2.42 (1H, m), 2.07-1.99 (1H, m), 1.69-1.59 (3H, m), 1.45 (1H, d, J = 10.4 Hz), 1.30-1.23 (1H, m), NH not observed. |
| Example 121 | 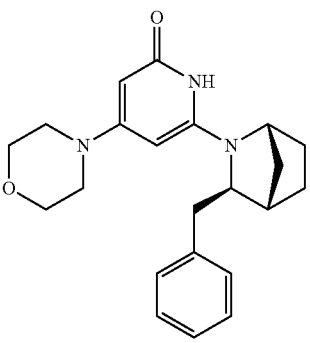<br>6-((1R,3R,4S)-3-benzyl-2-azabicyclo-[2.2.1]heptan-2-yl)-4-morpholino-pyridin-2-(1H)-one | LCMS (ES+) 366 (M + H)+, RT 2.94 min (Analytical Method A); RT 1.94 min (Analytical Method SFC1, YMC CELLULOSE-C, 30/70 MeOH + 0.1% DEAISO/CO$_2$); $^1$H NMR (400 MHz, CDCl$_3$): δ 7.32 (2H, dd, J = 7.2, 7.2 Hz), 7.22-7.18 (3H, m), 5.21 (1H, d, J = 2.0 Hz), 4.87 (1H, d, J = 2.0 Hz), 4.39 (1H, s), 3.79-3.74 (4H, m), 3.24-3.14 (5H, m), 2.97 (1H, dd, J =3.9, 14.3 Hz), 2.63 (1H, dd, J = 9.0, 14.3 Hz), 2.44 (1H, d, J = 1.5 Hz), 2.08-2.00 (1H, m), 1.68-1.59 (3H, m), 1.45 (1H, d, J = 10.1 Hz), 1.29-1.23 (1H, m), NH not observed. |

The following examples were prepared using a procedure analogous to that described for Example 115 starting from the listed Boc protected pyrrolidine and alkyl halide using Scaffolds 1 or 2 as required. Boc deprotection was achieved using 4M HCl in dioxane in place of TFA. For these examples the diastereomers were separated at the final step followed by the separation of the enantiomers of each diastereomer. The relative cis/trans stereochemistry was determined by NMR nOe experiments.

| Example | Structure | Amine | Alkyl halide | Analytical data |
|---|---|---|---|---|
| Example 122 | 6-((1R,3aR,6aS)-1-benzylhexahydro-cyclopenta[c]pyrrol-2(1H)-yl)-4-morpholinopyridin-2(1H)-one, | tert-butyl hexahydro-cyclopenta[c]-pyrrole-2(1H)-carboxylate | benzyl bromide | LCMS (ES+) 380 (M + H)+, RT 2.98 min (Analytical Method A); RT 0.90 min (Analytical Method SFC4, YMC AMYLOSE-C, 50/50 IPA + 0.1% DEAISO/CO$_2$); $^1$H NMR (400 MHz, CDCl$_3$): δ 7.31-7.19 (3H, m), 7.17-7.13 (2H, m), 5.20 (1H, d, J = 2.0 Hz), 4.84 (1H, d, J = 2.3 Hz), 4.03 (1H, dd, J = 3.8, 8.1 Hz), 3.81-3.77 (4H, m), 3.43 (1H, dd, J = 9.2, 9.2 Hz), 3.27-3.22 (4H, m), 3.02 (1H, dd, J = 4.7, 9.7 Hz), 2.92 (1H, dd, J = 3.8, 13.6 Hz), 2.73 (1H, dd, J = 8.2, 13.8 Hz), 2.57-2.45 (2H, m), 1.88-1.76 (2H, m), 1.72-1.60 (1H, m), 1.56-1.42 (2H, m), 1.37-1.27 (1H, m), NH not observed. |
| Example 123 | 6-((1S,3aS,6aR)-1-benzylhexahydro-cyclopenta[c]pyrrol-2-(1H)-yl)-4-morpholinopyridin-2(1H)-one | tert-butyl hexahydro-cyclopenta[c]-pyrrole-2(1H)-carboxylate | benzyl bromide | LCMS (ES+) 380 (M + H)+, RT 2.98 min (Analytical Method A); RT 1.71 min (Analytical Method SFC4, YMC AMYLOSE-C, 50/50 IPA + 0.1% DEAISO/CO$_2$); $^1$H NMR (400 MHz, CDCl$_3$): δ 7.30-7.19 (3H, m), 7.17-7.13 (2H, m), 5.20 (1H, d, J = 2.3 Hz), 4.84 (1H, d, J = 2.0 Hz), 4.06 (1H, dd, J = 3.8, 8.1 Hz), 3.81-3.77 (4H, m), 3.44 (1H, dd, J = 9.2, 9.2 Hz), 3.27-3.22 (4H, m), 3.03 (1H, dd, J = 4.7, 10.0 Hz), 2.92 (1H, dd, J = 3.8, 13.6 Hz), 2.72 (1H, dd, J = 8.3, 13.6 Hz), 2.57-2.45 (2H, m), 1.86-1.76 (2H, m), 1.71-1.60 (1H, m), 1.54-1.44 (2H, m), 1.37-1.27 (1H, m), NH not observed. |
| Example 124 | 6-((1S,3aR,6aS)-1-benzylhexahydro-cyclopenta[c]pyrrol-2(1H)-yl)-4-morpholinopyridin-2(1H)-one | tert-butyl hexahydro-cyclopenta[c]-pyrrole-2(1H)-carboxylate | benzyl bromide | LCMS (ES+) 380 (M + H)+, RT 3.0 min (Analytical Method A); RT 1.75 min (Analytical Method SFC4, YMC AMYLOSE-C, 35/65 MeOH + 0.1% DEAISO/CO$_2$); $^1$H NMR (400 MHz, CDCl$_3$): δ 7.31-7.27 (2H, m), 7.25-7.21 (3H, m), 5.22 (1H, d, J = 2.0 Hz), 4.89 (1H, d, J = 2.3 Hz), 4.19 (1H, ddd, J = 3.7, 6.4, 9.9 Hz), 3.77-3.73 (4H, m), 3.57 (1H, t, J = 9.3 Hz), 3.27-3.15 (6H, m), 2.71-2.62 (3H, m), 1.90-1.78 (2H, m), 1.72-1.54 (4H, m), NH not observed. |

| Example | Structure | Amine | Alkyl halide | Analytical data |
|---|---|---|---|---|
| Example 125 | 6-((1R,3aS,6aR)-1-benzylhexahydro-cyclopenta[c]pyrrol-2(1H)-yl)-4-morpholinopyridin-2(1H)-one | tert-butyl hexahydro-cyclopenta[c]-pyrrole-2(1H)-carboxylate | benzyl bromide | 6-((1R,3aS,6aR)-1-benzylhexahydrocyclopenta[c]pyrrol-2(1H)-yl)-4-morpholinopyridin-2(1H)-one as an off-white powder LCMS (ES+) 380 (M + H)$^+$, RT 3.00 min (Analytical Method A); RT 2.43 min (Analytical Method SFC4, YMC AMYLOSE-C, 35/65 MeOH + 0.1% DEAISO/CO$_2$); $^1$H NMR (400 MHz, CDCl$_3$) δ 7.32-7.27 (2H, m), 7.23 (3H, d, J = 7.1 Hz), 5.21 (1H, d, J = 2.3 Hz), 4.88 (1H, d, J = 2.3 Hz), 4.16 (1H, ddd, J = 3.9, 6.3, 9.8 Hz), 3.77-3.73 (4H, m), 3.56 (1H, dd, J = 9.2, 9.2 Hz), 3.24-3.15 (6H, m), 2.72-2.62 (3H, m), 1.93-1.79 (2H, m), 1.74-1.52 (4H, m), NH not observed. |
| Example 126 | 6-((1R,2S,5S)-2-(2-methoxybenzyl)-3-azabicyclo[3.1.0]hexan-3-yl)-4-morpholinopyridin-2(1H)-one, | tert-butyl 3-azabicyclo-[3.1.0]hexane-3-carboxylate | 1-(chloro methyl)-2-methoxy benzene | LCMS (ES+) 382 (M + H)$^+$, RT 3.08 min (Analytical Method B); RT 1.56 min (Analytical Method SFC4, YMC CELLULOSE-C, 35/65 IPA + 0.1% DEAISO/CO$_2$); $^1$H NMR (400 MHz, CDCl$_3$): δ 7.31-7.26 (1H, m), 7.14 (1H, dd, J = 1.6, 7.5 Hz), 6.97 (1H, d, J = 8.1 Hz), 6.92 (1H, ddd, J = 7.4, 7.4, 0.9 Hz), 5.22 (1H, d, J = 2.3 Hz), 4.79 (1H, d, J = 1.8 Hz), 4.16 (3H, s), 3.95 (1H, dd, J = 2.3, 10.6 Hz), 3.80-3.76 (5H, m), 3.49-3.39 (2H, m), 3.29-3.23 (5H, m), 2.39 (1H, dd, J = 10.7, 13.0 Hz), 1.69-1.63 (1H, m), 1.60-1.54 (1H, m), 0.66 (1H, dt, J = 5.2, 7.8 Hz), 0.14 (1H, dd, J = 4.2, 9.2 Hz). |
| Example 127 | 6-((1R,2R,5S)-2-(2-methoxybenzyl)-3-azabicyclo[3.1.0]hexan-3-yl)-4-morpholinopyridin-2(1H)-one, | tert-butyl 3-aza-bicyclo[3.1.0]-hexane-3-carboxylate | 1-(chloro methyl)-2-methoxy benzene | LCMS (ES+) 382 (M + H)$^+$, RT 3.05 min (Analytical Method A); RT 2.35 min (Analytical Method SFC4, YMC CELLULOSE-C, 35/65 IPA + 0.1% DEAISO/CO$_2$); $^1$H NMR (400 MHz, CDCl$_3$): δ 7.30-7.26 (1H, m), 7.21 (1H, dd, J = 1.5, 7.3 Hz), 6.96 (1H, d, J = 8.1 Hz), 6.92 (1H, dt, J = 1.0, 7.5 Hz), 5.26 (1H, d, J = 2.2 Hz), 4.95 (1H, d, J = 2.3 Hz), 4.15 (3H, s), 4.00 (1H, dq, J = 1.5, 4.9 Hz), 3.81-3.77 (4H, m), 3.61 (1H, d, J = 9.1 Hz), 3.48 (1H, dd, J = 1.4, 13.1 Hz), 3.42 (1H, dd, J = 4.7, 9.2 Hz), 3.28-3.24 (4H, m), 2.36 (1H, dd, J = 10.6, 13.1 Hz), 1.71-1.64 (2H, m), 0.84 (1H, dt, J = 5.1, 8.0 Hz), 0.60 (1H, q, J = 4.5 Hz). NH not observed. |

-continued

| Example | Structure | Amine | Alkyl halide | Analytical data |
|---|---|---|---|---|
| Example 128 | 6-((1S,2S,5R)-2-(2-methoxybenzyl)-3-azabicyclo[3.1.0]hexan-3-yl)-4-morpholinopyridin-2(1H)-one | tert-butyl 3-azabicyclo-[3.1.0]hexane-3-carboxylate | 1-(chloromethyl)-2-methoxybenzene | LCMS (ES+) 382 (M + H)+, RT 3.05 min (Analytical Method A); RT 1.63 min (Analytical Method SFC4, YMC CELLULOSE-C, 35/65 IP A + 0.1% DEAISO/CO$_2$); $^1$H NMR (400 MHz, CDCl$_3$): δ 7.31-7.26 (1H, m), 7.21 (1H, dd, J = 1.5, 7.3 Hz), 6.96 (1H, d, J = 8.2 Hz), 6.92 (1H, dt, J = 0.9, 7.4 Hz), 5.26 (1H, d, J = 2.3 Hz), 4.94 (1H, d, J = 2.0 Hz), 4.15 (3H, s), 4.02-3.96 (1H, m), 3.81-3.77 (4H, m), 3.60 (1H, d, J = 9.1 Hz), 3.47 (1H, dd, J = 1.5, 13.2 Hz), 3.42 (1H, dd, J = 4.8, 9.2 Hz), 3.28-3.24 (4H, m), 2.36 (1H, dd, J = 10.6, 13.1 Hz), 1.71-1.65 (2H, m), 0.84 (1H, dt, J = 5.3, 8.0 Hz), 0.60 (1H, q, J = 4.5 Hz), NH not observed. |
| Example 129 | 6-((1S,2R,5R)-2-(2-methoxybenzyl)-3-azabicyclo[3.1.0]hexan-3-yl)-4-morpholinopyridin-2(1H)-one | tert-butyl 3-azabicyclo-[3.1.0]hexane-3-carboxylate | 1-(chloromethyl)-2-methoxybenzene | LCMS (ES+) 382 (M + H)+, RT 3.20 min (Analytical Method B); RT 2.69 min (Analytical Method SFC4, YMC CELLULOSE-C, 35/65 IP A + 0.1% DEAISO/CO$_2$); $^1$H NMR (400 MHz, CDCl$_3$) δ 7.28-7.23 (1H, m), 7.14 (1H, dd, J = 1.5, 7.3 Hz), 6.90 (2H, dd, J = 7.7, 12.5 Hz), 5.76 (1H, s), 5.19 (1H, s), 4.20 (1H, dd, J = 4.0, 8.8 Hz), 3.89 (3H, s), 3.81-3.76 (4H, m), 3.57 (2H, s), 3.37-3.31 (4H, m), 3.16 (1H, dd, J = 3.5, 13.1 Hz), 2.59 (1H, dd, J = 8.8, 13.1 Hz), 1.69-1.63 (1H, m), 1.61-1.54 (1H, m), 0.74-0.67 (1H, m), 0.13 (1H, q, J = 4.3 Hz), NH not observed. |
| Example 130 | 6-((1R,3aR,6aS)-1-benzylhexahydro-cyclopenta[c]pyrrol-2(1H)-yl)-4-((R)-2-methylmorpholino)pyridin-2(1H)-one, | tert-butyl hexahydrocyclopenta[c]pyrrole-2(1H)-carboxylate | Benzyl bromide | LCMS (ES+) 394 (M + H)+, RT 3.44 min (Analytical Method B); RT 1.91 min (Analytical Method SFC4, YMC AMYLOSE-C, 30/70 MeOH + 0.1% DEAISO/CO$_2$); $^1$H NMR (400 MHz, CDCl$_3$): δ 7.32-7.27 (2H, m), 7.26-7.21 (3H, m), 5.21 (1H, d, J = 2.1 Hz), 4.89 (1H, d, J = 2.1 Hz), 4.16 (1H, ddd, J = 3.7, 6.4, 9.9 Hz), 3.93 (1H, ddt, J = 1.2, 5.0, 5.8 Hz), 3.70-3.55 (3H, m), 3.43 (2H, d, J = 12.8 Hz), 3.26-3.18 (2H, m), 2.90 (1H, dt, J = 3.5, 12.4 Hz), 2.72-2.62 (3H, m), 2.56 (1H, dd, J = 10.5, 12.6 Hz), 1.94-1.79 (2H, m), 1.76-1.53 (4H, m), 1.20 (3H, d, J = 6.1 Hz), NH not observed. |

-continued

| Example | Structure | Amine | Alkyl halide | Analytical data |
|---|---|---|---|---|
| Example 131 | 6-((1R,3aR,6aS)-1-benzylhexahydro-cyclopenta[c]pyrrol-2(1H)-yl)-4-((R)-2-methylmorpholino)pyridin-2(1H)-one | tert-butyl hexahydro-cyclopenta[c]-pyrrole-2(1H)-carboxylate | Benzyl bromide | LCMS (ES+) 394 (M + H)+, RT 3.40 min (Analytical Method B);. RT 1.10 min (Analytical Method SFC4, YMC AMYLOSE-C, 40/60 IP A + 0.1% DEAISO/CO$_2$); $^1$H NMR (400 MHz, CDCl$_3$): δ 7.31-7.26 (2H, m), 7.24-7.20 (1H, m), 7.15 (2H, d, J = 6.7 Hz), 5.20 (1H, d, J = 2.1 Hz), 4.84 (1H, d, J = 2.1 Hz), 4.03-3.95 (2H, m), 3.72-3.63 (2H, m), 3.55-3.41 (3H, m), 3.01 (1H, dd, J = 4.8, 9.8 Hz), 2.99-2.89 (2H, m), 2.73 (1H, dd, J = 8.2, 13.7 Hz), 2.63-2.46 (3H, m), 1.88-1.75 (2H, m), 1.72-1.63 (1H, m), 1.56-1.43 (2H, m), 1.36-1.27 (1H, m), 1.23 (3H, d, J = 6.3 Hz), NH not observed. |
| Example 132 | 6-((1S,3aS,6aR)-1-benzylhexahydro-cyclopenta[c]pyrrol-2(1H)-yl)-4-((R)-2-methylmorpholino)pyridin-2(1H)-one | tert-butyl hexahydro-cyclopenta[c]-pyrrole-2(1H)-carboxylate | Benzyl bromide | LCMS (ES+) 394 (M + H)+, RT 3.40 min (Analytical Method B); RT 1.80 min (Analytical Method SFC4, YMC AMYLOSE-C, 40/60 IP A + 0.1% DEAISO/CO$_2$); $^1$H NMR (400 MHz, CDCl$_3$): δ 7.31-7.20 (3H, m), 7.17-7.13 (2H, m), 5.20 (1H, d, J = 2.0 Hz), 4.84 (1H, d, J = 2.0 Hz), 4.00-3.95 (2H, m), 3.73-3.62 (2H, m), 3.54-3.46 (2H, m), 3.42 (1H, t, J = 9.1 Hz), 3.03-2.88 (3H, m), 2.74 (1H, dd, J = 8.1, 13.6 Hz), 2.61 (1H, dd, J = 10.4, 12.6 Hz), 2.57-2.46 (2H, m), 1.89-1.75 (2H, m), 1.72-1.61 (1H, m), 1.56-1.42 (2H, m), 1.36-1.26 (1H, m), 1.23 (3H, d, J = 6.3 Hz), NH not observed. |
| Example 133 | 6-((1R,3aS,6aR)-1-benzylhexahydro-cyclopenta[c]pyrrol-2(1H)-yl)-4-((R)-2-methylmorpholino)pyridin-2(1H)-one | tert-butyl hexahydro-cyclopenta[c]-pyrrole-2(1H)-carboxylate | Benzyl bromide | LCMS (ES+) 394 (M + H)+, RT 3.44 min (Analytical Method B); RT 2.72 min (Analytical Method SFC4, YMC AMYLOSE-C, 30/70 MeOH + 0.1% DEAISO/CO$_2$); $^1$H NMR (400 MHz, CDCl$_3$): δ 7.32-7.27 (2H, m), 7.26-7.21 (3H, m), 5.21 (1H, d, J = 2.1 Hz), 4.88 (1H, d, J = 2.1 Hz), 4.18-4.12 (1H, m), 3.93 (1H, dd, J = 2.2, 11.6 Hz), 3.67-3.54 (3H, m), 3.48 (1H, d, J = 12.5 Hz), 3.38 (1H, d, J = 12.7 Hz), 3.26-3.18 (2H, m), 2.94-2.86 (1H, m), 2.72-2.61 (3H, m), 2.56 (1H, dd, J = 10.6, 12.5 Hz), 1.92-1.80 (2H, m), 1.76-1.54 (4H, m), 1.20 (3H, d, J = 6.1 Hz), NH not observed. |

| Example | Structure | Amine | Alkyl halide | Analytical data |
|---|---|---|---|---|
| Example 134 | 6-((1S,2S,5R)-2-benzyl-3-azabicyclo-[3.2.1]octan-3-yl)-4-morpholinopyridin-2(1H)-one | 3-azabicyclo-[3.2.1]octane | Benzyl bromide | LCMS (ES+) 380 (M + H)+, RT 3.25 min (Analytical Method A); RT 3.05 min (Analytical Method SFC4, LUX CELLULOSE-4, 45/55 IPA + 0.1% DEAISO/CO$_2$); $^1$H NMR (400 MHz, CDCl$_3$): δ 8.80 (1H, s), 7.29-7.24 (2H, m), 7.22-7.16 (1H, m), 7.07 (2H, d, J = 6.8 Hz), 5.56 (1H, d, J = 2.3 Hz), 5.48 (1H, d, J = 2.0 Hz), 3.80-3.76 (4H, m), 3.24-3.10 (6H, m), 2.87 (1H, dd, J = 3.2, 13.9 Hz), 2.78 (1H, dd, J = L7, 10.7 Hz), 2.47 (1H, dd, J = 9.6, 14.1 Hz), 2.25 (1H, s), 2.06 (1H, dd, J = 6.3, 6.3 Hz), 1.99-1.91 (1H, m), 1.74-1.67 (2H, m), 1.66-1.58 (2H, m), 1.43 (1H, d, J = 11.4 Hz). |
| Example 135 | 6-((1R,2S,5S)-2-benzyl-3-azabicyclo-[3.2.1]octan-3-yl)-4-morpholinopyridin-2(1H)-one | 3-azabicyclo-[3.2.1]octane | Benzyl bromide | LCMS (ES+) 380 (M + H)+, RT 2.99 min (Analytical Method A); RT 2.11 min (Analytical Method SFC4, YMC AMYLOSE-C, 30/70 MeOH + 0.1% DEAISO/CO$_2$); $^1$H NMR (400 MHz, CDCl$_3$): δ 7.29-7.24 (2H, m), 7.21-7.14 (3H, m), 5.23 (1H, d, J = 2.3 Hz), 5.01 (1H, d, J = 2.3 Hz), 3.85-3.80 (1H, m), 3.80-3.76 (4H, m), 3.26-3.17 (6H, m), 2.84-2.72 (2H, m), 2.34 (1H, s), 2.12 (1H, dd, J = 6.9, 6.9 Hz), 2.02-1.95 (1H, m), 1.73-1.51 (4H, m), 1.42-1.35 (1H, m), NH not observed. |
| Example 136 | 6-((1R,2R,5S)-2-benzyl-3-azabicyclo-[3.2.1]octan-3-yl)-4-morpholinopyridin-2(1H)-one | 3-azabicyclo-[3.2.1]octane | Benzyl bromide | LCMS (ES+) 380 (M + H)+, RT 3.25 min (Analytical Method A); RT 3.75 min (Analytical Method SFC4, LUX CELLULOSE-4, 45/55 IPA + 0.1% DEAISO/CO$_2$); $^1$H NMR (400 MHz, CDCl$_3$): δ 8.60 (1H, s), 7.29-7.24 (2H, m), 7.21-7.17 (1H, m), 7.07 (2H, d, J = 6.8 Hz), 5.56 (1H, d, J = 2.3 Hz), 5.48 (1H, d, J = 2.3 Hz), 3.80-3.76 (4H, m), 3.27-3.15 (4H, m), 3.14-3.09 (2H, m), 2.86 (1H, dd, J = 3.2, 14.0 Hz), 2.78 (1H, dd, J = 1.5, 10.5 Hz), 2.47 (1H, dd, J = 9.7, 14.0 Hz), 2.26-2.23 (1H, m), 2.09-2.03 (1H, m), 1.98-1.91 (1H, m), 1.74-1.66 (1H, m), 1.65-1.57 (3H, m), 1.42 (1H, d, J = 11.7 Hz). |

| Example | Structure | Amine | Alkyl halide | Analytical data |
|---|---|---|---|---|
| Example 137 | 6-((1S,2R,5R)-2-benzyl-3-azabicyclo-[3.2.1]octan-3-yl)-4-morpholinopyridin-2(1H)-one | 3-azabicyclo-[3.2.1]octane | Benzyl bromide | LCMS (ES+) 380 (M + H)+, RT 2.99 min (Analytical Method A); RT 2.85 min (Analytical Method SFC4, YMC AMYLOSE-C, 30/70 MeOH + 0.1% DEAISO/CO₂); ¹H NMR (400 MHz, CDCl₃): δ 7.30-7.23 (2H, m), 7.22-7.14 (3H, m), 5.23 (1H, d, J = 2.0 Hz), 5.01 (1H, d, J = 2.3 Hz), 3.81-3.76 (5H, m), 3.26-3.20 (4H, m), 3.19-3.16 (2H, m), 2.83-2.72 (2H, m), 2.33 (1H, s), 2.14-2.10 (1H, m), 1.99 (1H, d, J = 11.9 Hz), 1.73-1.49 (4H, m), 1.43-1.35 (1H, m), NH not observed. |
| Example 138 | 6-((1R,2S,5S)-2-benzyl-3-azabicyclo[3.2.1]-octan-3-yl)-4-((R)-2-methylmorpholino)-pyridin-2(1H)-one | 3-azabicyclo-[3.2.1]octane | Benzyl bromide | LCMS (ES+) 394 (M + H)+, RT 3.29 min (Analytical Method B), RT 1.37 min (Analytical Method SFC4, YMC CELLULOSE-SC 55/45 IPA (0.1% DEAISO)/CO₂); ¹H NMR (400 MHz, CDCl₃): δ 7.29-7.24 (2H, m), 7.21-7.14 (3H, m), 5.23 (1H, d, J = 2.0 Hz), 5.01 (1H, d, J = 2.0 Hz), 3.96 (1H, dd, J = 2.4, 11.5 Hz), 3.81-3.77 (1H, m), 3.73-3.60 (2H, m), 3.51-3.45 (2H, m), 3.20-3.15 (2H, m), 2.93 (1H, dt, J = 3.4, 12.4 Hz), 2.83-2.72 (2H, m), 2.59 (1H, dd, J = 10.6, 12.6 Hz), 2.37-2.35 (1H, m), 2.14-2.11 (1H, m), 1.99 (1H, d, J = 11.6 Hz), 1.70-1.59 (2H, m), 1.56-1.50 (2H, m), 1.43-1.36 (1H, m), 1.23 (3H, d, J = 6.3 Hz), NH not observed. |
| Example 139 | 6-((1S,2S,5R)-2-benzyl-3-azabicyclo[3.2.1]-octan-3-yl)-4-((R)-2-methylmorpholino)-pyridin-2(1H)-one | 3-azabicyclo-[3.2.1]octane | Benzyl bromide | LCMS (ES+) 394 (M + H)+, RT 3.38 min (Analytical Method B), RT 2.17 min (Analytical Method SFC4, YMC AMYLOSE- C 20/80 MeOH (0.1 % DEAISO)/CO₂); ¹H NMR (400 MHz, CDCl₃) δ 8.72 (1H, br s), 7.29-7.25 (2H, m), 7.22-7.16 (1H, m), 7.07 (2H, d, J = 7.1 Hz), 5.55 (1H, d, J = 2.3 Hz), 5.47 (1H, d, J = 2.3 Hz), 3.97 (1H, dq, J = 1.2, 5.1 Hz), 3.69 (1H, dd, J = 2.6, 11.8 Hz), 3.66-3.58 (1H, m), 3.48-3.39 (2H, m), 3.16-3.08 (2H, m), 2.93 (1H, ddd, J = 12.1, 12.1, 3.7 Hz), 2.86 (1H, dd, J = 3.0, 13.9 Hz), 2.78 (1H, dd, J = 1.7, 10.5 Hz), 2.59 (1H, dd, J = 10.4, 12.6 Hz), 2.47 (1H, dd, J = 9.6, 13.9 Hz), 2.26 (1H, s), 2.07 (1H, dd, J = 5.3, 5.3 Hz), 1.98-1.90 (1H, m), 1.74-1.67 (2H, m), 1.61-1.49 (2H, m), 1.43 (1H, d, J = 11.9 Hz), 1.22 (3H, d, J = 6.3 Hz). |

| Example | Structure | Amine | Alkyl halide | Analytical data |
|---|---|---|---|---|
| Example 140 | 6-((1S,2R,5R)-2-benzyl-3-azabicyclo-[3.2.1]octan-3-yl)-4-((R)-2-methyl-morpholino)pyridin-2(1H)-one | 3-azabicyclo-[3.2.1]octane | Benzyl bromide | LCMS (ES+) 394 (M + H)+, RT 3.28 min (Analytical Method B), RT 1.85 min (Analytical Method SFC4, YMC CELLULOSE-SC 55/45 IP A (0.1% DEAISO)/CO$_2$); $^1$H NMR (400 MHz, CDCl$_3$): δ 7.30-7.25 (2H, m), 7.22-7.14 (3H, m), 5.23 (1H, d, J = 2.0 Hz), 5.01 (1H, d, J = 2.0 Hz), 3.96 (1H, ddd, J = 1.2, 3.5, 11.7 Hz), 3.80-3.74 (1H, m), 3.70-3.63 (2H, m), 3.52 (1H, td, J = 1.8, 12.5 Hz), 3.44 (1H, d, J = 12.1 Hz), 3.18 (2H, d, J = 2.3 Hz), 2.94 (1H, dt, J = 3.6, 12.2 Hz), 2.84-2.73 (2H, m), 2.59 (1H, dd, J = 10.5, 12.5 Hz), 2.38-2.35 (1H, m), 2.15 (1H, s), 1.99 (1H, d, J = 11.6 Hz), 1.74-1.58 (2H, m), 1.56-1.48 (2H, m), 1.44- 1.37 (1H, m), 1.23 (3H, d, J = 6.3 Hz), NH not observed. |
| Example 141 | 6-((1R,2R,5S)-2-benzyl-3-azabicyclo-[3.2.1]octan-3-yl)-4-((R)-2-methyl-morpholino)pyridin-2(1H)-one | 3-azabicyclo-[3.2.1]octane | Benzyl bromide | LCMS (ES+) 394 (M + H)+, RT 3.38 min (Analytical Method B), RT 3.04 min (Analytical Method SFC4, YMC AMYLOSE-C 20/80 MeOH (0.1% DEAISO)/CO$_2$); $^1$H NMR (400 MHz, CDCl$_3$): δ 8.89 (1H, br s), 7.29-7.24 (2H, m), 7.21-7.17 (1H, m), 7.08 (2H, d, J = 6.8 Hz), 5.55 (1H, d, J = 2.3 Hz), 5.47 (1H, d, J = 2.3 Hz), 3.96 (1H, dd, J = 2.2, 11.6 Hz), 3.69-3.61 (2H, m), 3.47 (1H, d, J = 12.5 Hz), 3.37 (1H, d, J = 12.7 Hz), 3.17-3.10 (2H, m), 2.93 (1H, dt, J = 3.7, 12.2 Hz), 2.87 (1H, dd, J = 2.8, 14.0 Hz), 2.78 (1H, dd, J = 1.7, 10.6 Hz), 2.58 (1H, dd, J = 10.5, 12.7 Hz), 2.48 (1H, dd, J = 9.6, 14.1 Hz), 2.26-2.26 (1H, m), 2.08 (1H, dd, J = 5.6, 5.6 Hz), 1.99-1.92 (1H, m), 1.74-1.69 (2H, m), 1.61-1.47 (2H, m), 1.44 (1H, d, J = 11.6 Hz), 1.23 (3H, d, J = 6.1 Hz). |

Example 142: 6-((1S,2R,4R,5R)-2-benzyl-4-methyl-3-azabicyclo[3.1.0]hexan-3-yl)-4-morpholinopyridin-2(1H)-one and Example 143: 6-((1R,2S,4S,5S)-2-benzyl-4-methyl-3-azabicyclo[3.1.0]hexan-3-yl)-4-morpholinopyridin-2(1H)-one

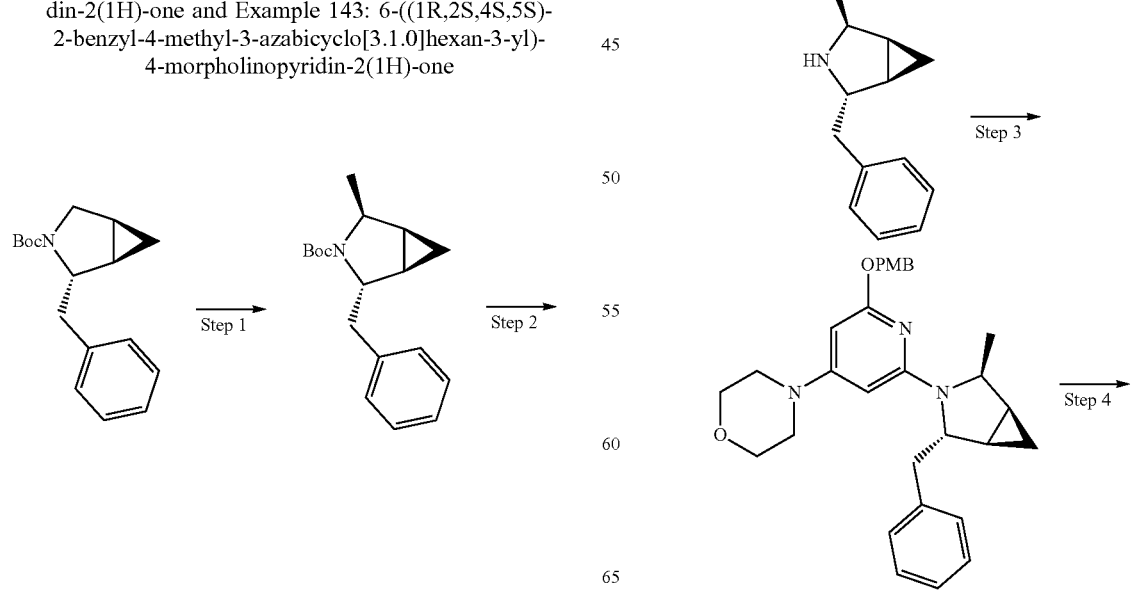

-continued

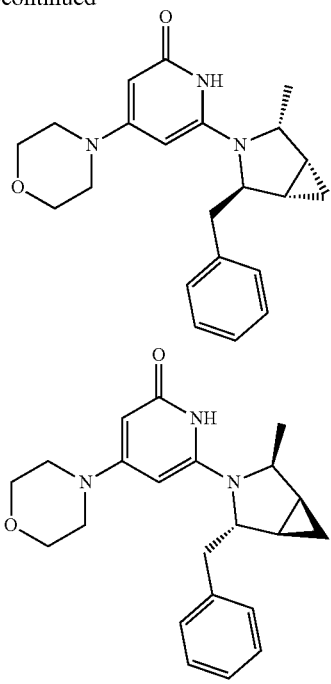

Step 1: tert-butyl(1R*,2S*,5S*)-2-benzyl-4-methyl-3-azabicyclo[3.1.0]hexane-3-carboxylate Tetramethylethylenediamine (540 μL, 3.6 mmol) was added to a solution of tert-butyl (JR*,2S*,5S*)-2-benzyl-3-azabicyclo[3.1.0]hexane-3-carboxylate (982 mg, 3.6 mmol, Intermediate 1 step 2) in Et₂O (12 mL) under nitrogen. The reaction was cooled to −78° C. and sec-BuLi (3.3 mL, 4.7 mmol, 1.4 M in cyclohexane) was added and the reaction warmed to −35° C. for 1 h. The reaction was cooled to −78° C. and methyl iodide (450 μL, 7.2 mmol) was added dropwise. After complete addition the reaction was allowed to slowly warm to rt overnight. The reaction was quenched with aqueous NH₄Cl solution, the layers separated and the aqueous further extracted with Et2O (×2). The combined organic extracts were dried (MgSO₄) and evaporated. Purification by silica gel column chromatography (gradient elution, 0-3% EtOAc/iso-hexane) afforded the title compound.

Step 2: (1R*,2S*,5S*)-2-benzyl-4-methyl-3-azabicyclo[3.1.0]hexane tert-Butyl (JR*,2S*,5S*)-2-benzyl-4-methyl-3-azabicyclo[3.1.0]hexane-3-carboxylate (130 mg, 0.45 mmol) was dissolved in HCl (3 mL, 4M in dioxane). After 1.5 hour the reaction was concentrated under reduced pressure. The residue was dissolved in DCM and washed with saturated NaHCO₃ (saturated aqueous solution). The DCM layer was dried (phase separator) and concentrated under reduced pressure to afford the title compound. Used without further purification in the next step.

Step 3: 4-(2-((1R*,2S*,5S*)-2-benzyl-4-methyl-3-azabicyclo[3.1.0]hexan-3-yl)-6-((4-methoxybenzyl)oxy)pyridin-4-yl)morpholine Following Method D from (R*,2S*,5S*)-2-benzyl-4-methyl-3-azabicyclo[3.1.0]hexane (75 mg, 0.40 mmol) and 4-(2-chloro-6-((4-methoxybenzyl)oxy)pyridin-4-yl)morpholine (134 mg, 0.40 mmol, Scaffold 1). Purification by silica gel column chromatography (gradient elution, 0-15% EtOAc/iso-hexane) afforded the title compound.

Step 4: 6-((1S,2R,4R,5R)-2-benzyl-4-methyl-3-azabicyclo[3.1.0]hexan-3-yl)-4-morpholinopyridin-2(1H)-one and 6-((1R,2S,4S,5S)-2-benzyl-4-methyl-3-azabicyclo[3.1.0]hexan-3-yl)-4-morpholinopyridin-2(1H)-one Following Method E from 4-(2-((1R*,2S*,5S*)-2-benzyl-4-methyl-3-azabicyclo[3.1.0]hexan-3-yl)-6-((4-methoxybenzyl)oxy)pyridin-4-yl)morpholine (53 mg, 0.11 mmol). The crude material was purified by chiral SFC for the separation of the isomers.

6-((1S,2R,4R,5R)-2-benzyl-4-methyl-3-azabicyclo [3.1.0]hexan-3-yl)-4-morpholinopyridin-2(1H)-one was freeze dried from MECN/H₂O to afford the title compound. LCMS (ES+) 366 (M+H)⁺, RT 3.10 min (Analytical Method B), RT 1.44 min (Analytical Method SFC4, YMC CELLULOSE-SC 35/65 MeOH [0.1% DEAISO]/CO₂); ¹H NMR (400 MHz, CDCl₃): δ 7.22-7.15 (3H, m), 7.15-7.10 (2H, m), 5.30 (1H, d, J=2.0 Hz), 4.99 (1H, d, J=2.0 Hz), 4.44 (1H, dd, J=3.2, 9.2 Hz), 3.83-3.71 (5H, m), 3.29-3.23 (4H, m), 2.97-2.89 (1H, m), 2.55 (1H, dd, J=9.3, 13.1 Hz), 1.61-1.54 (1H, m), 1.44-1.38 (1H, m), 1.21 (3H, d, J=5.6 Hz), 0.50-0.45 (2H, m), NH not observed.

6-((1R,2S,4S,5S)-2-benzyl-4-methyl-3-azabicyclo[3.1.0]hexan-3-yl)-4-morpholinopyridin-2(1H)-one was repurified by silica gel chromatography (gradient elution, 0-10% MeOH/EtOAc) and freeze dried from MECN/H₂O to afford the title compound. LCMS (ES+) 366 (M+H)⁺, RT 3.11 min (Analytical Method B), RT 3.16 min (Analytical Method SFC1, YMC CELLULOSE-SC 35/65 MeOH [0.1% DEAISO]/CO₂); ¹H NMR (400 MHz, CDCl₃): δ 7.22 (3H, dd, J=6.9, 13.3 Hz), 7.13 (2H, d, J=7.8 Hz), 5.29 (1H, d, J=1.5 Hz), 5.00 (1H, d, J=1.8 Hz), 4.27 (1H, dd, J=2.8, 8.8 Hz), 3.81 (4H, dd, J=4.8, 4.8 Hz), 3.73-3.67 (1H, m), 3.26 (4H, q, J=4.5 Hz), 2.93 (1H, dd, J=2.7, 13.5 Hz), 2.60 (1H, dd, J=9.1, 13.4 Hz), 1.63-1.56 (1H, m), 1.49-1.42 (1H, m), 1.21 (3H, d, J=5.8 Hz), 0.55-0.43 (2H, m), NH not observed.

Example 144: 6-((S)-2-(4-(((R)-1-methoxypropan-2-yl)oxy)benzyl)pyrrolidin-1-yl)-4-morpholinopyridin-2(1H)-one and Example 145: 6-((R)-2-(4-(((R)-1-methoxypropan-2-yl)oxy)benzyl)pyrrolidin-1-yl)-4-morpholinopyridin-2(1H)-one

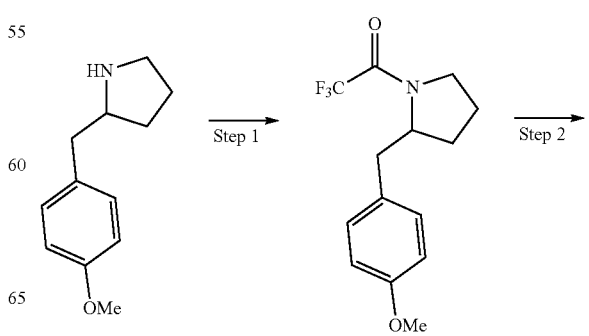

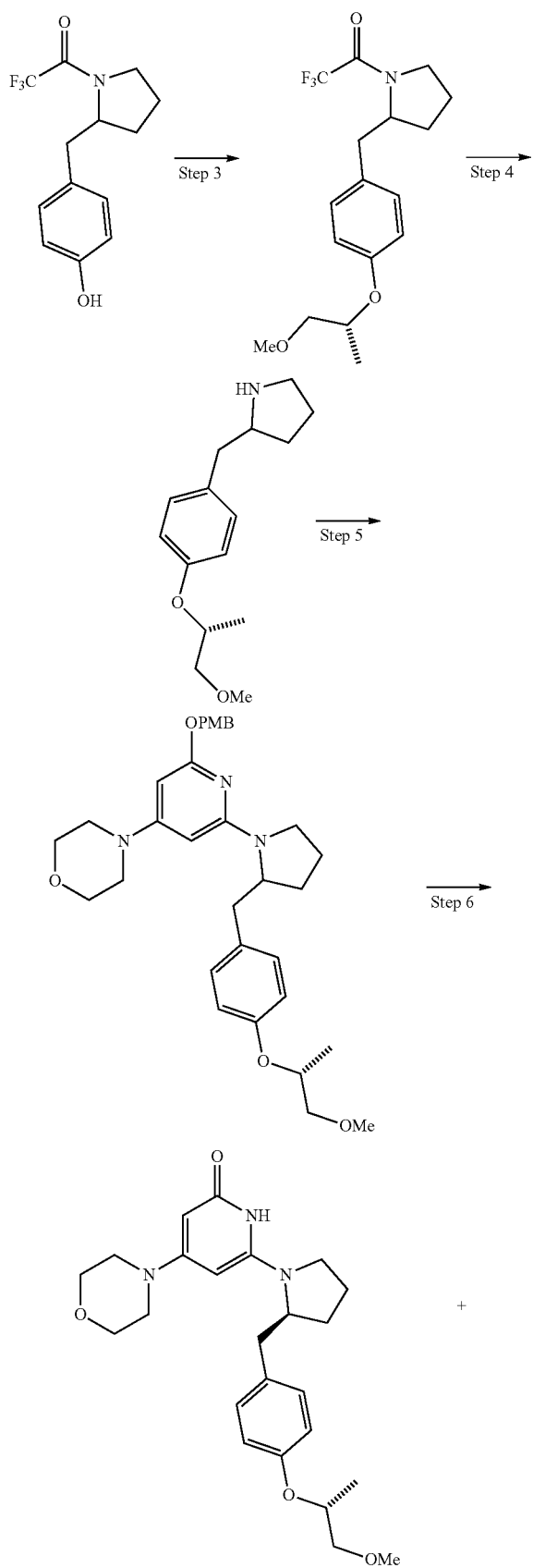
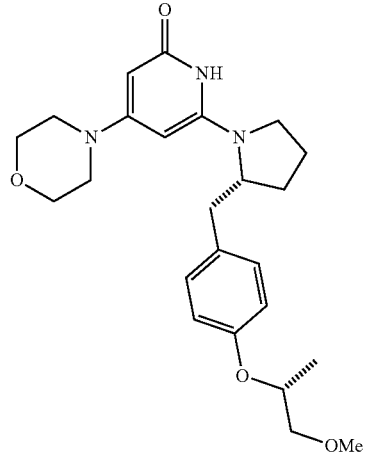

Step 1: 2,2,2-trifluoro-1-(2-(4-methoxybenzyl)pyrrolidin-1-yl)ethan-1-one

To a solution of 2-(4-methoxybenzyl)pyrrolidine (376 mg, 1.97 mmol) in dry DCM (0.1 M) at 0° C. under $N_2$ was added TFAA (2.0 eq.). The mixture was allowed to warm to rt with stirring over 24 h. The reaction was quenched by cooling to 0° C. and treatment with $H_2O$, followed by saturated aqueous $NaHCO_3$. The mixture was diluted with DCM and the layers separated. The organic layer was dried (phase separator) and concentrated under reduced pressure. The mixture was purified by silica gel column chromatography (gradient elution, 0-100% EtOAc/iso-hexane) to give impure title compound, which was used without further purification.

Step 2: 2,2,2-trifluoro-1-(2-(4-hydroxybenzyl)pyrrolidin-1-yl)ethan-1-one

A solution of 2,2,2-trifluoro-1-(2-(4-methoxybenzyl)pyrrolidin-1-yl)ethan-1-one (243 mg, 0.85 mmol) in dry DCM (0.2 M) was cooled to 0° C. under $N_2$. Boron tribromide (4.25 mL, 4.25 mmol, 1M solution in DCM) was added. After 2 h the reaction mixture was poured into saturated aqueous $NaHCO_3$ solution stirred vigourously for 1 h. The layers were separated, dried (phase separator) and concentrated under reduced pressure. The residue was purified by silica gel column chromatography (gradient elution, 0-100% EtOAc/iso-hexane) to give impure title compound, which was used without further purification.

Step 3: 2,2,2-trifluoro-1-(2-(4-(((R)-1-methoxypropan-2-yl)oxy)benzyl)pyrrolidin-1-yl)ethan-1-one A solution of 2,2,2-trifluoro-1-(2-(4-hydroxybenzyl)pyrrolidin-1-yl)ethan-1-one (250 mg, 0.92 mmol) and (S)-1-methoxypropan-2-ol (1.83 mmol) alcohol in dry THF (3 mL) was treated with $PPh_3$ (1.3 mmol) and DIAD (1.3 mmol) at r.t. The reaction was stirred for 3 hours at r.t. The mixture was concentrated and the residue purified by silica gel column chromatography (gradient elution, 0-100% EtOAc/iso-hexane) to give impure title compound, which was used without further purification.

Step 4: 2-(4-(((R)-1-methoxypropan-2-yl)oxy)benzyl)pyrrolidine

A solution of 2,2,2-trifluoro-1-(2-(4-(((R)-1-methoxypropan-2-yl)oxy)benzyl)pyrrolidin-1-yl)ethan-1-one (224 mg)

in MeOH (7 mL) was treated at rt with K$_2$CO$_3$ (420 mg, 3.04 mmol). The mixture was stirred at 60° C. for 1 h. After cooling to r.t., the mixture was concentrated and the residue as partitioned between DCM (20 mL) and water (10 mL), passed through a hydrophobic frit and the organic layer concentrated to give the title compound.

Step 5: 4-(2-((4-methoxybenzyl)oxy)-6-(2-(4-(((R)-1-methoxypropan-2-yl)oxy)benzyl)pyrrolidin-1-yl)pyridin-4-yl)morpholine Following Method C starting from 2-(4-(((R)-1-methoxypropan-2-yl)oxy)benzyl)pyrrolidine (155 mg, 0.62 mmol) and 4-(2-chloro-6-((4-methoxybenzyl)oxy)pyridin-4-yl)morpholine (211 mg, 0.63 mmol, Scaffold 1). After 16 h Further BINAP (0.13 mmol) and Pd$_2$(dba)$_3$ (64 µmol) were added, the tube was degassed three times with N$_2$, and heating continued at 100° C. for 22 h. After cooling to rt, the mixture was filtered through celite, washing with MeOH. The filtrate was concentrated and used without further purification.

Step 6: 6-((S)-2-(4-(((R)-1-methoxypropan-2-yl)oxy)benzyl)pyrrolidin-1-yl)-4-morpholinopyridin-2(1H)-one and 6-((R)-2-(4-(((R)-1-methoxypropan-2-yl)oxy)benzyl)pyrrolidin-1-yl)-4-morpholinopyridin-2(1H)-one A solution of 4-(2-((4-methoxybenzyl)oxy)-6-(2-(4-(((R)-1-methoxypropan-2-yl)oxy)benzyl)pyrrolidin-1-yl)pyridin-4-yl)morpholine (used crude from the previous step) in TFA (5 mL) was stirred at rt for 1-17 h. After which time the reaction mixture was concentrated. The crude mixture was purified by reverse phase preparative HPLC, followed by SFC to afford the title compounds.

6-((S)-2-(4-(((R)-1-methoxypropan-2-yl)oxy)benzyl)pyrrolidin-1-yl)-4-morpholinopyridin-2(1H)-one; LCMS (ES+) 428 (M+H)$^+$, RT 2.79 min (Analytical Method A); $^1$H NMR (400 MHz, CDCl$_3$): δ 7.06 (2H, d, J=8.5 Hz), 6.86 (2H, d, J=8.5 Hz), 5.21 (1H, d, J=2.0 Hz), 4.88 (1H, d, J=2.0 Hz), 4.55-4.46 (1H, m), 4.09-4.01 (1H, m), 3.79 (4H, dd, J=4.9, 4.9 Hz), 3.58 (1H, dd, J=5.9, 10.2 Hz), 3.49-3.42 (2H, m), 3.41 (3H, s), 3.32-3.23 (5H, m), 2.89 (1H, dd, J=3.7, 13.9 Hz), 2.63 (1H, dd, J=8.4, 13.9 Hz), 1.97-1.75 (5H, m), 1.30 (3H, d, J=6.3 Hz).

6-((R)-2-(4-(((R)-1-methoxypropan-2-yl)oxy)benzyl)pyrrolidin-1-yl)-4-morpholinopyridin-2(1H)-one; LCMS (ES+) 428 (M+H)$^+$, RT 2.79 min (Analytical Method A); $^1$H NMR (400 MHz, CDCl$_3$): δ 7.05 (2H, d, J=8.5 Hz), 6.86 (2H, d, J=8.7 Hz), 5.21 (1H, d, J=2.0 Hz), 4.87 (1H, d, J=2.0 Hz), 4.51 (1H, qt, J=5.6, 6.1 Hz), 4.05 (1H, dd, J=8.5, 8.5 Hz), 3.79 (4H, dd, J=4.9, 4.9 Hz), 3.58 (1H, dd, J=5.8, 10.2 Hz), 3.50-3.42 (2H, m), 3.41 (3H, s), 3.32-3.22 (5H, m), 2.89 (1H, dd, J=3.8, 13.9 Hz), 2.64 (1H, dd, J=8.3, 13.9 Hz), 1.97-1.75 (4H, m), 1.29 (3H, d, J=6.3 Hz), NH not observed.

Example 146: (R)-4-morpholino-6-(2-(3-((tetrahydro-2H-pyran-4-yl)oxy)benzyl)pyrrolidin-1-yl)pyridin-2(1H)-one and Example 147: (S)-4-morpholino-6-(2-(3-((tetrahydro-2H-pyran-4-yl)oxy)benzyl)pyrrolidin-1-yl)pyridin-2(1H)-one

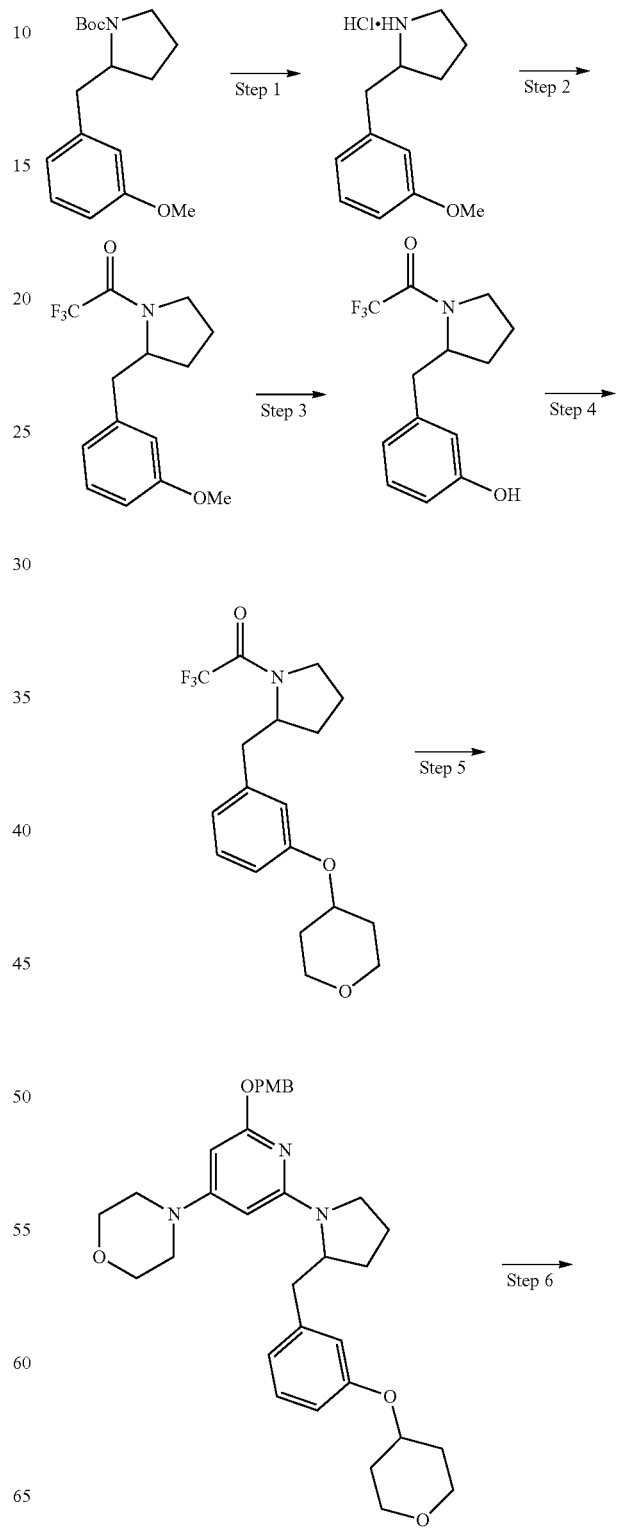

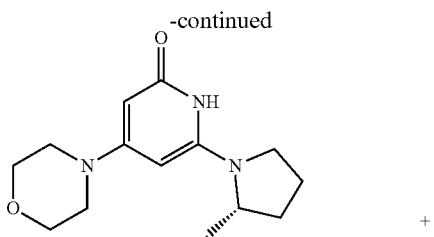

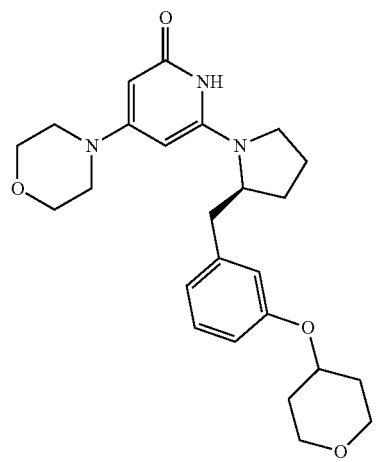 [SMILES: O=c1cc(N2CCOCC2)cc(N2CCC[C@H]2Cc2cccc(OC3CCOCC3)c2)[nH]1]

Step 1: 2-(3-methoxybenzyl)pyrrolidinium hydrochloride

A solution of tert-butyl 2-(3-methoxybenzyl)pyrrolidine-1-carboxylate (3.68 g, 12.6 mmol) in 4 M HCl/dioxane (25 mL) was stirred at rt for 1 h. The volatiles were evaporated to give impure title compound.

Step 2: 2,2,2-trifluoro-1-(2-(3-methoxybenzyl)pyrrolidin-1-yl)ethan-1-one

DIPEA (4.4 mL, 25.3 mmol) was added to a solution of 2-(3-methoxybenzyl)pyrrolidinium hydrochloride (2.87 g mixture from previous step) in dry DCM (120 mL) at 0° C. TFAA (3.5 mL, 25.2 mmol) was added over 5 minutes and the reaction allowed to warm to rt over 16 h. After 17 hours TFAA (3.5 mL, 25.2 mL) was added. After a further 4 hours TFAA (1.3 mL) was added at r.t. The reaction mixture was stirred at rt for a further 1.5 h before being cooled to 0° C. The reaction mixture was quenched with water (5 mL) and saturated aqueous $NaHCO_3$ solution (15 mL). The layers were separated and the organic extract dried (phase separator) and concentrated under reduced pressure. The residue was diluted with EtOAc (50 mL), washed with 1 M $Na_2CO_3$ (2×30 mL) and 1 M HCl (30 mL), dried ($Na_2SO_4$) and concentrated to give the title compound.

Step 3: 2,2,2-trifluoro-1-(2-(3-hydroxybenzyl)pyrrolidin-1-yl)ethan-1-one

Following the method described for the preparation of example 11 step 2 starting from 2,2,2-trifluoro-1-(2-(3-methoxybenzyl)pyrrolidin-1-yl)ethan-1-one (2.42 g, 8.42 mmol). The reaction mixture was quenched with 20 mL saturated aqueous $NaHCO_3$ solution. The residue was dried (phase separator) and concentrated to give the title compound.

Step 4: 2,2,2-trifluoro-1-(2-(3-((tetrahydro-2H-pyran-4-yl)oxy)benzyl)pyrrolidin-1-yl)ethan-1-one Following the method described for the preparation of example 11 step 3 starting from 2,2,2-trifluoro-1-(2-(3-hydroxybenzyl)pyrrolidin-1-yl)ethan-1-one (550 mg mixture from previous step) and tetrahydro-2H-pyran-4-ol (3.98 mmol). The mixture was concentrated and the residue purified by silica gel column chromatography (gradient elution, 0-100% EtOAc/iso-hexane) to afford impure title compound, which was used without further purification.

Step 5: 2-(3-((tetrahydro-2H-pyran-4-yl)oxy)benzyl)pyrrolidine

Following the method described for the preparation of example 11 step 4 starting from 2,2,2-trifluoro-1-(2-(3-((tetrahydro-2H-pyran-4-yl)oxy)benzyl) pyrrolidin-1-yl) ethan-1-one (564 mg mixture from previous step). Impure title compound was obtained, which was used without further purification.

Step 6: 4-(2-((4-methoxybenzyl)oxy)-6-(2-(3-((tetrahydro-2H-pyran-4-yl)oxy)benzyl)pyrrolidin-1-yl)pyridin-4-yl)morpholine Following Method D starting from 2-(3-((tetrahydro-2H-pyran-4-yl)oxy)benzyl)pyrrolidine (159 mg, 0.61 mmol) and 4-(2-chloro-6-((4-methoxybenzyl)oxy)pyridin-4-yl)morpholine (201 mg, 0.61 mmol, Scaffold 1). Purification by silica gel column chromatography (gradient elution, 0-40% EtOAc/iso-hexane) gave impure title compound, which was used without further purification.

Step 7: (R)-4-morpholino-6-(2-(3-((tetrahydro-2H-pyran-4-yl)oxy)benzyl)pyrrolidin-1-yl)pyridin-2(1H)-one and (S)-4-morpholino-6-(2-(3-((tetrahydro-2H-pyran-4-yl)oxy)benzyl)pyrrolidin-1-yl)pyridin-2(1H)-one Following Method E starting from 4-(2-((4-methoxybenzyl)oxy)-6-(2-(3-((tetrahydro-2H-pyran-4-yl)oxy)benzyl)pyrrolidin-1-yl)pyridin-4-yl)morpholine (171 mg from previous step). Purification by reverse phase HPLC, then chiral SFC to afford the title compounds.

(R)-4-morpholino-6-(2-(3-((tetrahydro-2H-pyran-4-yl)oxy)benzyl)pyrrolidin-1-yl)pyridin-2(1H)-one. LCMS (ES+) 440 (M+H)$^+$, RT 2.78 min (Analytical Method A), RT 1.92 min (Analytical Method SFC4, YMC AMYLOSE-C 50/50 IPA (0.1% DEAISO)/$CO_2$); $^1$H NMR (400 MHz, $CDCl_3$): δ 7.21 (1H, t, J=7.8 Hz), 6.82-6.73 (3H, m), 5.20 (1H, d, J=2.3 Hz), 4.85 (1H, d, J=2.0 Hz), 4.49-4.42 (1H, m), 4.05-3.93 (3H, m), 3.78 (4H, t, J=4.9 Hz), 3.60-3.53 (2H, m), 3.42 (1H, dd, J=6.7, 9.0 Hz), 3.29-3.25 (1H, m), 3.23 (4H, dd, J=4.2, 5.7 Hz), 2.92 (1H, dd, J=4.2, 13.8 Hz), 2.66 (1H, dd, J=8.3, 13.6 Hz), 2.04-1.86 (6H, m), 1.81-1.71 (3H, m).

(S)-4-morpholino-6-(2-(3-((tetrahydro-2H-pyran-4-yl)oxy)benzyl)pyrrolidin-1-yl)pyridin-2(1H)-one. LCMS (ES+) 440 (M+H)$^+$, RT 2.79 min (Analytical Method A), RT 0.94 min (Analytical Method SFC4, YMC AMYLOSE-C 50/50 IPA (0.1% DEAISO)/CO$_2$); $^1$H NMR (400 MHz, CDCl$_3$): δ 7.21 (1H, t, J=7.8 Hz), 6.82-6.73 (3H, m), 5.20 (1H, d, J=2.3 Hz), 4.85 (1H, d, J=2.0 Hz), 4.49-4.42 (1H, m), 4.05-3.93 (3H, m), 3.78 (4H, t, J=4.9 Hz), 3.60-3.53 (2H, m), 3.42 (1H, dd, J=6.7, 9.0 Hz), 3.29-3.25 (1H, m), 3.23 (4H, dd, J=4.2, 5.7 Hz), 2.92 (1H, dd, J=4.2, 13.8 Hz), 2.66 (1H, dd, J=8.3, 13.6 Hz), 2.04-1.86 (6H, m), 1.81-1.71 (3H, m).

Example 148: 6-((R)-2-(3-(((R)-1-methoxypropan-2-yl)oxy)benzyl)pyrrolidin-1-yl)-4-morpholinopyridin-2(1H)-one and Example 149: 6-((S)-2-(3-(((R)-1-methoxypropan-2-yl)oxy)benzyl)pyrrolidin-1-yl)-4-morpholinopyridin-2(1H)-one

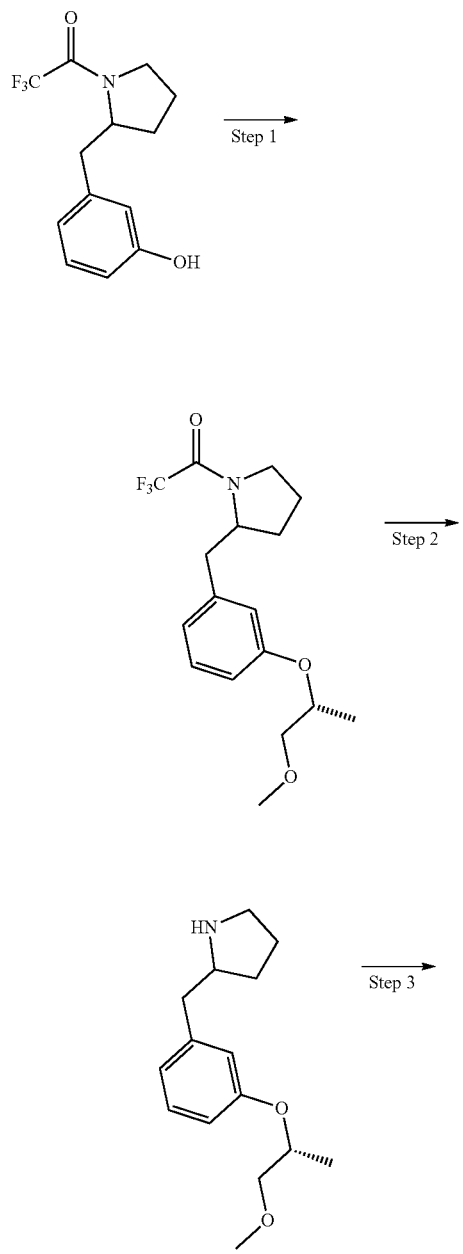

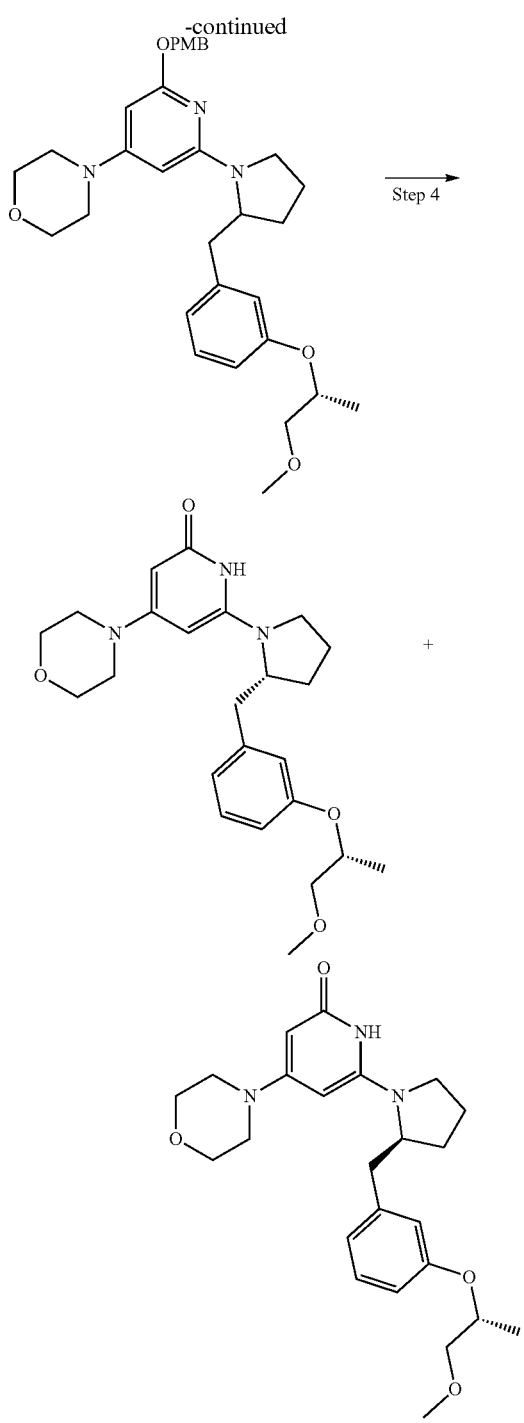

Step 1: 2,2,2-trifluoro-1-(2-(3-(((R)-1-methoxypropan-2-yl)oxy)benzyl)pyrrolidin-1-yl)ethan-1-one Following the method described for the preparation of example 11 step 3 starting from 2,2,2-trifluoro-1-(2-(3-hydroxybenzyl)pyrrolidin-1-yl)ethan-1-one (550 mg, Example 13 step 3) and (S)-1-methoxypropan-2-ol (3.99 mmol). The mixture was concentrated and the residue purified by silica gel column chromatography (gradient elution, 0-100% EtOAc/iso-hexane) to give the title compound.

Step 2: 2-(3-(((R)-1-methoxypropan-2-yl)oxy)benzyl)pyrrolidine

Following the method described for the preparation of example 11 step 4 starting from 2,2,2-trifluoro-1-(2-(3-(((R)-1-methoxypropan-2-yl)oxy)benzyl)pyrrolidin-1-yl)ethan-1-one (381 mg). The title compound was obtained.

Step 3: 4-(2-((4-methoxybenzyl)oxy)-6-(2-(3-(((R)-1-methoxypropan-2-yl)oxy)benzyl)pyrrolidin-1-yl)pyridin-4-yl)morpholine Following Method D from 2-(3-(((R)-1-methoxypropan-2-yl)oxy)benzyl)pyrrolidine (249 mg, 0.75 mmol) and 4-(2-chloro-6-((4-methoxybenzyl)oxy)pyridin-4-yl)morpholine (181 mg, 0.73 mmol, Scaffold 1). Purification by silica gel column chromatography (gradient elution, 0-50% EtOAc/iso-hexane) gave the title compound.

Step 4: 6-((R)-2-(3-(((R)-1-methoxypropan-2-yl)oxy)benzyl)pyrrolidin-1-yl)-4-morpholinopyridin-2(1H)-one and 6-((S)-2-(3-(((R)-1-methoxypropan-2-yl)oxy)benzyl)pyrrolidin-1-yl)-4-morpholinopyridin-2(1H)-one Following Method E from 4-(2-((4-methoxybenzyl)oxy)-6-(2-(3-(((R)-1-methoxypropan-2-yl)oxy)benzyl)pyrrolidin-1-yl)pyridin-4-yl)morpholine (289 mg, 0.53 mmol). Purification by reverse phase HPLC, then chiral SFC gave the title compounds.

6-((R)-2-(3-(((R)-1-methoxypropan-2-yl)oxy)benzyl)pyrrolidin-1-yl)-4-morpholinopyridin-2(1H)-one; LCMS (ES+) 428 (M+H)+, RT 2.83 min (Analytical Method A), RT 1.34 min (Analytical Method SFC4, YMC AMYLOSE-C 50/50 IPA (0.1% DEAISO)/CO2); $^1$H NMR (400 MHz, CDCl3): δ 7.20 (1H, t, J=8.0 Hz), 6.83-6.79 (1H, m), 6.77-6.73 (2H, m), 5.21 (1H, d, J=2.1 Hz), 4.88 (1H, d, J=2.1 Hz), 4.52 (1H, ddd, J=6.1, 10.5, 12.3 Hz), 4.04 (1H, dd, J=4.0, 8.0 Hz), 3.79 (4H, t, J=4.9 Hz), 3.57 (1H, dd, J=5.9, 10.2 Hz), 3.47 (2H, dd, J=4.4, 10.2 Hz), 3.41 (3H, s), 3.31-3.22 (6H, m), 2.95 (1H, dd, J=3.8, 13.7 Hz), 2.61 (1H, dd, J=8.6, 13.7 Hz), 1.99-1.84 (4H, m), 1.29 (3H, d, J=6.3 Hz).

6-((S)-2-(3-(((R)-1-methoxypropan-2-yl)oxy)benzyl)pyrrolidin-1-yl)-4-morpholinopyridin-2(1H)-one; LCMS (ES+) 428 (M+H)+, RT 2.84 min (Analytical Method A), RT 0.77 min (Analytical Method SFC4, YMC AMYLOSE-C 50/50 IPA (0.1% DEAISO)/CO2); $^1$H NMR (400 MHz, CDCl3): δ 7.20 (1H, t, J=7.8 Hz), 6.81 (1H, dd, J=2.1, 8.1 Hz), 6.78-6.73 (2H, m), 5.21 (1H, d, J=2.1 Hz), 4.89 (1H, d, J=2.1 Hz), 4.56-4.50 (1H, m), 4.02 (1H, dd, J=3.6, 8.0 Hz), 3.79 (4H, t, J=4.9 Hz), 3.57 (1H, dd, J=5.9, 10.2 Hz), 3.50-3.43 (2H, m), 3.41 (3H, s), 3.30-3.22 (5H, m), 2.94 (1H, dd, J=3.9, 13.7 Hz), 2.62 (1H, dd, J=8.6, 13.7 Hz), 2.00-1.84 (4H, m), 1.29 (3H, d, J=6.1 Hz), NH not observed.

Example 150: 6-((S)-2-(4-(((R)-1-methoxypropan-2-yl)oxy)benzyl)azepan-1-yl)-4-morpholinopyridin-2(1H)-one and Example 151: 6-((R)-2-(4-(((R)-1-methoxypropan-2-yl)oxy)benzyl)azepan-1-yl)-4-morpholinopyridin-2(1H)-one

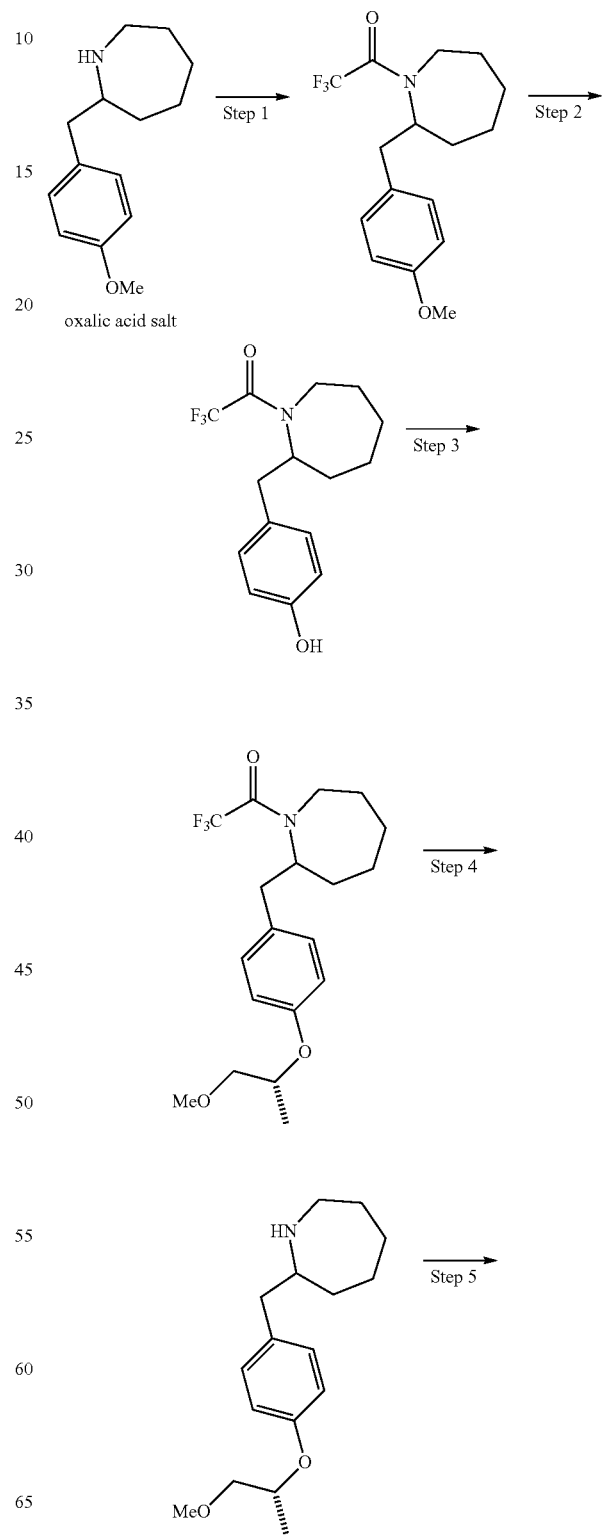

-continued

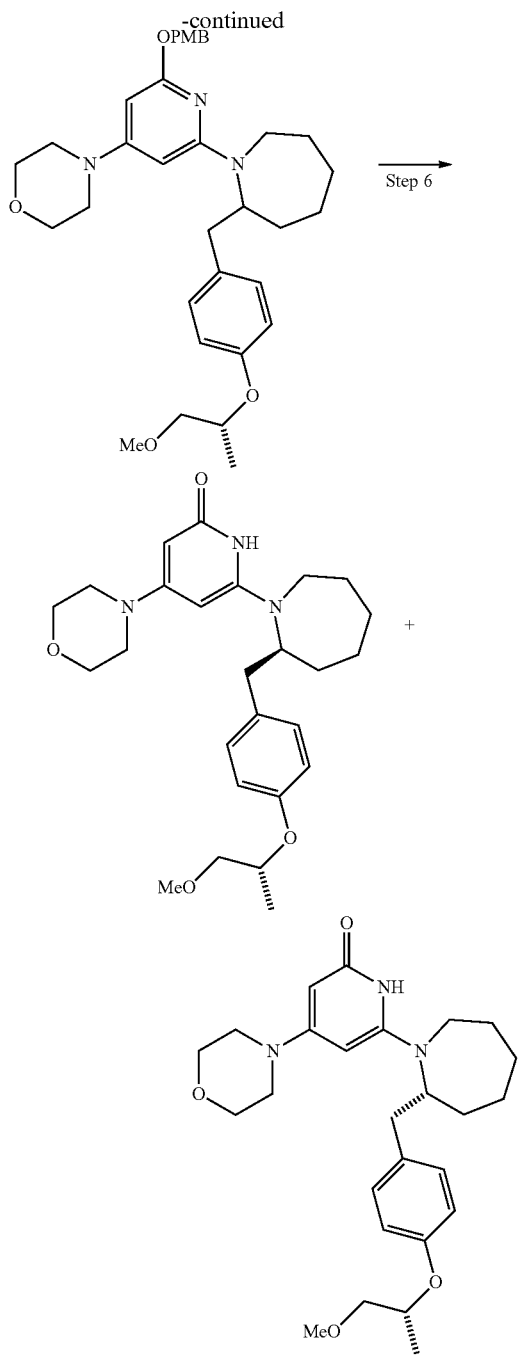

Step 1: 2,2,2-trifluoro-1-(2-(4-methoxybenzyl)azepan-1-yl)ethan-1-one

TFAA (0.63 mL, 4.53 mmol) was added to a solution of 2-(4-methoxybenzyl)azepane oxalic acid salt (619 mg, 2.00 mmol) in dry DCM (25 mL) at 0° C. under nitrogen. (NOTE: strongly exothermic). The mixture was stirred at rt for 18 h. DIPEA (3×199 μL, 3×1.14 mmol at 3-hourly intervals) was added until complete conversion observed. The reaction was quenched by cooling to 0° C. and treatment with 1 mL H$_2$O, followed by 1 mL saturated aqueous solution of NaHCO$_3$. The reaction mixture was diluted with 10 mL DCM and dried (phase separator). The crude material was purified by silica gel column chromatography (gradient elution, 0-60% EtOAc/iso-hexane) to give the product, which was used without further purification.

Step 2: 2,2,2-trifluoro-1-(2-(4-hydroxybenzyl)azepan-1-yl)ethan-1-one

Following the method described for the preparation of example 11 step 2 starting from 2,2,2-trifluoro-1-(2-(4-methoxybenzyl)azepan-1-yl)ethan-1-one. The organic layer was dried (phase separator) and concentrated under reduced pressure to afford the title compound.

Step 3: 2,2,2-trifluoro-1-(2-(4-(((R)-1-methoxypropan-2-yl)oxy)benzyl)azepan-1-yl)ethan-1-one Following the method described for the preparation of example 11 step 3 starting from 2,2,2-trifluoro-1-(2-(4-hydroxybenzyl)azepan-1-yl)ethan-1-one (1.37 mmol) and (S)-1-methoxypropan-2-ol (270 μL, 2.76 mmol). The mixture was purified by silica gel column chromatography (gradient elution, 0-50% EtOAc/iso-hexane) to give the title compound.

Step 4: 2-(4-(((R)-1-methoxypropan-2-yl)oxy)benzyl)pyrrolidine

Following the method described for the preparation of example 11 step 4 starting from 2,2,2-trifluoro-1-(2-(4-(((R)-1-methoxypropan-2-yl)oxy)benzyl)azepan-1-yl) ethan-1-one (0.93 mmol). After 18 h H$_2$O (2 mL) and KOH (3.70 mmol) were added and the reaction stirred at 60° C. After 43 h the reaction mixture was concentrated, diluted with 20 mL H$_2$O and 20 mL DCM, passed through a hydrophobic frit and the organic layer concentrated to yield the title compound.

Step 5: 4-(2-((4-methoxybenzyl)oxy)-6-(2-(4-(((R)-1-methoxypropan-2-yl)oxy)benzyl)azepan-1-yl)pyridin-4-yl)morpholine Following Method D starting from 4-(2-chloro-6-((4-methoxybenzyl)oxy)pyridin-4-yl)morpholine (221 mg, 0.66 mmol, Scaffold 1) and 2-(4-(((R)-1-methoxypropan-2-yl)oxy)benzyl)azepane (189 mg, 0.68 mmol,) added as a solution in dry dioxane (4.5 mL). The filtrate was concentrated then purified by silica gel column chromatography (gradient elution, 0-25% EtOAc/iso-hexane) to yield impure title compound, which was used without further purification.

Step 6: 6-((S)-2-(4-(((R)-1-methoxypropan-2-yl)oxy)benzyl)azepan-1-yl)-4-morpholinopyridin-2(1H)-one and 6-((R)-2-(4-(((R)-1-methoxypropan-2-yl)oxy)benzyl)azepan-1-yl)-4-morpholinopyridin-2(1H)-one Following Method E starting from 4-(2-((4-methoxybenzyl)oxy)-6-(2-(4-(((R)-1-methoxypropan-2-yl)oxy)benzyl) azepan-1-yl)pyridin-4-yl)morpholine (used crude from the previous step). The residue was partially purified by silica gel column chromatography (gradient elution, 0-20% MeOH/EtOAc), and the fractions containing the title compounds were further purified by SFC to yield the title compounds.

6-((R)-2-(4-(((R)-1-methoxypropan-2-yl)oxy)benzyl) azepan-1-yl)-4-morpholinopyridin-2(1H)-one; LCMS (ES+) 456 (M+H)$^+$, RT 2.90 min (Analytical Method A); $^1$H NMR (400 MHz, DMSO-d$_6$): δ 9.39 (1H, s), 7.18 (2H, d, J=8.3 Hz), 6.87 (2H, d, J=8.6 Hz), 5.34 (1H, s), 5.25 (1H, s), 4.62-4.55 (1H, m), 4.33 (1H, s), 3.72 (4H, t, J=4.8 Hz), 3.52 (1H, dd, J=5.7, 10.9 Hz), 3.45 (1H, dd, J=4.2, 10.4 Hz), 3.38 (3H, s), 3.19-3.13 (4H, m), 3.02-2.92 (1H, m), 2.78-2.72 (1H, m), 2.66-2.58 (1H, m), 1.90-1.86 (1H, m), 1.77-1.62 (3H, m), 1.48-1.38 (2H, m), 1.30-1.25 (1H, m), 1.23 (3H, d, J=6.1 Hz), 1.11-1.01 (1H, m), 1H not observed.

6-((S)-2-(4-(((R)-1-methoxypropan-2-yl)oxy)benzyl)azepan-1-yl)-4-morpholinopyridin-2(1H)-one; LCMS (ES+) 456 (M+H)$^+$, RT 2.91 min (Analytical Method A); $^1$H NMR (400 MHz, DMSO-d$_6$): δ 9.41 (1H, s), 7.18 (2H, d, J=8.6 Hz), 6.87 (2H, d, J=8.6 Hz), 5.38-5.31 (1H, m), 5.25 (1H, s), 4.62-4.55 (1H, m), 4.34 (1H, s), 3.72 (4H, t, J=4.9 Hz), 3.52 (1H, dd, J=5.8, 10.3 Hz), 3.45 (1H, dd, J=4.5, 10.3 Hz), 3.39 (3H, s), 3.19-3.13 (4H, m), 2.96 (1H, t, J=13.0 Hz), 2.74 (1H, dd, J=4.4, 13.0 Hz), 2.63 (1H, dd, J=8.0, 13.1 Hz), 1.91-1.83 (1H, m), 1.77-1.59 (3H, m), 1.51-1.38 (2H, m), 1.31-1.20 (4H, m), 1.12-1.01 (1H, m), 1H not observed.

Example 152: 6-[(2R)-2-Benzyl-2-(methoxymethyl)pyrrolidin-1-yl]-4-morpholino-1H-pyridin-2-one and
Example 153: 6-[(2S)-2-Benzyl-2-(methoxymethyl)pyrrolidin-1-yl]-4-morpholino-1H-pyridin-2-one

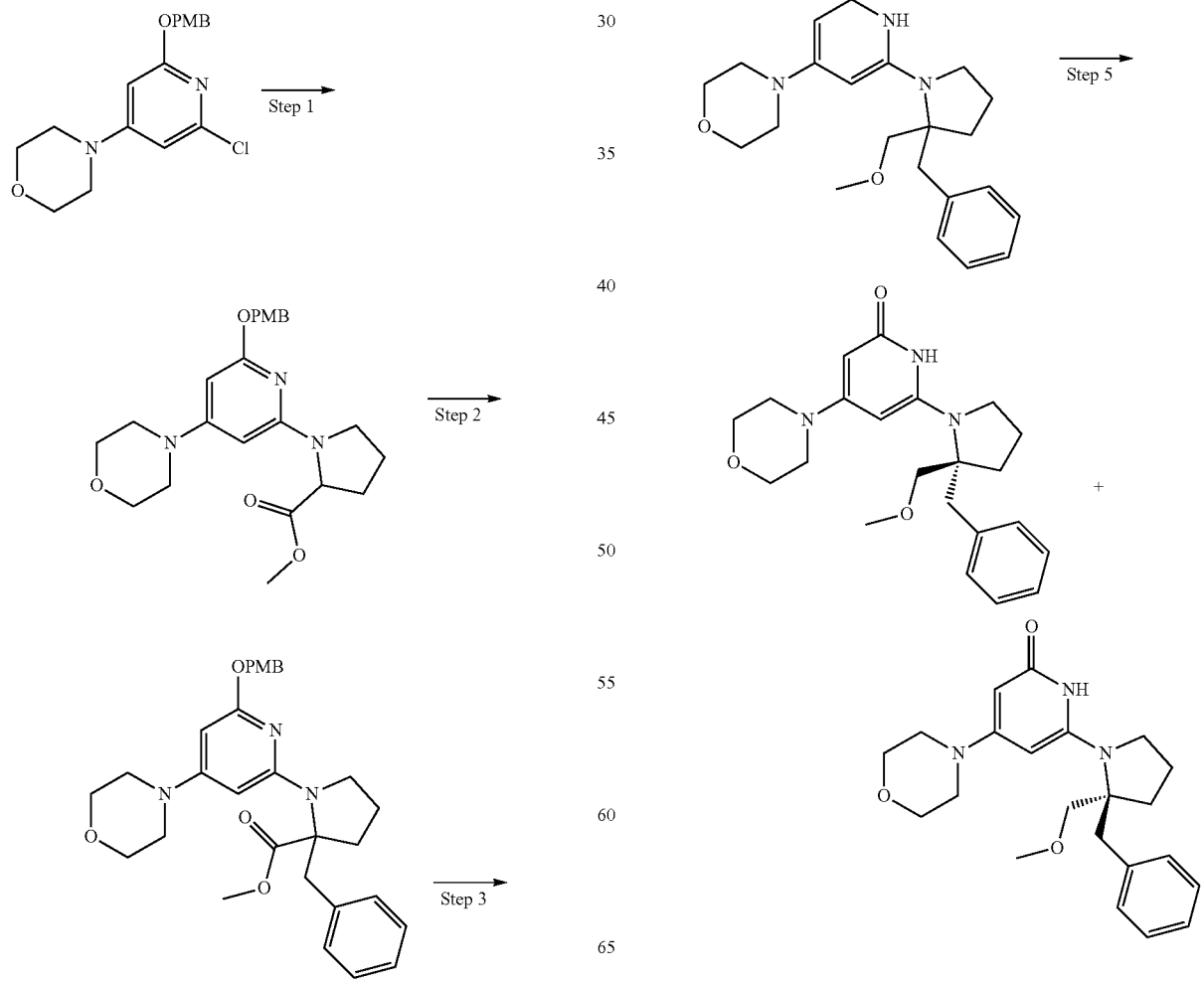

Step 1: Methyl-1-[6-[(4-methoxyphenyl)methoxy]-4-morpholino-2-pyridyl]pyrrolidine-2-carboxylate Following Method C starting from L-proline methyl ester hydrochloride (545 mg, 3.29 mmol) and 4-(2-chloro-6-((4-methoxybenzyl)oxy)pyridin-4-yl)morpholine (1.10 g, 3.29 mmol, Scaffold 1). The mixture was purified by silica gel column chromatography (gradient elution, 0-50% EtOAc/iso-hexane) to give impure title compound, which was reacted as such in the next step.

Step 2: Methyl 2-benzyl-1-[6-[(4-methoxyphenyl)methoxy]-4-morpholino-2-pyridyl]pyrrolidine-2-carboxylate LHMDS (3.1 mL, 3.06 mmol, 1M solution in THF) was added to a solution of methyl (2S)-1-[6-[(4-methoxyphenyl)methoxy]-4-morpholino-2-pyridyl]pyrrolidine-2-carboxylate (770 mg, 1.8 mmol) in dry THF (7 mL) at −25° C. under $N_2$ atmosphere. After 1 h, benzyl bromide (0.43 mL, 3.6 mmol) was added and allowed to warm to r.t. After 1 h the mixture was cooled to 0° C. and quenched with saturated aqueous $NH_4Cl$ solution. The reaction mixture was diluted with water (10 mL) and extracted with DCM (×2). The organic extracts were dried (phase separator) and concentrated under reduced pressure. The mixture was purified by silica gel column chromatography (gradient elution, 0-20% EtOAc/iso-hexane) to give the title compound.

Step 3: [2-Benzyl-1-[6-[(4-methoxyphenyl)methoxy]-4-morpholino-2-pyridyl]pyrrolidin-2-yl]methanol $LiAlH_4$ (0.68 mL, 1.36 mmol, 2M solution in THF) was added to a solution of methyl 2-benzyl-1-[6-[(4-methoxyphenyl)methoxy]-4-morpholino-2-pyridyl]pyrrolidine-2-carboxylate (701 mg, 1.36 mmol) in dry THF (6.8 mL) at r.t. After stirring for 1 h, the mixture was quenched with saturated aqueous $NH_4Cl$ solution and diluted with water (10 mL). The reaction mixture was extracted with DCM (×3). The organic extracts were dried (phase separator) and concentrated to give the title compound.

Step 4: 4-[2-[2-Benzyl-2-(methoxymethyl)pyrrolidin-1-yl]-6-[(4-methoxyphenyl)methoxy]-4-pyridyl]morpholine To a stirred solution of [2-benzyl-1-[6-[(4-methoxyphenyl)methoxy]-4-morpholino-2-pyridyl]pyrrolidin-2-yl]methanol (250 mg, 0.51 mmol) in dry DMF (3.4 mL) was added portionwise sodium hydride (31 mg, 0.77 mmol, 60% dispersion in mineral oil). The resulting mixture was stirred for 15 min, then iodomethane (35 μL, 0.56 mmol) was added. After 1.5 h, additional iodomethane (35 μL, 0.56 mmol) was added. After a further 1.5 h, more iodomethane (18 μL, 0.28 mmol) was added. After 2 hours the reaction mixture was partitioned between 4% aqueous LiCl solution and extracted with DCM (×3). The organic extracts were dried (phase separator) and concentrated to give the title compound.

Step 5: 6-[2-benzyl-2-(methoxymethyl)pyrrolidin-1-yl]-4-morpholino-1H-pyridin-2-one Following Method E starting from 4-[2-[2-benzyl-2-(methoxymethyl)pyrrolidin-1-yl]-6-[(4-methoxyphenyl)methoxy]-4-pyridyl]morpholine (259 mg, 0.51 mmol). The crude material was purified by reverse phase preparative HPLC followed by SFC to afford the title compounds.

6-[(2R)-2-benzyl-2-(methoxymethyl)pyrrolidin-1-yl]-4-morpholino-1H-pyridin-2-one; LCMS (ES+) 384 (M+H)$^+$, RT 2.97 min (Analytical Method A); RT 1.62 min (Analytical Method SFC1, YMC CELLULOSE-C, 45/55 IPA+0.1% DEAISO/CO$_2$); $^1$H NMR (400 MHz, CDCl$_3$): δ 10.89 (1H, s), 7.29-7.22 (3H, m), 7.15-7.12 (2H, m), 5.33 (1H, d, J=2.0 Hz), 4.91 (1H, d, J=2.1 Hz), 3.81-3.77 (4H, m), 3.58 (3H, s), 3.47 (1H, d, J=9.7 Hz), 3.38-3.22 (8H, m), 2.82 (1H, d, J=13.6 Hz), 2.11 (1H, ddd, J=7.1, 9.4, 13.0 Hz), 1.83-1.73 (1H, m), 1.72-1.66 (1H, m), 1.53 (1H, ddd, J=5.0, 7.3, 12.7 Hz).

6-[(2S)-2-benzyl-2-(methoxymethyl)pyrrolidin-1-yl]-4-morpholino-1H-pyridin-2-one; LCMS (ES+) 384 (M+H)$^+$, RT 2.98 min (Analytical Method A); RT 3.00 min (Analytical Method SFC1, YMC CELLULOSE-C, 45/55 IPA+0.1% DEAISO/CO$_2$); $^1$H NMR (400 MHz, CDCl$_3$): δ 10.89 (1H, s), 7.29-7.22 (3H, m), 7.15-7.12 (2H, m), 5.33 (1H, d, J=2.0 Hz), 4.91 (1H, d, J=2.1 Hz), 3.81-3.77 (4H, m), 3.58 (3H, s), 3.47 (1H, d, J=9.7 Hz), 3.38-3.22 (8H, m), 2.82 (1H, d, J=13.6 Hz), 2.11 (1H, ddd, J=7.1, 9.4, 13.0 Hz), 1.83-1.73 (1H, m), 1.72-1.66 (1H, m), 1.53 (1H, ddd, J=5.0, 7.3, 12.7 Hz).

Example 154: (S)-6-(2-benzyl-3,3-difluoropiperidin-1-yl)-4-morpholinopyridin-2(1H)-one and Example 155: (R)-6-(2-benzyl-3,3-difluoropiperidin-1-yl)-4-morpholinopyridin-2(1H)-one

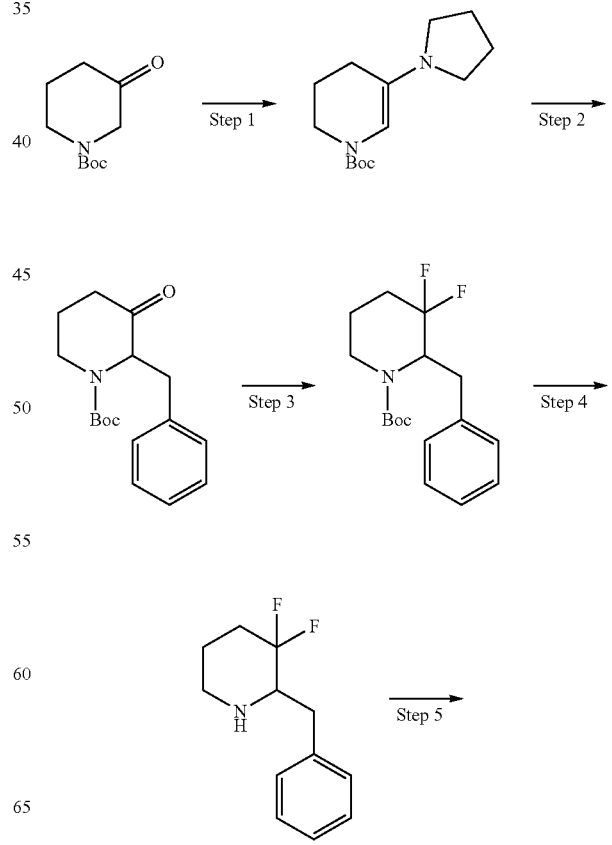

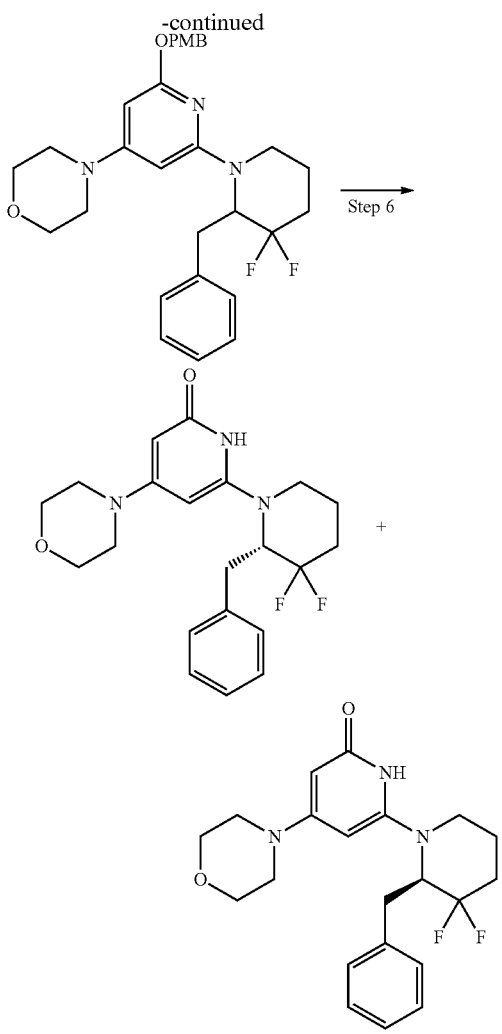

Step 1: tert-butyl 5-(pyrrolidin-1-yl)-3,4-dihydropyridine-1(2H)-carboxylate Pyrrolidine (3.13 mL, 37.5 mmol) was added to a solution of tert-butyl 3-oxopiperidine-1-carboxylate (5 g, 25 mmol) in toluene (50 mL). The reaction was heated at reflux with Dean stark apparatus. After 5.5 hours the reaction mixture was cooled to rt and concentrated under reduced pressure to afford the title compound. Used without further purification in the next step.

Step 2: tert-butyl 2-benzyl-3-oxopiperidine-1-carboxylate

Benzyl bromide (1.63 mL, 13.8 mmol) was added to a solution of tert-butyl 5-(pyrrolidin-1-yl)-3,4-dihydropyridine-1(2H)-carboxylate (3.15 g, 12.5 mmol) in acetonitrile (25 mL). The reaction mixture was heated at 65° C. After 15.5 hours the reaction was cooled to RT. Brine was added and the reaction mixture transferred to a separating funnel with EtOAc. The layers were separated and the aqueous layer extracted with EtOAc. The combined organics extracts were washed with saturated aqueous NH$_4$Cl solution, dried (MgSO$_4$), filtered and concentrated under reduced pressure. The resultant brown oil was purified by silica gel column chromatography (gradient elution 0-60% EtOAc/iso-hexane) to afford the title compound.

Step 3: tert-butyl 2-benzyl-3,3-difluoropiperidine-1-carboxylate

Following the method described for the preparation of example 40 step 3 starting from tert-butyl 2-benzyl-3-oxopiperidine-1-carboxylate (500 mg, 1.73 mmol). The crude material was purified by silica gel column chromatography (gradient 0-20% EtOAc/iso-hexane) to afford the title compound.

Step 4: 2-benzyl-3,3-difluoropiperidine

Following the method described for the preparation of example 5 step 2 starting from tert-butyl 2-benzyl-3,3-difluoropiperidine-1-carboxylate (320 mg, 1.03 mmol) to afford the title compound. Used without further purification in the next step.

Step 5: 4-(2-(2-benzyl-3,3-difluoropiperidin-1-yl)-6-((4-methoxybenzyl)oxy)pyridin-4-yl)morpholine Following Method D starting from 2-benzyl-3,3-difluoropiperidine (127 mg, 0.60 mmol) and 4-(2-chloro-6-((4-methoxybenzyl)oxy)pyridin-4-yl)morpholine (200 mg, 0.60 mmol, Scaffold 1). The residue was purified by silica gel column chromatography (gradient elution 0-55% Et$_2$O/iso-hexane) to afford the title compound.

Step 6: (S)-6-(2-benzyl-3,3-difluoropiperidin-1-yl)-4-morpholinopyridin-2(1H)-one and (R)-6-(2-benzyl-3,3-difluoropiperidin-1-yl)-4-morpholinopyridin-2(1H)-one TFA (29 µL, 0.38 mmol) was added to 4-(2-(2-benzyl-3,3-difluoropiperidin-1-yl)-6-((4-methoxybenzyl)oxy)pyridin-4-yl)morpholine (192 mg, 0.38 mmol) in DCM (2 mL). After 19 hours the reaction mixture was concentrated under reduced pressure. The oil was dissolved in DCM, washed with saturated aqueous sodium hydrogen carbonate solution, dried (phase separator) and concentrated under reduced pressure. The resultant oil was purified by silica gel column chromatography (gradient elution with 0-10% MeOH in EtOAc) followed by SFC for the separation of the enantiomers to afford the title compounds.

(S)-6-(2-benzyl-3,3-difluoropiperidin-1-yl)-4-morpholinopyridin-2(1H)-one; LCMS (ES+) 390 (M+H)$^+$, RT 2.83 min (Analytical Method A), RT 1.10 min (Analytical Method SFC4, YMC AMYLOSE-C 30% MeOH (0.1% DEAISO)/CO$_2$; $^1$H NMR (400 MHz, DMSO-d$_6$): δ 9.59 (1H, s), 7.37 (2H, d, J=7.1 Hz), 7.25 (2H, dd, J=7.3, 7.3 Hz), 7.20-7.15 (1H, m), 5.41-5.40 (1H, m), 5.32-5.28 (1H, m), 5.14-5.09 (1H, m), 4.12-4.03 (1H, m), 3.70-3.65 (4H, m), 3.15-2.99 (7H, m), 2.42-2.24 (1H, m), 2.13-2.04 (1H, m), 1.81-1.68 (2H, m). Rotamers observed.

(R)-6-(2-benzyl-3,3-difluoropiperidin-1-yl)-4-morpholinopyridin-2(1H)-one; LCMS (ES+) 390 (M+H)$^+$, RT 2.83 min (Analytical Method A), RT 1.85 min (Analytical Method SFC4, YMC AMYLOSE-C 30% MeOH (0.1% DEAISO)/C$_2$; $^1$H NMR (400 MHz, 105° C., DMSO-d$_6$): δ 9.04 (1H, s), 7.28 (2H, d, J=7.3 Hz), 7.19 (2H, dd, J=7.3, 7.3 Hz), 7.13-7.09 (1H, m), 5.30 (1H, s), 5.27 (1H, s), 4.97-4.95 (1H, m), 4.06-3.99 (1H, m), 3.65-3.62 (4H, m), 3.13-2.96 (6H, m), 2.32-2.14 (1H, m), 2.05-2.04 (1H, m), 1.78-1.70 (2H, m), NH not observed.

Example 156: (S)-6-(3,3-difluoro-2-(4-methoxybenzyl)piperidin-1-yl)-4-morpholinopyridin-2(1H)-one and Example 157: (R)-6-(3,3-difluoro-2-(4-methoxybenzyl)piperidin-1-yl)-4-morpholinopyridin-2(1H)-one

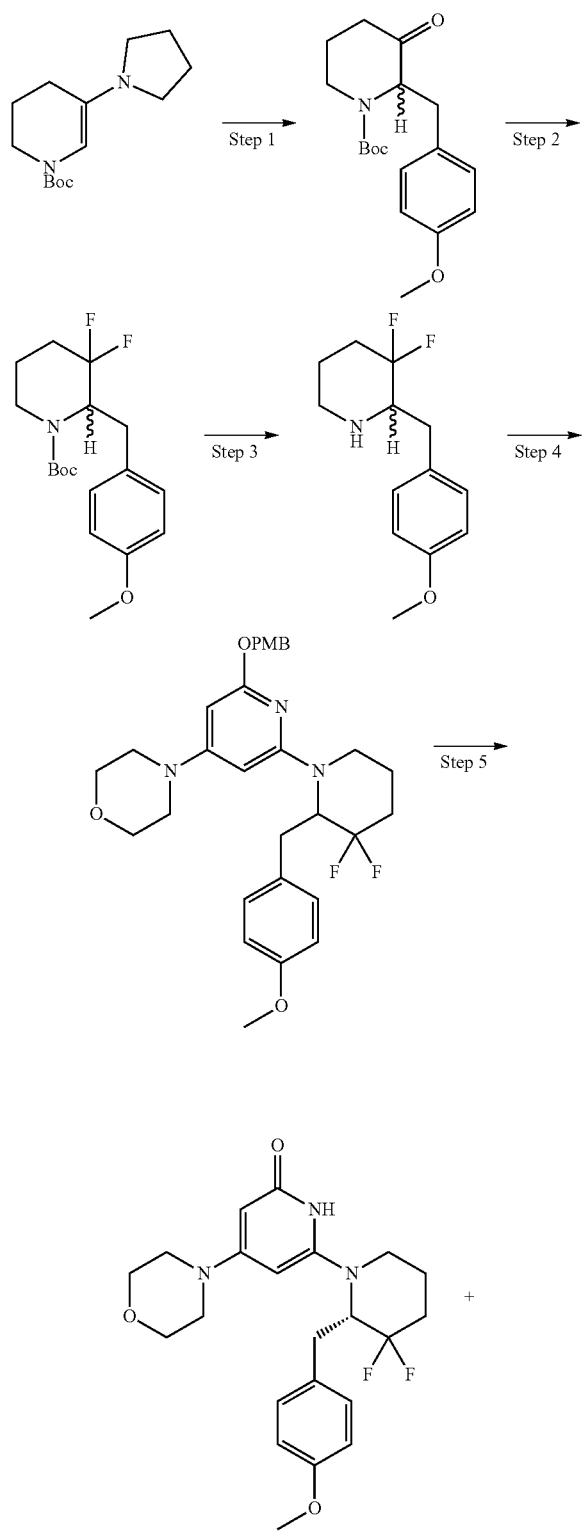

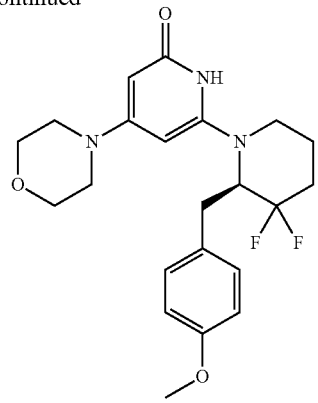

Step 1: tert-butyl 2-(4-methoxybenzyl)-3-oxopiperidine-1-carboxylate

4-Methoxy benzyl bromide (1.99 mL, 13.8 mmol) was added to a solution of tert-butyl 5-(pyrrolidin-1-yl)-3,4-dihydropyridine-1(2H)-carboxylate (3.15 g, 12.5 mmol, Example 132 step 1) in acetonitrile (25 mL). The reaction mixture was heated at 65° C. After 15.5 hours the reaction was cooled to RT. Brine was added and the reaction mixture transferred to a separating funnel with EtOAc. The layers were separated and the aqueous layer extracted with EtOAc. The combined organics extracts were washed with saturated aqueous $NH_4Cl$ solution, dried ($MgSO_4$), filtered and concentrated under reduced pressure. The resultant brown oil was purified by silica gel column chromatography (gradient elution 0-40% EtOAc/iso-hexane) to afford the title compound.

Step 2: tert-butyl 3,3-difluoro-2-(4-methoxybenzyl)piperidine-1-carboxylate

Following the method described for the preparation of example 40 step 3 starting from tert-butyl 2-(4-methoxybenzyl)-3-oxopiperidine-1-carboxylate (1.56 mmol). The mixture was purified by silica gel column chromatography (gradient elution 0-20% EtOAc/iso-hexane) to afford the title compound.

Step 3: 3,3-difluoro-2-(4-methoxybenzyl)piperidine

Following the method described for the preparation of example 5 step 3 starting from tert-butyl 3,3-difluoro-2-(4-methoxybenzyl)piperidine-1-carboxylate (313 mg, 0.92 mmol) to afford the title compound. Used without further purification in the next step.

Step 4: 4-(2-(2-benzyl-3,3-difluoropiperidin-1-yl)-6-((4-methoxybenzyl)oxy)pyridin-4-yl)morpholine Following Method D starting from 3,3-difluoro-2-(4-methoxybenzyl)piperidine (145 mg, 0.60 mmol) and 4-(2-chloro-6-((4-methoxybenzyl)oxy)pyridin-4-yl)morpholine (200 mg, 0.60 mmol, Scaffold 1). The residue was purified by silica gel column chromatography (gradient elution 0-55% $Et_2O$/iso-hexane) to afford the title compound.

Step 5: (S)-6-(3,3-difluoro-2-(4-methoxybenzyl)piperidin-1-yl)-4-morpholinopyridin-2(1H)-one and (R)-6-(3,3-difluoro-2-(4-methoxybenzyl)piperidin-1-yl)-4-morpholinopyridin-2(1H)-one Following the method described for the preparation of example 132 step 6 starting from 4-(2-(3,3-difluoro-2-(4- methoxybenzyl)piperidin-1-yl)-6-((4-methoxybenzyl)oxy) pyridin-4-yl)morpholine (129 mg, 0.24 mmol. The resultant oil was purified by silica gel column chromatography (gradient elution 0-10% MeOH/EtOAc). The two enantiomers were separated by SFC.

(S)-6-(3,3-difluoro-2-(4-methoxybenzyl)piperidin-1-yl)-4-morpholinopyridin-2(1H)-one; LCMS (ES+) 420 (M+H)$^+$, RT 2.82 min (Analytical Method A); RT 1.21 min (Analytical Method SFC4, YMC AMYLOSE-C 30% MeOH (0.1% DEAISO)/CO$_2$)); $^1$H NMR (400 MHz, DMSO-d$_6$): δ 9.52 (1H, s), 7.23 (2H, d, J=8.5 Hz), 6.77 (2H, d, J=8.7 Hz), 5.43-4.91 (3H, m), 4.18-3.94 (1H, m), 3.69 (3H, s), 3.66-3.61 (4H, m), 3.10-2.96 (6H, m), 2.90-2.85 (1H, m), 2.22 (1H, s), 2.07-2.02 (1H, m), 1.73-1.64 (2H, m). Rotamers observed.

(R)-6-(3,3-difluoro-2-(4-methoxybenzyl)piperidin-1-yl)-4-morpholinopyridin-2(1H)-one; LCMS (ES+) 420 (M+H)$^+$, RT 2.82 min (Analytical Method A); RT 1.96 min (Analytical Method SFC4, YMC AMYLOSE-C 30% MeOH (0.1% DEAISO)/CO$_2$; $^1$H NMR (400 MHz, 105° C., DMSO-d$_6$): δ 9.01 (1H, s), 7.18 (2H, d, J=8.0 Hz), 6.75 (2H, d, J=8.5 Hz), 5.30-5.23 (2H, m), 4.93-4.82 (1H, m), 4.05-3.98 (1H, m), 3.70 (3H, s), 3.66-3.61 (4H, m), 3.11-3.00 (6H, m), 2.28-2.12 (1H, m), 2.07-1.95 (1H, m), 1.77-1.72 (2H, m), 1H obscured by water peak.

Example 158: 6-((2S,3S)-2-benzyl-3-methoxypiperidin-1-yl)-4-morpholinopyridin-2(1H)-one and Example 159: 6-((2R,3R)-2-benzyl-3-methoxypiperidin-1-yl)-4-morpholinopyridin-2(1H)-one

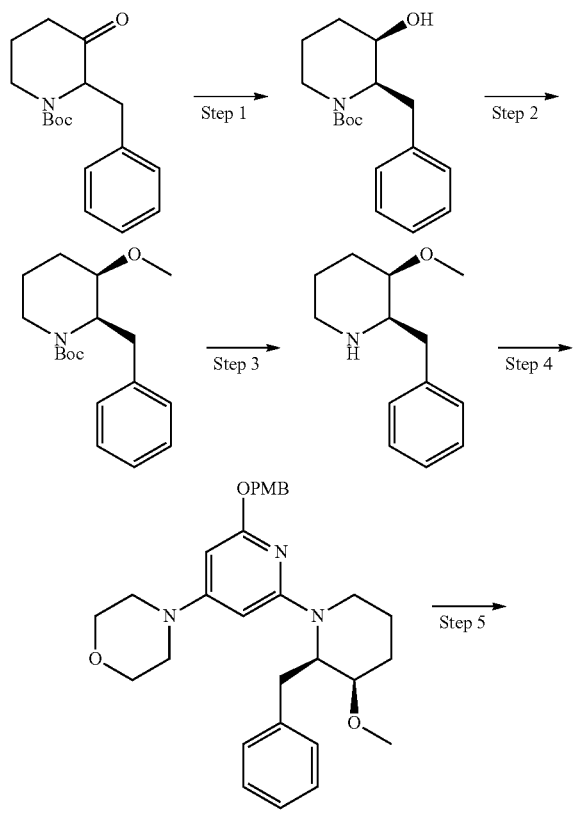

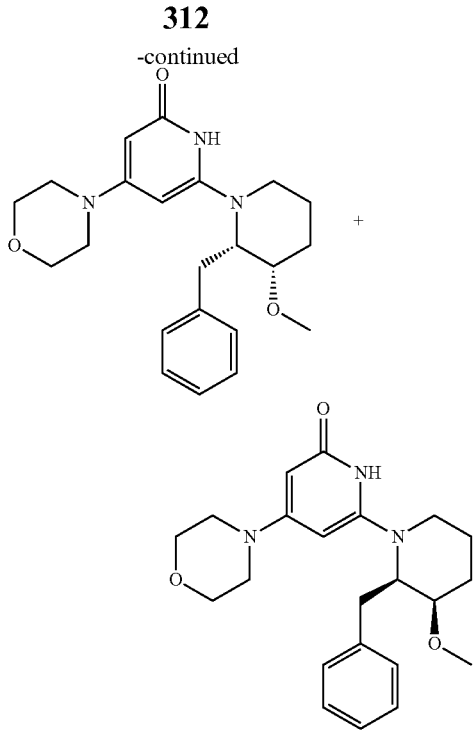

Step 1: tert-butyl (2R*,3R*)-2-benzyl-3-hydroxypiperidine-1-carboxylate

Following the method described for the preparation of example 30 step 2 starting from tert-butyl 2-benzyl-3-oxopiperidine-1-carboxylate (1.0 g, 3.45 mmol, step 2). The reaction mixture was purified by silica gel column chromatography (gradient elution 10-80% EtOAc/iso-hexane) to afford the title compound.

Step 2: tert-butyl (2R*,3R*)-2-benzyl-3-methoxypiperidine-1-carboxylate

Following the method described for the preparation of example 30 step 5 starting from tert-butyl (2R*,3R*)-2-benzyl-3-hydroxypiperidine-1-carboxylate (150 mg, 0.51 mmol). The reaction mixture was purified by silica gel column chromatography (gradient elution 10-80% EtOAc/iso-hexane) to afford the title compound.

Step 3: (2R*,3R*)-2-benzyl-3-methoxypiperidine

Following the method described for the preparation of example 73 step 5 starting from tert-butyl (2R*,3R*)-2-benzyl-3-methoxypiperidine-1-carboxylate (120 mg, 0.39 mmol). The reaction mixture was purified by SCX cartridge (1 g) eluting with 3 column volumes of DCM, 3 column volumes of methanol, 2 column volumes 9:1 DCM:7N NH$_3$ in MeOH and 2 column volumes of 4:1 DCM:7N NH$_3$ in MeOH. The ammonia fractions were combined and concentrated under reduced pressure to afford a colourless oil (40 mg). Further target material was isolated from the methanol layer. This was concentrated under reduced pressure, dissolved in DCM and washed with saturated NaHCO$_3$ aqueous solution. The organic extract was dried (phase separator) and concentrated under reduced pressure. The combined fractions afford the title compound.

Step 4: 4-(2-((2R*,3R*)-2-benzyl-3-methoxypiperidin-1-yl)-6-((4-methoxybenzyl)oxy)pyridin-4-yl)morpholine Following Method D starting from (2R*,3R*)-2-benzyl-3-methoxypiperidine (75 mg, 0.36 mmol) and 4-(2-chloro-6-((4-methoxybenzyl)oxy)pyridin-4-yl)morpholine (111 mg, 0.33 mmol, Scaffold 1). The crude material was purified by silica gel column chromatography (gradient elution 10-60% EtOAc/iso-hexane) to afford the title compound.

Step 5: 6-((2S,3S)-2-benzyl-3-methoxypiperidin-1-yl)-4-morpholinopyridin-2(1H)-one and 6-((2R,3R)-2-benzyl-3-methoxypiperidin-1-yl)-4-morpholinopyridin-2(1H)-one Following Method E starting from 4-(2-((2R*,3R*)-2-benzyl-3-methoxypiperidin-1-yl)-6-((4-methoxybenzyl)oxy)pyridin-4-yl)morpholine (110 mg, 0.22 mmol). The crude material was purified by silica gel column chromatography (gradient elution 0-25% methanol/EtOAc). The resultant product was purified by SFC for the separation of the enantiomers.

6-((2S,3S)-2-benzyl-3-methoxypiperidin-1-yl)-4-morpholinopyridin-2(1H)-one; LCMS (ES+) 384 (M+H)$^+$, RT 3.02 min (Analytical Method B), RT 2.34 min (Analytical Method SFC4, YMC CELLULOSE-C 35% IPA SOL4 (0.1% DEAISO)/CO$_2$); $^1$H NMR (400 MHz, CDCl3): δ 7.25-7.20 (2H, m), 7.18-7.13 (3H, m), 5.10 (1H, d, J=2.0 Hz), 4.71 (1H, d, J=2.3 Hz), 4.19-4.13 (1H, m), 3.71 (4H, dd, J=4.9, 4.9 Hz), 3.50-3.35 (5H, m), 3.28-3.20 (1H, m), 3.08-3.03 (4H, m), 3.00-2.85 (2H, m), 2.00-1.96 (1H, m), 1.86-1.81 (1H, m), 1.75-1.62 (2H, m), NH not observed.

6-((2R,3R)-2-benzyl-3-methoxypiperidin-1-yl)-4-morpholinopyridin-2(1H)-one; LCMS (ES+) 384 (M+H)$^+$, RT 2.92 min (Analytical Method B), RT 1.42 min (Analytical Method SFC14 YMC CELLULOSE-C 30% IPA SOL4 (0.1% DEAISO)/CO$_2$); $^1$H NMR (400 MHz, CDCl3): δ 7.23-7.11 (5H, m), 5.08 (1H, d, J=1.9 Hz), 4.68 (1H, s), 4.25-4.22 (1H, m), 3.72-3.69 (4H, m), 3.51-3.48 (1H, m), 3.42 (4H, s), 3.25-3.19 (1H, m), 3.07-3.01 (4H, m), 3.01-2.85 (2H, m), 2.01-1.97 (1H, m), 1.85-1.82 (1H, m), 1.74-1.60 (2H, m), NH not observed.

Example 160: 6-(2-benzyl-4,4-difluoropiperidin-1-yl)-4-morpholinopyridin-2(1H)-one

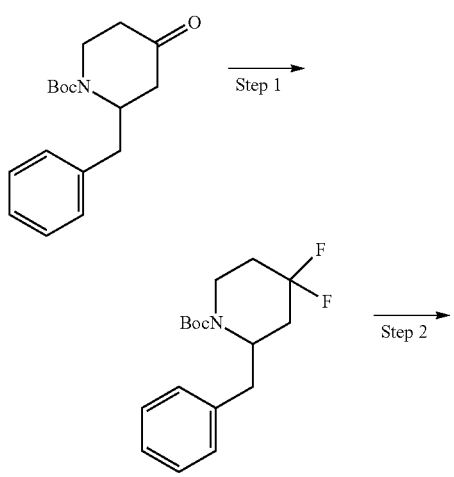

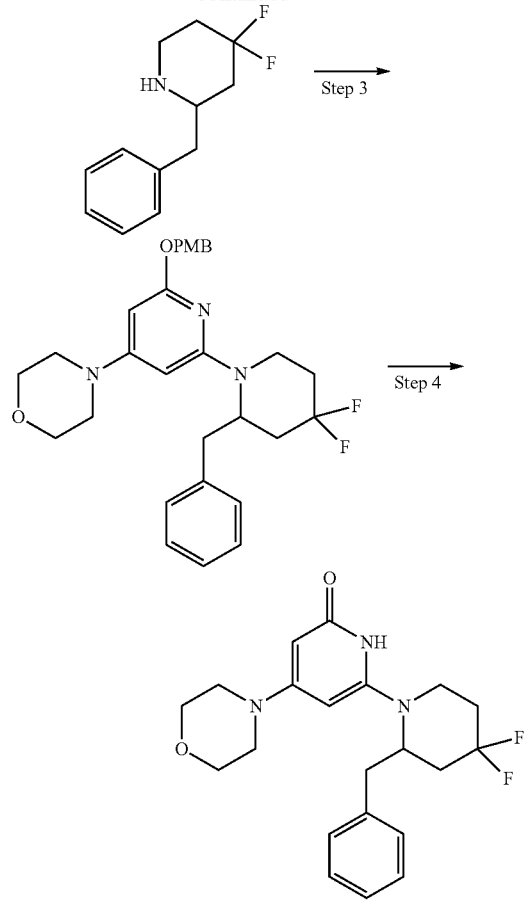

Step 1: tert-butyl 2-benzyl-4,4-difluoropiperidine-1-carboxylate

Following the method described for the preparation of example 132 step 3 starting from tert-butyl 2-benzyl-4-oxopiperidine-1-carboxylate (434 mg, 1.5 mmol). The reaction mixture was purified by silica gel column chromatography (gradient elution 5-40% EtOAc in iso-hexane) to afford the title compound.

Step 2: 2-benzyl-4,4-difluoropiperidine

Following the method described for the preparation of example 5 step 2 starting from tert-butyl 2-benzyl-4,4-difluoropiperidine-1-carboxylate (360 mg, 1.16 mmol) and using 5 eq. TFA. The reaction mixture was concentrated under reduced pressure. The residue was dissolved in DCM, washed with saturated NaHCO$_3$ aqueous solution and dried (phase separator) to afford the product. Used without further purification in the next step.

Step 3: 4-(2-(2-benzyl-4,4-difluoropiperidin-1-yl)-6-((4-methoxybenzyl)oxy)pyridin-4-yl)morpholine Following Method D starting from 2-benzyl-4,4-difluoropiperidine (186 mg, 0.88 mmol) and 4-(2-chloro-6-((4-methoxybenzyl)oxy)pyridin-4-yl)morpholine (267 mg, 0.80 mmol, Scaffold 1). The reaction mixture was purified by silica gel column chromatography (gradient elution 10-80%

EtOAc/iso-hexane) to afford the title compound contaminated with unreacted 4-(2-chloro-6-((4-methoxybenzyl)oxy)pyridin-4-yl)morpholine. Used without further purification in the next step.

Step 4: 6-(2-benzyl-4,4-difluoropiperidin-1-yl)-4-morpholinopyridin-2(1H)-one

Following Method E starting from 4-(2-(2-benzyl-4,4-difluoropiperidin-1-yl)-6-((4-methoxybenzyl)oxy)pyridin-4-yl)morpholine (260 mg, 0.51 mmol). The crude material was purified by reverse phase preparative HPLC to afford the title compound. LCMS (ES+) 390 (M+H)$^+$, RT 3.11 min (Analytical Method B); $^1$H NMR (400 MHz, CDCl$_3$): δ 7.25-7.22 (2H, m), 7.21-7.15 (3H, m), 5.29 (1H, d, J=2.0 Hz), 5.14 (1H, d, J=2.0 Hz), 4.36-4.32 (1H, m), 3.80-3.76 (4H, m), 3.65-3.60 (1H, m), 3.43-3.34 (1H, m), 3.24-3.19 (4H, m), 2.98-2.82 (2H, m), 2.20-1.98 (4H, m), NH not observed.

Example 161: (R)-2-benzyl-4-methyl-1-(4-morpholino-6-oxo-1,6-dihydropyridin-2-yl)-1,4-diazepan-5-one, Example 162: (S)-2-benzyl-4-methyl-1-(4-morpholino-6-oxo-1,6-dihydropyridin-2-yl)-1,4-diazepan-5-one, Example 163: 7-benzyl-4-methyl-1-(4-morpholino-6-oxo-1,6-dihydropyridin-2-yl)-1,4-diazepan-5-one

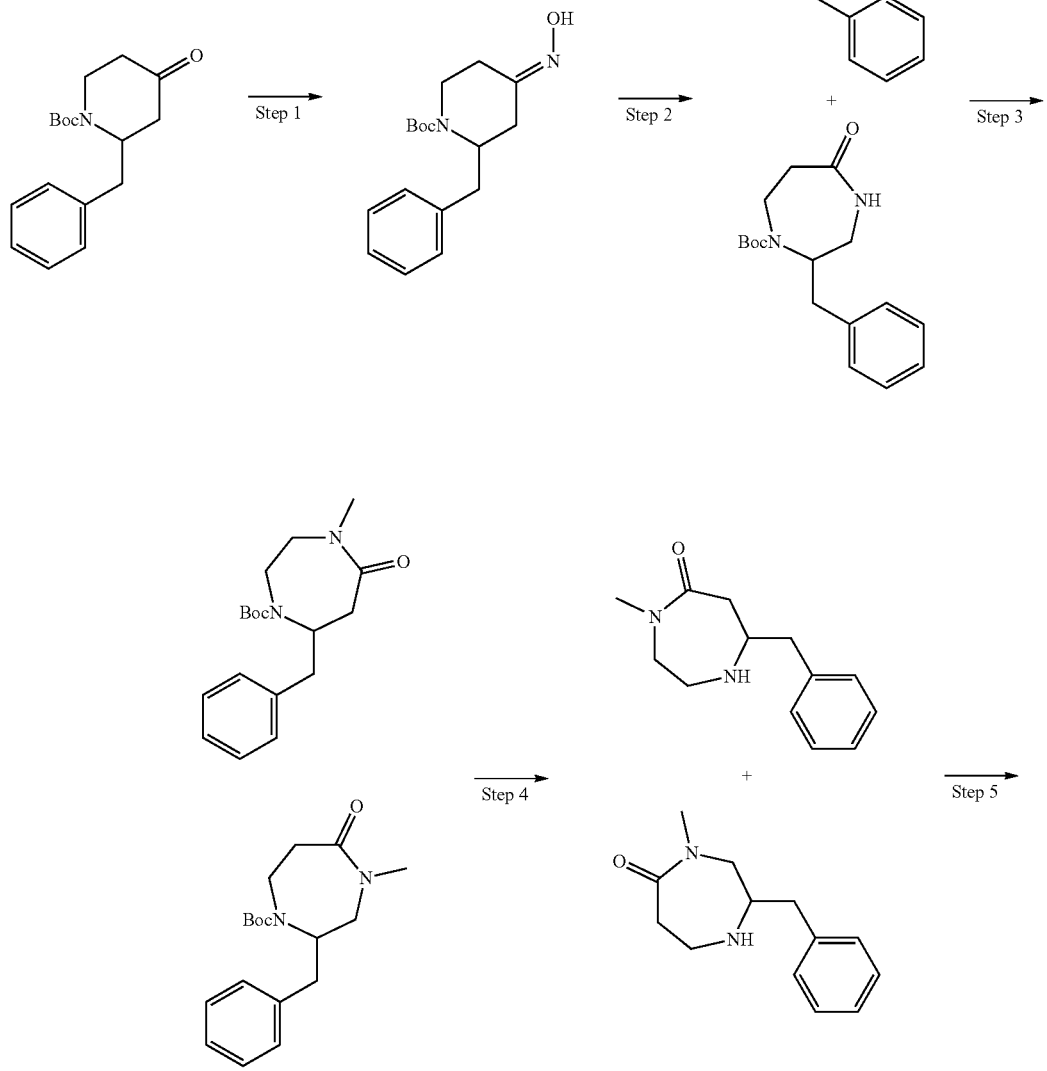

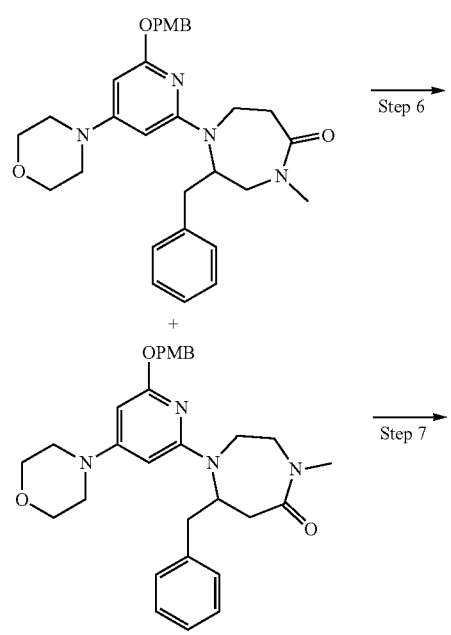
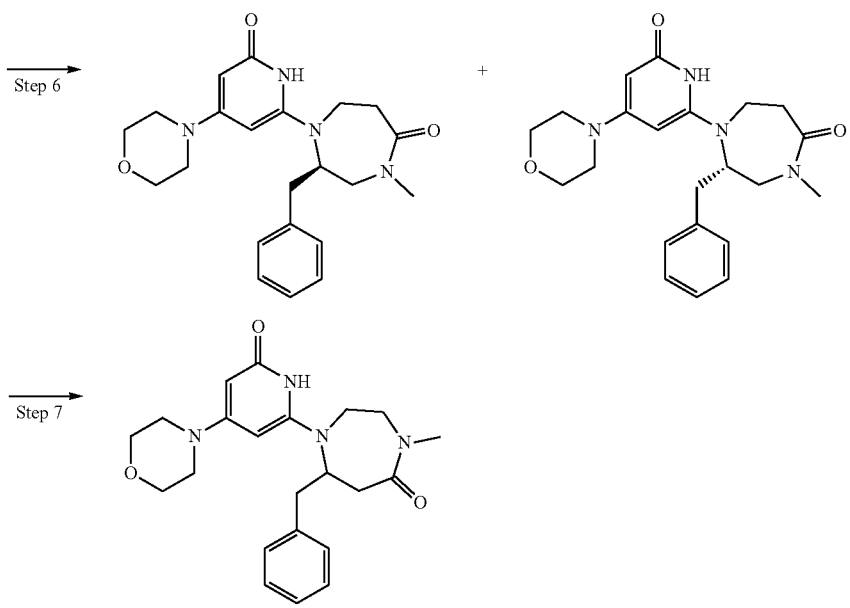

Step 1: tert-butyl 2-benzyl-4-(hydroxyimino)piperidine-1-carboxylate

Na$_2$CO$_3$ (2.20 g, 20.73 mmol) was added to a solution of tert-butyl 2-benzyl-4-oxopiperidine-1-carboxylate (2.0 g, 6.91 mmol) in MeOH (13 mL) and water (8 mL) at r.t. Hydroxylamine hydrochloride (960 mg, 13.8 mmol) was added and the reaction stirred for 21 h. The reaction mixture was concentrated under reduced pressure and diluted with DCM and washed with water. The organic extract was dried (phase separator) and concentrated under reduced pressure to afford the title compound. Used without further purification in the next step.

Step 2: tert-butyl 7-benzyl-5-oxo-1,4-diazepane-1-carboxylate and tert-butyl 2-benzyl-5-oxo-1,4-diazepane-1-carboxylate tert-Butyl 2-benzyl-4-(hydroxyimino)piperidine-1-carboxylate (2.07 g, 6.8 mmol) was dissolved in acetone (68 mL) and water (68 mL) and cooled to 0° C. Na$_2$CO$_3$ (2.88 g, 27.2 mmol) was added portionwise, followed by tosyl chloride (2.59 g, 13.6 mmol) portionwise. The reaction was allowed to warm to r.t. After 22 h the reaction was concentrated under reduced pressure. The residue was dissolved in DCM and washed with water. The organic extract was dried (phase separator) and concentrated under reduced pressure. The crude material was purified by silica gel column chromatography (gradient elution 5-80% EtOAc/iso-hexane to 10% MeOH/EtOAc) to afford the title compounds.

Step 3: tert-butyl 7-benzyl-4-methyl-5-oxo-1,4-diazepane-1-carboxylate and tert-butyl 2-benzyl-4-methyl-5-oxo-1,4-diazepane-1-carboxylate NaH (131 mg, 3.29 mmol, 60% dispersion in mineral oil) was added to an ice-cooled solution of tert-butyl 7-benzyl-5-oxo-1,4-diazepane-1-carboxylate and tert-butyl 2-benzyl-5-oxo-1,4-diazepane-1-carboxylate (500 mg, 1.64 mmol, inseparable mixture) in DMF (5 mL). After stirring at 0° C. for 20 min methyl iodide (123 µL, 1.97 mmol) was added and the reaction mixture warmed to RT. After 2 hours the reaction was cooled to 0° C. and cautiously quenched with water. The reaction mixture was diluted with DCM and the layers separated. The organic extracts were dried (phase separator) and concentrated under reduced pressure. Used without further purification in the next step.

Step 4: 7-benzyl-4-methyl-1,4-diazepan-5-one and 2-benzyl-4-methyl-1,4-diazepan-5-one Following the method described for the preparation of example 73 step 5 starting from impure tert-butyl 7-benzyl-4-methyl-5-oxo-1,4-diazepane-1-carboxylate and tert-butyl 2-benzyl-4-methyl-5-oxo-1,4-diazepane-1-carboxylate (1.64 mmol). The crude material was purified by 5 g SCX cartridge eluting with 3 column volumes of DCM, 3 column volumes of methanol, 2 column volumes 9:1 DCM:7N NH3 in MeOH and 2 column volumes of 4:1 DCM:7N NH3 in MeOH. The ammonia fractions were combined and concentrated under reduced pressure to afford the title compounds. This is an inseparable mixture which was used without further purification in the next step.

Step 5: 2-benzyl-1-(6-(((4-methoxybenzyl)oxy)-4-morpholinopyridin-2-yl)-4-methyl-1,4-diazepan-5-one and 7-benzyl-1-(6-(((4-methoxybenzyl)oxy)-4-morpholinopyridin-2-yl)-4-methyl-1,4-diazepan-5-one Following Method D starting from 7-benzyl-4-methyl-1,4-diazepan-5-one and 2-benzyl-4-methyl-1,4-diazepan-5-one (360 mg, 1.08 mmol) and 4-(2-chloro-6-((4-methoxybenzyl)oxy)pyridin-4-yl)morpholine (360 mg, 1.08 mmol, Scaffold 1). The crude material was purified by silica gel column chromatography (gradient elution 10-100% EtOAc/iso-hexane) to afford the title compounds. First eluting compound was 7-benzyl-1-(6-(((4-methoxybenzyl)oxy)-4-morpholinopyridin-2-yl)-4-methyl-1,4-diazepan-5-one, and second eluting compound was 2-benzyl-1-(6-((4-methoxybenzyl)oxy)-4-morpholinopyridin-2-yl)-4-methyl-1,4-diazepan-5-one.

Step 6: (S)-2-benzyl-4-methyl-1-(4-morpholino-6-oxo-1,6-dihydropyridin-2-yl)-1,4-diazepan-5-one and (R)-2-benzyl-4-methyl-1-(4-morpholino-6-oxo-1,6-dihydropyridin-2-yl)-1,4-diazepan-5-one Following Method E starting from 2-benzyl-1-(6-((4-methoxybenzyl)oxy)-4-morpholinopyridin-2-yl)-4-methyl-1,4-diazepan-5-one (253 mg, 0.49 mmol). The crude material was purified by silica gel column chromatography (gradient elution 0-4% 7N NH3 in MeOH/DCM). This resultant product was purified by SFC for the separation of the enantiomers, which were freeze dried from acetonitrile/water.

(S)-2-benzyl-4-methyl-1-(4-morpholino-6-oxo-1,6-dihydropyridin-2-yl)-1,4-diazepan-5-one; LCMS (ES+) 397 (M+H)$^+$, RT 2.72 min (Analytical Method B), RT 1.35 min (Analytical Method SFC1, YMC AMYLOSE-C+0.1% DEAISO 35% MeOH SOL3); $^1$H NMR (400 MHz, CDCl3): δ 7.27-7.17 (5H, m), 5.21 (1H, d, J=2.0 Hz), 4.88 (1H, d, J=2.0 Hz), 4.53-4.45 (1H, m), 3.78-3.73 (5H, m), 3.64-3.55 (1H, m), 3.49-3.35 (2H, m), 3.18-3.13 (4H, m), 2.91-2.90 (7H, m), NH no observed.

(R)-2-benzyl-4-methyl-1-(4-morpholino-6-oxo-1,6-dihydropyridin-2-yl)-1,4-diazepan-5-one; LCMS (ES+) 397 (M+H)$^+$, RT 2.72 min (Analytical Method B), RT 2.02 min (Analytical Method SFC1, YMC AMYLOSE-C+0.1% DEAISO 35% MeOH SOL3); $^1$H NMR (400 MHz, CDCl3): δ 7.25-7.17 (5H, m), 5.21 (1H, d, J=2.0 Hz), 4.88 (1H, d, J=1.8 Hz), 4.51-4.45 (1H, m), 3.81-3.74 (5H, m), 3.62-3.55 (1H, m), 3.48-3.35 (2H, m), 3.17-3.13 (4H, m), 3.06-2.73 (7H, m), NH not observed.

Step 7: 7-benzyl-4-methyl-1-(4-morpholino-6-oxo-1,6-dihydropyridin-2-yl)-1,4-diazepan-5-one Following Method E starting from 7-benzyl-1-(6-((4-methoxybenzyl)oxy)-4-morpholinopyridin-2-yl)-4-methyl-1,4-diazepan-5-one (76 mg, 0.15 mmol). The crude material was purified by silica gel column chromatography (gradient elution 0-4% 7N NH$_3$ in MeOH/DCM). This material was purified by reverse phase preparative HPLC to afford the title compound.

LCMS (ES+) 397 (M+H)$^+$, RT 2.60 min (Analytical Method A); $^1$H NMR (400 MHz, CDCl3): δ 7.26-7.19 (5H, m), 5.23 (1H, d, J=2.0 Hz), 4.87 (1H, d, J=1.8 Hz), 4.19-4.14 (1H, m), 3.87-3.77 (2H, m), 3.74 (4H, dd, J=4.9, 4.9 Hz), 3.49-3.43 (1H, m), 3.43-3.35 (1H, m), 3.13 (4H, dd, J=3.7, 5.9 Hz), 3.05 (3H, s), 2.97-2.88 (3H, m), 2.81-2.74 (1H, m), NH not observed.

Example 164: (S)-6-(3-benzyl-1,4-oxazepan-4-yl)-4-morpholinopyridin-2(1H)-one

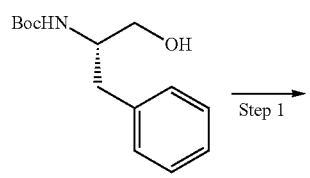

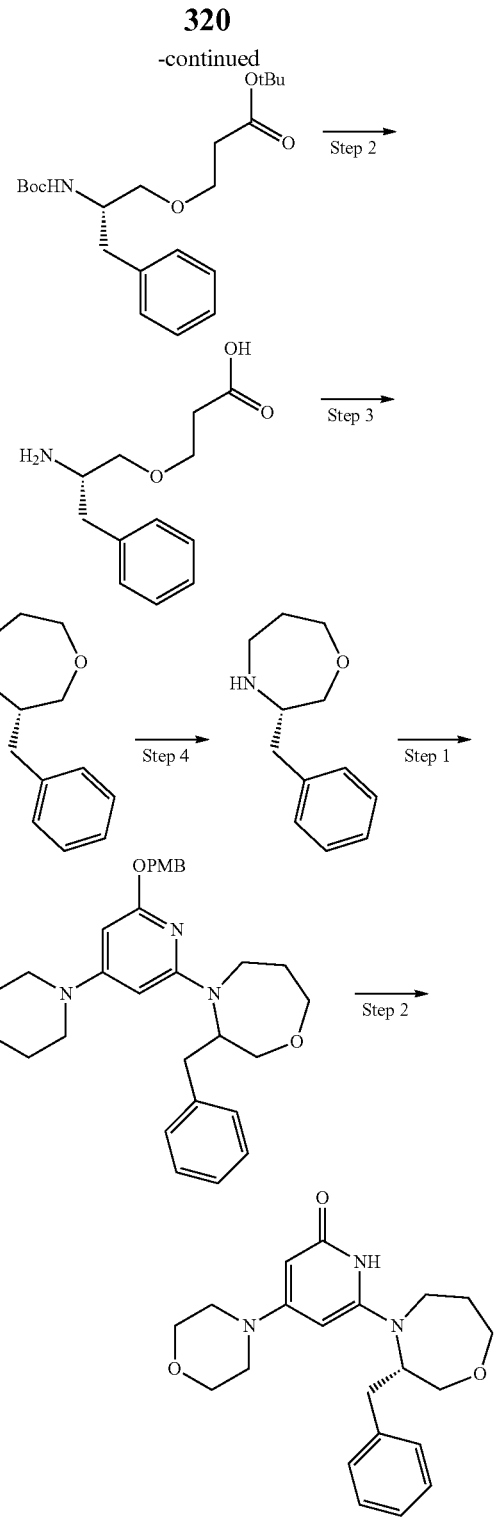

Step 1: tert-butyl (S)-3-(2-((tert-butoxycarbonyl)amino)-3-phenylpropoxy)propanoate tert-Butyl acrylate (2.52 mL, 17.19 mmol) was added to a solution of tert-butyl (S)-(1-hydroxy-3-phenylpropan-2-yl)carbamate (2.88 g, 11.45 mmol) in NaOH (445 µL, 5 M aqueous solution) and dioxane (3 mL). Dioxane (1.5 mL) was added after 30 min and stirring continued at rt for 18 h. NaOH (445 L) and tert-butyl acrylate (0.5 mL) were added and stirring continued. After 7.5 h NaOH (100 L) and tert-butyl acrylate (0.5 mL) were added and stirring continued for 18 h. The reaction mixture was partitioned between DCM and water. The layers were separated, dried (phase separator) and concentrated under reduced pressure. The reaction mixture was purified by silica gel column chromatography (gradient elution 10-60% EtOAc/iso-hexane) to afford the title compound.

Step 2: (S)-3-(2-amino-3-phenylpropoxy)propanoic acid

TFA (2 mL) was added to a solution of tert-butyl (S)-3-(2-((tert-butoxycarbonyl)amino)-3-phenylpropoxy)propanoate (546 mg, 1.44 mmol) in DCM (2 mL) at rt with stirring. After 2 h the reaction was concentrated under reduced pressure to afford the title compound as a TFA salt. The oil was dissolved in EtOAc (5 mL). Et$_3$N (200 μL, 1.44 mmol) was added at rt with stirring. After 2 h the resultant white precipitate was collected by filtration and air dried to afford the title compound. Used without further purification.

Step 3: (S)-3-benzyl-1,4-oxazepan-5-one (S)-3-(2-amino-3-phenylpropoxy)propanoic acid (230 mg, 1.03 mmol) was dissolved in DMF (5 mL) and cooled to 0° C. N-methyl morpholine (226 μL, 2.06 mmol), HOBt (139 mg, 1.03 mmol) and EDC (296 mg, 1.54 mmol) were added and the reaction warmed to rt after stirring for 15 min. After 25 h the reaction mixture was concentrated under reduced pressure and purified by silica gel column chromatography (gradient elution 20-100% EtOAc/iso-hexane). The product containing fractions were reduced to approximately 50 mL. EtOAc (20 mL) was added and the organics washed with NaHCO$_3$ (saturated aqueous solution). The organic extracts were dried (phase separator) and concentrated under reduced pressure to afford the product.

Step 4: (S)-3-benzyl-1,4-oxazepane

Lithium aluminium hydride (1.22 mL, 1.22 mmol, 1M solution in THF) was added to (S)-3-benzyl-1,4-oxazepan-5-one (125 mg, 0.61 mmol) in THF (4 mL) at 0° C. The reaction was warmed to rt and stirred for 19 h. The reaction mixture was cooled to 0° C. and cautiously quenched with water. The THF was removed under reduced pressure. The crude mixture was diluted with EtOAc/water and the layers separated. The aqueous layer was extracted with EtOAc. The combined organic extracts were dried (phase separator) and concentrated under reduced pressure. The crude material was purified by SCX eluting with 3 column volumes of DCM, 3 column volumes of methanol, 2 column volumes 9:1 DCM:7N NH$_3$ in MeOH and 2 column volumes of 4:1 DCM:7N NH$_3$ in MeOH. The ammonia fractions were combined and concentrated under reduced pressure to afford the product.

Step 5: (S)-3-benzyl-4-(6-((4-methoxybenzyl)oxy)-4-morpholinopyridin-2-yl)-1,4-oxazepane Following Method D starting from (S)-3-benzyl-1,4-oxazepane (110 mg, 0.57 mmol) and 4-(2-chloro-6-((4-methoxybenzyl)oxy)pyridin-4-yl)morpholine (175 mg, 0.52 mmol, Scaffold 1). The reaction mixture was purified by silica gel column chromatography (gradient elution 10-50% diethyl ether in iso-hexane) to afford the title compound.

Step 6: (S)-6-(3-benzyl-1,4-oxazepan-4-yl)-4-morpholinopyridin-2(1H)-one

Following Method E starting from (S)-3-benzyl-4-(6-((4-methoxybenzyl)oxy)-4-morpholinopyridin-2-yl)-1,4-oxazepane (160 mg, 0.33 mmol). The crude material was purified by reverse phase preparative HPLC to afford the title compound as a salt. The solid was dissolved in DCM, washed with NaHCO$_3$ (saturated aqueous solution), dried (phase separator) and concentrated under reduced pressure to afford the title compound.

(S)-6-(3-benzyl-1,4-oxazepan-4-yl)-4-morpholinopyridin-2(1H)-one; LCMS (ES+) 370 (M+H)$^+$, RT 2.76 min (Analytical Method A); $^1$H NMR (400 MHz, CDCl3): δ 7.32-7.21 (3H, m), 7.18-7.14 (2H, m), 5.20 (1H, d, J=2.0 Hz), 4.91 (1H, d, J=1.8 Hz), 4.10-3.91 (3H, m), 3.75 (4H, dd, J=4.9, 4.9 Hz), 3.67-3.48 (3H, m), 3.30-3.21 (1H, m), 3.19-3.14 (4H, m), 2.92-2.78 (2H, m), 2.03-1.93 (1H, m), 1.78-1.70 (1H, m), NH not observed.

Example 165: 6-(2-benzylazepan-1-yl)-4-((2R,6R)-2,6-dimethylmorpholino)pyridin-2(1H)-one Stereoisomer 1

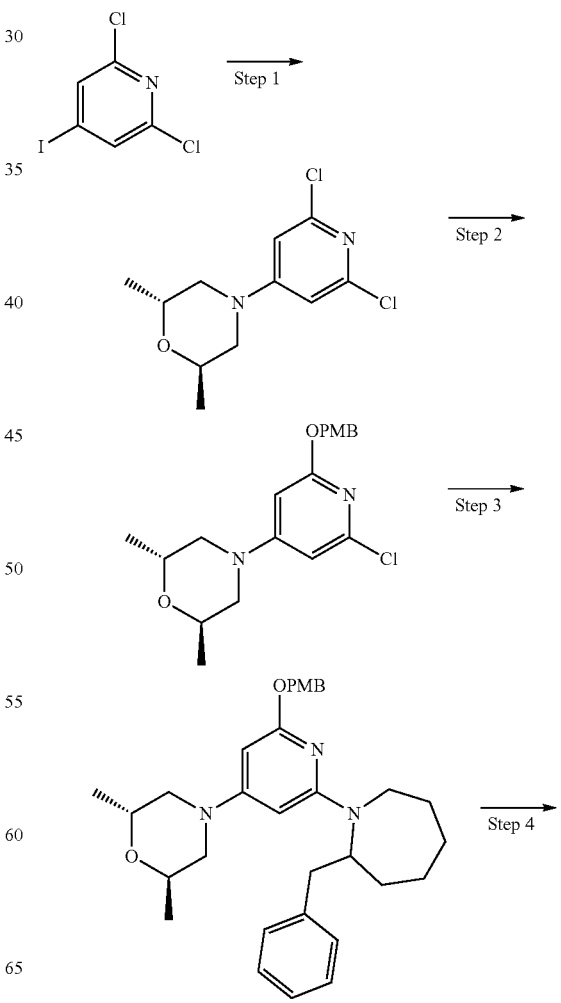

323

-continued

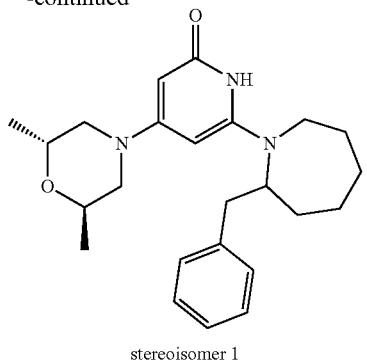

stereoisomer 1

Step 1: (2R,6R)-4-(2,6-Dichloropyridin-4-yl)-2,6-dimethylmorpholine

Following Method B starting from (2R,6R)-2,6-dimethylmorpholine (0.5 g, 4.5 mmol) and 2,6-dichloro-4-iodopyridine (1.3 g, 4.5 mmol). Purified by silica gel column chromatography (gradient elution, 2-20% EtOAc/iso-hexane) to afford the title compound.

Step 2: (2R,6R)-4-(2-Chloro-6-((4-methoxybenzyl)oxy)pyridin-4-yl)-2,6-dimethylmorpholine Following Method A starting from (2R,6R)-4-(2,6-dichloropyridin-4-yl)-2,6-dimethylmorpholine (0.4 g, 1.5 mmol) and (4-methoxyphenyl)methanol (231 mg, 2.1 mmol). Purified by silica gel column chromatography (gradient elution, 1-25% EtOAc/iso-hexane) to afford the title compound.

Step 3: (2R,6R)-4-(2-(2-Benzylazepan-1-yl)-6-((4-methoxybenzyl)oxy)pyridin-4-yl)-2,6-dimethyl morpholine Following Method D starting from (2R,6R)-4-(2-chloro-6-((4-methoxybenzyl)oxy)pyridin-4-yl)-2,6-dimethylmorpholine (0.21 g, 1.1 mmol) and 2-benzylazepane (209 mg, 1.1 mmol). Purified by silica gel column chromatography (gradient elution, 10-30% EtOAc/iso-hexane) to afford the title compound.

Step 4: 6-(2-benzylazepan-1-yl)-4-((2R,6R)-2,6-dimethylmorpholino)pyridin-2(1H)-one stereoisomer 1

Following Method E starting from (2R,6R)-4-(2-(2-benzylazepan-1-yl)-6-((4-methoxybenzyl)oxy)pyridin-4-yl)-2,6-dimethylmorpholine (0.31 g, 0.6 mmol). The crude material was purified by reverse phase HPLC to give a brown solid. The sample was further purified by SFC chiral chromatography to give the title compound as a single isomer. LCMS (ES+) 396 (M+H)+, RT 2.99 min 97% (Analytical Method A); $^1$H NMR δ (ppm) (400 MHz, CDCl$_3$) 7.31-7.21 (3H, m), 7.16-7.13 (2H, m), 5.11 (1H, dd, J=2.0, 2.0 Hz), 4.84 (1H, dd, J=2.0, 16.1 Hz), 4.12-4.05 (2H, m), 3.82-3.73 (1H, m), 3.43 (1H, d, J=15.7 Hz), 3.33-3.25 (1H, m), 3.05-2.95 (3H, m), 2.89-2.74 (2H, m), 2.16-2.04 (1H, m), 1.86-1.72 (4H, m), 1.56-1.44 (2H, m), 1.32-1.13 (8H, m); NH not visible.

Example 166: 6-(2-Benzylazepan-1-yl)-4-(2-(difluoromethyl)morpholino)pyridin-2(1H)-one

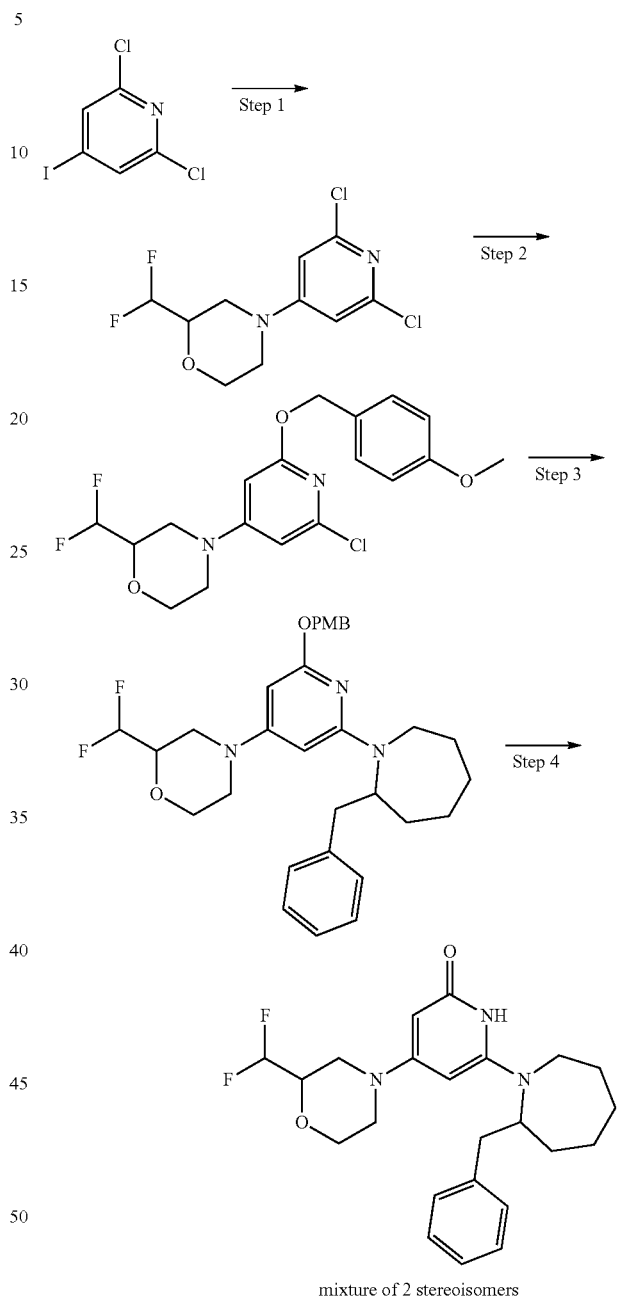

mixture of 2 stereoisomers

Step 1: 4-(2,6-Dichloropyridin-4-yl)-2-(difluoromethyl)morpholine

Following Method B starting from 2-difluoromethyl morpholine (0.4 g, 2.9 mmol) 2,6-dichloro-4-iodopyridine (822 mg, 3 mmol). Purified by silica gel column chromatography (gradient elution 10-40% EtOAc/iso-hexane) to afford the title compound.

Step 2: 4-(2-Chloro-6-((4-methoxybenzyl)oxy)pyridin-4-yl)-2-(difluoromethyl)morpholine Following Method A starting from 4-(2,6-dichloropyridin-4-yl)-2-(difluoromethyl)morpholine (0.5 g, 1.8 mmol) and (4-methoxyphenyl)methanol (269 mg, 1.95 mmol). Purified by silica gel column chromatography (gradient elution, 1-20% EtOAc/iso-hexane) to afford the title compound.

Step 3: 4-(2-(2-benzylazepan-1-yl)-6-((4-methoxybenzyl)oxy)pyridin-4-yl)-2-(difluoromethyl) morpholine Following Method D starting from 4-(2-chloro-6-((4-methoxybenzyl)oxy)pyridin-4-yl)-2-(difluoromethyl)morpholine (0.19 g, 1.0 mmol) and 2-benzylazepane (190 mg, 1 mmol) (Example 3 step 2). Purification by silica gel column chromatography (gradient elution 10-25% EtOAc/iso-hexane) afforded the title compound.

Step 4: 6-(2-benzylazepan-1-yl)-4-(2-(difluoromethyl)morpholino)pyridin-2(1H)-one mixture of two stereoisomers Following Method E starting from 4-(2-(2-benzylazepan-1-yl)-6-((4-methoxybenzyl)oxy)pyridin-4-yl)-2-(difluoromethyl) morpholine (0.4 g, 0.74 mmol). The crude material was purified by reverse phase preparative HPLC to give the title compound. LCMS (ES+) 418 (M+H)+, RT 3.12 min, 98% (Analytical Method A); $^1$H NMR δ (ppm) (400 MHz, CDCl$_3$) 7.30-7.20 (3H, m), 7.14 (2H, d, J=7.7 Hz), 5.92 (1H, dd, J=2.1, 4.1 Hz), 5.80 (1H, dddd, J=55.0 Hz; J=2.1 Hz; J=4.0 Hz), 5.19-5.18 (1H, m), 4.88 (1H, dd, J=2.0, 7.2 Hz), 4.05-4.01 (1H, m), 3.83-3.57 (4H, m), 3.43 (2H, d, J=13.1 Hz), 3.09-2.73 (4H, m), 2.17-2.00 (1H, m), 1.84-1.79 (3H, m), 1.58-1.45 (2H, m), 1.32-1.13 (2H, m); NH not visible.

Example 167: (R)-6-(2-benzylazepan-1-yl)-4-(3,6-dihydro-2H-pyran-4-yl)pyridin-2(1H)-one and Example 168: (S)-6-(2-benzylazepan-1-yl)-4-(3,6-dihydro-2H-pyran-4-yl)pyridin-2(1H)-one

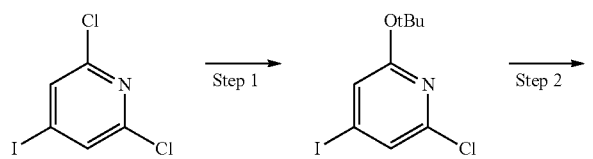

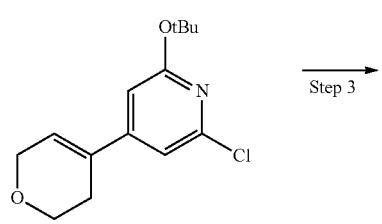

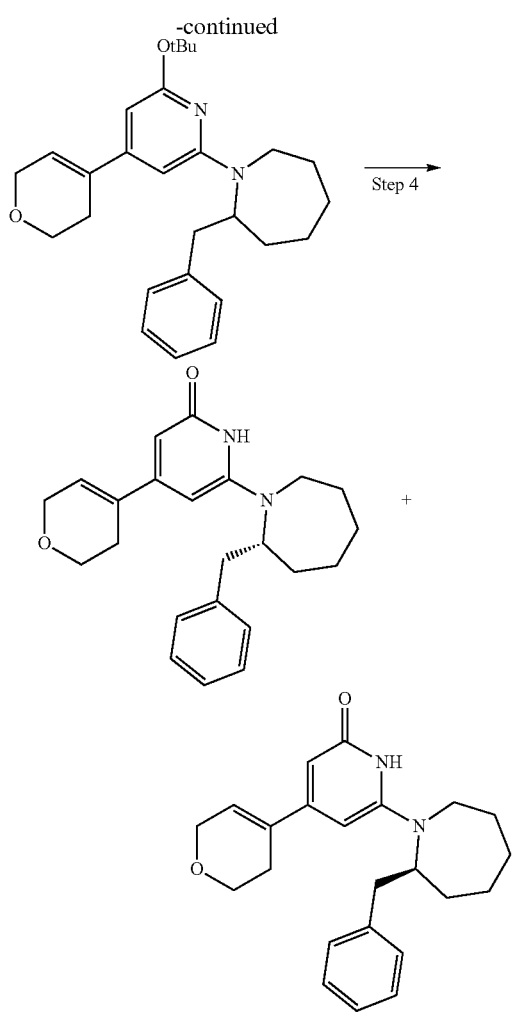

Step 1: 2-(tert-Butoxy)-6-chloro-4-iodopyridine

A solution of 2,6-dichloro-4-iodopyridine (1.0 g, 3.65 mmol) in dry THF (15 mL) was treated with KOtBu (4.0 mL, 4.0 mmol, 1 M in THF) at rt. The mixture was heated at reflux for 2 h. After cooling to rt the reaction was diluted with EtOAc (100 mL), washed with water (30 mL), brine (30 mL) and dried (Na$_2$SO$_4$). The mixture was concentrated to give the title compound.

Step 2: 2-(tert-Butoxy)-6-chloro-4-(3,6-dihydro-2H-pyran-4-yl)pyridine

A mixture of 2-(tert-butoxy)-6-chloro-4-iodopyridine (661 mg, 2.12 mmol), 2-(3,6-dihydro-2H-pyran-4-yl)-4,4,5,5-tetramethyl-1,3,2-dioxaborolane (540 mg, 2.57 mmol), XPhos PdG2 (23.3 mg, 30 μmol), K$_2$CO$_3$ (885 mg, 6.40 mmol), dioxane (9.4 mL) and water (2.4 mL) was degassed three times with N$_2$, sealed and heated to 80° C. for 45 min. After cooling to rt, the mixture was filtered through Celite, washing with MeOH. The filtrate was concentrated and purified by silica gel chromatography (gradient elution, 0-50% EtOAc/iso-hexane) to give impure title compound, which was used without further purification.

Step 3: 2-Benzyl-1-(6-(tert-butoxy)-4-(3,6-dihydro-2H-pyran-4-yl)pyridin-2-yl)azepane Following Method D starting from 2-(tert-butoxy)-6-chloro-4-(3,6-dihydro-2H-pyran-4-yl)pyridine (447 mg, 1.67 mmol) and 2-benzylazepane (316 mg, 1.67 mmol, Example 3 step 2). The mixture was purified by silica gel column chromatography (gradient elution, 0-100% EtOAc/iso-hexane) to give impure title compound, which was used without further purification.

Step 4: (R)-6-(2-Benzylazepan-1-yl)-4-(3,6-dihydro-2H-pyran-4-yl)pyridin-2(1H)-one and (S)-6-(2-benzylazepan-1-yl)-4-(3,6-dihydro-2H-pyran-4-yl)pyridin-2(1H)-one A solution of 2-benzyl-1-(6-(tert-butoxy)-4-(3,6-dihydro-2H-pyran-4-yl)pyridin-2-yl)azepane (148 mg, 0.35 mmol) in DCM (1.5 mL) at 0° C. under $N_2$ was treated with $TiCl_4$ (0.53 mL, 0.53 mmol, 1 M in DCM) and stirred for 2.5 h. The reaction was quenched with 2 mL saturated aqueous $NaHCO_3$ solution, diluted with DCM (10 mL) and the layers separated. The organic extracts were dried (phase separator) and concentrated under reduced pressure. The crude material was purified by silica gel column chromatography (gradient elution, 0-100% EtOAc/iso-hexane then 0-20% MeOH/DCM). The target material was further purified by reverse phase preparative HPLC followed by SFC to yield the title compounds.

(R)-6-(2-benzylazepan-1-yl)-4-(3,6-dihydro-2H-pyran-4-yl)pyridin-2(1H)-one; LCMS (ES+) 365 (M+H)$^+$ 3.31 min (Analytical Method A), RT 1.75 min (Analytical Method SFC4, YMC AMYLOSE-C 50/50 MeOH (0.1% DEA)/$CO_2$); $^1$H NMR (400 MHz, $CDCl_3$): δ 7.31-7.26 (2H, m), 7.25-7.20 (1H, m), 7.17-7.13 (2H, m), 6.17-6.15 (1H, m), 5.76 (1H, d, J=1.3 Hz), 5.44 (1H, d, J=1.3 Hz), 4.30 (2H, q, J=2.8 Hz), 3.97-3.91 (1H, m), 3.89 (2H, t, J=5.4 Hz), 3.51-3.43 (1H, m), 3.01 (1H, dd, J=11.7, 15.5 Hz), 2.86 (1H, dd, J=5.5, 13.4 Hz), 2.79 (1H, dd, J=7.5, 13.4 Hz), 2.43-2.37 (2H, m), 2.14-2.04 (1H, m), 1.87-1.69 (3H, m), 1.60-1.45 (3H, m), 1.33-1.12 (2H, m).

(S)-6-(2-benzylazepan-1-yl)-4-(3,6-dihydro-2H-pyran-4-yl)pyridin-2(1H)-one; LCMS (ES+) 365 (M+H)$^+$, RT 3.31 min (Analytical Method A), RT 1.28 (Analytical Method SFC4, YMC AMYLOSE-C 50/50 MeOH (0.1% DEA)/$CO_2$); $^1$H NMR (400 MHz, $CDCl_3$): δ 7.31-7.26 (2H, m), 7.25-7.20 (1H, m), 7.17-7.13 (2H, m), 6.17-6.15 (1H, m), 5.76 (1H, d, J=1.3 Hz), 5.44 (1H, d, J=1.3 Hz), 4.30 (2H, q, J=2.8 Hz), 3.97-3.91 (1H, m), 3.89 (2H, t, J=5.4 Hz), 3.51-3.43 (1H, m), 3.01 (1H, dd, J=11.7, 15.5 Hz), 2.86 (1H, dd, J=5.5, 13.4 Hz), 2.79 (1H, dd, J=7.5, 13.4 Hz), 2.43-2.37 (2H, m), 2.14-2.04 (1H, m), 1.87-1.69 (3H, m), 1.60-1.45 (3H, m), 1.33-1.12 (2H, m).

Example 169: (R)-2-(2-(2-methoxybenzyl)piperidin-1-yl)-6-morpholinopyrimidin-4(3H)-one

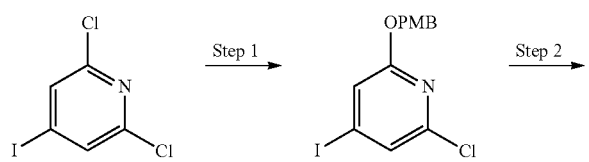

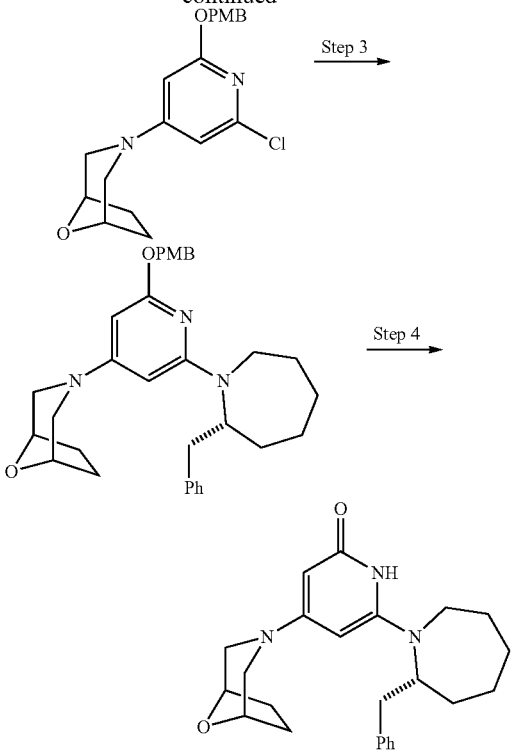

Step 1: 2-Chloro-4-iodo-6-((4-methoxybenzyl)oxy)pyridine

NaH (0.68 g, 17.1 mmol, 60% dispersion in mineral oil) was suspended in THF (17 mL) and cooled to 0° C. (4-Methoxyphenyl)methanol (1.4 mL, 11.25 mmol) was added and the reaction stirred at 0° C. for 20 minutes. 2,6-Dichloro-4-iodopyridine (2.8 g, 10.2 mmol) in THF (10 mL) was added slowly to the reaction and the mixture warmed to r.t. After 18 h the reaction was cooled to 0° C. and cautiously quenched with $NH_4Cl$ (saturated aqueous solution). The reaction was warmed to rt and extracted with EtOAc. The combined organic extracts were dried (phase separator) and concentrated under reduced pressure. The residue was purified by silica gel column chromatography (gradient elution, 2-20% EtOAc/iso-hexane) to afford the title compound.

Step 2: (1R,5S)-3-(2-Chloro-6-((4-methoxybenzyl)oxy)pyridin-4-yl)-8-oxa-3-azabicyclo[3.2.1]octane A reaction tube containing 2-chloro-4-iodo-6-((4-methoxybenzyl)oxy)pyridine (292 mg, 0.78 mmol), (1R,5S)-8-oxa-3-azabicyclo[3.2.1]octane hydrochloride (121 mg, 0.81 mmol), $Pd(OAc)_2$ (10.2 mg, 45 μmol), $PPh_3$ (23.9 mg, 91 μmol) and $K_3PO_4$ (765 mg, 3.60 mmol) in dry DMF (5 mL) was evacuated and backfilled with $N_2$ three times. The reaction was stirred at 100° C. for 1 h. After cooling to rt, the reaction mixture was diluted with DCM (40 mL) and water (20 mL). The layers were separated by passage through a hydrophobic frit and the DCM layer was concentrated. The residue was purified by silica gel column chromatography (gradient elution, 0-100% EtOAc/iso-hexane) to give the title compound.

329

Step 3: (1R,5S)-3-(2-((R)-2-Benzylazepan-1-yl)-6-((4-methoxybenzyl)oxy)pyridin-4-yl)-8-oxa-3-azabicyclo[3.2.1]octane Following Method D from (1R,5S)-3-(2-chloro-6-((4-methoxybenzyl)oxy)pyridin-4-yl)-8-oxa-3-azabicyclo[3.2.1]octane (102 mg, 0.28 mmol) and (R)-2-benzylazepane (57.3 mg, 0.30 mmol, Example 3 step 2). Additional (R)-2-benzylazepane (0.86 equiv), RuPhos Pd G1 (0.06 equiv), RuPhos (0.06 equiv) and NaOtBu (1 equiv) were added after 16 h to completely convert the heteroaryl chloride. Purification by silica gel chromatography (gradient elution, 0-100% EtOAc/iso-hexane) gave impure title compound, which was used without further purification.

Step 4: (R)-2-(2-(2-methoxybenzyl)piperidin-1-yl)-6-morpholinopyrimidin-4(3H)-one Following Method E from (1R,5S)-3-(2-((R)-2-benzylazepan-1-yl)-6-((4-methoxybenzyl)oxy)pyridin-4-yl)-8-oxa-3-azabicyclo[3.2.1]octane (116 mg from previous step). Purification by reverse phase HPLC gave the title compound. LCMS (ES+) 394 (M+H)+, RT 2.97 min (Analytical method A); 1H NMR (400 MHz, CDCl3) 7.32-7.20 (3H, m), 7.17-7.10 (2H, m), 5.11 (1H, d, J=1.8 Hz), 4.82 (1H, d, J=1.3 Hz), 4.48-4.41 (2H, m), 3.82-3.73 (1H, m), 3.37 (1H, d, J=16.4 Hz), 3.25 (2H, dd, J=2.9, 11.7 Hz), 3.12-2.94 (3H, m), 2.85-2.74 (2H, m), 2.15-2.05 (1H, m), 1.97-1.70 (7H, m), 1.60-1.44 (2H, m), 1.31-1.14 (2H, m), NH not observed.

Example 170: 6-((R)-2-Benzylazepan-1-yl)-4-((1S,4S)-2-oxa-5-azabicyclo[2.2.1]heptan-5-yl)pyridin-2(1H)-one

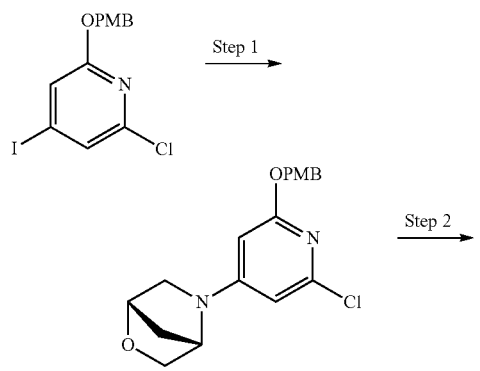
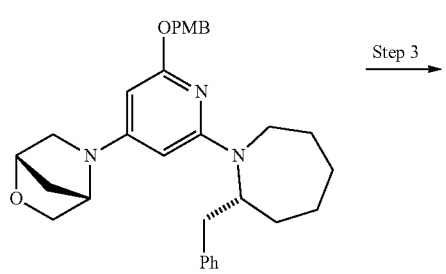
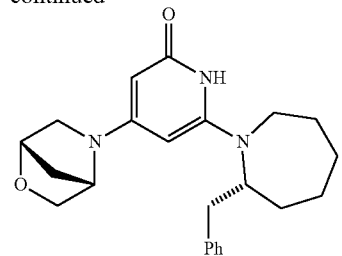

Step 1: (1S,4S)-5-(2-Chloro-6-((4-methoxybenzyl)oxy)pyridin-4-yl)-2-oxa-5-azabicyclo[2.2.1]heptane A tube containing 2-chloro-4-iodo-6-((4-methoxybenzyl)oxy)pyridine (304 mg, 0.81 mmol, step 1), (1S,4S)-2-oxa-5-azabicyclo[2.2.1]heptane hydrochloride (116 mg, 0.86 mmol), Pd(OAc)2 (20.7 mg, 92 µmol), PPh3 (44.8 mg, 0.17 mmol) and K3PO4 (753 mg, 3.55 mmol) in dry DMF (5 mL) was evacuated and backfilled with N2 three times. The reaction was stirred at 100° C. for 1 h. After cooling to RT, the reaction mixture was diluted with DCM (40 mL) and water (20 mL). The layers were separated by passage through a hydrophobic frit and the DCM layer was concentrated. The residue was purified by silica gel column chromatography (gradient elution, 0-100% EtOAc/iso-hexane) to give the title compound.

Step 2: (1S,4S)-5-(2-((R)-2-Benzylazepan-1-yl)-6-((4-methoxybenzyl)oxy)pyridin-4-yl)-2-oxa-5-azabicyclo[2.2.1]heptane Following Method D from (1S,4S)-5-(2-Chloro-6-((4-methoxybenzyl)oxy)pyridin-4-yl)-2-oxa-5-azabicyclo[2.2.1]heptane (231 mg, 0.67 mmol) and (R)-2-benzylazepane (124 mg, 0.66 mmol). Purification by silica gel chromatography (gradient elution, 0-100% EtOAc/iso-hexane) gave impure title compound, which was used without further purification.

Step 3: 6-((R)-2-Benzylazepan-1-yl)-4-((1S,4S)-2-oxa-5-azabicyclo[2.2.1]heptan-5-yl)pyridin-2(1H)-one Following Method E from (1S,4S)-5-(2-((R)-2-benzylazepan-1-yl)-6-((4-methoxybenzyl)oxy)pyridin-4-yl)-2-oxa-5-azabicyclo[2.2.1]heptane (118 mg from previous step). Purification by reverse phase HPLC gave the title compound. LCMS (ES+) 380 (M+H)+, RT 2.85 min (Analytical method A); 1H NMR (400 MHz, DMSO) 9.25 (1H, s), 7.36-7.19 (5H, m), 5.05 (1H, s), 4.95 (1H, s), 4.65 (1H, s), 4.55 (1H, s), 4.30 (1H, br s), 3.76 (2H, d, J=7.1 Hz), 3.68 (1H, d, J=7.1 Hz), 3.43 (1H, d, J=9.6 Hz), 3.08 (1H, d, J=10.4 Hz), 3.00 (1H, t, J=12.7 Hz), 2.84 (1H, dd, J=4.5, 12.9 Hz), 2.68 (1H, dd, J=8.5, 12.8 Hz), 1.95-1.82 (3H, m), 1.78-1.60 (3H, m), 1.53-1.39 (2H, m), 1.26 (1H, dd, J=3.4, 11.5 Hz), 1.09 (1H, q, J=11.7 Hz).

Example 171: (R)-6-(2-benzylazepan-1-yl)-3-fluoro-4-morpholinopyridin-2(1H)-one

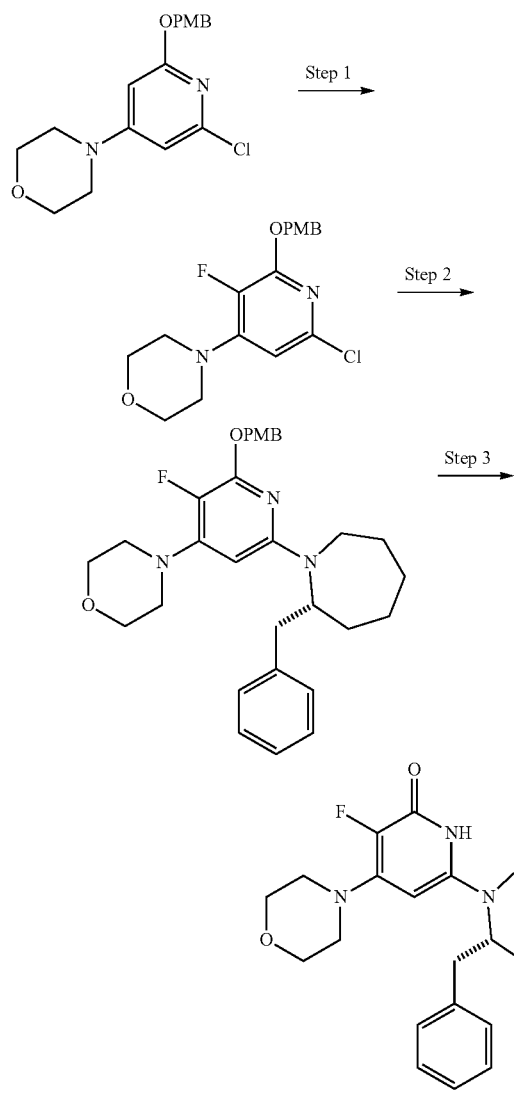

Step 1: 4-(6-chloro-3-fluoro-2-((4-methoxybenzyl)oxy)pyridin-4-yl)morpholine A mixture of 4-(2-chloro-6-((4-methoxybenzyl)oxy)pyridin-4-yl)morpholine (1.00 g, 2.99 mmol, Scaffold 1) and Selectfluor (1.27 g, 3.58 mmol) in DMF (6 mL) and MeCN (6 mL) was stirred at rt for 18 h. The mixture was partitioned between EtOAc (50 mL) and water (30 mL). The layers were separated and the aqueous extracted with further EtOAc (2×40 mL). The combined organics were dried (Na$_2$SO$_4$) and concentrated. Trituration with Et$_2$O afforded the title compound. $^1$H NMR (400 MHz, CDCl$_3$): δ 7.41 (2H, d, J=8.6 Hz), 6.90 (2H, d, J=8.6 Hz), 6.42 (1H, d, J=4.6 Hz), 5.33 (2H, s), 3.84-3.79 (7H, m), 3.26-3.22 (4H, m).

Step 2: (R)-4-(6-(2-benzylazepan-1-yl)-3-fluoro-2-((4-methoxybenzyl)oxy)pyridin-4-yl)morpholine Following Method D from 4-(6-chloro-3-fluoro-2-((4-methoxybenzyl)oxy)pyridin-4-yl)morpholine (107 mg, 0.30 mmol) and (R)-2-benzylazepane (62.3 mg, 0.33 mmol) and heated at 80° C. for 17 h. After cooling to rt the mixture was filtered through Celite, washing with MeOH, and the filtrate concentrated. The residue was purified by silica gel column chromatography (gradient elution, 0-100% EtOAc/isohexane) to give impure title compound, which was used without further purification.

Step 3: (R)-6-(2-benzylazepan-1-yl)-3-fluoro-4-morpholinopyridin-2(1H)-one

A mixture of (R)-4-(6-(2-benzylazepan-1-yl)-3-fluoro-2-((4-methoxybenzyl)oxy)pyridin-4-yl)morpholine (70 mg), 1-methyl-1,4-cyclohexadiene (156 μL, 1.39 mmol) and 5% Pd/C (50 wt % H$_2$O, 86.2 mg) in EtOH (1.4 mL) was deoxygenated by evacuation of the reaction vessel and refilling with N$_2$ four times. The reaction was stirred at 75° C. for 3.5 h. After cooling to rt the mixture was filtered through Celite, washing with MeOH, and the filtrate concentrated. The residue was purified by reverse phase HPLC to give the title compound. LCMS (ES+) 386 (M+H)$^+$, RT 3.25 min (Analytical Method A); H NMR (400 MHz, CDCl$_3$): δ 7.30-7.20 (3H, m), 7.15-7.10 (2H, m), 4.72 (1H, d, J=4.8 Hz), 3.80 (5H, dd, J=4.7, 4.7 Hz), 3.50-3.42 (1H, m), 3.22-3.17 (4H, m), 3.03 (1H, dd, J=12.4, 15.4 Hz), 2.85-2.73 (2H, m), 2.16-2.07 (1H, m), 1.86-1.70 (3H, m), 1.56-1.44 (2H, m), 1.32-1.12 (2H, m), NH not observed.

Example 172 (S)-6-(2-benzylpyrrolidin-1-yl)-1-methyl-4-morpholinopyridin-2(1H)-one and Example 173: (R)-6-(2-benzylpyrrolidin-1-yl)-1-methyl-4-morpholinopyridin-2(1H)-one

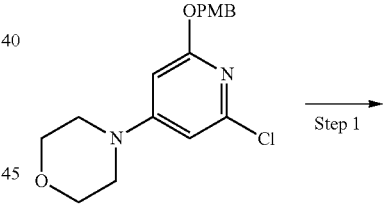

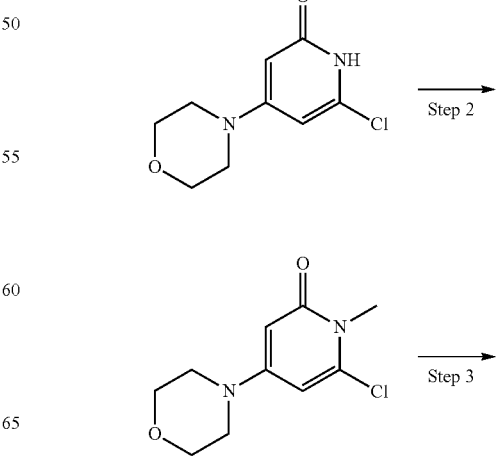

333

-continued

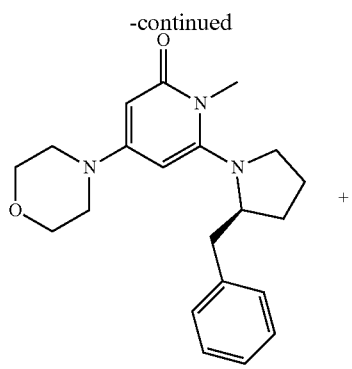

+

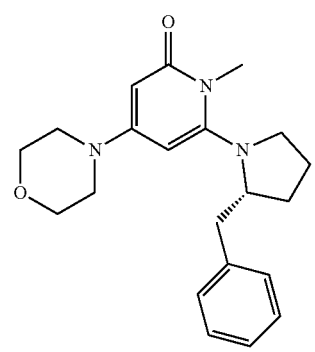

Step 1: 6-chloro-4-morpholinopyridin-2(1H)-one 4-(2-Chloro-6-((4-methoxybenzyl)oxy)pyridin-4-yl)morpholine (1 g, 2.99 mmol, Scaffold 1) was dissolved in DCM (10 mL). TFA (0.23 mL, 2.99 mmol) was added and the reaction stirred at rt for 5 hours. A white precipitate was formed during the reaction, this was collected by filtration. The filtrate was diluted with DCM and washed with saturated sodium hydrogen carbonate solution. The layers were separated, dried (phase separator) and concentrated under reduced pressure. The resultant product was triturated with diethyl ether to afford another product. The two products were combined and used without further purification in the next step.

Step 2: 6-chloro-1-methyl-4-morpholinopyridin-2(1H)-one

6-Chloro-4-morpholinopyridin-2(1H)-one (400 mg, 1.87 mmol) was dissolved in dioxane (5 mL). Lithium tert-butoxide (299 mg, 3.74 mmol) followed by iodomethane (116 μL, 1.87 mmol) were added to the reaction mixture at rt with stirring. The reaction mixture was then heated at 85° C. for 22.5 hours. After this time the reaction mixture was cooled to rt and quenched with water. The reaction was transferred to a separating funnel and diluted with DCM. The layers were separated and the aqueous layer extracted with DCM. The combined organics were dried (phase separator) and concentrated under reduced pressure. The crude mixture was purified by silica gel column chromatography (gradient elution 0-9% MeOH/EtOAc) to afford the title compound.

334

Step 3: (S)-6-(2-benzylpyrrolidin-1-yl)-1-methyl-4-morpholinopyridin-2(1H)-one and (R)-6-(2-benzylpyrrolidin-1-yl)-1-methyl-4-morpholinopyridin-2(1H)-one DIPEA (91 μL, 0.53 mmol) was added to a solution of 6-chloro-1-methyl-4-morpholinopyridin-2(1H)-one (80 mg, 0.35 mmol) and 2-benzyl pyrrolidine (56 mg, 0.35 mmol) in NMP (0.5 mL) in a stem block tube. The reaction mixture was sealed and heated at 150° C. for 53.5 hours. After this time the reaction was cooled to rt and diluted with EtOAc and water. The layers were separated, the organic extracts dried (phase separator) and concentrated under reduced pressure. The crude material was purified by silica gel column chromatography (gradient elution 0-10% MeOH/EtOAc) to afford the target compound. This material was purified by SFC to afford the two enantiomers.

(R)-6-(2-benzylpyrrolidin-1-yl)-1-methyl-4-morpholinopyridin-2(1H)-one; CMS (ES+) 354 (M+H)$^+$, RT 3.09 min (Analytical Method A), RT 2.76 min (Analytical Method SFC1, YMC AMYLOSE-C 30% IPA (0.1% DEA)/CO$_2$); $^1$H NMR δ (ppm) (400 MHz, DMSO-d$_6$) $^1$H NMR δ (ppm) (400 MHz, DMSO-d$_6$) 7.35-7.29 (2H, m), 7.26-7.21 (1H, m), 7.20-7.17 (2H, m), 5.74 (1H, d, J=2.5 Hz), 5.35 (1H, d, J=2.3 Hz), 3.99-3.90 (1H, m), 3.73 (4H, dd, J=4.8, 4.8 Hz), 3.52-3.43 (1H, m), 3.32-3.17 (7H, m), 2.89-2.82 (2H, m), 2.62-2.58 (1H, m), 1.96-1.87 (2H, m), 1.82-1.59 (2H, m).

(S)-6-(2-benzylpyrrolidin-1-yl)-1-methyl-4-morpholinopyridin-2(1H)-one; LCMS (ES+) 354 (M+H)$^+$, RT 3.09 min (Analytical Method A), RT 2.23 min (Analytical Method SFC1, YMC AMYLOSE-C 30% IPA (0.1% DEA)/CO$_2$); $^1$H NMR δ (ppm) (400 MHz, DMSO-d$_6$) $^1$H NMR (400 MHz, DMSO) 7.34-7.30 (2H, m), 7.24 (1H, dd, J=7.3, 7.3 Hz), 7.20-7.17 (2H, m), 5.74 (1H, d, J=2.5 Hz), 5.35 (1H, d, J=2.3 Hz), 3.99-3.90 (1H, m), 3.75-3.71 (4H, m), 3.51-3.43 (1H, m), 3.32-3.17 (7H, m), 2.89-2.82 (2H, m), 2.62-2.57 (1H, m), 1.97-1.86 (2H, m), 1.82-1.58 (2H, m).

Example 174: 6-((2R*,3S*)-2-Benzyl-3-methylpyrrolidin-1-yl)-1-(3-methoxypropyl)-4-morpholinopyridin-2(1H)-one Stereoisomer 1 and Example 175: 6-((2R*,3S*)-2-Benzyl-3-methylpyrrolidin-1-yl)-1-(3-methoxypropyl)-4-morpholinopyridin-2(1H)-one Stereoisomer 2

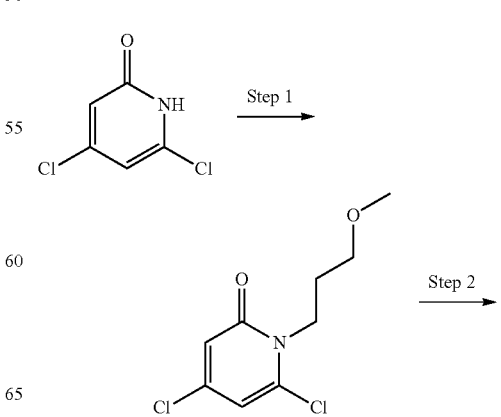

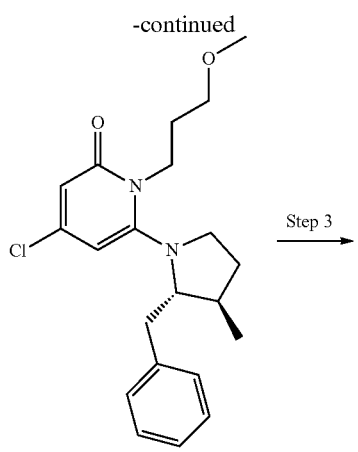

Step 3

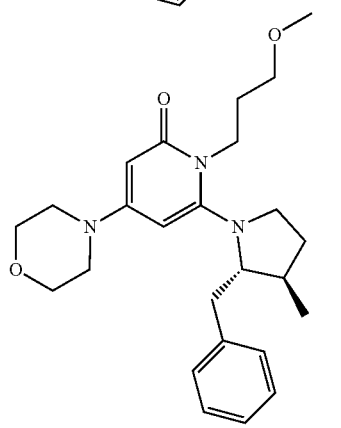

+

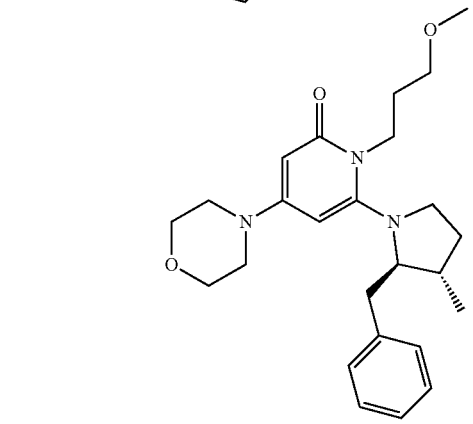

Step 1:
4,6-Dichloro-1-(3-methoxypropyl)pyridin-2(1H)-one

1-Bromo-3-methoxypropane (0.56 mL, 5.00 mmol) was added to 4,6-dichloropyridin-2(1H)-one (410 mg, 2.50 mmoL) and potassium carbonate (691 mg, 5.0 mmol) in acetone (8 mL) and heated at 60° C. After 24 h the reaction was cooled to r.t., filtered and the filtrate concentrated under reduced pressure. The residue was purified by silica gel column chromatography (gradient elution, 7-60% EtOAc in iso-hexane) to afford the title compound.

Step 2: 6-((2S*,3R*)-2-benzyl-3-methylpyrrolidin-1-yl)-4-chloro-1-(3-methoxypropyl)pyridin-2(1H)-one 4,6-Dichloro-1-(3-methoxypropyl)pyridin-2(1H)-one (73 mg, 0.31 mmol), (2R*,3S*)-2-benzyl-3-methylpyrrolidine (60 mg, 0.34 mmol, Intermediate 6) and DIPEA (59 μL, 0.34 mmol) in NMP (1.7 mL) were heated at 100° C. After 20 h the reaction was cooled to rt and diluted with EtOAc and water. The layers were separated and the aqueous layer extracted with EtOAc. The organic extracts were washed with brine, dried (phase separator) and concentrated under reduced pressure. The residue was purified by silica gel column chromatography (gradient elution, 2-100% EtOAc in iso-hexane) to afford the title compound.

Step 3: 6-((2R*,3S*)-2-Benzyl-3-methylpyrrolidin-1-yl)-1-(3-methoxypropyl)-4-morpholinopyridin-2(1H)-one Stereoisomer 1 and Example 175: 6-((2R*,3S*)-2-Benzyl-3-methylpyrrolidin-1-yl)-1-(3-methoxypropyl)-4-morpholinopyridin-2(1H)-one Stereoisomer 2

Following method D from 6-((2S*,3R*)-2-benzyl-3-methylpyrrolidin-1-yl)-4-chloro-1-(3-methoxypropyl)pyridin-2(1H)-one (38 mg, 0.10 mmol) and morpholine (9.8 μL, 0.11 mmol) in dioxane (4 mL). The crude material was purified by reverse phase preparative HPLC followed by SFC to separate the enantiomers to afford the title compounds.

6-((2R*,3S*)-2-Benzyl-3-methylpyrrolidin-1-yl)-1-(3-methoxypropyl)-4-morpholinopyridin-2(1H)-one stereoisomer 1; LCMS (ES+) 426 (M+H)+, RT 3.32 min (Analytical Method A); RT 3.45 min (Analytical Method SFC1, LUX CELLULOSE-4+0.1% DEAISO 40% MeOH SOL4); 1H NMR (400 MHz, CDCl3), 7.25-7.15 (3H, m), 7.04 (2H, d, J=7.1 Hz), 5.51 (1H, d, J=2.3 Hz), 5.44 (1H, d, J=2.3 Hz), 4.25-4.15 (1H, m), 3.91-3.80 (1H, m), 3.80-3.74 (4H, m), 3.50-3.42 (3H, m), 3.33-3.25 (4H, m), 3.20-3.09 (4H, m), 2.91-2.70 (3H, m), 2.27-2.17 (1H, m), 2.08-1.98 (2H, m), 1.91-1.80 (1H, m), 1.53-1.43 (1H, m), 0.94 (3H, d, J=6.1 Hz)

6-((2R*,3S*)-2-Benzyl-3-methylpyrrolidin-1-yl)-1-(3-methoxypropyl)-4-morpholinopyridin-2(1H)-one stereoisomer 2; LCMS (ES+) 426 (M+H)+, RT 3.32 min (Analytical Method A); RT 2.74 min (Analytical Method SFC4, LUX CELLULOSE-4+0.1% DEAISO 35% MeOH SOL3); 1H NMR (400 MHz, CDCl3), 7.24-7.15 (3H, m), 7.04 (2H, d, J=7.1 Hz), 5.51 (1H, d, J=2.3 Hz), 5.44 (1H, d, J=2.3 Hz), 4.24-4.16 (1H, m), 3.91-3.83 (1H, m), 3.80-3.73 (4H, m), 3.50-3.41 (3H, m), 3.33-3.25 (4H, m), 3.20-3.09 (4H, m), 2.91-2.71 (3H, m), 2.27-2.17 (1H, m), 2.06-1.98 (2H, m), 1.91-1.81 (1H, m), 1.52-1.46 (1H, m), 0.94 (3H, d, J=6.3 Hz).

Example 176: (R)-2-(2-benzylpyrrolidin-1-yl)-3-methyl-6-morpholinopyrimidin-4(3H)-one and
Example 177: (S)-2-(2-benzylpyrrolidin-1-yl)-3-methyl-6-morpholinopyrimidin-4(3H)-one

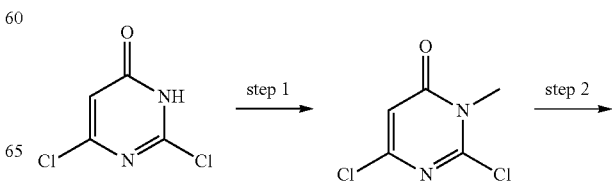

-continued

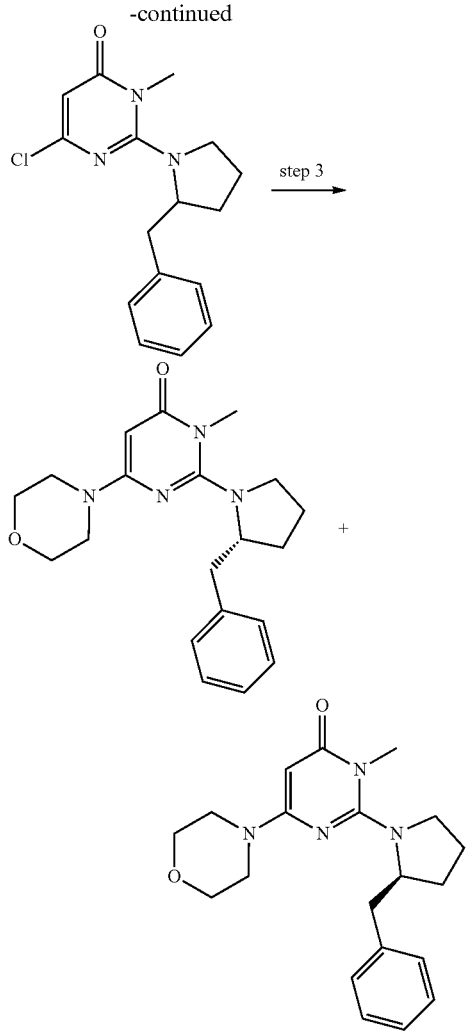

step 3

Step 1: 2,6-dichloro-3-methylpyrimidin-4(3H)-one

Methyl iodide (43 μL, 0.69 mmol) was added to 2,6-dichloropyrimidin-4(3H)-one (100 mg, 0.61 mmol) and potassium carbonate (168 mg, 1.21 mmol) in DMF (2.0 mL) at r.t. After 23 h the reaction was diluted with water and extracted with EtOAc (×2). The combined organic extracts were washed with brine, dried (phase separator) and concentrated under reduced pressure. The residue was purified by purified by silica gel column chromatography (gradient elution, 10-80% EtOAc/iso-hexane) to afford the title compound.

Step 2: 2-(2-benzylpyrrolidin-1-yl)-6-chloro-3-methylpyrimidin-4(3H)-one

2-Benzyl pyrrolidine (130 mg, 0.80 mmol) was added to a solution of 2,6-dichloro-3-methylpyrimidin-4(3H)-one (72 mg, 0.40 mmol) in EtOH (0.5 mL) and DCM (1.5 mL) at r.t. After 1 h the reaction was diluted with water and DCM. The layers were separated, the organic extracts dried (phase separator) and concentrated under reduced pressure. The residue was purified by silica gel column chromatography (gradient elution, 0-80% EtOAc in iso-hexane) to afford the title compound.

Step 3: (R)-2-(2-benzylpyrrolidin-1-yl)-3-methyl-6-morpholinopyrimidin-4(3H)-one and (S)-2-(2-benzylpyrrolidin-1-yl)-3-methyl-6-morpholinopyrimidin-4(3H)-one Following method D from 2-(2-benzylpyrrolidin-1-yl)-6-chloro-3-methylpyrimidin-4(3H)-one (84 mg, 0.28 mmol) and morpholine (27 μL, 0.30 mmol) using 1,4-dioxane (10 mL). The crude reaction mixture was purified by preparative HPLC followed by SFC for the separation of the enantiomers.

(R)-2-(2-benzylpyrrolidin-1-yl)-3-methyl-6-morpholinopyrimidin-4(3H)-one; LCMS (ES+) 355 (M+H)+, RT 3.27 min (Analytical Method B); RT 2.63 min (Analytical Method SFC4, LUX CELLULOSE-3+0.1% DEAISO 15% IPA SOL4); $^1$H NMR (400 MHz, CDCl3) 7.31-7.18 (3H, m), 7.10 (2H, d, J=7.1 Hz), 5.21 (1H, s), 4.49-4.40 (1H, m), 3.79-3.73 (4H, m), 3.54-3.46 (5H, m), 3.35 (3H, s), 3.22 (1H, dd, J=8.0, 8.0 Hz), 3.08 (1H, dd, J=3.5, 13.1 Hz), 2.69 (1H, dd, J=8.3, 13.1 Hz), 2.05-1.85 (2H, m), 1.75-1.62 (2H, m).

(S)-2-(2-benzylpyrrolidin-1-yl)-3-methyl-6-morpholinopyrimidin-4(3H)-one; LCMS (ES+) 355 (M+H)+, RT 3.27 min (Analytical Method B); RT 1.85 min (Analytical Method SFC4, LUX CELLULOSE-3+0.1% DEAISO 15% IPA SOL4); $^1$H NMR (400 MHz, CDCl3) 7.31-7.19 (3H, m), 7.12-7.08 (2H, m), 5.21 (1H, s), 4.50-4.40 (1H, m), 3.76 (4H, dd, J=4.9, 4.9 Hz), 3.57-3.42 (5H, m), 3.35 (3H, s), 3.25-3.18 (1H, m), 3.08 (1H, dd, J=3.5, 13.1 Hz), 2.69 (1H, dd, J=8.3, 13.1 Hz), 2.06-1.84 (2H, m), 1.78-1.65 (2H, m).

Example 178: (R)-2-(2-benzylpyrrolidin-1-yl)-6-morpholinopyrimidin-4-ol and Example 179: (S)-2-(2-benzylpyrrolidin-1-yl)-6-morpholinopyrimidin-4-ol

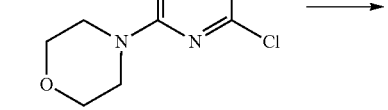

Step 1

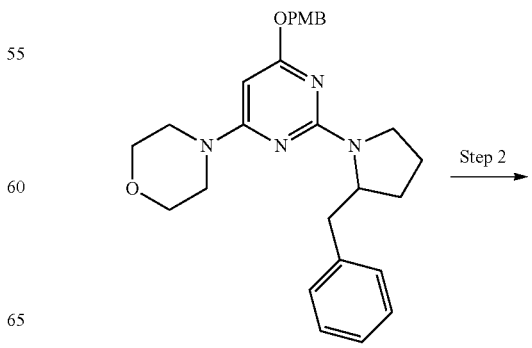

Step 2

-continued

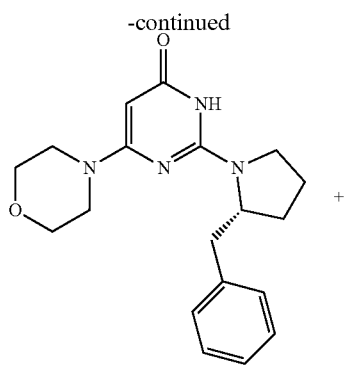

+

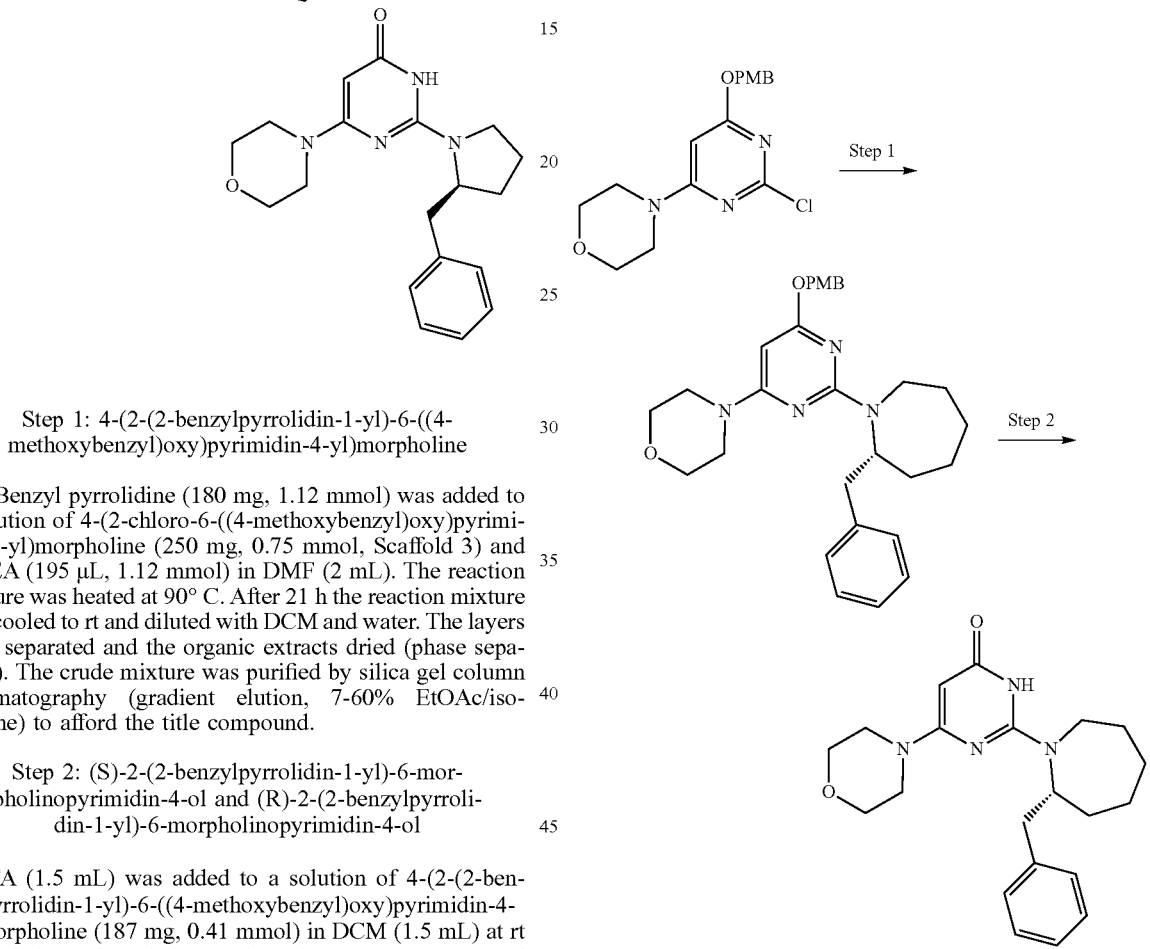

Step 1: 4-(2-(2-benzylpyrrolidin-1-yl)-6-((4-methoxybenzyl)oxy)pyrimidin-4-yl)morpholine 2-Benzyl pyrrolidine (180 mg, 1.12 mmol) was added to a solution of 4-(2-chloro-6-((4-methoxybenzyl)oxy)pyrimidin-4-yl)morpholine (250 mg, 0.75 mmol, Scaffold 3) and DIPEA (195 µL, 1.12 mmol) in DMF (2 mL). The reaction mixture was heated at 90° C. After 21 h the reaction mixture was cooled to rt and diluted with DCM and water. The layers were separated and the organic extracts dried (phase separator). The crude mixture was purified by silica gel column chromatography (gradient elution, 7-60% EtOAc/iso-hexane) to afford the title compound.

Step 2: (S)-2-(2-benzylpyrrolidin-1-yl)-6-morpholinopyrimidin-4-ol and (R)-2-(2-benzylpyrrolidin-1-yl)-6-morpholinopyrimidin-4-ol TFA (1.5 mL) was added to a solution of 4-(2-(2-benzylpyrrolidin-1-yl)-6-((4-methoxybenzyl)oxy)pyrimidin-4-yl)morpholine (187 mg, 0.41 mmol) in DCM (1.5 mL) at rt with stirring. After 4 h the reaction mixture was concentrated under reduced pressure. The crude residue was dissolved in DCM, washed with saturated $NaHCO_3$ aqueous solution, dried (phase separator) and concentrated under reduced pressure. The resultant oil was purified by silica gel column chromatography (gradient elution, 2-20% methanol in DCM) to afford the product. The enantiomers were separated by SFC followed by preparative HPLC to afford the title compounds which were freeze dried from MeCN/water.

(R)-2-(2-benzylpyrrolidin-1-yl)-6-morpholinopyrimidin-4-ol; LCMS (ES+) 341 (M+H)$^+$, RT 3.12 min (Analytical Method A), RT 1.37 min (Analytical Method SFC4, LMC CELLULOSE-3 20% MeOH SOL3 (0.1% DEAISO)/$CO_2$); $^1$H NMR (400 MHz, DMSO): δ 10.23 (1H, s), 7.38-7.33 (2H, m), 7.29-7.23 (3H, m), 4.85 (1H, s), 4.41-4.35 (1H, m), 3.70 (4H, dd, J=4.8, 4.8 Hz), 3.50 (5H, dd, J=3.7, 3.7 Hz), 3.33-3.30 (1H, m), 3.17-3.11 (1H, m), 2.67-2.59 (1H, m), 1.90-1.71 (4H, m).

(S)-2-(2-benzylpyrrolidin-1-yl)-6-morpholinopyrimidin-4-ol; LCMS (ES+) 341 (M+H)$^+$, RT 3.12 min (Analytical Method A), RT 0.94 min (Analytical Method SFC4, LMC CELLULOSE-3 20% MeOH SOL3 (0.1% DEAISO)/$CO_2$); $^1$H NMR (400 MHz, DMSO): δ 10.25 (1H, s), 7.36 (2H, dd, J=7.5, 7.5 Hz), 7.29-7.23 (3H, m), 4.86 (1H, s), 4.40-4.33 (1H, m), 3.72-3.67 (4H, m), 3.53-3.48 (5H, m), 3.34-3.30 (1H, m), 3.17-3.10 (1H, m), 2.68-2.60 (1H, m), 1.90-1.69 (4H, m).

Example 180: (R)-2-(2-benzylazepan-1-yl)-6-morpholinopyrimidin-4(3H)-one

Step 1: (R)-4-(2-(2-benzylazepan-1-yl)-6-((4-methoxybenzyl)oxy)pyrimidin-4-yl)morpholine 2-(R)-Benzyl azepane (169 mg, 0.89 mmol, Example 3 step 2) was added to a solution of 4-(2-chloro-6-((4-methoxybenzyl)oxy)pyrimidin-4-yl)morpholine (200 mg, 0.60 mmol, Scaffold 3) and DIPEA (156 µL, 0.89 mmol) in DMF (1.6 mL). The reaction mixture was heated at 100° C. After 66.5 h the reaction mixture was cooled to rt and diluted with DCM and water. The layers were separated and the organic extracts dried (phase separator). The crude mixture was purified by silica gel column chromatography (gradient elution, 10-80% EtOAc/iso-hexane) to afford the title compound.

Step 2: (R)-2-(2-benzylazepan-1-yl)-6-morpholino-pyrimidin-4(3H)-one

TFA (1 mL) was added to a solution of (R)-4-(2-(2-benzylazepan-1-yl)-6-((4-methoxybenzyl)oxy)pyrimidin-4-yl)morpholine (144 mg, 0.295 mmol) in DCM (1 mL) at rt with stirring. After 5 h the reaction mixture was concentrated under reduced pressure. The crude residue was dissolved in DCM, washed with saturated NaHCO$_3$ aqueous solution, dried (phase separator) and concentrated under reduced pressure. The resultant oil was dissolved in DMSO and purified by reverse phase preparative HPLC. The resultant solid was dissolved in DCM and washed with saturated aqueous solution of NaHCO$_3$. The organic extracts were dried (phase separator) and concentrated under reduced pressure followed by freeze drying from MeCN:water to afford the title compound. LCMS (ES+) 369 (M+H)$^+$, RT 3.26 min (Analytical Method A), $^1$H NMR (400 MHz, CDCl$_3$): δ 7.25-7.19 (3H, m), 7.16-7.11 (2H, m), 4.90 (1H, s), 4.71 (1H, br s), 3.75-3.60 (5H, m), 3.53-3.47 (4H, m), 2.92-2.82 (2H, m), 2.78-2.70 (1H, m), 2.08-1.98 (1H, m), 1.82-1.75 (3H, m), 1.49-1.39 (2H, m), 1.28-1.12 (2H, m), NH not observed.

The general scheme for the synthesis of pyrimidinone target compounds is as follows:

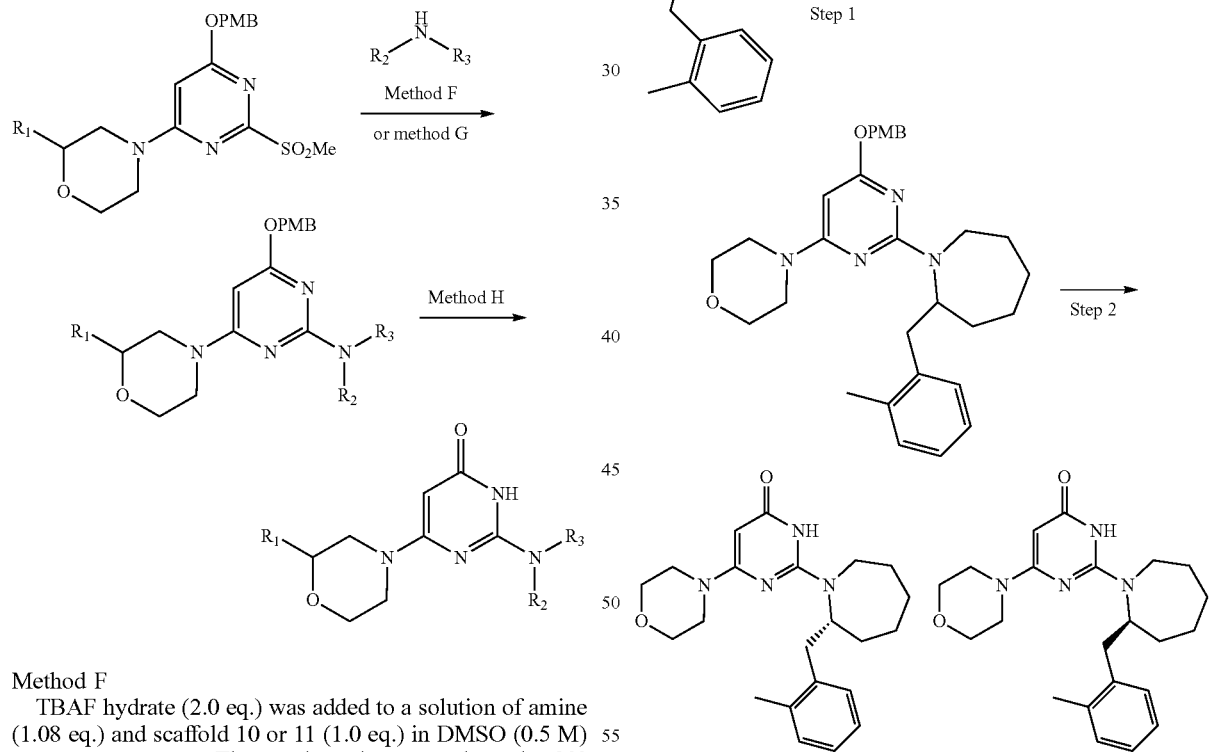

Method F

TBAF hydrate (2.0 eq.) was added to a solution of amine (1.08 eq.) and scaffold 10 or 11 (1.0 eq.) in DMSO (0.5 M) at room temperature. The reaction mixture was heated at 80° C. for 18-70 h. After this time the reaction was diluted with DCM and water and the layers were separated. The organic extracts were dried (phase separator) and concentrated under reduced pressure. Used without further purification in the next step.

Method G

TBAF hydrate (2.0 eq.) was added to a solution of amine (1.08 eq.), scaffold 10 or 11 (1.0 eq.) and DIPEA (2.0 eq.) in DMSO (0.5 M) at room temperature. The reaction mixture was heated at 80° C. for 18-70 h. After this time the reaction was diluted with DCM and water and the layers were separated. The organic extracts were dried (phase separator) and concentrated under reduced pressure. Used without further purification in the next step.

Method H

TFA (0.24 M) was added to a solution of the PMB protected scaffold in DCM (0.24 M). The reaction was stirred at room temperature for 1-4 hours before concentrating under reduced pressure. The residue was dissolved in DCM, washed with saturated sodium bicarbonate solution, dried (phase separator) and concentrated under reduced pressure. The crude material was purified by reverse phase preparative HPLC.

Example 181: (R)-2-(2-(2-methylbenzyl)azepan-1-yl)-6-morpholinopyrimidin-4(3H)-one and Example 182: (S)-2-(2-(2-methylbenzyl)azepan-1-yl)-6-morpholinopyrimidin-4(3H)-one

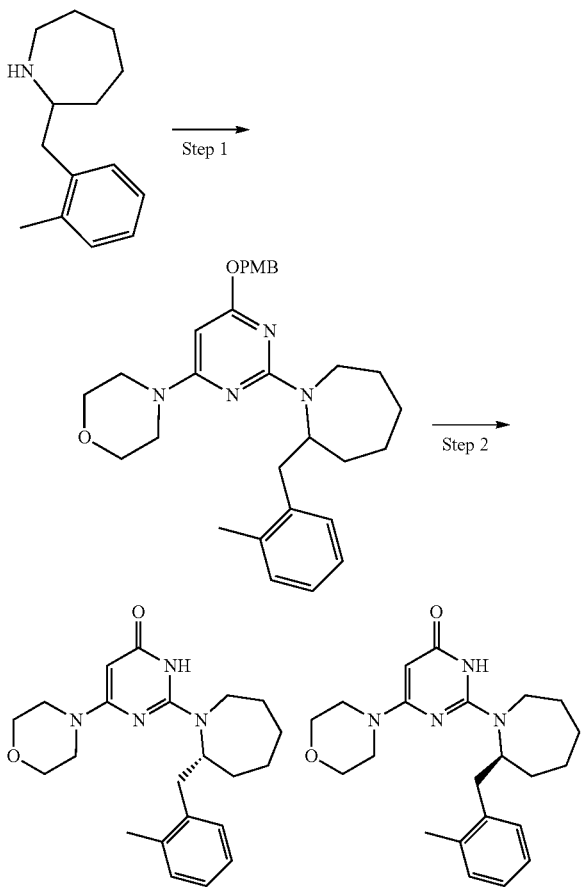

Step 1: 4-(6-((4-methoxybenzyl)oxy)-2-(2-(2-methylbenzyl)azepan-1-yl)pyrimidin-4-yl)morpholine Following Method F from 2-(2-methylbenzyl)azepane (107 mg, 0.53 mmol) and 4-(6-((4-methoxybenzyl)oxy)-2-(methylsulfonyl)pyrimidin-4-yl)morpholine (100 mg, 0.26 mmol, Scaffold 4). Used in the next step without further purification.

Step 2: (R)-2-(2-(2-methylbenzyl)azepan-1-yl)-6-morpholinopyrimidin-4(3H)-one and (S)-2-(2-(2-methylbenzyl)azepan-1-yl)-6-morpholinopyrimidin-4(3H)-one Following Method H from 4-(6-((4-methoxybenzyl)oxy)-2-(2-(2-methylbenzyl)azepan-1-yl)pyrimidin-4-yl)morpholine. After 1 h the reaction was concentrated under reduced pressure. The residue was dissolved in DCM and washed with saturated NaHCO$_3$ (saturated aqueous solution). The DCM layer was dried (phase separator) and concentrated under reduced pressure. The crude material was purified by reverse phase preparative HPLC followed by Chiral SFC for the separation of the enantiomers.

(R)-2-(2-(2-methylbenzyl)azepan-1-yl)-6-morpholinopyrimidin-4(3H)-one; LCMS (ES+) 383 (M+H)$^+$, RT 3.40 min (Analytical Method B); RT 1.26 min (Analytical Method SFC4, YMC AMYLOSE-C 40% MeOH SOL3 (0.1% DEA)/CO$_2$); $^1$H NMR (400 MHz, CDCl$_3$): δ 10.11 (1H, s), 7.17 (1H, dd, J=7.6, 7.6 Hz), 7.02 (3H, d, J=7.6 Hz), 4.83-4.80 (2H, br m), 3.89-3.85 (1H, br m), 3.67 (4H, dd, J=4.5, 4.5 Hz), 3.43 (4H, dd, J=6.1, 6.1 Hz), 3.00-2.99 (1H, br m), 2.77 (1H, dd, J=5.3, 12.9 Hz), 2.64 (1H, dd, J=8.3, 12.9 Hz), 2.29 (3H, s), 1.91-1.80 (1H, m), 1.76-1.68 (3H, m), 1.49-1.21 (3H, m), 1.10-0.98 (1H, m).

(S)-2-(2-(2-methylbenzyl)azepan-1-yl)-6-morpholinopyrimidin-4(3H)-one; LCMS (ES+) 383 (M+H)$^+$, RT 3.40 min (Analytical Method B); RT 0.90 min (Analytical Method SFC4, YMC AMYLOSE-C 40% MeOH SOL3 (0.1% DEA)/CO$_2$); $^1$H NMR (400 MHz, CDCl$_3$): δ 10.14 (1H, s), 7.19 (1H, dd, J=7.6, 7.6 Hz), 7.08-7.01 (3H, m), 4.88-4.72 (2H, br m), 3.91-3.87 (1H, br m), 3.69 (4H, dd, J=4.5, 4.5 Hz), 3.49-3.42 (4H, m), 3.02-3.01 (1H, m), 2.79 (1H, dd, J=5.2, 12.8 Hz), 2.66 (1H, dd, J=8.3, 12.9 Hz), 2.31 (3H, s), 1.92-1.82 (1H, m), 1.78-1.72 (3H, m), 1.50-1.21 (3H, m), 1.11-1.00 (1H, m).

The following examples were prepared using a procedure analogous to that described for Example 129 starting from the reported amine and Scaffold 4. Methyl sulfonyl displacement conditions Method F or Method G were used, followed by Method H to deprotect the scaffold. The chirally pure isomers were isolated after purification by Chiral SFC unless otherwise stated (*), these cases the amine used was chirally pure.

| Example | Structure and Name | Amine | Displacement conditions | Analytical data |
|---|---|---|---|---|
| Example 183 | 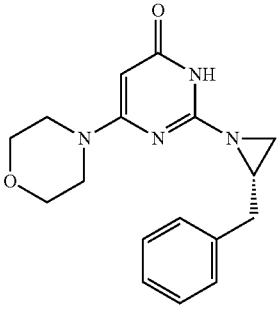<br>2-[(2S)-2-benzylaziridin-1-yl]-4-morpholino-1H-pyrimidin-6-one | (S)-2-benzyl aziridine | Method F | LCMS (ES+) 313 (M + H)$^+$, RT 2.42 min (Analytical Method A); $^1$H NMR (400 MHz, CDCl$_3$): δ 7.38-7.31 (2H, m), 7.31-7.24 (1H, m), 7.19 (2H, d, J = 7.1 Hz), 5.30 (1H, s), 4.51-4.43 (1H, m), 3.91-3.76 (4H, m), 3.70-3.58 (2H, m), 3.27 (1H, dd, J = 3.5, 13.3 Hz), 3.21-3.11 (2H, m), 2.93-2.81 (3H, m). NH not observed. |
| Example 184 | 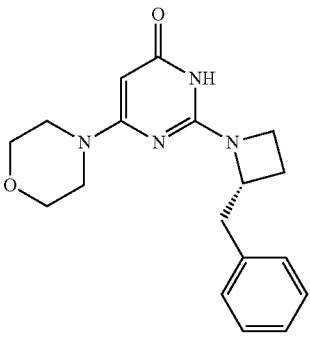<br>2-[(2S)-2-benzylazetidin-1-yl]-4-morpholino-1H-pyrimidin-6-one | 2-benzyl azetidine | Method F | LCMS (ES+) 327 (M + H)$^+$, RT 2.99 min (Analytical Method B) RT 3.09 min (Analytical Method SFC1, YMC AMYLOSE-C, 25/75 IPA (0.1% DEAISO)/CO$_2$); $^1$H NMR (400 MHz, CDCl$_3$): δ 11.14-11.14 (1H, br s), 7.33-7.20 (5H, m), 4.91 (1H, s), 4.72-4.64 (1H, m), 4.09-3.92 (2H, m), 3.75-3.69 (4H, m), 3.54-3.41 (4H, m), 3.34 (1H, dd, J = 4.4, 13.7 Hz), 2.98 (1H, dd, J = 8.5, 13.5 Hz), 2.35-2.25 (1H, m), 2.14-2.03 (1H, m) |

| Example | Structure and Name | Amine | Displacement conditions | Analytical data |
|---|---|---|---|---|
| Example 185 | 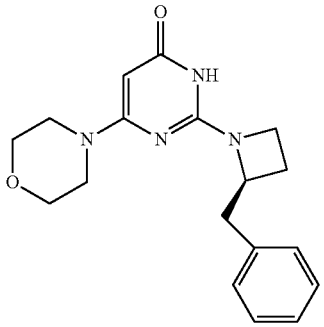<br>2-[(2R)-2-benzylazetidin-1-yl]-4-morpholino-1H-pyrimidin-6-one | 2-benzyl azetidine | Method F | LCMS (ES+) 327 (M + H)+, RT 2.99 min (Analytical Method By, RT 2.19 min (Analytical Method SFC1, YMC AMYLOSE-C, 25/75 IPA (0.1% DEAISO)/$CO_2$); $^1$H NMR (400 MHz, $CDCl_3$): δ 11.04 (1H, br s), 7.34-7.17 (5H, m), 4.91 (1H, s), 4.72-4.64 (1H, m), 4.08-3.92 (2H, m), 3.75-3.69 (4H, m), 3.54-3.41 (4H, m), 3.34 (1H, dd, J = 4.3, 13.6 Hz), 2.99 (1H, dd, J = 8.5, 13.5 Hz), 2.36-2.25 (1H, m), 2.13-2.00 (1H, m) |
| Example 186 | 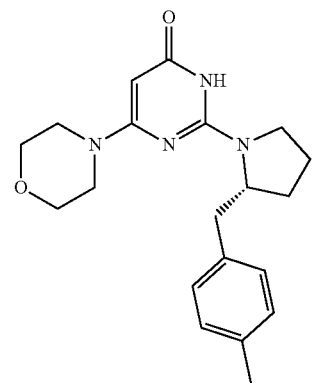<br>(R)-2-(2-(4-methylbenzyl)pyrrolidin-1-yl)-6-morpholinopyrimidin-4(3H)-one | 2-(4-methylbenzyl) pyrrolidine | Method G | LCMS (ES+) 355 (M + H)+, RT 3.23 min (Analytical Method B), RT 2.69 min (Analytical Method SFC4, YMC AMYLOSE-C 20/80 MeOH [0.1% DEAISO]/$CO_2$); $^1$H NMR (400 MHz, $CDCl_3$): δ 10.10-10.09 (1H, br s), 7.12-7.03 (4H, m), 4.96 (1H, s), 4.45-4.38 (1H, m), 3.75 (4H, dd, J = 4.9, 4.9 Hz), 3.63-3.52 (5H, m), 3.42 (1H, dd, J = 7.9, 17.1 Hz), 3.15 (1H, dd, J = 3.2, 13.3 Hz), 2.59 (1H, dd, J = 9.3, 13.1 Hz), 2.32 (3H, s), 1.95-1.80 (4H, m) |
| Example 187 | 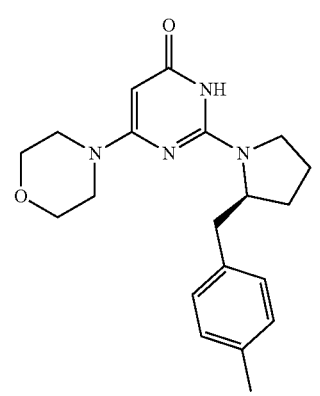<br>(S)-2-(2-(4-methylbenzyl)pyrrolidin-1-yl)-6-morpholinopyrimidin-4(3H)-one | 2-(4-methylbenzyl) pyrrolidine | Method G | LCMS (ES+) 355 (M + H)+, RT 3.23 min (Analytical Method B), RT 2.19 min (Analytical Method SFC4, YMC AMYLOSE-C 20/80 MeOH [0.1% DEAISO]/$CO_2$); $^1$H NMR (400 MHz, $CDCl_3$): δ 9.94-9.29 (1H, br s), 7.12-7.03 (4H, m), 4.96 (1H, s), 4.43-4.38 (1H, m), 3.76 (4H, dd, J = 4.8, 4.8 Hz), 3.59-3.52 (5H, m), 3.40 (1H, dd, J = 8.0, 17.1 Hz), 3.14 (1H, dd, J = 2.8, 13.4 Hz), 2.61 (1H, dd, J = 9.2, 13.3 Hz), 2.32 (3H, s), 1.93-1.80 (4H, m) |

| Example | Structure and Name | Amine | Displacement conditions | Analytical data |
|---|---|---|---|---|
| Example 188 | 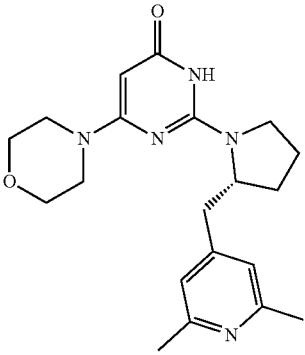<br>(R)-2-(2-((2,6-dimethylpyridin-4-yl)methyl)pyrrolidin-1-yl)-6-morpholinopyrimidin-4(3H)-one | 2,6-dimethyl-4-(pyrrolidin-2-ylmethyl)-pyridine | Method G | LCMS (ES+) 370 (M + H)⁺, RT 2.71 min (Analytical Method B), RT 1.88 min (Analytical Method SFC4, YMC AMYLOSE-C 30/70 MeOH [0.1% DEAISO]/CO$_2$); ¹H NMR (400 MHz, CDCl$_3$): δ 6.81 (2H, s), 4.97 (1H, s), 4.48-4.45 (1H, m), 3.78-3.73 (4H, m), 3.65-3.42 (6H, m), 3.16 (1H, dd, J = 3.3,13.1 Hz), 2.52-2.44 (7H, m), 2.02-1.74 (4H, m), NH not observed. |
| Example 189 | 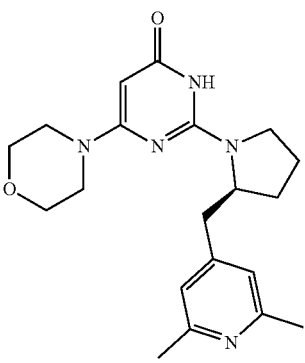<br>(S)-2-(2-((2,6-dimethylpyridin-4-yl)methyl)pyrrolidin-1-yl)-6-morpholinopyrimidin-4(3H)-one | 2,6-dimethyl-4-(pyrrolidin-2-ylmethyl)-pyridine | Method G | LCMS (ES+) 370 (M + H)⁺, RT 2.71 min (Analytical Method B), RT 1.05 min (Analytical Method SFC4, YMC AMYLOSE-C 30/70 MeOH [0.1% DEAISO]/CO$_2$); ¹H NMR (400 MHz, CDCl$_3$): δ 10.73 (1H, s), 6.82 (2H, s), 4.97 (1H, s), 4.73-4.47 (1H, m), 3.78-3.74 (4H, m), 3.68 (1H, qdt, J = 3.3, 3.6, 3.5 Hz), 3.61-3.42 (5H, m), 3.17 (1H, dd, J = 3.5, 13.1 Hz), 2.51-2.44 (7H, m), 2.02-1.72 (4H, m) |
| Example 190 | 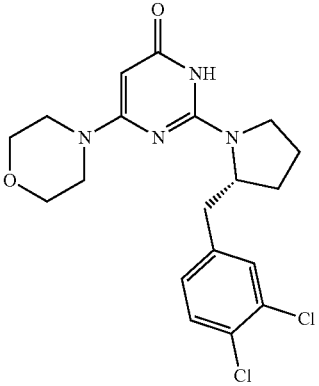<br>(R)-2-(2-(3,4-dichlorobenzyl)pyrrolidin-1-yl)-6-morpholinopyrimidin-4(3H)-one | 2-(3,4-dichlorobenzyl)pyrrolidine | Method G | LCMS (ES+) 409 (M + H)⁺, RT 3.37 min (Analytical Method B), RT 2.35 min (Analytical Method SFC4, YMC AMYLOSE-C 30/70 MeOH [0.1% DEAISO]/CO$_2$); ¹H NMR (400 MHz, CDCl$_3$): δ 7.40-7.38 (1H, m), 7.35 (1H, d, J = 8.3 Hz), 7.01 (1H, dd, J = 1.5, 8.3 Hz), 4.98 (1H, s), 4.51-4.45 (1H, m), 3.76 (4H, dd, J = 4.9, 4.9 Hz), 3.64-3.44 (6H, m), 3.16 (1H, dd, J = 3.8, 13.4 Hz), 2.56 (1H, dd, J = 9.5, 13.5 Hz), 1.99-1.83 (3H, m), 1.83-1.73 (1H, m), NH not observed |

-continued

| Example | Structure and Name | Amine | Displacement conditions | Analytical data |
|---|---|---|---|---|
| Example 191 | (S)-2-(2-(3,4-dichlorobenzyl)-pyrrolidin-1-yl)-6-morpholino-pyrimidin-4(3H)-one | 2-(3,4-dichlorobenzyl) pyrrolidine | Method G | LCMS (ES+) 409 (M + H)+, RT 3.72 min (Analytical Method A), RT 1.88 min (Analytical Method SFC4, YMC AMYLOSE-C 30/70 MeOH [0.1% DEAISO]/CO$_2$); $^1$H NMR (400 MHz, CDCl$_3$): δ 7.42-7.37 (1H, m), 7.34 (1H, d, J = 8.1 Hz), 7.01 (1H, d, J = 7.1 Hz), 4.98 (1H, s), 4.49 (1H, s), 3.76 (4H, dd, J = 4.9, 4.9 Hz), 3.65-3.44 (6H, m), 3.16 (1H, dd, J = 3.8, 13.4 Hz), 2.55 (1H, dd, J = 9.9, 13.1 Hz), 1.99-1.73 (4H, m), NH not observed |
| Example 192 | 2(2-((1H-benzo[d]imidazol-1-yl)-methyl)pyrrolidin-1-yl)-6-morpholinopyrimidin-4(3H)-one | 1-(pyrrolidin-2-ylmethyl)-1H-benzo[d]-imidazole | Method G | LCMS (ES+) 381 (M + H)+, RT 2.29 min (Analytical Method A); $^1$H NMR (400 MHz, CDCl$_3$): δ 8.02 (1H, s), 7.83-7.80 (1H, m), 7.41-7.36 (1H, m), 7.32-7.27 (2H, m), 5.00 (1H, s), 4.79-4.79 (1H, m), 4.48 (1H, dd, J = 4.1, 14.4 Hz), 4.35 (1H, dd, J = 6.6, 14.0 Hz), 3.76-3.72 (4H, m), 3.71-3.61 (1H, m), 3.57-3.44 (5H, m), 2.01-1.92 (2H, m), 1.85-1.79 (1H, m), 1.67-1.56 (1H, m), NH not observed |
| Example 193 | 2-[(2R)-2-[(4-fluorophenyl)methyl]-pyrrolidin-1-yl]-4-morpholino-1H-pyrimidin-6-one | 2-(4-fluorobenzyl)-pyrrolidine | Method F | LCMS (ES+) 359 (M + H)+, RT 3.11 min (Analytical Method B) RT 2.83 min (Analytical Method SFC4, YMC AMYLOSE-C, 20/80 EtOH (0.1% DEAISO)/CO$_2$); $^1$H NMR (400 MHz, CDCl$_3$): δ 10.43-10.42 (1H, br s), 7.17-7.10 (2H, m), 7.00-6.94 (2H, m), 4.95 (1H, s), 4.43 (1H, d, J = 2.0 Hz), 3.78-3.73 (4H, m), 3.61-3.44 (6H, m), 3.13 (1H, dd, J = 3.5, 13.6 Hz), 2.66 (1H, dd, J = 9.1, 13.4 Hz), 1.97-1.77 (4H, m) |

| Example | Structure and Name | Amine | Displacement conditions | Analytical data |
|---|---|---|---|---|
| Example 194 | 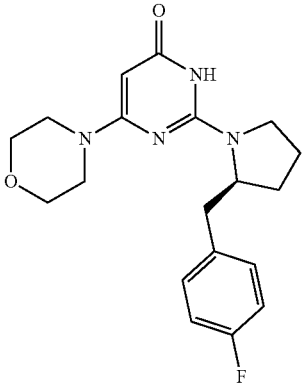<br>2-[(2S)-2-[(4-fluorophenyl)methyl]-pyrrolidin-1-yl]-4-morpholino-1H-pyrimidin-6-one | 2-(4-fluorobenzyl)-pyrrolidine | Method F | LCMS (ES+) 359 (M + H)$^+$, RT 3.11 min (Analytical Method By, RT 2.16 min (Analytical Method SFC4, YMC AMYLOSE-C, 20/80 EtOH (0.1% DEAISO)/CO$_2$); $^1$H NMR (400 MHz, CDCl$_3$): δ 10.58 (1H, br s), 7.16-7.10 (2H, m), 7.00-6.95 (2H, m), 5.01 (1H, s), 4.45-4.44 (1H, m), 3.78-3.73 (4H, m), 3.61-3.51 (5H, m), 3.47-3.40 (1H, m), 3.12 (1H, dd, J = 3.7, 13.5 Hz), 2.66 (1H, dd, J = 9.0, 13.5 Hz), 1.96-1.80 (4H, m) |
| Example 195 | 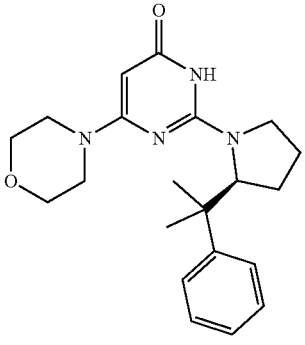<br>2-[(2S)-2-(1-methyl-1-phenyl-ethyl)-pyrrolidin-1-yl]-4-morpholino-1H-pyrimidin-6-one | 2-(2-phenyl propan-2-yl)pyrrolidine | Method F | LCMS (ES+) 369 (M + H)$^+$, RT 3.22 min (Analytical Method By RT 1.49 min (Analytical Method SFC4, YMC AMYLOSE-C, 55/45 IPA (0.1% DEAISO)/CO$_2$); $^1$H NMR (400 MHz, CDCl$_3$): δ 9.78 (1H, br s), 7.42-7.39 (2H, m), 7.34 - 7.29 (2H, m), 7.25-7.21 (1H, m), 4.97 (1H, s), 4.68 (1H, dd, J = 3.5, 6.5 Hz), 3.81-3.71 (4H, m), 3.62-3.56 (2H, m), 3.55-3.45 (3H, m), 3.39 (1H, dt, J = 4.2, 9.9 Hz), 1.79-1.73 (2H, m), 1.69-1.63 (1H, m), 1.39 (6H, s), 1.23-1.13 (1H, m) |
| Example 196 | 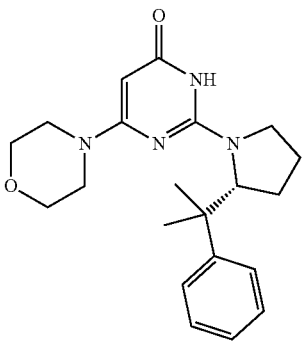<br>2-[(2R)-2-(1-methyl-1-phenyl-ethyl)-pyrrolidin-1-yl]-4-morpholino-1H-pyrimidin-6-one | 2-(2-phenyl propan-2-yl)pyrrolidine | Method F | LCMS (ES+) 369 (M + H)$^+$, RT 3.22 min (Analytical Method By RT 1.92 min (Analytical Method SFC4, YMC AMYLOSE-C, 55/45 IPA (0.1% DEAISO)/CO$_2$); $^1$H NMR (400 MHz, CDCl$_3$): δ 9.95-9.94 (1H, m), 7.42-7.40 (2H, m), 7.31 (2H, dd, J = 7.6, 7.6 Hz), 7.25-7.21 (1H, m), 4.97 (1H, s), 4.70 (1H, dd, J = 2.9, 6.7 Hz), 3.82-3.71 (4H, m), 3.63-3.55 (2H, m), 3.55-3.44 (3H, m), 3.41 (1H, dt, J = 3.8, 9.6 Hz), 1.78-1.71 (2H, m), 1.71-1.61 (1H, m), 1.38 (6H, d, J = 1.8Hz), 1.26-1.12 (1H, m) |

| Example | Structure and Name | Amine | Displacement conditions | Analytical data |
|---|---|---|---|---|
| Example 197 | (R)-2-(2-(2-methoxybenzyl)piperidin-1-yl)-6-morpholinopyrimidin-4(3H)-one | 2-(2-methoxy-benzyl)-piperidine | Method F | LCMS (ES+) 385 (M + H)+, RT 3.29 min (Analytical method By, RT 3.04 min (Analytical method SFC1, LUX CELLULOSE-3, 10/90 MeOH [0.1% DEA]/CO$_2$); $^1$H NMR (400 MHz, CDCl$_3$): δ 8.92 (1H, s), 7.29-7.22 (1H, m), 7.07 (1H, d, J = 6.1 Hz), 6.98-6.88 (2H, m), 4.94 (1H, s), 4.60-4.54 (1H, m), 4.16 (3H, s), 4.06-3.98 (1H, m), 3.77-3.72 (4H, m), 3.52-3.46 (4H, m), 3.01-2.88 (3H, m), 1.85-1.43 (6H, m) |
| Example 198 | (S)-2-(2-(2-methoxybenzyl)piperidin-1-yl)-6-morpholinopyrimidin-4(3H)-one | 2-(2-methoxy-benzyl)-piperidine | Method F | LCMS (ES+) 385 (M + H)+, RT 3.29 min (Analytical method By RT 2.32 min (Analytical method SFC1, LUX CELLULOSES, 10/90 MeOH [0.1% DEA]/CO$_2$); $^1$H NMR (400 MHz, CDCl$_3$): δ 8.89 (1H, s), 7.29-7.23 (1H, m), 7.08-7.05 (1H, m), 6.98-6.88 (2H, m), 4.94 (1H, s), 4.62-4.54 (1H, m), 4.16 (3H, s), 4.04-3.97 (1H, m), 3.77-3.71 (4H, m), 3.51-3.47 (4H, m), 3.01-2.88 (3H, m), 1.82-1.74 (2H, m), 1.67-1.62 (2H, m), 1.60-1.44 (2H, m) |
| Example 199 | (R)-2-(2-benzylpiperidin-1-yl)-6-morpholinopyrimidin-4(3H)-one | 2-benzyl piperidine | Method G | LCMS (ES+) 355 (M + H)+, RT 3.15 min (Analytical Method A); RT 3.08 min (Analytical Method SFC4, YMC AMYLOSE-C + 0.1% DEAISO 25% IPA SOL4; $^1$H NMR (400 MHz, DMSO): δ 10.26 (1H, br s), 7.29-7.24 (4H, m), 7.21-7.15 (1H, m), 4.89-4.80 (2H, m), 4.23 (1H, d, J = 12.7 Hz), 3.65-3.61 (4H, m), 3.41-3.38 (4H, m), 3.07-2.89 (2H, m), 2.80 (1H, dd, J = 6.3, 13.2 Hz), 1.83-1.65 (2H, m), 1.58-1.30 (4H, m) |

| Example | Structure and Name | Amine | Displacement conditions | Analytical data |
|---|---|---|---|---|
| Example 200 | (S)-2-(2-benzylpiperidin-1-yl)-6-morpholinopyrimidin-4(3H)-one | 2-benzyl piperidine | Method G | LCMS (ES+) 355 (M + H)+, RT 3.15 min (Analytical Method A); RT 2.37 min (Analytical Method SFC4, YMC AMYLOSE-C + 0.1% DEAISO 25% IPA SOL4; $^1$H NMR (400 MHz, DMSO): δ 10.30 (1H, br s), 7.28-7.24 (4H, m), 7.20-7.15 (1H, m), 4.84-4.80 (2H, m), 4.24 (1H, d, J = 12.0 Hz), 3.63 (4H, dd, J = 4.8, 4.8 Hz), 3.41-3.36 (4H, m), 3.06-2.89 (2H, m), 2.79 (1H, dd, J = 6.3, 13.2 Hz), 1.83-1.65 (2H, m), 1.57-1.32 (4H, m) |
| Example 201 | (R)-2-(2-(2-methoxybenzyl)azepan-1-yl)-6-morpholinopyrimidin-4(3H)-one | 2-(2-methoxy-benzyl)-azepane | Method F | LCMS (ES+) 399 (M + H)+, RT 3.43 min (Analytical Method By RT 1.54 min (Analytical Method SFC4, YMC AMYLOSE-C 40% MeOH SOL3 (0.1% DEA)/CO$_2$); $^1$H NMR (400 MHz, DMSO, 105° C.): δ 7.22-7.12 (2H, m), 6.97 (1H, d, J = 7.9 Hz), 6.86 (1H, dd, J = 7.3, 7.3 Hz), 4.78 (1H, s), 4.45 (1H, br s), 4.05-4.00 (1H, m), 3.89 (3H, s), 3.60-3.68 (4H, s), 3.43-3.39 (4H, m), 3.09-3.02 (1H, m), 2.88-2.67 (2H, m), 1.92-1.86 (1H, m), 1.74-1.68 (3H, m), 1.56-1.47 (2H, m), 1.36-1.10 (2H, m), NH not observed |
| Example 202 | (S)-2-(2-(2-methoxybenzyl)azepan-1-yl)-6-morpholinopyrimidin-4(3H)-one | 2-(2-methoxy-benzyl)-azepane | Method F | LCMS (ES+) 399 (M + H)+, RT 3.43 min (Analytical Method By, RT 1.12 min (Analytical Method SFC4, YMC AMYLOSE-C 40% MeOH SOL3 (0.1% DEA)/CO$_2$); $^1$H NMR (400 MHz, DMSO, 105° C.): δ 9.19 (1H, s), 7.21-7.12 (2H, m), 6.96 (1H, d, J = 8.2 Hz), 6.88-6.83 (1H, m), 4.78 (1H, s), 4.43 (1H, s), 4.06-3.98 (1H, m), 3.89 (3H, s), 3.67-3.62 (4H, m), 3.43-3.39 (4H, m), 3.08-3.01 (1H, m), 2.91-2.68 (2H, m), 1.92-1.89 (1H, m), 1.73-1.66 (3H, m), 1.57-1.47 (2H, m), 1.37-1.25 (1H, m), 1.20-1.08 (1 H, m) |

-continued

| Example | Structure and Name | Amine | Displacement conditions | Analytical data |
|---|---|---|---|---|
| Example 203 | (R)-2-(2-(3-methoxybenzyl)azepan-1-yl)-6-morpholinopyrimidin-4(3H)-one | 2-(3-methoxybenzyl)azepane | Method F | LCMS (ES+) 399 (M + H)+, RT 3.24 min (Analytical Method B) RT 1.40 min (Analytical Method SFC4, YMC AMYLOSE-C 40% MeOH SOL3 (0.1% DEA)/CO$_2$); $^1$H NMR (400 MHz, CDCl$_3$): δ 10.07 (1H, s), 7.17 (1H, dd, J = 8.0, 8.0 Hz), 6.76-6.72 (3H, m), 4.74-4.74 (2H, m), 3.90 (1H, s), 3.72 (3H, s), 3.65-3.60 (4H, m), 3.43-3.35 (4H, m), 2.96 (1H, s), 2.78-2.60 (2H, m), 1.87-1.81 (1H, m), 1.70-1.67 (2H, m), 1.46- 1.16 (3H, m), 1.07-0.97 (1H, m) NH not visible |
| Example 204 | (S)-2-(2-(3-methoxybenzyl)azepan-1-yl)-6-morpholinopyrimidin-4(3H)-one | 2-(3-methoxybenzyl)azepane | Method F | LCMS (ES+) 399 (M + H)+, RT 3.24 min (Analytical Method B) RT 0.96 min (Analytical Method SFC4, YMC AMYLOSE-C 40% MeOH SOL3 (0.1% DEA)/CO$_2$); $^1$H NMR (400 MHz, CDCl$_3$): δ 10.07 (1H, s), 7.17 (1H, dd, J = 8.0, 8.0 Hz), 6.77-6.72 (3H, m), 4.75-4.75 (2H, m), 3.86-3.80 (1H, m), 3.72 (3H, s), 3.65-3.60 (4H, m), 3.42-3.36 (4H, m), 2.97-2.97 (1H, m), 2.79-2.72 (1H, m), 2.64 (1H, dd, J = 8.4, 13.4 Hz), 1.88-1.83 (1H, m), 1.73-1.67 (2H, m), 1.46-1.17 (3H, m), 1.05-0.96 (1H, m) NH not visible |
| Example 205 | 2-[(2R)-2-[(2-chlorophenyl)methyl]-azepan-1-yl]-4-morpholino-1H-pyrimidin-6-one | 2-(2-chlorobenzyl)-azepane | Method F | 3.37 min (Analytical Method A); RT 1.68 min (Analytical Method SFC1,YMC AMYLOSE- C, 55/45 IPA (0.1% DEAISO)/CO$_2$); $^1$H NMR (400 MHz, CDCl$_3$): δ 7.31-7.29 (1H, m), 7.15-7.08 (3H, m), 4.82 (1H, s), 3.71-3.68 (5H, m), 3.45-3.38 (4H, m), 3.12-3.06 (1H, m), 3.02-2.95 (1H, m), 2.88-2.80 (1H, m), 2.16-2.06 (1H, m), 1.84-1.75 (3H, m), 1.54-1.45 (3H, m), 1.36-1.13 (2H, m), NH not observed |

| Example | Structure and Name | Amine | Displacement conditions | Analytical data |
|---|---|---|---|---|
| Example 206 | 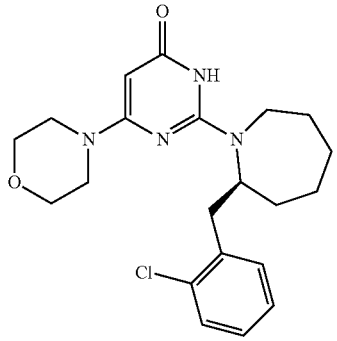<br>2-[(2S)-2-[(2-chlorophenyl)methyl]-azepan-1-yl]-4-morpholino-1H-pyrimidin-6-one | 2-(2-chlorobenzy)-azepane | Method F | LCMS (ES+) 403 (M + H)+, RT 3.37 min (Analytical Method A); RT 0.92 min (Analytical Method SFC1, YMC AMYLOSE-C, 55/45 IPA (0.1% DEAISO)/CO$_2$); $^1$H NMR (400 MHz, CDCl$_3$): δ 7.31-7.29 (1H, m), 7.15-7.09 (3H, m), 4.82 (1H, s), 3.71-3.68 (5H, m), 3.45-3.38 (4H, m), 3.13-3.04 (1H, m), 2.97 (1H, dd, J = 5.9, 13.3 Hz), 2.88 -2.79 (1H, m), 2.16-2.06 (1H, m), 1.85-1.73 (3H, m), 1.55-1.41 (3H, m), 1.30-1.13 (2H, m), NH not observed |
| Example 207 | 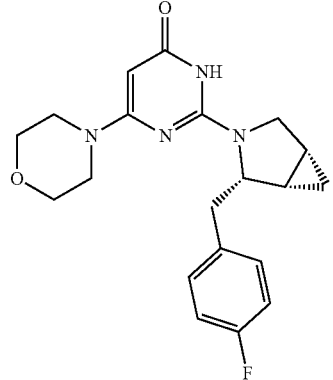<br>2-[(1R,4S,5S)-4-[(4-fluorophenyl)-methyl]-3-azabicyclo[3.1.0]hexan-3-yl]-4-morpholino-1H-pyrimidin-6-one | Intermediate 3 | Method G | LCMS (ES+) 371 (M + H)+, RT 3.13 min (Analytical Method A); RT 2.57 min (Analytical Method SFC4, YMC AMYLOSE-C, 30/70 IPA (0.1% DEAISO)/CO$_2$); $^1$H NMR (400 MHz, CDCl$_3$): δ 10.42 (1H, br s), 7.15-7.15 (2H, m), 6.96 (2H, dd, J = 8.6, 8.6 Hz), 4.94 (1H, s), 4.51 (1H, dd, J = 3.4, 8.0 Hz), 3.78-3.72 (4H, m), 3.66-3.45 (5H, m), 3.23 (1H, dd, J = 3.8, 10.4 Hz), 3.04 (1H, dd, J = 3.0, 13.4 Hz), 2.82-2.81 (1H, m), 1.51-1.39 (2H, m), 0.70-0.62 (1H, m), 0.19-0.15 (1H, m). |
| Example 208 | 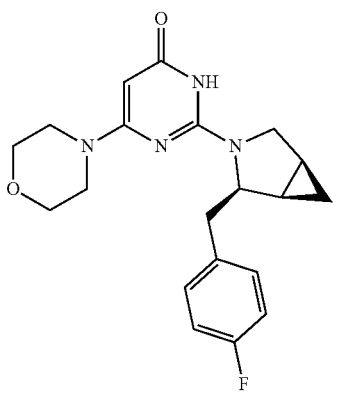<br>2-[(1S,4R,5R)-4-[(4-fluorophenyl)-methyl]-3-azabicyclo[3.1.0]hexan-3-yl]-4-morpholino-1H-pyrimidin-6-one | Intermediate 3 | Method G | LCMS (ES+) 371 (M + H)+, RT 3.12 min (Analytical Method By, RT 1.83 min (Analytical Method SFC4, YMC AMYLOSE-C, 30/70 IPA (0.1% DEAISO)/CO$_2$); $^1$H NMR (400 MHz, CDCl$_3$): δ 10.28 (1H, br s), 7.15-7.15 (2H, m), 6.96 (2H, dd, J = 8.6, 8.6 Hz), 4.94 (1H, s), 4.50 (1H, dd, J = 3.5, 7.8 Hz), 3.78-3.72 (4H, m), 3.58-3.47 (5H, m), 3.23 (1H, dd, J = 3.4, 10.2 Hz), 3.04 (1H, dd, J = 3.0, 13.1 Hz), 2.85-2.81 (1H, m), 1.48-1.40 (2H, m), 0.66 (1H, dd, J = 7.7, 13.0 Hz), 0.17 (1H, q, J = 4.2 Hz). |

| Example | Structure and Name | Amine | Displacement conditions | Analytical data |
|---------|-------------------|-------|------------------------|-----------------|
| Example 209 | 2-[(1R,4S,5R)-4-[(4-fluorophenyl)-methyl]-3-azabicyclo[3.1.0]hexan-3-yl]-4-morpholino-1H-pyrimidin-6-one | Intermediate 4 | Method G | LCMS (ES+) 371 (M + H)+, RT 3.21 min (Analytical Method A); RT 2.11 min (Analytical Method SFC4, YMC AMYLOSE-C, 20/80 MeOH (0.1% DEAISO)/CO$_2$); $^1$H NMR (400 MHz, CDCl$_3$): δ 10.34 (1H, br s), 7.25-7.21 (2H, m), 7.02-6.97 (2H, m), 5.00 (1H, s), 4.39-4.32 (1H, m), 3.87 (1H, d, J = 9.5 Hz), 3.82-3.74 (5H, m), 3.64-3.51 (5H, m), 2.37 (1H, dd, J = 10.4, 12.8 Hz), 1.74-1.67 (1H, m), 1.54-1.48 (1H, m), 0.78 (1H, dt, J = 5.1, 7.9 Hz), 0.55 (1H, q, J = 4.5 Hz). |
| Example 210 | 2-[(1S,4R,5S)-4-[(4-fluorophenyl)-methyl]-3-azabicyclo[3.1.0]hexan-3-yl]-4-morpholino-1H-pyrimidin-6-one | Intermediate 4 | Method G | LCMS (ES+) 371 (M + H)+, RT 3.17 min (Analytical Method By, RT 4.36 min (Analytical Method SFC4, YMC AMYLOSE-C, 15/85 MeOH (0.1% DEAISO)/CO$_2$); $^1$H NMR (400 MHz, CDCl$_3$): δ 10.37-10.36 (1H, br s), 7.23 (2H, dd, J = 5.6, 8.3 Hz), 6.99 (2H, dd, J = 8.6, 8.6 Hz), 5.00 (1H, s), 4.36 (1H, tt, J = 4.9, 4.7 Hz), 3.87 (1H, d, J = 9.6 Hz), 3.79-3.74 (5H, m), 3.64-3.51 (5H, m), 2.37 (1H, dd, J = 10.6, 12.6 Hz), 1.75-1.67 (1H, m), 1.55-1.48 (1H, m), 0.81-0.74 (1H, m), 0.56 (1H, q, J = 4.2 Hz). |
| Example 211 | 2-((1S,2S,5R)-2-benzyl-3-azabicyclo-[3.1.0]hexan-3-yl)-6-morpholino-pyrimidin-4(3H)-one | Intermediate 1 | Method G | LCMS (ES+) 353 (M + H)+, RT 3.16 min (Analytical Method B), RT 8.50 min (Analytical Method SFC1, LUX CELLULOSE-4 30/70 MeOH [0.1% DEAISO]/CO$_2$); $^1$H NMR (400 MHz, CDCl$_3$): δ 7.34-7.21 (5H, m), 5.00 (1H, s), 4.42-4.36 (1H, m), 3.85-3.74 (6H, m), 3.64-3.52 (5H, m), 2.40 (1H, dd, J = 10.4, 12.6 Hz), 1.74-1.66 (1H, m), 1.58-1.50 (1H, m), 0.82-0.75 (1H, m), 0.58 (1H, q, J = 4.5 Hz), NH not observed. |

| Example | Structure and Name | Amine | Displacement conditions | Analytical data |
|---|---|---|---|---|
| Example 212 | 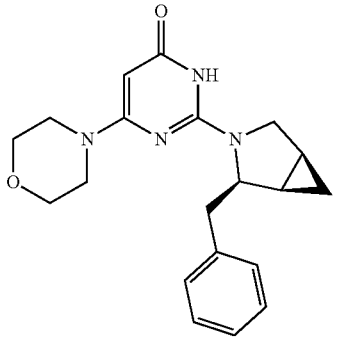<br>2-((1R,2R,5S)-2-benzyl-3-azabicyclo-[3.1.0]hexan-3-yl)-6-morpholino-pyrimidin-4(3H)-one | Intermediate 1 | Method G | LCMS (ES+) 353 (M + H)$^+$, RT 3.16 min (Analytical Method B), RT 9.75 min (Analytical Method SFC1, LUX CELLULOSE-4 30/70 MeOH [0.1% DEAISO]/CO$_2$); $^1$H NMR (400 MHz, CDCl$_3$): δ 7.34-7.22 (5H, m), 5.00 (1H, s), 4.42-4.35 (1H, m), 3.83-3.74 (6H, m), 3.64-3.52 (5H, m), 2.40 (1H, dd, J = 10.5, 12.5 Hz), 1.73-1.67 (1H, m), 1.55-1.52 (1H, m), 0.83-0.76 (1H, m), 0.58 (1H, q, J = 4.5 Hz), NH not observed. |
| Example 213 | 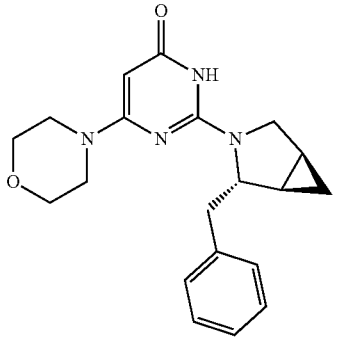<br>2-((1R,2S,5S)-2-benzyl-3-azabicyclo-[3.1.0]hexan-3-yl)-6-morpholino-pyrimidin-4(3H)-one | Intermediate 2 | Method G | LCMS (ES+) 353 (M + H)$^+$, RT 3.31 min (Analytical Method A), RT 2.71 min (Analytical Method SFC1, YMC AMYLOSE-C 40/60 IPA [0.1% DEAISO]/CO$_2$); $^1$H NMR (400 MHz, CDCl$_3$): δ 7.32-7.26 (2H, m), 7.25-7.16 (3H, m), 4.94 (1H, s), 4.49 (1H, dd, J = 3.0, 7.8 Hz), 3.75 (4H, dd, J = 4.9, 4.9 Hz), 3.59-3.48 (5H, m), 3.26 (1H, dd, J = 3.3, 10.1 Hz), 3.12-3.06 (1H, m), 2.80 (1H, dd, J = 8.5, 13.0 Hz), 1.50-1.43 (2H, m), 0.68-0.61 (1H, m), 0.18-0.13 (1H, m), NH not observed. |
| Example 214 | 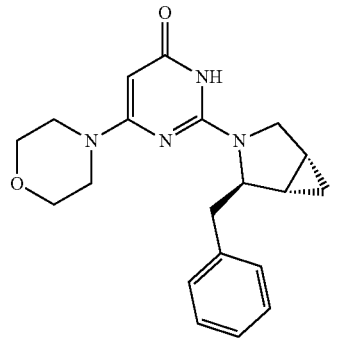<br>2-((1S,2R,5R)-2-benzyl-3-azabicyclo-[3.1.0]hexan-3-yl)-6-morpholino-pyrimidin-4(3H)-one | Intermediate 2 | Method G | LCMS (ES+) 353 (M + H)$^+$, RT 3.31 min (Analytical Method A), RT 1.69 min (Analytical Method SFC1, YMC AMYLOSE-C 40/60 IPA [0.1% DEAISO]/CO$_2$); $^1$H NMR (400 MHz, CDCl$_3$): δ 10.26-10.25 (1H, br s), 7.29 (2H, d, J = 6.8 Hz), 7.25-7.19 (3H, m), 4.94 (1H, s), 4.51 (1H, dd, J = 3.7, 8.5 Hz), 3.75 (4H, dd, J = 4.9, 4.9 Hz), 3.64-3.46 (5H, m), 3.28 (1H, dd, J = 3.4, 10.0 Hz), 3.12-3.09 (1H, m), 2.78 (1H, dd, J = 8.7, 13.0 Hz), 1.48-1.43 (2H, m), 0.68-0.60 (1H, m), 0.18-0.13 (1H, m). |

| Example | Structure and Name | Amine | Displacement conditions | Analytical data |
|---|---|---|---|---|
| Example 215 | 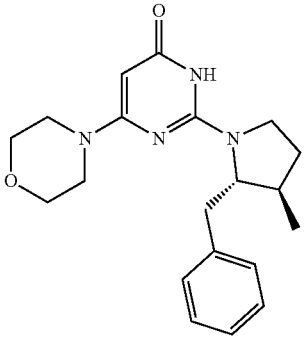<br>2-((2S,3R)-2-benzyl-3-methyl-pyrrolidin-1-yl)-6-morpholino-pyrimidin-4(3H)-one | Intermediate 6 | Method F | LCMS (ES+) 355 (M + H)+, RT 3.18 min (Analytical Method B), RT 2.71 min (Analytical Method SFC4, YMC AMYLOSE-C + 0.1% DEAISO 25% IPA SOL4; $^1$H NMR (400 MHz, DMSO): δ 10.22 (1H, br s), 7.31 (2H, dd, J = 7.4, 7.4 Hz), 7.20 (3H, dd, J = 7.0, 13.2 Hz), 4.81 (1H, s), 3.93(1H, br d, J = 7.9 Hz), 3.67-3.62 (4H, m), 3.48-3.42 (6H, m), 3.08 (1H, dd, J = 2.6, 13.1 Hz), 2.68 (1H, dd, J = 9.2, 12.9 Hz), 2.08-1.94 (2H, m), 1.51-1.44 (1H, m), 0.80 (3H, d, J = 6.8 Hz). |
| Example 216 | 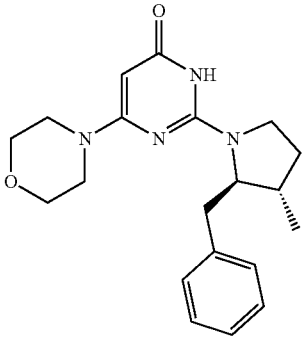<br>2-((2R,3S)-2-benzyl-3-methyl-pyrrolidin-1-yl)-6-morpholino-pyrimidin-4(3H)-one | Intermediate 6 | Method F | LCMS (ES+) 355 (M + H)+, RT 3.18 min (Analytical Method A); RT 2.06 min (Analytical Method SFC4, YMC AMYLOSE-C + 0.1% DEAISO 25% IPA SOL4; $^1$H NMR (400 MHz, DMSO): δ 10.24 (1H, br s), 7.33-7.28 (2H, m), 7.24-7.17 (3H, m), 4.81 (1H, s), 3.92 (1H, br d, J = 8.7 Hz), 3.68-3.62 (4H, m), 3.47 3.36 (6H, m), 3.09 (1H, dd, J = 3.3, 13.1 Hz), 2.68 (1H, dd, J = 9.2, 12.9 Hz), 2.08-1.92 (2H, m), 1.50-1.43 (1H, m), 0.80 (3H, d, J = 6.8 Hz). |
| Example 217 | 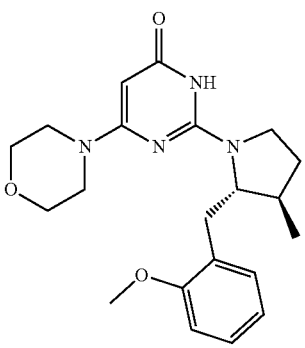<br>2-((2S,3R)-2-(2-methoxybenzyl)-3-methylpyrrolidin-1-yl)-6-morpholino-pyrimidin-4(3H)-one | Intermediate 7 | Method F | Silica column, SFC then further purified by preparative HPLC product. LCMS (ES+) 385 (M + H)+, RT 3.31 min (Analytical Method By, RT 1.55 min (Analytical Method SFC1, YMC AMYLOSE-C + 0.1% DEAISO 50% IPA SOL6); $^1$H NMR (400 MHz, DMSO): δ 9.89 (1H, s), 7.18-7.05 (2H, m), 6.91 (1H, d, J = 7.8 Hz), 6.82 (1H, dd, J = 7.2, 7.2 Hz), 4.71 (1H, s), 3.76 (4H, s), 3.60-3.53 (4H, m), 3.4-3.34 (6H, m), 3.20-3.19 (1H, m), 2.65-2.58 (1H, m), 2.18-2.06 (2H, m), 1.57-1.51 (1H, m), 0.79 (3H, d, J = 6.6 Hz). |

-continued

| Example | Structure and Name | Amine | Displacement conditions | Analytical data |
|---|---|---|---|---|
| Example 218 | 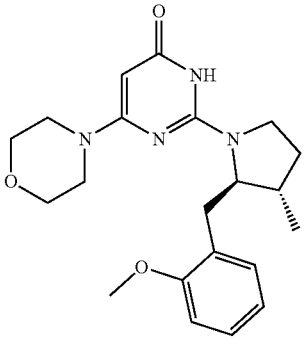<br>2-((2R,3S)-2-(2-methoxybenzyl)-3-methylpyrrolidin-1-yl)-6-morpholino-pyrimidin-4(3H)-one | Intermediate 7 | Method F | LCMS (ES+) 385 (M + H)+, RT 3.31 min (Analytical Method By RT 2.73 min (Analytical Method SFC1, YMC AMYLOSE-C + 0.1% DEAISO 50% IPA SOL6); $^1$H NMR (400 MHz, CDCl$_3$): δ 9.02 (1H, br s), 7.31-7.28 (1H, m), 7.08 (1H, dd, J = 1.5, 7.3 Hz), 6.99-6.90 (2H, m), 4.97 (1H, s), 4.20 (3H, s), 3.77-3.73 (4H, m), 3.67-3.63 (2H, m), 3.55-3.50 (4H, m), 3.43-3.43 (1H, m), 3.19 (1H, d, J = 13.3 Hz), 2.35-2.19(3H, m), 1.68-1.54 (1H, m under water peak), 0.85 (3H, d, J = 7.0 Hz). |
| Example 219 | 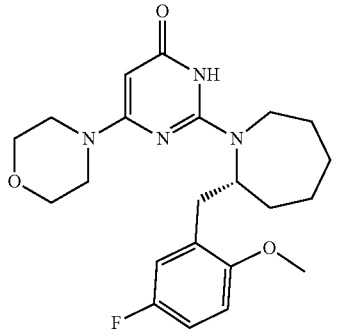<br>(R)-2-(2-(5-fluoro-2-methoxybenzyl)-azepan-1-yl)-6-morpholinopyrimidin-4(3H)-one | Intermediate 13 | Method F | LCMS (ES+) 417 (M + H)+, RT 3.38 min (Analytical Method By, RT 2.34 min (Analytical Method SFC4, YMC AMYLOSE-C, 30/70 MeOH (0.1% DEAISO)/CO$_2$); $^1$H NMR (400 MHz, CDCl$_3$): δ 9.04(1H, br s), 6.96-6.86 (2H, m), 6.81 (1H, dd, J = 3.0, 8.7 Hz), 4.96 (1H, s), 4.26-4.19 (4H, m), 3.76-3.63 (5H, m), 3.56-3.45 (4H, m), 3.12-2.99 (2H, m), 2.46-2.40 (1H, m), 2.04-1.96 (1H, m), 1.85-1.76 (3H, m), 1.69-1.65 (1H, m), 1.50-1.40 (1H, m), 1.36-1.26 (1H, m), 1.18-1.09 (1H, m) |
| Example 220 | 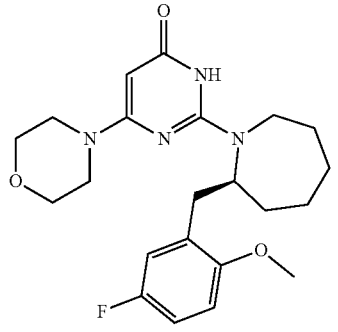<br>(S)-2-(2-(5-fluoro-2-methoxybenzyl)-azepan-1-yl)-6-morpholinopyrimidin-4(3H)-one | Intermediate 13 | Method F | LCMS (ES+) 417 (M + H)+, RT 3.4 min (Analytical Method A); RT 1.33 min (Analytical Method SFC4, YMC AMYLOSE-C, 30/70 MeOH (0.1% DEAISO)/CO$_2$); $^1$H NMR (400 MHz, CDCl$_3$): δ 9.04 (1H, br s), 6.96-6.86 (2H, m), 6.81 (1H, dd, J = 3.0, 8.7 Hz), 4.96 (1H, s), 4.26-4.19 (4H, m), 3.76-3.63 (5H, m), 3.56-3.45 (4H, m), 3.12-2.99 (2H, m), 2.46-2.40 (1H, m), 2.04-1.96 (1H, m), 1.85-1.76 (3H, m), 1.69-1.65 (1H, m), 1.50-1.40 (1H, m), 1.36-1.26 (1H, m), 1.18-1.09 (1H, m) |

-continued

| Example | Structure and Name | Amine | Displacement conditions | Analytical data |
|---|---|---|---|---|
| Example 221 | (S)-2-(2-(4-fluorobenzyl)azepan-1-yl)-6-morpholinopyrimidin-4(3H)-one | Intermediate 15 | Method F | LCMS (ES+) 387 (M + H)+, RT 3.26 min (Analytical Method A); RT 0.84 min (Analytical Method SFC4, YMC AMYLOSE-C, 50/50 MeOH (0.1% DEAISO)/CO$_2$); $^1$H NMR (400 MHz, CDCl$_3$): δ 9.46 (1H, br s), 7.10-7.07 (2H, m), 6.93 (2H, t, J = 9.0 Hz), 4.90 (1H, s), 4.71 (1H, brs), 3.74 (4H, t, J = 4.8 Hz), 3.66-3.44 (5H, m), 2.94-2.71 (3H, m), 2.07-1.98 (1H, m), 1.81-1.75 (3H, m), 1.46-1.37 (2H, m), 1.28-1.13 (2H, m) |
| Example 222 | (R)-2-(2-(4-fluorobenzyl)azepan-1-yl)-6-morpholinopyrimidin-4(3H)-one | Intermediate 15 | Method F | LCMS (ES+) 387 (M + H)+, RT 3.26 min (Analytical Method A); RT 1.38 min (Analytical Method SFC4, YMC AMYLOSE-C, 50/50 MeOH (0.1% DEAISO)/CO$_2$); $^1$H NMR (400 MHz, CDCl$_3$): δ 9.46 (1H, br s), 7.10-7.07 (2H, m), 6.93 (2H, t, J = 9.0 Hz), 4.90 (1H, s), 4.71 (1H, brs), 3.74 (4H, t, J = 4.8 Hz), 3.66-3.44 (5H, m), 2.94-2.71 (3H, m), 2.07-1.98 (1H, m), 1.81-1.75 (3H, m), 1.46-1.37 (2H, m), 1.28-1.13 (2H, m). |
| Example 223 | (R)-2-(2-(2,3-difluorobenzyl)-azepan-1-yl)-6-morpholino-pyrimidin-4(3H)-one | Intermediate 14 | Method F | LCMS (ES+) 405 (M + H)+, RT 3.28 min (Analytical Method A); RT 2.19 min (Analytical Method SFC4, YMC AMYLOSE-C, 30/70 MeOH (0.1% DEAISO)/CO$_2$); $^1$H NMR (400 MHz, CDCl$_3$): δ 9.37 (1H, br s), 7.02-6.80 (3H, m), 5.01-4.78 (2H, m), 3.77-3.61 (5H, m), 3.46 (4H, t, J = 4.9 Hz), 3.10-2.99 (1H, m), 2.85 (2H, d, J = 6.9 Hz), 2.11-2.04 (1H, m), 1.85-1.76 (3H, m), 1.47-1.37 (2H, m), 1.31-1.14 (2H, m) |

| Example | Structure and Name | Amine | Displacement conditions | Analytical data |
|---|---|---|---|---|
| Example 224 | (S)-2-(2-(2,3-difluorobenzyl)azepan-1-yl)-6-morpholinopyrimidin-4(3H)-one | Intermediate 14 | Method F | LCMS (ES+) 405 (M + H)+, RT 3.28 min (Analytical Method A); RT 1.16 min (Analytical Method SFC4, YMC AMYLOSE-C, 30/70 MeOH (0.1% DEAISO)/CO$_2$); $^1$H NMR (400 MHz, CDCl$_3$): δ 9.37 (1H, br s), 7.02-6.80 (3H, m), 5.01-4.78 (2H, m), 3.77-3.61 (5H, m), 3.46 (4H, t, J = 4.9 Hz), 3.10-2.99 (1H, m), 2.85 (2H, d, J = 6.9 Hz), 2.11-2.04 (1H, m), 1.85-1.76 (3H, m), 1.47-1.37 (2H, m), 1.31-1.14 (2H, m) |
| Example 225 | (R)-2-(2-((2,3-dihydrobenzofuran-7-yl)methyl)azepan-1-yl)-6-morpholino-pyrimidin-4(3H)-one | Intermediate 13 | Method F | LCMS (ES+) 411 (M + H)+, RT 3.36 min (Analytical Method A); RT 1.93 min (Analytical Method SFC4, YMC AMYLOSE-C, 35/65 MeOH (0.1% DEAISO)/CO$_2$); $^1$H NMR (400 MHz, CDCl$_3$): δ 9.44 (1H, br s), 7.11 (1H, d, J = 7.0 Hz), 6.86 (1H, d, J = 9.0 Hz), 6.78 (1H, t, J = 7.5 Hz), 4.95-4.74 (3H, m), 4.28-4.10 (1H, m), 3.79-3.66 (5H, m), 3.55-3.43 (4H, m), 3.24 (2H, t, J = 8.7 Hz), 3.07-2.97 (2H, m), 2.93 (1H, dd, J = 3.3, 13.3 Hz), 2.58 (1H, dd, J = 10.0, 13.3 Hz), 2.12-2.02 (1H, m), 1.86-1.71 (3H, m), 1.51-1.40 (1H, m), 1.36-1.23 (1H, m), 1.18-1.08 (1H, m) |
| Example 226 | (S)-2-(2-((2,3-dihydrobenzofuran-7-yl)methyl)azepan-1-yl)-6-morpholino-pyrimidin-4(3H)-one | Intermediate 13 | Method F | LCMS (ES+) 411 (M + H)+, RT 3.36 min (Analytical Method A); RT 1.51 min (Analytical Method SFC4, YMC AMYLOSE-C, 35/65 MeOH (0.1% DEAISO)/CO$_2$); $^1$H NMR (400 MHz, CDCl$_3$): δ 9.44 (1H, br s), 7.11 (1H, d, J = 7.0 Hz), 6.86 (1H, d, J = 9.0 Hz), 6.78 (1H, t, J = 7.5 Hz), 4.95-4.74 (3H, m), 4.28-4.10 (1H, m), 3.79-3.66 (5H, m), 3.55-3.43 (4H, m), 3.24 (2H, t, J = 8.7 Hz), 3.07-2.97 (2H, m), 2.93 (1H, dd, J = 3.3, 13.3 Hz), 2.58 (1H, dd, J = 10.0, 13.3 Hz), 2.12-2.02 (1H, m), 1.86-1.71 (3H, m), 1.51-1.40 (1H, m), 1.36-1.23 (1H, m), 1.18-1.08 (1H, m) |

| Example | Structure and Name | Amine | Displacement conditions | Analytical data |
|---|---|---|---|---|
| Example 227 | (S)-2-(2-(4-fluoro-2-methoxybenzyl)-azepan-1-yl)-6-morpholinopyrimidin-4(3H)-one | Intermediate 8 | Method F | LCMS (ES+) 417 (M + H)+, RT 3.4 min (Analytical Method By, RT 4.15 min (Analytical Method SFC4, YMC AMYLOSE-C, 15/85 MeOH (0.1% DEAISO)/CO$_2$); $^1$H NMR δ (400 MHz, CDCl$_3$): δ 8.97 (1H, br s), 7.00 (1H, t, J = 7.6 Hz), 6.70 (1H, d, J = 10.5 Hz), 6.60 (1H, t, J = 7.6 Hz), 4.96 (1H, s), 4.27-4.16 (4H, m), 3.74 (4H, t, J = 4.9 Hz), 3.66-3.46 (5H, m), 3.09-2.98 (2H, m), 2.49-2.40 (1H, m), 2.01-1.94 (1H, m), 1.86-1.63 (4H, m), 1.48-1.24 (2H, m), 1.17-1.07 (1H, m) |
| Example 228 | (R)-2-(2-(4-fluoro-2-methoxybenzyl)-azepan-1-yl)-6-morpholinopyrimidin-4(3H)-one | Intermediate 8 | Method F | LCMS (ES+) 417 (M + H)+, RT 3.4 min (Analytical Method By RT 5.86 min (Analytical Method SFC4, YMC AMYLOSE-C, 15/85 MeOH (0.1% DEAISO)/CO$_2$); $^1$H NMR (400 MHz, CDCl$_3$): δ 8.97 (1H, br s), 7.00 (1H, t, J = 7.6 Hz), 6.70 (1H, d, J = 10.5 Hz), 6.60 (1H, t, J = 7.6 Hz), 4.96 (1H, s), 4.27-4.16 (4H, m), 3.74 (4H, t, J = 4.9 Hz), 3.66-3.46 (5H, m), 3.09-2.98 (2H, m), 2.49-2.40 (1H, m), 2.01-1.94 (1H, m), 1.86-1.63 (4H, m), 1.48-1.24 (2H, m), 1.17-1.07 (1H, m) |
| Example 229 | (S)-2-(2-(2,3-dimethoxybenzyl)azepan-1-yl)-6-morpholinopyrimidin-4(3H)-one | Intermediate 10 | Method F | LCMS (ES+) 429 (M + H)+, RT 3.34 min (Analytical Method By RT 0.08 min (Analytical Method SFC4, YMC AMYLOSE-C, 25/75 MeOH (0.1% DEAISO)/CO$_2$); $^1$H NMR (400 MHz, CDCl$_3$): δ 9.13(1H, br s), 0.97 (1H, t, J = 7.7 Hz), 0.85 (1H, d, J = 8.2 Hz), 0.70 (1H, d, J = 0.1 Hz), 4.90 (1H, s), 4.29-4.03 (4H, m), 3.87 (3H, s), 3.74 (4H, t, J = 4.9 Hz), 3.55-3.45 (5H, m), 3.06-2.99 (2H, m), 2.52-2.40 (1H, m), 1.97-1.88 (1H, m), 1.83-1.68 (4H, m), 1.46-1.22 (2H, m), 1.14-1.04 (1H, m) |

| Example | Structure and Name | Amine | Displacement conditions | Analytical data |
|---|---|---|---|---|
| Example 230 | 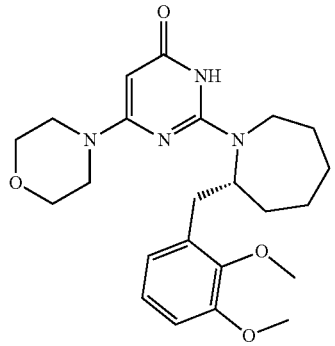<br>(R)-2-(2-(2,3-dimethoxybenzyl)azepan-1-yl)-6-morpholinopyrimidin-4(3H)-one | Intermediate 10 | Method F | LCMS (ES+) 429 (M + H)+, RT 3.34 min (Analytical Method By, RT 2.09 min (Analytical Method SFC4, YMC AMYLOSE-C, 25/75 MeOH (0.1% DEAISO)/CO$_2$); $^1$H NMR (400 MHz, CDCl$_3$): δ 9.13 (1H, br s), 6.97 (1H, t, J = 7.7 Hz), 6.85 (1H, d, J = 8.2 Hz), 6.70 (1H, d, J = 6.1 Hz), 4.96 (1H, s), 4.29-4.03 (4H, m), 3.87 (3H, s), 3.74 (4H, t, J = 4.9 Hz), 3.55-3.45 (5H, m), 3.06-2.99 (2H, m), 2.52-2.40 (1H, m), 1.97-1.88 (1H, m), 1.83-1.68 (4H, m), 1.46-1.22 (2H, m), 1.14-1.04 (1H, m) |
| Example 231 | 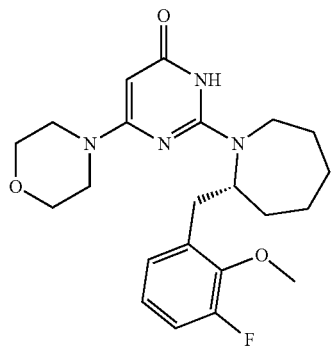<br>(R)-2-(2-(3-fluoro-2-methoxybenzyl)-azepan-1-yl)-6-morpholinopyrimidin-4(3H)-one | Intermediate 12 | Method F | LCMS (ES+) 417 (M + H)+, RT 3.34 min (Analytical Method By RT 2.23 min (Analytical Method SFC4, YMC AMYLOSE-C, 20/80 MeOH (0.1% DEAISO)/CO$_2$); $^1$H NMR (400 MHz, CDCl$_3$): δ 8.95 (1H, s), 7.05-6.82 (3H, m), 4.97 (1H, s), 4.34-4.18 (4H, m), 3.74 (4H, t, J = 4.9 Hz), 3.64-3.46 (5H, m), 3.06-2.98 (2H, m), 2.57-2.43 (1H, m), 1.99-1.72 (4H, m), 1.48-1.06 (4H, m) |
| Example 232 | 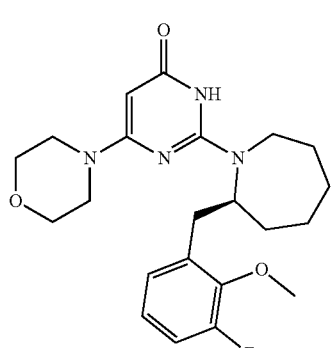<br>(S)-2-(2-(3-fluoro-2-methoxybenzyl)-azepan-1-yl)-6-morpholinopyrimidin-4(3H)-one | Intermediate 12 | Method F | LCMS (ES+) 417 (M + H)+, RT 3.34 min (Analytical Method By RT 1.59 min (Analytical Method SFC4, YMC AMYLOSE-C, 20/80 MeOH (0.1% DEAISO)/CO$_2$); $^1$H NMR (400 MHz, CDCl$_3$): δ 8.95 (1H, s), 7.05-6.82 (3H, m), 4.97 (1H, s), 4.34-4.18 (4H, m), 3.74 (4H, t, J = 4.9 Hz), 3.64-3.46 (5H, m), 3.06-2.98 (2H, m), 2.57-2.43 (1H, m), 1.99-1.72 (4H, m), 1.48-1.06 (4H, m) |

| Example | Structure and Name | Amine | Displacement conditions | Analytical data |
| --- | --- | --- | --- | --- |
| Example 233 | 2-((2R,4S)-2-benzyl-4-methylazepan-1-yl)-6-morpholinopyrimidin-4(3H)-one | Intermediate 23 | Method F | LCMS (ES+) 383 (M + H)+, RT 3.4 min (Analytical Method By, RT 2.75 min (Analytical Method SFC4, LUX CELLULOSE-3, 15/85 MeOH (0.1% DEAISO)/CO$_2$); $^1$H NMR (400 MHz, CDCl$_3$): δ 7.29-7.19 (3H, m), 7.14 (2H, d, J = 7.1 Hz), 4.90 (1H, s), 4.84-4.65 (1H, m), 3.74 (4H, t, J = 4.9 Hz), 3.55-3.45 (5H, m), 2.97-2.73 (3H, m), 1.72-1.40 (6H, m), 1.11-1.00 (1H, m), 0.91 (3H, d, J = 6.2 Hz), NH not observed. |
| Example 234 | 2-((2S,4R)-2-benzyl-4-methylazepan-1-yl)-6-morpholinopyrimidin-4(3H)-one | Intermediate 23 | Method F | LCMS (ES+) 383 (M + H)+, RT 3.39 min (Analytical Method A); RT 3.12 min (Analytical Method SFC4, YMC AMYLOSE-C, 15/85 MeOH (0.1% DEAISO)/CO$_2$); $^1$H NMR (400 MHz, CDCl$_3$): δ 7.29-7.19 (3H, m), 7.14 (2H, d, J = 7.1 Hz), 4.90 (1H, s), 4.84-4.65 (1H, m), 3.74 (4H, t, J = 4.9 Hz), 3.55-3.45 (5H, m), 2.97-2.73 (3H, m), 1.72-1.40 (6H, m), 1.11-1.00 (1H, m), 0.91 (3H, d, J = 6.2 Hz), NH not observed |
| Example 235 | 2-((2R,4S)-2-(4-fluorobenzyl)-4-methylazepan-1-yl)-6-morpholinopyrimidin-4(3H)-one | Intermediate 25 | Method F | LCMS (ES+) 401 (M + H)+, RT 3.36 min (Analytical Method By RT 4.02 min (Analytical Method SFC4, LUX CELLULOSE-3, 15/85 MeOH (0.1% DEAISO)/CO$_2$); $^1$H NMR (400 MHz, CDCl$_3$): δ 7.12-7.03 (2H, m), 6.94 (2H, t, J = 8.9 Hz), 4.90 (1H, s), 4.83-4.58 (1H, m), 3.75 (4H, t, J = 4.4 Hz), 3.54-3.43 (5H, m), 2.96-2.69 (3H, m), 1.70-1.37 (6H, m), 1.11-0.98 (1H, m), 0.92 (3H, d, J = 6.4 Hz), NH not observed |

| Example | Structure and Name | Amine | Displacement conditions | Analytical data |
|---------|-------------------|-------|------------------------|-----------------|
| Example 236 | 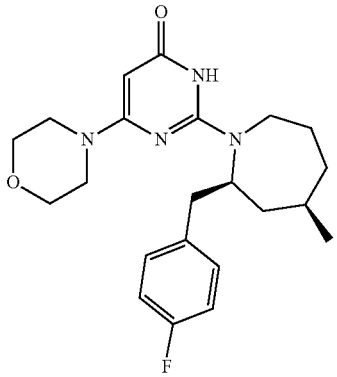<br>2-((2S,4R)-2-(4-fluorobenzyl)-4-methylazepan-1-yl)-6-morpholino-pyrimidin-4(3H)-one | Intermediate 25 | Method F | LCMS (ES+) 401 (M + H)+, RT 3.39 min (Analytical Method A); RT 2.48 min (Analytical Method SFC4, YMC AMYLOSE-C, 15/85 MeOH (0.1% DEAISO)/$CO_2$); $^1$H NMR (400 MHz, $CDCl_3$): δ 7.12-7.03 (2H, m), 6.94 (2H, t, J = 8.9 Hz), 4.90 (1H, s), 4.83-4.58 (1H, m), 3.75 (4H, t, J = 4.4 Hz), 3.54-3.43 (5H, m), 2.96-2.69 (3H, m), 1.70-1.37 (6H, m), 1.11-0.98 (1H, m), 0.92 (3H, d, J = 6.4 Hz), NH not observed |
| Example 237 | 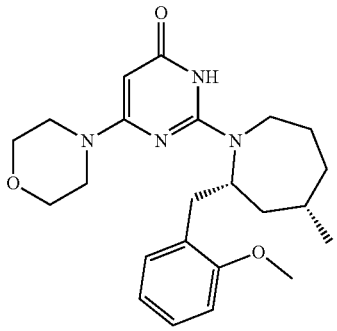<br>2-((2R,4S)-2-(2-methoxybenzyl)-4-methylazepan-1-yl)-6-morpholino-pyrimidin-4-(3H)-one | Intermediate 28 | Method F | LCMS (ES+) 413 (M + H)+, RT 3.51 min (Analytical Method B) RT 5.24 min (Analytical Method SFC4, LUX CELLULOSES, 10/90 IPA (0.1% DEAISO)/$CO_2$); $^1$H NMR δ (ppm) (400 MHz, $CDCl_3$) 9.08 (1H, s), 7.29-7.25 (1H, m), 7.07-7.05 (1H, m), 6.98 (1H, d, J = 7.2 Hz), 6.91 (1H, J = 7.6 Hz), 4.96 (1H, s), 4.28-4.19 (4H, m), 3.78-3.69 (5H, m), 3.56-3.44 (4H, m), 3.11-32.48-2.42 (1H, m), 1.75-1.63.01 (2H, m), (4H, m), 1.50-1.39 (2H, m), 1.19-1.08 (1H, m), 0.86 (3H, d, J = 5.7 Hz) |
| Example 238 | 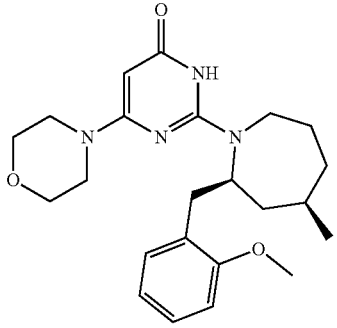<br>2-((2S,4R)-2-(2-methoxybenzyl)-4-methylazepan-1-yl)-6-morpholino-pyrimidin-4(3H)-one | Intermediate 28 | Method F | LCMS (ES+) 413 (M + H)+, RT 3.51 min (Analytical Method B) RT 2.89 min (Analytical Method SFC4, LUX CELLULOSES, 10/90 IPA (0.1% DEAISO)/$CO_2$); $^1$H NMR δ (ppm) (400 MHz, $CDCl_3$) 9.08 (1H, s), 7.29-7.25 (1H, m), 7.07-7.05 (1H, m), 6.98 (1H, d, J = 7.2 Hz), 6.91 (1H, J = 7.6 Hz), 4.96 (1H, s), 4.28-4.19 (4H, m), 3.78-3.69 (5H, m), 3.56-3.44 (4H, m), 3.11-3.01 (2H, m), 2.48-2.42 (1H, m), 1.75-1.63 (4H, m), 1.50-1.39 (2H, m), 1.19-1.08 (1H, m), 0.86 (3H, d, J = 5.7 Hz). |

| Example | Structure and Name | Amine | Displacement conditions | Analytical data |
|---|---|---|---|---|
| Example 239 | 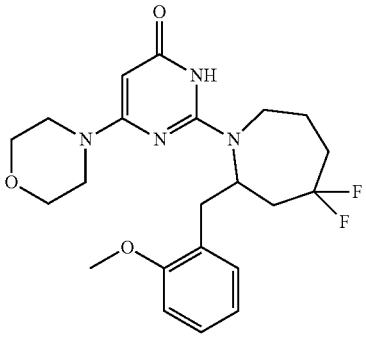  2-(4,4-difluoro-2-(2-methoxybenzyl)-azapan-1-yl)-6-morpholinpyrimidin-4(3H)-one | Intermediate 27 | Method F | LCMS (ES+) 435 (M + H)+, RT 3.21 min (Analytical Method A); $^1$H NMR δ (ppm) (400 MHz, CDCl$_3$) 9.15 (1H, s), 7.30 (1H, t, J = 7.8 Hz), 7.06-6.90 (3H, m), 4.98 (1H, s), 4.45-4.35 (1H, m), 4.22 (3H, s), 4.00-3.90 (1H, m), 3.76 (4H, t, J = 5.2 Hz), 3.55-3.44 (4H, m), 3.20-3.08 (2H, m), 2.55-2.46 (1H, m), 2.41-2.10 (3H, m), 1.97-1.70 (3H, m). |
| Example 240 | 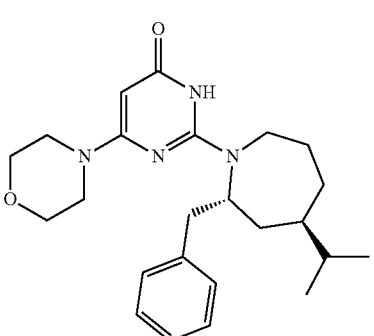  2-((2R,4R)-2-benzyl-4-isopropylazepan-1-yl)-6-morpholinopyrimidin-4(3H)-one | Intermediate 22 | Method F | LCMS (ES+) 411 (M + H)+, RT 3.89 min (Analytical Method A); $^1$H NMR (400 MHz, DMSO) 9.98 (1H, br s), 7.21-7.05 (5H, m), 4.75-4.52 (2H, m), 4.03-3.68 (1H, m), 3.58-3.52 (4H, m), 3.33-3.26 (4H, m), 2.84-2.84 (1H, m), 2.72-2.59 (2H, m), 1.61-1.38 (2H, m), 1.28-1.16 (2H, m), 1.07-0.93 (2H, m), 0.65 (6H, dd, J = 3.8, 6.8 Hz); |
| Example 241 | 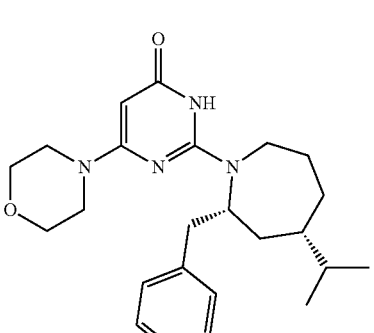  2-((2R,4S)-2-benzyl-4-isopropylazepan-1-yl)-6-morpholinopyrimidin-4(3H)-one | Intermediate 22 | Method F | LCMS (ES+) 411 (M + H)+, RT 3.84 min (Analytical Method A); MIXTURE OF ENANTIOMERS Not a full NH $^1$H NMR (400 MHz, DMSO) 10.04 (1H, br s), 7.22-7.08 (5H, m), 4.71 (1H, s), 3.79-3.79 (1H, m), 3.59-3.53 (4H, m), 3.36-3.29 (4H, m), 2.96-2.96 (1H, m), 2.81-2.71 (1H, m), 2.63-2.57 (1H, m), 1.74-1.63 (1H, m), 1.59-1.52 (2H, m), 1.47-1.41 (2H, m), 1.27-1.21 (3H, m), 0.67 (6H, dd, J = 5.9, 13.0 Hz). |

| Example | Structure and Name | Amine | Displacement conditions | Analytical data |
| --- | --- | --- | --- | --- |
| Example 242 | (R)-2-(2-benzyl-4,4-dimethylazepan-1-yl)-6-morpholinopyrimidin-4(3H)-one | Intermediate 20 | Method F | LCMS (ES+) 397 (M + H)+, RT 3.45 min (Analytical Method B) RT 2.08 min (Analytical Method SFC4, LUX CELLULOSE-3 15% MeOH SOL3 (0.1% DEA)/$CO_2$); $^1$H NMR (400 MHz, DMSO, 125° C.) 7.25-7.14 (5H, m), 4.85 (1H, s), 4.70-4.64 (1H, m), 4.03-4.00 (1H, m), 3.64 (4H, dd, J = 5.0, 5.0 Hz), 3.42-3.39 (4H, m), 2.92-2.69 (2H, m), 1.68-1.45 (4H, m), 1.38-1.18 (3H, m), 0.87 (3H, s), 0.76 (3H, s). |
| Example 243 | (S)-2-(2-benzyl-4,4-dimethylazepan-1-yl)-6-morpholinopyrimidin-4(3H)-one | Intermediate 20 | Method F | LCMS (ES+) 397 (M + H)+, RT 3.45 min (Analytical Method B); RT 0.97 min (Analytical Method SFC4, LUX CELLULOSE-3 15% MeOH SOL3 (0.1% DEA)/$CO_2$); $^1$H NMR (400 MHz, DMSO, 125° C.) 7.25-7.12 (5H, m), 4.83 (1H, d, J = 10.4 Hz), 4.65 (1H, dd, J = 9.7, 24.6 Hz), 4.04-3.94 (1H, m), 3.66-3.63 (4H, m), 3.43-3.39 (4H, m), 2.90-2.64 (2H, m), 1.65-1.18 (7H, m), 0.87 (3H, s), 0.76 (3H, s). |
| Example 244 | (S)-2-(2-benzyl-4,4-difluoroazepan-1-yl)-6-morpholinopyrimidin-4(3H)-one | Intermediate 21 | Method F | LCMS (ES+) 405 (M + H)+, RT 3.10 min (Analytical Method B) RT 2.38 min (Analytical Method SFC4, LUX CELLULOSE-3, 15/85 MeOH (0.1% DEAISO)/$CO_2$); $^1$H NMR (400 MHz, CDCl$_3$): δ 7.31-7.22 (3H, m), 7.14 (2H, d, J = 7.5 Hz), 4.94-4.71 (2H, m), 4.01-3.90 (1H, m), 3.76 (4H, t, J = 4.7 Hz), 3.56-3.48 (4H, m), 2.90-2.82 (3H, m), 2.42-2.06 (3H, m), 1.88-1.66 (3H, m), NH not observed. |

-continued

| Example | Structure and Name | Amine | Displacement conditions | Analytical data |
|---|---|---|---|---|
| Example 245 | 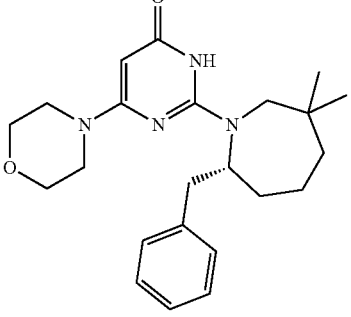<br>2-[(2R)-2-benzyl-6,6-dimethyl-azepan-1-yl]-4-morpholino-1H-pyrimidin-6-one | Intermediate 29 | Method F | LCMS (ES+) 397 (M + H)$^+$, RT 3.51 min (Analytical Method A); RT 2.14 min (Analytical Method SFC1, LUX CELLULOSE-C, 55/45 IPA (0.1% DEAISO)/CO$_2$); $^1$H NMR (400 MHz, CDCl$_3$): δ 7.29-7.18 (3H, m), 7.12 (2H, d, J = 6.8 Hz), 4.93 (1H, s), 4.81-4.60 (1H, m), 3.80-3.73 (4H, m), 3.58-3.33 (5H, m), 2.91-2.86 (2H, m), 2.69 (1H, dd, J = 8.6, 12.9 Hz), 2.01-1.95 (1H, m), 1.67-1.25 (4H, m), 1.18-1.10 (1H, m), 0.91 (6H, d, J = 21.7 Hz), NH not observed. |
| Example 246 | 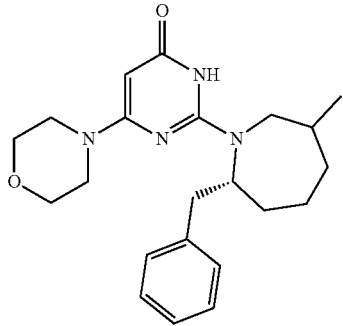<br>2-((2R)-2-benzyl-6-methylazepan-1-yl)-6-morpholinopyrimidin-4(3H)-one stereoisomer 2 | Intermediate 31 | Method F | LCMS (ES+) 383 (M + H)$^+$, RT 3.36 min (Analytical Method By, RT 1.70 min (Analytical Method SFC4, YMC AMYLOSE-C, 30/70 IPA (0.1% DEAISO)/CO$_2$); $^1$H NMR (400 MHz, CDCl$_3$): δ 9.92 (1H, br s), 7.27-7.16 (3H, m), 7.12 (2H, d, J = 7.1 Hz), 4.93 (1H, s), 4.40-4.38 (1H, m), 3.79-3.73 (4H, m), 3.67-3.47 (5H, m), 3.30-3.15 (1H, m), 3.04-3.00 (1H, m), 2.77 (1H, dd, J = 7.8, 13.1 Hz), 2.02-2.01 (1H, m), 1.92-1.88 (1H, m), 1.57-1.38 (5H, m), 0.90 (3H, d, J = 7.1 Hz) |
| Example 247 | 2-((2R)-2-benzyl-6-methylazepan-1-yl)-6-morpholinopyrimidin-4(3H)-one stereoisomer 1 | Intermediate 30 | Method F | LCMS (ES+) 383 (M + H)$^+$, RT 3.36 min (Analytical Method By RT 1.21 min (Analytical Method SFC4, YMC AMYLOSE-C, 30/70 IPA (0.1% DEAISO)/CO$_2$); $^1$H NMR (400 MHz, CDCl$_3$): δ 8.63 (1H, br s), 7.29-7.17 (3H, m), 7.14 (2H, d, J = 6.8 Hz), 4.92-4.71 (2H, m), 3.77-3.71 (4H, m), 3.56-3.20 (5H, m), 2.87-2.73 (3H, m), 2.00-1.99 (1H, m), 1.84 (1H, d, J = 12.1 Hz), 1.77-1.62 (2H, m), 1.43-1.39 (1H, m), 1.28-1.17 (1H, m), 0.99-0.89 (4H, m). |

| Example | Structure and Name | Amine | Displacement conditions | Analytical data |
|---|---|---|---|---|
| Example 248 | 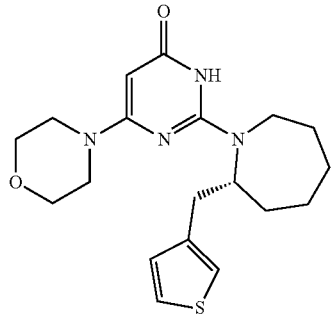<br>(R)-6-morpholino-2-(2-(thiophen-3-ylmethyl)azepan-1-yl)pyrimidin-4(3H)-one | Intermediate 26 | Method F | LCMS (ES+) 375 (M + H)+, RT 3.28 min (Analytical Method A); RT 0.94 min (Analytical Method SFC4, YMC AMYLOSE-C, 50/50 MeOH (0.1% DEAISO)/$CO_2$); $^1$H NMR δ (ppm) (400 MHz, $CDCl_3$) 9.04 (1H, s), 7.27-7.23 (1H, m, partially obscured by chloroform), 6.95-6.88 (2H, m), 4.91 (1H, s), 4.78-4.47 (1H, m), 3.76-3.73 (4H, m), 3.56-3.45 (5H, m), 2.94-2.84 (3H, m), 2.11-2.02 (1H, m), 1.82-1.71 (3H, m), 1.53-1.40 (2H, m), 1.30-1.14 (2H, m). |
| Example 249 | 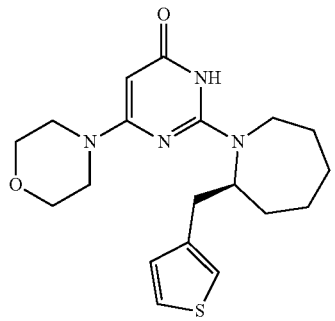<br>(S)-6-morpholino-2-(2-(thiophen-3-ylmethyl)azepan-1-yl)pyrimidin-4(3H)one | Intermediate 26 | Method F | LCMS (ES+) 375 (M + H)+, RT 3.28 min (Analytical Method A); RT 2.03 min (Analytical Method SFC4, YMC AMYLOSE-C, 50/50 MeOH (0.1% DEAISO)/$CO_2$); $^1$H NMR δ (ppm) (400 MHz, $CDCl_3$) 7.27-7.23 (1H, m, partially obscured by chloroform), 6.95-6.88 (2H, m), 4.91 (1H, s), 4.78-4.47 (1H, m), 3.76-3.73 (4H, m), 3.56-3.45 (5H, m), 2.94-2.84 (3H, m), 2.11-2.02 (1H, m), 1.82-1.71 (3H, m), 1.53-1.40 (2H, m), 1.30-1.14 (2H, m). |

Example 250: 6-morpholino-2-((S)-2-((S)-1-phenyl-ethyl)pyrrolidin-1-yl)pyrimidin-4(3H)-one),
Example 251: 6-morpholino-2-((R)-2-((R)-1-phenylethyl)pyrrolidin-1-yl)pyrimidin-4(3H)-one, and
Example 252: 6-morpholino-2-((R*)-2(S*)-1-phenylethyl)pyrrolidin-1-yl)pyrimidin-4(3H)-one

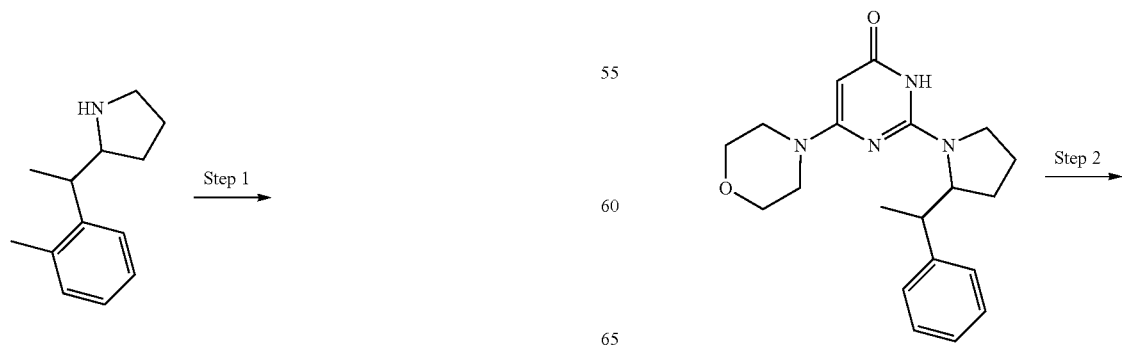

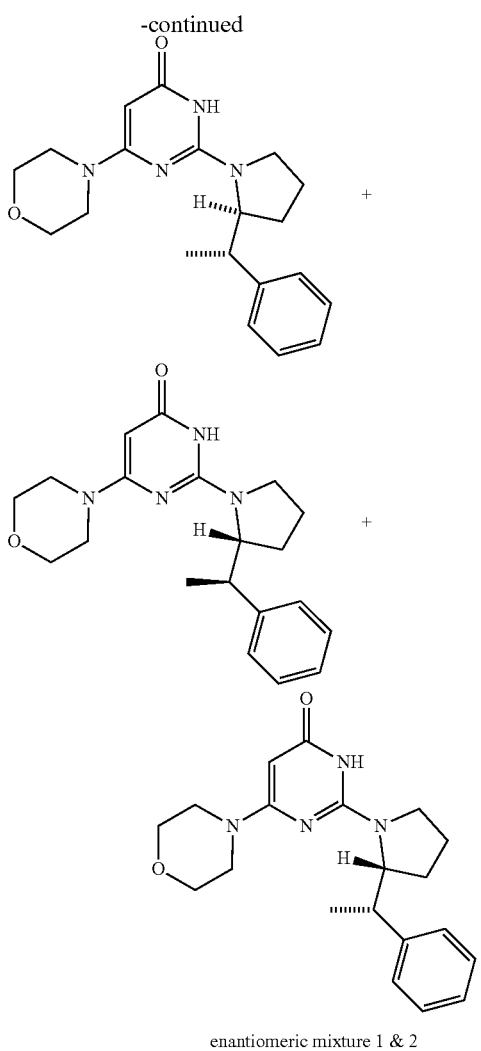

enantiomeric mixture 1 & 2

Step 1: 4-(6-((4-methoxybenzyl)oxy)-2-(2-(1-phenylethyl)pyrrolidin-1-yl)pyrimidin-4-yl)morpholine Following Method F from 4-(6-((4-methoxybenzyl)oxy)-2-(methylthio)pyrimidin-4-yl)morpholine (270 mg, 0.71 mmol, Scaffold 4) and 2-(1-phenylethyl)pyrrolidine (143 mg, 0.82 mmol). The reaction was heated for 16 h. After cooling to r.t., the mixture was diluted with 5 mL water and 5 mL EtOAc. The tube was shaken to dissolve all solids and the layers separated. The organic layer was dried (Na₂SO₄) and concentrated. The residue was purified by silica gel column chromatography (gradient elution, 0-100% EtOAc/iso-hexane) to give the title compound as a mixture of diastereomers.

Step 2: 6-morpholino-2-((S)-2-((S)-1-phenylethyl)pyrrolidin-1-yl)pyrimidin-4(3H)-one, 6-morpholino-2-((R)-2-((R)-1-phenylethyl)pyrrolidin-1-yl)pyrimidin-4(3H)-one and 6-morpholino-2-((R*)-2-((S*)-1-phenylethyl)pyrrolidin-1-yl)pyrimidin-4(3H)-one Following Method H from 4-(6-((4-methoxybenzyl)oxy)-2-(2-(1-phenylethyl)pyrrolidin-1-yl)pyrimidin-4-yl)morpholine (79 mg, 0.17 mmol). Successive purifications by reverse phase HPLC and chiral SFC gave the title compounds.

6-morpholino-2-((S)-2-((S)-1-phenylethyl)pyrrolidin-1-yl)pyrimidin-4(3H)-one: LCMS (ES+) 355 (M+H)+, RT 3.13 min (10 cm_Bicarb_AQ); RT 6.16 min (Analytical method SFC4, YMC AMYLOSE-C, 10/90 MeOH (0.1% DEAISO)/CO₂); $^1$H NMR (400 MHz, CDCl₃): δ 9.17 (1H, s), 7.34-7.19 (5H, m), 4.93 (1H, s), 4.39 (1H, d, J=3.5 Hz), 3.75 (4H, dd, J=4.8, 4.8 Hz), 3.54 (7H, dd, J=4.7, 9.2 Hz), 2.02-1.88 (3H, m), 1.78-1.70 (1H, m), 1.23 (3H, d, J=7.3 Hz).

6-morpholino-2-((R)-2-((R)-1-phenylethyl)pyrrolidin-1-yl)pyrimidin-4(3H)-one: LCMS (ES+) 355 (M+H)+, RT 3.13 min (10 cm_Formic_AQ); RT 8.23 min (Analytical method SFC4, YMC AMYLOSE-C, 10/90 MeOH (0.1% DEAISO)/CO₂); $^1$H NMR (400 MHz, CDCl₃): δ 9.17 (1H, s), 7.34-7.19 (5H, m), 4.93 (1H, s), 4.39 (1H, d, J=3.5 Hz), 3.75 (4H, dd, J=4.8, 4.8 Hz), 3.54 (7H, dd, J=4.7, 9.2 Hz), 2.02-1.88 (3H, m), 1.78-1.70 (1H, m), 1.23 (3H, d, J=7.3 Hz).

6-morpholino-2-((R*)-2-((S*)-1-phenylethyl)pyrrolidin-1-yl)pyrimidin-4(3H)-one enantiomeric mixture 1 & 2: LCMS (ES+) 355 (M+H)+, RT 3.18 min (10 cm_Bicarb_AQ); $^1$H NMR (400 MHz, CDCl₃): δ 8.93 (1H, s), 7.30-7.10 (5H, m), 4.98 (1H, s), 4.40-4.36 (1H, m), 3.76 (4H, dd, J=4.8, 4.8 Hz), 3.63-3.46 (5H, m), 3.31-3.25 (1H, m), 3.16-3.09 (1H, m), 1.84-1.77 (2H, m), 1.66 (1H, d, J=5.8 Hz), 1.32 (3H, d, J=7.3 Hz), 1.11-0.99 (1H, m).

Example 253: (S)-2-(2-benzyl-3,3-difluoropyrrolidin-1-yl)-6-morpholinopyrimidin-4(3H)-one

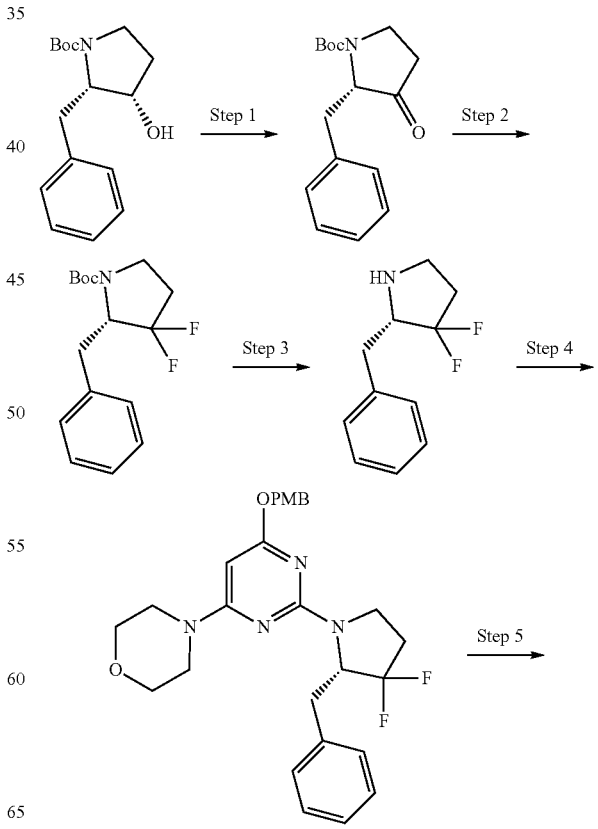

-continued

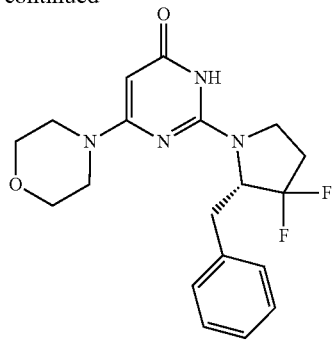

Step 1: tert-butyl (S)-2-benzyl-3-oxopyrrolidine-1-carboxylate

Dess Martin (4.95 g, 11.7 mmol) was added to tert-butyl (2S,3S)-2-benzyl-3-hydroxypyrrolidine-1-carboxylate (2.69 g, 9.7 mmol, prepared according to the procedure reported in Perkin Trans. 1, 2001, 1421-1430) in DCM (98 mL) at 0° C. and the reaction was warmed to r.t. After 25.5 h the reaction was diluted with brine and EtOAc. The organic layer was washed with sodium thiosulfate, dried (Na2SO4), filtered and concentrated under reduced pressure. The residue was purified by silica gel column chromatography (gradient elution, 7-60% ethyl acetate in iso-hexane) to afford the title compound.

Step 2: tert-butyl (S)-2-benzyl-3,3-difluoropyrrolidine-1-carboxylate

50% Deoxofluor in THF (2.22 mL, 5.22 mmol) was added dropwise to a solution of tert-butyl (S)-2-benzyl-3-oxopyrrolidine-1-carboxylate (288 mg, 1.04 mmol) in DCM (10 mL) at 0° C. After complete addition reaction was warmed to rt and stirred for 18 h. The reaction was cooled in an ice-bath and quenched by addition of saturated NaHCO$_3$. The aqueous layer was extracted with DCM and the layers separated using a phase separator. The DCM was removed in vacuo to give a residue oil, which was purified by silica chromatography (gradient elution, 0-20% EtOAc/isohexane) yielded of the title compound.

Step 3: (S)-2-benzyl-3,3-difluoropyrrolidine tert-Butyl (S)-2-benzyl-3,3-difluoropyrrolidine-1-carboxylate (320 mg, 1.1 mmol) was dissolved in 4M hydrochloric acid in dioxane (10 mL) and stirred at rt for 2 h. The solvent was removed in vacuo to give a residue, which was dissolved in DCM and washed with saturated NaHCO$_3$. The layers were separated using a phase separator and the DCM layer concentrated in vacuo to give the title compound.

Step 4: (S)-4-(2-(2-benzyl-3,3-difluoropyrrolidin-1-yl)-6-((4-methoxybenzyl)oxy)pyrimidin-4-yl)morpholine Following Method F from 4-(6-((4-methoxybenzyl)oxy)-2-(methylthio)pyrimidin-4-yl)morpholine (270 mg, 0.71 mmol, Scaffold 4) and (S)-2-benzyl-3,3-difluoropyrrolidine (143 mg, 0.82 mmol).

Step 5: (S)-2-(2-benzyl-3,3-difluoropyrrolidin-1-yl)-6-morpholinopyrimidin-4(3H)-one Following Method H from (S)-4-(2-(2-benzyl-3,3-difluoropyrrolidin-1-yl)-6-((4-methoxybenzyl)oxy)pyrimidin-4-yl)morpholine (79 mg, 0.17 mmol). LCMS (ES+) 377 (M+H)+, RT 3.07 min (Analytical Method B); RT 2.82 min (Analytical Method SFC4, LUX CELLULOSE-3, 55/45 MeOH (0.1% DEAISO)/CO$_2$); $^1$H NMR (400 MHz, CDCl$_3$): δ 7.28-7.20 (3H, m), 7.14 (2H, d, J=7.8 Hz), 4.96 (1H, s), 4.69-4.63 (1H, m), 3.73 (4H, t, J=5.1 Hz), 3.54-3.43 (6H, m), 3.33 (1H, dd, J=6.1, 14.2 Hz), 2.98 (1H, td, J=2.8, 14.2 Hz), 2.30-2.20 (1H, m), 1.84-1.66 (1H, m), NH not observed.

Example 254: 2-((2S,3S)-2-benzyl-3-methoxy-3-methylpyrrolidin-1-yl)-6-morpholinopyrimidin-4(3H)-one

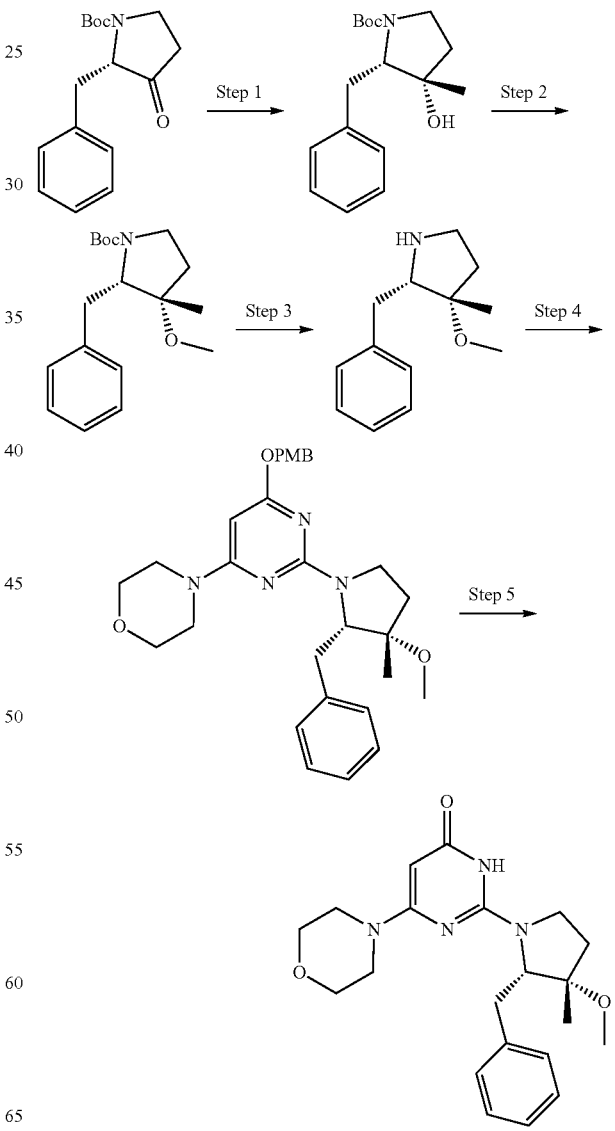

Step 1: tert-butyl (2S,3S)-2-benzyl-3-hydroxy-3-methylpyrrolidine-1-carboxylate Cerium trichloride (1.30 g, 5.28 mmol) was suspended in THF (13 mL) at −78° C. Methyl magnesium bromide (1.41 mL, 4.8 mmol, 3.4 M solution in THF) was added dropwise over 30 minutes maintaining the temperature at −78° C. tert-Butyl (S)-2-benzyl-3-oxopyrrolidine-1-carboxylate (600 mg, 2.18 mmol) was dissolved in THF (13 mL) and cooled to −78° C. The solution was added dropwise to the suspension of cerium trichloride/methyl magnesium bromide. After complete addition the reaction was stirred at −78° C. for 40 min. The reaction was warmed to 0° C. over 3 h. After this time EtOAc was added and the suspension filtered through celite. THF was removed under reduced pressure and the residue was dissolved in EtOAc, washed with water, brine, dried (MgSO$_4$) and concentrated under reduced pressure. The residue was purified by silica gel column chromatography (gradient elution, 0-80% EtOAc/iso-hexane) to afford the title compound.

Step 2: tert-butyl (2S,3S)-2-benzyl-3-methoxy-3-methylpyrrolidine-1-carboxylate NaH (40 mg, 0.99 mmol, 60% dispersion in mineral oil) was added to tert-butyl (2S,3S)-2-benzyl-3-hydroxy-3-methylpyrrolidine-1-carboxylate (145 mg, 0.50 mmol) in DMF (1.4 mL) at 0° C. After 15 min iodomethane (39 µL, 0.62 mmol) was added and the reaction warmed to r.t. After 17 h the reaction was cooled to 0° C. and quenched with water. The mixture was transferred to a separation funnel, diluted with water and DCM. The layers were separated. The DCM layer was washed with brine, dried (phase separator) and concentrated under reduced pressure. The residue was purified by silica gel column chromatography (gradient elution, 0-80% EtOAc/iso-hexane) to afford the title compound.

Step 3: (2S,3S)-2-benzyl-3-methoxy-3-methylpyrrolidine tert-Butyl (2S,3S)-2-benzyl-3-methoxy-3-methylpyrrolidine-1-carboxylate (140 mg, 0.46 mmol) was dissolved in 4 M in dioxane HCl (3 mL). After 3 h the reaction was concentrated under reduced pressure. The crude material was purified by SCX column eluting with 3 CV DCM, 3 CV MeOH, 3 CV MeOH; 7 N NH$_3$ in MeOH (4:1). The ammonia fractions were combined and concentrated under reduced pressure to afford the title compound. Used without further purification in the next step.

Step 4: 4-(2-((2S,3S)-2-benzyl-3-methoxy-3-methylpyrrolidin-1-yl)-6-((4-methoxybenzyl)oxy)pyrimidin-4-yl)morpholine Following Method G starting from (2S,3S)-2-benzyl-3-methoxy-3-methylpyrrolidine (35 mg, 0.17 mmol) and 4-(6-((4-methoxybenzyl)oxy)-2-(methylsulfonyl)pyrimidin-4-yl)morpholine (60 mg, 0.16 mmol, scaffold 4). The crude material was used without further purification in the next step.

Step 5: 2-((2S,3S)-2-benzyl-3-methoxy-3-methylpyrrolidin-1-yl)-6-morpholinopyrimidin-4(3H)-one Following Method H from 4-(2-((2S,3S)-2-benzyl-3-methoxy-3-methylpyrrolidin-1-yl)-6-((4-methoxybenzyl)oxy)pyrimidin-4-yl)morpholine (0.16 mmol). Purified by preparative HPLC to afford the title compound. LCMS (ES+) 385 (M+H)$^+$, RT 3.07 min (Analytical Method A); $^1$H NMR (400 MHz, CDCl$_3$): δ 7.25-7.16 (5H, m), 4.88 (1H, s), 4.10 (1H, br s), 3.71 (4H, dd, J=4.8, 4.8 Hz), 3.49-3.35 (6H, m), 3.28 (3H, s), 3.17 (1H, dd, J=5.6, 13.7 Hz), 2.88-2.85 (1H, m), 1.88-1.80 (2H, m), 1.21 (3H, s), NH not observed

Example 255: 2-((2S,3S)-2-benzyl-3-hydroxypyrrolidin-1-yl)-6-morpholinopyrimidin-4(3H)-one

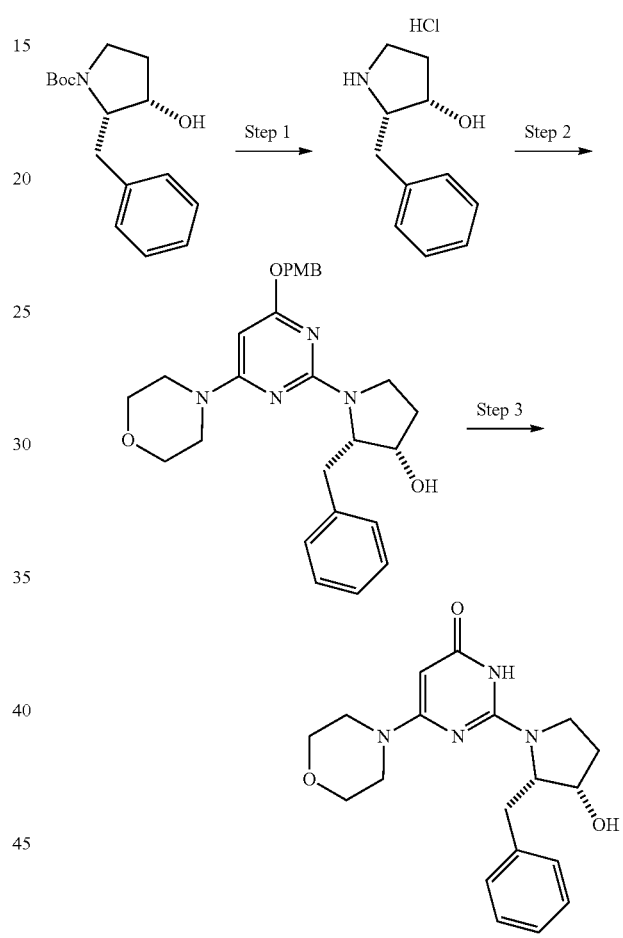

Step 1: (2S,3S)-2-benzylpyrrolidin-3-ol hydrochloride

A solution of tert-butyl (2S,3S)-2-benzyl-3-hydroxypyrrolidine-1-carboxylate (118 mg, 0.43 mmol) in 4 M HCl/dioxane (1 mL) was stirred at rt for 1.5 h. The solvent was removed by evaporation to give impure title compound, which was used without further purification.

Step 2: (2S,3S)-2-benzyl-1-(4-((4-methoxybenzyl)oxy)-6-morpholinopyrimidin-2-yl)pyrrolidin-3-ol Following Method G from 4-(6-((4-methoxybenzyl)oxy)-2-(methylsulfonyl)pyrimidin-4-yl)morpholine (165 mg, 0.43 mmol, scaffold 4) and (2S,3S)-2-benzylpyrrolidin-3-ol hydrochloride (95 mg). The reaction was stirred at 90° C. for 38 h. The title compound was obtained and was used without further purification.

Step 3: 2-((2S,3S)-2-benzyl-3-hydroxypyrrolidin-1-yl)-6-morpholinopyrimidin-4(3H)-one Following Method H from (2S,3S)-2-benzyl-1-(4-((4-methoxybenzyl)oxy)-6-morpholinopyrimidin-2-yl)pyrrolidin-3-ol (156 mg). The title compound was obtained. LCMS (ES+) 357 (M+H)+, RT 2.68 min (Analytical method A); $^1$H NMR (400 MHz, CDCl$_3$): δ 10.01 (1H, s), 7.30-7.18 (5H, m), 4.93 (1H, s), 4.49-4.34 (2H, m), 3.77-3.61 (5H, m), 3.56-3.44 (5H, m), 3.26 (1H, dd, J=4.4, 13.5 Hz), 3.01 (1H, dd, J=8.3, 13.6 Hz), 2.14-2.04 (1H, m), 1.92-1.82 (1H, m), one exchangeable not observed.

Example 256: 2-((2S,3R)-2-benzyl-3-(cyclopropylmethoxy)pyrrolidin-1-yl)-6-morpholino pyrimidin-4(3H)-one

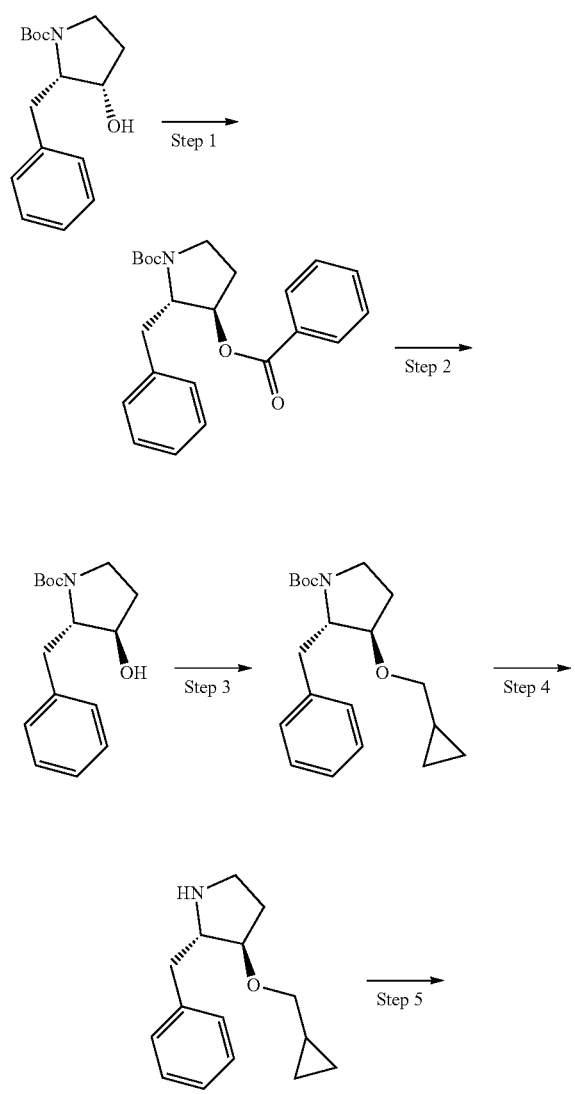

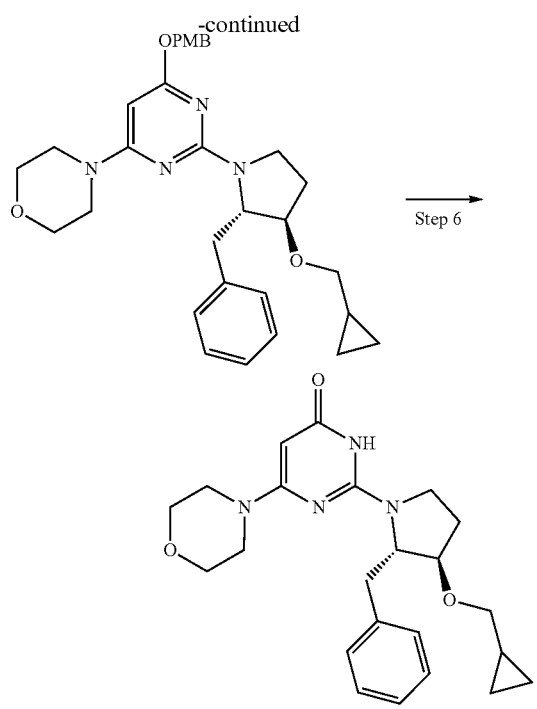

Step 1: tert-butyl (2S,3R)-3-(benzoyloxy)-2-benzylpyrrolidine-1-carboxylate tert-Butyl (2S,3S)-2-benzyl-3-hydroxypyrrolidine-1-carboxylate (940 mg, 3.39 mmol, *J. Chem. Soc., Perkin Trans 1*, 2001, 1421-1430) was dissolved in THF (20 mL) and cooled to 0° C. Triphenyl phosphine (1.16 g, 4.41 mmol), benzoic acid (538 mg, 4.41 mmol) and DIAD (868 µL, 4.41 mmol) were added sequentially. After 6 h the reaction mixture was concentrated under reduced pressure. Purified by silica gel column chromatography (gradient elution, 10-80% EtOAc/iso-hexane) to afford the title compound.

Step 2: tert-butyl (2S,3R)-2-benzyl-3-hydroxypyrrolidine-1-carboxylate

Lithium hydroxide (126 mg, 3.0 mmol) was added to tert-butyl (2S,3R)-3-(benzoyloxy)-2-benzylpyrrolidine-1-carboxylate (763 mg, 2.0 mmol) in methanol and water. The reaction was heated at 50° C. After 5 h the reaction was cooled to rt and the solvents removed under reduced pressure. The aqueous layer was extracted with DCM. The organic extract was dried (phase separator) and concentrated under reduced pressure to afford the product. Used without further purification in the next step.

Step 3: tert-butyl (2S,3R)-2-benzyl-3-(cyclopropylmethoxy)pyrrolidine-1-carboxylate NaH (63 mg, 1.59 mmol, 60% wt dispersion in mineral oil) was added to a solution of tert-butyl (2S,3R)-2-benzyl-3-hydroxypyrrolidine-1-carboxylate (220 mg, 0.79 mmol) in DMF (2 mL) at 0° C. After 15 min (bromomethyl)cyclopropane (92 µL, 0.95 mmol) was added and the reaction allowed to slowly warm to r.t. After 3 h the reaction was cooled to 0° C. and quenched with water. The solvent was removed under reduced pressure. The residue was dissolved in DCM and washed with water. The organic extract was dried (phase separator) and concentrated under reduced pressure. Purified by silica gel column chromatography (gradient elution, 5-40% EtOAc/iso-hexane) to afford the title compound.

Step 4: (2S,3R)-2-benzyl-3-(cyclopropylmethoxy)pyrrolidine tert-butyl (2S,3R)-2-benzyl-3-(cyclopropylmethoxy)pyrrolidine-1-carboxylate (184 mg, 0.56 mmol) was dissolved in 4 M HCl in dioxane (3.65 mL) and stirred at r.t. After 2 h the reaction was concentrated under reduced pressure. The residue was dissolved in DCM and washed with saturated NaHCO$_3$ (aq. solution). The organic extracts were dried (phase separator) and concentrated under reduced pressure to afford the product. Used without further purification in the next step.

Step 5: 4-(2-((2S,3R)-2-benzyl-3-(cyclopropylmethoxy)pyrrolidin-1-yl)-6-((4-methoxybenzyl)oxy)pyrimidin-4-yl)morpholine Following Method F from (2S,3R)-2-benzyl-3-(cyclopropylmethoxy)pyrrolidine (110 mg, 0.47 mmol) and 4-(6-((4-methoxybenzyl)oxy)-2-(methylsulfonyl)pyrimidin-4-yl)morpholine (167 mg, 0.44 mmol, Scaffold 4) heating for 70 h. Used in the next step without further purification.

Step 6: 2-((2S,3R)-2-benzyl-3-(cyclopropylmethoxy)pyrrolidin-1-yl)-6-morpholinopyrimidin-4(3H)-one Following Method H from 4-(2-((2S,3R)-2-benzyl-3-(cyclopropylmethoxy)pyrrolidin-1-yl)-6-((4-methoxybenzyl)oxy) pyrimidin-4-yl)morpholine (0.44 mmol) stirring for 1 h. The crude material was purified by reverse phase preparative HPLC and freeze dried from acetonitrile to afford the title compound.

2-((2S,3R)-2-benzyl-3-(cyclopropylmethoxy)pyrrolidin-1-yl)-6-morpholino pyrimidin-4(3H)-one: LCMS (ES+) 411 (M+H)$^+$, RT 3.47 min (Analytical Method A); $^1$H NMR (400 MHz, DMSO) 10.34 (1H, s), 7.42-7.36 (2H, m), 7.33-7.26 (3H, m), 4.89 (1H, s), 4.35 (1H, s), 3.85 (1H, s), 3.71 (4H, dd, J=4.7, 4.7 Hz), 3.64-3.58 (1H, m), 3.51 (4H, dd, J=4.9, 4.9 Hz), 3.15-3.08 (2H, m), 2.99 (1H, dd, J=7.1, 10.6 Hz), 2.64-2.59 (2H, m, under DMSO peak), 2.06-2.04 (2H, m), 0.86-0.78 (1H, m), 0.38 (2H, dd, J=1.8, 8.1 Hz), 0.07--0.05 (2H, m).

Example 257: 2-((2S,3R)-2-benzyl-3-methoxypyrrolidin-1-yl)-6-morpholinopyrimidin-4(3H)-one

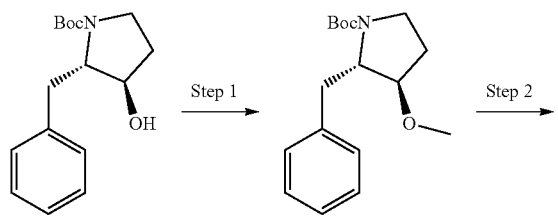

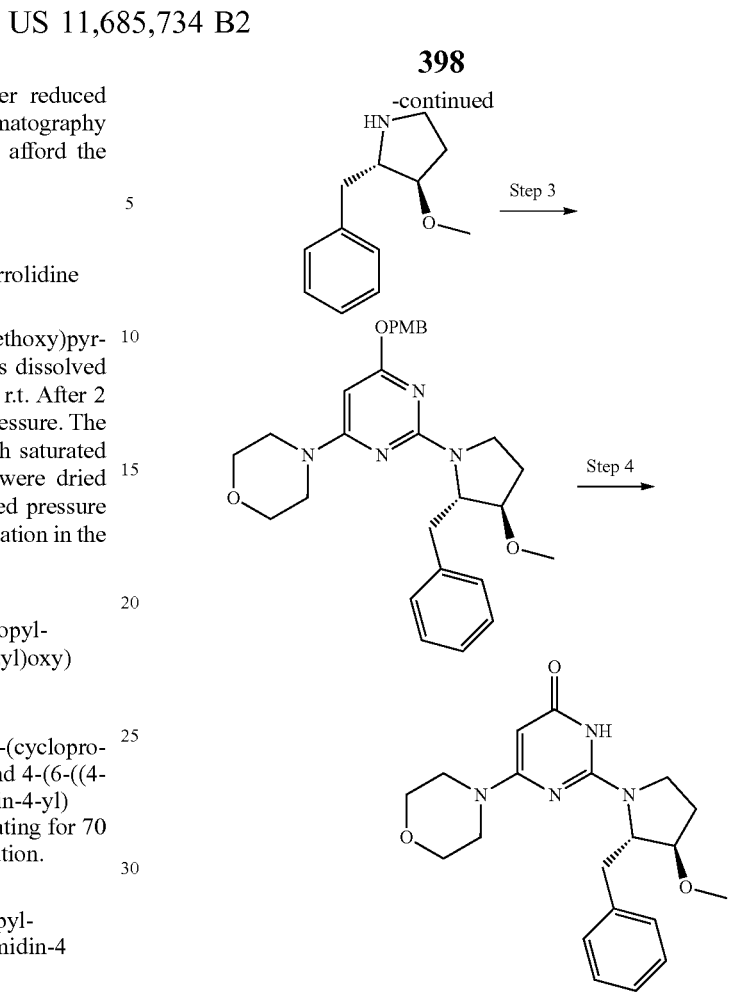

Step 1: tert-butyl (2S,3R)-2-benzyl-3-methoxypyrrolidine-1-carboxylate

NaH (43 mg, 1.08 mmol, 60% dispersion in mineral oil) was added to tert-butyl (2S,3R)-2-benzyl-3-hydroxypyrrolidine-1-carboxylate (150 mg, 0.54 mmol, Example 256 step 2) in DMF (1.4 mL) at 0° C. After 15 min Iodomethane (42 μL, 0.68 mmol) was added and the reaction warmed to r.t. After 4 h the reaction was cooled to 0° C. and quenched with water. The mixture was diluted with DCM. The layers were separated and the DCM layer washed with brine, dried (phase separator) and concentrated under reduced pressure. The crude material was purified by silica gel column chromatography (gradient elution, 5-40% EtOAc/DCM) to afford the title compound.

Step 2: (2S,3R)-2-benzyl-3-methoxypyrrolidine

4 M in dioxane Hydrochloric acid (3 mL) was added to tert-butyl (2S,3R)-2-benzyl-3-methoxypyrrolidine-1-carboxylate (140 mg, 0.48 mmol). After 3 h the reaction was concentrated under reduced pressure. The crude material was purified by SCX column to afford the title compound.

Step 3: 4-(2-((2S,3R)-2-benzyl-3-methoxypyrrolidin-1-yl)-6-((4-methoxybenzyl)oxy)pyrimidin-4-yl)morpholine Following Method G from (2S,3R)-2-benzyl-3-methoxypyrrolidine (55 mg, 0.29 mmol) and 4-(6-((4-methoxybenzyl)oxy)-2-(methylsulfonyl)pyrimidin-4-yl)morpholine (101 mg, 0.27 mmol, scaffold 4). Used without further purification in the next step.

Step 4: 2-((2S,3R)-2-benzyl-3-methoxypyrrolidin-1-yl)-6-morpholinopyrimidin-4(3H)-one Following Method H from 4-(2-((2S,3R)-2-benzyl-3-methoxypyrrolidin-1-yl)-6-((4-methoxybenzyl)oxy)pyrimidin-4-yl)morpholine ("0.27 mmol"). The crude material was purified by preparative HPLC to afford the resulting product. LCMS (ES+) 371 (M+H)+, RT 2.99 min (Analytical Method B); $^1$H NMR (400 MHz, CDCl$_3$): δ 7.33-7.28 (2H, m), 7.25-7.21 (1H, m), 7.18 (2H, d, J=7.1 Hz), 4.96 (1H, s), 4.45 (1H, dd, J=3.5, 9.6 Hz), 3.79-3.71 (4H, m), 3.68 (1H, d, J=4.0 Hz), 3.64-3.48 (6H, m), 3.26-3.17 (1H, m), 3.12 (3H, s), 2.59 (1H, dd, J=9.6, 13.6 Hz), 2.11 (1H, dd, J=6.8, 13.6 Hz), 1.95-1.84 (1H, m), NH not observed.

Example 258: 2-((2S,3R)-2-benzyl-3-hydroxypyrrolidin-1-yl)-6-morpholinopyrimidin-4(3H)-one

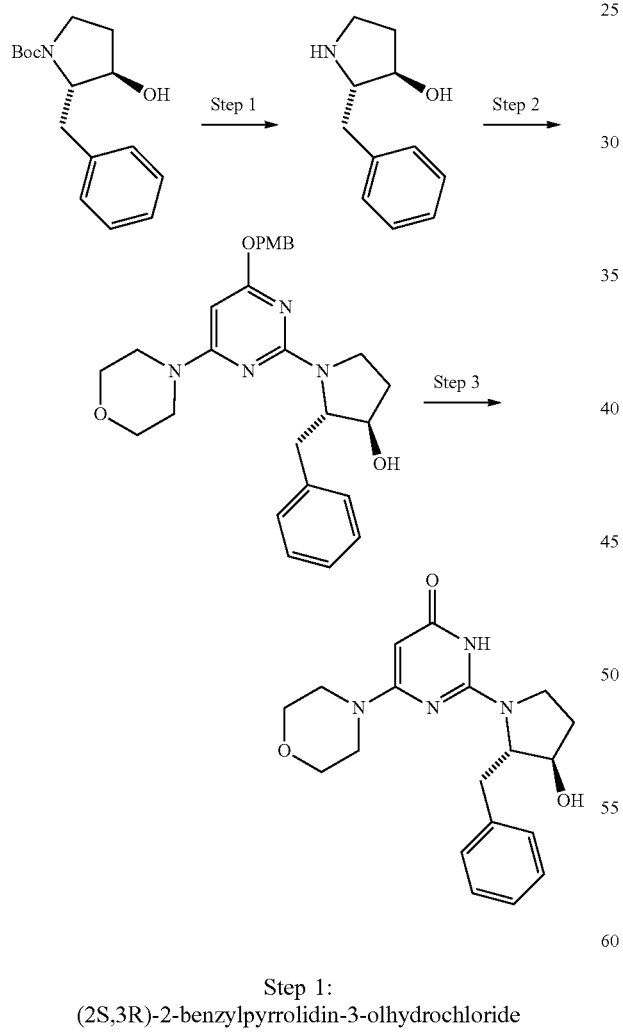

Step 1: (2S,3R)-2-benzylpyrrolidin-3-ol hydrochloride

A solution of tert-butyl (2S,3R)-2-benzyl-3-hydroxypyrrolidine-1-carboxylate (125 mg, 0.45 mmol, Example 256 step 2) in 4 M HCl in dioxane (1 mL) was stirred at rt for 1.5 h. The solvent was removed by evaporation to give impure title compound, which was used without further purification.

Step 2: (2S,3R)-2-benzyl-1-(4-((4-methoxybenzyl)oxy)-6-morpholinopyrimidin-2-yl)pyrrolidin-3-ol Following Method G from 4-(6-((4-methoxybenzyl)oxy)-2-(methylsulfonyl)pyrimidin-4-yl)morpholine (194 mg, 0.51 mmol, scaffold 4) and (2S,3R)-2-benzylpyrrolidin-3-ol hydrochloride (111 mg). The reaction was stirred at 90° C. for 38 h. The title compound was obtained and used without further purification.

Step 3: 2-((2S,3R)-2-benzyl-3-hydroxypyrrolidin-1-yl)-6-morpholinopyrimidin-4(3H)-one Following Method H from (2S,3R)-2-benzyl-1-(4-((4-methoxybenzyl)oxy)-6-morpholinopyrimidin-2-yl)pyrrolidin-3-ol (220 mg). The title compound was obtained. LCMS (ES+) 357 (M+H)+, RT 2.75 min (Analytical method B); $^1$H NMR (400 MHz, CDCl$_3$) 9.97 (1H, br s), 7.31-7.27 (2H, m), 7.25-7.21 (1H, m), 7.16 (2H, d, J=6.8 Hz), 4.93 (1H, s), 4.37 (1H, dd, J=4.1, 9.3 Hz), 4.23 (1H, d, J=1.8 Hz), 3.74 (4H, dd, J=4.8, 4.8 Hz), 3.72-3.56 (2H, m), 3.56-3.50 (4H, m), 3.17 (1H, dd, J=3.8, 13.7 Hz), 2.62-2.54 (1H, m), 2.03-1.95 (2H, m), one exchangeable proton not observed.

Example 259: 2-((2S,3R)-2-benzyl-3-(cyclopropylmethoxy)pyrrolidin-1-yl)-6-morpholinopyrimidin-4(3H)-one

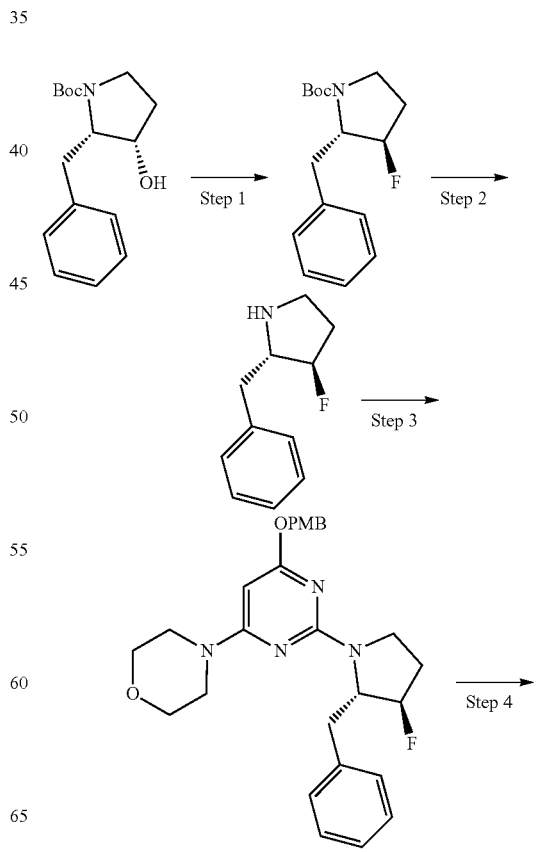

-continued

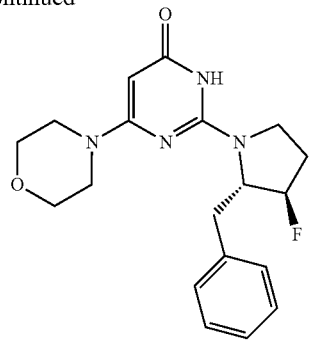

Step 1: tert-butyl (2S,3R)-2-benzyl-3-fluoropyrrolidine-1-carboxylate

DAST (417 µL, 3.15 mmol) was added dropwise to a solution of tert-butyl (2S,3S)-2-benzyl-3-hydroxypyrrolidine-1-carboxylate (400 mg, 1.44 mmol, prepared according to the procedure reported in Perkin Trans. 1, 2001, 1421-1430) in DCM (22 mL) at −78° C. After complete addition the reaction temperature was maintained at −78° C. for 2 h before warming to r.t. After 18 h the reaction was cooled to 0° C. and cautiously quenched with saturated NaHCO$_3$ (aq. solution) and the layers separated. The organic extracts were dried (phase separator) and concentrated under reduced pressure. Purified by silica gel column chromatography (gradient elution, 0-20% EtOAc/iso-hexane) to afford the title compound.

Step 2: (2S,3R)-2-benzyl-3-fluoropyrrolidine tert-butyl (2S,3R)-2-benzyl-3-fluoropyrrolidine-1-carboxylate (193 mg, 0.69 mmol) was dissolved in 4M HCl in dioxane (4.5 mL). After 2.5 h the reaction was concentrated under reduced pressure. The residue was dissolved in DCM and washed with saturated NaHCO$_3$ (aq. solution). The organic extracts were dried (phase separator) and concentrated under reduced pressure to afford the title compound.

Step 3: 4-(2-((2S,3R)-2-benzyl-3-fluoropyrrolidin-1-yl)-6-((4-methoxybenzyl)oxy)pyrimidin-4-yl)morpholine Following Method F from (2S,3R)-2-benzyl-3-fluoropyrrolidine (50 mg, 0.28 mmol) and 4-(6-((4-methoxybenzyl)oxy)-2-(methylthio)pyrimidin-4-yl)morpholine (98 mg, 0.26 mmol, Scaffold 4). Used in the next step without further purification.

Step 4: 2-((2S,3R)-2-benzyl-3-fluoropyrrolidin-1-yl)-6-morpholinopyrimidin-4(3H)-one Following Method H from 4-(2-((2S,3R)-2-benzyl-3-fluoropyrrolidin-1-yl)-6-((4-methoxybenzyl)oxy)pyrimidin-4-yl)morpholine. The crude material was purified by reverse phase preparative HPLC to afford the title compound. LCMS (ES+) 359 (M+H)$^+$, RT 3.00 min (Analytical Method B); $^1$H NMR (400 MHz, DMSO): δ 10.39 (1H, s), 7.37-7.31 (2H, m), 7.25 (3H, dd, J=7.0, 7.0 Hz), 5.09-4.87 (2H, m), 4.50-4.41 (1H, m), 3.65 (5H, dd, J=4.8, 4.8 Hz), 3.48-3.39 (5H, m), 3.08 (1H, d, J=13.4 Hz), 2.66-2.59 (1H, m), 2.18-2.08 (2H, m).

Example 260: 2-((2R,3R)-2-benzyl-3-methylpyrrolidin-1-yl)-6-morpholinopyrimidin-4(3H)-one and Example 261: 2-((2S,3S)-2-benzyl-3-methylpyrrolidin-1-yl)-6-morpholinopyrimidin-4(3H)-one

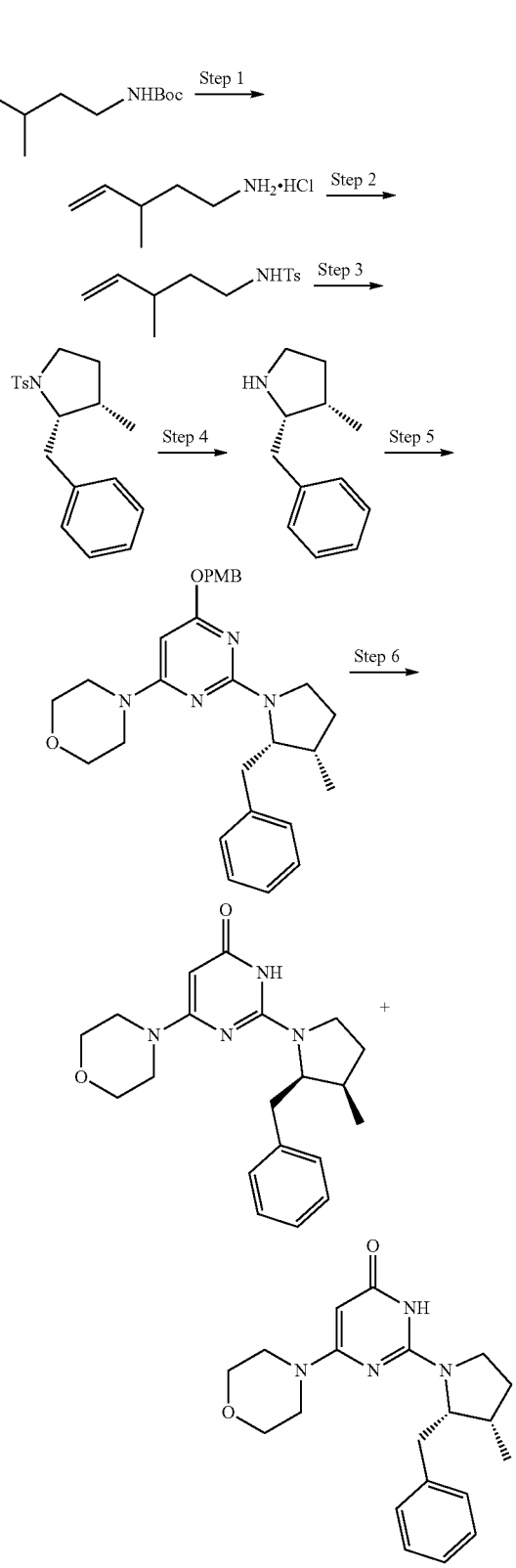

Step 1: 3-methylpent-4-en-1-amine hydrochloride

Hydrochloric acid (18.8 mL, 75.3 mmol, 4 M in dioxane) was added to tert-butyl (3-methylpent-4-en-1-yl)carbamate (1.50 g, 7.5 mmol) at r.t. After 2 h the reaction was concentrated under reduced pressure to the title compound. Used without further purification in the next step.

Step 2: 4-methyl-N-(3-methylpent-4-en-1-yl)benzenesulfonamide p-Toluenesulfonyl chloride (1.39 g, 7.31 mmol) was added to a solution of 3-methylpent-4-en-1-amine hydrochloride (991 mg, 7.31 mmol) and pyridine (1.8 mL, 21.9 mmol) in DCM (15 mL). After 24 h the reaction was diluted with water and extracted with Et$_2$O (×3). The combined organic extracts were washed with brine, dried (phase separator) and concentrated under reduced pressure. The crude material was purified by silica gel column chromatography (gradient elution, 5-40% EtOAc/iso-hexane) to afford the title compound.

Step 3: (2R*,3R*)-2-benzyl-3-methyl-1-tosylpyrrolidine

Prepared following the procedure described in Advanced Synthesis & Catalysis, 2015, 357(10), 2339-2344 from 4-methyl-N-(3-methylpent-4-en-1-yl)benzenesulfonamide (500 mg, 1.97 mmol) and phenyl trifluoromethanesulfonate (0.64 mL, 3.95 mmol). After 24 h the reaction was cooled to rt and diluted with NH$_4$Cl and ethyl acetate. The layers were separated and the aqueous layer extracted with EtOAc. The combined organic extracts were dried (phase separator) and concentrated under reduced pressure. The crude material was purified by silica gel column chromatography (gradient elution, 0-40% EtOAc/iso-hexane) to afford the title compound.

Step 4: (2R*,3R*)-2-benzyl-3-methylpyrrolidine

LiAlH$_4$ (4.2 mL, 4.3 mmol, 1.0 M in THF) was added dropwise to (2R*,3R*)-2-benzyl-3-methyl-1-tosylpyrrolidine (350 mg, 1.06 mmol) in THF (4 mL) at 0° C. After complete addition the reaction mixture was heated at reflux. After 22 h the reaction was cooled to rt then 0° C. The reaction was cautiously quenched with water followed by sodium hydroxide. After 5 minutes the reaction was filtered through celite, washing with Et$_2$O. The solvents were concentrated under reduced pressure and purified by SCX column to afford the title compound.

Step 5: 4-(2-((2R*,3R*)-2-benzyl-3-methylpyrrolidin-1-yl)-6-((4-methoxybenzyl)oxy)pyrimidin-4-yl)morpholine Following Method G from (2R*,3R*)-2-benzyl-3-methylpyrrolidine (111 mg, 0.63 mmol) and 4-(6-((4-methoxybenzyl)oxy)-2-(methylsulfonyl)pyrimidin-4-yl)morpholine (222 mg, 0.59 mmol, scaffold 4). Used in the next step without further purification.

Step 6: 2-((2R,3R)-2-benzyl-3-methylpyrrolidin-1-yl)-6-morpholinopyrimidin-4(3H)-one and 2-((2S,3S)-2-benzyl-3-methylpyrrolidin-1-yl)-6-morpholinopyrimidin-4(3H)-one Following Method H from 4-(2-((2R*,3R*)-2-benzyl-3-methylpyrrolidin-1-yl)-6-((4-methoxybenzyl)oxy)pyrimidin-4-yl)morpholine (278 mg, 0.59 mmol). Purified by preparative HPLC to separate the diastereomers followed by SFC for the separation of the enantiomers. Structure confirmed by NMR analysis.

2-((2R,3R)-2-benzyl-3-methylpyrrolidin-1-yl)-6-morpholinopyrimidin-4(3H)-one: LCMS (ES+) 355 (M+H)$^+$, RT 3.18 min (Analytical Method B); RT 6.26 min (Analytical Method SFC4, LUX CELLULOSE-4+0.1% DEAISO 25% MeOH SOL3); $^1$H NMR (400 MHz, CDCl3) 7.26-7.23 (2H, m, under CDCl3), 7.22-7.15 (3H, m), 4.84 (1H, s), 4.41 (1H, s), 3.71-3.66 (4H, m), 3.52-3.36 (6H, m), 2.93 (1H, dd, J=6.3, 13.9 Hz), 2.79 (1H, dd, J=5.7, 13.5 Hz), 2.39-2.29 (1H, m), 2.07-1.99 (1H, m), 1.74-1.64 (1H, m, under water peak), 1.09 (3H, d, J=6.8 Hz). NH not observed.

2-((2S,3S)-2-benzyl-3-methylpyrrolidin-1-yl)-6-morpholinopyrimidin-4(3H)-one: LCMS (ES+) 355 (M+H)$^+$, RT 3.18 min (Analytical Method B); RT 5.36 min (Analytical Method SFC4, LUX CELLULOSE-4+0.1% DEAISO 25% MeOH SOL3); $^1$H NMR (400 MHz, CDCl$_3$): δ 7.25-7.21 (2H, m), 7.21-7.15 (3H, m), 4.85 (1H, s), 4.43 (1H, s), 3.68 (4H, dd, J=4.4, 4.4 Hz), 3.57-3.50 (1H, m), 3.48-3.35 (5H, m), 2.92 (1H, dd, J=6.6, 14.1 Hz), 2.84-2.76 (1H, m), 2.38-2.29 (1H, m), 2.07-2.00 (1H, m), 1.73-1.64 (1H, m, under water peak), 1.08 (3H, d, J=7.1 Hz) NH not observed.

Example 262: (S)-2-(6-benzyl-5-azaspiro[2.4]heptan-5-yl)-6-morpholinopyrimidin-4(3H)-one and
Example 263: (R)-2-(6-benzyl-5-azaspiro[2.4]heptan-5-yl)-6-morpholinopyrimidin-4(3H)-one

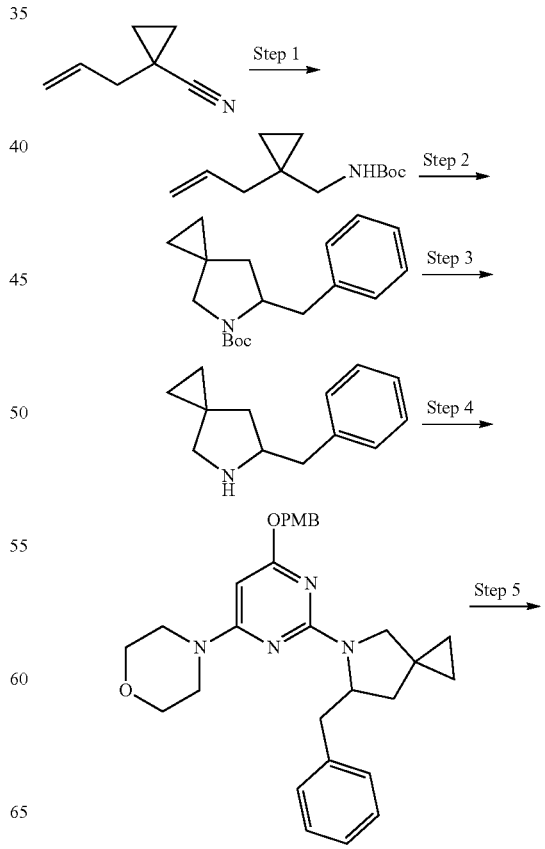

-continued

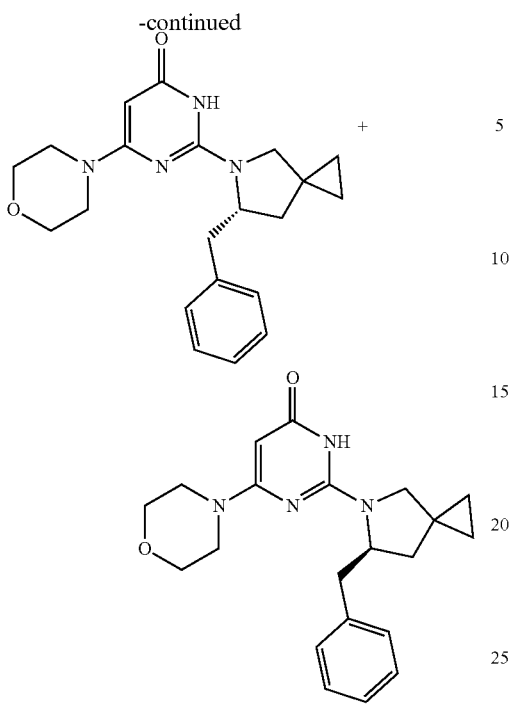

Step 1: 1-allylcyclopropane-1-carboxamide

LiAlH₄ (53.4 mL, 1.0 M solution in THF) was added dropwise to a solution of 1-allylcyclopropane-1-carbonitrile (CAS No 22566-35-4), 2.86 g, 26.69 mmol) in THF (35 mL) at 0° C. After complete addition the reaction was warmed to rt and then refluxed for 1 h. The reaction was cooled to r.t. After 15.5 h the reaction was cooled to 0° C. and quenched with NaOH (53.4 mL, 2 M aqueous solution). After complete addition di-tert-butyl dicarbonate (11.65 g, 53.38 mmol) was added with stirring. After 24 h the reaction mixture was filtered through celite, washing with water and EtOAc. The layers were separated and the aqueous layer extracted with EtOAc (x3). The combined organics were dried (phase separator) and concentrated under reduced pressure to afford the product.

Step 2: tert-butyl 6-benzyl-5-azaspiro[2.4]heptane-5-carboxylate

Palladium (II) acetate (13 mg, 0.06 mmol), Dpe-phos (65 mg, 0.12 mmol) and NaOtBu (663 mg, 6.90 mmol) were placed in a reaction tube. The tube was sealed and degassed. tert-Butyl ((1-allylcyclopropyl)methyl)carbamate (634 mg, 3.0 mmol) dissolved in dioxane (12 mL) was degassed and added to the reaction tube followed by bromobenzene (0.38 mL, 3.60 mmoL) and the reaction heated at 100° C. for 18 h. The reaction mixture was cooled to r.t., diluted with NH₄Cl and DCM. The layers were separated and the organic extracts dried (phase separator). The solvents were removed under reduced pressure. The crude product was purified by silica gel column chromatography (gradient elution, 2-20% EtOAc/iso-hexane) to afford the title compound.

Step 3: 6-benzyl-5-azaspiro[2.4]heptane

Hydrochloric acid (1.5 mL, 4 M in dioxane) was added to tert-butyl 6-benzyl-5-azaspiro[2.4]heptane-5-carboxylate (173 mg, 0.60 mmol) at rt with stirring. After 2 h the reaction mixture was concentrated under reduced pressure. The residue was dissolved in DCM and washed with NaHCO₃ (saturated aqueous solution). The organic extract was dried (phase separator) and concentrated under reduced pressure. Used without further purification in the next step.

Step 4: 4-(2-(6-benzyl-5-azaspiro[2.4]heptan-5-yl)-6-((4-methoxybenzyl)oxy)pyrimidin-4-yl)morpholine Following Method G from 6-benzyl-5-azaspiro[2.4]heptane (56 mg, 0.30 mmol) and 4-(6-((4-methoxybenzyl)oxy)-2-(methylsulfonyl)pyrimidin-4-yl)morpholine (105 mg, 0.28 mmol, scaffold 4) heating at 80° C. for 68 h. Used without further purification in the next step.

Step 5: (R)-2-(6-benzyl-5-azaspiro[2.4]heptan-5-yl)-6-morpholinopyrimidin-4(3H)-one and (S)-2-(6-benzyl-5-azaspiro[2.4]heptan-5-yl)-6-morpholinopyrimidin-4(3H)-one Following Method H from 4-(2-(6-benzyl-5-azaspiro[2.4]heptan-5-yl)-6-((4-methoxybenzyl)oxy)pyrimidin-4-yl)morpholine (135 mg, 0.278 mmol). The crude material was purified by silica gel column chromatography (gradient elution, 2-20% MeOH/EtOAc). The enantiomers were separated by SFC to afford the title compounds.

(S)-2-(6-benzyl-5-azaspiro[2.4]heptan-5-yl)-6-morpholinopyrimidin-4(3H)-one LCMS (ES+) 367 (M+H)⁺, RT 3.26 min (Analytical Method A); RT 1.96 min (Analytical Method SFC4, LUX CELLULOSE-3+0.5% DEAISO 20% MeOH SOL3; ¹H NMR (400 MHz, DMSO): δ 10.19 (1H, br s), 7.35-7.29 (2H, m), 7.27-7.20 (3H, m), 4.84-4.84 (1H, m), 4.48-4.44 (1H, m), 3.66 (4H, dd, J=4.7, 4.7 Hz), 3.53-3.45 (5H, m), 3.28-3.22 (2H, m), 2.76-2.68 (1H, m), 1.99 (1H, dd, J=7.5, 12.4 Hz), 1.37 (1H, d, J=12.8 Hz), 0.68-0.63 (2H, m), 0.58-0.51 (2H, m).

(R)-2-(6-benzyl-5-azaspiro[2.4]heptan-5-yl)-6-morpholinopyrimidin-4(3H)-one LCMS (ES+) 367 (M+H)⁺, RT 3.26 min (Analytical Method A); RT 1.04 min (Analytical Method SFC4, LUX CELLULOSE-3+0.5% DEAISO 20% MeOH SOL3; ¹H NMR (400 MHz, DMSO) 10.20 (1H, br s), 7.39-7.33 (2H, m), 7.31-7.23 (3H, m), 4.88-4.88 (1H, m), 4.51-4.49 (1H, m), 3.72-3.67 (4H, m), 3.57-3.51 (5H, m), 3.32-3.26 (2H, m), 2.76 (1H, dd, J=10.7, 12.5 Hz), 2.03 (1H, dd, J=7.6, 12.4 Hz), 1.41 (1H, d, J=12.1 Hz), 0.72-0.67 (2H, m), 0.62-0.55 (2H, m)

Example 264: (R)-2-(6-(2-methoxybenzyl)-5-azaspiro[2.4]heptan-5-yl)-6-morpholinopyrimidin-4(3H)-one and Example 265: (S)-2-(6-(2-methoxybenzyl)-5-azaspiro[2.4]heptan-5-yl)-6-morpholinopyrimidin-4(3H)-one

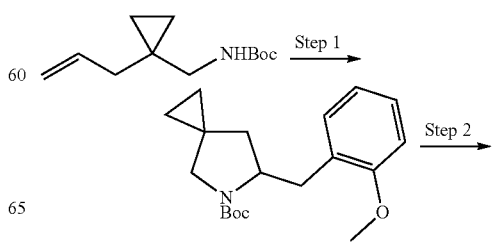

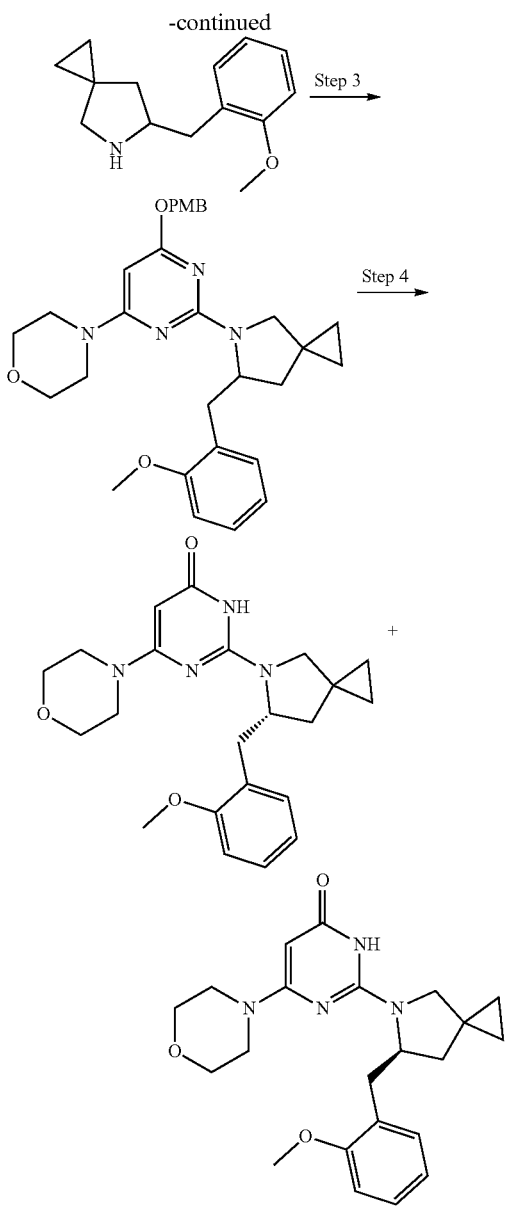

Step 1: tert-butyl 6-(2-methoxybenzyl)-5-azaspiro[2.4]heptane-5-carboxylate

Following the method described for Example 262 step 2 from tert-butyl ((1-allylcyclopropyl)methyl)carbamate (317 mg, 1.5 mmol) and 2-bromoanisole (0.22 mL, 1.8 mmol). The crude material was purified by silica gel column chromatography (gradient elution, 2-20% EtOAc/iso-hexane) to afford the title compound.

Step 2: 6-(2-methoxybenzyl)-5-azaspiro[2.4]heptane

Hydrochloric acid (1.0 mL, 4.1 mmol, 4M in dioxane) was added to tert-butyl 6-(2-methoxybenzyl)-5-azaspiro[2.4]heptane-5-carboxylate (131 mg, 0.41 mmol) at r.t. After 2 h the reaction was concentrated under reduced pressure. The residue was dissolved in DCM and washed with NaHCO₃ (saturated aqueous solution). The organic extract was dried (phase separator) and concentrated under reduced pressure to afford the title compound. Used without further purification in the next step Step 3: 4-(2-(6-(2-methoxybenzyl)-5-azaspiro[2.4] heptan-5-yl)-6-((4-methoxybenzyl)oxy)pyrimidin-4-yl)morpholine Following Method G from 6-(2-methoxybenzyl)-5-azaspiro[2.4]heptane (90 mg, 0.41 mmol) and 4-(6-((4-methoxybenzyl)oxy)-2-(methylsulfonyl)pyrimidin-4-yl) morpholine (146 mg, 0.38 mmol, scaffold 4) heating at 85° C. for 23 h. Purified by silica gel column chromatography (gradient elution, 0-65% EtOAc/iso-hexane) to afford the title compound.

Step 4: (R)-2-(6-(2-methoxybenzyl)-5-azaspiro[2.4] heptan-5-yl)-6-morpholinopyrimidin-4(3H)-one and (S)-2-(6-(2-methoxybenzyl)-5-azaspiro[2.4]heptan-5-yl)-6-morpholinopyrimidin-4(3H)-one Following Method H from 4-(2-(6-(2-methoxybenzyl)-5-azaspiro[2.4]heptan-5-yl)-6-((4-methoxybenzyl)oxy)pyrimidin-4-yl)morpholine (98 mg, 0.19 mmol). The crude product was purified by preparative HPLC followed by SFC for the separation of the enantiomers to afford the title compounds.

(R)-2-(6-(2-methoxybenzyl)-5-azaspiro[2.4]heptan-5-yl)-6-morpholinopyrimidin-4(3H)-one LCMS (ES+) 397 (M+H)⁺, RT 3.36 min (Analytical Method B); RT 1.38 min (Analytical Method SFC4, LUX CELLULOSE-3+0.1% DEAISO 20% MeOH SOL3); ¹H NMR (400 MHz, CDCl₃): δ 9.05 (1H, br s), 7.31-7.26 (1H, m), 7.04 (1H, d, J=7.3 Hz), 6.97 (1H, d, J=8.6 Hz), 6.91 (1H, dd, J=7.3, 7.3 Hz), 4.97 (1H, s), 4.21 (3H, s), 4.02-3.91 (1H, m), 3.76-3.68 (5H, m), 3.53-3.47 (4H, m), 3.29-3.23 (2H, m), 2.72-2.61 (1H, m), 2.22 (1H, dd, J=8.0, 12.5 Hz), 1.45 (1H, d, J=12.9 Hz), 0.86-0.75 (2H, m), 0.70-0.60 (2H, m).

(S)-2-(6-(2-methoxybenzyl)-5-azaspiro[2.4]heptan-5-yl)-6-morpholinopyrimidin-4(3H)-one LCMS (ES+) 397 (M+H)⁺, RT 3.41 min (Analytical Method B); RT 0.77 min (Analytical Method SFC4, LUX CELLULOSE-3+0.1% DEAISO 20% MeOH SOL3); ¹H NMR (400 MHz, CDCl₃): δ 9.04 (1H, br s), 7.31-7.27 (1H, m), 7.04 (1H, d, J=7.1 Hz), 6.97 (1H, d, J=8.1 Hz), 6.94-6.88 (1H, m), 4.97 (1H, s), 4.21 (3H, s), 3.96-3.90 (1H, m), 3.73 (5H, dd, J=4.9, 4.9 Hz), 3.53-3.48 (4H, m), 3.29-3.23 (2H, m), 2.73-2.64 (1H, m), 2.22 (1H, dd, J=7.7, 12.5 Hz), 1.46 (1H, d, J=12.6 Hz), 0.86-0.75 (2H, m), 0.69-0.59 (2H, m).

Example 266: (S)-2-(3-benzyl-2-azaspiro[4.4] nonan-2-yl)-6-morpholinopyrimidin-4(3H)-one and
Example 267: (R)-2-(3-benzyl-2-azaspiro[4.4] nonan-2-yl)-6-morpholinopyrimidin-4(3H)-one

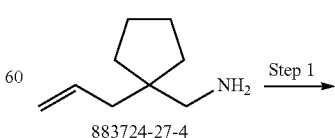

883724-27-4

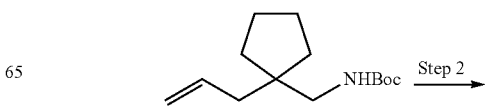

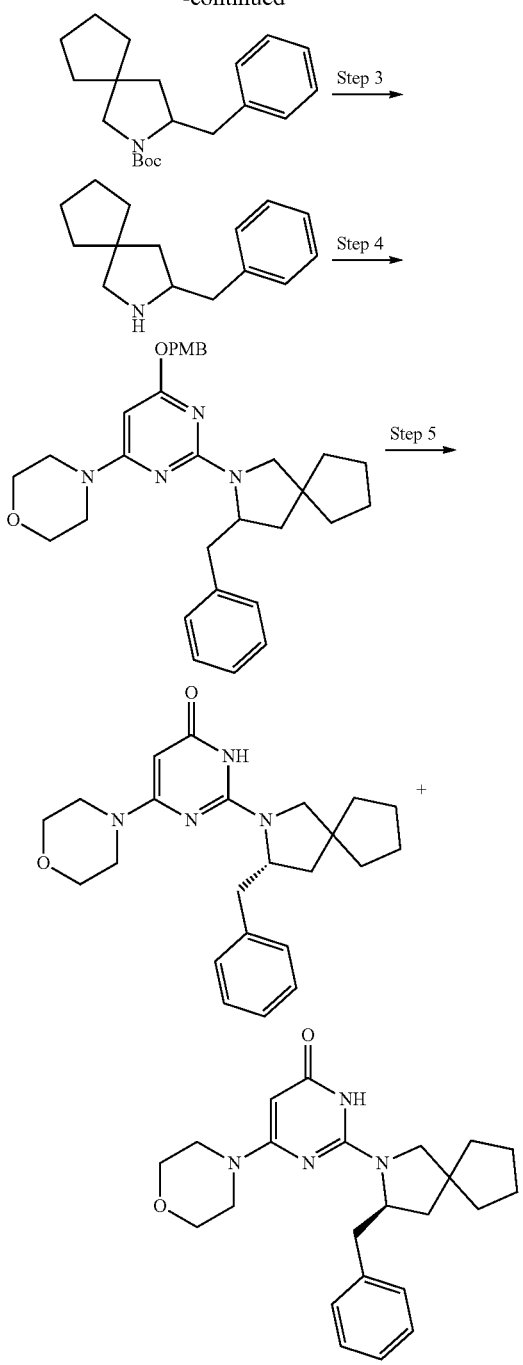

Step 2: tert-butyl 3-benzyl-2-azaspiro[4.4]nonane-2-carboxylate

Following the method described for Example 262 step 2 from tert-butyl ((1-allylcyclopentyl)methyl)carbamate (359 mg, 1.50 mmol) and bromobenzene (0.19 mL, 1.80 mmol). The crude material was purified by silica gel column chromatography (gradient elution, 2-20% EtOAc/iso-hexane) to afford the title compound.

Step 3: 3-benzyl-2-azaspiro[4.4]nonane

Hydrochloric acid (2.6 mL, 10.6 mmol) was added to tert-butyl 3-benzyl-2-azaspiro[4.4]nonane-2-carboxylate (334 mg, 1.06 mmol) at room temperature with stirring. After 2 h the reaction was concentrated under reduced pressure. The residue was dissolved in DCM and 1.0 eq PS-carbonate (3.28 mmol/g) was added. The mixture was stirred for 1 h before filtering and concentrating under reduced pressure to afford the title compound. Used without further purification in the next step.

Step 4: 4-(2-(3-benzyl-2-azaspiro[4.4]nonan-2-yl)-6-((4-methoxybenzyl)oxy)pyrimidin-4-yl)morpholine Following Method G from 3-benzyl-2-azaspiro[4.4] nonane (105 mg, 0.49 mmol) and 4-(6-((4-methoxybenzyl) oxy)-2-(methylsulfonyl)pyrimidin-4-yl)morpholine (171 mg, 0.45 mmol, scaffold 4). Used without further purification in the next step.

Step 5: (R)-2-(3-benzyl-2-azaspiro[4.4]nonan-2-yl)-6-morpholinopyrimidin-4(3H)-one and (S)-2-(3-benzyl-2-azaspiro[4.4]nonan-2-yl)-6-morpholinopyrimidin-4(3H)-one Following Method H from 4-(2-(3-benzyl-2-azaspiro[4.4] nonan-2-yl)-6-((4-methoxybenzyl)oxy)pyrimidin-4-yl)morpholine (0.45 mmol). Purified by silica gel column chromatography (gradient elution, 2-20% MeOH in EtOAc) followed by SFC for the separation of the enantiomers.

(S)-2-(3-benzyl-2-azaspiro[4.4]nonan-2-yl)-6-morpholinopyrimidin-4(3H)-one LCMS (ES+) 395 (M+H)+, RT 3.51 min (Analytical Method A); RT 1.67 min (Analytical Method SFC4, LUX CELLULOSE-3+0.1% DEAISO 20% MeOH SOL3); $^1$H NMR (400 MHz, DMSO): δ 10.28 (1H, br s), 7.39-7.32 (2H, m), 7.29-7.20 (3H, m), 4.88 (1H, s), 4.35-4.29 (1H, m), 3.73-3.66 (4H, m), 3.58-3.41 (6H, m), 3.21 (1H, d, J=10.6 Hz), 2.65 (1H, dd, J=9.9, 12.4 Hz), 1.78-1.56 (8H, m), 1.44-1.39 (2H, m).

(R)-2-(3-benzyl-2-azaspiro[4.4]nonan-2-yl)-6-morpholinopyrimidin-4(3H)-one LCMS (ES+) 395 (M+H)+, RT 3.49 min (Analytical Method B); RT 1.12 min (Analytical Method SFC4, LUX CELLULOSE-3+0.1% DEAISO 20% MeOH SOL3); $^1$H NMR (400 MHz, DMSO): δ 10.30 (1H, br s), 7.39-7.31 (2H, m), 7.29-7.19 (3H, m), 4.88 (1H, s), 4.32 (1H, d, J=5.8 Hz), 3.69 (4H, dd, J=4.7, 4.7 Hz), 3.56-3.39 (6H, m), 3.21 (1H, d, J=10.6 Hz), 2.65 (1H, dd, J=9.9, 12.4 Hz), 1.82-1.57 (8H, m), 1.44-1.35 (2H, m).

Step 1: tert-butyl((1-allylcyclopentyl)methyl)carbamate

Di-tert-butyl dicarbonate (862 mg, 3.95 mmol) was added to (1-allylcyclopentyl)methanamine (500 mg, 3.59 mmol) and trimethylamine (1.1 mL, 7.90 mmol) in DCM (10 mL) at rt with stirring. After 24 hours the reaction mixture was diluted with water and the layers separated. The DCM layer was dried (phase separator) and concentrated under reduced pressure to afford the product. Used without further purification in the next step.

Example 268: (S)-2-(2-benzyl-3,3-dimethylpyrrolidin-1-yl)-6-morpholinopyrimidin-4(3H)-one and Example 269: (R)-2-(2-benzyl-3,3-dimethylpyrrolidin-1-yl)-6-morpholinopyrimidin-4(3H)-one

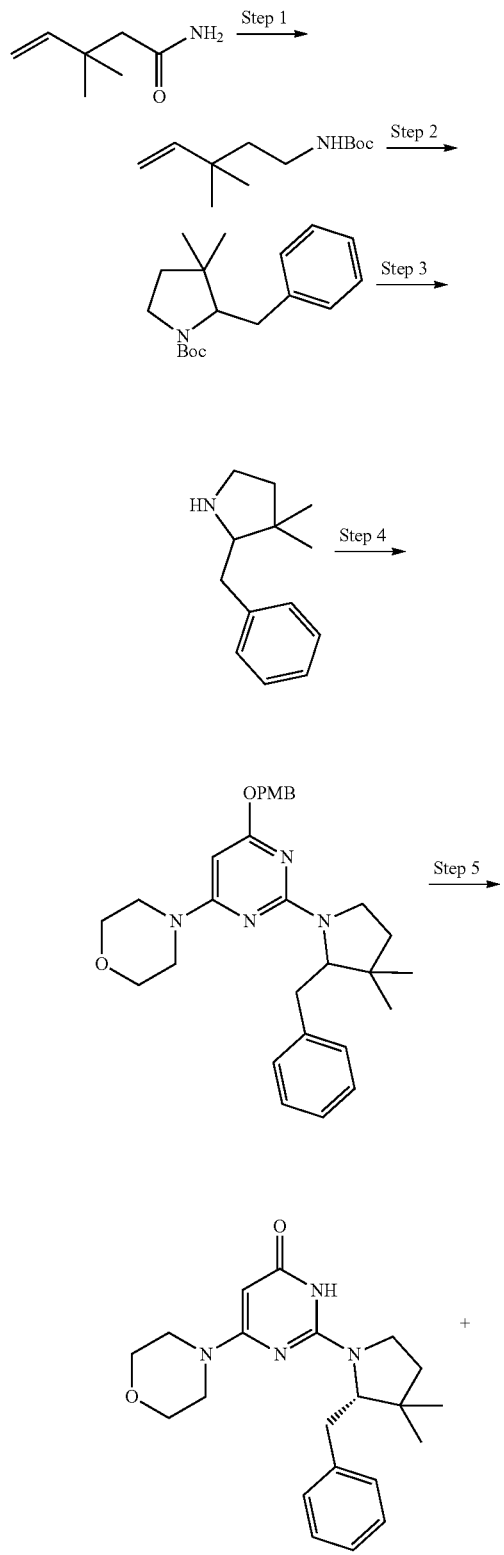

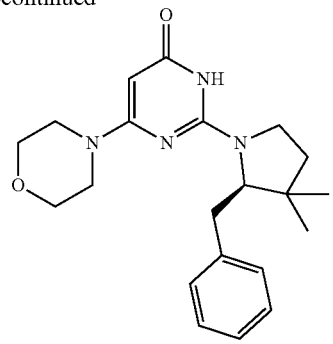

Step 1: tert-butyl (3,3-dimethylpent-4-en-1-yl)carbamate

Lithium aluminium hydride (15.7 mL, 15.7 mmol, 1 M solution in THF) was added dropwise to a solution of 3,3-dimethylpent-4-enamide (1.0 g, 7.86 mmol) in THF (15 mL) at 0° C. and the reaction mixture was warmed to r.t. After 23 h the reaction was cooled to 0° C. and cautiously quenched with NaOH (15.7 mL, 31.4 mmol, 2 M aqueous solution). After complete addition di-tert-butyl dicarbonate (3.43 g, 15.7 mmol) was added and the reaction warmed to rt After 24 h the reaction was filtered through celite. Water was added and the layers separated. The aqueous layer was extracted with EtOAc (×3). The organic extracts were dried (MgSO$_4$ filtered and concentrated under reduced pressure. The crude product was purified by silica gel column chromatography (gradient elution, 12-20% EtOAc/iso-hexane) to afford the title compound.

Step 2: tert-butyl 2-benzyl-3,3-dimethylpyrrolidine-1-carboxylate

Following the method described for Example 262 step 2 tert-butyl (3,3-dimethylpent-4-en-1-yl)carbamate (427 mg, 2.00 mmol) and bromobenzene (0.25 mL, 2.40 mmol). Purified by silica gel column chromatography (gradient elution, 2-20% EtOAc/iso-hexane) to afford the product.

Step 3: 2-benzyl-3,3-dimethylpyrrolidine

Hydrochloric acid (2.8 mL, 11.0 mmol, 4M in dioxane) was added to tert-butyl 2-benzyl-3,3-dimethylpyrrolidine-1-carboxylate (319 mg, 1.10 mmol) at room temperature. After 3 h the reaction was concentrated under reduced pressure. The residue was dissolved in DCM and PS-carbonate (1.0 eq., 3.28 mmol/g) added. After 30 min the mixture was filtered and concentrated under reduced pressure to afford the title compound. Used without further purification in the next step.

Step 4: 4-(2-(2-benzyl-3,3-dimethylpyrrolidin-1-yl)-6-((4-methoxybenzyl)oxy)pyrimidin-4-yl)morpholine Following Method G from 2-benzyl-3,3-dimethylpyrrolidine (92 mg, 0.49 mmol) and scaffold 10 (171 mg, 0.45 mmol). Used without further purification in the next step.

Step 5: (R)-2-(2-benzyl-3,3-dimethylpyrrolidin-1-yl)-6-morpholinopyrimidin-4(3H)-one and (S)-2-(2-benzyl-3,3-dimethylpyrrolidin-1-yl)-6-morpholinopyrimidin-4(3H)-one Following Method H from 4-(2-(2-benzyl-3,3-dimethylpyrrolidin-1-yl)-6-((4-methoxybenzyl)oxy)pyrimidin-4- yl)morpholine (0.45 mmol). The crude material was purified by silica gel column chromatography (gradient elution, 2-20% MeOH in EtOAc) followed by SFC for the separation of the enantiomers.

(S)-2-(2-benzyl-3,3-dimethylpyrrolidin-1-yl)-6-morpholinopyrimidin-4(3H)-one LCMS (ES+) 369 (M+H)+, RT 3.23 min (Analytical Method B); RT 2.13 min (Analytical Method SFC4, LUX CELLULOSE-3+0.1% DEAISO 10% MeOH SOL3); $^1$H NMR (400 MHz, DMSO): δ 9.95 (1H, br s), 7.29-7.24 (4H, m), 7.22-7.15 (1H, m), 4.73 (1H, s), 4.22 (1H, dd, J=5.9, 5.9 Hz), 3.62-3.50 (5H, m), 3.42-3.30 (5H, m, under water peak), 2.93-2.85 (2H, m), 1.90-1.81 (1H, m), 1.67-1.61 (1H, m), 1.04 (3H, s), 0.93 (3H, s).

(R)-2-(2-benzyl-3,3-dimethylpyrrolidin-1-yl)-6-morpholinopyrimidin-4(3H)-one LCMS (ES+) 369 (M+H)+, RT 3.21 min (Analytical Method B); RT 1.76 min (Analytical Method SFC1, LUX CELLULOSE-3+0.1% DEAISO 10% MeOH SOL4); $^1$H NMR (400 MHz, DMSO): δ 9.92 (1H, br s), 7.26-7.21 (4H, m), 7.17-7.12 (1H, m), 4.69 (1H, s), 4.18 (1H, dd, J=6.3, 6.3 Hz), 3.63-3.53 (4H, m), 3.51-3.47 (1H, m), 3.39-3.26 (5H, m, under water peak), 2.90-2.81 (2H, m), 1.85-1.76 (1H, m), 1.63-1.58 (1H, m), 1.00 (3H, s), 0.89 (3H, s).

Example 270: 2-((R)-2-benzylazepan-1-yl)-6-((R)-2-methylmorpholino)pyrimidin-4(3H)-one

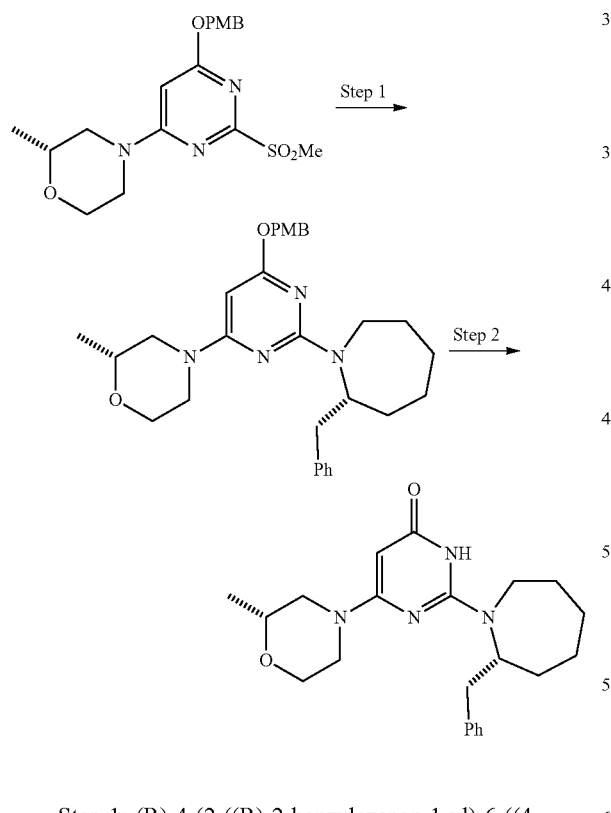

Step 1: (R)-4-(2-((R)-2-benzylazepan-1-yl)-6-((4-methoxybenzyl)oxy)pyrimidin-4-yl)-2-methylmorpholine (R)-4-(6-((4-methoxybenzyl)oxy)-2-(methylsulfonyl)pyrimidin-4-yl)-2-methylmorpholine (128 mg, 0.33 mmol, Scaffold 5), (R)-2-benzylazepane (40 mg, 0.21 mmol, Example 3 step 2) and TBAF hydrate (131 mg, 0.50 mmol) in DMSO (0.7 mL). The reaction was heated at 80° C. for 6 days. After 42 h at 80° C., further TBAF hydrate (50 mg, 0.19 mmol) was added, and after 68 h at 80° C. DIPEA (120 μL, 0.69 mmol) was added to the reaction. On completion of the reaction, and after cooling to rt, water (2 mL) was added, whereupon a gum formed. The liquid supernatant was decanted off and the gum dissolved in a 1:1 mixture of DCM and water. The biphasic mixture was separated by passage through a hydrophobic frit; the DCM layer was concentrated to give the title compound, which was used without further purification.

Step 2: 2-((R)-2-benzylazepan-1-yl)-6-((R)-2-methylmorpholino)pyrimidin-4(3H)-one Following Method H from (R)-4-(2-((R)-2-benzylazepan-1-yl)-6-((4-methoxybenzyl)oxy)pyrimidin-4-yl)-2-methylmorpholine. The reaction was stirred at rt for 4.5 h. The reaction was quenched with MeOH and concentrated. Purification by reverse phase preparative HPLC was followed by freeze-drying gave the title compound. LCMS (ES+) 383 (M+H)$^+$, RT 3.52 min (Analytical Method A); $^1$H NMR (400 MHz, CDCl$_3$): δ 7.29-7.12 (5H, m), 4.90 (1H, s), 4.70 (1H, br s), 4.08 (1H, br s), 3.98-3.91 (2H, m), 3.67-3.54 (3H, m), 3.00-2.86 (3H, m), 2.75-2.68 (1H, m), 2.61 (1H, dd, J=10.5, 13.0 Hz), 2.07-2.00 (1H, m), 1.83-1.73 (4H, m), 1.48-1.41 (2H, m), 1.31-1.12 (5H, m)

Example 271: 2-((R)-2-benzylpyrrolidin-1-yl)-6-((R)-2-methylmorpholino)pyrimidin-4(3H)-one and Example 272: 2-((S)-2-benzylpyrrolidin-1-yl)-6-((R)-2-methylmorpholino)pyrimidin-4(3H)-one

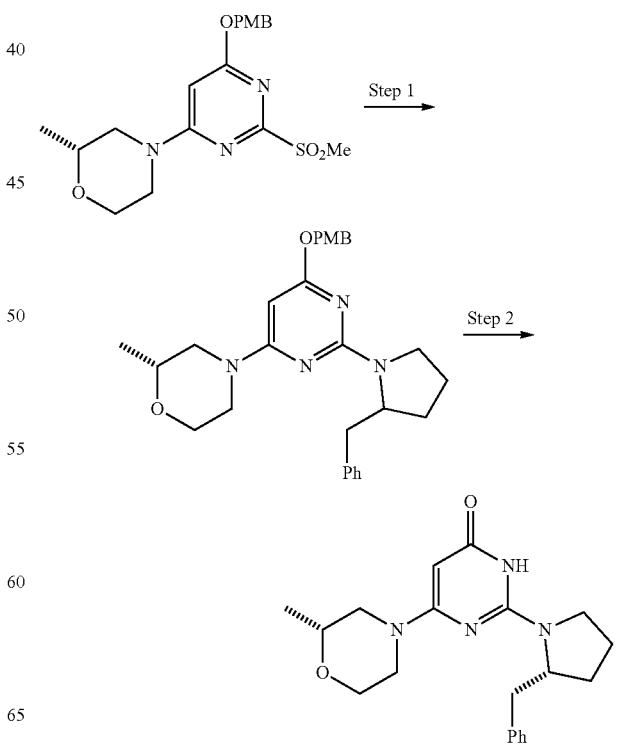

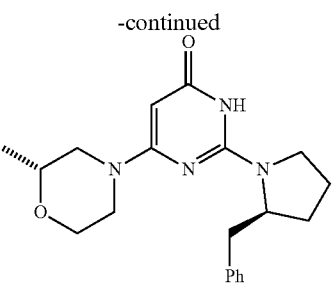

Step 1: (2R)-4-(2-(2-benzylpyrrolidin-1-yl)-6-((4-methoxybenzyl)oxy)pyrimidin-4-yl)-2-methylmorpholine Following Method F from Scaffold 5 (128 mg, 0.33 mmol), 2-benzylpyrrolidine (170 mg, 0.43 mmol) and TBAF hydrate (276 mg, 1.06 mmol) in DMSO (0.7 mL). The reaction was heated at 80° C. for 21 h. After cooling to r.t., water (2 mL) was added and the resulting precipitate collected by filtration, washing with water, to give the title compound, which was used without further purification.

Step 2: 2-((R)-2-benzylpyrrolidin-1-yl)-6-((R)-2-methylmorpholino)pyrimidin-4(3H)-one and 2-((S)-2-benzylpyrrolidin-1-yl)-6-((R)-2-methylmorpholino)pyrimidin-4(3H)-one Following Method H from (2R)-4-(2-(2-benzylpyrrolidin-1-yl)-6-((4-methoxybenzyl)oxy)pyrimidin-4-yl)-2-methylmorpholine (106 mg). The reaction mixture was stirred at rt for 3 h. The reaction was quenched with MeOH and concentrated. The residue was dissolved in DCM (5 mL) and washed with water (5 mL). Concentration of the DCM layer provided a pale brown solid which was purified by reverse phase HPLC, then SFC to give two isomers. The compounds were freeze-dried from MeCN—H$_2$O to give the title compounds.

2-((R)-2-benzylpyrrolidin-1-yl)-6-((R)-2-methylmorpholino)pyrimidin-4(3H)-one: LCMS (ES+) 355 (M+H)$^+$, RT 3.21 min (Analytical Method B); $^1$H NMR (400 MHz, CDCl$_3$): δ 8.93 (1H, s), 7.39-7.15 (5H, m), 4.95 (1H, s), 4.44-4.41 (1H, m), 4.20-4.11 (1H, m), 4.03-3.93 (2H, m), 3.69-3.47 (3H, m), 3.42-3.34 (1H, m), 3.23-3.19 (1H, m), 3.03-2.96 (1H, m), 2.69-2.60 (2H, m), 1.98-1.82 (4H, m), 1.22 (3H, d, J=6.3 Hz).

2-((S)-2-benzylpyrrolidin-1-yl)-6-((R)-2-methylmorpholino)pyrimidin-4(3H)-one: LCMS (ES+) 355 (M+H)$^+$, RT 3.21 min (Analytical Method B); $^1$H NMR (400 MHz, CDCl$_3$): δ 9.45 (1H, s), 7.33-7.16 (5H, m), 4.95 (1H, s), 4.45-4.40 (1H, m), 4.23-4.20 (1H, m), 3.99-3.91 (2H, m), 3.67-3.52 (3H, m), 3.44-3.36 (1H, m), 3.25-3.19 (1H, m), 3.05-2.96 (1H, m), 2.67-2.58 (2H, m), 1.97-1.82 (4H, m), 1.23 (3H, d, J=6.3 Hz).

The following examples were prepared using a procedure analogous to that described for Example 271 starting from the reported amine and Scaffold 5. Methyl sulfonyl displacement conditions Method F or Method G were used, followed by Method H to deprotect the scaffold. The chirally pure isomers were isolated after purification by Chiral SFC unless otherwise stated (*), these cases the amine was chirally pure.

| Example | Structure and Name | Amine | Displacement conditions | Analytical data |
|---|---|---|---|---|
| Example 273 | 2-[2-(benzimidazol-1-ylmethyl)pyrrolidin-1-yl]-4-[(2R)-2-methylmorpholin-4-yl]-1H-pyrimidin-6-one | 1-(pyrrolidin-2-ylmethyl)-1H-benzo[d]imidazole | Method F | LCMS (ES+) 395 (M + H)$^+$, RT 2.71 min (Analytical Method B); $^1$H NMR (400 MHz, CDCl$_3$): δ 7.97 (1H, s), 7.83-7.78 (1H, m), 7.41-7.37 (1H, m), 7.31-7.23 (2H, m), 5.00 (1H, s), 4.78-4.76 (1H, m), 4.50 (1H, dd, J = 3.8, 14.4 Hz), 4.35 (1H, dd, J = 6.7, 13.9 Hz), 4.02-3.91 (3H, m), 3.68-3.57 (3H, m), 3.46 (1H, dd, J = 9.7, 17.3 Hz), 2.94 (1H, dt, J = 3.5, 12.3 Hz), 2.65 (1H, dd, J = 10.6, 12.9 Hz), 2.00-1.93 (2H, m), 1.85-1.79 (1H, m), 1.62-1.54 (1H, m), 1.21 (3H, d, J = 6.3 Hz), NH not observed |

| Example | Structure and Name | Amine | Displacement conditions | Analytical data |
|---|---|---|---|---|
| Example 274 | 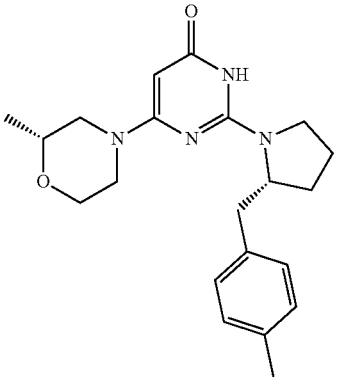 [SMILES: Cc1ccc(C[C@H]2CCCN2c2nc(N3CCO[C@H](C)C3)cc(=O)[nH]2)cc1]<br>4-[(2R)-2-methylmorpholin-4-yl]-2-[(2R)-2-(p-tolylmethyl)pyrrolidin-1-yl]-1H-pyrimidin-6-one | 2-(4-methylbenzyl)pyrrolidine | Method F | LCMS (ES+) 369 (M + H)$^+$, RT 3.35 min (Analytical Method A); RT 4.36 min (Analytical Method SFC4, YMC CELLULOSE-C, 10/90 MeOH (0.1% DEAISO)/CO$_2$); $^1$H NMR (400 MHz, CDCl$_3$): δ 9.80-9.79 (1H, br s), 7.12-7.04 (4H, m), 4.95 (1H, s), 4.44-4.37 (1H, m), 4.19-4.15 (1H, m), 4.04-3.92 (2H, m), 3.68-3.54 (3H, m), 3.41 (1H, q, J = 8.8 Hz), 3.21-3.14 (1H, m), 3.03-2.95 (1H, m), 2.68-2.51 (2H, m), 2.32 (3H, s), 1.95-1.78 (4H, m), 1.22 (3H, d, J = 6.3 Hz) |
| Example 275 | 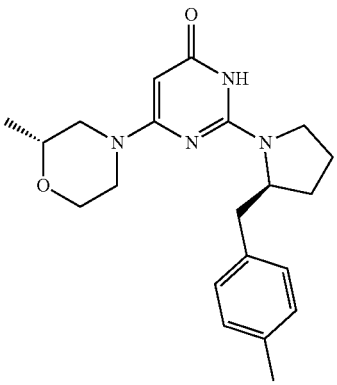 [SMILES: Cc1ccc(C[C@@H]2CCCN2c2nc(N3CCO[C@H](C)C3)cc(=O)[nH]2)cc1]<br>4-[(2R)-2-methylmorpholin-4-yl]-2-[(2S)-2-(p-tolylmethyl)pyrrolidin-1-yl]-1H-pyrimidin-6-one | 2-(4-methylbenzyl)pyrrolidine | Method F | LCMS (ES+) 369 (M + H)$^+$, RT 3.35 min (Analytical Method A); RT 4.98 min (Analytical Method SFC4, YMC CELLULOSE-C, 10/90 MeOH (0.1% DEAISO)/CO$_2$); $^1$H NMR (400 MHz, CDCl$_3$): δ 10.32-10.28 (1H, br s), 7.10-7.07 (4H, m), 4.95 (1H, s), 4.45-4.39 (1H, m), 4.25-4.23 (1H, m), 3.94 (2H, dd, J = 2.5, 11.4 Hz), 3.66-3.56 (3H, m), 3.43 (1H, q, J = 8.7 Hz), 3.21-3.15 (1H, m), 3.00 (1H, dt, J = 3.5, 12.4 Hz), 2.63 (1H, dd, J = 10.6, 12.8 Hz), 2.54 (1H, dd, J = 9.9, 13.5 Hz), 2.32 (3H, s), 1.97-1.93 (2H, m), 1.85-1.77 (2H, m), 1.23 (3H, d, J = 6.3 Hz) |
| Example 276 | 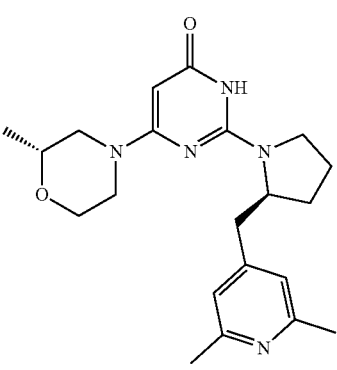<br>2-[(2S)-2-[(2,6-dimethyl-4-pyridyl)methyl]pyrrolidin-1-yl]-4-[(2R)-2-methylmorpholin-4-yl]-1H-pyrimidin-6-one | 2,6-dimethyl-4-(pyrrolidin-2-ylmethyl)pyridine | Method F | LCMS (ES+) 384 (M + H)$^+$, RT 2.33 min (Analytical Method A); RT 0.78 min (Analytical Method SFC4, YMC AMYLOSE-C, 40/60 IPA (0.1% DEAISO)/CO$_2$); $^1$H NMR (400 MHz, CDCl$_3$): δ 10.51 (1H, br s), 6.81 (2H, s), 4.96 (1H, s), 4.49-4.43 (1H, m), 4.21-4.17 (1H, m), 3.98-3.92 (2H, m), 3.71-3.59 (3H, m), 3.46 (1H, dd, J = 8.3, 17.7 Hz), 3.22 (1H, dd, J = 3.2, 12.8 Hz), 3.00 (1H, dt, J = 3.2, 12.4 Hz), 2.63 (1H, dd, J = 10.5, 12.8 Hz), 2.50-2.40 (7H, m), 2.02-1.96 (2H, m), 1.91-1.73 (2H, m), 1.22 (3H, d, J = 6.1 Hz) |

| Example | Structure and Name | Amine | Displacement conditions | Analytical data |
|---|---|---|---|---|
| Example 277 | 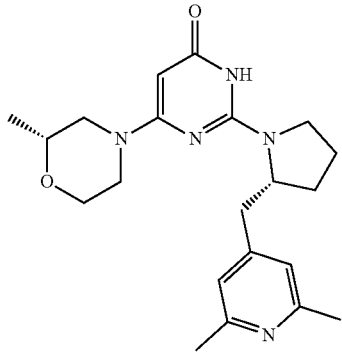<br>2-[(2R)-2-[(2,6-dimethyl-4-pyridyl)methyl]pyrrolidin-1-yl]-4-[(2R)-2-methylmorpholin-4-yl]-1H-pyrimidin-6-one | 2,6-dimethyl-4-(pyrrolidin-2-ylmethyl)pyridine | Method F | LCMS (ES+) 384 (M + H)+, RT 2.32 min (Analytical Method A); RT 2.01 min (Analytical Method SFC4, YMC AMYLOSE-C, 40/60 IPA (0.1% DEAISO)/CO$_2$); $^1$H NMR (400 MHz, CDCl$_3$): δ 6.82 (2H, s), 4.96 (1H, s), 4.48-4.47 (1H, m), 4.07 (1H, dd, J = 11.1, 32.7 Hz), 3.95 (2H, dd, J = 3.6, 12.5 Hz), 3.68-3.56 (3H, m), 3.45 (1H, dd, J = 8.0, 17.1 Hz), 3.22 (1H, dd, J = 2.7, 13.0 Hz), 2.99 (1H, dt, J = 2.9, 12.4 Hz), 2.65 (1H, dd, J = 10.7, 12.8 Hz), 2.49-2.43 (7H, m), 2.03-1.97 (2H, m), 1.91-1.81 (1H, m), 1.76-1.73 (1H, m), 1.21 (3H, d, J = 6.1 Hz), NH not observed |
| Example 278 | 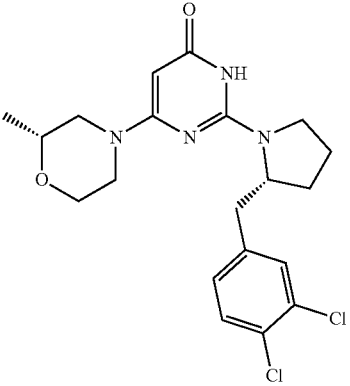 [SMILES: C[C@@H]1CN(c2cc(=O)[nH]c(N3CCC[C@@H]3Cc3ccc(Cl)c(Cl)c3)n2)CCO1]<br>2-[(2R)-2-[(3,4-dichlorophenyl)methyl]pyrrolidin-1-yl]-4-[(2R)-2-methylmorpholin-4-yl]-1H-pyrimidin-6-one | 2-(3,4-dichlorobenzyl)pyrrolidine | Method F | LCMS (ES+) 423 (M + H)+, RT 3.49 min (Analytical Method B); RT 2.74 min (Analytical Method SFC4, YMC AMYLOSE-C, 25/75 EtOH (0.1% DEAISO)/CO$_2$); $^1$H NMR (400 MHz, CDCl$_3$): δ 7.42-7.34 (1H, m), 7.03 (1H, d, J = 7.3 Hz), 4.98 (1H, s), 4.49-4.45 (1H, m), 4.10-3.92 (3H, m), 3.70-3.57 (3H, m), 3.49-3.44 (1H, m), 3.22 (1H, dd, J = 3.7, 13.3 Hz), 2.98 (1H, dt, J = 3.2, 12.4 Hz), 2.64 (1H, dd, J = 10.8, 12.8 Hz), 2.51 (1H, dd, J = 10.0, 13.0 Hz), 1.97-1.82 (3H, m), 1.76-1.72 (1H, m), 1.23 (3H, d, J = 6.3 Hz), NH not observed |
| Example 279 | 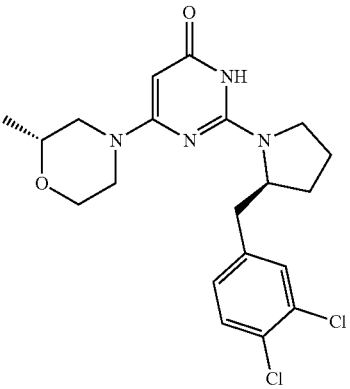 [SMILES: C[C@@H]1CN(c2cc(=O)[nH]c(N3CCC[C@H]3Cc3ccc(Cl)c(Cl)c3)n2)CCO1]<br>2-[(2S)-2-[(3,4-dichlorophenyl)methyl]pyrrolidin-1-yl]-4-[(2R)-2-methylmorpholin-4-yl]-1H-pyrimidin-6-one | 2-(3,4-dichlorobenzyl)pyrrolidine | Method F | LCMS (ES+) 423 (M + H)+, RT 3.48 min (Analytical Method B); RT 1.87 min (Analytical Method SFC4, YMC AMYLOSE-C, 25/75 EtOH (0.1% DEAISO)/CO$_2$); $^1$H NMR (400 MHz, CDCl$_3$): δ 7.40-7.32 (2H, m), 7.03-7.01 (1H, m), 4.97 (1H, s), 4.46-4.44 (1H, m), 4.14-4.14 (1H, m), 3.99-3.91 (2H, m), 3.68-3.59 (3H, m), 3.50-3.42 (1H, m), 3.21 (1H, dd, J = 3.7, 13.3 Hz), 3.00 (1H, dt, J = 3.3, 12.4 Hz), 2.63 (2H, dd, J = 10.3, 13.0 Hz), 2.51 (1H, dd, J = 9.8, 13.2 Hz), 2.00-1.83 (3H, m), 1.78-1.75 (1H, m), 1.24 (3H, d, J = 6.3 Hz). |

-continued

| Example | Structure and Name | Amine | Displacement conditions | Analytical data |
|---|---|---|---|---|
| Example 280 | 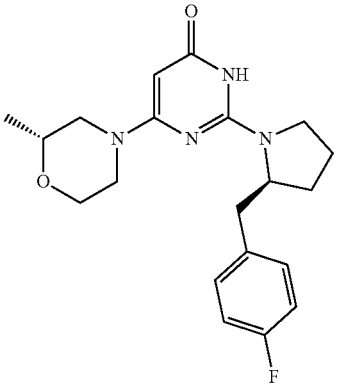 [SMILES: C[C@@H]1CN(c2cc(=O)[nH]c(N3CCC[C@H]3Cc3ccc(F)cc3)n2)CCO1]<br>2-[(2S)-2-[(4-fluorophenyl)methyl]pyrrolidin-1-yl]-4-[(2R)-2-methylmorpholin-4-yl]-1H-pyrimidin-6-one | 2-(4-fluorobenzyl) pyrrolidine | Method F | LCMS (ES+) 373 (M + H)+, RT 3.22 min (Analytical Method A); RT 1.63 min (Analytical Method SFC4, LUX CELLULOSE-C, 10/90 MeOH (0.1% DEAISO)/$CO_2$); $^1$H NMR (400 MHz, $CDCl_3$): δ 10.21-10.20 (1H, br s), 7.17-7.12 (2H, m), 6.97 (2H, t, J = 8.7 Hz), 4.95 (1H, s), 4.45-4.40 (1H, m), 4.19-4.15 (1H, m), 3.95 (2H, dd, J = 2.8, 11.1 Hz), 3.66-3.56 (3H, m), 3.46-3.39 (1H, m), 3.16 (1H, dd, J = 3.2, 13.3 Hz), 3.00 (1H, dt, J = 3.3, 12.4 Hz), 2.66-2.58 (2H, m), 1.95-1.78 (4H, m), 1.22 (3H, d, J = 6.1 Hz) |
| Example 281 | 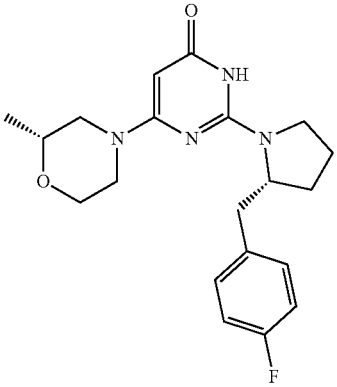 [SMILES: C[C@@H]1CN(c2cc(=O)[nH]c(N3CCC[C@@H]3Cc3ccc(F)cc3)n2)CCO1]<br>2-[(2R)-2-[(4-fluorophenyl)methyl]pyrrolidin-1-yl]-4-[(2R)-2-methylmorpholin-4-yl]-1H-pyrimidin-6-one | 2-(4-fluorobenzyl) pyrrolidine | Method F | LCMS (ES+) 373 (M + H)+, RT 3.22 min (Analytical Method A); RT 2.56 min (Analytical Method SFC1, LUX-CELLULOSE-C, 10/90 MeOH (0.1% DEAISO)/$CO_2$); $^1$H NMR (400 MHz, $CDCl_3$): δ 10.28 (1H, br s), 7.18-7.11 (2H, m), 6.98 (2H, t, J = 8.6 Hz), 4.95 (1H, s), 4.48-4.43 (1H, m), 4.15-4.10 (1H, m), 4.02-3.92 (2H, m), 3.67-3.57 (3H, m), 3.45-3.38 (1H, m), 3.17 (1H, dd, J = 2.8, 12.9 Hz), 2.98 (1H, dt, J = 2.7, 12.3 Hz), 2.68-2.59 (2H, m), 1.95-1.79 (4H, m), 1.27-1.19 (3H, m) |
| Example 282 | 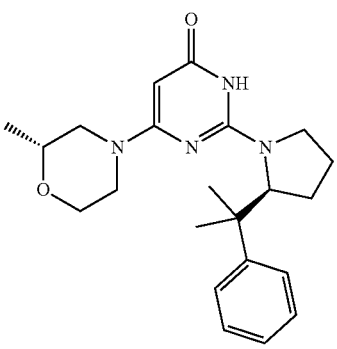 [SMILES: C[C@@H]1CN(c2cc(=O)[nH]c(N3CCC[C@H]3C(C)(C)c3ccccc3)n2)CCO1]<br>4-[(2R)-2-methylmorpholin-4-yl]-2-[(2S)-2-(1-methyl-1-phenyl-ethyl)pyrrolidin-1-yl]-1H-pyrimidin-6-one | 2-(2-phenyl propan-2-yl)pyrrolidine | Method F | LCMS (ES+) 383 (M + H)+, RT 3.34 min (Analytical Method B); RT 4.07 min (Analytical Method SFC4, YMC AMYLOSE-C, 15/85 IPA (0.1% DEAISO)/$CO_2$); $^1$H NMR (400 MHz, $CDCl_3$): δ 9.44 (1H, br s), 7.42-7.40 (2H, m), 7.34-7.29 (2H, m), 7.25-7.21 (1H, m), 4.96 (1H, s), 4.66 (1H, t, J = 4.6 Hz), 4.15 (1H, d, J = 12.2 Hz), 3.99-3.93 (2H, m), 3.65-3.57 (2H, m), 3.48 (1H, dd, J = 8.7, 18.2 Hz), 3.39 (1H, dt, J = 3.7, 9.6 Hz), 3.00 (1H, dq, J = 12.0, 5.5 Hz), 2.63 (1H, dd, J = 10.4, 13.1 Hz), 1.79-1.63 (3H, m), 1.39 (6H, s), 1.26-1.17 (4H, m) |

-continued

| Example | Structure and Name | Amine | Displacement conditions | Analytical data |
|---|---|---|---|---|
| Example 283 | 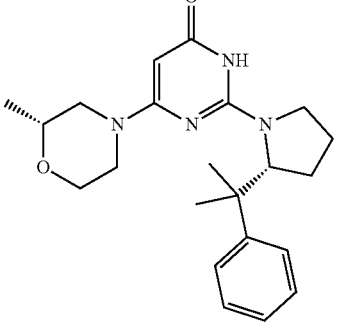<br>4-[(2R)-2-methylmorpholin-4-yl]-2-[(2R)-2-(1-methyl-1-phenyl-ethyl)pyrrolidin-1-yl]-1H-pyrimidin-6-one | 2-(2-phenyl propan-2-yl)pyrrolidine | Method F | LCMS (ES+) 383 (M + H)$^+$, RT 3.34 min (Analytical Method B); RT 5.02 min (Analytical Method SFC4, YMC AMYLOSE-C, 15/85 IPA (0.1% DEAISO)/CO$_2$); $^1$H NMR (400 MHz, CDCl$_3$): δ 9.62-9.62 (1H, br s), 7.42-7.40 (2H, m), 7.34-7.29 (2H, m), 7.25-7.21 (1H, m), 4.96 (1H, s), 4.72-4.67 (1H, m), 4.09 (2H, d, J = 11.9 Hz), 3.96 (1H, ddt, J = 1.1, 4.9, 5.7 Hz), 3.65 (1H, dt, J = 2.7, 11.7 Hz), 3.61-3.54 (1H, m), 3.52-3.45 (1H, m), 3.40 (1H, dt, J = 3.7, 9.6 Hz), 2.98 (1H, dq, J = 12.0, 5.5 Hz), 2.65 (1H, dd, J = 10.4, 12.9 Hz), 1.78-1.63 (3H, m), 1.39-1.37 (6H, m), 1.25-1.18 (4H, m) |
| Example 284 | 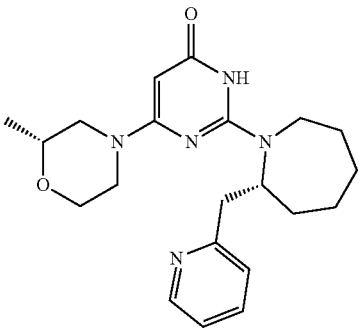 [SMILES: C[C@@H]1CN(c2cc(=O)[nH]c(N3CCCCC[C@@H]3Cc3ccccn3)n2)CCO1]<br>4-[(2R)-2-methylmorpholin-4-yl]-2-[(2R)-2-(2-pyridylmethyl)azepan-1-yl]-1H-pyrimidin-6-one | 2-(pyridin-2-ylmethyl) azepane | Method F | LCMS (ES+) 384 (M + H)$^+$, RT 2.97 min (Analytical Method B); RT 2.09 min (Analytical Method SFC4, YMC AMYLOSE-C, 25/75 MeOH (0.1% DEAISO)/CO$_2$); $^1$H NMR (400 MHz, CDCl$_3$): δ 8.71 (1H, s), 7.59 (1H, dd, J = 7.6, 7.6 Hz), 7.19-7.13 (1H, m), 7.08 (1H, d, J = 7.6 Hz), 4.90 (1H, s), 4.43 (1H, br s), 4.02-3.88 (3H, m), 3.64-3.50 (2H, m), 3.08-2.85 (4H, m), 2.56 (1H, dd, J = 11.1, 12.1 Hz), 2.18-2.09 (1H, m), 1.84-1.71 (4H, m), 1.63-1.52 (3H, m), 1.33-1.15 (5H, m) |
| Example 285 | 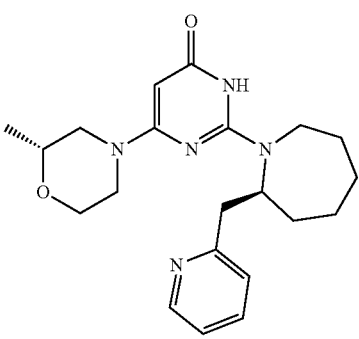 [SMILES: C[C@@H]1CN(c2cc(=O)[nH]c(N3CCCCC[C@H]3Cc3ccccn3)n2)CCO1]<br>4-[(2R)-2-methylmorpholin-4-yl]-2-[(2S)-2-(2-pyridylmethyl)azepan-1-yl]-1H-pyrimidin-6-one | 2-(pyridin-2-ylmethyl) azepane | Method F | LCMS (ES+) 384 (M + H)$^+$, RT 2.46 min (Analytical Method A); RT 1.62 min (Analytical Method SFC4, YMC AMYLOSE-C, 25/75 MeOH (0.1% DEAISO)/CO$_2$); $^1$H NMR (400 MHz, CDCl$_3$): δ 8.70-8.66 (1H, m), 7.59 (1H, dd, J = 7.3, 7.3 Hz), 7.19-7.14 (1H, m), 7.08 (1H, d, J = 7.8 Hz), 4.90 (1H, br s), 4.43 (1H, s), 4.02-3.88 (4H, m), 3.63-3.54 (2H, m), 3.08-3.00 (2H, m), 2.95-2.86 (2H, m), 2.55 (1H, dd, J = 11.0, 12.5 Hz), 2.14-2.14 (1H, m), 1.86-1.74 (4H, m), 1.65-1.51 (3H, m), 1.36-1.18 (4H, m) |
| Example 286 | 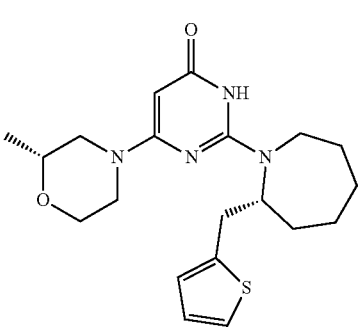 [SMILES: C[C@@H]1CN(c2cc(=O)[nH]c(N3CCCCC[C@@H]3Cc3cccs3)n2)CCO1]<br>6-((R)-2-methylmorpholino)-2-((S)-2-(thiophen-2-ylmethyl)azepan-1-yl)pyrimidin-4(3H)-one | 2-(thiophen-2-ylmethyl) azepane | method G | LCMS (ES+) 389 (M + H)$^+$, RT 3.32 min (Analytical Method B), RT 1.50 min (Analytical Method SFC4, YMC AMYLOSE-C 50/50 MeOH [0.1% DEAISO]/CO$_2$); $^1$H NMR (400 MHz, CDCl$_3$): δ 9.13 (1H, br s), 7.15 (1H, dd, J = 0.9, 5.1 Hz), 6.92 (1H, dd, J = 3.3, 5.1 Hz), 6.79 (1H, d, J = 2.8 Hz), 4.92 (1H, s), 4.64-4.64 (1H, m), 4.11-4.07 (1H, m), 4.00-3.92 (2H, m), 3.67-3.55 (3H, m), 3.11-3.06 (1H, m), 3.01-2.91 (3H, m), 2.61 (1H, dd, J = 10.5, 13.0 Hz), 2.13-2.06 (1H, m), 1.86-1.76 (3H, m), 1.48-1.40 (2H, m), 1.30-1.15 (5H, m) |

| Example | Structure and Name | Amine | Displacement conditions | Analytical data |
|---|---|---|---|---|
| Example 287 | 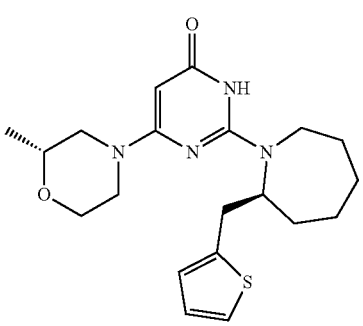 [SMILES: C[C@@H]1CN(c2cc(=O)[nH]c(N3CCCCC[C@H]3Cc3cccs3)n2)CCO1]<br>6-((R)-2-methylmorpholino)-2-((S)-2-(thiophen-2-ylmethyl)azepan-1-yl)pyrimidin-4(3H)-one | 2-(thiophen-2-ylmethyl)azepane | method G | LCMS (ES+) 389 (M + H)+, RT 3.32 min (Analytical Method B), RT 0.82 min (Analytical Method SFC4, YMC AMYLOSE-C 50/50 MeOH [0.1% DEAISO]/$CO_2$); $^1$H NMR (400 MHz, $CDCl_3$): δ 7.15 (1H, dd, J = 1.1, 5.2 Hz), 6.92 (1H, dd, J = 3.4, 5.2 Hz), 6.79 (1H, d, J = 3.3 Hz), 4.92 (1H, s), 4.64 (1H, s), 4.12-4.08 (1H, m), 3.99-3.92 (2H, m), 3.65-3.57 (3H, m), 3.12-3.02 (1H, m), 3.01-2.91 (3H, m), 2.61 (1H, dd, J = 10.4, 13.1 Hz), 2.17-2.06 (1H, m), 1.84-1.76 (3H, m), 1.49-1.41 (2H, m), 1.24 (5H, d, J = 6.1 Hz), NH not observed |
| Example 288 | 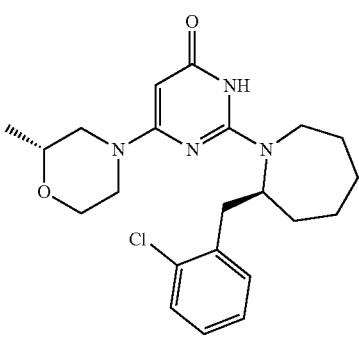 [SMILES: C[C@@H]1CN(c2cc(=O)[nH]c(N3CCCCC[C@H]3Cc3ccccc3Cl)n2)CCO1]<br>2-[(2S)-2-[(2-chlorophenyl)methyl]azepan-1-yl]-4-[(2R)-2-methylmorpholin-4-yl]-1H-pyrimidin-6-one | 2-(2-chlorobenzyl)azepane | method F | LCMS (ES+) 417 (M + H)+, RT 3.50 min (Analytical Method A); RT 0.83 min (Analytical Method SFC4, YMC AMYLOSE-C, 50/50 IPA (0.1% DEAISO)/$CO_2$); $^1$H NMR (400 MHz, $CDCl_3$): δ 7.29-7.28 (1H, m), 7.12-7.08 (3H, m), 4.81 (1H, s), 3.98-3.86 (3H, m), 3.72-3.50 (3H, m), 3.18-3.10 (1H, m), 2.97 (1H, dd, J = 5.9, 12.5 Hz), 2.90-2.81 (2H, m), 2.47-2.41 (1H, m), 2.16-2.06 (1H, m), 1.85-1.75 (3H, m), 1.54-1.41 (3H, m), 1.31-1.25 (1H, m), 1.25-1.18 (4H, m), NH not observed |
| Example 289 | 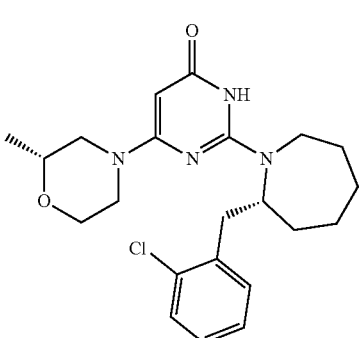<br>2-[(2R)-2-[(2-chlorophenyl)methyl]azepan-1-yl]-4-[(2R)-2-methylmorpholin-4-yl]-1H-pyrimidin-6-one | 2-(2-chlorobenzyl)azepane | method F | LCMS (ES+) 417 (M + H)+, RT 3.50 min (Analytical Method A); RT 1.31 min (Analytical Method SFC4, YMC AMYLOSE-C, 50/50 IPA (0.1% DEAISO)/$CO_2$); $^1$H NMR (400 MHz, $CDCl_3$): δ 7.32-7.29 (1H, m), 7.14-7.08 (3H, m), 4.81 (1H, s), 3.99 (2H, d, J = 11.7 Hz), 3.94-3.88 (1H, m), 3.87-3.80 (1H, m), 3.70-3.50 (2H, m), 3.14-3.07 (1H, m), 2.97 (1H, dd, J = 5.6, 13.6 Hz), 2.84 (2H, t, J = 12.2 Hz), 2.51 (1H, dd, J = 11.5, 11.5 Hz), 2.15-2.06 (1H, m), 1.86-1.77 (3H, m), 1.56-1.42 (3H, m), 1.33-1.25 (1H, m), 1.23 (3H, d, J = 6.3 Hz), 1.20-1.13 (1H, m), NH not observed |

| Example | Structure and Name | Amine | Displacement conditions | Analytical data |
|---|---|---|---|---|
| Example 290 | 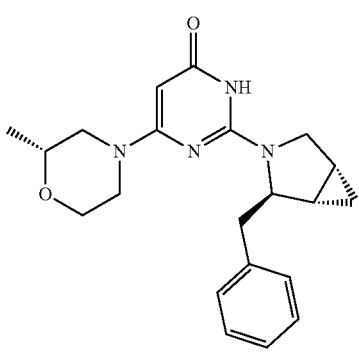 [SMILES: C[C@@H]1CN(c2cc(=O)[nH]c(N3C[C@@H]4C[C@@H]4[C@H]3Cc3ccccc3)n2)CCO1]<br>2-((1S,2R,5R)-2-benzyl-3-azabicyclo[3.1.0]hexan-3-yl)-6-((R)-2-methylmorpholino)pyrimidin-4(3H)-one | Intermediate 2 | Method G | LCMS (ES+) 367 (M + H)+, RT 3.45 min (Analytical Method A), RT 1.73 min (Analytical Method SFC1, YMC AMYLOSE-C 35/65 IPA [0.1% DEAISO]/CO2); $^1$H NMR (400 MHz, CDCl$_3$): δ 10.25-10.24 (1H, br s), 7.31-7.26 (2H, m), 7.25-7.19 (3H, m), 4.94 (1H, s), 4.50 (1H, dd, J = 3.6, 8.7 Hz), 4.16-4.16 (1H, m), 3.95 (2H, dd, J = 2.8, 11.2 Hz), 3.67-3.58 (3H, m), 3.33 (1H, d, J = 6.9 Hz), 3.14 (1H, d, J = 12.3 Hz), 2.98 (1H, dt, J = 3.1, 12.4 Hz), 2.74 (1H, dd, J = 8.8, 13.1 Hz), 2.62 (1H, dd, J = 10.5, 12.9 Hz), 1.52-1.45 (2H, m), 1.24 (3H, d, J = 6.1 Hz), 0.68-0.61 (1H, m), 0.18-0.14 (1H, m). |
| Example 291 | 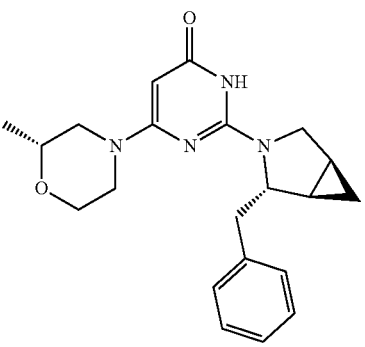 [SMILES: C[C@@H]1CN(c2cc(=O)[nH]c(N3C[C@H]4C[C@H]4[C@@H]3Cc3ccccc3)n2)CCO1]<br>2-((1R,2S,5S)-2-benzyl-3-azabicyclo[3.1.0]hexan-3-yl)-6-((R)-2-methylmorpholino)pyrimidin-4(3H)-one | Intermediate 2 | Method G | LCMS (ES+) 367 (M + H)$^+$, RT 3.45 min (Analytical Method A), RT 2.48 min (Analytical Method SFC1, YMC AMYLOSE-C 35/65 IPA [0.1% DEAISO]/CO$_2$); H NMR (400 MHz, CDCl$_3$): δ 10.42-10.42 (1H, br s), 7.31-7.26 (2H, m), 7.25-7.18 (3H, m), 4.94 (1H, s), 4.52 (1H, dd, J = 3.6, 8.7 Hz), 4.08-3.94 (3H, m), 3.68-3.56 (3H, m), 3.35-3.34 (1H, m), 3.14 (1H, d, J = 12.2 Hz), 2.97 (1H, dt, J = 3.1, 12.4 Hz), 2.74 (1H, dd, J = 8.8, 13.2 Hz), 2.63 (1H, dd, J = 10.5, 12.8 Hz), 1.61-1.44 (2H, m), 1.23 (3H, d, J = 6.1 Hz), 0.67-0.60 (1H, m), 0.19-0.14 (1H, m). |
| Example 292 | 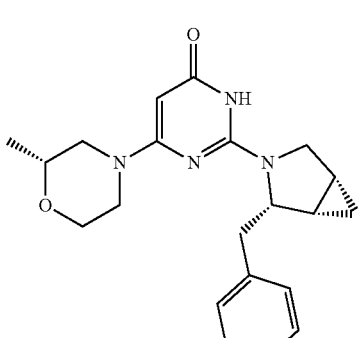<br>2-((1S,2S,5R)-2-benzyl-3-azabicyclo[3.1.0]hexan-3-yl)-6-((R)-2-methylmorpholino)pyrimidin-4(3H)-one | Intermediate 1 | Method G | LCMS (ES+) 367 (M + H)+, RT 3.32 min (Analytical Method A), RT 7.68 min (Analytical Method SFC1, LUX CELLULOSE-4 30/70 MeOH [0.1% DEAISO]/CO2); $^1$H NMR (400 MHz, CDCl$_3$): δ 10.32-10.32 (1H, br s), 7.32-7.29 (4H, m), 7.25-7.21 (1H, m), 5.00 (1H, s), 4.43-4.36 (1H, m), 4.21 (1H, d, J = 11.9 Hz), 4.04-3.94 (2H, m), 3.89 (2H, d, J = 9.5 Hz), 3.83 (1H, dd, J = 3.4, 12.9 Hz), 3.70-3.56 (2H, m), 3.01 (1H, dt, J = 3.5, 12.4 Hz), 2.67 (1H, dd, J = 10.5, 13.0 Hz), 2.38 (1H, dd, J = 10.6, 12.6 Hz), 1.74-1.66 (1H, m), 1.57-1.50 (1H, m), 1.22 (3H, d, J = 6.3 Hz), 0.82-0.75 (1H, m), 0.59 (1H, q, J = 4.4 Hz). |

| Example | Structure and Name | Amine | Displacement conditions | Analytical data |
|---|---|---|---|---|
| Example 293 | 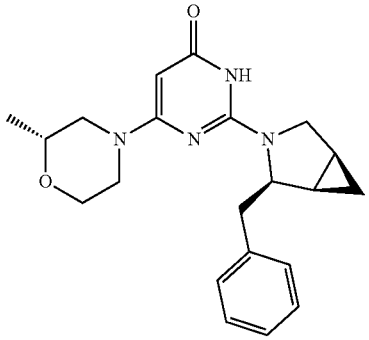 [SMILES: C[C@@H]1CN(c2cc(=O)[nH]c(N3C[C@H]4C[C@H]4[C@H]3Cc3ccccc3)n2)CCO1]<br>2-((1R,2R,5S)-2-benzyl-3-azabicyclo[3.1.0]hexan-3-yl)-6-((R)-2-methylmorpholino)pyrimidin-4(3H)-one | Intermediate 1 | Method G | LCMS (ES+) 367 (M + H)+, RT 3.28 min (Analytical Method B), RT 9.02 min (Analytical Method SFC1, LUX CELLULOSE-4 30/70 MeOH [0.1% DEAISO]/CO$_2$); $^1$H NMR (400 MHz, CDCl$_3$): δ 10.65-10.55 (1H, br s), 7.31 (4H, d, J = 4.5 Hz), 7.26-7.21 (1H, m), 5.00 (1H, s), 4.43-4.36 (1H, m), 4.32-4.27 (1H, m), 3.99-3.88 (3H, m), 3.82 (1H, dd, J = 3.3, 12.6 Hz), 3.68-3.58 (3H, m), 3.03 (1H, dt, J = 3.5, 12.4 Hz), 2.65 (1H, dd, J = 10.4, 12.9 Hz), 2.39 (1H, dd, J = 10.5, 12.5 Hz), 1.74-1.67 (1H, m), 1.58-1.51 (1H, m), 1.24 (3H, d, J = 6.3 Hz), 0.79 (1H, dt, J = 5.2, 7.9 Hz), 0.59 (1H, q, J = 4.5 Hz). |
| Example 294 | 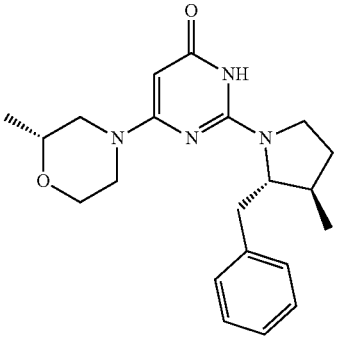 [SMILES: C[C@@H]1CN(c2cc(=O)[nH]c(N3CC[C@@H](C)[C@@H]3Cc3ccccc3)n2)CCO1]<br>2-((2S,3R)-2-benzyl-3-methylpyrrolidin-1-yl)-6-((R)-2-methylmorpholino)pyrimidin-4(3H)-one | Intermediate 6 | Method F | LCMS (ES+) 369 (M + H)+, RT 3.30 min (Analytical Method A); RT 2.19 min (Analytical Method SFC4, LUX CELLULOSE-3 + 0.1% DEAISO 10% MeOH SOL3); $^1$H NMR (400 MHz, DMSO): δ 10.25 (1H, br s), 7.34-7.29 (2H, m), 7.26-7.19 (3H, m), 4.83 (1H, s), 4.15 (1H, d, J = 12.0 Hz), 4.03-3.83 (3H, m), 3.54-3.38 (4H, m), 3.14 (1H, d, J = 11.7 Hz), 2.88-2.79 (1H, m), 2.67-2.60 (1H, m), 2.56-2.48 (1H, m, under DMSO peak), 2.08-1.99 (2H, m), 1.55-1.47 (1H, m), 1.12 (3H, d, J = 6.1 Hz), 0.79 (3H, d, J = 6.7 Hz); |
| Example 295 | 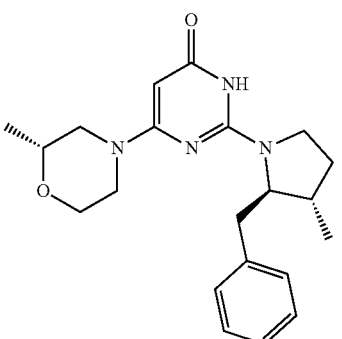<br>2-((2R,3S)-2-benzyl-3-methylpyrrolidin-1-yl)-6-((R)-2-methylmorpholino)pyrimidin-4(3H)-one | Intermediate 6 | Method F | LCMS (ES+) 369 (M + H)+, RT 3.30 min (Analytical Method A); RT 1.27 min (Analytical Method SFC4, LUX CELLULOSE-3 + 0.5% DEAISO 10% MeOH SOL3); $^1$H NMR (400 MHz, DMSO): δ 10.30 (1H, br s), 7.39-7.31 (2H, m), 7.28-7.21 (3H, m), 4.87 (1H, s), 4.22 (1H, d, J = 12.1 Hz), 4.02-3.87 (3H, m), 3.60-3.42 (4H, m), 3.19 (1H, d, J = 11.6 Hz), 2.93-2.83 (1H, m), 2.70-2.59 (1H, m), 2.55-2.50 (1H, m), 2.15-2.05 (2H, m), 1.59-1.50 (1H, m), 1.18 (3H, d, J = 6.1 Hz), 0.82 (3H, d, J = 6.6 Hz) |

-continued

| Example | Structure and Name | Amine | Displacement conditions | Analytical data |
|---|---|---|---|---|
| Example 296 | 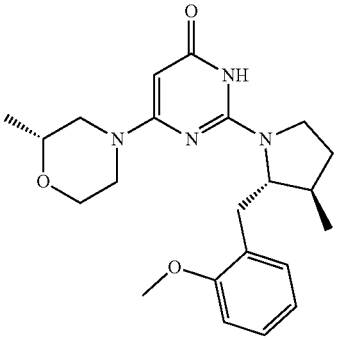 [SMILES: COc1ccccc1C[C@H]1[C@H](C)CCN1c1nc(N2CCO[C@H](C)C2)cc(=O)[nH]1]<br>2-((2S,3R)-2-(2-methoxybenzyl)-3-methylpyrrolidin-1-yl)-6-((R)-2-methylmorpholino)pyrimidin-4(3H)-one | Intermediate 7 | Method F | LCMS (ES+) 399 (M + H)+, RT 3.38 min (Analytical Method B); RT 0.86 min (Analytical Method SFC4, YMC AMYLOSE-C + 0.1% DEAISO 50% IPA SOL4; $^1$H NMR (400 MHz, CDCl$_3$): δ 9.03 (1H, br s), 7.29 (1H, d, J = 7.8 Hz), 7.08 (1H, d, J = 7.3 Hz), 6.99-6.89 (2H, m), 4.97 (1H, s), 4.18 (3H, s), 4.05 (2H, d, J = 13.1 Hz), 3.97-3.91 (1H, m), 3.66-3.56 (4H, m), 3.45 (1H, s), 3.18 (1H, d, J = 12.9 Hz), 3.00-2.90 (1H, m), 2.65-2.57 (1H, m), 2.36-2.20 (3H, m), 1.67-1.52 (1H, m), 1.22 (3H, d, J = 6.1 Hz), 0.85 (3H, d, J = 6.6 Hz). |
| Example 297 | 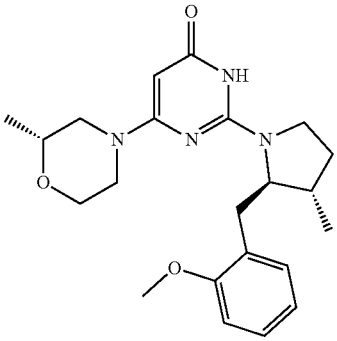 [SMILES: COc1ccccc1C[C@@H]1[C@@H](C)CCN1c1nc(N2CCO[C@H](C)C2)cc(=O)[nH]1]<br>2-((2R,3S)-2-(2-methoxybenzyl)-3-methylpyrrolidin-1-yl)-6-((R)-2-methylmorpholino)pyrimidin-4(3H)-one | Intermediate 7 | Method F | LCMS (ES+) 399 (M + H)+, RT 3.42 min (Analytical Method B); RT 2.27 min (Analytical Method SFC4, YMC AMYLOSE-C + 0.1% DEAISO 50% IPA SOL4); $^1$H NMR (400 MHz, CDCl$_3$): δ 9.02 (1H, br s), 7.31-7.27 (1H, m), 7.08 (1H, dd, J = 1.6, 7.3 Hz), 6.99-6.90 (2H, m), 4.97 (1H, s), 4.18 (3H, s), 4.06-4.03 (2H, m), 3.94 (1H, dd, J = 2.4, 11.6 Hz), 3.68-3.57 (4H, m), 3.43-3.43 (1H, m), 3.18 (1H, d, J = 12.3 Hz), 3.00-2.91 (1H, m), 2.64-2.57 (1H, m), 2.31-2.22 (3H, m), 1.67-1.57 (1H, m), 1.23 (3H, d, J = 6.1 Hz), 0.85 (3H, d, J = 7.0 Hz). |
| Example 298 | 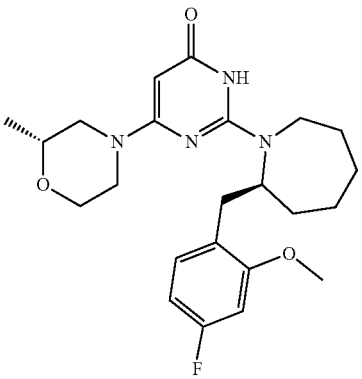 [SMILES: COc1cc(F)ccc1C[C@@H]1CCCCCN1c1nc(N2CCO[C@H](C)C2)cc(=O)[nH]1]<br>2-((S)-2-(4-fluoro-2-methoxybenzyl)azepan-1-yl)-6-((R)-2-methylmorpholino)pyrimidin-4(3H)-one | Intermediate 8 | Method F | LCMS (ES+) 431 (M + H)+, RT 3.5 min (Analytical Method B); RT 3.1 min (Analytical Method SFC4, YMC AMYLOSE-C, 15/85 MeOH (0.1% DEAISO)/CO$_2$); $^1$H NMR (400 MHz, CDCl$_3$): δ 8.95 (1H, br s), 7.01 (1H, t, J = 7.0 Hz), 6.69 (1H, d, J = 10.2 Hz), 6.60 (1H, t, J = 7.6 Hz), 4.96 (1H, s), 4.27-4.14 (4H, m), 4.03-3.92 (3H, m), 3.64-3.57 (3H, m), 3.05-2.91 (3H, m), 2.62 (1H, t, J = 11.1 Hz), 2.48-2.41 (1H, m), 2.01-1.94 (1H, m), 1.84-1.73 (3H, m), 1.70-1.54 (1H, m), 1.48-1.38 (1H, m), 1.36-1.07 (5H, m) |

-continued

| Example | Structure and Name | Amine | Displacement conditions | Analytical data |
|---|---|---|---|---|
| Example 299 | 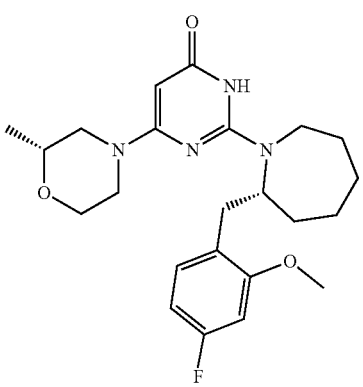 [SMILES: COc1cc(F)ccc1C[C@H]1CCCCCN1c1nc(N2CCO[C@H](C)C2)cc(=O)[nH]1]<br>2-((R)-2-(4-fluoro-2-methoxybenzyl)azepan-1-yl)-6-((R)-2-methylmorpholino)pyrimidin-4(3H)-one | Intermediate 8 | Method F | LCMS (ES+) 431 (M + H)+, RT 3.51 min (Analytical Method B); RT 4.56 min (Analytical Method SFC4, YMC AMYLOSE-C, 15/85 MeOH (0.1% DEAISO)/CO$_2$); $^1$H NMR (400 MHz, CDCl$_3$): δ 8.95 (1H, br s), 7.00 (1H, t, J = 6.6 Hz), 6.71 (1H, d, J = 9.1 Hz), 6.60 (1H, t, J = 7.9 Hz), 4.95 (1H, s), 4.26-3.92 (7H, m), 3.65-3.54 (3H, m), 3.06-2.91 (3H, m), 2.62 (1H, t, J = 11.6 Hz), 2.48-2.40 (1H, m), 2.00-1.93 (1H, m), 1.85-1.73 (3H, m), 1.48-1.07 (7H, m). |
| Example 300 | 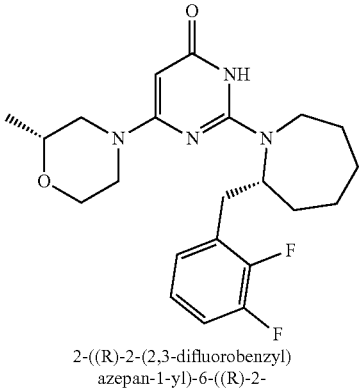<br>2-((R)-2-(2,3-difluorobenzyl)azepan-1-yl)-6-((R)-2-methylmorpholino)pyrimidin-4(3H)-one | Intermediate 14 | Method F | LCMS (ES+) 419 (M + H)+, RT 3.38 min (Analytical Method B); RT 1.79 min (Analytical Method SFC4, YMC AMYLOSE-C, 25/75 MeOH (0.1% DEAISO)/CO$_2$); $^1$H NMR (400 MHz, CDCl$_3$): δ 9.42 (1H, br s), 7.03-6.79 (3H, m), 5.01-4.80 (2H, m), 4.16-3.52 (6H, m), 3.14-2.98 (1H, m), 2.94-2.79 (3H, m), 2.56 (1H, t, J = 12.1 Hz), 2.10-2.03 (1H, m), 1.85-1.71 (3H, m), 1.49-1.14 (7H, m) |
| Example 301 | 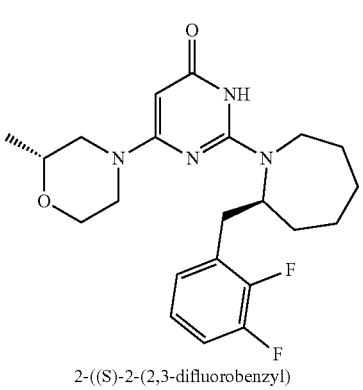<br>2-((S)-2-(2,3-difluorobenzyl)azepan-1-yl)-6-((R)-2-methylmorpholino)pyrimidin-4(3H)-one | Intermediate 14 | Method F | LCMS (ES+) 419 (M + H)+, RT 3.41 min (Analytical Method A); RT 1.17 min (Analytical Method SFC4, YMC AMYLOSE-C, 25/75 MeOH (0.1% DEAISO)/CO$_2$); $^1$H NMR (400 MHz, CDCl$_3$): δ 9.68 (1H, br s), 7.02-6.79 (3H, m), 5.01-4.80 (2H, m), 4.09-3.54 (6H, m), 3.16-3.00 (1H, m), 2.95-2.79 (3H, m), 2.53 (1H, t, J = 11.0 Hz), 2.10-2.03 (1H, m), 1.85-1.75 (3H, m), 1.46-1.13 (7H, m) |

-continued

| Example | Structure and Name | Amine | Displacement conditions | Analytical data |
|---|---|---|---|---|
| Example 302 | 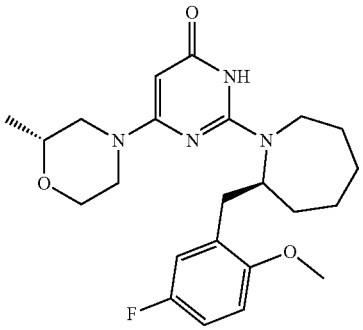 [SMILES: COc1ccc(F)cc1C[C@@H]1CCCCCN1c1nc(N2CCO[C@H](C)C2)cc(=O)[nH]1]<br>2-((S)-2-(5-fluoro-2-methoxybenzyl)azepan-1-yl)-6-((R)-2-methylmorpholino)pyrimidin-4(3H)-one | Intermediate 13 | Method F | LCMS (ES+) 431 (M + H)+, RT 3.48 min (Analytical Method B); RT 1.55 min (Analytical Method SFC4, YMC AMYLOSE-C, 25/75 MeOH (0.1% DEAISO)/CO$_2$); $^1$H NMR (400 MHz, CDCl$_3$): δ 9.03 (1H, br s), 6.97-6.79 (3H, m), 4.95 (1H, s), 4.28-4.13 (4H, m), 4.03-3.92 (3H, m), 3.73-3.55 (3H, m), 3.11-2.91 (3H, m), 2.64-2.57 (1H, m), 2.48-2.39 (1H, m), 2.04-1.95 (1H, m), 1.86-1.73 (3H, m), 1.50-1.08 (7H, m) |
| Example 303 | 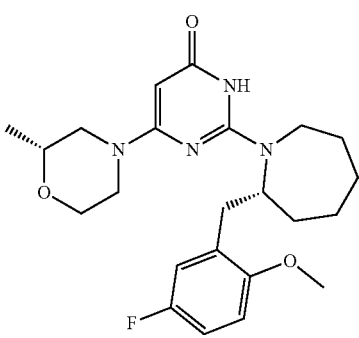 [SMILES: COc1ccc(F)cc1C[C@H]1CCCCCN1c1nc(N2CCO[C@H](C)C2)cc(=O)[nH]1]<br>2-((R)-2-(5-fluoro-2-methoxybenzyl)azepan-1-yl)-6-((R)-2-methylmorpholino)pyrimidin-4(3H)-one | Intermediate 13 | Method F | LCMS (ES+) 431 (M + H)+, RT 3.51 min (Analytical Method A); RT 2.64 min (Analytical Method SFC4, YMC AMYLOSE-C, 25/75 EtOH (0.1% DEAISO)/CO$_2$); $^1$H NMR (400 MHz, CDCl$_3$): δ 9.03 (1H, s), 6.97-6.80 (3H, m), 4.95 (1H, s), 4.25-4.14 (4H, m), 4.09-4.04 (1H, m), 3.99-3.92 (2H, m), 3.72-3.54 (3H, m), 3.12-2.90 (3H, m), 2.61 (1H, dd, J = 10.7, 13.3 Hz), 2.48-2.38 (1H, m), 2.03-1.96 (1H, m), 1.85-1.64 (4H, m), 1.50-1.40 (1H, m), 1.37-1.08 (5H, m). |
| Example 304 | 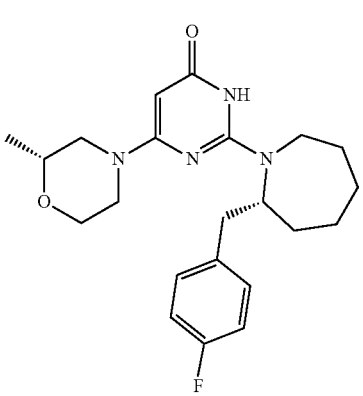 [SMILES: C[C@@H]1CN(c2cc(=O)[nH]c(N3CCCCC[C@@H]3Cc3ccc(F)cc3)n2)CCO1]<br>2-((R)-2-(4-fluorobenzyl)azepan-1-yl)-6-((R)-2-methylmorpholino)pyrimidin-4(3H)-one | Intermediate 15 | Method F | LCMS (ES+) 401 (M + H)+, RT 3.38 min (Analytical Method A); RT 4.02 min (Analytical Method SFC4, YMC AMYLOSE-C, 20/80 IPA (0.1% DEAISO)/CO$_2$); $^1$H NMR (400 MHz, CDCl$_3$): δ 9.36 (1H, br s), 7.11-7.06 (2H, m), 6.96-6.91 (2H, m), 4.89 (1H, s), 4.78-4.55 (1H, m), 4.09-3.88 (3H, m), 3.65-3.52 (3H, m), 2.98-2.56 (5H, m), 2.06-1.95 (1H, m), 1.86-1.70 (3H, m), 1.47-1.13 (7H, m) |

-continued

| Example | Structure and Name | Amine | Displacement conditions | Analytical data |
|---|---|---|---|---|
| Example 305 | 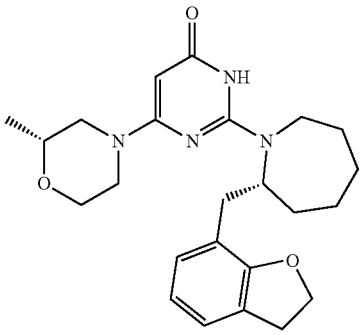 [SMILES: C[C@@H]1CN(c2cc(=O)[nH]c(N3CCCCC[C@@H]3Cc3cccc4c3OCC4)n2)CCO1]<br>2-((R)-2-((2,3-dihydrobenzofuran-7-yl)methyl)azepan-1-yl)-6-((R)-2-methylmorpholino)pyrimidin-4(3H)-one | Intermediate 13 | Method F | LCMS (ES+) 425 (M + H)+, RT 3.48 min (Analytical Method B); RT 2.74 min (Analytical Method SFC4, YMC AMYLOSE-C, 25/75 MeOH (0.1% DEAISO)/CO$_2$); $^1$H NMR (400 MHz, CDCl$_3$): δ 9.42 (1H, br s), 7.11-7.09 (1H, m), 6.86 (1H, d, J = 8.0 Hz), 6.80-6.76 (1H, m), 4.93-4.75 (3H, m), 4.28-3.91 (4H, m), 3.79-3.54 (3H, m), 3.26-3.22 (2H, m), 3.08-2.88 (3H, m), 2.62-2.56 (2H, m), 2.13-2.03 (1H, m), 1.85-1.71 (3H, m), 1.51-1.41 (2H, m), 1.35-1.08 (5H, m) |
| Example 306 | 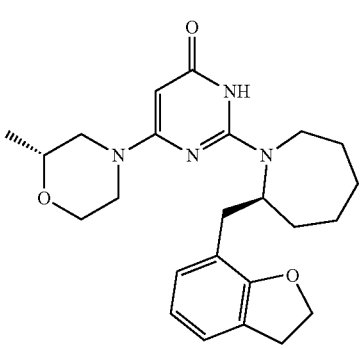 [SMILES: C[C@@H]1CN(c2cc(=O)[nH]c(N3CCCCC[C@H]3Cc3cccc4c3OCC4)n2)CCO1]<br>2-((S)-2-((2,3-dihydrobenzofuran-7-yl)methyl)azepan-1-yl)-6-((R)-2-methylmorpholino)pyrimidin-4(3H)-one | Intermediate 13 | Method F | LCMS (ES+) 425 (M + H)+, RT 3.47 min (Analytical Method A); RT 2.14 min (Analytical Method SFC4, YMC AMYLOSE-C, 25/75 MeOH (0.1% DEAISO)/CO$_2$); $^1$H NMR (400 MHz, CDCl$_3$): δ 9.44 (1H, br s), 7.11-7.09 (1H, m), 6.88-6.76 (2H, m), 4.93-4.77 (3H, m), 4.27-3.91 (4H, m), 3.80-3.57 (3H, m), 3.27-3.22 (2H, m), 3.07-2.90 (3H, m), 2.62-2.56 (2H, m), 2.10-2.04 (1H, m), 1.83-1.71 (4H, m), 1.50-1.41 (1H, m), 1.31-1.09 (5H, m) |
| Example 307 | 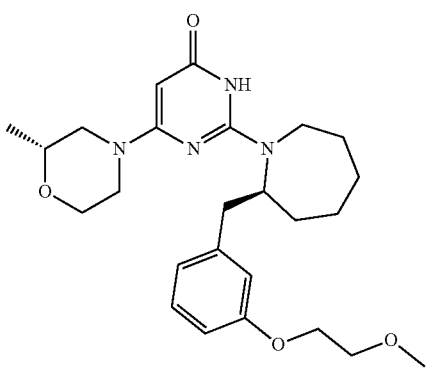<br>2-((S)-2-(3-(2-methoxyethoxy)benzyl)azepan-1-yl)-6-((R)-2-methylmorpholino)pyrimidin-4(3H)-one | Intermediate 16 | Method F | LCMS (ES+) 457.2 (M + H)+, RT 3.29 min (Analytical Method B); ); RT 1.71 min (Analytical Method SFC4, YMC AMYLOSE-C, 30/70 IPA (0.1% DEAISO)/CO$_2$); $^1$H NMR (400 MHz, CDCl$_3$): δ 7.18 (1H, t, J = 7.9 Hz), 6.78-6.74 (3H, m), 4.91 (1H, s), 4.77-4.55 (1H, m), 4.14-4.06 (3H, m), 3.97-3.91 (2H, m), 3.74-3.71 (2H, m), 3.65-3.58 (3H, m), 3.45 (3H, s), 3.00-2.84 (3H, m), 2.68-2.58 (2H, m), 2.04-1.96 (1H, m), 1.84-1.73 (3H, m), 1.46-1.36 (2H, m), 1.31-1.12 (5H, m), NH not observed |

| Example | Structure and Name | Amine | Displacement conditions | Analytical data |
|---|---|---|---|---|
| Example 308 | 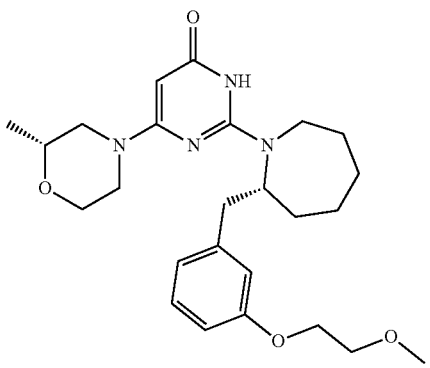<br>2-((R)-2-(3-(2-methoxyethoxy)benzyl)azepan-1-yl)-6-((R)-2-methylmorpholino)pyrimidin-4(3H)-one | Intermediate 16 | Method F | LCMS (ES+) 457.3 (M + H)+, RT 3.29 min (Analytical Method B); RT 2.61 min (Analytical Method SFC4, YMC AMYLOSE-C, 30/70 IPA (0.1% DEAISO)/CO$_2$); $^1$H NMR (400 MHz, CDCl$_3$): δ 7.17 (1H, t, J = 8.3 Hz), 6.77-6.73 (3H, m), 4.91 (1H, s), 4.78-4.59 (1H, m), 4.10-3.93 (5H, m), 3.73 (2H, t, J = 4.7 Hz), 3.67-3.55 (3H, m), 3.45 (3H, s), 3.00-2.85 (3H, m), 2.68-2.59 (2H, m), 2.03-1.94 (1H, m), 1.83-1.72 (3H, m), 1.47-1.36 (2H, m), 1.29-1.11 (5H, m), NH not observed |
| Example 309 | 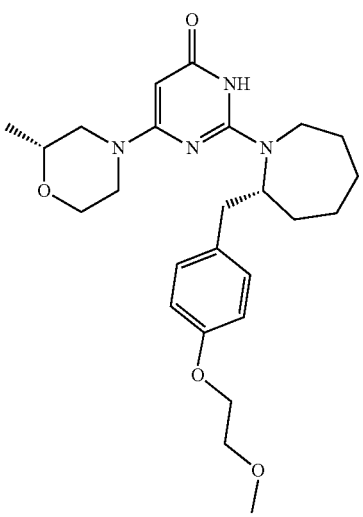 [SMILES: COCCOc1ccc(C[C@H]2CCCCCN2c2nc(N3CCO[C@H](C)C3)cc(=O)[nH]2)cc1]<br>2-((R)-2-(4-(2-methoxyethoxy)benzyl)azepan-1-yl)-6-((R)-2-methylmorpholino)pyrimidin-4(3H)-one | Intermediate 17 | Method F | LCMS (ES+) 457 (M + H)+, RT 3.28 min (Analytical Method B); RT 2.09 min (Analytical Method SFC4, LUX CELLULOSE-3, 25/75 EtOH (0.1% DEAISO)/CO$_2$); $^1$H NMR (400 MHz, CDCl$_3$): δ 7.04 (2H, d, J = 8.1 Hz), 6.84 (2H, d, J = 8.1 Hz), 4.90 (1H, s), 4.78-4.44 (1H, m), 4.10-3.92 (5H, m), 3.75-3.73 (2H, m), 3.66-3.55 (2H, m), 3.45 (3H, s), 2.99-2.58 (5H, m), 2.05-1.94 (1H, m), 1.81-1.71 (3H, m), 1.46-1.36 (2H, m), 1.26-1.12 (6H, m), NH not observed |
| Example 310 | 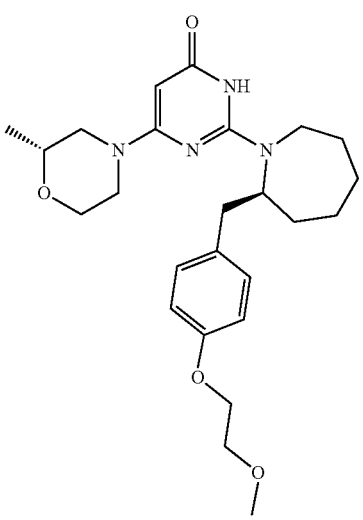 [SMILES: COCCOc1ccc(C[C@@H]2CCCCCN2c2nc(N3CCO[C@H](C)C3)cc(=O)[nH]2)cc1]<br>2-((S)-2-(4-(2-methoxyethoxy)benzyl)azepan-1-yl)-6-((R)-2-methylmorpholino)pyrimidin-4(3H)-one | Intermediate 17 | Method F | LCMS (ES+) 457 (M + H)+, RT 3.28 min (Analytical Method B); RT 0.96 min (Analytical Method SFC4, LUX CELLULOSE-3, 25/75 EtOH (0.1% DEAISO)/CO$_2$); $^1$H NMR (400 MHz, CDCl$_3$): δ 7.05 (2H, d, J = 8.0 Hz), 6.84 (2H, d, J = 8.0 Hz), 4.91 (1H, s), 4.79-4.49 (1H, m), 4.16-4.08 (3H, m), 3.97-3.89 (2H, m), 3.75-3.73 (2H, m), 3.65-3.58 (2H, m), 3.45 (3H, s), 2.99-2.77 (3H, m), 2.71-2.58 (2H, m), 2.05-1.96 (1H, m), 1.84-1.71 (3H, m), 1.50-1.35 (2H, m), 1.29-1.12 (6H, m), NH not observed |

| Example | Structure and Name | Amine | Displacement conditions | Analytical data |
|---|---|---|---|---|
| Example 311 | 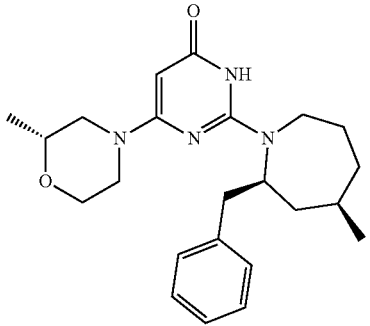<br>2-((2S,4R)-2-benzyl-4-methylazepan-1-yl)-6-((R)-2-methylmorpholino)pyrimidin-4(3H)-one | Intermediate 23 | Method F | LCMS (ES+) 397.2 (M + H)+, RT 3.48 min (Analytical Method B); RT 2.79 min (Analytical Method SFC4, YMC AMYLOSE-C, 15/85 MeOH (0.1% DEAISO)/CO$_2$); $^1$H NMR (400 MHz, CDCl$_3$): δ 7.29-7.19 (3H, m), 7.14 (2H, d, J = 7.3 Hz), 4.90 (1H, s), 4.83-4.60 (1H, m), 4.16-4.03 (1H, m), 3.97-3.89 (2H, m), 3.64-3.49 (3H, m), 3.00-2.81 (3H, m), 2.75-2.68 (1H, m), 2.60 (1H, dd, J = 10.5, 13.0 Hz), 1.74-1.38 (6H, m), 1.25 (3H, d, J = 5.4 Hz), 1.12-1.02 (1H, m), 0.92 (3H, d, J = 5.7 Hz), NH not observed |
| Example 312 | 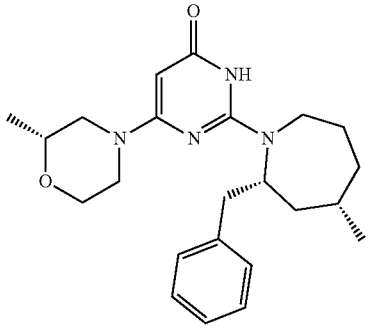<br>2-((2R,4S)-2-benzyl-4-methylazepan-1-yl)-6-((R)-2-methylmorpholino)pyrimidin-4(3H)-one | Intermediate 23 | Method F | LCMS (ES+) 397.2 (M + H)+, RT 3.48 min (Analytical Method B); RT 2.92 min (Analytical Method SFC1, YMC AMYLOSE-C, 20/80 MeOH (0.1% DEAISO)/CO$_2$); $^1$H NMR (400 MHz, CDCl$_3$): δ 7.29-7.18 (3H, m), 7.15 (2H, d, J = 6.7 Hz), 4.89 (1H, s), 4.84-4.64 (1H, m), 4.15-3.92 (3H, m), 3.66-3.55 (3H, m), 3.01-2.81 (3H, m), 2.76-2.68 (1H, m), 2.60 (1H, dd, J = 10.3, 13.0 Hz), 1.75-1.65 (3H, m), 1.51-1.41 (3H, m), 1.24 (3H, d, J = 6.0 Hz), 1.12-1.02 (1H, m), 0.92 (3H, d, J = 6.0 Hz), NH not observed |
| Example 313 | 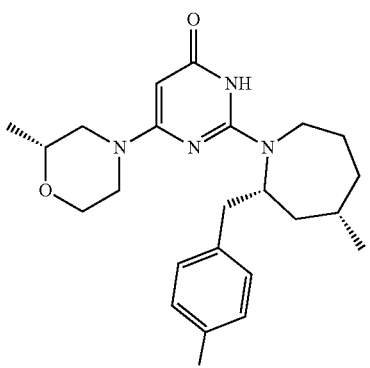<br>2-((2R,4S)-2-(4-fluorobenzyl)-4-methylazepan-1-yl)-6-((R)-2-methylmorpholino)pyrimidin-4(3H)-one | Intermediate 25 | Method F | LCMS (ES+) 415.2 (M + H)+, RT 3.47 min (Analytical Method B); RT 1.70 min (Analytical Method SFC4, LUX CELLULOSE-3, 15/85 MeOH (0.1% DEAISO)/CO$_2$); $^1$H NMR (400 MHz, CDCl$_3$): δ 7.11-7.06 (2H, m), 6.95 (2H, t, J = 8.2 Hz), 4.90 (1H, s), 4.82-5.57 (1H, m), 4.09-3.93 (3H, m), 3.66-3.37 (3H, m), 2.98-2.69 (4H, m), 2.64-2.58 (1H, m), 1.74-1.64 (3H, m), 1.54-1.33 (3H, m), 1.23 (3H, d, J = 5.8Hz), 1.12-1.01 (1H, m), 0.92 (3H, d, J = 5.8 Hz), NH not observed |

| Example | Structure and Name | Amine | Displacement conditions | Analytical data |
|---|---|---|---|---|
| Example 314 | 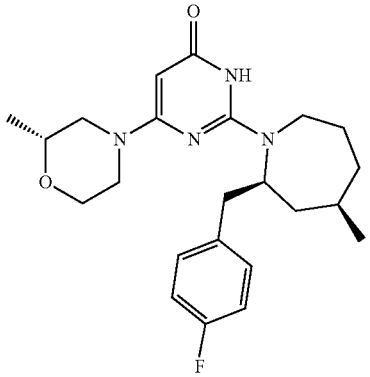<br>2-((2S,4R)-2-(4-fluorobenzyl)-4-methylazepan-1-yl)-6-((R)-2-methylmorpholino)pyrimidin-4(3H)-one | Intermediate 25 | Method F | LCMS (ES+) 415.2 (M + H)+, RT 3.55 min (Analytical Method A); RT 2.88 min (Analytical Method SFC4, YMC AMYLOSE-C, 15/75 MeOH (0.1% DEAISO)/CO$_2$); $^1$H NMR (400 MHz, CDCl$_3$): δ 7.11-7.08 (2H, m), 6.95 (2H, t, J = 8.8 Hz), 4.90 (1H, s), 4.79-4.65 (1H, m), 4.11-3.88 (3H, m), 3.64-3.57 (3H, m), 2.98-2.91 (2H, m), 2.82-2.67 (2H, m), 2.59 (1H, dd, J = 10.6, 12.7 Hz), 1.76-1.65 (3H, m), 1.52-1.36 (3H, m), 1.25 (3H, d, J = 5.8 Hz), 1.11-1.00 (1H, m), 0.91 (3H, d, J = 6.4 Hz), NH not observed. |
| Example 315 | 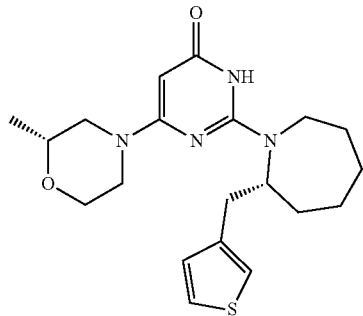 [SMILES: C[C@@H]1CN(c2cc(=O)[nH]c(N3CCCCC[C@@H]3Cc3ccsc3)n2)CCO1]<br>6-((R)-2-methylmorpholino)-2-((R)-2-(thiophen-3-ylmethyl)azepan-1-yl)pyrimidin-4(3H)-one | Intermediate 26 | Method F | LCMS (ES+) 389 (M + H)+, RT 3.45 min (Analytical Method B); RT 1.53 min (Analytical Method SFC4, YMC AMYLOSE-C, 40/60 IPA (0.1% DEAISO)/CO$_2$); $^1$H NMR (400 MHz, CDCl$_3$): δ 8.94 (1H, s), 7.27-7.24 (1H, m, partially obscured by chloroform), 6.95 (1H, s), 6.89 (1H, d, J = 4.4 Hz), 4.90 (1H, s), 4.78-4.43 (1H, m), 4.05-3.92 (3H, m), 3.66-3.54 (3H, m), 2.99-2.78 (4H, m), 2.61 (1H, dd, J = 10.5, 13.0 Hz), 2.10-2.02 (1H, m), 1.82-1.74 (3H, m), 1.50-1.39 (2H, m), 1.29-1.14 (5H, m) |
| Example 316 | 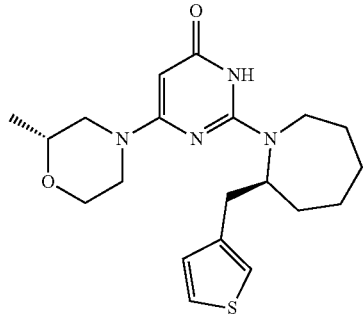 [SMILES: C[C@@H]1CN(c2cc(=O)[nH]c(N3CCCCC[C@H]3Cc3ccsc3)n2)CCO1]<br>6-((R)-2-methylmorpholino)-2-((S)-2-(thiophen-3-ylmethyl)azepan-1-yl)pyrimidin-4(3H)-one | Intermediate 26 | Method F | LCMS (ES+) 389 (M + H)+, RT 3.45 min (Analytical Method B); RT 0.93 min (Analytical Method SFC4, YMC AMYLOSE-C, 40/60 IPA (0.1% DEAISO)/CO$_2$); $^1$H NMR (400 MHz, CDCl$_3$): δ 9.06 (1H, s), 7.27-7.23 (1H, m, partially obscured by chloroform), 6.95 (1H, s), 6.89 (1H, d, J = 4.9 Hz), 4.91 (1H, s), 4.76-4.51 (1H, m), 4.08-4.03 (1H, m), 3.95-3.92 (2H, m), 3.64-3.57 (3H, m), 2.99-2.78 (4H, m), 2.60 (1H, dd, J = 10.2, 13.5 Hz), 2.10-2.01 (1H, m), 1.83-1.73 (3H, m), 1.50-1.39 (2H, m), 1.30-1.14 (5H, m) |

-continued

| Example | Structure and Name | Amine | Displacement conditions | Analytical data |
|---|---|---|---|---|
| Example 317 | 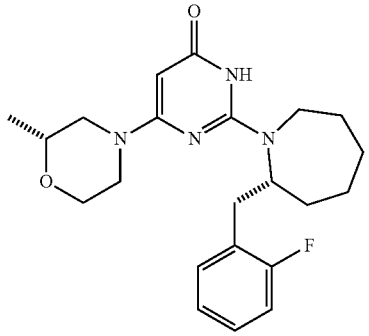 [SMILES: C[C@@H]1CN(c2cc(=O)[nH]c(N3CCCCC[C@@H]3Cc3ccccc3F)n2)CCO1]<br>2-((R)-2-(2-fluorobenzyl)azepan-1-yl)-6-((R)-2-methylmorpholino)pyrimidin-4(3H)-one | (R)-2-(2-fluorobenzyl)azepane | Method F | LCMS (ES+) 401 (M + H)$^+$, RT 3.60 min (Analytical Method A); $^1$H NMR δ (ppm) (400 MHz, CDCl$_3$) 8.26 (1H, s), 7.21-7.17 (1H, m), 7.12-7.09 (1H, m), 7.05-6.96 (2H, m), 4.87 (1H, s), 4.13-4.01 (1H, m), 3.94 (2H, dd, J = 2.6, 11.3 Hz), 3.65-3.53 (2H, m), 3.16-3.02 (1H, m), 2.96-2.87 (2H, m), 2.76 (1H, dd, J = 7.8, 13.4 Hz), 2.57 (1H, dd, J = 10.6, 12.9 Hz), 2.09-2.01 (1H, m), 1.88-1.74 (3H, m), 1.48-1.36 (2H, m), 1.33-1.12 (5H, m). 2 protons obscured by water peak. |
| Example 318 | 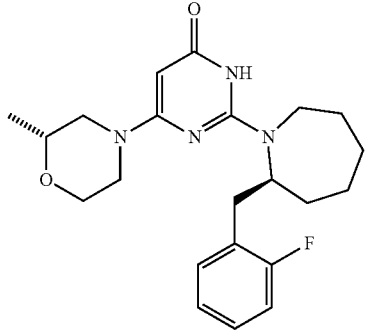 [SMILES: C[C@@H]1CN(c2cc(=O)[nH]c(N3CCCCC[C@H]3Cc3ccccc3F)n2)CCO1]<br>2-((S)-2-(2-fluorobenzyl)azepan-1-yl)-6-((R)-2-methylmorpholino)pyrimidin-4(3H)-one | (S)-2-(2-fluorobenzyl)azepane | Method F | LCMS (ES+) 401 (M + H)$^+$, RT 3.61 min (Analytical Method A); $^1$H NMR δ (ppm) (400 MHz, CDCl$_3$) 8.37 (1H, s), 7.21-7.16 (1H, m), 7.13-7.09 (1H, m), 7.04-6.96 (2H, m), 4.88 (1H, s), 4.11-4.02 (1H, m), 3.97-3.91 (2H, m), 3.63-3.56 (2H, m), 3.18-3.01 (1H, m), 2.96-2.87 (2H, m), 2.76 (1H, dd, J = 7.8, 13.3 Hz), 2.55 (1H, dd, J = 10.7, 12.7 Hz), 2.08-2.00 (1H, m), 1.85-1.76 (3H, m), 1.47-1.41 (1H, m), 1.32-1.13 (5H, m). 3 protons obscured by water peak. |
| Example 319 | 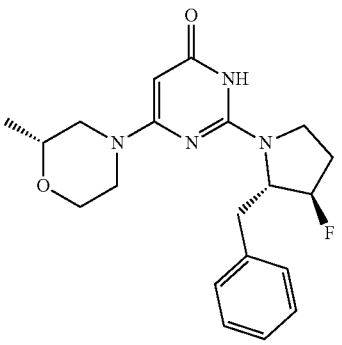 [SMILES: C[C@@H]1CN(c2cc(=O)[nH]c(N3CC[C@@H](F)[C@@H]3Cc3ccccc3)n2)CCO1]<br>2-((2S,3R)-2-benzyl-3-fluoropyrrolidin-1-yl)-6-((R)-2-methylmorpholino)pyrimidin-4(3H)-one | Example 259 step 2 | Method F | LCMS (ES+) 373 (M + H)$^+$, RT 3.11 min (Analytical Method B); $^1$H NMR (400 MHz, DMSO): δ 10.40 (1H, s), 7.37-7.32 (2H, m), 7.29-7.25 (3H, m), 5.08-4.90 (2H, m), 4.49-4.41 (1H, m), 4.16 (1H, d, J = 12.8 Hz), 3.96 (1H, d, J = 12.8 Hz), 3.86 (1H, dd, J = 2.4, 11.5 Hz), 3.71-3.64 (1H, m), 3.53-3.40 (3H, m), 3.12 (1H, d, J = 13.6 Hz), 2.88-2.79 (1H, m), 2.61-2.54 (2H, m, under DMSO peak), 2.21-2.14 (2H, m), 1.13 (3H, d, J = 6.1 Hz) |

| Example | Structure and Name | Amine | Displacement conditions | Analytical data |
|---|---|---|---|---|
| Example 320 | 2-((2R)-2-benzyl-4-methylpyrrolidin-1-yl)-6-((R)-2-methylmorpholino)pyrimidin-4(3H)-one stereoisomer 1 | Example 100 step 6 | Method F | LCMS (ES+) 369 (M + H)+, RT 3.34 min (Analytical Method B); $^1$H NMR (400 MHz, CDCl$_3$): δ 9.52 (1H, s), 7.31-7.27 (2H, m), 7.24-7.20 (1H, m), 7.17-7.14 (2H, m), 4.96 (1H, s), 4.39-4.30 (1H, m), 4.18-4.10 (1H, m), 4.07-4.00 (1H, m), 3.95 (1H, dd, J = 2.5, 11.7 Hz), 3.73-3.47 (4H, m), 3.00 (1H, dt, J = 3.4, 12.4 Hz), 2.92 (1H, t, J = 9.6 Hz), 2.69-2.58 (2H, m), 2.18-2.06 (2H, m), 1.44-1.35 (1H, m), 1.21 (3H, d, J = 6.3 Hz), 1.06 (3H, d, J = 6.3 Hz). |
| Example 321 | 2-((2R)-2-benzyl-4-methylpyrrolidin-1-yl)-6-((R)-2-methylmorpholino)pyrimidin-4(3H)-one stereoisomer 2 | Example 100 step 6 | Method F | LCMS (ES+) 369 (M + H)+, RT 3.54 min (Analytical Method A); $^1$H NMR (400 MHz, CDCl$_3$): δ 8.84 (1H, s), 7.32-7.28 (2H, m), 7.25-7.21 (1H, m), 7.18 (2H, d, J = 6.9 Hz), 4.95 (1H, s), 4.46-4.38 (1H, m), 4.19-4.11 (1H, m), 4.04-3.92 (2H, m), 3.68-3.56 (3H, m), 3.26-3.19 (1H, m), 3.03-2.89 (2H, m), 2.67-2.60 (2H, m), 2.44-2.34 (1H, m), 1.92 (1H, dd, J = 6.2, 12.7 Hz), 1.54-1.47 (1H, m), 1.22 (3H, d, J = 6.1 Hz), 1.07 (3H, d, J = 6.5 Hz). |
| Example 322 | 2-((S)-2-benzyl-3,3-difluoropyrrolidin-1-yl)-6-((R)-2-methylmorpholino)pyrimidin-4(3H)-one | Example 98 step 2 | Method F | LCMS (ES+) 391 (M + H)+, RT 3.17 min (Analytical Method B); $^1$H NMR (400 MHz, CDCl$_3$): δ 7.17-7.12 (2H, m), 4.97 (1H, s), 4.69-4.61 (1H, m), 4.01-3.87 (3H, m), 3.65-3.47 (4H, m), 3.29 (1H, dd, J = 5.9, 14.5 Hz), 3.03-2.90 (2H, m), 2.62 (1H, dd, J = 10.4, 12.9 Hz), 2.32-2.22 (1H, m), 1.87-1.73 (1H, m), 1.20 (3H, d, J = 6.3 Hz), NH not observed, 3 protons obscured by CHCl$_3$ peak. |
| Example 323 | 2-((R)-2-benzyl-3,3-difluoropyrrolidin-1-yl)-6-((R)-2-methylmorpholino)pyrimidin-4(3H)-one | Example 98 step 2 | Method F | LCMS (ES+) 391 (M + H)+, RT 3.17 min (Analytical Method B); $^1$H NMR δ (ppm) (400 MHz, CDCl$_3$) 7.17-7.13 (2H, m), 4.97 (1H, s), 4.69-4.61 (1H, m), 4.07-4.02 (1H, m), 3.95-3.89 (2H, m), 3.63-3.49 (4H, m), 3.33-3.25 (1H, m), 3.04-2.93 (2H, m), 2.59 (1H, dd, J = 10.5, 13.0 Hz), 2.33-2.22 (1H, m), 1.91-1.74 (1H, m), 1.21 (3H, d, J = 6.3 Hz), NH not observed, 3 protons obscured by CHCl$_3$ peak. |

Example 324: 2-((2S,3S)-3-fluoro-2-(2-methoxybenzyl)pyrrolidin-1-yl)-6-morpholinopyrimidin-4(3H)-one and Example 325: 2-((2R,3R)-3-fluoro-2-(2-methoxybenzyl)pyrrolidin-1-yl)-6-morpholinopyrimidin-4(3H)-one

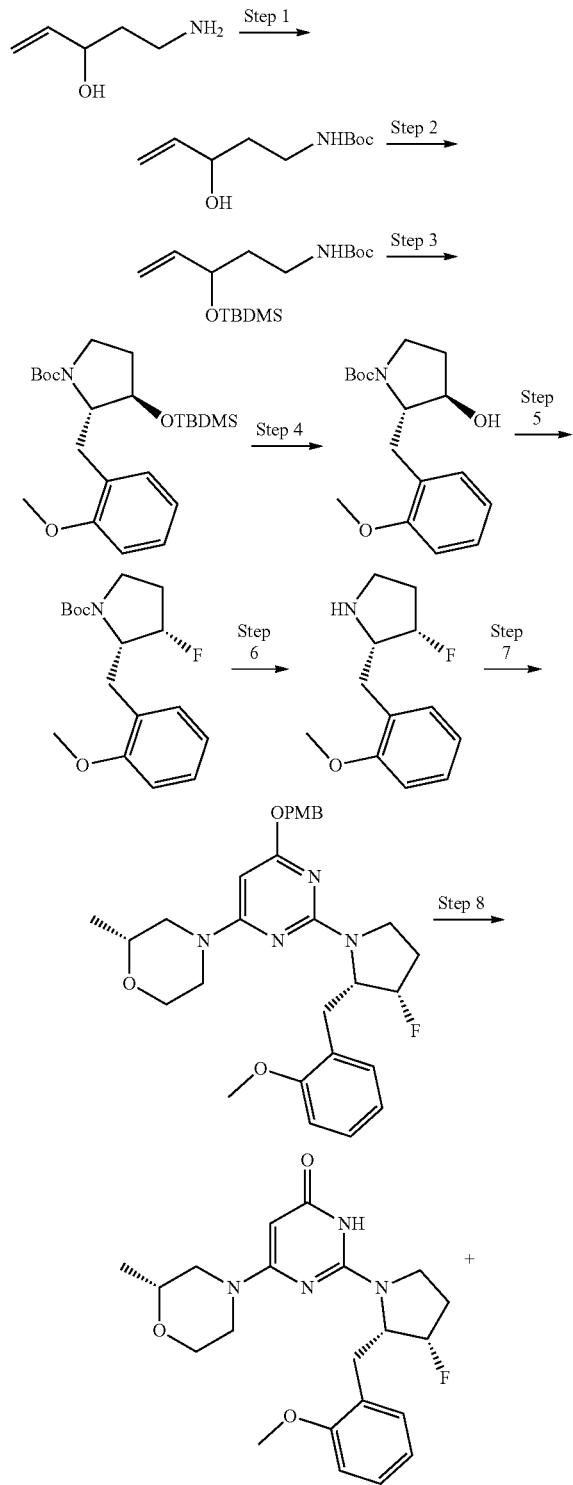

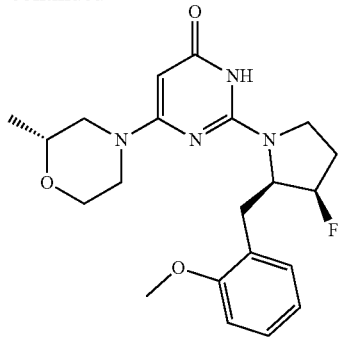 [SMILES: COc1ccccc1C[C@@H]1[C@H](F)CCN1c1nc(N2CCO[C@H](C)C2)cc(=O)[nH]1]

Step 1: tert-Butyl (3-hydroxypent-4-en-1-yl)carbamate

Di-tert-butyl dicarbonate (2.0 g, 19.8 mmol) was added to 5-aminopent-1-en-3-ol (2.0 g, 19.8 mmol) in DCM (50 mL). After 2 hours trimethylamine (2.76 mL, 19.8 mmol) was added. After 18 hours the reaction was diluted with water and the layers separated. The DCM was dried (phase separator) and concentrated under reduced pressure. The crude material was purified by silica gel column chromatography (gradient elution, 5-20% ethyl acetate in iso-hexane) to afford the title compound.

Step 2: tert-Butyl (3-((tert-butyldimethylsilyl)oxy)pent-4-en-1-yl)carbamate tert-Butyldimethylsilyl chloride (4.07 g, 27.03 mmol) was added to a solution of tert-butyl (3-hydroxypent-4-en-1-yl)carbamate (3.40 g, 16.89 mmol) and imidazole (2.30 g, 33.79 mmol) dissolved in DMF (34 mL) at 0° C. The reaction mixture was warmed to room temperature. After 18 hours the reaction was diluted with water and extracted with ethyl acetate (×3). The combined organic extracts were dried (phase separator) and concentrated under reduced pressure. The crude product was purified by silica gel column chromatography (gradient elution 2-15% ethyl acetate in iso-hexane) to afford the title compound.

Step 3: tert-Butyl 3-((tert-butyldimethylsilyl)oxy)-2-(2-methoxybenzyl)pyrrolidine-1-carboxylate Palladium (II) acetate (9.0 mg, 0.04 mmol), Dpe-phos (43 mg, 0.08 mmol) and sodium tert-butoxide (442 mg, 4.60 mmol) were placed in a stem block tube and sealed. The reaction tube was degassed. tert-butyl (3-((tert-butyldimethylsilyl)oxy)pent-4-en-1-yl)carbamate (631 mg, 2.00 mmol) dissolved in toluene (8 mL) and degassed. The solution was added to the stem block tube followed by 2-bromoanisole (0.30 mL, 2.40 mmol). The reaction was heated at 100° C. After 28 hours the reaction mixture was cooled to room temperature, diluted with NH₄Cl and DCM. The layers were separated and the organic extracts dried (phase separator), filtered and concentrated under reduced pressure. The crude material was purified by silica gel column chromatography (gradient elution, 0-30% ethyl acetate in iso-hexane) to afford the title compound.

Step 4: tert-Butyl (2S*,3R*)-3-hydroxy-2-(2-methoxybenzyl)pyrrolidine-1-carboxylate To a solution of tert-butyl (2S,3R)-3-((tert-butyldimethylsilyl)oxy)-2-(2-methoxybenzyl)pyrrolidine-1-carboxylate (229 mg, 0.54 mmol) in THF (10 mL) was added TBAF (284 mg, 1.09 mmol) and the reaction was stirred at rt overnight. The solvent was removed in vacuo and the residue was dissolved in DCM and washed with water. The DCM layer was separated using a phase separator and concentrated in vacuo. The residue was purified by purified by silica chromatography (gradient elution, 0-30% EtOAc/iso-hexane) to yield the title compound.

Step 5: tert-Butyl (2S*,3S*)-3-fluoro-2-(2-methoxybenzyl)pyrrolidine-1-carboxylate A solution of tert-butyl (2S,3R)-3-hydroxy-2-(2-methoxybenzyl)pyrrolidine-1-carboxylate (54 mg, 0.18 mmol) in DCM (2 mL) was cooled to −78° C. DAST (99 mg, 0.61 mmol) was added and the cooling bath was removed. The reaction was stirred overnight allowing the reaction to reach RT. Saturated sodium hydrogencarbonate was added and once effervescence had subsided the mixture was further diluted with DCM. The DCM layer was separated using a phase separator and concentrated in vacuo. The residue was purified by silica gel column chromatography (gradient elution, 0-20% EtOAc/iso-hexane) to yield the title compound.

Step 6: (2S*,3S*)-3-Fluoro-2-(2-methoxybenzyl)pyrrolidine

A solution of tert-butyl (2S*,3S*)-3-fluoro-2-(2-methoxybenzyl)pyrrolidine-1-carboxylate (51 mg, 0.16 mmol) in 4N hydrogen chloride in dioxane (2 mL) was stirred at rt for 2 hours. The solvent was removed in vacuo to give a residue, which was dissolved in DCM (10 mL). The DCM was washed with saturated sodium hydrogen carbonate and the layers separated using a phase separator. The DCM layer was concentrated in vacuo to give the title compound.

Step 7: (R)-4-(2-((2S*,3S*)-3-fluoro-2-(2-methoxybenzyl)pyrrolidin-1-yl)-6-((4-methoxybenzyl)oxy)pyrimidin-4-yl)-2-methylmorpholine Following Method G from (R)-4-(6-((4-methoxybenzyl)oxy)-2-(methylsulfonyl)pyrimidin-4-yl)-2-methylmorpholine (32 mg, 0.15 mmol) and (2S*,3S*)-3-Fluoro-2-(2-methoxybenzyl)pyrrolidine (60 mg, 0.15 mmol). The reaction was stirred at 85° C. for 17 h. Purification by silica gel column chromatography (gradient elution, 0-30% EtOAc/iso-hexane) gave the title compound as a clear oil (65 mg, 81%).

Step 8: 2-((2S,3S)-3-fluoro-2-(2-methoxybenzyl)pyrrolidin-1-yl)-6-((R)-2-methylmorpholino)pyrimidin-4(3H)-one and 2-((2R,3R)-3-fluoro-2-(2-methoxybenzyl)pyrrolidin-1-yl)-6-morpholinopyrimidin-4(3H)-one Following Method H from (R)-4-(2-((2S*,3S*)-3-fluoro-2-(2-methoxybenzyl)pyrrolidin-1-yl)-6-((4-methoxybenzyl)oxy)pyrimidin-4-yl)-2-methylmorpholine. Purification by reverse phase preparative HPLC was followed by SFC for the separation of isomers to afford the title compounds.

2-((2S,3S)-3-fluoro-2-(2-methoxybenzyl)pyrrolidin-1-yl)-6-morpholinopyrimidin-4(3H)-one: LCMS (ES+) 403 (M+H)+, RT 3.19 min (Analytical Method A); RT 2.67 min (Analytical Method SFC4, YMC AMYLOSE-C, 20/80 MeOH (0.1% DEAISO)/CO₂); ¹H NMR δ (ppm) (400 MHz, CDCl₃) 9.05 (1H, s), 7.31 (1H, t, J=7.9 Hz), 7.06-6.92 (3H, m), 5.08-4.95 (2H, m), 4.28-3.93 (7H, m), 3.84-3.58 (4H, m), 3.24-3.18 (1H, m), 3.00-2.93 (1H, m), 2.63 (1H, t, J=12.2 Hz), 2.35-2.15 (3H, m), 1.23 (3H, d, J=7.3 Hz).

2-((2R,3R)-3-fluoro-2-(2-methoxybenzyl)pyrrolidin-1-yl)-6-morpholinopyrimidin-4(3H)-one: LCMS (ES+) 403 (M+H)+, RT 3.19 min (Analytical Method A); RT 1.93 min (Analytical Method SFC4, YMC AMYLOSE-C, 20/80 MeOH (0.1% DEAISO)/CO₂); ¹H NMR δ (ppm) (400 MHz, CDCl₃) 9.05 (1H, s), 7.31 (1H, t, J=7.9 Hz), 7.06-6.92 (3H, m), 5.08-4.95 (2H, m), 4.28-3.93 (7H, m), 3.84-3.58 (4H, m), 3.24-3.18 (1H, m), 3.00-2.93 (1H, m), 2.63 (1H, t, J=12.2 Hz), 2.35-2.15 (3H, m), 1.23 (3H, d, J=7.3 Hz).

Example 326: 2-(2-benzylpyrrolidin-1-yl)-6-(2-(difluoromethyl)morpholino)pyrimidin-4(3H)-one, Stereoisomer 1, Example 327: 2-(2-benzylpyrrolidin-1-yl)-6-(2-(difluoromethyl)morpholino)pyrimidin-4(3H)-one, Stereoisomer 2 and Example 328: 2-(2-benzylpyrrolidin-1-yl)-6-(2-(difluoromethyl)morpholino)pyrimidin-4(3H)-one, Stereoisomer 3

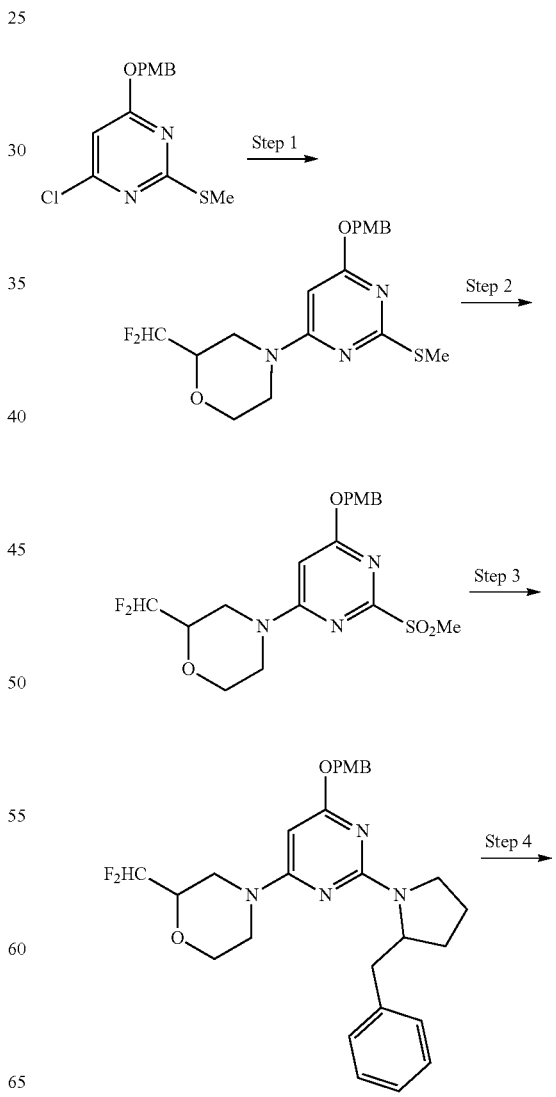

-continued

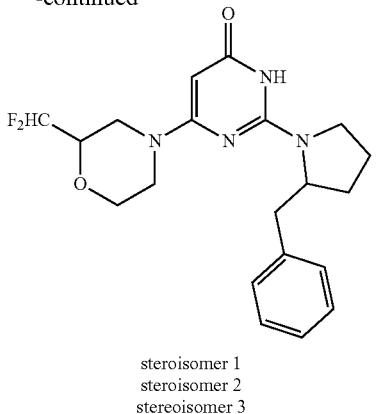

stereoisomer 1
stereoisomer 2
stereoisomer 3

Step 1: 2-(difluoromethyl)-4-(6-((4-methoxybenzyl) oxy)-2-(methylthio)pyrimidin-4-yl)morpholine A solution of 2-(difluoromethyl)morpholine hydrochloride (315 mg, 1.81 mmol) and 4-chloro-6-((4-methoxybenzyl)oxy)-2-(methylthio)pyrimidine (501 mg, 1.69 mmol, Scaffold 5, step 1) in dry THF (4.2 mL) was treated at rt with DIPEA (0.73 mL, 4.19 mmol). The mixture was stirred at 60° C. for 19 h. After cooling to r.t., the solvent was removed by evaporation and the residue partitioned between DCM (20 mL) and water (20 mL). The layers were separated by passage through a hydrophobic frit and the DCM layer was concentrated. The residue was purified by silica gel column chromatography (gradient elution, 0-50% EtOAc/isohexane) to give the title compound.

Step 2: 2-(difluoromethyl)-4-(6-((4-methoxybenzyl) oxy)-2-(methylsulfonyl)pyrimidin-4-yl)morpholine A mixture of 2-(difluoromethyl)-4-(6-((4-methoxybenzyl)oxy)-2-(methylthio)pyrimidin-4-yl)morpholine (346 mg, 0.87 mmol) in DCM (9 mL) was treated at rt with mCPBA (674 mg, 1.95 mmol, ~50 wt % in water). After stirring at rt for 24 h, the reaction was diluted with 2 M NaOH (10 mL), with vigorous stirring. The layers were then separated by passage through a hydrophobic frit. The DCM layer was concentrated to give the title compound.

Step 3: 4-(2-(2-benzylpyrrolidin-1-yl)-6-((4-methoxybenzyl)oxy)pyrimidin-4-yl)-2-(difluoromethyl)morpholine Following Method G from 2-(difluoromethyl)-4-(6-((4-methoxybenzyl)oxy)-2-(methylsulfonyl)pyrimidin-4-yl) morpholine (368 mg, 0.86 mmol) and 2-benzylpyrrolidine (157 mg, 0.97 mmol). The reaction was stirred at 80° C. for 18 h. Impure title compound was obtained, which was used without further purification.

Step 4: 2-(2-benzylpyrrolidin-1-yl)-6-(2-(difluoromethyl)morpholino)pyrimidin-4(3H)-one, Stereoisomer 1, 2-(2-benzylpyrrolidin-1-yl)-6-(2-(difluoromethyl)morpholino)pyrimidin-4(3H)-one, Stereoisomer 2 and 2-(2-benzylpyrrolidin-1-yl)-6-(2-(difluoromethyl)morpholino)pyrimidin-4(3H)-one, Stereoisomer 3

Following Method H from 4-(2-(2-benzylpyrrolidin-1-yl)-6-((4-methoxybenzyl)oxy)pyrimidin-4-yl)-2-(difluoromethyl)morpholine (190 mg from previous step). Successive purification by reverse phase HPLC and SFC gave the title compounds.

2-(2-benzylpyrrolidin-1-yl)-6-(2-(difluoromethyl)morpholino)pyrimidin-4(3H)-one, stereoisomer 1: LCMS (ES+) 391 (M+H)+, RT 3.24 min (Analytical method B); RT 2.36 min (Analytical method SFC4, LUX CELLULOSE-3 10% MeOH SOL3 (0.1% DEAISO)/CO$_2$); $^1$H NMR δ (ppm) (400 MHz, CDCl$_3$) 10.42 (1H, s), 7.31-7.27 (2H, m), 7.25-7.17 (3H, m), 5.78 (1H, dt, J=4.1, 55.3 Hz), 4.99 (1H, s), 4.58-4.43 (2H, m), 4.04 (1H, dd, J=2.3, 11.4 Hz), 3.91-3.73 (2H, m), 3.71-3.61 (2H, m), 3.50-3.41 (1H, m), 3.24 (1H, dd, J=3.0, 13.1 Hz), 3.13-3.04 (1H, m), 2.94 (1H, dd, J=10.9, 13.1 Hz), 2.55 (1H, dd, J=9.9, 13.1 Hz), 2.01-1.94 (2H, m), 1.86-1.78 (2H, m).

2-(2-benzylpyrrolidin-1-yl)-6-(2-(difluoromethyl)morpholino)pyrimidin-4(3H)-one, stereoisomer 2: LCMS (ES+) 391 (M+H)+, RT 3.24 min (Analytical method B); RT 2.66 min (Analytical method SFC4, LUX CELLULOSE-3 10% MeOH SOL3 (0.1% DEAISO)/CO$_2$); $^1$H NMR δ (ppm) (400 MHz, CDCl$_3$) 10.36 (1H, s), 7.31-7.27 (2H, m), 7.25-7.17 (3H, m), 5.78 (1H, dt, J=4.1, 55.2 Hz), 4.99 (1H, s), 4.51-4.39 (2H, m), 4.04 (1H, dd, J=2.1, 11.5 Hz), 3.93 (1H, d, J=12.9 Hz), 3.80-3.60 (3H, m), 3.49-3.40 (1H, m), 3.22 (1H, dd, J=2.8, 12.6 Hz), 3.06 (1H, ddd, J=3.6, 11.7, 13.1 Hz), 2.97 (1H, dd, J=10.7, 13.0 Hz), 2.58 (1H, dd, J=9.6, 13.1 Hz), 2.01-1.90 (2H, m), 1.86-1.80 (2H, m).

2-(2-benzylpyrrolidin-1-yl)-6-(2-(difluoromethyl)morpholino)pyrimidin-4(3H)-one, stereoisomer 3: LCMS (ES+) 391 (M+H)+, RT 3.27 min (Analytical method A); RT 4.83 min (Analytical method SFC4, LUX CELLULOSE-3 10% MeOH SOL3 (0.1% DEAISO)/CO$_2$); $^1$H NMR δ (ppm) (400 MHz, CDCl$_3$) 10.39 (1H, s), 7.36-7.14 (5H, m), 5.78 (1H, dt, J=4.4, 55.0 Hz), 4.99 (1H, s), 4.50-4.39 (2H, m), 4.05 (1H, d, J=10.4 Hz), 3.93 (1H, d, J=12.9 Hz), 3.77-3.60 (3H, m), 3.44 (1H, q, J=8.8 Hz), 3.24-3.18 (1H, m), 3.08 (1H, dt, J=3.2, 12.4 Hz), 2.97 (1H, dd, J=10.8, 12.8 Hz), 2.58 (1H, dd, J=9.7, 13.0 Hz), 2.01-1.89 (2H, m), 1.86-1.76 (2H, m).

Example 329: 2-(2-benzylpyrrolidin-1-yl)-6-(2-(trifluoromethyl)morpholino)pyrimidin-4(3H)-one Enantiomeric Mixture 1 & 2 and Example 330: 2-(2-benzylpyrrolidin-1-yl)-6-(2-(trifluoromethyl) morpholino)pyrimidin-4(3H)-one Enantiomeric Mixture 3 & 4

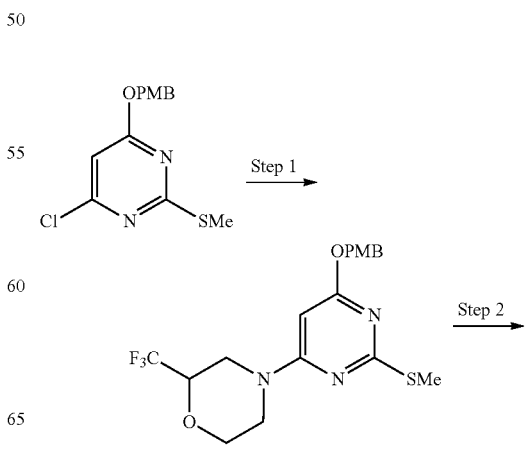

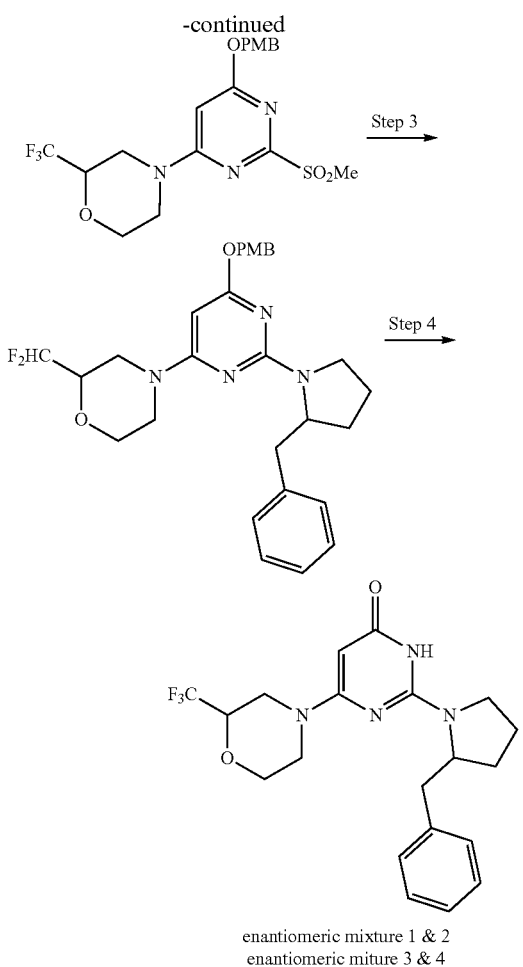

Step 1: 4-(6-((4-methoxybenzyl)oxy)-2-(methylthio) pyrimidin-4-yl)-2-(trifluoromethyl)morpholine A mixture of 4-chloro-6-((4-methoxybenzyl)oxy)-2-(methylthio)pyrimidine (502 mg, 1.69 mmol, Scaffold 5, step 1), 2-(trifluoromethyl)morpholine hydrochloride (360 mg, 1.88 mmol) and DIPEA (0.73 mL, 2.5 mmol) in dry THF (4.2 mL) was stirred at 60° C. for 19 h. After cooling to rt, the solvent was removed by evaporation and the residue was partitioned between DCM (20 mL) and water (20 mL). The layers were separated by passage through a hydrophobic frit and the DCM layer concentrated. The residue was purified by silica gel column chromatography (gradient elution, 0-50% EtOAc/iso-hexane) to give the title compound.

Step 2: 4-(6-((4-methoxybenzyl)oxy)-2-(methylsulfonyl)pyrimidin-4-yl)-2-(trifluoromethyl)morpholine A mixture of 4-(6-((4-methoxybenzyl)oxy)-2-(methylthio)pyrimidin-4-yl)-2-(trifluoromethyl)morpholine (350 mg, 0.84 mmol) and mCPBA (50 wt % in water, 680 mg, 1.97 mmol) in DCM (8 mL) was stirred at rt for 24 h. The reaction was diluted with 10 mL 2 M NaOH and stirred vigorously. The layers were separated by passage through a hydrophobic frit and the DCM layer concentrated to give the title compound. $^1$H NMR δ (ppm) (400 MHz, CDCl$_3$) 7.38-7.34 (2H, m), 6.91-6.88 (2H, m), 5.95 (1H, s), 5.37 (2H, s), 4.39-4.26 (1H, m), 4.16-4.04 (2H, m), 3.99-3.88 (1H, m), 3.80 (3H, s), 3.72-3.63 (1H, m), 3.26 (3H, s), 3.23-3.03 (2H, m).

Step 3: 4-(2-(2-benzylpyrrolidin-1-yl)-6-((4-methoxybenzyl)oxy)pyrimidin-4-yl)-2-(trifluoromethyl)morpholine Following Method G from 4-(6-((4-methoxybenzyl)oxy)-2-(methylsulfonyl)pyrimidin-4-yl)-2-(trifluoromethyl)morpholine (313 mg, 0.70 mmol) and 2-benzylpyrrolidine (130 mg, 0.81 mmol). Purification by silica gel column chromatography (gradient elution, 0-60% EtOAc/iso-hexane) gave impure title compound, which was used without further purification.

Step 4: 2-(2-benzylpyrrolidin-1-yl)-6-(2-(trifluoromethyl)morpholino)pyrimidin-4(3H)-one diastereomeric mixture Following Method H from 4-(2-(2-benzylpyrrolidin-1-yl)-6-((4-methoxybenzyl)oxy)pyrimidin-4-yl)-2-(trifluoromethyl)morpholine (194 mg). Successive purification by reverse phase HPLC and SFC gave the title compounds.

2-(2-benzylpyrrolidin-1-yl)-6-(2-(trifluoromethyl)morpholino)pyrimidin-4(3H)-one enantiomeric mixture 1 & 2 LCMS (ES+) 409 (M+H)+, RT 3.38 min (Analytical method B); RT 1.40 min (Analytical method SFC4, LUX CELLULOSE-3 10% MeOH SOL3 (0.1% DEAISO)/CO$_2$); $^1$H NMR δ (ppm) (400 MHz, CDCl$_3$) 10.47 (1H, s), 7.32-7.27 (2H, m), 7.25-7.15 (3H, m), 4.99 (1H, s), 4.59 (1H, dd, J=13.1, 37.9 Hz), 4.50-4.42 (1H, m), 4.09 (1H, d, J=11.4 Hz), 3.98-3.83 (2H, m), 3.75-3.61 (2H, m), 3.45 (1H, q, J=8.9 Hz), 3.20 (1H, d, J=12.8 Hz), 3.16-2.97 (2H, m), 2.63-2.52 (1H, m), 2.00-1.97 (2H, m), 1.86-1.80 (2H, m).

2-(2-benzylpyrrolidin-1-yl)-6-(2-(trifluoromethyl)morpholino)pyrimidin-4(3H)-one enantiomeric mixture 3 & 4 LCMS (ES+) 409 (M+H)+, RT 3.38 min (Analytical method B); RT 1.66 min (Analytical method SFC4, LUX CELLULOSE-3 10% MeOH SOL3 (0.1% DEAISO)/CO$_2$); $^1$H NMR δ (ppm) (400 MHz, CDCl$_3$) 9.96 (1H, s), 7.32-7.27 (2H, m), 7.25-7.21 (1H, m), 7.19-7.15 (2H, m), 4.99 (1H, s), 4.59 (1H, dd, J=12.6, 36.6 Hz), 4.49-4.41 (1H, m), 4.09 (1H, d, J=11.1 Hz), 3.98-3.84 (2H, m), 3.74-3.57 (2H, m), 3.47-3.39 (1H, m), 3.23-2.97 (3H, m), 2.64-2.54 (1H, m), 2.02-1.92 (2H, m), 1.87-1.81 (2H, m).

Example 331: 2-((R)-2-benzylpyrrolidin-1-yl)-6-((S)-2-methylmorpholino)pyrimidin-4(3H)-one and Example 332: 2-((S)-2-benzylpyrrolidin-1-yl)-6-((S)-2-methylmorpholino)pyrimidin-4(3H)-one

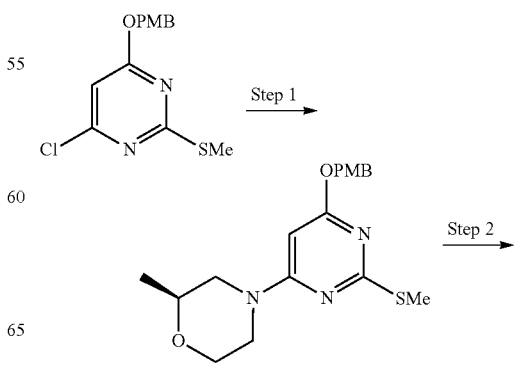

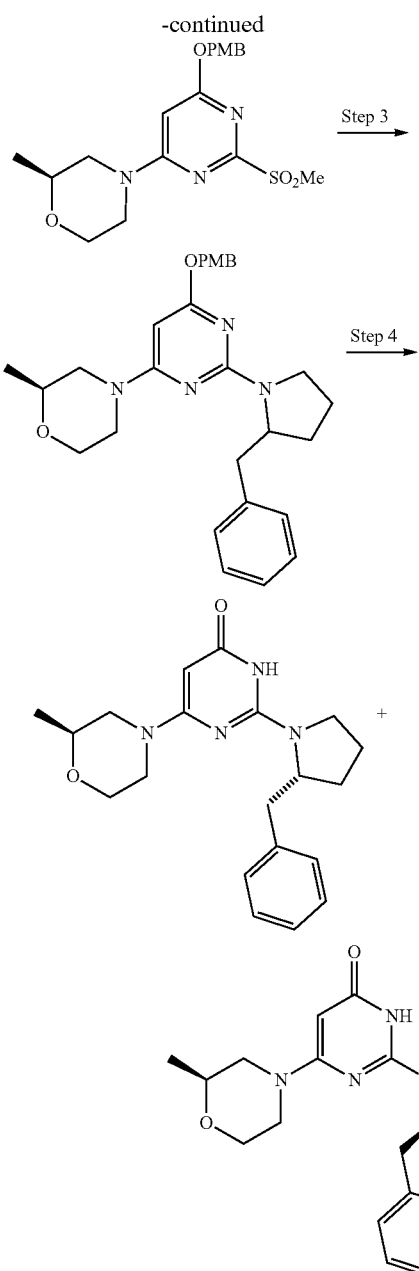

Step 1: (S)-4-(6-((4-methoxybenzyl)oxy)-2-(methylthio)pyrimidin-4-yl)-2-methylmorpholine A mixture of 4-chloro-6-((4-methoxybenzyl)oxy)-2-(methylthio)pyrimidine (506 mg, 1.71 mmol, Scaffold 5, step 1), (S)-2-methylmorpholine (190 mg, 1.88 mmol) and DIPEA (0.32 mL, 1.84 mmol) in dry THF (4.2 mL) was stirred at 60° C. After 19 h the reaction was cooled to rt and the solvent removed by evaporation. The residue was partitioned between DCM (20 mL) and water (20 mL). The layers were separated by passage through a hydrophobic frit and the DCM layer concentrated. The residue was purified by silica gel column chromatography (gradient elution, 0-50% EtOAc/iso-hexane) to give the title compound.

Step 2: (S)-4-(6-((4-methoxybenzyl)oxy)-2-(methylsulfonyl)pyrimidin-4-yl)-2-methylmorpholine A mixture of (S)-4-(6-((4-methoxybenzyl)oxy)-2-(methylthio)pyrimidin-4-yl)-2-methylmorpholine (282 mg, 0.78 mmol) and mCPBA (611 mg, 1.77 mmol, 50 wt % in water) in DCM (8 mL) was stirred at rt. After 24 h the reaction was diluted with 2 M NaOH (10 mL) and stirred vigorously. The layers were separated by passage through a hydrophobic frit and the DCM layer concentrated to give the title compound, which was used without further purification.

Step 3: (2S)-4-(2-(2-benzylpyrrolidin-1-yl)-6-((4-methoxybenzyl)oxy)pyrimidin-4-yl)-2-methylmorpholine Following Method G from (S)-4-(6-((4-methoxybenzyl)oxy)-2-(methylsulfonyl)pyrimidin-4-yl)-2-methylmorpholine (307 mg) and 2-benzylpyrrolidine (143 mg, 0.89 mmol). Purification by silica gel column chromatography (gradient elution, 0-60% EtOAc/iso-hexane) gave impure title compound, which was used without further purification.

Step 4: 2-((R)-2-benzylpyrrolidin-1-yl)-6-((S)-2-methylmorpholino)pyrimidin-4(3H)-one and 2-((S)-2-benzylpyrrolidin-1-yl)-6-((S)-2-methylmorpholino)pyrimidin-4(3H)-one Following Method H from (2S)-4-(2-(2-benzylpyrrolidin-1-yl)-6-((4-methoxybenzyl)oxy)pyrimidin-4-yl)-2-methylmorpholine (165 mg). Successive purification by reverse phase HPLC and SFC gave the title compounds.

2-((R)-2-benzylpyrrolidin-1-yl)-6-((S)-2-methylmorpholino)pyrimidin-4(3H)-one LCMS (ES+) 355 (M+H)+, RT 3.21 min (Analytical method B); $^1$H NMR δ (ppm) (400 MHz, CDCl$_3$) 9.32 (1H, s), 7.32-7.27 (2H, m), 7.25-7.17 (3H, m), 4.95 (1H, s), 4.46-4.38 (1H, m), 4.22 (1H, d, J=14.5 Hz), 3.95 (2H, dd, J=2.6, 11.4 Hz), 3.67-3.51 (3H, m), 3.40 (1H, q, J=8.6 Hz), 3.22 (1H, dd, J=2.9, 13.1 Hz), 3.05-2.96 (1H, m), 2.67-2.58 (2H, m), 2.00-1.81 (4H, m), 1.23 (3H, d, J=6.3 Hz).

2-((S)-2-benzylpyrrolidin-1-yl)-6-((S)-2-methylmorpholino)pyrimidin-4(3H)-one LCMS (ES+) 355 (M+H)+, RT 3.21 min (Analytical method B); $^1$H NMR δ (ppm) (400 MHz, CDCl$_3$) 9.39 (1H, s), 7.32-7.28 (2H, m), 7.25-7.21 (1H, m), 7.20-7.18 (2H, m), 4.95 (1H, s), 4.46-4.40 (1H, m), 4.16 (1H, d, J=12.2 Hz), 4.04-3.93 (2H, m), 3.68-3.52 (3H, m), 3.40 (1H, q, J=8.6 Hz), 3.21 (1H, dd, J=3.2, 13.0 Hz), 3.03-2.95 (1H, m), 2.68-2.58 (2H, m), 1.99-1.81 (4H, m), 1.22 (3H, d, J=6.1 Hz).

Example 333: 2-(2-benzylpyrrolidin-1-yl)-6-(2-ethylmorpholino)pyrimidin-4(3H)-one Stereoisomer 1 Example 334: 2-(2-benzylpyrrolidin-1-yl)-6-(2-ethylmorpholino)pyrimidin-4(3H)-one Stereoisomer 2, Example 335: 2-(2-benzylpyrrolidin-1-yl)-6-(2-ethylmorpholino)pyrimidin-4(3H)-one Stereoisomer 3, and Example 336: 2-(2-benzylpyrrolidin-1-yl)-6-(2-ethylmorpholino)pyrimidin-4(3H)-one Stereoisomer 4

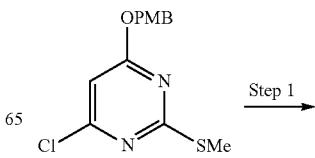

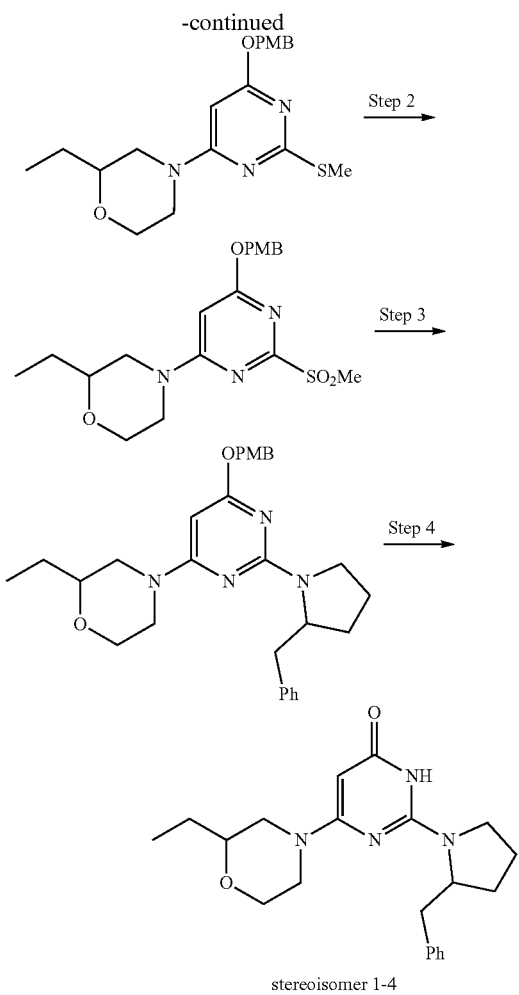

stereoisomer 1-4

Step 1: 2-Ethyl-4-(6-((4-methoxybenzyl)oxy)-2-(methylthio)pyrimidin-4-yl)morpholine A mixture of 4-chloro-6-((4-methoxybenzyl)oxy)-2-(methylthio)pyrimidine (501 mg, 1.69 mmol, Scaffold 5, step 1), 2-ethylmorpholine (203 mg, 1.76 mmol) and DIPEA (0.32 mL, 1.84 mmol) in dry THF (4.2 mL) was stirred at 60° C. for 25 h. After cooling to rt, the solvent was removed by evaporation and the residue was partitioned between DCM (20 mL) and water (20 mL). The layers were separated by passage through a hydrophobic frit and the DCM layer concentrated. The residue was purified by silica gel column chromatography (gradient elution, 0-100% EtOAc/isohexane) to give the title compound.

Step 2: 2-Ethyl-4-(6-((4-methoxybenzyl)oxy)-2-(methylsulfonyl)pyrimidin-4-yl)morpholine A mixture of 2-ethyl-4-(6-((4-methoxybenzyl)oxy)-2-(methylthio)pyrimidin-4-yl)morpholine (424 mg, 1.13 mmol) and mCPBA (854 mg, 2.47 mmol, 50 wt % in water) in DCM (8 mL) was stirred at rt. After 21 h the reaction was diluted with 2 M NaOH (10 mL) and stirred vigorously. The layers were separated by passage through a hydrophobic frit and the DCM layer concentrated to give the title compound, which was used without further purification.

Step 3: 4-(2-(2-benzylpyrrolidin-1-yl)-6-((4-methoxybenzyl)oxy)pyrimidin-4-yl)-2-ethylmorpholine Following Method G from 2-ethyl-4-(6-((4-methoxybenzyl)oxy)-2-(methylsulfonyl)pyrimidin-4-yl)morpholine (169 mg, 0.41 mmol) and 2-benzylpyrrolidine (77.7 mg, 0.48 mmol). The reaction mixture was stirred at 85° C. for 20 h. The title compound was obtained, which was used without further purification.

Step 4: Four stereoisomers of 2-(2-benzylpyrrolidin-1-yl)-6-(2-ethylmorpholino)pyrimidin-4(3H)-one Following Method H from 4-(2-(2-benzylpyrrolidin-1-yl)-6-((4-methoxybenzyl)oxy)pyrimidin-4-yl)-2-ethylmorpholine. Successive purification by reverse phase preparative HPLC and SFC gave the four stereoisomers. Absolute and relative stereochemistry was assigned arbitrarily. The enantiomeric pairs were identifiable from their identical $^1$H NMR spectra (abs1/abs3 and abs2/abs4).

2-(2-benzylpyrrolidin-1-yl)-6-(2-ethylmorpholino)pyrimidin-4(3H)-one stereoisomer 1: LCMS (ES+) 369 (M+H)$^+$, RT 3.35 min (Analytical method B); RT 4.80 min (Analytical method SFC4, YMC CELLULOSE-C, 10/90 MeOH [0.1% DEAISO]/CO$_2$); $^1$H NMR (400 MHz, CDCl$_3$) 9.36 (1H, s), 7.33-7.15 (5H, m), 4.96 (1H, s), 4.47-4.39 (1H, m), 4.15-4.12 (1H, m), 4.06-4.02 (1H, m), 3.97 (1H, dd, J=3.0, 11.6 Hz), 3.62 (1H, dt, J=2.1, 11.3 Hz), 3.57-3.50 (1H, m), 3.43-3.34 (2H, m), 3.20 (1H, dd, J=2.4, 13.0 Hz), 2.99 (1H, dt, J=3.2, 12.4 Hz), 2.70-2.61 (2H, m), 1.96-1.80 (4H, m), 1.56-1.46 (2H, m), 0.98 (3H, t, J=7.3 Hz).

2-(2-benzylpyrrolidin-1-yl)-6-(2-ethylmorpholino)pyrimidin-4(3H)-one stereoisomer 2 LCMS (ES+) 369 (M+H)$^+$, RT 3.35 min (Analytical method B); RT 5.61 min (Analytical method SFC4, YMC CELLULOSE-C, 10/90 MeOH [0.1% DEAISO]/CO$_2$); $^1$H NMR (400 MHz, CDCl$_3$) 9.00 (1H, s), 7.33-7.15 (5H, m), 4.96 (1H, s), 4.46-4.37 (1H, m), 4.27-4.15 (1H, m), 4.00-3.93 (2H, m), 3.61 (1H, dt, J=2.6, 11.8 Hz), 3.55-3.48 (1H, m), 3.42-3.35 (2H, m), 3.23-3.15 (1H, m), 3.02 (1H, dt, J=3.5, 12.5 Hz), 2.69-2.60 (2H, m), 2.01-1.81 (4H, m), 1.00 (3H, t, J=7.6 Hz), 2 protons obscured by water peak.

2-(2-benzylpyrrolidin-1-yl)-6-(2-ethylmorpholino)pyrimidin-4(3H)-one stereoisomer 3 LCMS (ES+) 369 (M+H)$^+$, RT 3.37 min (Analytical method B); RT 4.84 min (Analytical method SFC1, YMC AMYLOSE-C, 10/5/5/80 ACN [0.1% DEAISO]/EtOH [0.1% DEAISO]/IPA [0.1% DEAISO]/CO$_2$); $^1$H NMR (400 MHz, CDCl$_3$) 7.33-7.15 (5H, m), 4.96 (1H, s), 4.47-4.39 (1H, m), 4.17-4.09 (1H, m), 4.08-4.01 (1H, m), 3.97 (1H, dd, J=2.8, 11.0 Hz), 3.63 (1H, dt, J=2.7, 11.6 Hz), 3.56-3.48 (1H, m), 3.44-3.32 (2H, m), 3.19 (1H, dd, J=2.5, 13.1 Hz), 3.04-2.95 (1H, m), 2.70-2.61 (2H, m), 1.96-1.83 (4H, m), 1.55-1.45 (2H, m), 0.98 (3H, t, J=7.6 Hz), NH not observed.

2-(2-benzylpyrrolidin-1-yl)-6-(2-ethylmorpholino)pyrimidin-4(3H)-one stereoisomer 4 LCMS (ES+) 369 (M+H)$^+$, RT 3.37 min (Analytical method B); RT 5.52 min (Analytical method SFC1, YMC AMYLOSE-C, 10/5/5/80 ACN [0.1% DEAISO]/EtOH [0.1% DEAISO]/IPA [0.1% DEAISO]/CO$_2$); $^1$H NMR (400 MHz, CDCl$_3$) 9.32 (1H, s), 7.33-7.15 (5H, m), 4.96 (1H, s), 4.47-4.41 (1H, m), 4.26-4.16 (1H, m), 4.03-3.92 (2H, m), 3.65-3.51 (2H, m), 3.44-3.34 (2H, m), 3.20 (1H, dd, J=2.4, 13.3 Hz), 3.01 (1H, dt, J=3.2, 12.4 Hz), 2.69-2.60 (2H, m), 1.98-1.81 (4H, m), 1.00 (3H, t, J=7.5 Hz), 2 protons obscured by water peak.

Example 337: 2-(2-benzylpyrrolidin-1-yl)-6-(2-cyclopropylmorpholino)pyrimidin-4(3H)-one Stereoisomer 1 and Example 338: 2-(2-benzylpyrrolidin-1-yl)-6-(2-cyclopropylmorpholino)pyrimidin-4(3H)-one Stereoisomer 2

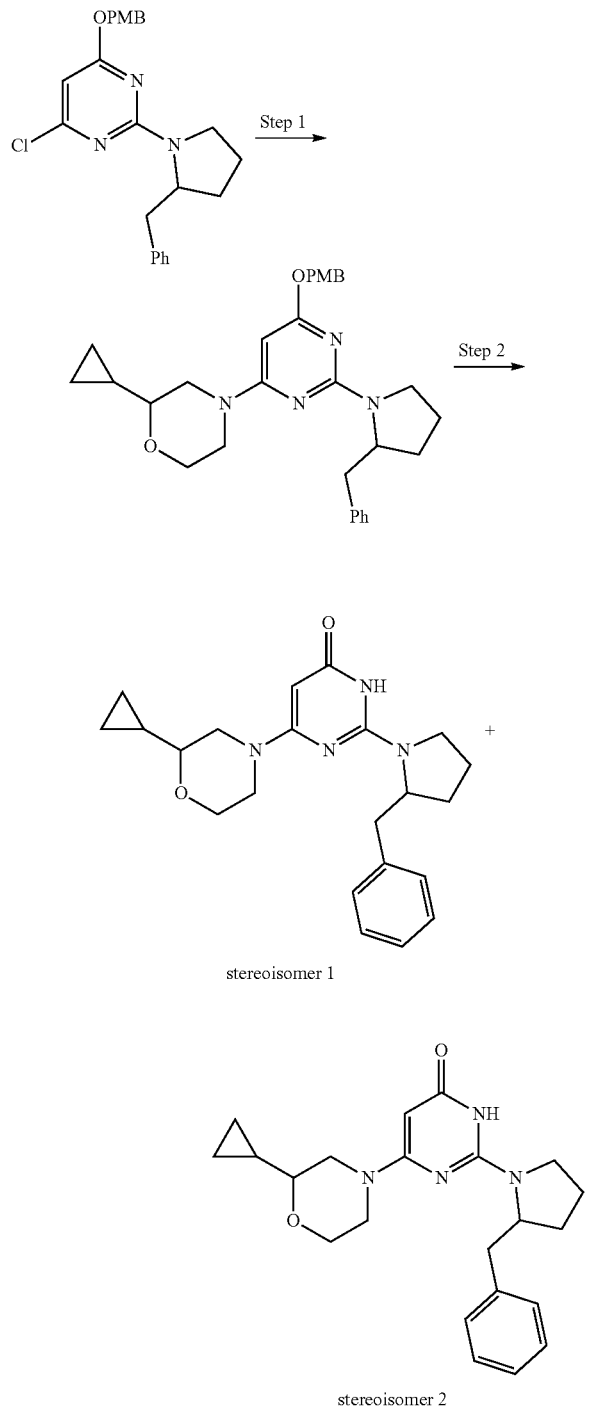

Step 1: 4-(2-(2-benzylpyrrolidin-1-yl)-6-((4-methoxybenzyl)oxy)pyrimidin-4-yl)-2-cyclopropylmorpholine Following Method D from 2-(2-Benzylpyrrolidin-1-yl)-4-chloro-6-((4-methoxybenzyl)oxy)pyrimidine (50 mg, 0.12 mmol, Scaffold 6) and 2-cyclopropylmorpholine (29.3 mg, 0.23 mmol). Purification by silica gel column chromatography (gradient elution, 0-100% EtOAc/iso-hexane) gave the title compound.

Step 2: 2-(2-benzylpyrrolidin-1-yl)-6-(2-cyclopropylmorpholino)pyrimidin-4(3H)-one Stereoisomer 1 and 2-(2-benzylpyrrolidin-1-yl)-6-(2-cyclopropylmorpholino)pyrimidin-4(3H)-one Stereoisomer 2

Following Method H from 4-(2-(2-benzylpyrrolidin-1-yl)-6-((4-methoxybenzyl)oxy)pyrimidin-4-yl)-2-cyclopropylmorpholine (56 mg, 0.11 mmol, 1 equiv). The mixture was stirred at rt for 26 h. The reaction was quenched with MeOH and purified by reverse phase HPLC, then chiral SFC to give two individual stereoisomers which were diastereomeric to each other. Absolute and relative stereochemistry was assigned arbitrarily.

2-(2-benzylpyrrolidin-1-yl)-6-(2-cyclopropylmorpholino)pyrimidin-4(3H)-one (single isomer) stereoisomer 1 LCMS (ES+) 381 (M+H)+, RT 3.31 min (Analytical method A); RT 2.87 min (Analytical method SFC1, YMC CELLULOSE-C, 20/80 MeOH [0.1% DEAISO]/CO$_2$); $^1$H NMR (400 MHz, CDCl$_3$) 9.56 (1H, s), 7.33-7.27 (2H, m), 7.24-7.16 (3H, m), 4.97 (1H, s), 4.49-4.42 (1H, m), 4.33-4.24 (1H, m), 3.98 (2H, dd, J=2.5, 11.1 Hz), 3.61-3.53 (2H, m), 3.41 (1H, q, J=8.5 Hz), 3.25 (1H, dd, J=2.4, 13.0 Hz), 3.02 (1H, dt, J=2.9, 12.3 Hz), 2.87 (1H, dd, J=10.6, 12.9 Hz), 2.76-2.68 (1H, m), 2.61 (1H, dd, J=9.6, 13.1 Hz), 1.99-1.81 (4H, m), 0.97-0.88 (1H, m), 0.63-0.49 (2H, m), 0.45-0.37 (1H, m), 0.27-0.19 (1H, m).

2-(2-benzylpyrrolidin-1-yl)-6-(2-cyclopropylmorpholino)pyrimidin-4(3H)-one (single isomer) stereoisomer 2 LCMS (ES+) 381 (M+H)+, RT 3.31 min (Analytical method 1); RT 3.58 min (Analytical method SFC1, YMC CELLULOSE-C, 20/80 MeOH [0.1% DEAISO]/CO$_2$); $^1$H NMR (400 MHz, CDCl$_3$) 9.60 (1H, s), 7.33-7.27 (2H, m), 7.24-7.17 (3H, m), 4.97 (1H, s), 4.45-4.35 (2H, m), 4.01-3.89 (2H, m), 3.62-3.52 (2H, m), 3.41 (1H, q, J=8.6 Hz), 3.27 (1H, d, J=12.6 Hz), 3.05 (1H, dt, J=3.1, 12.2 Hz), 2.91-2.82 (1H, m), 2.78-2.71 (1H, m), 2.58 (1H, dd, J=9.9, 13.1 Hz), 2.01-1.93 (2H, m), 1.86-1.79 (2H, m), 0.97-0.88 (1H, m), 0.65-0.57 (2H, m), 0.48-0.43 (1H, m), 0.34-0.28 (1H, m).

The following examples were prepared using a procedure analogous to that described for Example 13 starting from the reported amine and Scaffold 6 or Scaffold 7 as appropriate. Buchwald conditions Method D were used to couple the amine and deprotection achieved following Method H. The isomers were isolated after purification by Chiral SFC.

| Example | Structure and Name | Amine | Scaffold | Data |
|---|---|---|---|---|
| Example 339 | 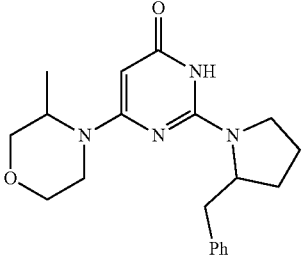 [SMILES: CC1COCCN1c1cc(=O)[nH]c(N2CCCC2Cc2ccccc2)n1]<br>2-(2-benzylpyrrolidin-1-yl)-6-(3-methylmorpholino)pyrimidin-4(3H)-one stereoisomer 1 | 3-methyl-morpholine | Scaffold 6 | LCMS (ES+) 355 (M + H)$^+$, RT 3.17 min (Analytical method A); RT 2.37 min (Analytical method SFC4, LUX CELLULOSE-3, 10/90 MeOH [0.5% DEAISO]/CO$_2$); $^1$H NMR (400 MHz, CDCl$_3$) 8.96 (1H, s), 7.33-7.13 (5H, m), 4.94 (1H, s), 4.43-4.36 (2H, m), 3.97 (1H, dd, J = 3.4, 11.5 Hz), 3.83-3.69 (3H, m), 3.60-3.46 (2H, m), 3.40-3.34 (1H, m), 3.27-3.14 (2H, m), 2.68 (1H, dd, J = 9.2, 13.3 Hz), 1.94-1.83 (4H, m), 1.26 (3H, d, J = 6.8 Hz). |
| Example 340 | 2-(2-benzylpyrrolidin-1-yl)-6-(3-methylmorpholino)pyrimidin-4(3H)-one stereoisomer 2 | 3-methyl-morpholine | Scaffold 6 | LCMS (ES+) 355 (M + H)$^+$, RT 3.17 min (Analytical method A); RT 3.37 min (Analytical method SFC4, LUX CELLULOSE-3, 10/90 MeOH [0.5% DEAISO]/CO$_2$); $^1$H NMR (400 MHz, CDCl$_3$) 8.65 (1H, s), 7.34-7.11 (5H, m), 4.93 (1H, s), 4.40-4.37 (1H, m), 4.23-4.21 (1H, m), 3.99-3.93 (2H, m), 3.77-3.66 (2H, m), 3.60-3.52 (1H, m), 3.50-3.44 (1H, m), 3.42-3.33 (1H, m), 3.25-3.16 (2H, m), 2.67 (1H, dd, J = 9.0, 13.3 Hz), 1.96-1.84 (4H, m), 1.29 (3H, d, J = 6.8 Hz). Stereochemistry arbitrarily assigned |
| Example 341 | 2-(2-benzylpyrrolidin-1-yl)-6-(3-methylmorpholino)pyrimidin-4(3H)-one stereoisomer 3 | 3-methyl-morpholine | Scaffold 6 | LCMS (ES+) 355 (M + H)$^+$, RT 3.18 min (Analytical method B); RT 3.39 min (Analytical method SFC4, YMC AMYLOSE-C, 55/45 MeCN [0.1% DEAISO]/CO$_2$); $^1$H NMR (400 MHz, CDCl$_3$) 7.33-7.14 (5H, m), 4.93 (1H, s), 4.42-4.37 (1H, m), 4.26-4.19 (1H, m), 3.99-3.93 (2H, m), 3.77-3.66 (2H, m), 3.60-3.45 (2H, m), 3.40-3.33 (1H, m), 3.25-3.15 (2H, m), 2.67 (1H, dd, J = 9.2, 13.3 Hz), 1.96-1.83 (4H, m), 1.29 (3H, d, J = 6.8 Hz), NH not observed. Stereochemistry arbitrarily assigned |
| Example 342 | 2-(2-benzylpyrrolidin-1-yl)-6-(3-methylmorpholino)pyrimidin-4(3H)-one stereoisomer 4 | 3-methyl-morpholine | Scaffold 6 | LCMS (ES+) 355 (M + H)$^+$, RT 3.17 min (Analytical method A); RT 2.50 min (Analytical method SFC1, LUX CELLULOSE-4, 10/90 MeOH [0.1% DEAISO]/CO$_2$); $^1$H NMR (400 MHz, CDCl$_3$) 9.76 (1H, s), 7.33-7.14 (5H, m), 4.94 (1H, s), 4.48-4.33 (2H, m), 3.96 (1H, dd, J = 3.3, 11.4 Hz), 3.85-3.69 (3H, m), 3.61-3.51 (2H, m), 3.46-3.37 (1H, m), 3.27-3.18 (2H, m), 2.65 (1H, dd, J = 9.3, 13.4 Hz), 1.94-1.79 (4H, m), 1.27 (3H, d, J = 6.8 Hz). Stereochemistry arbitrarily assigned |
| Example 343 | 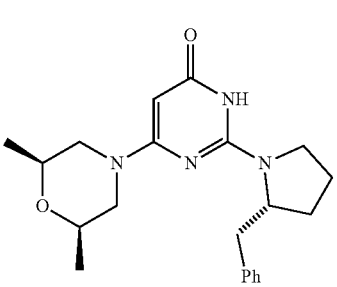 [SMILES: C[C@@H]1CN(c2cc(=O)[nH]c(N3CCC[C@@H]3Cc3ccccc3)n2)C[C@H](C)O1]<br>2-((R)-2-benzylpyrrolidin-1-yl)-6-((2S,6R)-2,6-dimethylmorpholino)pyrimidin-4(3H)-one: | cis-2,6-dimethyl-morpholine | Scaffold 6 | LCMS (ES+) 369 (M + H)$^+$, RT 3.32 min (Analytical method B); RT 8.04 min (Analytical method HPLC, YMC-CELLULOSE-SC, 40/60 IPA/HEPTANE); $^1$H NMR (400 MHz, CDCl$_3$) 8.70 (1H, s), 7.34-7.17 (5H, m), 4.95 (1H, s), 4.44-4.36 (1H, m), 4.24-4.04 (2H, m), 3.68-3.61 (2H, m), 3.53-3.48 (1H, m), 3.41-3.34 (1H, m), 3.26-3.21 (1H, m), 2.63-2.52 (3H, m), 2.01-1.94 (2H, m), 1.88-1.81 (2H, m), 1.26-1.20 (6H, m). |

| Example | Structure and Name | Amine | Scaffold | Data |
|---|---|---|---|---|
| Example 344 | 2-((S)-2-benzylpyrrolidin-1-yl)-6-((2S,6R)-2,6-dimethylmorpholino)pyrimidin-4(3H)-one: | cis-2,6-dimethyl-morpholine | Scaffold 6 | LCMS (ES+) 369 (M + H)+, RT 3.32 min (Analytical method B); RT 9.13 min (Analytical method HPLC, YMC-CELLULOSE-SC, 40/60 IPA/HEPTANE); 1H NMR (400 MHz, CDCl3) 9.03 (1H, s), 7.34-7.16 (5H, m), 4.95 (1H, s), 4.46-4.37 (1H, m), 4.24-4.02 (2H, m), 3.69-3.61 (2H, m), 3.57-3.50 (1H, m), 3.38 (1H, q, J = 8.4 Hz), 3.26-3.21 (1H, m), 2.62-2.51 (3H, m), 2.01-1.94 (2H, m), 1.87-1.81 (2H, m), 1.23 (6H, t, J = 5.4 Hz). |
| Example 345 | 2-((R)-2-benzylpyrrolidin-1-yl)-6-((2S,6S)-2,6-dimethylmorpholino)pyrimidin-4(3H)-one: | (2S,6S)-dimethyl-morpholine | Scaffold 6 | LCMS (ES+) 369 (M + H)+, RT 3.30 min (Analytical method B); RT 8.14 min (Analytical method HPLC, YMC-CELLULOSE-SC, 35/65 IPA/HEPTANE); 1H NMR (400 MHz, CDCl3) 9.63 (1H, s), 7.34-7.15 (5H, m), 4.93 (1H, s), 4.47-4.40 (1H, m), 4.10-4.04 (2H, m), 3.72 (2H, d, J = 11.6 Hz), 3.61-3.54 (1H, m), 3.41 (1H, q, J = 8.6 Hz), 3.35-3.19 (3H, m), 2.60 (1H, dd, J = 9.9, 13.1 Hz), 2.02-1.78 (4H, m), 1.23 (6H, d, J = 6.6 Hz). |
| Example 346 | 2-((S)-2-benzylpyrrolidin-1-yl)-6-((2S,6S)-2,6-dimethylmorpholino)pyrimidin-4(3H)-one: | (2S,6S)-dimethyl-morpholine | Scaffold 6 | LCMS (ES+) 369 (M + H)+, RT 3.30 min (Analytical method B); RT 9.80 min (Analytical method HPLC, YMC-CELLULOSE-SC, 35/65 IPA/HEPTANE); 1H NMR (400 MHz, CDCl3) 9.32 (1H, s), 7.34-7.14 (5H, m), 4.92 (1H, s), 4.44-4.39 (1H, m), 4.09-4.01 (2H, m), 3.74-3.67 (2H, m), 3.59-3.52 (1H, m), 3.40 (1H, q, J = 8.6 Hz), 3.31-3.20 (3H, m), 2.61 (1H, dd, J = 9.6, 13.4 Hz), 2.01-1.79 (4H, m), 1.23 (6H, d, J = 6.6 Hz). |
| Example 347 | 2-((R)-2-benzylpyrrolidin-1-yl)-6-((2R,6R)-2,6-dimethylmorpholino)pyrimidin-4(3H)-one: | (2R,6R)-2,6-dimethyl-morpholine | Scaffold 6 | LCMS (ES+) 369 (M + H)+, RT 3.30 min (Analytical method B); RT 2.57 min (Analytical method SFC1, LUX CELLULOSE-3, 10/90 MeOH [0.1% DEA]/CO2); 1H NMR (400 MHz, CDCl3) 9.37 (1H, s), 7.33-7.15 (5H, m), 4.92 (1H, s), 4.44-4.38 (1H, m), 4.09-4.02 (2H, m), 3.73 (2H, d, J = 12.1 Hz), 3.59-3.52 (1H, m), 3.45-3.36 (1H, m), 3.32-3.21 (3H, m), 2.61 (1H, dd, J = 9.5, 13.3 Hz), 1.98-1.80 (4H, m), 1.23 (6H, d, J = 6.3 Hz). |

| Example | Structure and Name | Amine | Scaffold | Data |
|---|---|---|---|---|
| Example 348 | 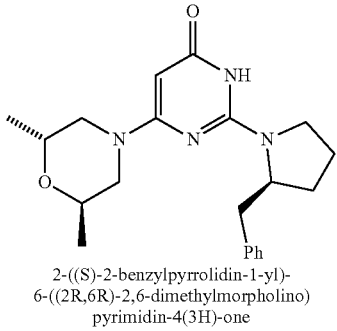<br>2-((S)-2-benzylpyrrolidin-1-yl)-6-((2R,6R)-2,6-dimethylmorpholino)pyrimidin-4(3H)-one | (2R,6R)-2,6-dimethyl-morpholine | Scaffold 6 | LCMS (ES+) 369 (M + H)+, RT 3.26 min (Analytical method A); RT 2.04 min (Analytical method SFC1, LUX CELLULOSE-3, 10/90 MeOH [0.1% DEA]/CO$_2$); $^1$H NMR (400 MHz, CDCl$_3$) 10.00 (1H, s), 7.34-7.15 (5H, m), 4.93 (1H, s), 4.48-4.42 (1H, m), 4.11-4.04 (2H, m), 3.74-3.71 (2H, m), 3.63-3.57 (1H, m), 3.43 (1H, q, J = 8.7 Hz), 3.34-3.23 (3H, m), 2.59 (1H, dd, J = 9.6, 13.1 Hz), 2.00-1.78 (4H, m), 1.22 (6H, d, J = 6.3 Hz). |
| Example 349 | 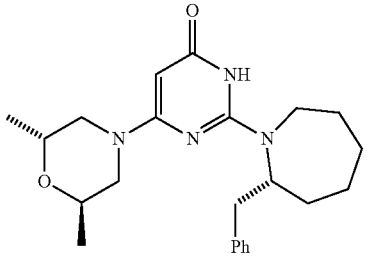 [SMILES: C[C@@H]1CN(c2cc(=O)[nH]c(N3CCCCC[C@@H]3Cc3ccccc3)n2)C[C@@H](C)O1]<br>2-((R)-2-benzylazepan-1-yl)-6-((2R,6R)-2,6-dimethylmorpholino)pyrimidin-4(3H)-one | (2R,6R)-2,6-dimethyl-morpholine | Scaffold 7 | LCMS (ES+) 397 (M + H)+, RT 3.42 min (Analytical method A); $^1$H NMR (400 MHz, CDCl$_3$) 7.29-7.12 (5H, m), 4.86 (1H, s), 4.07-4.01 (2H, m), 3.73-3.64 (3H, m), 3.21 (2H, dd, J = 6.4, 12.8 Hz), 3.05-2.84 (2H, m), 2.73-2.68 (1H, m), 2.10-1.98 (1H, m), 1.84-1.74 (3H, m), 1.48-1.36 (3H, m), 1.29-1.14 (8H, m), NH not observed. |
| Example 350 | 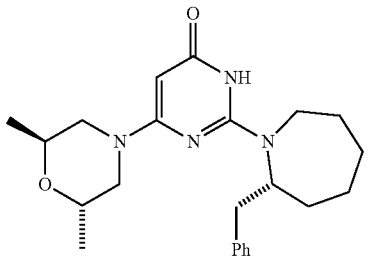 [SMILES: C[C@H]1CN(c2cc(=O)[nH]c(N3CCCCC[C@@H]3Cc3ccccc3)n2)C[C@H](C)O1]<br>2-((R)-2-benzylazepan-1-yl)-6-((2S,6S)-2,6-dimethylmorpholino)pyrimidin-4(3H)-one | (2S,6S)-2,6-dimethyl-morpholine | Scaffold 7 | LCMS (ES+) 397 (M + H)+, RT 3.46 min (Analytical method A); $^1$H NMR (400 MHz, CDCl$_3$) 7.32-7.11 (5H, m), 4.89 (1H, s), 4.68 (1H, br s), 4.10-4.03 (2H, m), 3.72-3.45 (3H, m), 3.32-3.24 (2H, m), 3.00-2.84 (2H, m), 2.75-2.68 (1H, m), 2.07-1.92 (1H, m), 1.87-1.69 (3H, m), 1.50-1.35 (3H, m), 1.29-1.16 (8H, m). |
| Example 351 | 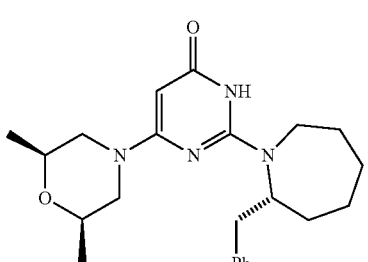<br>2-((R)-2-benzylazepan-1-yl)-6-((2S,6R)-2,6-dimethylmorpholino)pyrimidin-4(3H)-one | cis-2,6-dimethyl-morpholine | Scaffold 7 | LCMS (ES+) 397 (M + H)+, RT 3.53 min (Analytical method A); $^1$H NMR (400 MHz, CDCl$_3$) 7.31-7.13 (5H, m), 4.90 (1H, s), 4.68 (1H, br s), 4.13-3.98 (2H, m), 3.71-3.48 (3H, m), 3.08-2.88 (2H, m), 2.71-2.65 (1H, m), 2.53 (2H, dd, J = 11.7, 11.7 Hz), 2.07-1.98 (1H, m), 1.84-1.75 (3H, m), 1.48-1.36 (3H, m), 1.31-1.13 (8H, m). |

Example 352: 2-(2-benzylpyrrolidin-1-yl)-6-(2,3-dimethylmorpholino)pyrimidin-4(3H)-one, Stereoisomer 1, Example 353: 2-(2-benzylpyrrolidin-1-yl)-6-(2,3-dimethylmorpholino)pyrimidin-4(3H)-one, Stereoisomer 2, Example 354: 2-(2-benzylpyrrolidin-1-yl)-6-(2,3-dimethylmorpholino)pyrimidin-4(3H)-one, Stereoisomer 3, and Example 355: 2-(2-benzylpyrrolidin-1-yl)-6-(2,3-dimethylmorpholino)pyrimidin-4(3H)-one, Stereoisomer 4

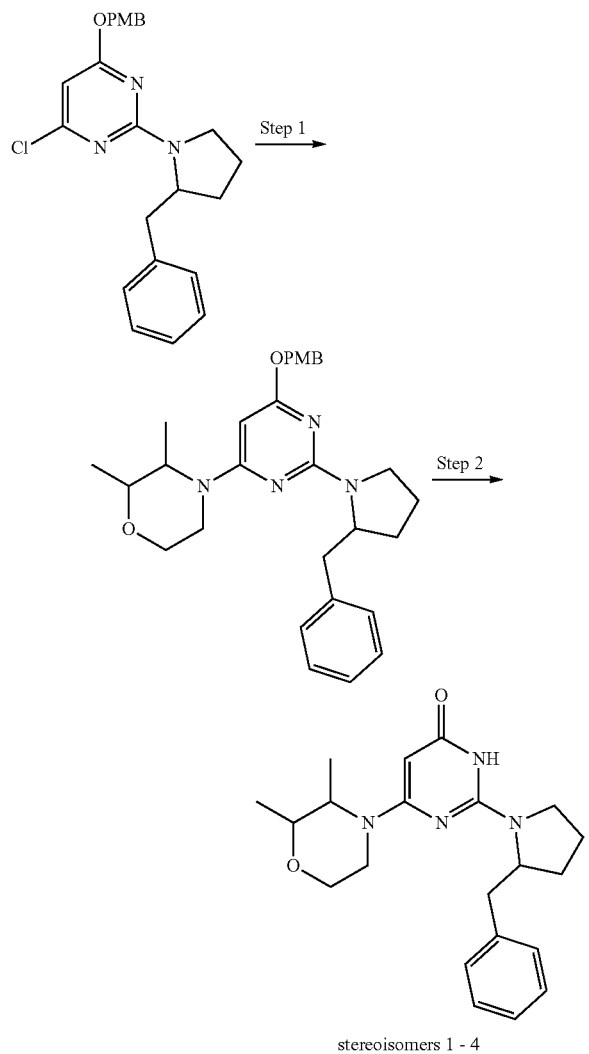

stereoisomers 1 - 4

Step 1: 4-(2-(2-benzylpyrrolidin-1-yl)-6-((4-methoxybenzyl)oxy)pyrimidin-4-yl)-2,3-dimethylmorpholine Following Method D from Scaffold 6 (100 mg, 0.24 mmol, 1 equiv) and 2,3-dimethylmorpholine (33.3 mg, 0.29 mmol, 1.2 equiv). The material was used without chromatography.

Step 2: Four stereoisomers of 2-(2-benzylpyrrolidin-1-yl)-6-(2,3-dimethylmorpholino)pyrimidin-4(3H)-one Following Method H from 4-(2-(2-benzylpyrrolidin-1-yl)-6-((4-methoxybenzyl)oxy)pyrimidin-4-yl)-2,3-dimethylmorpholine (169 mg). The mixture was stirred at rt for 21 h. The reaction was quenched with MeOH and purified by reverse phase HPLC, then chiral SFC to give four individual stereoisomers.

2-(2-benzylpyrrolidin-1-yl)-6-(2,3-dimethylmorpholino)pyrimidin-4(3H)-one, stereoisomer 1: LCMS (ES+) 369 (M+H)$^+$, RT 3.22 min (Analytical method A); RT 2.30 min (Analytical method SFC4, LUX CELLULOSE-3, 10/90 MeOH [0.1% DEAISO]/CO$_2$); $^1$H NMR (400 MHz, CDCl$_3$) 10.00 (1H, s), 7.33-7.14 (5H, m), 4.94 (1H, s), 4.45-4.40 (1H, m), 4.15-4.11 (1H, m), 3.98-3.79 (3H, m), 3.69-3.55 (2H, m), 3.48-3.38 (1H, m), 3.30-3.18 (2H, m), 2.63 (1H, dd, J=9.9, 12.9 Hz), 1.95-1.78 (4H, m), 1.35 (3H, d, J=6.6 Hz), 1.28 (3H, d, J=6.8 Hz).

2-(2-benzylpyrrolidin-1-yl)-6-(2,3-dimethylmorpholino)pyrimidin-4(3H)-one, stereoisomer 2: LCMS (ES+) 369.2 (M+H)$^+$, RT 3.24 min (Analytical method B); RT 5.39 min (Analytical method SFC1, YMC AMYLOSE-C, 10/10/80 MeOH [0.1% DEAISO]/MeCN [0.1% DEAISO]/CO$_2$); $^1$H NMR (400 MHz, CDCl$_3$) 7.33-7.14 (5H, m), 4.93 (1H, s), 4.44-4.36 (1H, m), 4.10-3.79 (4H, m), 3.68 (1H, dd, J=4.3, 11.4 Hz), 3.50-3.45 (1H, m), 3.37 (1H, q, J=8.3 Hz), 3.28-3.18 (2H, m), 2.66 (1H, dd, J=9.2, 13.3 Hz), 1.96-1.82 (4H, m), 1.31 (6H, dd, J=1.9, 6.7 Hz), NH not observed.

2-(2-benzylpyrrolidin-1-yl)-6-(2,3-dimethylmorpholino)pyrimidin-4(3H)-one, stereoisomer 3: LCMS (ES+) 369 (M+H)$^+$, RT 3.23 min (Analytical method B); RT 7.28 min (Analytical method SFC1, YMC AMYLOSE-C, 10/10/80 MeOH [0.1% DEAISO]/MeCN [0.1% DEAISO]/CO$_2$); $^1$H NMR (400 MHz, CDCl$_3$) 7.33-7.14 (5H, m), 4.94 (1H, s), 4.43-4.36 (1H, m), 4.16-4.09 (1H, m), 3.96-3.79 (3H, m), 3.71-3.64 (1H, m), 3.53-3.46 (1H, m), 3.40-3.34 (1H, m), 3.29-3.17 (2H, m), 2.66 (1H, dd, J=9.2, 13.3 Hz), 1.94-1.83 (4H, m), 1.34 (3H, d, J=6.7 Hz), 1.28 (3H, d, J=6.8 Hz), NH not observed.

2-(2-benzylpyrrolidin-1-yl)-6-(2,3-dimethylmorpholino)pyrimidin-4(3H)-one, stereoisomer 4: LCMS (ES+) 369 (M+H)$^+$, RT 3.24 min (Analytical method B); RT 2.33 min (Analytical method SFC4, LUX CELLULOSE-4, 40/60 MeOH [0.1% DEAISO]/CO$_2$); $^1$H NMR (400 MHz, CDCl$_3$) 9.58 (1H, s), 7.33-7.15 (5H, m), 4.93 (1H, s), 4.44-4.40 (1H, m), 4.11-3.80 (4H, m), 3.67 (1H, dd, J=3.8, 11.4 Hz), 3.58-3.52 (1H, m), 3.44-3.37 (1H, m), 3.28-3.18 (2H, m), 2.63 (1H, dd, J=9.5, 13.0 Hz), 1.95-1.80 (4H, m), 1.31 (6H, dd, J=1.6, 6.7 Hz).

Example 356: 2-(2-benzylpyrrolidin-1-yl)-6-(3,6-dihydro-2H-pyran-4-yl)pyrimidin-4(3H)-one

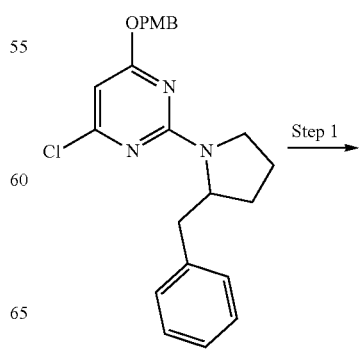

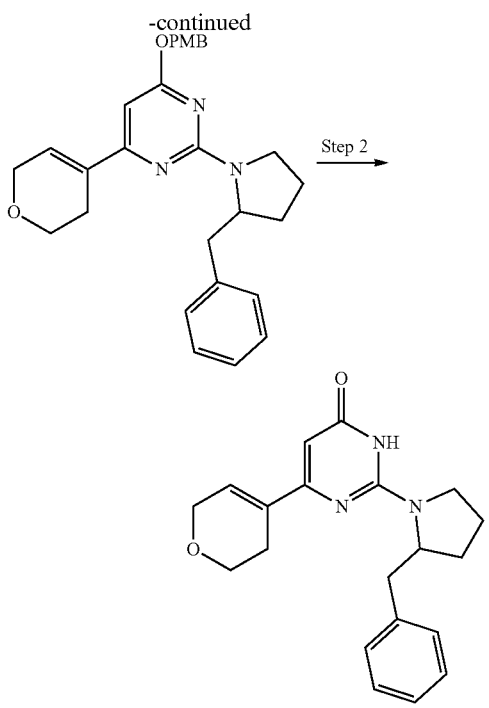

Step 1: 2-(2-benzylpyrrolidin-1-yl)-4-(3,6-dihydro-2H-pyran-4-yl)-6-((4-methoxybenzyl)oxy)pyrimidine A reaction tube containing Scaffold 6 (150 mg, 0.37 mmol), 2-(3,6-dihydro-2H-pyran-4-yl)-4,4,5,5-tetramethyl-1,3,2-dioxaborolane (91.7 mg, 0.44 mmol), Pd(PPh$_3$)$_4$ (42.2 mg, 37 µmol) and Na$_2$CO$_3$ (0.55 mL, 1.1 mmol, 2 M in H$_2$O) in DME (1.8 mL) was evacuated and backfilled with N$_2$ four times. The mixture was stirred at 80° C. for 16 h. After cooling to rt the mixture was filtered through Celite, washing with MeOH. The filtrate was concentrated and purified by silica gel column chromatography (gradient elution, 0-100% EtOAc/iso-hexane) to give impure title compound, which was used without further purification.

Step 2: 2-(2-benzylpyrrolidin-1-yl)-6-(3,6-dihydro-2H-pyran-4-yl)pyrimidin-4(3H)-one Following Method H from 2-(2-benzylpyrrolidin-1-yl)-4-(3,6-dihydro-2H-pyran-4-yl)-6-((4-methoxybenzyl)oxy)pyrimidine (48 mg). After 21 h the reaction was quenched with MeOH and purified by reverse phase preparative HPLC to give the title compound. LCMS (ES+) 338 (M+H)$^+$, RT 3.22 min (Analytical method B); $^1$H NMR (400 MHz, CDCl$_3$) 9.71 (1H, s), 7.34-7.28 (2H, m), 7.24-7.19 (3H, m), 6.98 (1H, s), 5.80 (1H, s), 4.52 (1H, d, J=4.8 Hz), 4.38 (2H, d, J=2.5 Hz), 3.93-3.88 (2H, m), 3.60-3.54 (1H, m), 3.47-3.41 (1H, m), 3.24 (1H, dd, J=2.8, 12.6 Hz), 2.68 (1H, dd, J=9.2, 13.3 Hz), 2.50-2.46 (2H, m), 2.00-1.84 (4H, m).

Biological Examples

ATM: Recombinant, full length human FLAG-tagged ATM activity (Eurofins 14-933) was measured in an ELISA for p53 S15 phosphorylation, in a 384 well V-bottom polypropylene plate (Greiner Bio One 781280). Reactions contained 0.75 nM ATM, 25 nM full length myc tagged p53 (Eurofins 23-034), 10 µM UltraPure ATP (Promega V915B) and serial dilutions of inhibitors (0.1% DMSO final) in 25 mM HEPES, pH 7.5. 5 mM MgCl2, 2.5 mM MnCl2, 0.006% Brij-35, 0.5% glycerol, 0.1 mg/ml BSA, 0.5 mM DTT and were allowed to proceed for 30 min at 20° C. 70 mM EDTA final terminated the kinase reactions. An aliquot of the terminated reaction (25 µl) was transferred to a 384-well, high binding microplate (Greiner Bio One 781061), precoated with anti-myc capture antibody overnight (Millipore 05-724) diluted in 1:1000 in PBS, then blocked with Odyssey blocking buffer (LI-COR Biosciences 92740000) for 60 min at 20° C. The terminated reaction was allowed to capture for 2 h at 20° C. Phosphorylation was measured using an antibody specific to p53 S15 phosphorylation (1:5000 Abcam ab38497), anti-rabbit HRP (1:1000 Cell Signalling Technology, 7074) and TMB (ab171522). Antibodies were diluted in Odyssey blocking buffer and incubated for 60 min at 20° C. Three washes with PBS containing 0.05% (v/v) Tween 20 (PBS-T) were performed between each incubation. The TMB reaction was stopped with an equal volume of 0.2 M sulfuric acid and absorbance read at 450 nm on the Perkin Elmer Envision within 30 min of terminating the reaction. The percentage of inhibition was calculated for each concentration of compound using 0.1% DMSO control wells as 0% inhibition and 1 µM KU60019 as 100% inhibition. IC50 values represent the mean from at least two independent experiments.

Inhibition of cellular ATM activity was determined by changes in etoposide-stimulated KAP1 phosphorylation, based on the work of Guo et al. 2014. Phosphorylation of KAP1, ATM, H2AX and p53 were evaluated in-house with comparable results, but the greater assay window was observed with KAP1.

Cryopreserved U20S cells were plated overnight at 6 k cells/well in black walled, clear bottomed 384 well plates (Greiner Bio One 781090). After overnight incubation (37 C, 5% CO2), cells were incubated with titrations of test compounds (0.3% DMSO final) in the presence of 100 µM etoposide (Sigma E1383) to stimulate ATM via induction of double stranded DNA breaks. After 60 min, cells were fixed using 100% cold methanol and incubated at −20° C. for 10 min. Fixed cells were washed with PBS containing 0.05% (v/v) Tween 20 (PBS-T) prior to a 60 minute blocking step in Odyssey blocking buffer (LI-COR Biosciences 92740000). Primary antibodies (1:1000 phosphorylated KAP1: Cell Signalling Technology 4127, 1:5000 total KAP1: Cell Signaling Technology 5868) were diluted in Odyssey blocking buffer and incubated overnight at 4° C., before addition of IRDye(R) conjugated secondary antibodies (LI-COR Biociences 926-32211, LI-COR Biosciences 926-68070) diluted 1:2000 in Odyssey blocking buffer for 60 min at room temperature and detection by LI-COR Odyssey (ImageStudio version 2.1.10, focus offset 4 mm, resolution 169 µm, lowest quality, intensities of 1 and 3 for 700 and 800 channels respectively). Immunoreactivity was quantified and the ratio of phosphorylated KAP1 calculated by dividing by the total KAP1 immunoreactivity. The percentage of inhibition was calculated for each concentration of compound using 100% (100 µM etoposide+30 µM KU-60019) and 0% effect controls (100 µM etoposide+DMSO). IC50 values represent the mean from at least two independent experiments.

Measured assay activity for a number of Example compounds is presented in the Table below:

| Example | ATM BIO IC50 (μM) | ATM CELL IC50 (μM) |
|---|---|---|
| Example 1 | 0.0362 | 3.381 |
| Example 7 | 0.0446 | 1.025 |
| Example 13 | 0.0705 | 4.492 |
| Example 16 | 0.0894 | 4.16 |
| Example 20 | 0.0541 | 2.929 |
| Example 22 | 0.0553 | 2.684 |
| Example 23 | 0.0065 | 0.527 |
| Example 25 | 0.0137 | 0.53 |
| Example 27 | 0.0166 | 0.501 |
| Example 29 | 0.0325 | 0.371 |
| Example 31 | 0.0123 | 0.26 |
| Example 33 | 0.0924 | 1.778 |
| Example 35 | 0.0532 | 2.484 |
| Example 39 | 0.0262 | 0.517 |
| Example 41 | 0.0691 | 1.043 |
| Example 43 | 0.0096 | 0.293 |
| Example 47 | 0.0083 | 0.347 |
| Example 50 | 0.023 | 0.977 |
| Example 52 | 0.0353 | 0.839 |
| Example 57 | 0.018 | 0.292 |
| Example 62 | 0.0405 | 1.25 |
| Example 64 | 0.0428 | 0.933 |
| Example 66 | 0.0187 | 0.603 |
| Example 70 | 0.0024 | 0.274 |
| Example 74 | 0.0112 | 0.498 |
| Example 76 | 0.0702 | 2.685 |
| Example 78 | 0.0108 | 0.318 |
| Example 84 | 0.0476 | 0.864 |
| Example 86 | 0.065 | 1.383 |
| Example 88 | 0.053 | 1.665 |
| Example 90 | 0.0391 | 0.874 |
| Example 96 | 0.0055 | 0.27 |
| Example 98 | 0.0384 | 0.925 |
| Example 100 | 0.0331 | 1.627 |
| Example 101 | 0.0171 | 1.41 |
| Example 102 | 0.0396 | 2.223 |
| Example 117 | 0.0728 | 0.684 |
| Example 123 | 0.0212 | 0.861 |
| Example 124 | 0.0033 | 0.248 |
| Example 126 | 0.0069 | 0.388 |
| Example 128 | 0.0147 | 0.711 |
| Example 134 | 0.0139 | 0.581 |
| Example 135 | 0.0087 | 0.178 |
| Example 145 | 0.0656 | 2.031 |
| Example 146 | 0.0742 | 1.86 |
| Example 148 | 0.0418 | 1.167 |
| Example 151 | 0.0209 | 1.017 |
| Example 167 | 0.0387 | 1.54 |
| Example 173 | 0.0378 | 1.897 |
| Example 176 | 0.0051 | 0.462 |
| Example 178 | 0.008 | 0.451 |
| Example 181 | 0.0012 | 0.548 |
| Example 186 | 0.0144 | 0.852 |
| Example 188 | 0.0287 | 1.059 |
| Example 190 | 0.0042 | 0.939 |
| Example 192 | 0.03 | 1.337 |
| Example 193 | 0.0097 | 0.598 |
| Example 196 | 0.0469 | 0.975 |
| Example 197 | 0.0149 | 0.711 |
| Example 199 | 0.0028 | 0.125 |
| Example 201 | 0.0141 | 0.693 |
| Example 203 | 0.0019 | 0.427 |
| Example 205 | 0.0396 | 0.797 |
| Example 207 | 0.0044 | 0.207 |
| Example 209 | 0.0089 | 0.377 |
| Example 211 | 0.0037 | 0.446 |
| Example 213 | 0.0011 | 0.134 |
| Example 215 | 0.001 | 0.074 |
| Example 217 | 0.0071 | 0.499 |
| Example 222 | 0.0057 | 0.163 |
| Example 223 | 0.0263 | 0.512 |
| Example 225 | 0.0039 | 0.26 |
| Example 228 | 0.0695 | 0.756 |
| Example 230 | 0.0712 | 0.881 |
| Example 231 | 0.084 | 1.089 |
| Example 233 | 0.0012 | 0.327 |
| Example 235 | 0.0053 | 0.436 |
| Example 237 | 0.0356 | 0.592 |
| Example 239 | 0.0365 | 2.015 |
| Example 242 | 0.0845 | 9.76 |
| Example 244 | 0.0102 | 0.273 |
| Example 245 | 0.0173 | 1.237 |
| Example 246 | 0.0225 | 1.072 |
| Example 247 | 0.0015 | 0.194 |
| Example 248 | 0.0039 | 0.421 |
| Example 250 | 0.005 | 0.153 |
| Example 252 | 0.0637 | 2.289 |
| Example 253 | 0.0113 | 0.434 |
| Example 255 | 0.0709 | 1.265 |
| Example 257 | 0.004 | 0.411 |
| Example 258 | 0.0068 | 0.881 |
| Example 259 | 0.0017 | 0.196 |
| Example 261 | 0.0613 | 3.045 |
| Example 262 | 0.0098 | 0.282 |
| Example 264 | 0.0053 | 0.35 |
| Example 270 | 0.0074 | 0.818 |
| Example 271 | 0.0241 | 2.138 |
| Example 274 | 0.0327 | 0.41 |
| Example 277 | 0.057 | 0.417 |
| Example 278 | 0.0897 | 0.969 |
| Example 281 | 0.0349 | 0.627 |
| Example 286 | 0.0246 | 1.018 |
| Example 291 | 0.0111 | 0.562 |
| Example 292 | 0.0055 | 1.307 |
| Example 294 | 0.0209 | 0.423 |
| Example 296 | 0.0405 | 1.85 |
| Example 300 | 0.0937 | 0.586 |
| Example 304 | 0.0192 | 0.957 |
| Example 305 | 0.039 | 0.569 |
| Example 308 | 0.0143 | 0.56 |
| Example 309 | 0.0062 | 0.256 |
| Example 312 | 0.0447 | 1.742 |
| Example 313 | 0.0423 | 1.655 |
| Example 315 | 0.0164 | 0.813 |
| Example 317 | 0.0461 | 0.857 |
| Example 319 | 0.0053 | 0.538 |
| Example 320 | 0.0909 | 1.678 |
| Example 322 | 0.0332 | 2.837 |
| Example 324 | 0.0054 | 1.677 |
| Example 339 | 0.0345 | 1.565 |
| Example 347 | 0.0237 | 0.528 |
| Example 349 | 0.0075 | 0.345 |
| Example 352 | 0.024 | 1.533 |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention.

The materials, methods, and examples provided here are representative of preferred embodiments, are exemplary, and are not intended as limitations on the scope of the invention.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed:

1. A compound of Formula I:

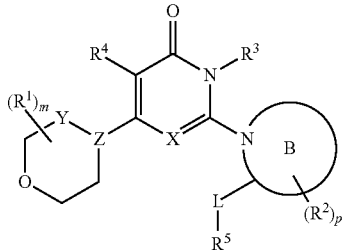

I or a pharmaceutically acceptable salt, stereoisomer, or mixture of stereoisomers thereof;
wherein:
ring B is a heterocycloalkyl ring optionally having 1 to 3 additional heteroatoms selected from O, N, and S;
X is CH or N;
(i) Z is N and Y is —CH($R^1$)— or —CH$_2$—; or
(ii) Z—Y is —C═C($R^1$)— or —C═C(H)—;
L is $C_{1-3}$ alkylene optionally substituted with $C_{1-4}$alkoxy;
each $R^1$ is independently $C_{1-4}$alkyl, halo-$C_{1-4}$alkyl, $C_{1-4}$alkoxy, halo-$C_{1-4}$alkoxy, or $C_{3-6}$ cycloalkyl;
or two $R^1$, together with the carbon atoms to which they are attached, join to form a cycloalkyl ring;
each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;
or two $R^2$, when present on the same carbon atom, join to form oxo;
or two $R^2$, together with the carbon atoms to which they are attached, join to form a $C_{3-7}$ cycloalkyl ring optionally substituted with 1 to 3 halo or a 3- to 7-membered heterocycloalkyl ring optionally substituted with 1 to 3 halo, wherein the heterocycloalkyl ring contains 1 to 3 heteroatoms selected from N, O, and S;
$R^3$ is H or $C_{1-6}$alkyl optionally substituted with —N($R^8$)($R^9$), $C_{1-4}$alkoxy, or $C_{3-6}$ cycloalkyl;
$R^4$ is H or halo;
$R^5$ is an aryl or 5- to 10-membered heteroaryl having 1, 2, 3, or 4 heteroatoms selected from N, O, and S, each of which is optionally substituted with 1 to 3 $R^6$;
each $R^6$ is independently halo, $C_{1-6}$alkyl, halo-$C_{1-6}$alkyl, or —O$R^7$;

each $R^7$ is independently selected from heterocycloalkyl and $C_{1-6}$alkyl optionally substituted with $C_{1-4}$alkoxy or halo;
$R^8$ and $R^9$ are each independently selected from H and $C_{1-6}$alkyl;
p is 0, 1, 2, or 3; and
m is 0, 1, 2, or 3.

2. The compound of claim 1, wherein the compound is of Formula II:

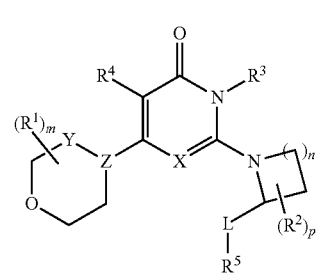

II or a pharmaceutically acceptable salt, stereoisomer, or mixture of stereoisomers thereof;
wherein:
n is 0, 1, 2, 3, or 4.

3. The compound of claim 2, wherein the compound is a compound of Formula II(a):

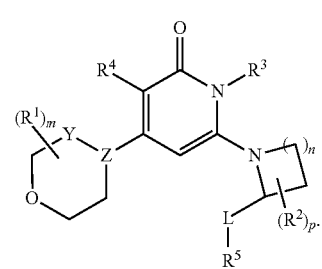

II(a)

4. The compound of claim 2, wherein the compound is a compound of Formula II(b):

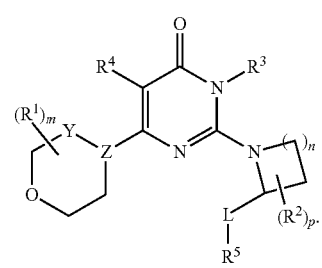

II(b)

5. The compound of claim 3, wherein the compound is a compound of Formula II(a)(i):

II(a)(i)

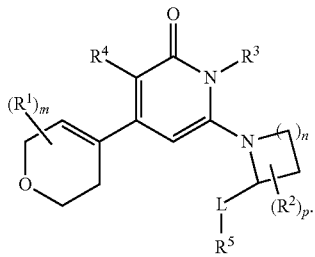

6. The compound of claim 3, wherein the compound is a compound of Formula II(a)(ii):

II(a)(ii)

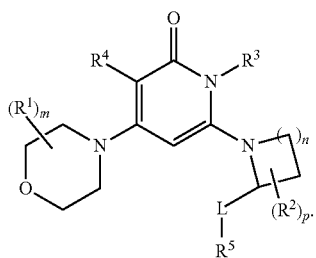

7. The compound of claim 4, wherein the compound is a compound of Formula II(b)(i):

II(b)(i)

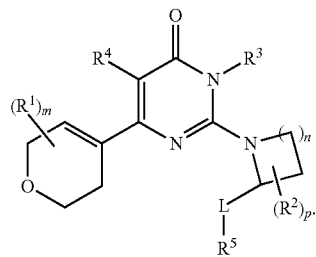

8. The compound of claim 4, wherein the compound is a compound of Formula II(b)(ii):

II(b)(ii)

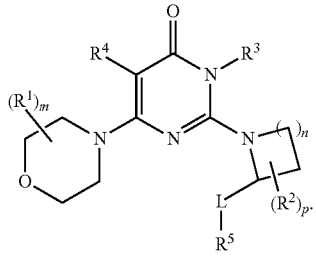

9. A compound of Formula III:

III

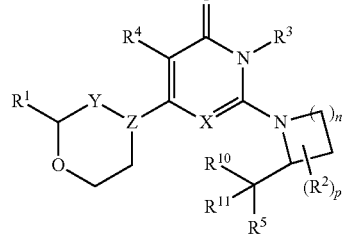

or a pharmaceutically acceptable salt, stereoisomer, or mixture of stereoisomers thereof;

wherein:

X is CH or N;

(i) Z is N and Y is —CH($R^1$)— or —CH$_2$—; or (ii) Z—Y is —C=C($R^1$)—;

each $R^1$ is independently H, $C_{1-4}$alkyl, halo-$C_{1-4}$alkyl, $C_{1-4}$alkoxy, halo-$C_{1-4}$alkoxy, or $C_{3-6}$ cycloalkyl;

or two $R^1$, together with the carbon atoms to which they are attached, join to form a cycloalkyl ring;

each $R^2$ is independently selected from hydroxy, halo, $C_{1-4}$alkyl optionally substituted with $C_{1-4}$alkoxy, halo-$C_{1-4}$alkyl optionally substituted with $C_{1-4}$alkoxy, $C_{1-4}$alkoxy optionally substituted with cycloalkyl, halo-$C_{1-4}$alkoxy, $C_{3-6}$ cycloalkyl, and $C_{3-6}$ cycloalkoxy;

or two $R^2$, when present on the same carbon atom, join to form oxo;

or two $R^2$, together with the carbon atoms to which they are attached, join to form a $C_{3-7}$ cycloalkyl ring optionally substituted with 1 to 3 halo or a 3- to 7-membered hereocycloalkyl ring optionally substituted with 1 to 3 halo, wherein the heterocycloalkyl ring contains 1 to 3 heteroatoms selected from N, O, and S;

$R^3$ is H or $C_{1-3}$alkyl optionally substituted with —N($R^8$)($R^9$), $C_{1-4}$alkoxy, or $C_{3-6}$ cycloalkyl;

$R^4$ is H or halo;

$R^5$ is an aryl or 5- to 10-membered heteroaryl having 1, 2, 3, or 4 heteroatoms selected from N, O, and S, each of which is optionally substituted with 1 to 3 $R^6$;

each $R^6$ is independently halo, $C_{1-6}$alkyl, halo-$C_{1-6}$alkyl, or —OR$^7$;

each $R^7$ is independently selected from heterocycloalkyl and $C_{1-6}$alkyl optionally substituted with $C_{1-4}$alkoxy or halo;

$R^8$ and $R^9$ are each independently selected from H and $C_{1-6}$alkyl;

$R^{10}$ and $R^{11}$ are each independently selected from H or $C_{1-3}$alkyl;

p is 0, 1, 2, or 3; and n is 0, 1, 2, 3, or 4.

10. The compound of claim 9, wherein the compound is a compound of Formula III(a):

11. The compound of claim 9, wherein the compound is a compound of Formula III(b):

III(a)

III(b)

12. The compound of claim 10, wherein the compound is a compound of Formula III(a)(i):

III(a)(i)

13. The compound of claim 10, wherein the compound is a compound of Formula III(a)(ii):

III(a)(ii)

14. The compound of claim 11, wherein the compound is a compound of Formula III(b)(i):

III(b)(i)

15. The compound of claim 11, wherein the compound is a compound of Formula III(b)(ii):

III(b)(ii)

16. The compound of claim 9, wherein the compound is of Formula IV:

IV or a pharmaceutically acceptable salt, stereoisomer, or mixture of stereoisomers thereof;
wherein:
$R^1$ is H or $C_{1-3}$alkyl;
$R^3$ is H or $C_{1-3}$alkyl;
$R^{10}$ and $R^{11}$ are each independently selected from H or methyl;
and
n is 2, 3, or 4.

17. The compound of claim 1, wherein m is 1, and $R^1$ is methyl.

18. The compound of claim 1, wherein $R^1$ is H or methyl.

19. The compound of claim 18, wherein $R^1$ is H.

20. The compound of claim 1, wherein $R^3$ is H or methyl.

21. The compound of claim 1, wherein $R^4$ is H or fluoro.

22. The compound of claim 1, wherein $R^5$ is aryl optionally substituted with 1 to 3 $R^6$.

23. The compound of claim 1, wherein $R^5$ is aryl.

24. The compound of claim 1, wherein $R^5$ is phenyl optionally substituted with 1 to 3 $R^6$.

25. The compound of claim 1, wherein $R^5$ is phenyl.

26. The compound of claim 2, wherein n is 2, 3, or 4.

27. The compound of claim 2, wherein n is 2.

28. The compound of claim 2, wherein n is 3.

29. The compound of claim 2, wherein n is 4.

30. The compound of claim 1, wherein the compound is:

| Example | Structure |
|---|---|
| 1 | 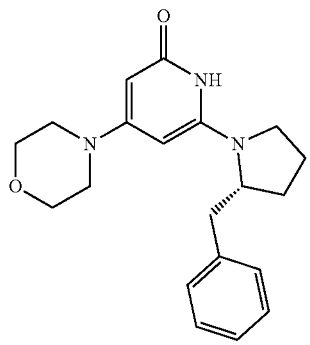 [SMILES: O=c1cc(N2CCOCC2)cc(N2CCC[C@@H]2Cc2ccccc2)[nH]1] |
| 2 | 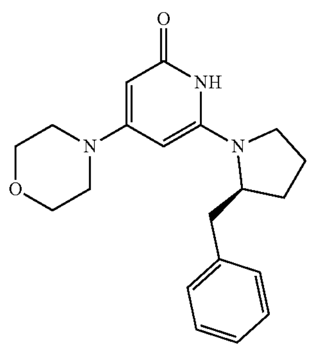 [SMILES: O=c1cc(N2CCOCC2)cc(N2CCC[C@H]2Cc2ccccc2)[nH]1] |
| 3 | 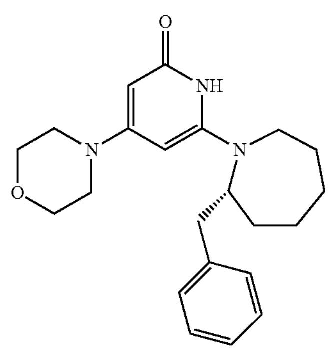 [SMILES: O=c1cc(N2CCOCC2)cc(N2CCCCC[C@@H]2Cc2ccccc2)[nH]1] |
| 4 | 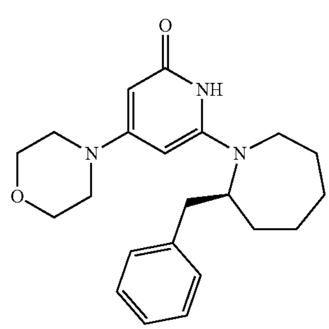 [SMILES: O=c1cc(N2CCOCC2)cc(N2CCCCC[C@H]2Cc2ccccc2)[nH]1] |
| 5 | |
| 6 | |
| 7 | |
| 8 | |

-continued

| Example | Structure |
|---------|-----------|
| 9 | 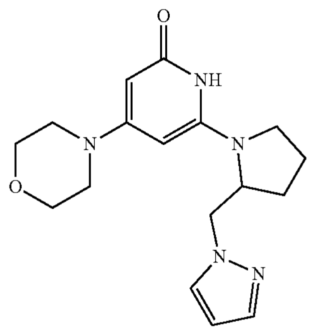 [SMILES: O=c1cc(N2CCOCC2)cc(N2CCCC2Cn2cccn2)[nH]1] |
| 10 | 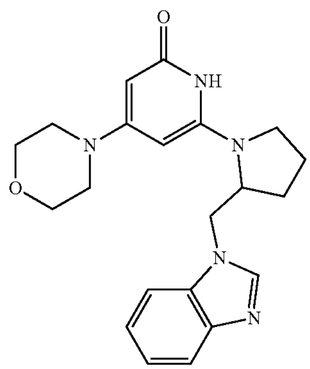 [SMILES: O=c1cc(N2CCOCC2)cc(N2CCCC2Cn2cnc3ccccc32)[nH]1] |
| 11 | 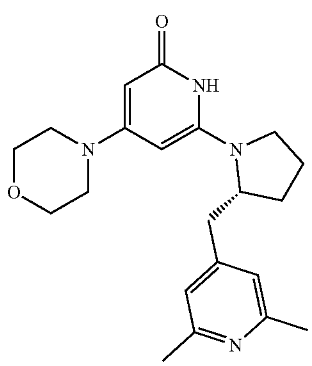 [SMILES: Cc1cc(C[C@H]2CCCN2c2cc(N3CCOCC3)cc(=O)[nH]2)cc(C)n1] |
| 12 | 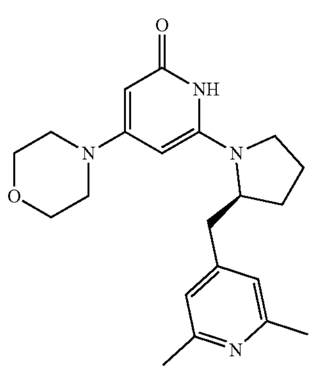 [SMILES: Cc1cc(C[C@@H]2CCCN2c2cc(N3CCOCC3)cc(=O)[nH]2)cc(C)n1] |

-continued

| Example | Structure |
|---------|-----------|
| 13 | 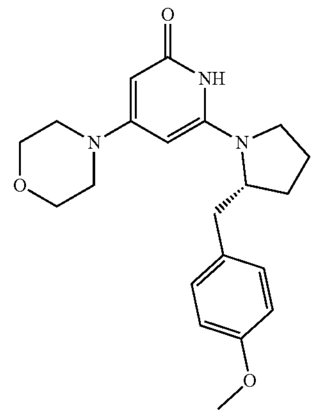 [SMILES: COc1ccc(C[C@H]2CCCN2c2cc(N3CCOCC3)cc(=O)[nH]2)cc1] |
| 14 | 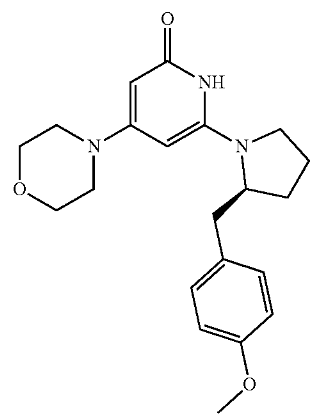 [SMILES: COc1ccc(C[C@@H]2CCCN2c2cc(N3CCOCC3)cc(=O)[nH]2)cc1] |
| 15 | 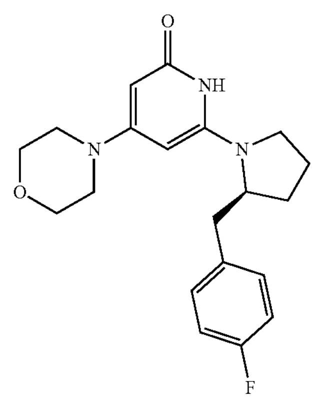 [SMILES: O=c1cc(N2CCOCC2)cc(N2CCC[C@H]2Cc2ccc(F)cc2)[nH]1] |
| 16 | 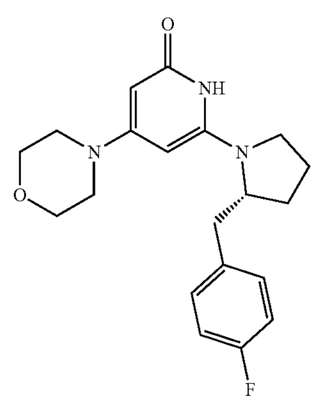 [SMILES: O=c1cc(N2CCOCC2)cc(N2CCC[C@@H]2Cc2ccc(F)cc2)[nH]1] |

485
-continued
| Example | Structure |
|---|---|
| 17 | 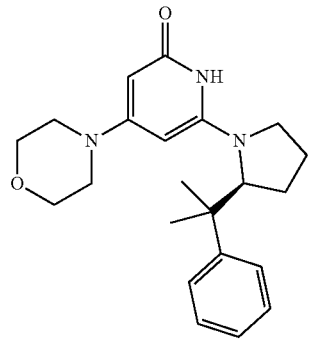 [SMILES: CC(C)(c1ccccc1)[C@@H]1CCCN1c1cc(N2CCOCC2)cc(=O)[nH]1] |
| 18 | 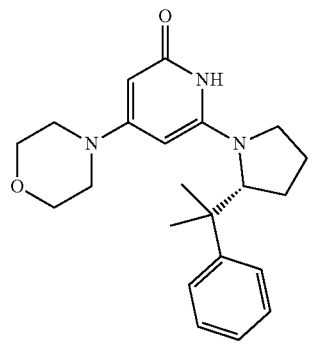 [SMILES: CC(C)(c1ccccc1)[C@H]1CCCN1c1cc(N2CCOCC2)cc(=O)[nH]1] |
| 19 | 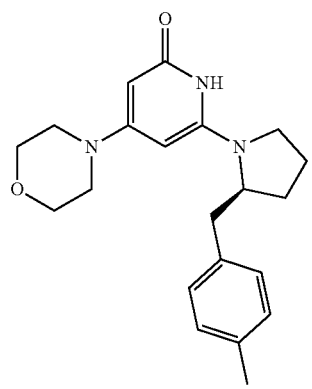 [SMILES: Cc1ccc(C[C@@H]2CCCN2c2cc(N3CCOCC3)cc(=O)[nH]2)cc1] |
| 20 | 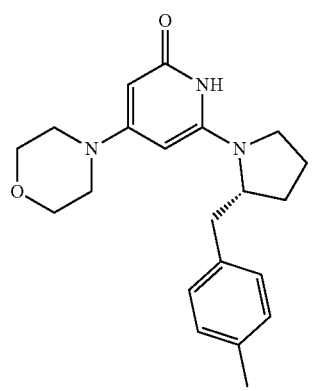 [SMILES: Cc1ccc(C[C@H]2CCCN2c2cc(N3CCOCC3)cc(=O)[nH]2)cc1] |
486
-continued
| Example | Structure |
|---|---|
| 21 | 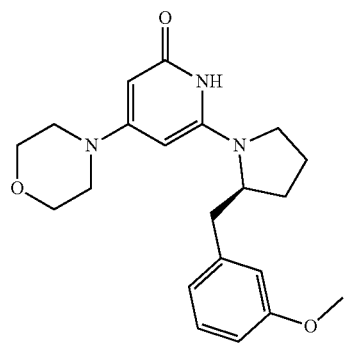 [SMILES: COc1cccc(C[C@@H]2CCCN2c2cc(N3CCOCC3)cc(=O)[nH]2)c1] |
| 22 | 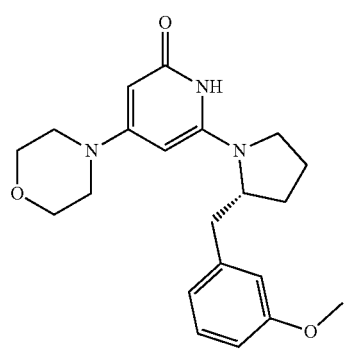 [SMILES: COc1cccc(C[C@H]2CCCN2c2cc(N3CCOCC3)cc(=O)[nH]2)c1] |
| 23 | 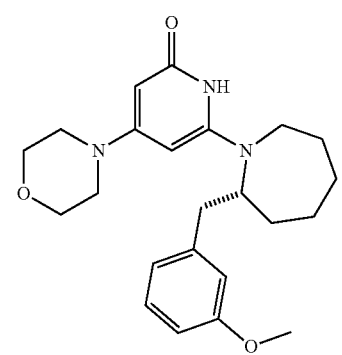 [SMILES: COc1cccc(C[C@H]2CCCCCN2c2cc(N3CCOCC3)cc(=O)[nH]2)c1] |
| 24 | 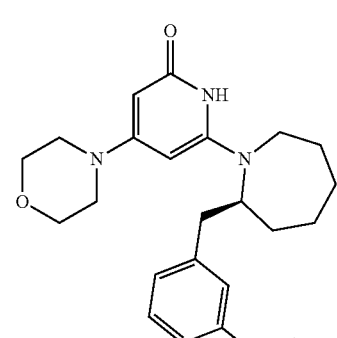 |

-continued
| Example | Structure |
|---------|-----------|
| 25 | 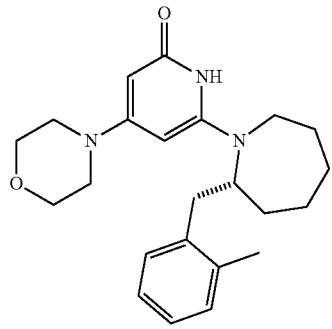 [SMILES: Cc1ccccc1C[C@H]1CCCCCN1c1cc(N2CCOCC2)cc(=O)[nH]1] |
| 26 | 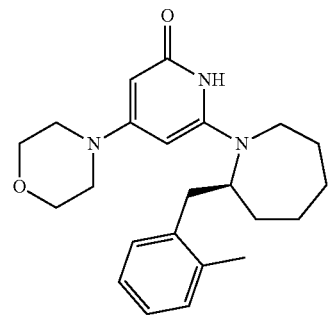 [SMILES: Cc1ccccc1C[C@@H]1CCCCCN1c1cc(N2CCOCC2)cc(=O)[nH]1] |
| 27 | 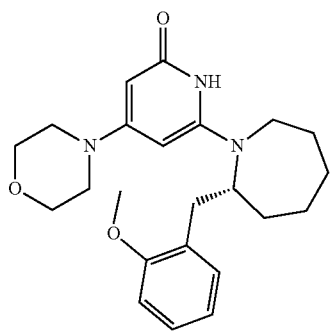 [SMILES: COc1ccccc1C[C@H]1CCCCCN1c1cc(N2CCOCC2)cc(=O)[nH]1] |
| 28 | 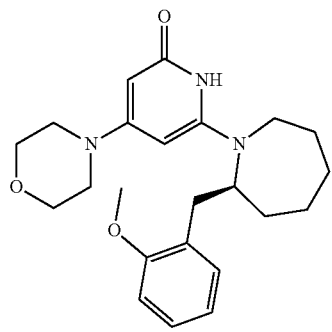 [SMILES: COc1ccccc1C[C@@H]1CCCCCN1c1cc(N2CCOCC2)cc(=O)[nH]1] |
-continued
| Example | Structure |
|---------|-----------|
| 29 | 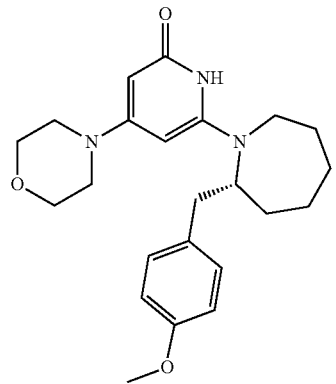 [SMILES: COc1ccc(C[C@H]2CCCCCN2c2cc(N3CCOCC3)cc(=O)[nH]2)cc1] |
| 30 | 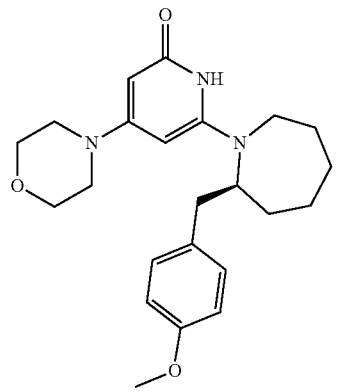 [SMILES: COc1ccc(C[C@@H]2CCCCCN2c2cc(N3CCOCC3)cc(=O)[nH]2)cc1] |
| 31 | 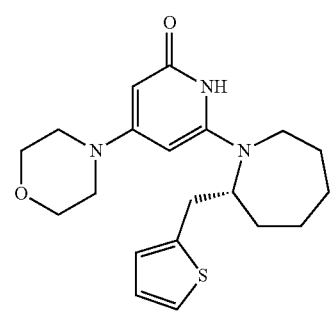 [SMILES: O=c1cc(N2CCOCC2)cc(N2CCCCC[C@@H]2Cc2cccs2)[nH]1] |
| 32 | 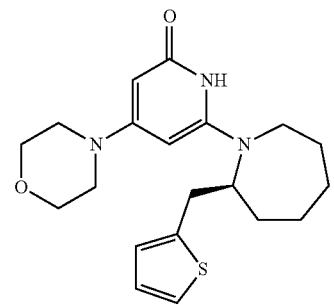 [SMILES: O=c1cc(N2CCOCC2)cc(N2CCCCC[C@H]2Cc2cccs2)[nH]1] |

| Example | Structure |
|---|---|
| 33 | 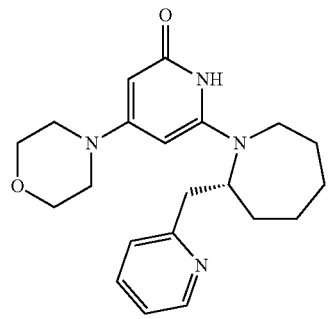 [SMILES: O=c1cc(N2CCOCC2)cc(N2CCCCC[C@@H]2Cc2ccccn2)[nH]1] |
| 34 | 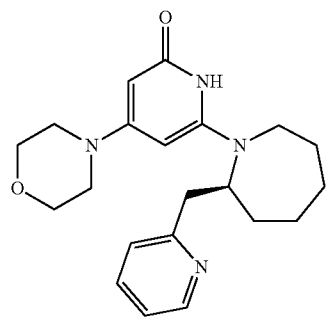 [SMILES: O=c1cc(N2CCOCC2)cc(N2CCCCC[C@H]2Cc2ccccn2)[nH]1] |
| 35 | 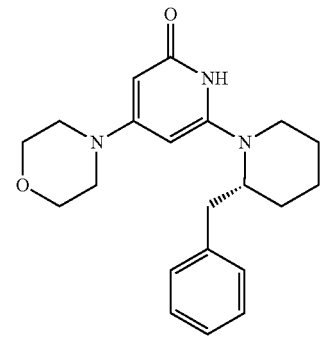 [SMILES: O=c1cc(N2CCOCC2)cc(N2CCCC[C@@H]2Cc2ccccc2)[nH]1] |
| 36 | 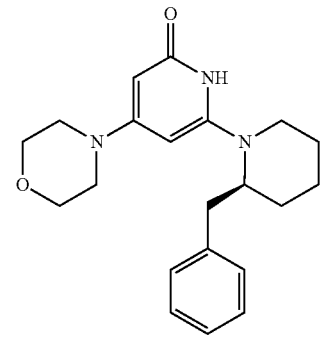 [SMILES: O=c1cc(N2CCOCC2)cc(N2CCCC[C@H]2Cc2ccccc2)[nH]1] |
| Example | Structure |
|---|---|
| 37 | 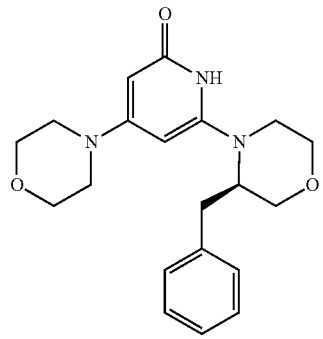 [SMILES: O=c1cc(N2CCOCC2)cc(N2CCOC[C@H]2Cc2ccccc2)[nH]1] |
| 38 | 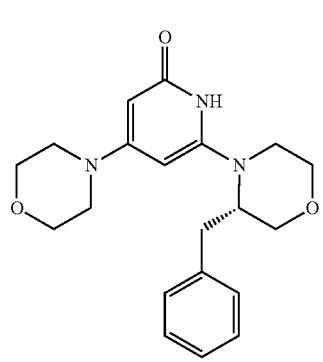 [SMILES: O=c1cc(N2CCOCC2)cc(N2CCOC[C@@H]2Cc2ccccc2)[nH]1] |
| 39 | 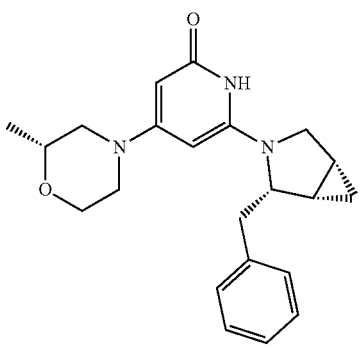 [SMILES: C[C@@H]1CN(c2cc(N3C[C@@H]4C[C@@H]4[C@@H]3Cc3ccccc3)[nH]c(=O)c2)CCO1] |
| 40 | 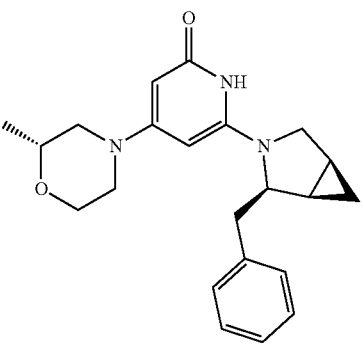 [SMILES: C[C@@H]1CN(c2cc(N3C[C@H]4C[C@H]4[C@H]3Cc3ccccc3)[nH]c(=O)c2)CCO1] |

| Example | Structure |
|---|---|
| 41 | 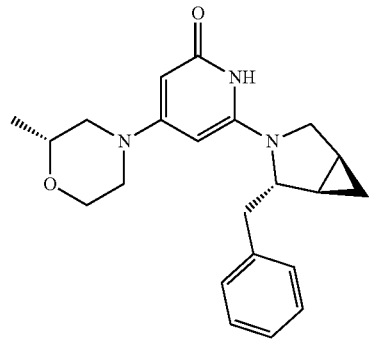 [SMILES: C[C@@H]1CN(c2cc(N3C[C@H]4C[C@H]4[C@@H]3Cc3ccccc3)[nH]c(=O)c2)CCO1] |
| 42 | 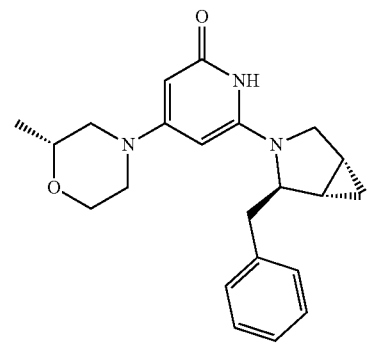 [SMILES: C[C@@H]1CN(c2cc(N3C[C@@H]4C[C@@H]4[C@H]3Cc3ccccc3)[nH]c(=O)c2)CCO1] |
| 43 | 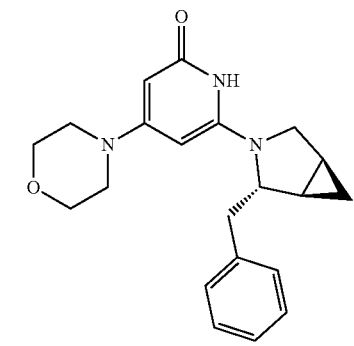 [SMILES: O=c1cc(N2CCOCC2)cc(N2C[C@H]3C[C@H]3[C@@H]2Cc2ccccc2)[nH]1] |
| 44 | 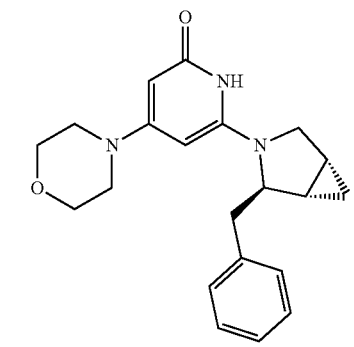 [SMILES: O=c1cc(N2CCOCC2)cc(N2C[C@@H]3C[C@@H]3[C@H]2Cc2ccccc2)[nH]1] |
| Example | Structure |
|---|---|
| 45 | 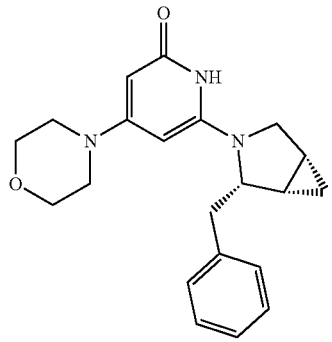 [SMILES: O=c1cc(N2CCOCC2)cc(N2C[C@@H]3C[C@@H]3[C@@H]2Cc2ccccc2)[nH]1] |
| 46 | 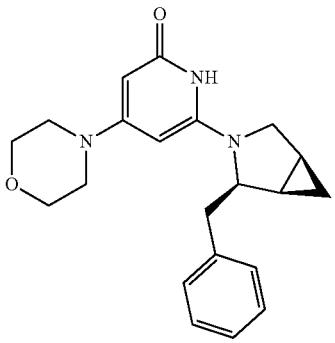 [SMILES: O=c1cc(N2CCOCC2)cc(N2C[C@H]3C[C@H]3[C@H]2Cc2ccccc2)[nH]1] |
| 47 | 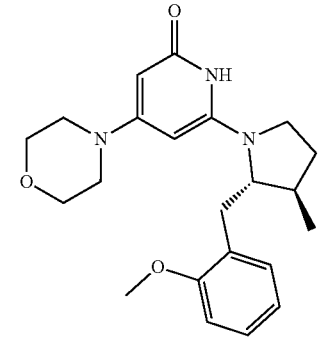 [SMILES: COc1ccccc1C[C@H]1[C@H](C)CCN1c1cc(N2CCOCC2)cc(=O)[nH]1] |
| 48 | 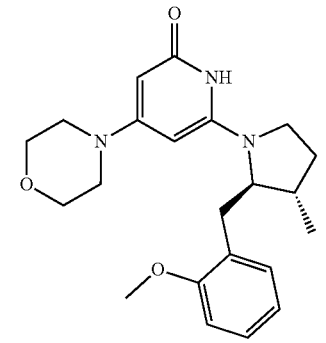 [SMILES: COc1ccccc1C[C@@H]1[C@@H](C)CCN1c1cc(N2CCOCC2)cc(=O)[nH]1] |

-continued
| Example | Structure |
|---|---|
| 49 | 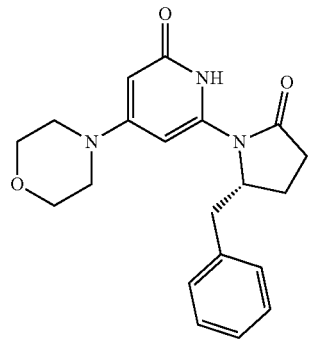 [SMILES: O=C1CC[C@H](Cc2ccccc2)N1c1cc(N2CCOCC2)cc(=O)[nH]1] |
| 50 | 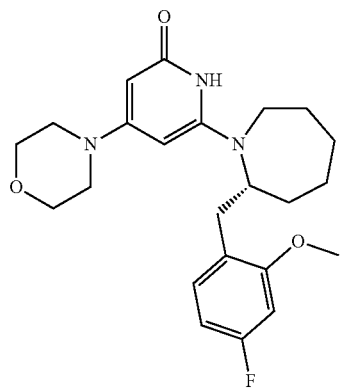 [SMILES: COc1cc(F)ccc1C[C@H]1CCCCCN1c1cc(N2CCOCC2)cc(=O)[nH]1] |
| 51 | 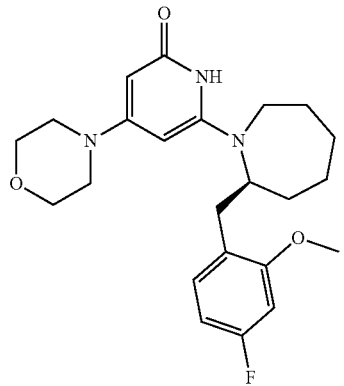 [SMILES: COc1cc(F)ccc1C[C@@H]1CCCCCN1c1cc(N2CCOCC2)cc(=O)[nH]1] |
| 52 | 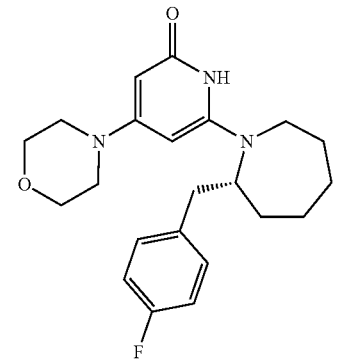 [SMILES: O=c1cc(N2CCOCC2)cc(N2CCCCC[C@@H]2Cc2ccc(F)cc2)[nH]1] |
-continued
| Example | Structure |
|---|---|
| 53 | 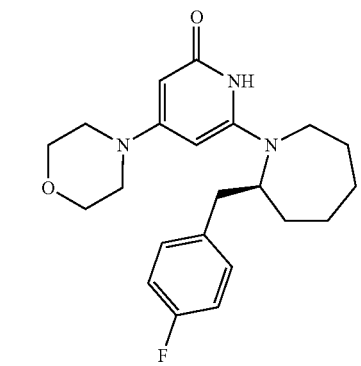 [SMILES: O=c1cc(N2CCOCC2)cc(N2CCCCC[C@H]2Cc2ccc(F)cc2)[nH]1] |
| 54 | 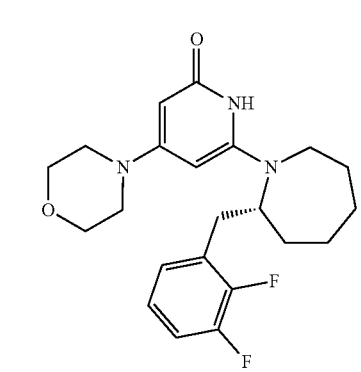 [SMILES: O=c1cc(N2CCOCC2)cc(N2CCCCC[C@@H]2Cc2cccc(F)c2F)[nH]1] |
| 55 | 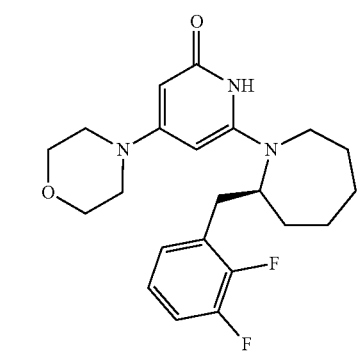 [SMILES: O=c1cc(N2CCOCC2)cc(N2CCCCC[C@H]2Cc2cccc(F)c2F)[nH]1] |
| 58 | 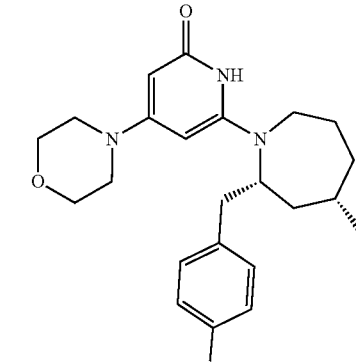 |

-continued
| Example | Structure |
|---|---|
| 59 | 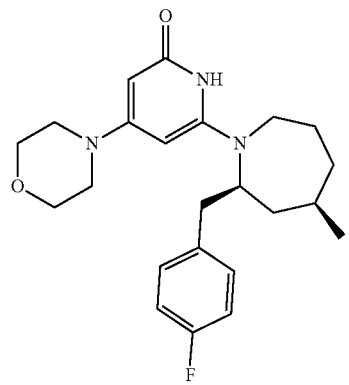 [SMILES: C[C@@H]1CCCN(c2cc(N3CCOCC3)cc(=O)[nH]2)[C@H](Cc2ccc(F)cc2)C1] |
| 60 | 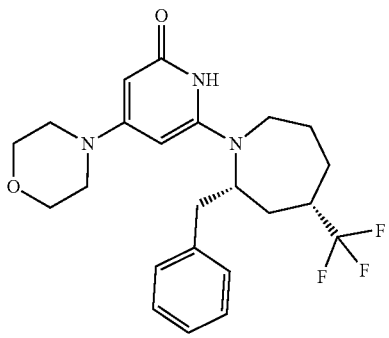 [SMILES: O=c1cc(N2CCOCC2)cc(N2CCC[C@H](C(F)(F)F)C[C@@H]2Cc2ccccc2)[nH]1] |
| 61 | 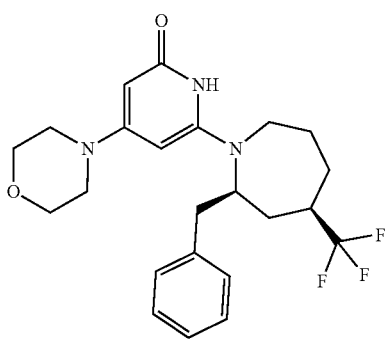 [SMILES: O=c1cc(N2CCOCC2)cc(N2CCC[C@@H](C(F)(F)F)C[C@H]2Cc2ccccc2)[nH]1] |
| 62 | 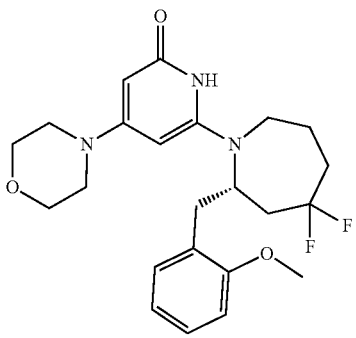 [SMILES: COc1ccccc1C[C@H]1CC(F)(F)CCCN1c1cc(N2CCOCC2)cc(=O)[nH]1] |
-continued
| Example | Structure |
|---|---|
| 63 | 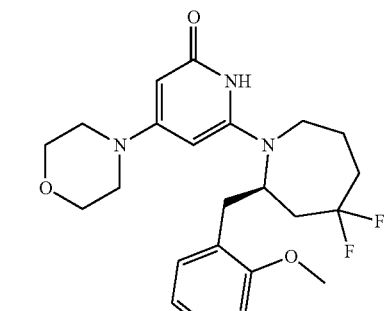 |
| 64 | 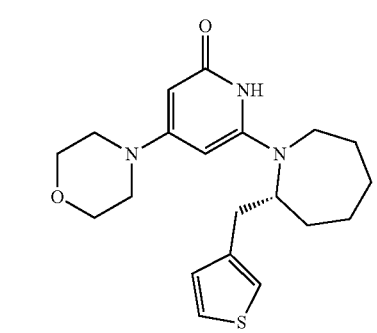 [SMILES: O=c1cc(N2CCOCC2)cc(N2CCCCC[C@@H]2Cc2ccsc2)[nH]1] |
| 65 | 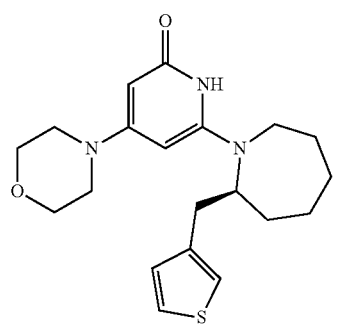 [SMILES: O=c1cc(N2CCOCC2)cc(N2CCCCC[C@H]2Cc2ccsc2)[nH]1] |
| 66 | 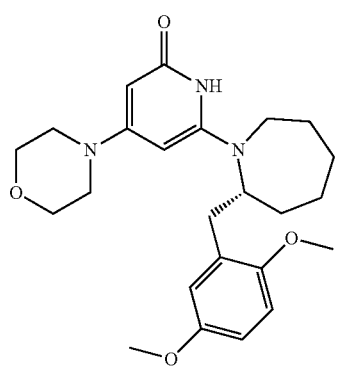 [SMILES: COc1ccc(OC)c(C[C@H]2CCCCCN2c2cc(N3CCOCC3)cc(=O)[nH]2)c1] |

-continued
| Example | Structure |
|---------|-----------|
| 67 | 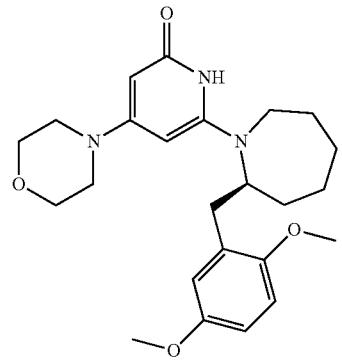 [SMILES: COc1ccc(OC)c(C[C@@H]2CCCCCN2c2cc(N3CCOCC3)cc(=O)[nH]2)c1] |
| 68 | 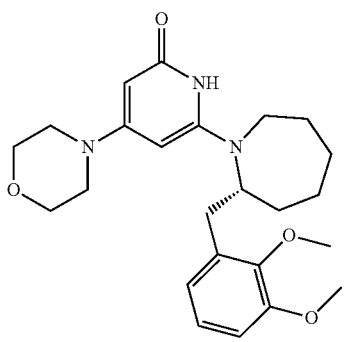 [SMILES: COc1cccc(C[C@H]2CCCCCN2c2cc(N3CCOCC3)cc(=O)[nH]2)c1OC] |
| 69 | 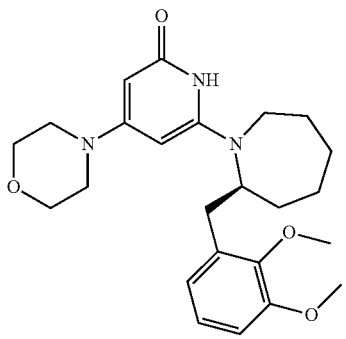 [SMILES: COc1cccc(C[C@@H]2CCCCCN2c2cc(N3CCOCC3)cc(=O)[nH]2)c1OC] |
| 72 | 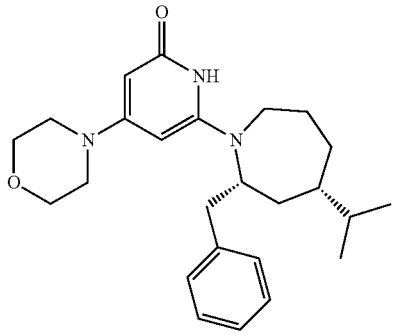 [SMILES: CC(C)[C@H]1CCCN(c2cc(N3CCOCC3)cc(=O)[nH]2)[C@@H](Cc2ccccc2)C1] |
-continued
| Example | Structure |
|---------|-----------|
| 73 | 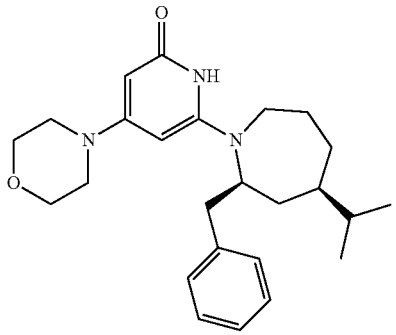 [SMILES: CC(C)[C@@H]1CCCN(c2cc(N3CCOCC3)cc(=O)[nH]2)[C@H](Cc2ccccc2)C1] |
| 74 | 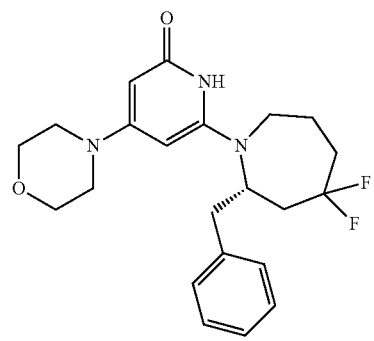 [SMILES: O=c1cc(N2CCOCC2)cc(N2CCCC(F)(F)C[C@@H]2Cc2ccccc2)[nH]1] |
| 75 | 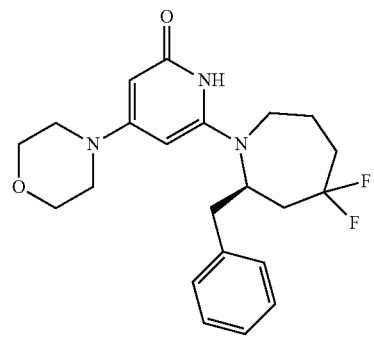 [SMILES: O=c1cc(N2CCOCC2)cc(N2CCCC(F)(F)C[C@H]2Cc2ccccc2)[nH]1] |
| 76 | 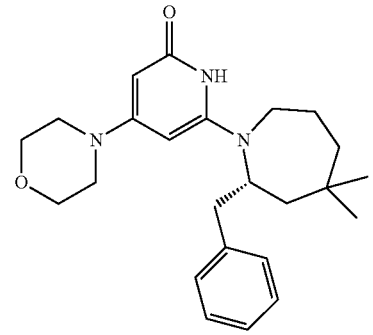 [SMILES: CC1(C)CCCN(c2cc(N3CCOCC3)cc(=O)[nH]2)[C@@H](Cc2ccccc2)C1] |

499
-continued
| Example | Structure |
|---|---|
| 77 | 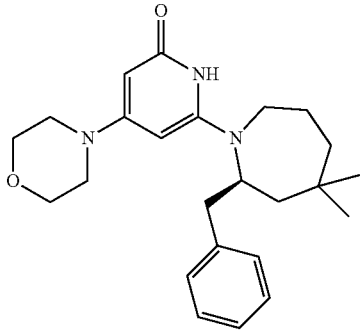 [SMILES: CC1(C)CCCN(c2cc(N3CCOCC3)cc(=O)[nH]2)[C@H](Cc2ccccc2)C1] |
| 78 | 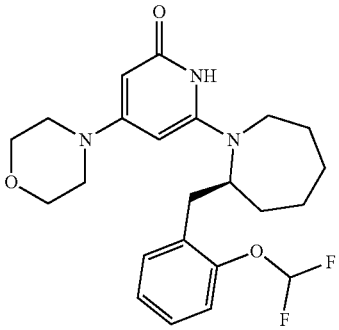 |
| 79 | 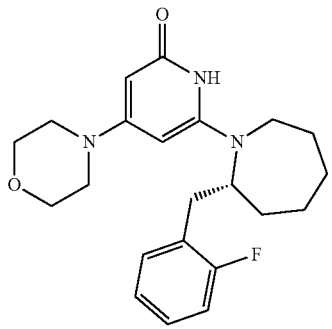 [SMILES: O=c1cc(N2CCOCC2)cc(N2CCCCC[C@@H]2Cc2ccccc2F)[nH]1] |
| 80 | 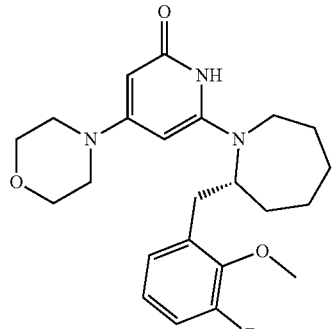 |
500
-continued
| Example | Structure |
|---|---|
| 81 | 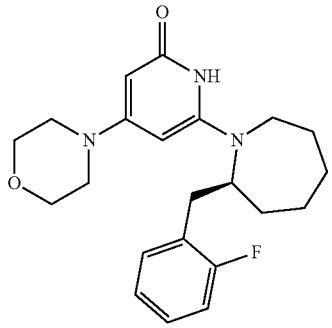 [SMILES: O=c1cc(N2CCOCC2)cc(N2CCCCC[C@H]2Cc2ccccc2F)[nH]1] |
| 82 | 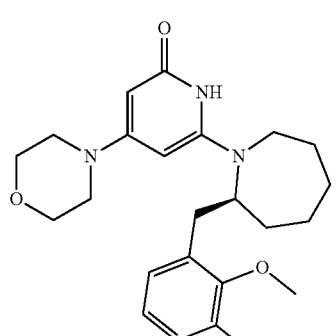 |
| 83 | 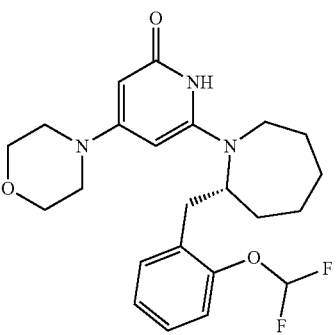 [SMILES: O=c1cc(N2CCOCC2)cc(N2CCCCC[C@@H]2Cc2ccccc2OC(F)F)[nH]1] |
| 84 | 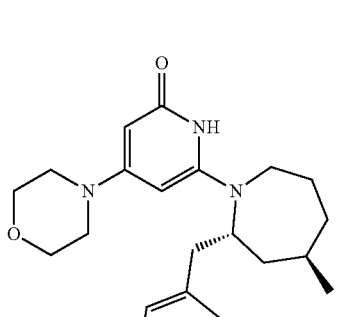 |

| Example | Structure |
|---------|-----------|
| 85 | 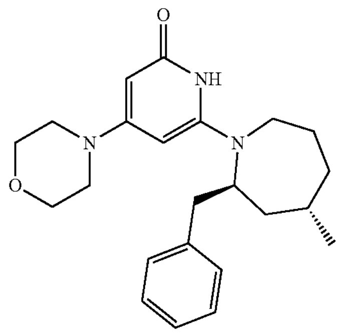 [SMILES: C[C@H]1CCCN(c2cc(N3CCOCC3)cc(=O)[nH]2)[C@H](Cc2ccccc2)C1] |
| 86 | 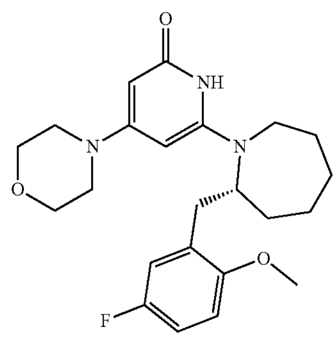 [SMILES: COc1ccc(F)cc1C[C@H]1CCCCCN1c1cc(N2CCOCC2)cc(=O)[nH]1] |
| 87 | 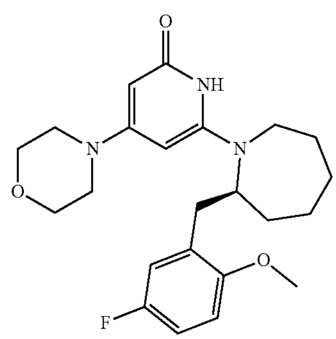 [SMILES: COc1ccc(F)cc1C[C@@H]1CCCCCN1c1cc(N2CCOCC2)cc(=O)[nH]1] |
| 88 | 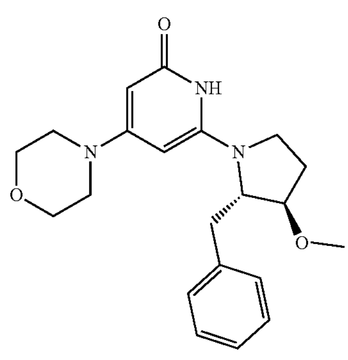 [SMILES: CO[C@@H]1CCN(c2cc(N3CCOCC3)cc(=O)[nH]2)[C@H]1Cc1ccccc1] |
| 89 | 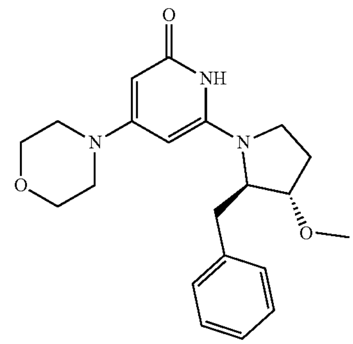 [SMILES: CO[C@H]1CCN(c2cc(N3CCOCC3)cc(=O)[nH]2)[C@@H]1Cc1ccccc1] |
| 90 | 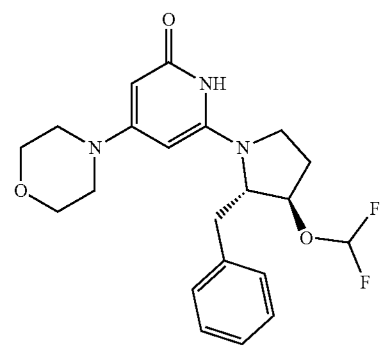 [SMILES: O=c1cc(N2CCOCC2)cc(N2CC[C@@H](OC(F)F)[C@@H]2Cc2ccccc2)[nH]1] |
| 91 | 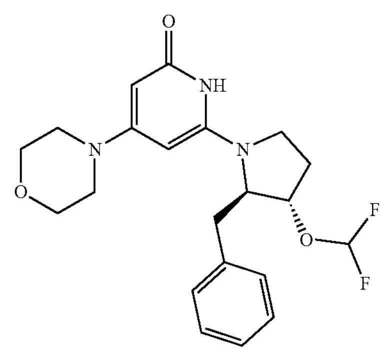 [SMILES: O=c1cc(N2CCOCC2)cc(N2CC[C@H](OC(F)F)[C@H]2Cc2ccccc2)[nH]1] |
| 92 | 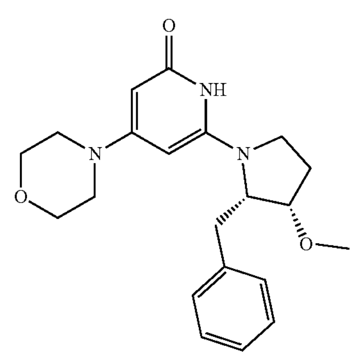 [SMILES: CO[C@H]1CCN(c2cc(N3CCOCC3)cc(=O)[nH]2)[C@H]1Cc1ccccc1] |

| Example | Structure |
|---|---|
| 93 | 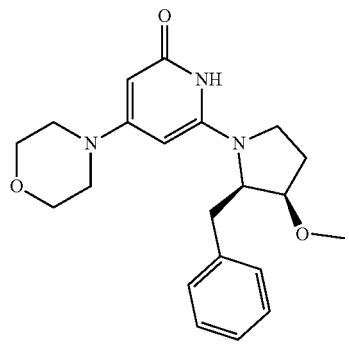 [SMILES: CO[C@@H]1CCN(c2cc(N3CCOCC3)cc(=O)[nH]2)[C@@H]1Cc1ccccc1] |
| 94 | 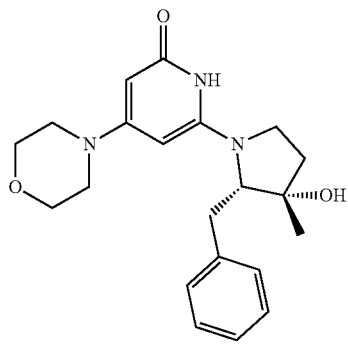 [SMILES: C[C@]1(O)CCN(c2cc(N3CCOCC3)cc(=O)[nH]2)[C@H]1Cc1ccccc1] |
| 95 | 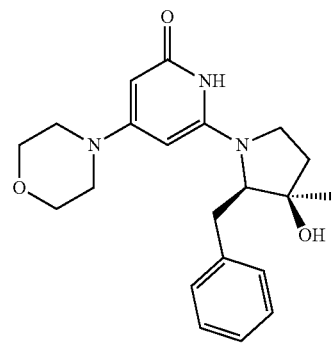 [SMILES: C[C@@]1(O)CCN(c2cc(N3CCOCC3)cc(=O)[nH]2)[C@@H]1Cc1ccccc1] |
| 96 | 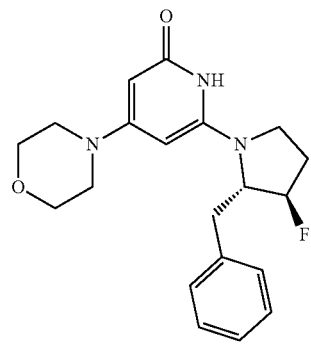 [SMILES: O=c1cc(N2CCOCC2)cc(N2CC[C@@H](F)[C@@H]2Cc2ccccc2)[nH]1] |
| Example | Structure |
|---|---|
| 97 | 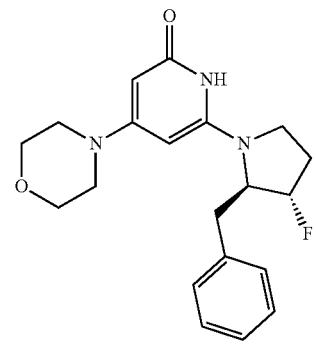 [SMILES: O=c1cc(N2CCOCC2)cc(N2CC[C@H](F)[C@H]2Cc2ccccc2)[nH]1] |
| 98 | 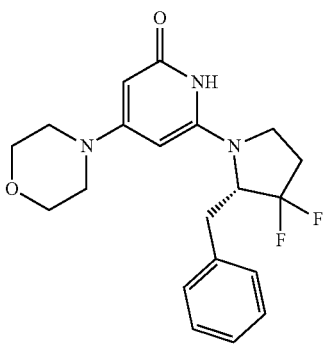 [SMILES: O=c1cc(N2CCOCC2)cc(N2CCC(F)(F)[C@@H]2Cc2ccccc2)[nH]1] |
| 99 | 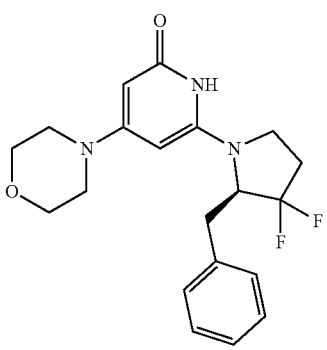 [SMILES: O=c1cc(N2CCOCC2)cc(N2CCC(F)(F)[C@H]2Cc2ccccc2)[nH]1] |
| 100 | 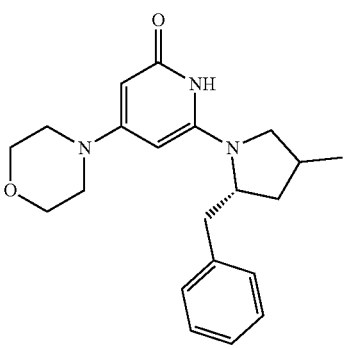 [SMILES: CC1C[C@H](Cc2ccccc2)N(c2cc(N3CCOCC3)cc(=O)[nH]2)C1] |

| Example | Structure |
|---|---|
| 101 | (structure) |
| 102 | (structure) |
| 103 | (structure) |
| 104 | (structure) |
| 105 | (structure) |
| 106 | (structure) |
| 107 | (structure) |
| 108 | (structure) |

507
-continued

| Example | Structure |
|---------|-----------|
| 109 | 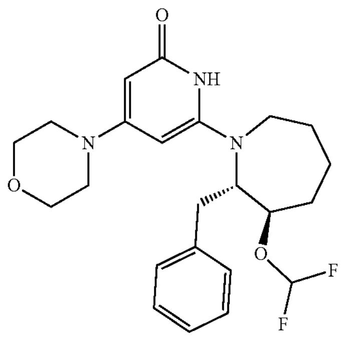 [SMILES: O=c1cc(N2CCOCC2)cc(N2CCCC[C@@H](OC(F)F)[C@@H]2Cc2ccccc2)[nH]1] |
| 110 | 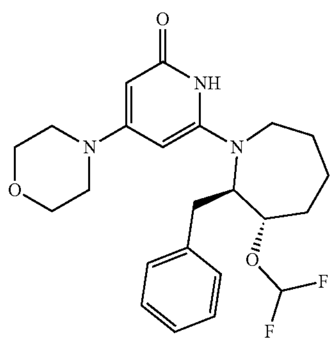 [SMILES: O=c1cc(N2CCOCC2)cc(N2CCCC[C@H](OC(F)F)[C@H]2Cc2ccccc2)[nH]1] |
| 111 | 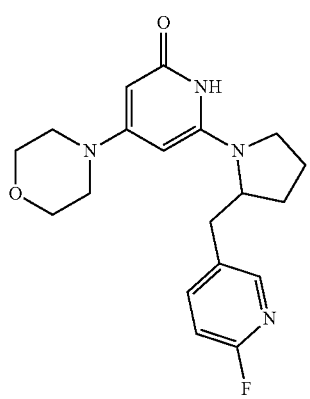 [SMILES: O=c1cc(N2CCOCC2)cc(N2CCCC2Cc2ccc(F)nc2)[nH]1] |
| 113 | 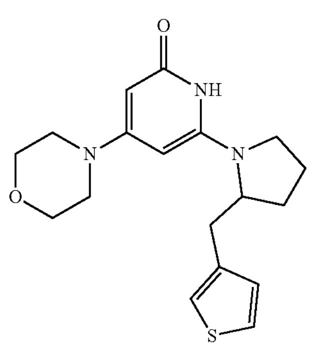 [SMILES: O=c1cc(N2CCOCC2)cc(N2CCCC2Cc2ccsc2)[nH]1] |

508
-continued

| Example | Structure |
|---------|-----------|
| 114 | 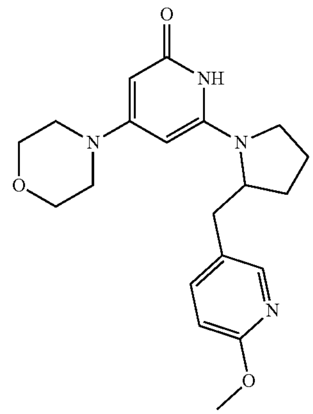 [SMILES: COc1ccc(CC2CCCN2c2cc(N3CCOCC3)cc(=O)[nH]2)cn1] |
| 115 | 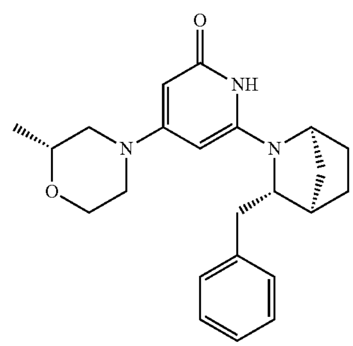 [SMILES: C[C@@H]1CN(c2cc(N3[C@H]4CC[C@H](C4)[C@@H]3Cc3ccccc3)[nH]c(=O)c2)CCO1] |
| 116 | 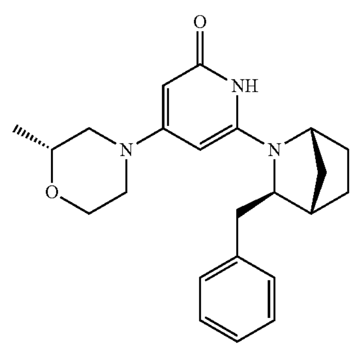 [SMILES: C[C@@H]1CN(c2cc(N3[C@@H]4CC[C@@H](C4)[C@H]3Cc3ccccc3)[nH]c(=O)c2)CCO1] |
| 117 | 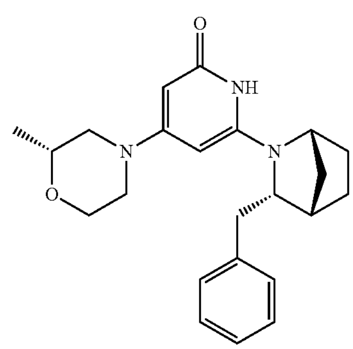 [SMILES: C[C@@H]1CN(c2cc(N3[C@@H]4CC[C@@H](C4)[C@@H]3Cc3ccccc3)[nH]c(=O)c2)CCO1] |

509
-continued
| Example | Structure |
|---|---|
| 118 | 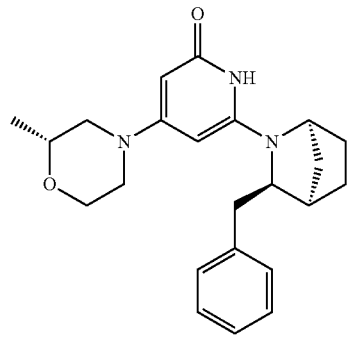 [SMILES: C[C@@H]1CN(c2cc(N3[C@H]4CC[C@H](C4)[C@H]3Cc3ccccc3)[nH]c(=O)c2)CCO1] |
| 119 | 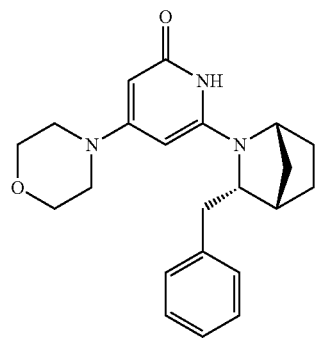 |
| 120 | 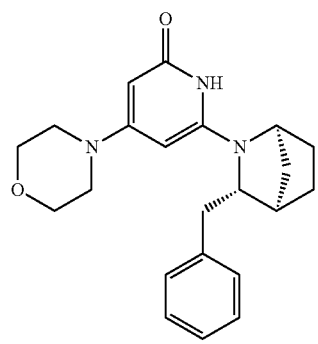 |
| 121 | 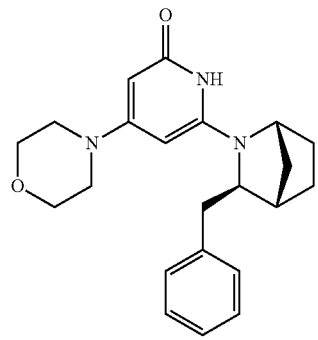 |
510
-continued
| Example | Structure |
|---|---|
| 122 | 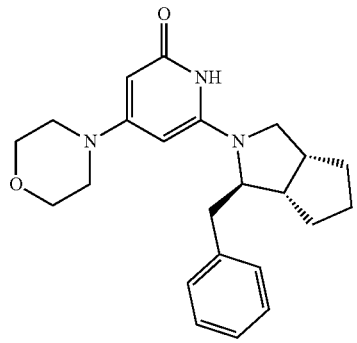 [SMILES: O=c1cc(N2CCOCC2)cc(N2C[C@@H]3CCC[C@@H]3[C@H]2Cc2ccccc2)[nH]1] |
| 123 | 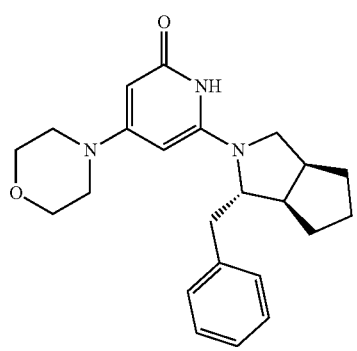 [SMILES: O=c1cc(N2CCOCC2)cc(N2C[C@H]3CCC[C@H]3[C@@H]2Cc2ccccc2)[nH]1] |
| 124 | 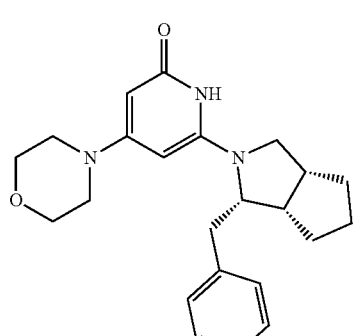 |
| 125 | 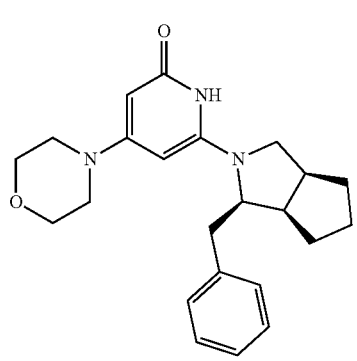 [SMILES: O=c1cc(N2CCOCC2)cc(N2C[C@H]3CCC[C@H]3[C@H]2Cc2ccccc2)[nH]1] |

| 511 -continued | | 512 -continued | |
|---|---|---|---|
| Example | Structure | Example | Structure |
| 126 | | 130 | |
| 127 | | 131 | |
| 128 | | 132 | |
| 129 | | 133 | |

513
-continued
| Example | Structure |
|---|---|
| 134 | 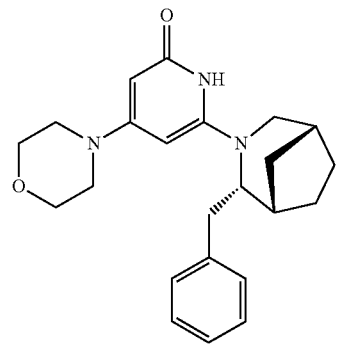 [SMILES: O=c1cc(N2CCOCC2)cc(N2C[C@@H]3CC[C@@H](C3)[C@@H]2Cc2ccccc2)[nH]1] |
| 135 | 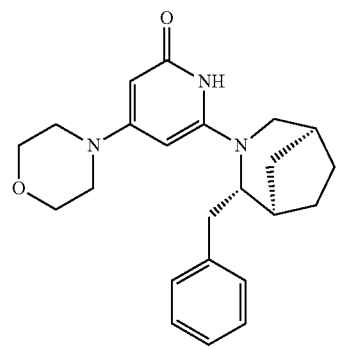 [SMILES: O=c1cc(N2CCOCC2)cc(N2C[C@H]3CC[C@H](C3)[C@@H]2Cc2ccccc2)[nH]1] |
| 136 | 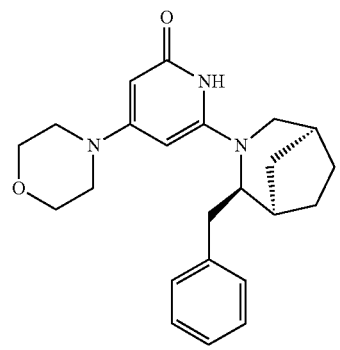 [SMILES: O=c1cc(N2CCOCC2)cc(N2C[C@H]3CC[C@H](C3)[C@H]2Cc2ccccc2)[nH]1] |
| 137 | 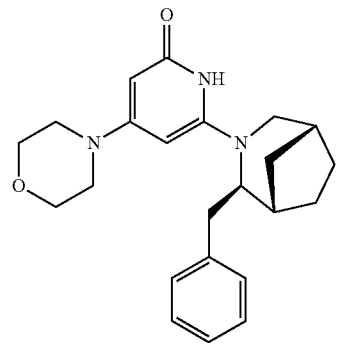 [SMILES: O=c1cc(N2CCOCC2)cc(N2C[C@@H]3CC[C@@H](C3)[C@H]2Cc2ccccc2)[nH]1] |
514
-continued
| Example | Structure |
|---|---|
| 138 | 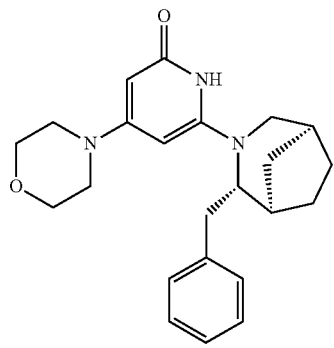 [SMILES: O=c1cc(N2CCOCC2)cc(N2C[C@H]3CC[C@H](C3)[C@@H]2Cc2ccccc2)[nH]1] |
| 139 | 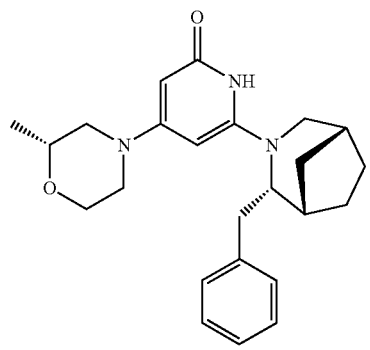 [SMILES: C[C@@H]1CN(c2cc(N3C[C@@H]4CC[C@@H](C4)[C@@H]3Cc3ccccc3)[nH]c(=O)c2)CCO1] |
| 140 | 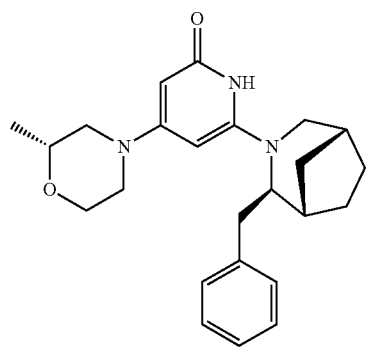 [SMILES: C[C@@H]1CN(c2cc(N3C[C@@H]4CC[C@@H](C4)[C@H]3Cc3ccccc3)[nH]c(=O)c2)CCO1] |
| 141 | 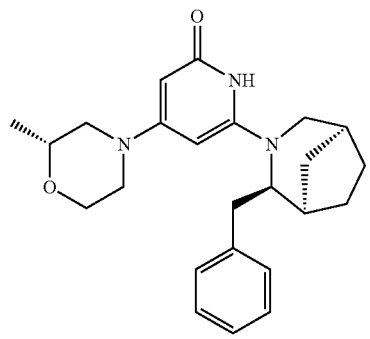 [SMILES: C[C@@H]1CN(c2cc(N3C[C@H]4CC[C@H](C4)[C@H]3Cc3ccccc3)[nH]c(=O)c2)CCO1] |

515
-continued
| Example | Structure |
|---|---|
| 142 | 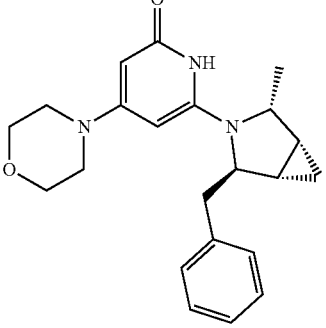 |
| 143 | 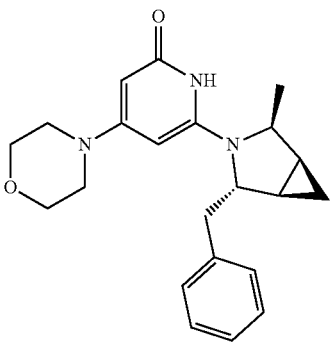 [SMILES: C[C@H]1[C@H]2C[C@H]2[C@H](Cc2ccccc2)N1c1cc(N2CCOCC2)cc(=O)[nH]1] |
| 144 | 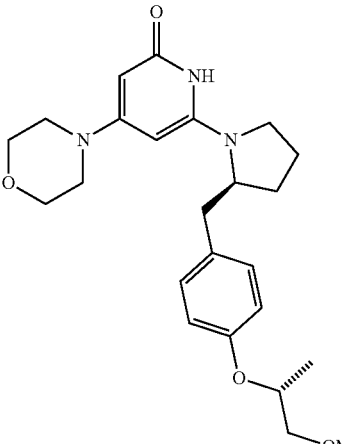 |
| 145 | 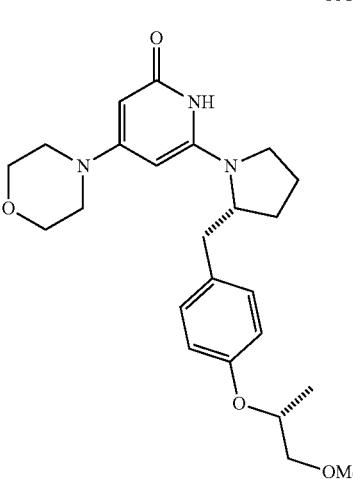 |
516
-continued
| Example | Structure |
|---|---|
| 146 | 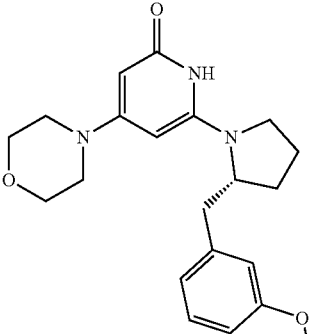 |
| 147 | 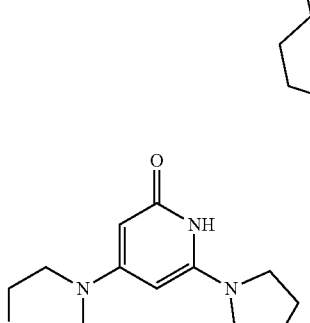 |
| 148 | 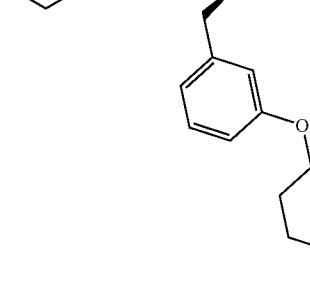 |

-continued
| Example | Structure |
|---|---|
| 149 | 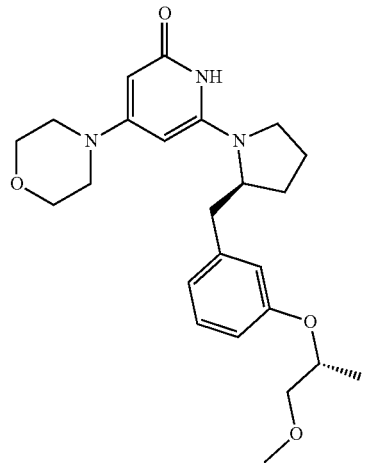 [SMILES: COC[C@@H](C)Oc1cccc(C[C@@H]2CCCN2c2cc(N3CCOCC3)cc(=O)[nH]2)c1] |
| 150 | 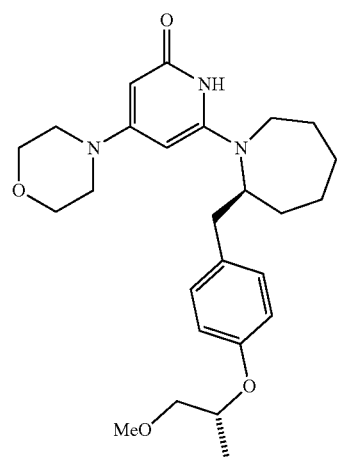 [SMILES: COC[C@@H](C)Oc1ccc(C[C@@H]2CCCCCN2c2cc(N3CCOCC3)cc(=O)[nH]2)cc1] |
| 151 | 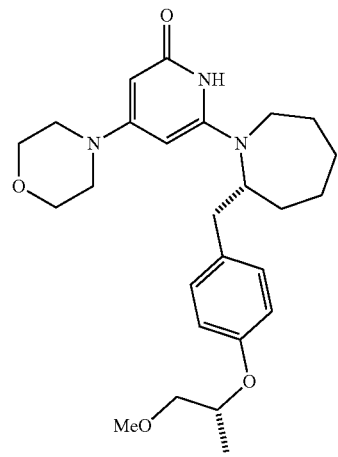 [SMILES: COC[C@@H](C)Oc1ccc(C[C@H]2CCCCCN2c2cc(N3CCOCC3)cc(=O)[nH]2)cc1] |
-continued
| Example | Structure |
|---|---|
| 152 | 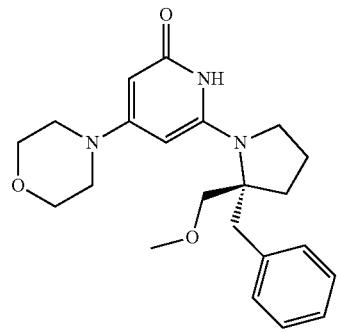 [SMILES: COC[C@]1(Cc2ccccc2)CCCN1c1cc(N2CCOCC2)cc(=O)[nH]1] |
| 153 | 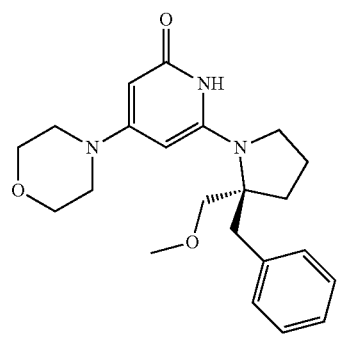 [SMILES: COC[C@@]1(Cc2ccccc2)CCCN1c1cc(N2CCOCC2)cc(=O)[nH]1] |
| 154 | 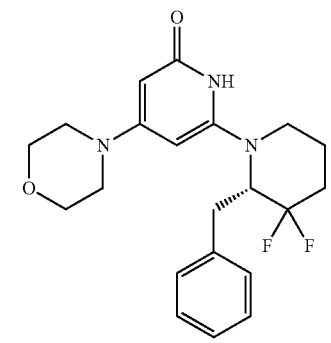 [SMILES: O=c1cc(N2CCOCC2)cc(N2CCCC(F)(F)[C@@H]2Cc2ccccc2)[nH]1] |
| 155 | 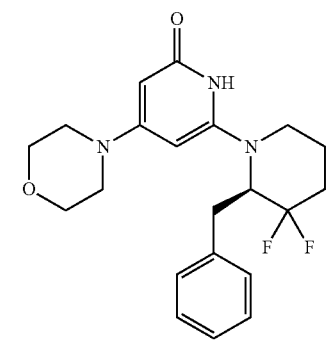 [SMILES: O=c1cc(N2CCOCC2)cc(N2CCCC(F)(F)[C@H]2Cc2ccccc2)[nH]1] |

| Example | Structure |
|---|---|
| 156 | (4-morpholino-6-[(2S)-2-(3,3-difluoro-2-(4-methoxybenzyl)piperidin-1-yl)]pyridin-2(1H)-one) |
| 157 | (4-morpholino-6-[(2R)-2-(3,3-difluoro-2-(4-methoxybenzyl)piperidin-1-yl)]pyridin-2(1H)-one) |
| 158 | (4-morpholino-6-[(2S,3R)-2-benzyl-3-methoxypiperidin-1-yl]pyridin-2(1H)-one) |
| 159 | (4-morpholino-6-[(2R,3S)-2-benzyl-3-methoxypiperidin-1-yl]pyridin-2(1H)-one) |

| Example | Structure |
|---|---|
| 160 | (4-morpholino-6-[2-benzyl-4,4-difluoropiperidin-1-yl]pyridin-2(1H)-one) |
| 161 | (4-morpholino-6-[(S)-3-benzyl-1-methyl-2-oxo-1,4-diazepan-4-yl]pyridin-2(1H)-one) |
| 162 | (4-morpholino-6-[(R)-3-benzyl-1-methyl-2-oxo-1,4-diazepan-4-yl]pyridin-2(1H)-one) |
| 163 | (4-morpholino-6-[5-benzyl-1-methyl-6-oxo-1,4-diazepan-4-yl]pyridin-2(1H)-one) |

-continued
| Example | Structure |
|---|---|
| 164 | 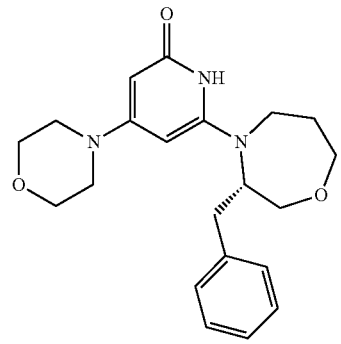 [SMILES: O=c1cc(N2CCOCC2)cc(N2CCCOC[C@@H]2Cc2ccccc2)[nH]1] |
| 165 | 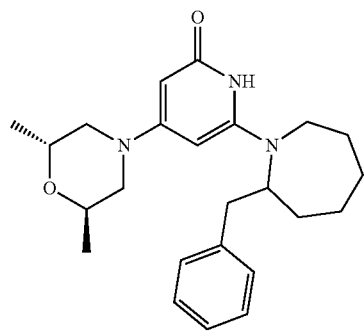 [SMILES: C[C@@H]1CN(c2cc(N3CCCCCC3Cc3ccccc3)[nH]c(=O)c2)C[C@@H](C)O1] |
| 166 | 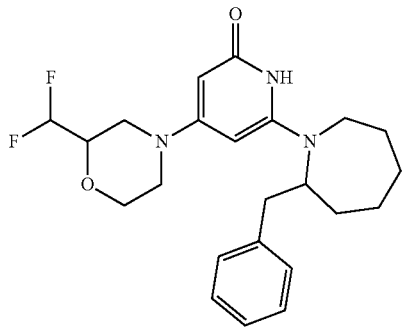 [SMILES: O=c1cc(N2CCOC(C(F)F)C2)cc(N2CCCCCC2Cc2ccccc2)[nH]1] |
| 167 | 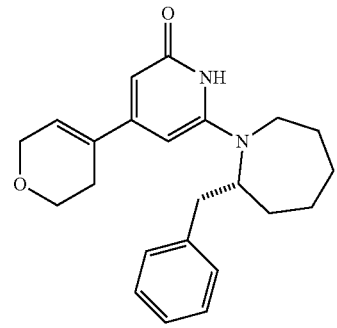 [SMILES: O=c1cc(C2=CCOCC2)cc(N2CCCCC[C@@H]2Cc2ccccc2)[nH]1] |
-continued
| Example | Structure |
|---|---|
| 168 | 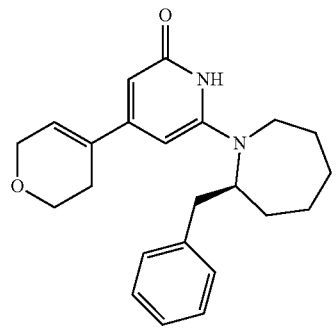 [SMILES: O=c1cc(C2=CCOCC2)cc(N2CCCCC[C@H]2Cc2ccccc2)[nH]1] |
| 171 | 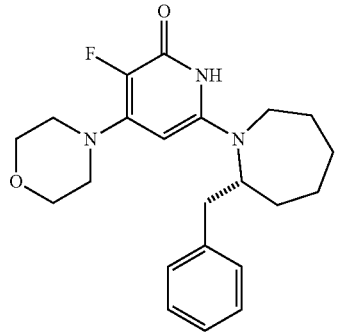 [SMILES: O=c1[nH]c(N2CCCCC[C@@H]2Cc2ccccc2)cc(N2CCOCC2)c1F] |
| 172 | 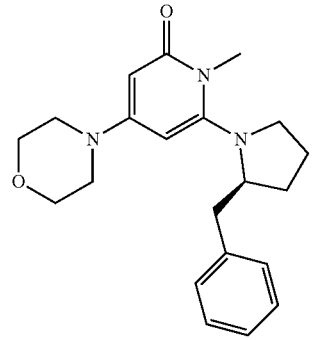 [SMILES: Cn1c(N2CCC[C@H]2Cc2ccccc2)cc(N2CCOCC2)cc1=O] |
| 173 | 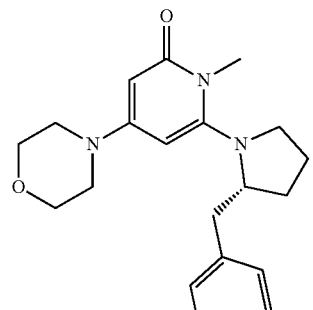 |

-continued

| Example | Structure |
|---------|-----------|
| 174 | 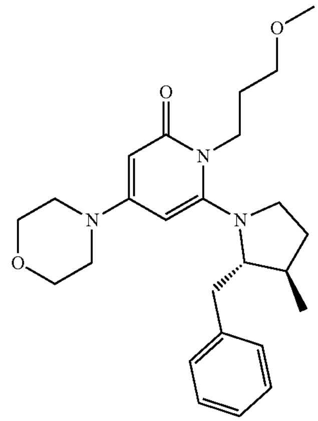 [SMILES: COCCCn1c(N2CC[C@@H](C)[C@@H]2Cc2ccccc2)cc(N2CCOCC2)cc1=O] |
| 175 | 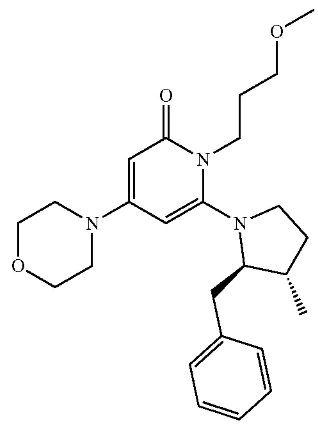 [SMILES: COCCCn1c(N2CC[C@H](C)[C@H]2Cc2ccccc2)cc(N2CCOCC2)cc1=O] |
| 176 | 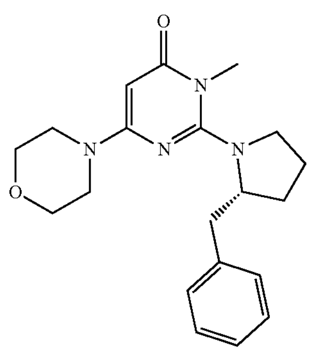 [SMILES: Cn1c(N2CCC[C@@H]2Cc2ccccc2)nc(N2CCOCC2)cc1=O] |
| 177 | 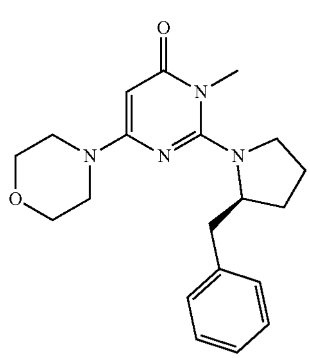 [SMILES: Cn1c(N2CCC[C@H]2Cc2ccccc2)nc(N2CCOCC2)cc1=O] |
| 178 | |
| 179 | |
| 180 | |
| 181 | |

525
-continued

| Example | Structure |
|---------|-----------|
| 182 | 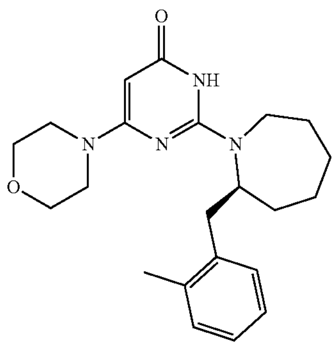 [SMILES: Cc1ccccc1C[C@@H]1CCCCCN1c1nc(N2CCOCC2)cc(=O)[nH]1] |
| 183 | 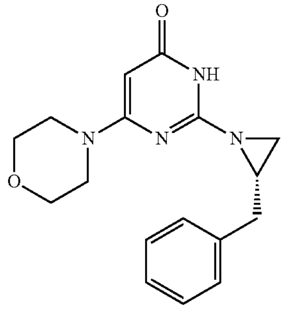 [SMILES: O=c1cc(N2CCOCC2)nc(N2C[C@@H]2Cc2ccccc2)[nH]1] |
| 184 | 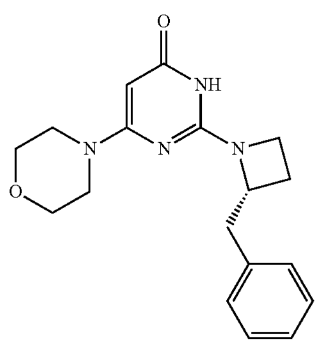 [SMILES: O=c1cc(N2CCOCC2)nc(N2CC[C@@H]2Cc2ccccc2)[nH]1] |
| 185 | 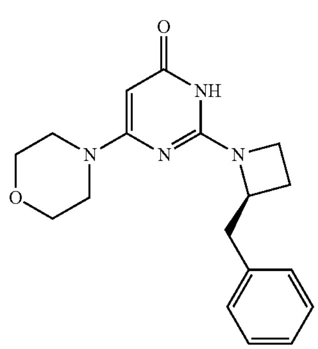 [SMILES: O=c1cc(N2CCOCC2)nc(N2CC[C@H]2Cc2ccccc2)[nH]1] |

526
-continued

| Example | Structure |
|---------|-----------|
| 186 | 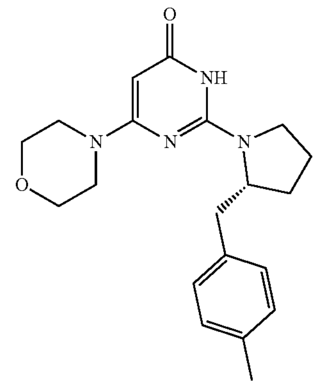 |
| 187 | 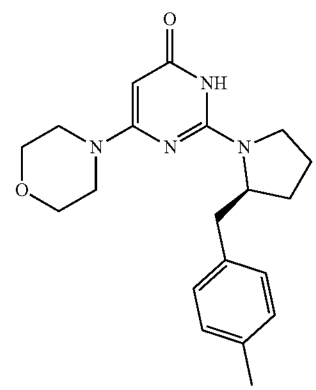 |
| 188 | 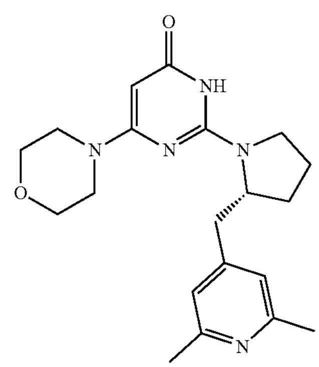 |
| 189 | 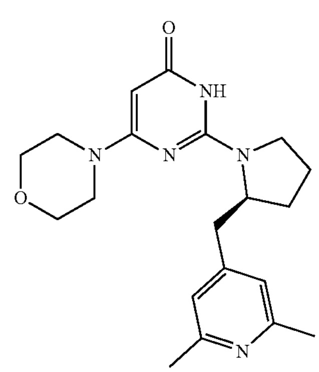 |

-continued
| Example | Structure |
|---|---|
| 190 | 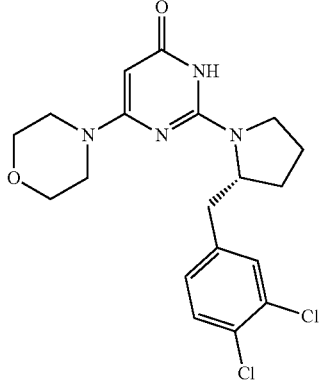 [SMILES: O=c1cc(N2CCOCC2)nc(N2CCC[C@@H]2Cc2ccc(Cl)c(Cl)c2)[nH]1] |
| 191 | 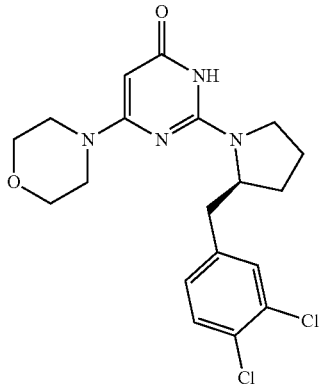 [SMILES: O=c1cc(N2CCOCC2)nc(N2CCC[C@H]2Cc2ccc(Cl)c(Cl)c2)[nH]1] |
| 192 | 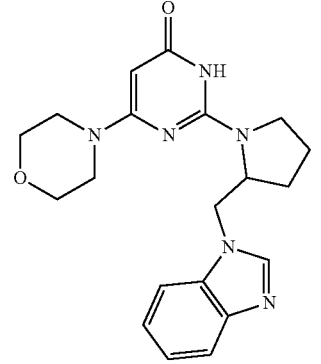 [SMILES: O=c1cc(N2CCOCC2)nc(N2CCCC2Cn2cnc3ccccc32)[nH]1] |
| 193 | 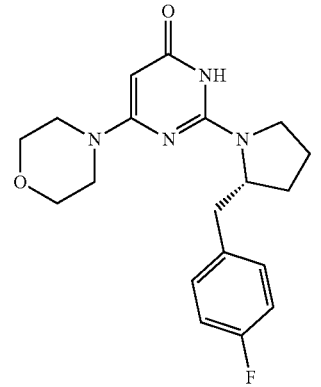 |
-continued
| Example | Structure |
|---|---|
| 194 | 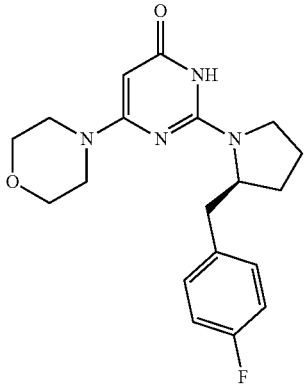 |
| 195 | 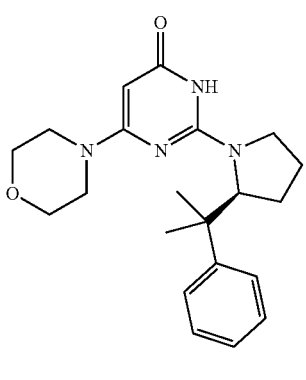 |
| 196 | 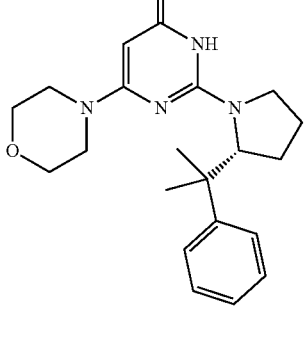 |
| 197 | 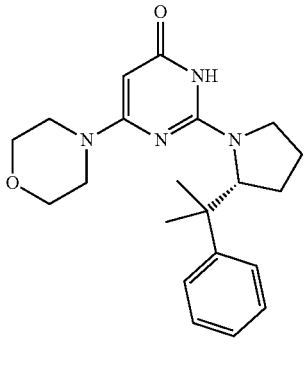 |

| Example | Structure |
|---|---|
| 198 | 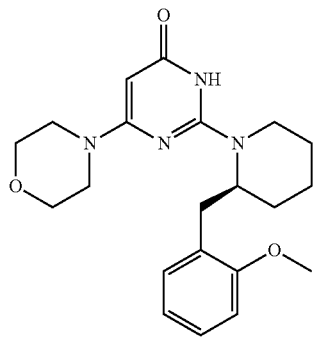 [SMILES: COc1ccccc1C[C@@H]1CCCCN1c1nc(N2CCOCC2)cc(=O)[nH]1] |
| 199 | 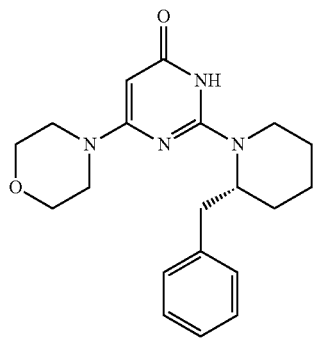 |
| 200 | 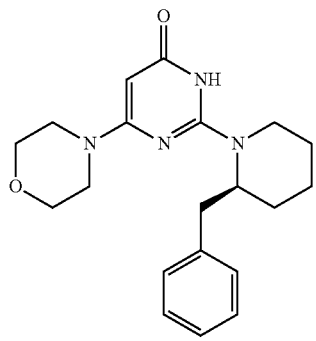 [SMILES: O=c1cc(N2CCOCC2)nc(N2CCCC[C@H]2Cc2ccccc2)[nH]1] |
| 201 | 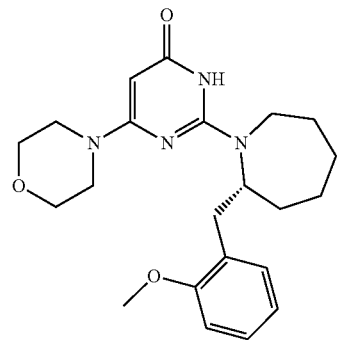 [SMILES: COc1ccccc1C[C@H]1CCCCCN1c1nc(N2CCOCC2)cc(=O)[nH]1] |
| Example | Structure |
|---|---|
| 202 | 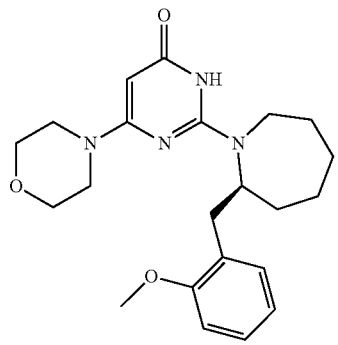 [SMILES: COc1ccccc1C[C@@H]1CCCCCN1c1nc(N2CCOCC2)cc(=O)[nH]1] |
| 203 | 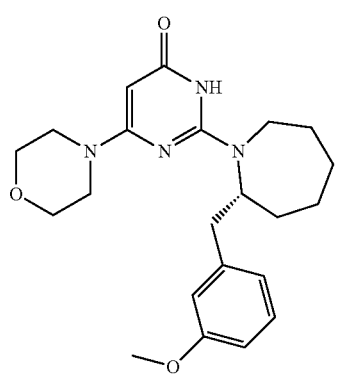 [SMILES: COc1cccc(C[C@H]2CCCCCN2c2nc(N3CCOCC3)cc(=O)[nH]2)c1] |
| 204 | 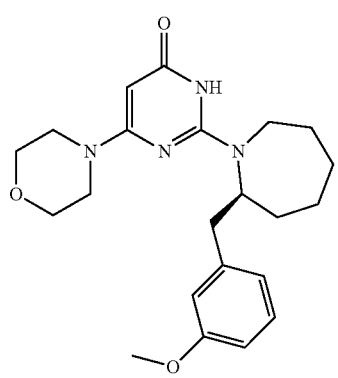 [SMILES: COc1cccc(C[C@@H]2CCCCCN2c2nc(N3CCOCC3)cc(=O)[nH]2)c1] |
| 205 | 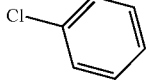 |

| Example | Structure |
|---|---|
| 206 | 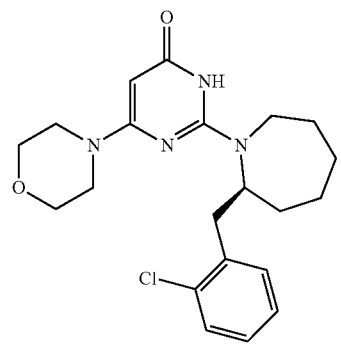 [SMILES: O=c1cc(N2CCOCC2)nc(N2CCCCC[C@H]2Cc2ccccc2Cl)[nH]1] |
| 207 | 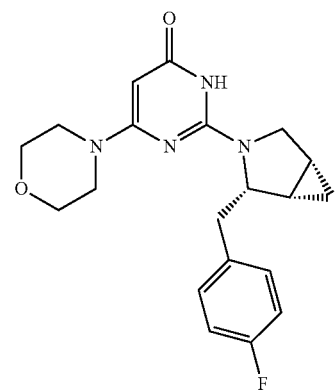 [SMILES: O=c1cc(N2CCOCC2)nc(N2C[C@@H]3C[C@@H]3[C@@H]2Cc2ccc(F)cc2)[nH]1] |
| 208 | 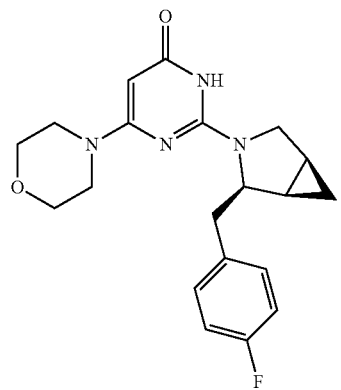 [SMILES: O=c1cc(N2CCOCC2)nc(N2C[C@H]3C[C@H]3[C@H]2Cc2ccc(F)cc2)[nH]1] |
| 209 | 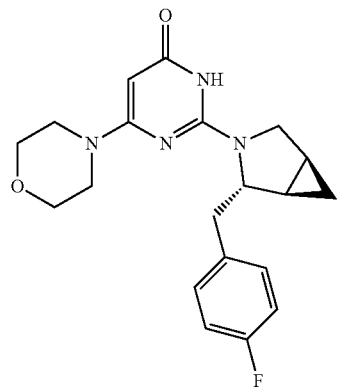 [SMILES: O=c1cc(N2CCOCC2)nc(N2C[C@H]3C[C@H]3[C@@H]2Cc2ccc(F)cc2)[nH]1] |
| Example | Structure |
|---|---|
| 210 | 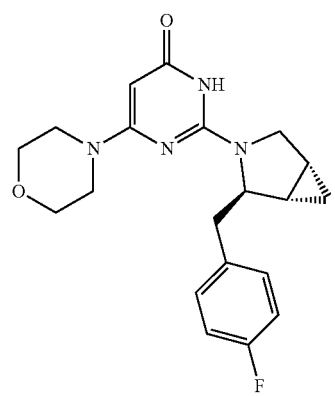 [SMILES: O=c1cc(N2CCOCC2)nc(N2C[C@@H]3C[C@@H]3[C@H]2Cc2ccc(F)cc2)[nH]1] |
| 211 | 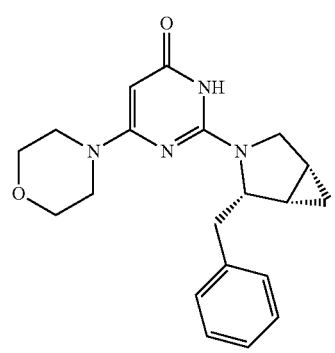 |
| 212 | 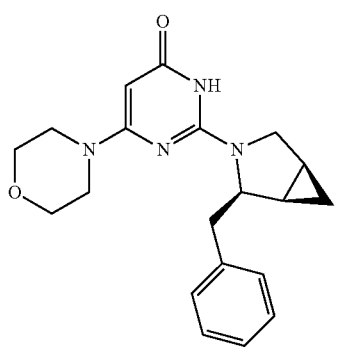 |
| 213 | 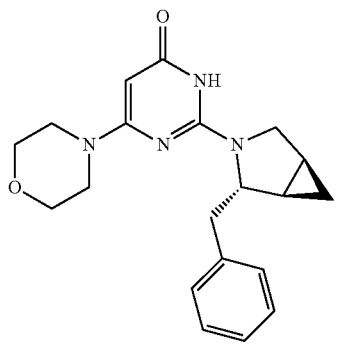 |

-continued
| Example | Structure |
|---------|-----------|
| 214 | 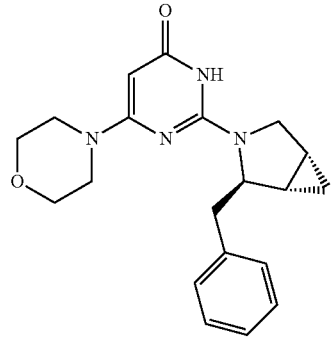 [SMILES: O=c1cc(N2CCOCC2)nc(N2C[C@@H]3C[C@@H]3[C@H]2Cc2ccccc2)[nH]1] |
| 215 | 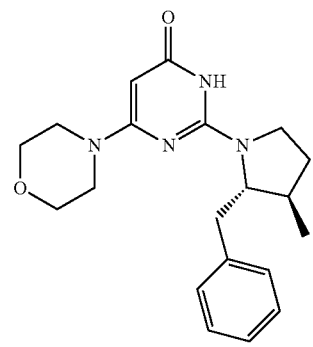 [SMILES: C[C@@H]1CCN(c2nc(N3CCOCC3)cc(=O)[nH]2)[C@H]1Cc1ccccc1] |
| 216 | 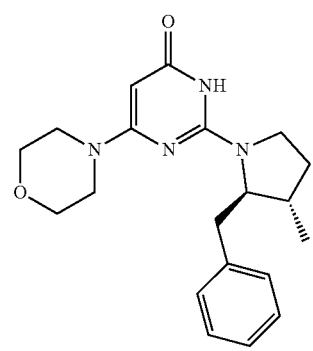 [SMILES: C[C@H]1CCN(c2nc(N3CCOCC3)cc(=O)[nH]2)[C@@H]1Cc1ccccc1] |
| 217 | 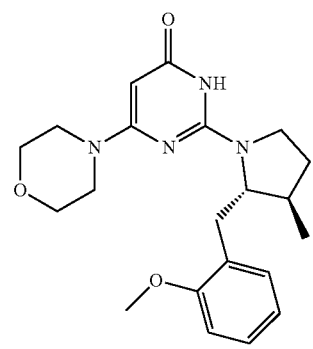 [SMILES: COc1ccccc1C[C@H]1[C@H](C)CCN1c1nc(N2CCOCC2)cc(=O)[nH]1] |
-continued
| Example | Structure |
|---------|-----------|
| 218 | 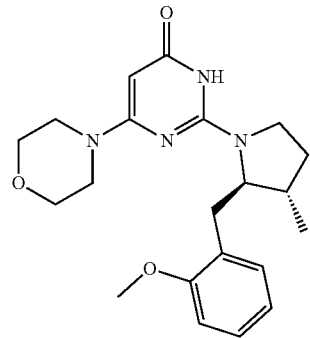 |
| 219 | 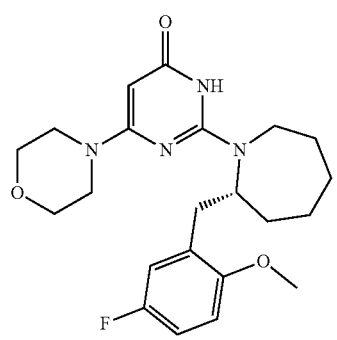 |
| 220 | 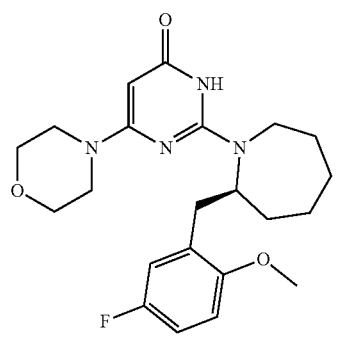 |
| 221 | 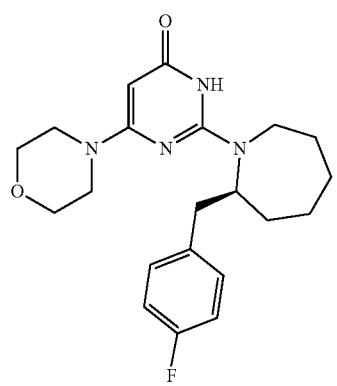 |

535
-continued
| Example | Structure |
|---|---|
| 222 | 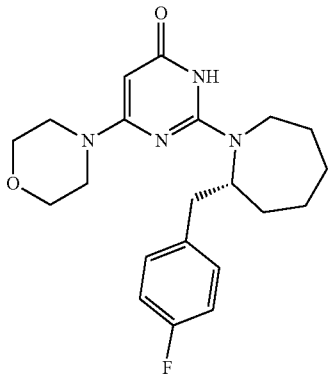 [SMILES: O=c1cc(N2CCOCC2)nc(N2CCCCC[C@@H]2Cc2ccc(F)cc2)[nH]1] |
| 223 | 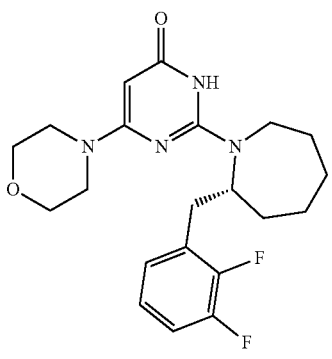 |
| 224 | 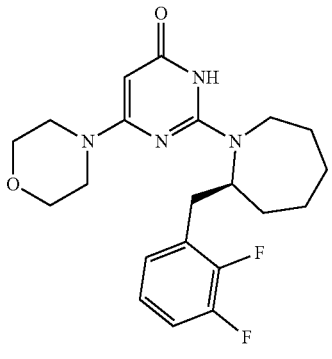 [SMILES: O=c1cc(N2CCOCC2)nc(N2CCCCC[C@H]2Cc2cccc(F)c2F)[nH]1] |
| 227 | 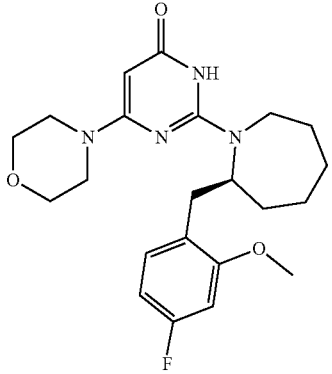 [SMILES: COc1cc(F)ccc1C[C@@H]1CCCCCN1c1nc(N2CCOCC2)cc(=O)[nH]1] |
536
-continued
| Example | Structure |
|---|---|
| 228 | 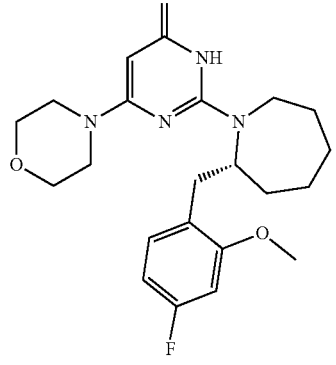 |
| 229 | 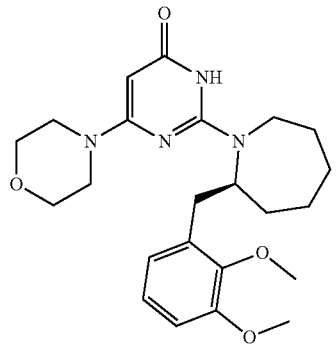 [SMILES: COc1cccc(C[C@@H]2CCCCCN2c2nc(N3CCOCC3)cc(=O)[nH]2)c1OC] |
| 230 | 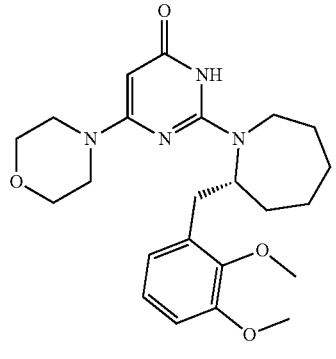 [SMILES: COc1cccc(C[C@H]2CCCCCN2c2nc(N3CCOCC3)cc(=O)[nH]2)c1OC] |
| 231 | 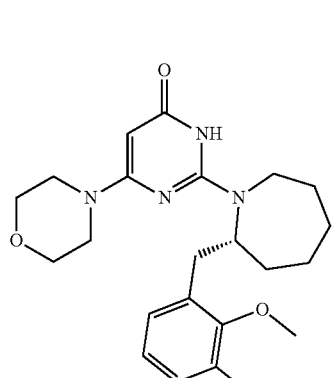 |

US 11,685,734 B2
537
-continued
| Example | Structure |
|---|---|
| 232 | 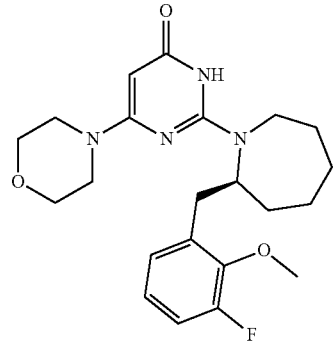 |
| 233 | 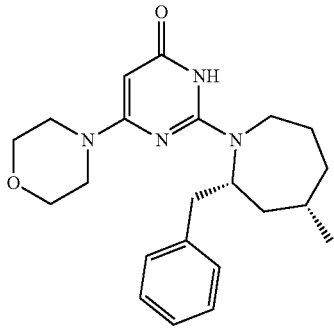 [SMILES: C[C@H]1CCCN(c2nc(N3CCOCC3)cc(=O)[nH]2)[C@@H](Cc2ccccc2)C1] |
| 234 | 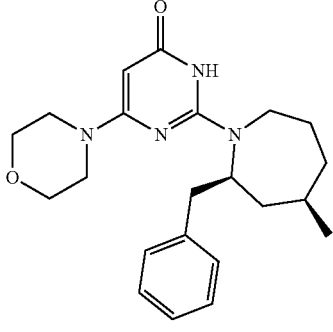 [SMILES: C[C@@H]1CCCN(c2nc(N3CCOCC3)cc(=O)[nH]2)[C@H](Cc2ccccc2)C1] |
| 235 | 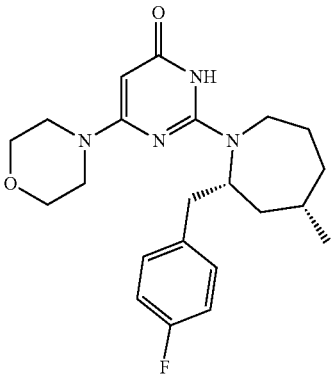 [SMILES: C[C@H]1CCCN(c2nc(N3CCOCC3)cc(=O)[nH]2)[C@@H](Cc2ccc(F)cc2)C1] |
538
-continued
| Example | Structure |
|---|---|
| 236 | 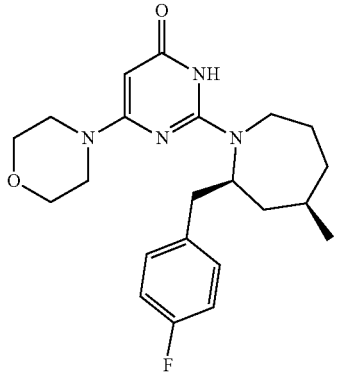 [SMILES: C[C@@H]1CCCN(c2nc(N3CCOCC3)cc(=O)[nH]2)[C@H](Cc2ccc(F)cc2)C1] |
| 237 | 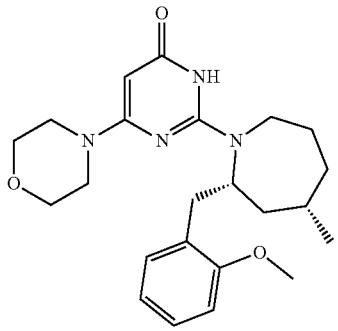 [SMILES: COc1ccccc1C[C@H]1C[C@@H](C)CCCN1c1nc(N2CCOCC2)cc(=O)[nH]1] |
| 238 | 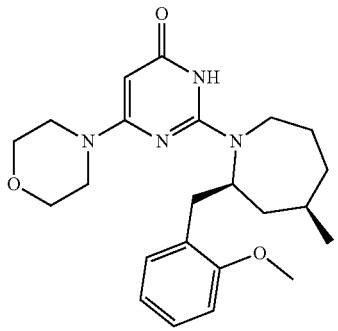 [SMILES: COc1ccccc1C[C@@H]1C[C@H](C)CCCN1c1nc(N2CCOCC2)cc(=O)[nH]1] |
| 239 | 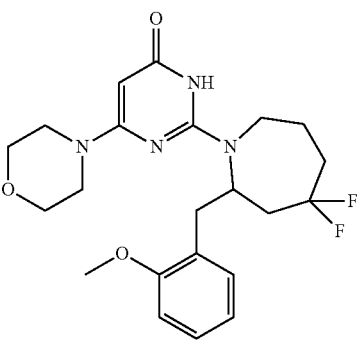 [SMILES: COc1ccccc1CC1CC(F)(F)CCCN1c1nc(N2CCOCC2)cc(=O)[nH]1] |

TABLE 539-continued
| Example | Structure |
|---|---|
| 240 | 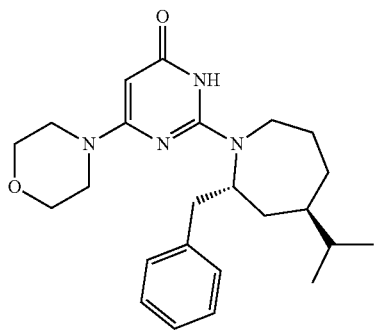 [SMILES: CC(C)[C@@H]1CCCN(c2nc(N3CCOCC3)cc(=O)[nH]2)[C@@H](Cc2ccccc2)C1] |
| 241 | 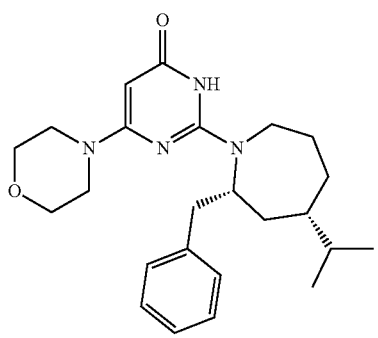 [SMILES: CC(C)[C@H]1CCCN(c2nc(N3CCOCC3)cc(=O)[nH]2)[C@@H](Cc2ccccc2)C1] |
| 242 | 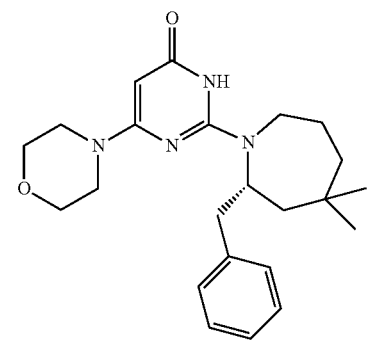 [SMILES: CC1(C)CCCN(c2nc(N3CCOCC3)cc(=O)[nH]2)[C@@H](Cc2ccccc2)C1] |
| 243 | 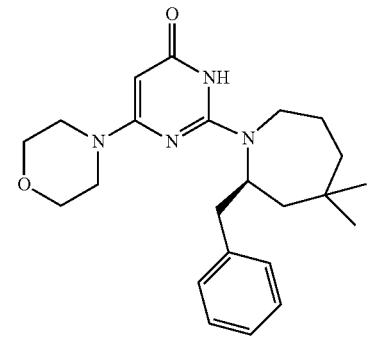 [SMILES: CC1(C)CCCN(c2nc(N3CCOCC3)cc(=O)[nH]2)[C@H](Cc2ccccc2)C1] |
TABLE 540-continued
| Example | Structure |
|---|---|
| 244 | 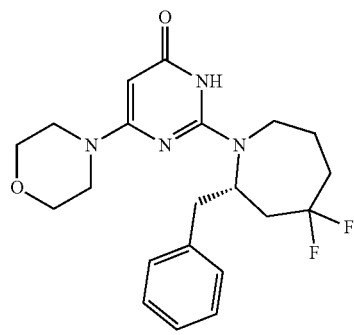 [SMILES: O=c1cc(N2CCOCC2)nc(N2CCCC(F)(F)C[C@@H]2Cc2ccccc2)[nH]1] |
| 245 | 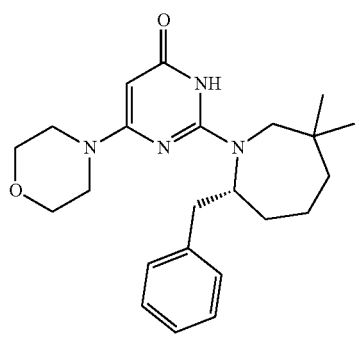 [SMILES: CC1(C)CCC[C@H](Cc2ccccc2)N(c2nc(N3CCOCC3)cc(=O)[nH]2)C1] |
| 246 | 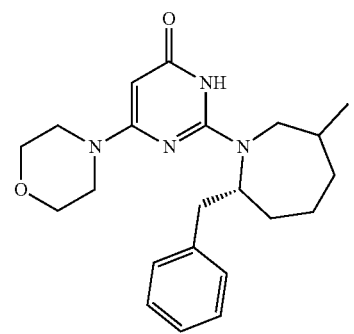 [SMILES: CC1CCC[C@H](Cc2ccccc2)N(c2nc(N3CCOCC3)cc(=O)[nH]2)C1] |
| 247 | 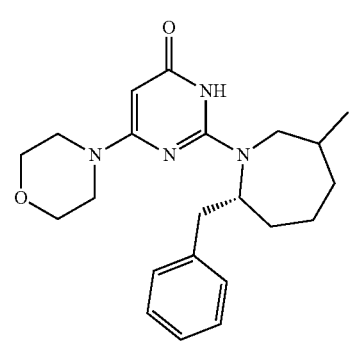 [SMILES: CC1CCC[C@H](Cc2ccccc2)N(c2nc(N3CCOCC3)cc(=O)[nH]2)C1] |

| Example | Structure |
|---------|-----------|
| 248 | 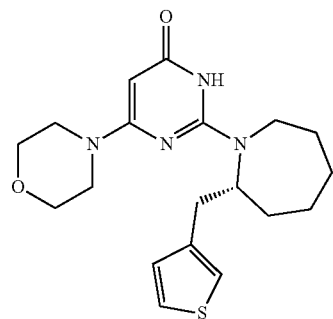 [SMILES: O=c1cc(N2CCOCC2)nc(N2CCCCC[C@@H]2Cc2ccsc2)[nH]1] |
| 249 | 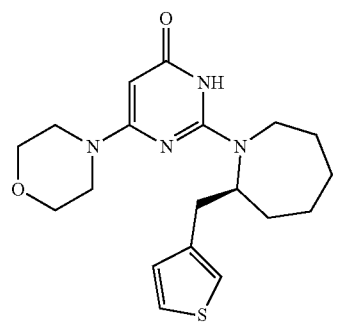 [SMILES: O=c1cc(N2CCOCC2)nc(N2CCCCC[C@H]2Cc2ccsc2)[nH]1] |
| 250 | 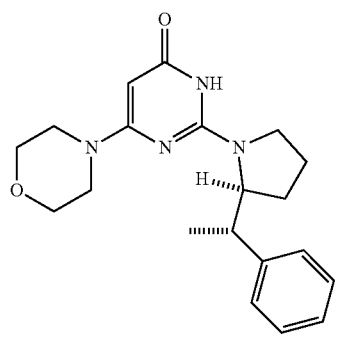 [SMILES: C[C@@H](c1ccccc1)[C@@H]1CCCN1c1nc(N2CCOCC2)cc(=O)[nH]1] |
| 251 | 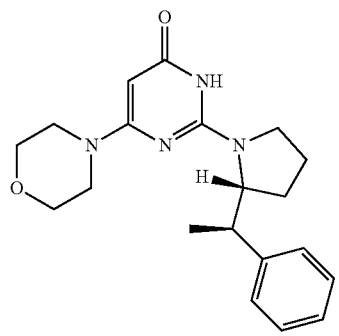 [SMILES: C[C@H](c1ccccc1)[C@H]1CCCN1c1nc(N2CCOCC2)cc(=O)[nH]1] |
| Example | Structure |
|---------|-----------|
| 252 | 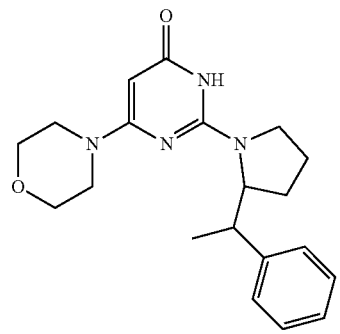 [SMILES: CC(c1ccccc1)C1CCCN1c1nc(N2CCOCC2)cc(=O)[nH]1] |
| 253 | 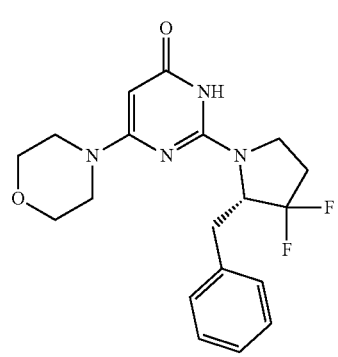 [SMILES: O=c1cc(N2CCOCC2)nc(N2CCC(F)(F)[C@@H]2Cc2ccccc2)[nH]1] |
| 254 | 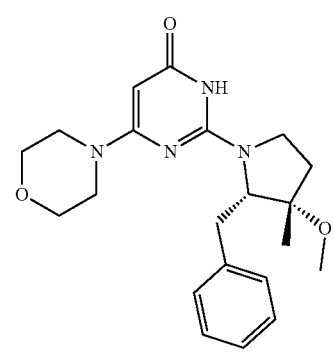 [SMILES: CO[C@@]1(C)CCN(c2nc(N3CCOCC3)cc(=O)[nH]2)[C@H]1Cc1ccccc1] |
| 255 | 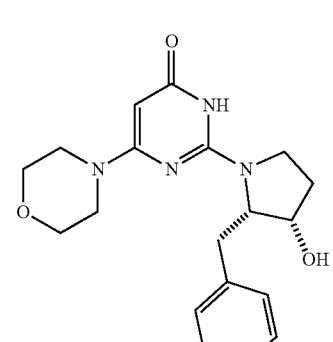 |

TABLE -continued

| Example | Structure |
|---------|-----------|
| 256 | 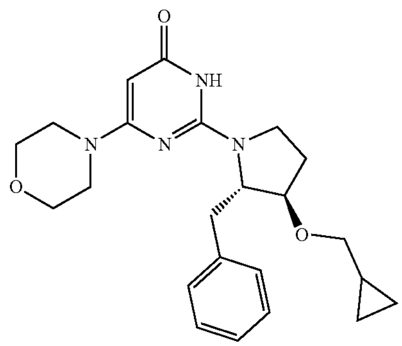 [SMILES: O=c1cc(N2CCOCC2)nc(N2CC[C@@H](OCC3CC3)[C@@H]2Cc2ccccc2)[nH]1] |
| 257 | 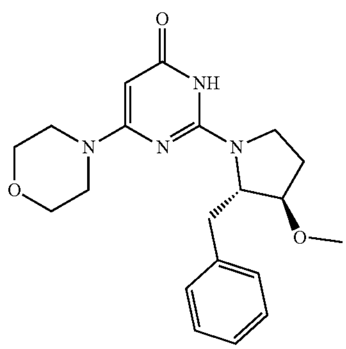 [SMILES: CO[C@@H]1CCN(c2nc(N3CCOCC3)cc(=O)[nH]2)[C@H]1Cc1ccccc1] |
| 258 | 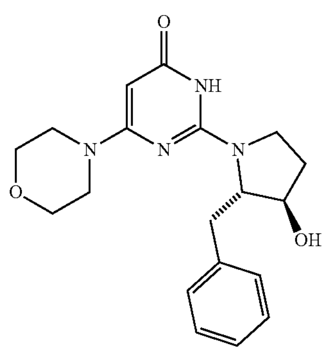 [SMILES: O=c1cc(N2CCOCC2)nc(N2CC[C@@H](O)[C@@H]2Cc2ccccc2)[nH]1] |
| 259 | 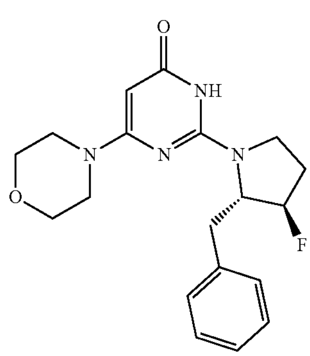 [SMILES: O=c1cc(N2CCOCC2)nc(N2CC[C@@H](F)[C@@H]2Cc2ccccc2)[nH]1] |
| 260 | 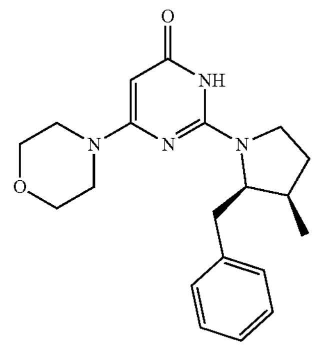 [SMILES: C[C@@H]1CCN(c2nc(N3CCOCC3)cc(=O)[nH]2)[C@@H]1Cc1ccccc1] |
| 261 | 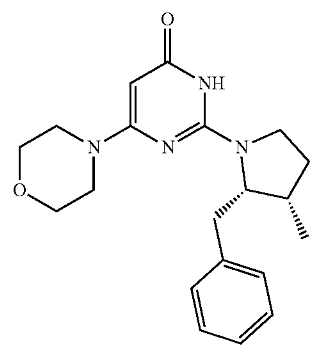 [SMILES: C[C@H]1CCN(c2nc(N3CCOCC3)cc(=O)[nH]2)[C@H]1Cc1ccccc1] |
| 262 | 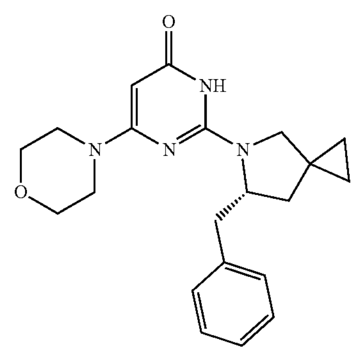 [SMILES: O=c1cc(N2CCOCC2)nc(N2CC3(CC3)C[C@@H]2Cc2ccccc2)[nH]1] |
| 263 | 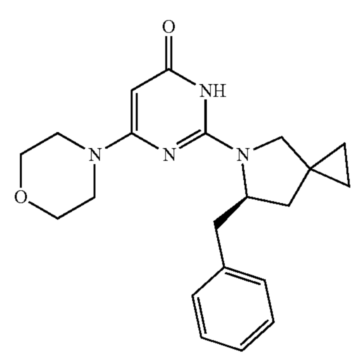 [SMILES: O=c1cc(N2CCOCC2)nc(N2CC3(CC3)C[C@H]2Cc2ccccc2)[nH]1] |

545
-continued
| Example | Structure |
|---|---|
| 264 | 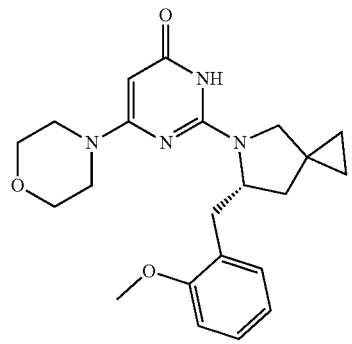 [SMILES: COc1ccccc1C[C@H]1CC2(CC2)CN1c1nc(N2CCOCC2)cc(=O)[nH]1] |
| 265 | 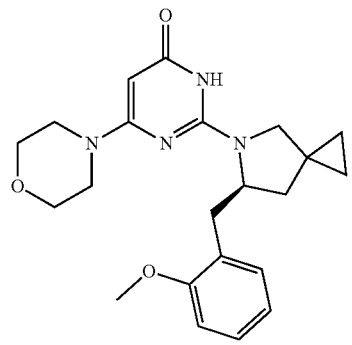 [SMILES: COc1ccccc1C[C@@H]1CC2(CC2)CN1c1nc(N2CCOCC2)cc(=O)[nH]1] |
| 266 | 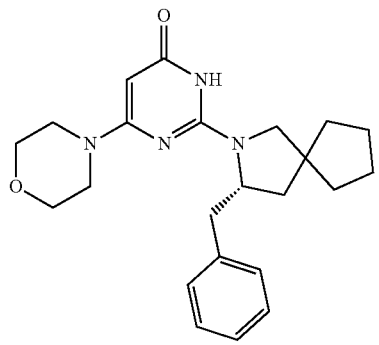 [SMILES: O=c1cc(N2CCOCC2)nc(N2CC3(CCCC3)C[C@@H]2Cc2ccccc2)[nH]1] |
| 267 | 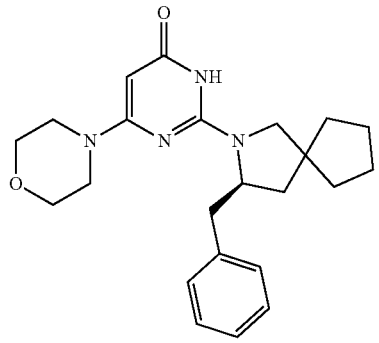 [SMILES: O=c1cc(N2CCOCC2)nc(N2CC3(CCCC3)C[C@H]2Cc2ccccc2)[nH]1] |
546
-continued
| Example | Structure |
|---|---|
| 268 | 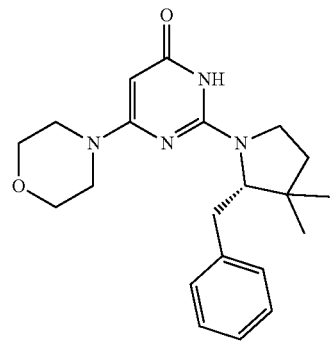 [SMILES: CC1(C)CCN(c2nc(N3CCOCC3)cc(=O)[nH]2)[C@H]1Cc1ccccc1] |
| 269 | 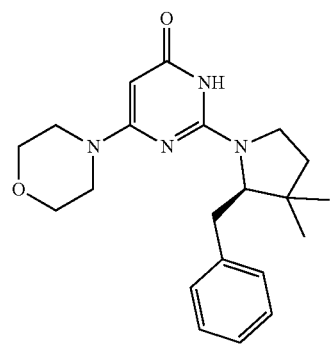 [SMILES: CC1(C)CCN(c2nc(N3CCOCC3)cc(=O)[nH]2)[C@@H]1Cc1ccccc1] |
| 270 | 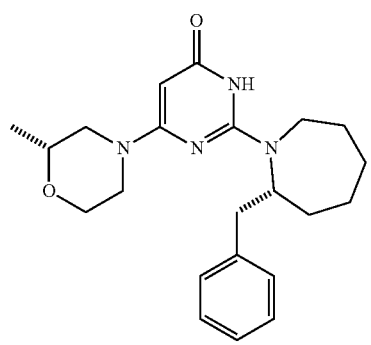 |
| 271 | 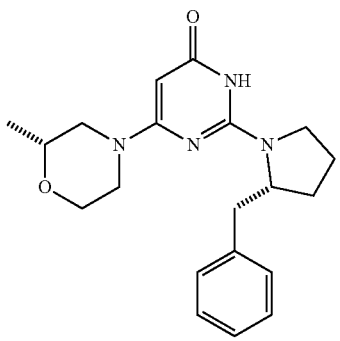 [SMILES: C[C@@H]1CN(c2cc(=O)[nH]c(N3CCC[C@@H]3Cc3ccccc3)n2)CCO1] |

547
-continued

| Example | Structure |
|---|---|
| 272 | (structure) |
| 273 | (structure) |
| 274 | (structure) |
| 275 | (structure) |

548
-continued

| Example | Structure |
|---|---|
| 276 | (structure) |
| 277 | (structure) |
| 278 | (structure) |
| 279 | (structure) |

| Example | Structure |
|---|---|
| 280 | 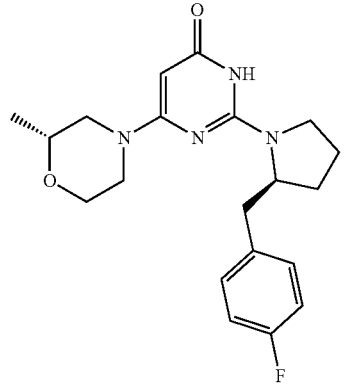 [SMILES: C[C@@H]1CN(c2cc(=O)[nH]c(N3CCC[C@H]3Cc3ccc(F)cc3)n2)CCO1] |
| 281 | 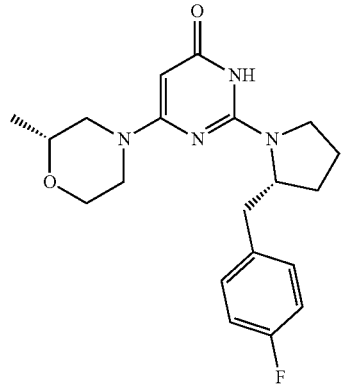 [SMILES: C[C@@H]1CN(c2cc(=O)[nH]c(N3CCC[C@@H]3Cc3ccc(F)cc3)n2)CCO1] |
| 282 | 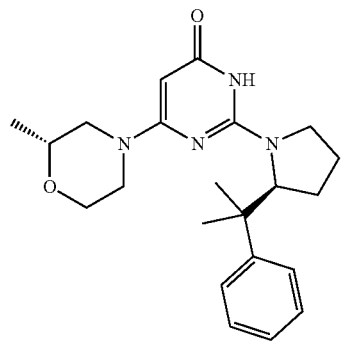 [SMILES: C[C@@H]1CN(c2cc(=O)[nH]c(N3CCC[C@H]3C(C)(C)c3ccccc3)n2)CCO1] |
| 283 | 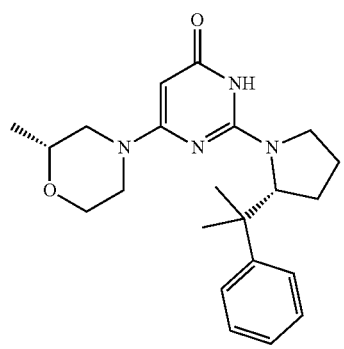 [SMILES: C[C@@H]1CN(c2cc(=O)[nH]c(N3CCC[C@@H]3C(C)(C)c3ccccc3)n2)CCO1] |
| Example | Structure |
|---|---|
| 284 | 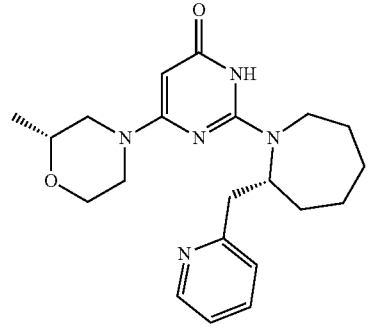 [SMILES: C[C@@H]1CN(c2cc(=O)[nH]c(N3CCCCC[C@@H]3Cc3ccccn3)n2)CCO1] |
| 285 | 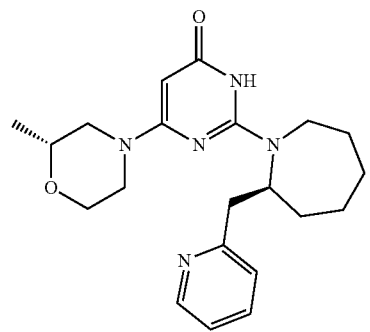 [SMILES: C[C@@H]1CN(c2cc(=O)[nH]c(N3CCCCC[C@H]3Cc3ccccn3)n2)CCO1] |
| 286 | 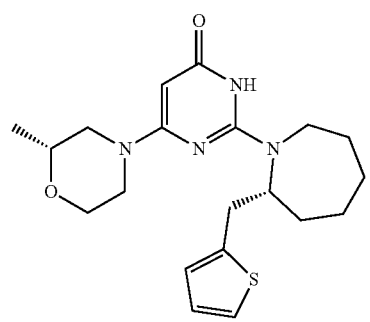 [SMILES: C[C@@H]1CN(c2cc(=O)[nH]c(N3CCCCC[C@@H]3Cc3cccs3)n2)CCO1] |
| 287 | 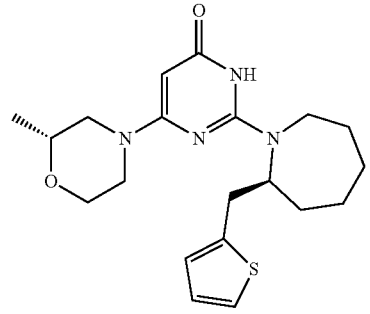 [SMILES: C[C@@H]1CN(c2cc(=O)[nH]c(N3CCCCC[C@H]3Cc3cccs3)n2)CCO1] |

551
-continued

| Example | Structure |
|---|---|
| 288 | (structure) |
| 289 | (structure) |
| 290 | (structure) |
| 291 | (structure) |

552
-continued

| Example | Structure |
|---|---|
| 292 | (structure) |
| 293 | (structure) |
| 294 | (structure) |
| 295 | (structure) |

-continued

| Example | Structure |
|---------|-----------|
| 296 | 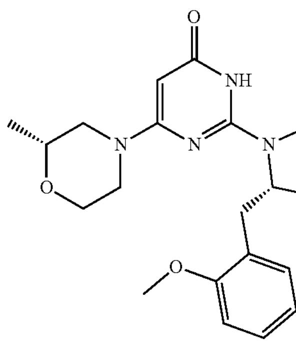 |
| 297 | 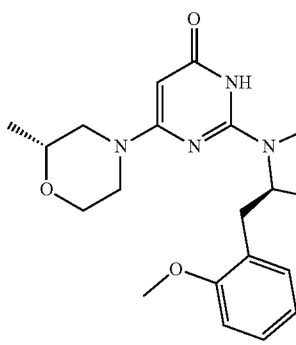 |
| 298 | 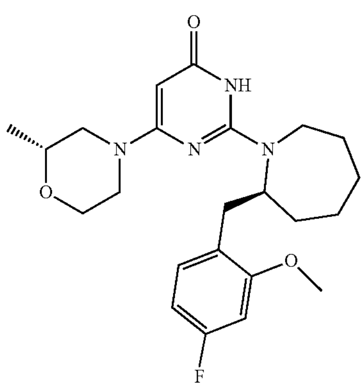 [SMILES: COc1cc(F)ccc1C[C@@H]1CCCCCN1c1nc(N2CCO[C@H](C)C2)cc(=O)[nH]1] |
| 299 | 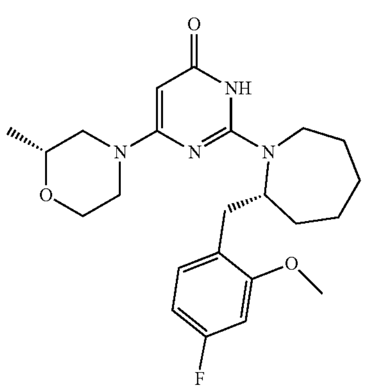 [SMILES: COc1cc(F)ccc1C[C@H]1CCCCCN1c1nc(N2CCO[C@H](C)C2)cc(=O)[nH]1] |

-continued

| Example | Structure |
|---------|-----------|
| 300 | 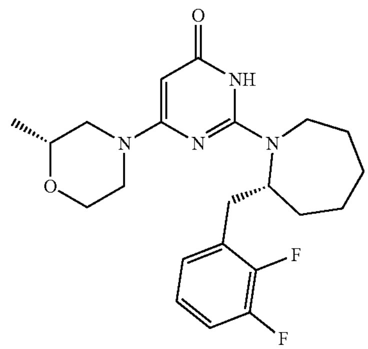 [SMILES: C[C@@H]1CN(c2cc(=O)[nH]c(N3CCCCC[C@@H]3Cc3cccc(F)c3F)n2)CCO1] |
| 301 | 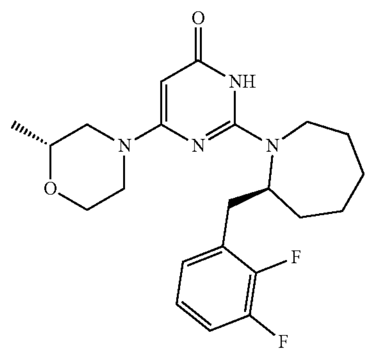 [SMILES: C[C@@H]1CN(c2cc(=O)[nH]c(N3CCCCC[C@H]3Cc3cccc(F)c3F)n2)CCO1] |
| 302 | 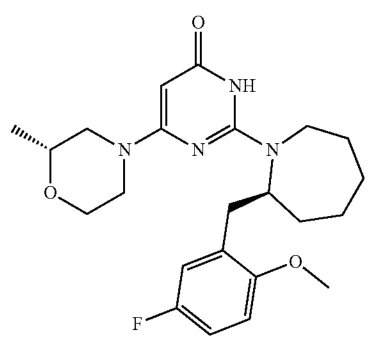 [SMILES: COc1ccc(F)cc1C[C@@H]1CCCCCN1c1nc(N2CCO[C@H](C)C2)cc(=O)[nH]1] |
| 303 | 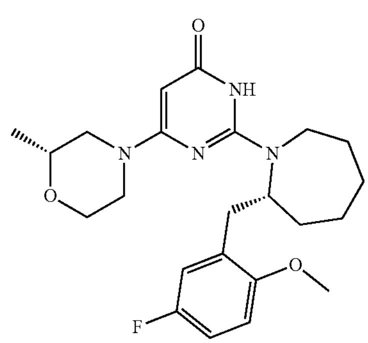 [SMILES: COc1ccc(F)cc1C[C@H]1CCCCCN1c1nc(N2CCO[C@H](C)C2)cc(=O)[nH]1] |

| Example | Structure |
|---|---|
| 304 | 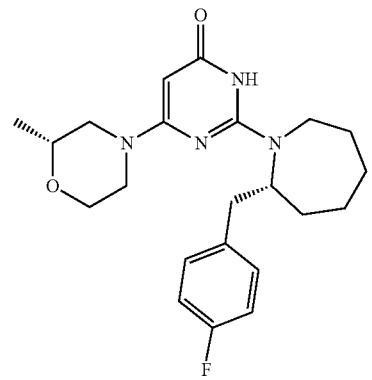 [SMILES: C[C@@H]1CN(c2cc(=O)[nH]c(N3CCCCC[C@@H]3Cc3ccc(F)cc3)n2)CCO1] |
| 307 | 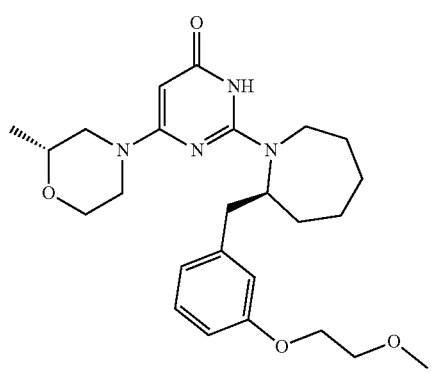 |
| 308 | 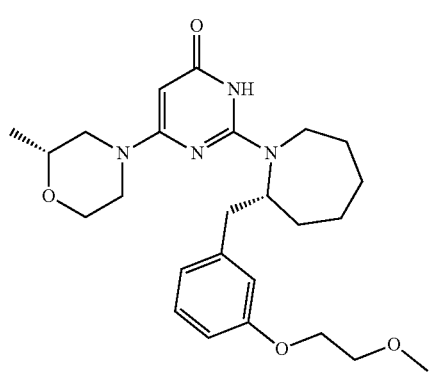 |
| Example | Structure |
|---|---|
| 309 | 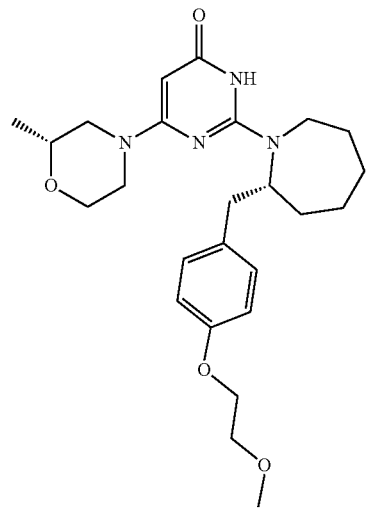 [SMILES: COCCOc1ccc(C[C@H]2CCCCCN2c2nc(N3CCO[C@H](C)C3)cc(=O)[nH]2)cc1] |
| 310 | |
| 311 | 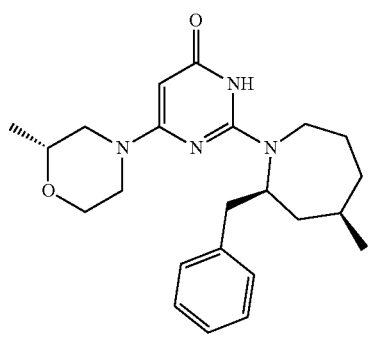 |

557
-continued
| Example | Structure |
|---|---|
| 312 | 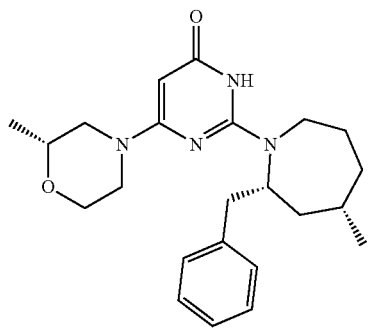 |
| 313 | 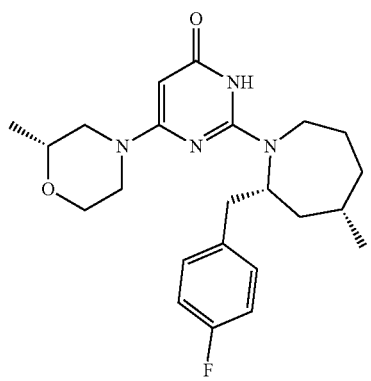 |
| 314 | 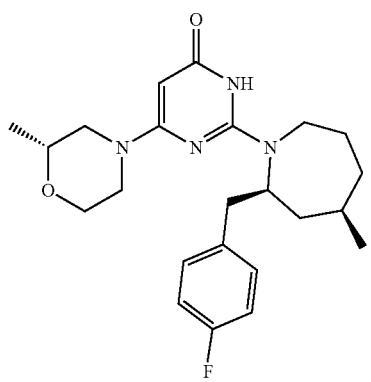 |
| 315 | 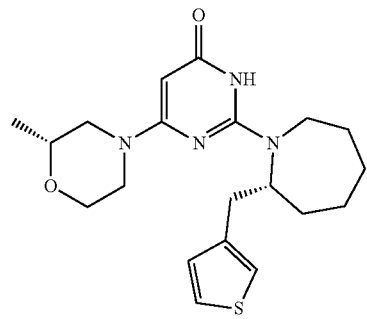 [SMILES: C[C@@H]1CN(c2cc(=O)[nH]c(N3CCCCC[C@@H]3Cc3ccsc3)n2)CCO1] |
558
-continued
| Example | Structure |
|---|---|
| 316 | 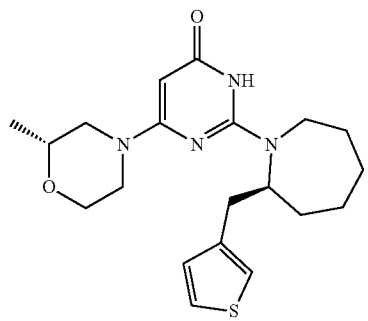 [SMILES: C[C@@H]1CN(c2cc(=O)[nH]c(N3CCCCC[C@H]3Cc3ccsc3)n2)CCO1] |
| 317 | 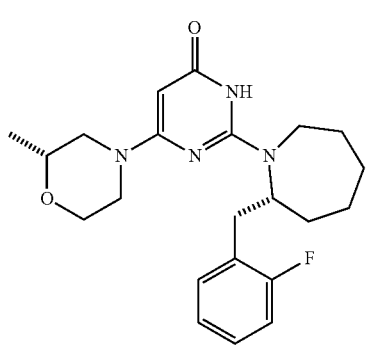 [SMILES: C[C@@H]1CN(c2cc(=O)[nH]c(N3CCCCC[C@@H]3Cc3ccccc3F)n2)CCO1] |
| 318 | 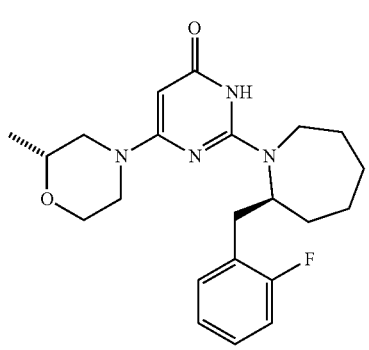 [SMILES: C[C@@H]1CN(c2cc(=O)[nH]c(N3CCCCC[C@H]3Cc3ccccc3F)n2)CCO1] |
| 319 | 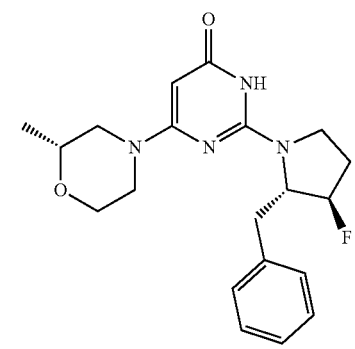 [SMILES: C[C@@H]1CN(c2cc(=O)[nH]c(N3CC[C@@H](F)[C@@H]3Cc3ccccc3)n2)CCO1] |

| Example | Structure |
|---|---|
| 320 | 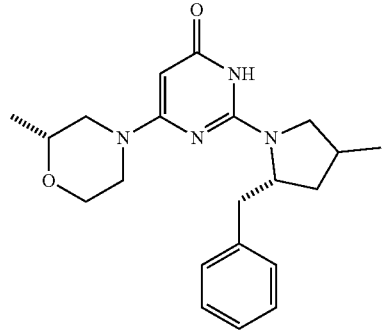 |
| 321 | 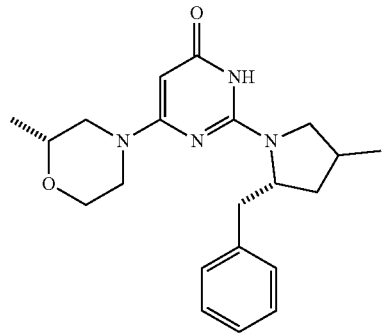 |
| 322 | 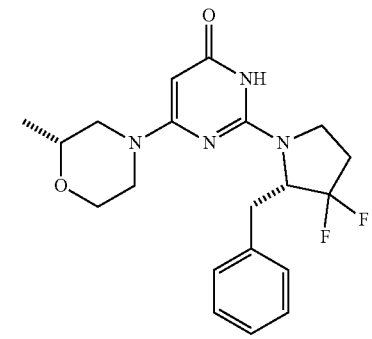 [SMILES: C[C@@H]1CN(c2cc(=O)[nH]c(N3CCC(F)(F)[C@@H]3Cc3ccccc3)n2)CCO1] |
| 323 | 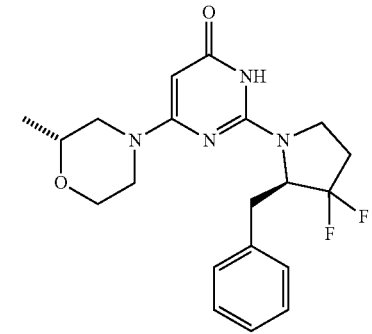 [SMILES: C[C@@H]1CN(c2cc(=O)[nH]c(N3CCC(F)(F)[C@H]3Cc3ccccc3)n2)CCO1] |
| Example | Structure |
|---|---|
| 324 | 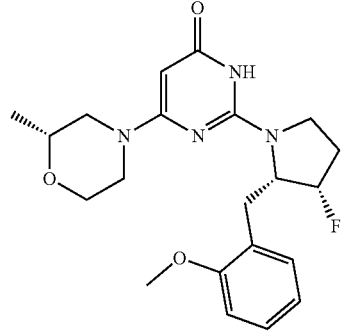 [SMILES: COc1ccccc1C[C@H]1[C@@H](F)CCN1c1nc(N2CCO[C@H](C)C2)cc(=O)[nH]1] |
| 325 | 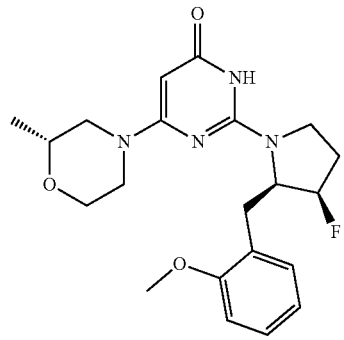 [SMILES: COc1ccccc1C[C@@H]1[C@H](F)CCN1c1nc(N2CCO[C@H](C)C2)cc(=O)[nH]1] |
| 326 | 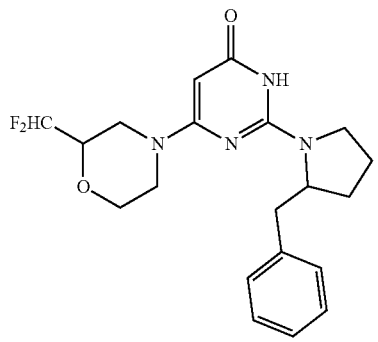 [SMILES: O=c1cc(N2CCOC(C(F)F)C2)nc(N2CCCC2Cc2ccccc2)[nH]1] |
| 327 | 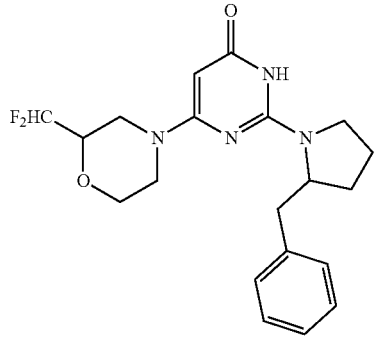 [SMILES: O=c1cc(N2CCOC(C(F)F)C2)nc(N2CCCC2Cc2ccccc2)[nH]1] |

| Example | Structure |
|---|---|
| 328 | 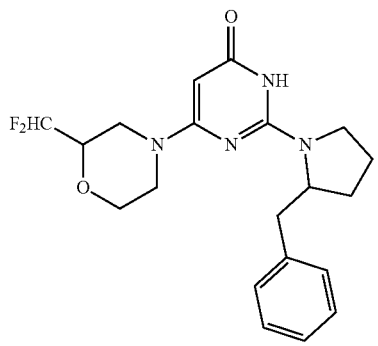 [SMILES: O=c1cc(N2CCOC(C(F)F)C2)nc(N2CCCC2Cc2ccccc2)[nH]1] |
| 329 | 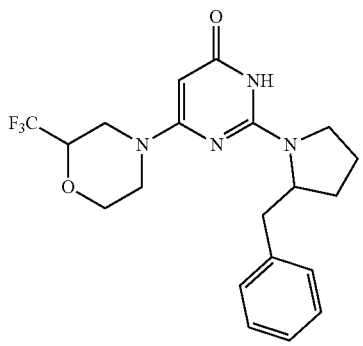 |
| 330 | 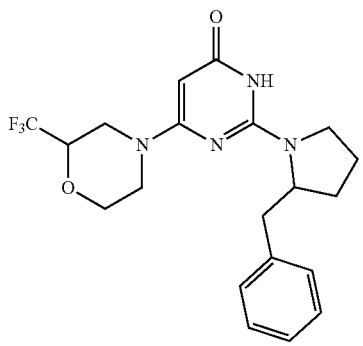 [SMILES: O=c1cc(N2CCOC(C(F)(F)F)C2)nc(N2CCCC2Cc2ccccc2)[nH]1] |
| 331 | 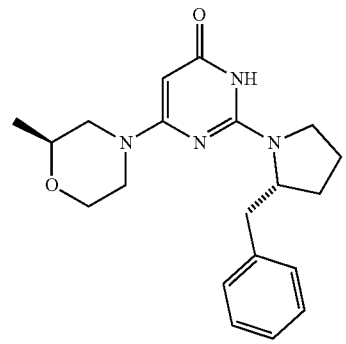 [SMILES: C[C@H]1CN(c2cc(=O)[nH]c(N3CCC[C@@H]3Cc3ccccc3)n2)CCO1] |
| Example | Structure |
|---|---|
| 332 | 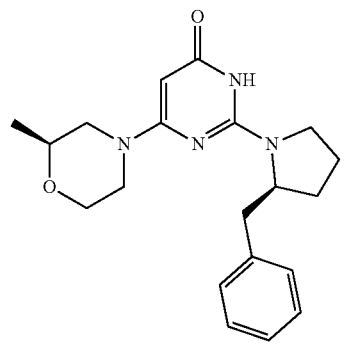 [SMILES: C[C@H]1CN(c2cc(=O)[nH]c(N3CCC[C@H]3Cc3ccccc3)n2)CCO1] |
| 333 | 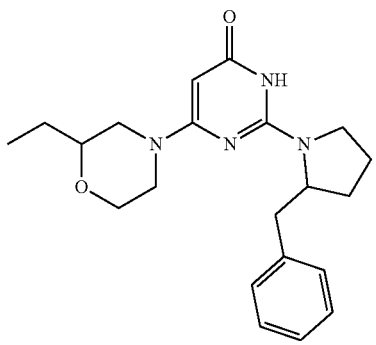 [SMILES: CCC1CN(c2cc(=O)[nH]c(N3CCCC3Cc3ccccc3)n2)CCO1] |
| 334 | 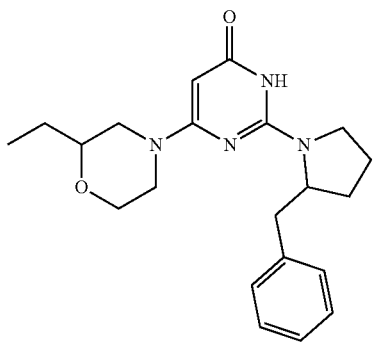 [SMILES: CCC1CN(c2cc(=O)[nH]c(N3CCCC3Cc3ccccc3)n2)CCO1] |
| 335 | 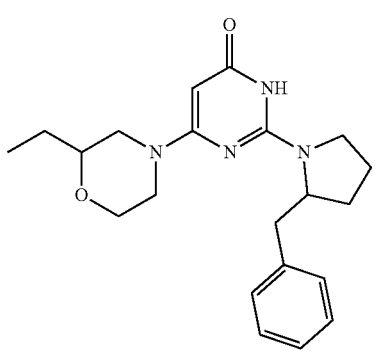 [SMILES: CCC1CN(c2cc(=O)[nH]c(N3CCCC3Cc3ccccc3)n2)CCO1] |

| Example | Structure |
|---|---|
| 336 | *(6-(2-ethylmorpholin-4-yl)-2-(2-benzylpyrrolidin-1-yl)pyrimidin-4(3H)-one)* |
| 337 | *(6-(2-cyclopropylmorpholin-4-yl)-2-(2-benzylpyrrolidin-1-yl)pyrimidin-4(3H)-one)* |
| 338 | *(6-(2-cyclopropylmorpholin-4-yl)-2-(2-benzylpyrrolidin-1-yl)pyrimidin-4(3H)-one isomer)* |
| 339 | *(6-(3-methylmorpholin-4-yl)-2-(2-benzylpyrrolidin-1-yl)pyrimidin-4(3H)-one)* |
| 340 | *(6-(3-methylmorpholin-4-yl)-2-(2-benzylpyrrolidin-1-yl)pyrimidin-4(3H)-one isomer)* |
| 341 | *(6-(3-methylmorpholin-4-yl)-2-(2-benzylpyrrolidin-1-yl)pyrimidin-4(3H)-one isomer)* |
| 342 | *(6-(3-methylmorpholin-4-yl)-2-(2-benzylpyrrolidin-1-yl)pyrimidin-4(3H)-one isomer)* |
| 343 | *(6-((2S,6R)-2,6-dimethylmorpholin-4-yl)-2-((S)-2-benzylpyrrolidin-1-yl)pyrimidin-4(3H)-one)* |

TABLE-continued

| Example | Structure |
|---------|-----------|
| 344 | 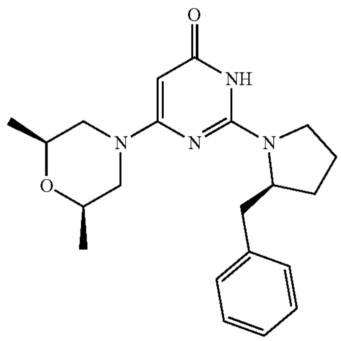 [SMILES: C[C@@H]1CN(c2cc(=O)[nH]c(N3CCC[C@H]3Cc3ccccc3)n2)C[C@H](C)O1] |
| 345 | 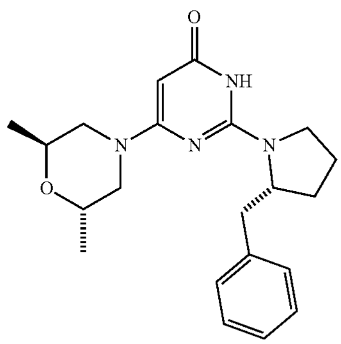 [SMILES: C[C@H]1CN(c2cc(=O)[nH]c(N3CCC[C@@H]3Cc3ccccc3)n2)C[C@H](C)O1] |
| 346 | 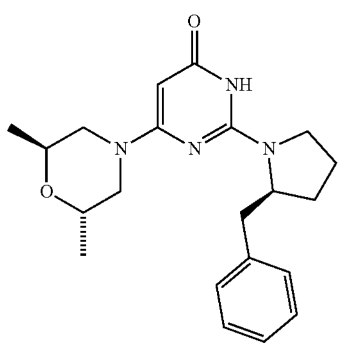 [SMILES: C[C@H]1CN(c2cc(=O)[nH]c(N3CCC[C@H]3Cc3ccccc3)n2)C[C@H](C)O1] |
| 347 | 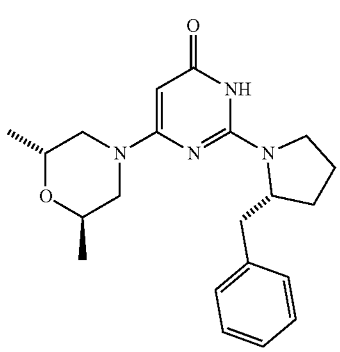 [SMILES: C[C@@H]1CN(c2cc(=O)[nH]c(N3CCC[C@@H]3Cc3ccccc3)n2)C[C@@H](C)O1] |
| 348 | |
| 349 | |
| 350 | |
| 351 | |

| Example | Structure |
|---|---|
| 352 | 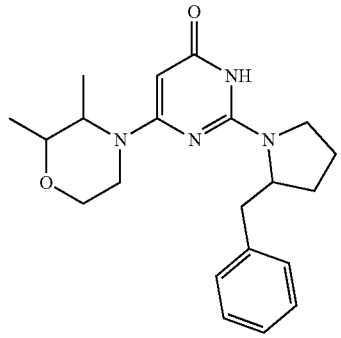 [SMILES: CC1OCCN(c2cc(=O)[nH]c(N3CCCC3Cc3ccccc3)n2)C1C] |
| 353 | 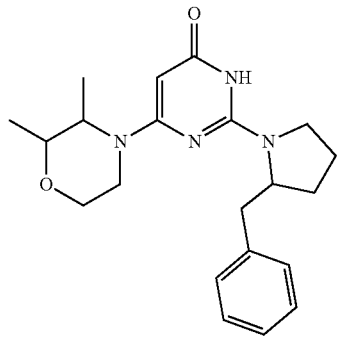 [SMILES: CC1OCCN(c2cc(=O)[nH]c(N3CCCC3Cc3ccccc3)n2)C1C] |
| 354 | 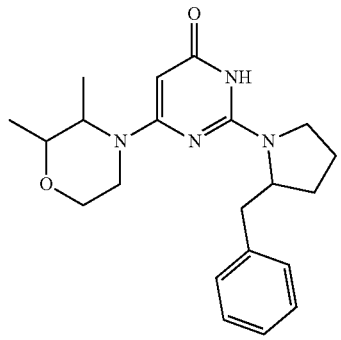 [SMILES: CC1OCCN(c2cc(=O)[nH]c(N3CCCC3Cc3ccccc3)n2)C1C] |
| 355 | 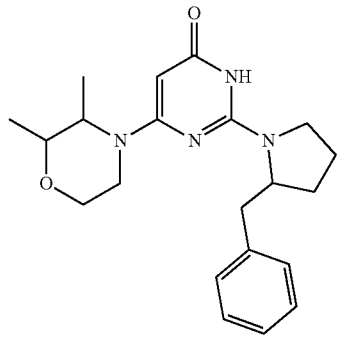 [SMILES: CC1OCCN(c2cc(=O)[nH]c(N3CCCC3Cc3ccccc3)n2)C1C] |

| Example | Structure |
|---|---|
| 356 | 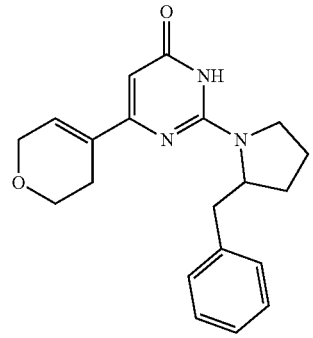 [SMILES: O=c1cc(C2=CCOCC2)nc(N2CCCC2Cc2ccccc2)[nH]1] | or a pharmaceutically acceptable salt thereof.

31. A pharmaceutical composition comprising a compound of claim 1, or a pharmaceutically acceptable salt thereof, and a pharmaceutically acceptable carrier.

32. A method for treating a condition or disorder mediated by an ATM kinase in a patient in need thereof comprising administering to the patient a therapeutically effective amount of a compound of claim 1, wherein the condition or disorder is Huntington's disease.

33. A compound which is:

| | |
|---|---|
| 56 | 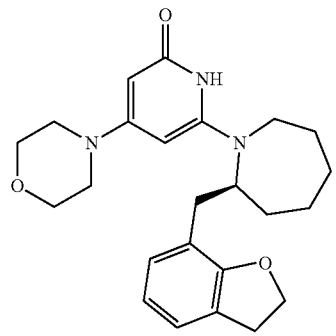 [SMILES: O=c1cc(N2CCOCC2)cc(N2CCCCC[C@H]2Cc2cccc3c2OCC3)[nH]1] |
| 57 | 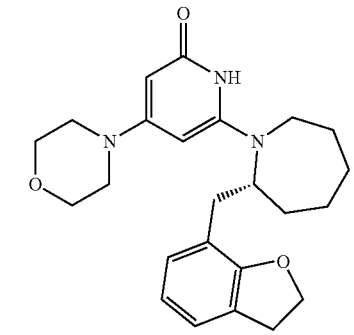 [SMILES: O=c1cc(N2CCOCC2)cc(N2CCCCC[C@@H]2Cc2cccc3c2OCC3)[nH]1] |

| | | | |
|---|---|---|---|
| 70 | 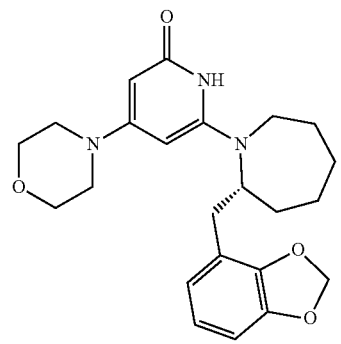 [SMILES: O=c1cc(N2CCOCC2)cc(N2CCCCC[C@@H]2Cc2cccc3c2OCO3)[nH]1] | 170 | 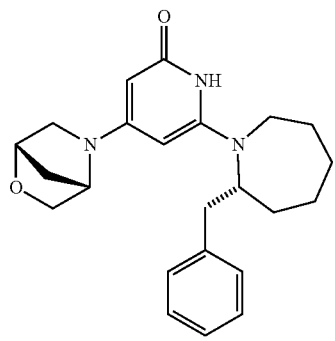 |
| 71 | 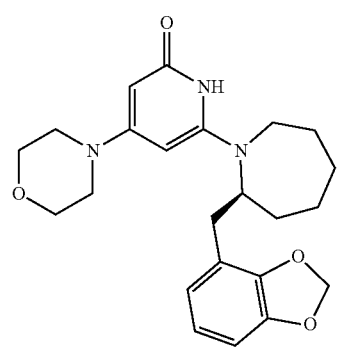 [SMILES: O=c1cc(N2CCOCC2)cc(N2CCCCC[C@H]2Cc2cccc3c2OCO3)[nH]1] | 225 | 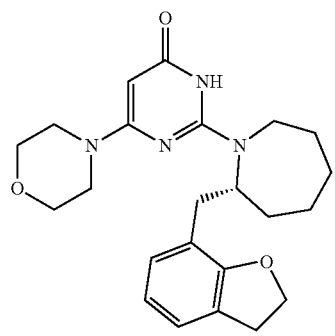 |
| 112 | 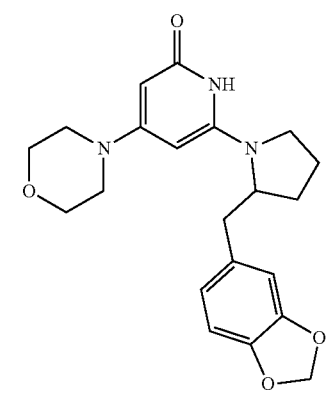 [SMILES: O=c1cc(N2CCOCC2)cc(N2CCCC2Cc2ccc3c(c2)OCO3)[nH]1] | 226 | 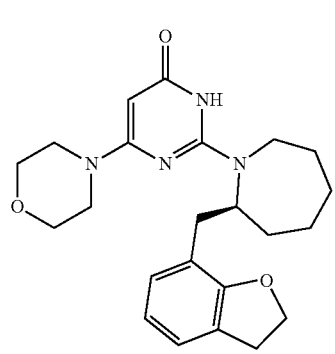 |
| 169 | 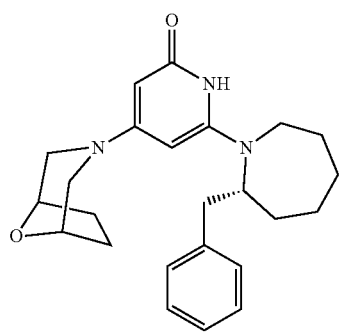 [SMILES: O=c1cc(N2CC3CCC(C2)O3)cc(N2CCCCC[C@@H]2Cc2ccccc2)[nH]1] | 305 | 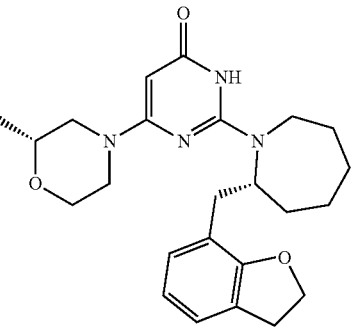 [SMILES: C[C@@H]1CN(c2cc(=O)[nH]c(N3CCCCC[C@@H]3Cc3cccc4c3OCC4)n2)CCO1] |

| 306 | [Chemical structure: 2-{2-[(2,3-dihydro-1-benzofuran-7-yl)methyl]azepan-1-yl}-6-[(2S)-2-methylmorpholin-4-yl]pyrimidin-4(3H)-one] |
|---|---| or a pharmaceutically acceptable salt thereof.

34. A pharmaceutical composition comprising a compound of claim 30, or a pharmaceutically acceptable salt thereof, and a pharmaceutically acceptable carrier.

35. A pharmaceutical composition comprising a compound of claim 33, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 11,685,734 B2  
APPLICATION NO. : 17/111307  
DATED : June 27, 2023  
INVENTOR(S) : Leticia M. Toledo-Sherman et al.

Page 1 of 27

It is certified that error appears in the above-identified patent and that said Letters Patent is hereby corrected as shown below:

In the Claims

In Claim 9, Column 478, Line 43, please replace "hereocycloalkyl ring" with --heterocycloalkyl ring--.

In Claim 30, Column 486, Lines 34-48, please replace " 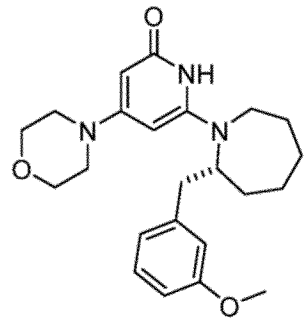 " with

-- 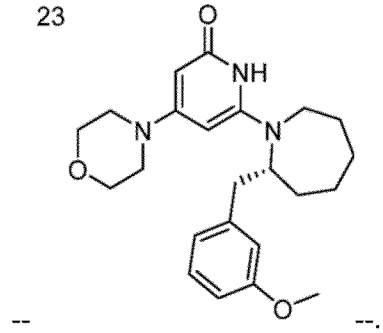 --.

Signed and Sealed this  
Twelfth Day of November, 2024

Katherine Kelly Vidal  
*Director of the United States Patent and Trademark Office*

In Claim 30, Column 487, Lines 5-18, please replace " 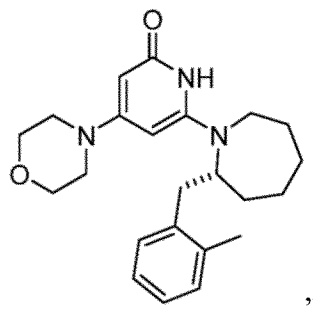 " with
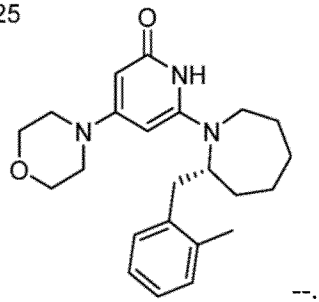
-- --.
In Claim 30, Column 514, Lines 5-18, please replace " 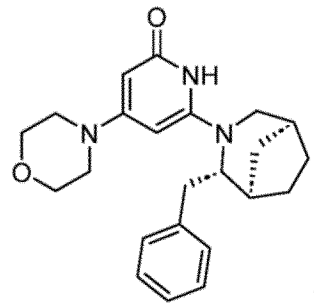 " with
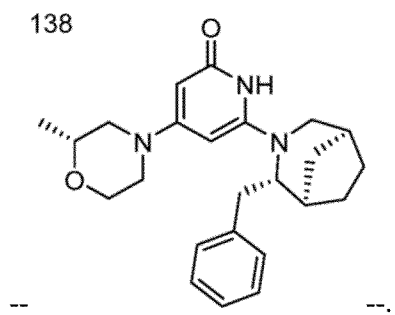
-- --.

CERTIFICATE OF CORRECTION (continued)
U.S. Pat. No. 11,685,734 B2

In Claim 30, Column 515, Lines 31-48, please replace " 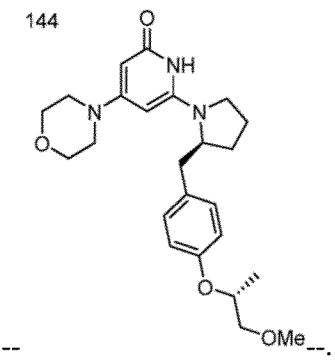 " with 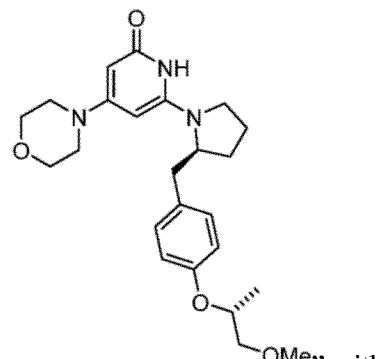 --.

In Claim 30, Column 515, Lines 50-66, please replace " 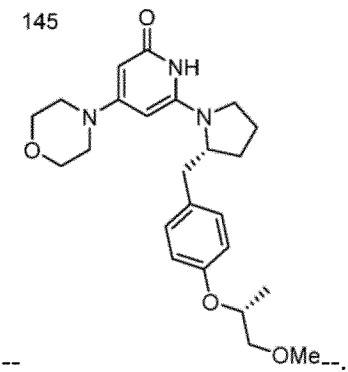 " with 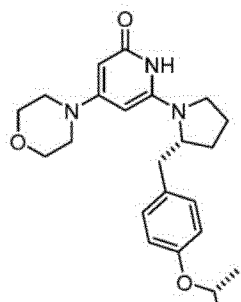 --.

CERTIFICATE OF CORRECTION (continued)
U.S. Pat. No. 11,685,734 B2

In Claim 30, Column 517, Lines 25-42, please replace " 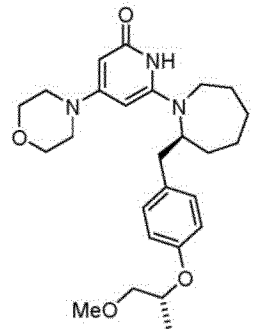 " with

-- --.

In Claim 30, Column 517, Lines 47-64, please replace " 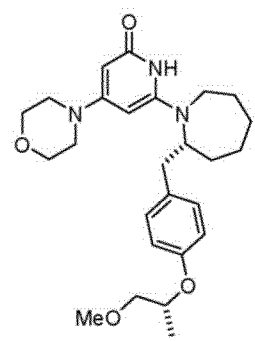 " with

151

-- --.

CERTIFICATE OF CORRECTION (continued)
U.S. Pat. No. 11,685,734 B2

In Claim 30, Column 521, Lines 52-64, please replace " 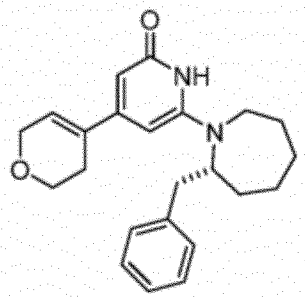 " with 

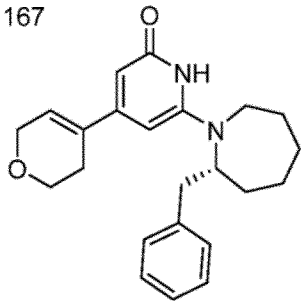

--        --.

In Claim 30, Column 522, Lines 19-33, please replace " 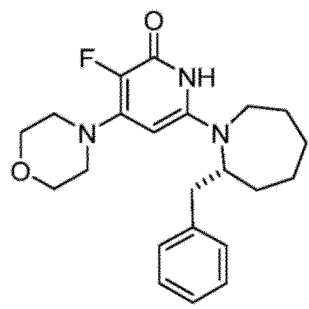 " with 

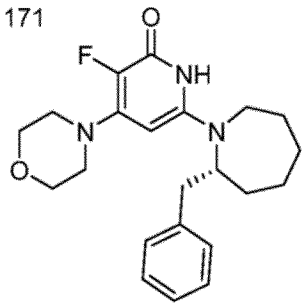

--        --.

In Claim 30, Column 528, Lines 53-64, please replace " 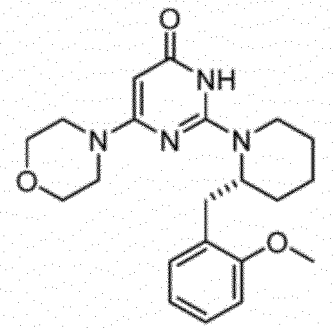 " with
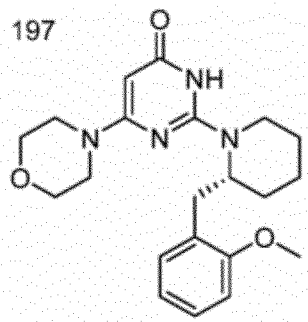
-- --.
In Claim 30, Column 541, Lines 32-44, please replace " 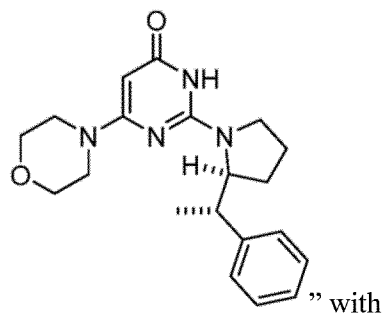 " with
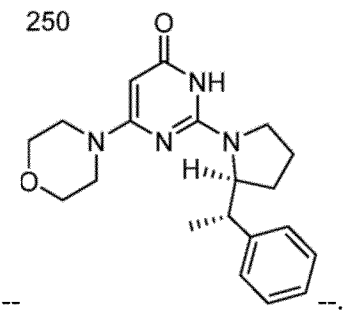
-- --.

CERTIFICATE OF CORRECTION (continued)
U.S. Pat. No. 11,685,734 B2

In Claim 30, Column 542, Lines 5-18, please replace " 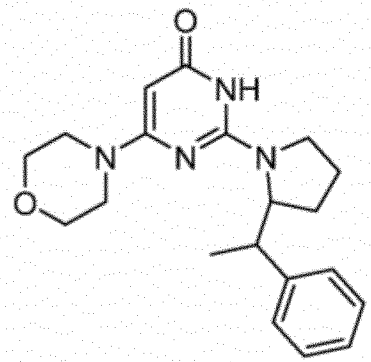 " with

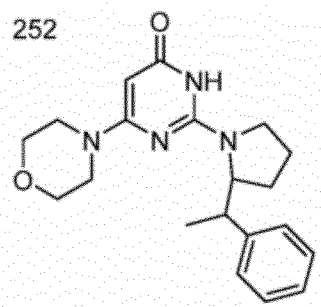

-- --.

In Claim 30, Column 542, Lines 51-63, please replace " 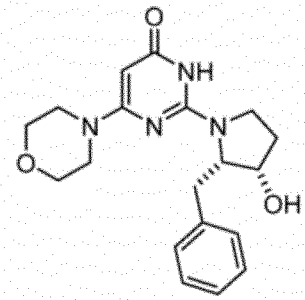 " with

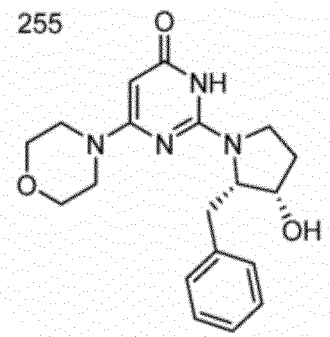

-- --.

CERTIFICATE OF CORRECTION (continued)
U.S. Pat. No. 11,685,734 B2

In Claim 30, Column 543, Lines 34-47, please replace " 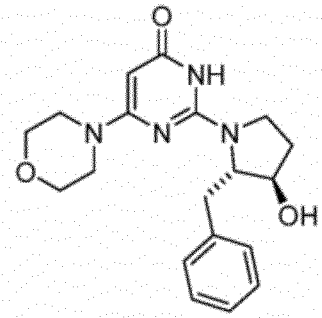 " with

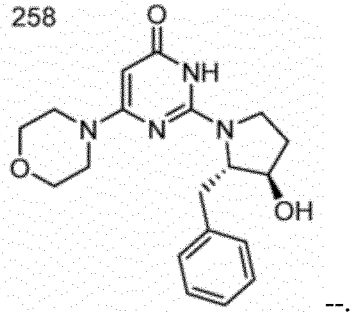

-- --.

In Claim 30, Column 546, Lines 34-48, please replace " 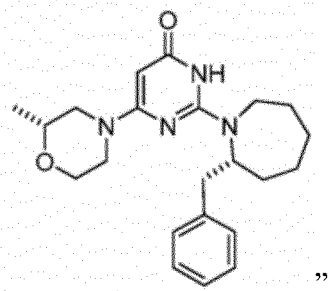 " with

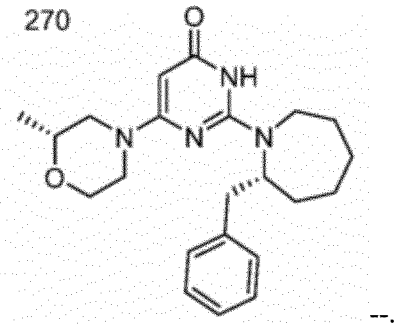

-- --.

In Claim 30, Column 546, Lines 50-64, please replace " 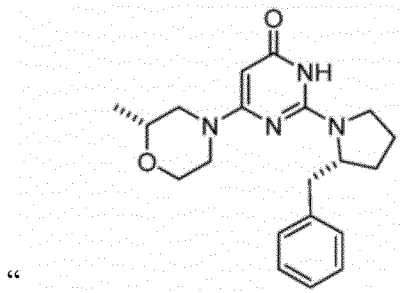 " with 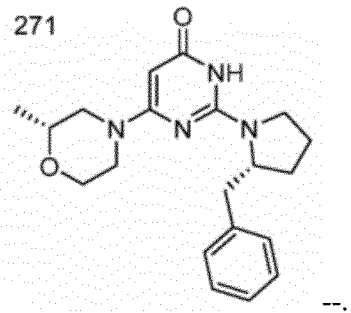 --.
In Claim 30, Column 547, Lines 5-18, please replace " 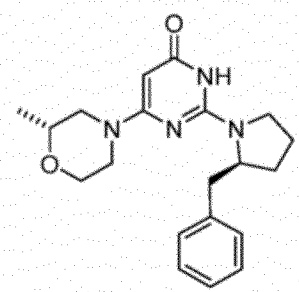 " with 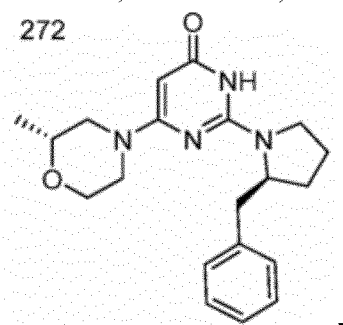 --.

In Claim 30, Column 558, Lines 19-31, please replace " 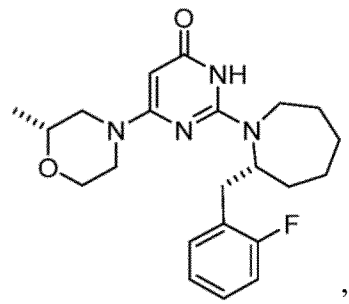 " with
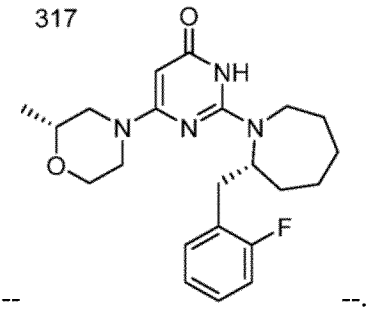
--              --.
In Claim 30, Column 558, Lines 33-45, please replace " 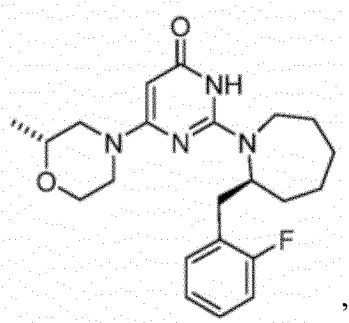 " with
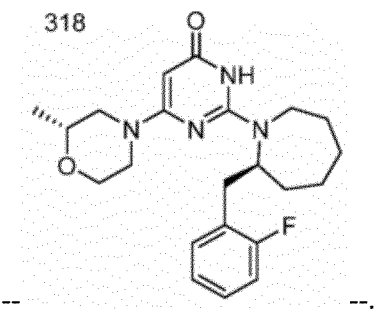
--              --.

In Claim 30, Column 559, Lines 5-18, please replace " 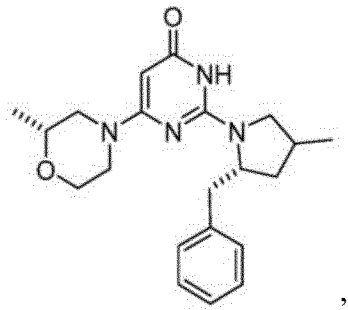 " with
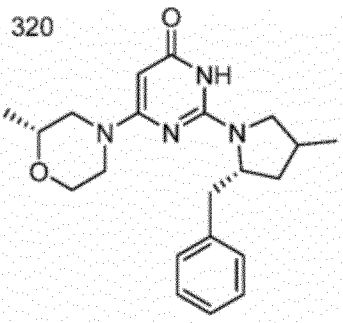 --.
In Claim 30, Column 559, Lines 20-32, please replace " 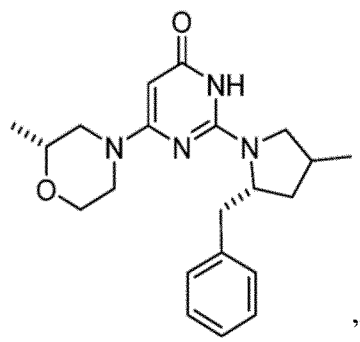 " with
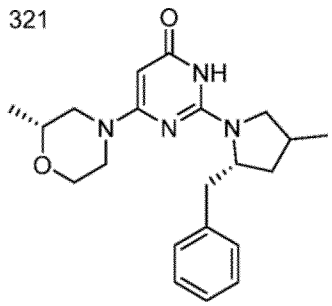 --.

CERTIFICATE OF CORRECTION (continued)
U.S. Pat. No. 11,685,734 B2

In Claim 30, Column 559, Lines 34-46, please replace " 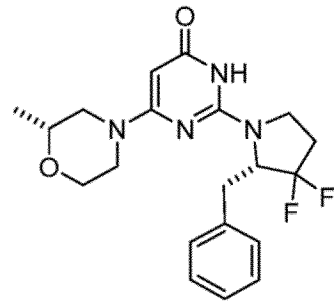 " with

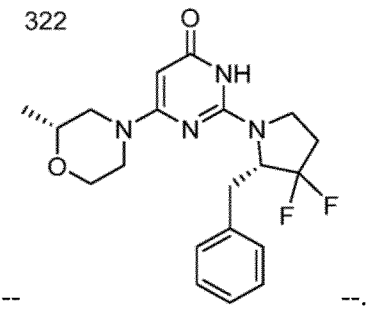

--        --.

In Claim 30, Column 559, Lines 52-64, please replace " 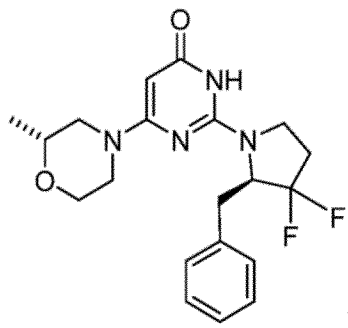 " with

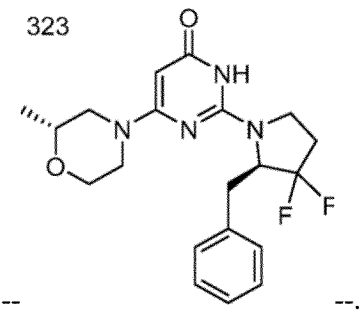

--        --.

CERTIFICATE OF CORRECTION (continued)
U.S. Pat. No. 11,685,734 B2

In Claim 30, Column 560, Lines 34-46, please replace " 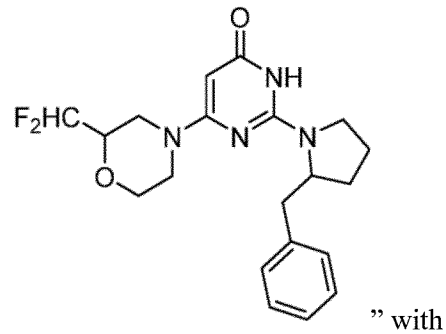 " with

-- 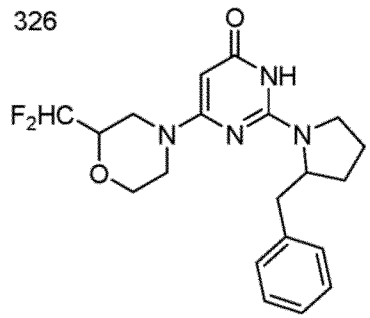 --.

In Claim 30, Column 560, Lines 52-65, please replace " 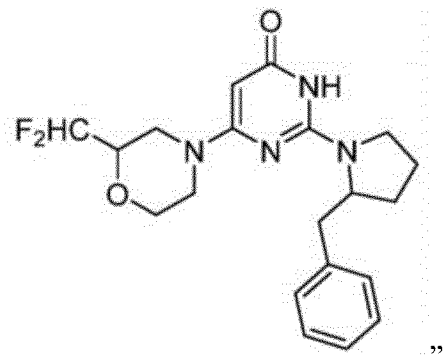 "

with -- 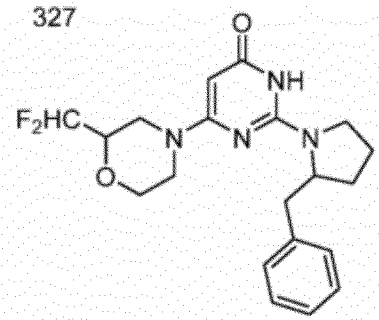 --.

CERTIFICATE OF CORRECTION (continued)
U.S. Pat. No. 11,685,734 B2

In Claim 30, Column 561, Lines 5-18, please replace " 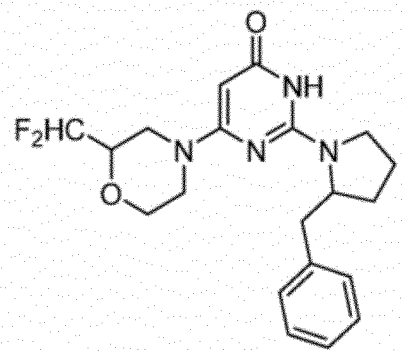 " with 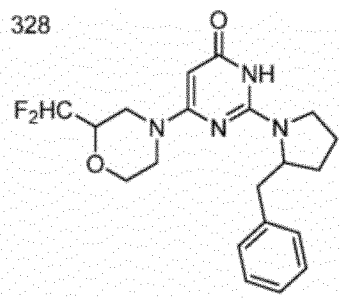 --.

In Claim 30, Column 561, Lines 20-33, please replace " 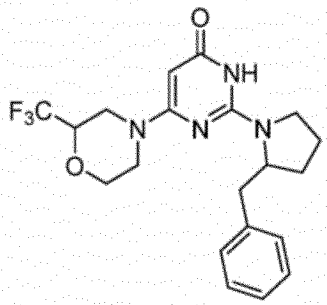 " with 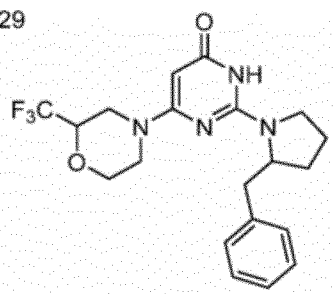 --.

In Claim 30, Column 561, Lines 34-47, please replace " 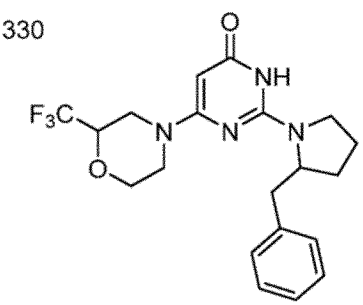 " with 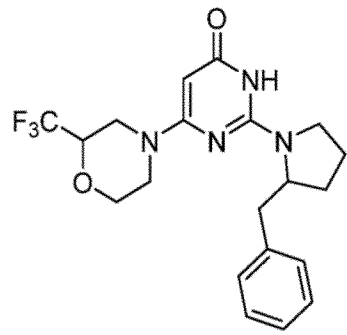
-- enantiomeric mixture 3 & 4 --.
In Claim 30, Column 561, Lines 52-64, please replace " 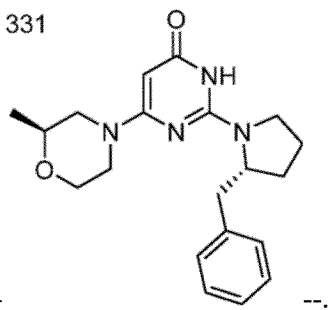 " with 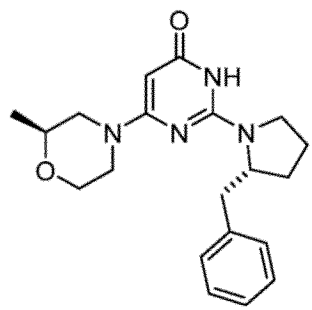
-- --.

CERTIFICATE OF CORRECTION (continued)
U.S. Pat. No. 11,685,734 B2

In Claim 30, Column 562, Lines 20-33, please replace " 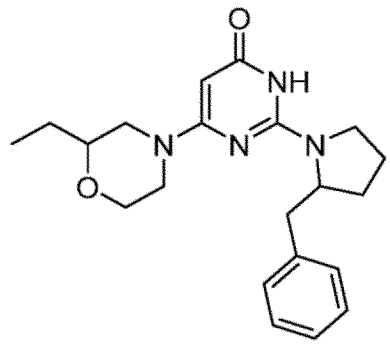 " with

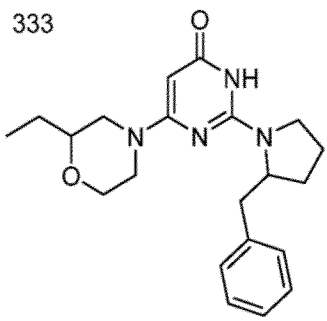

-- --.

In Claim 30, Column 562, Lines 34-48, please replace " 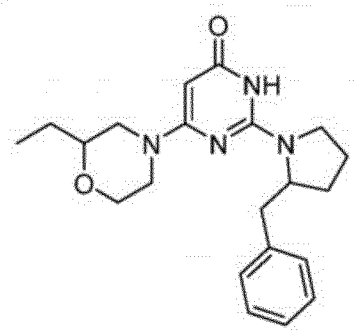 " with

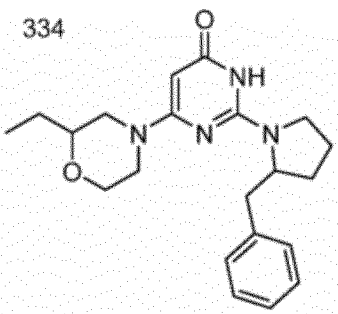

-- --.

335
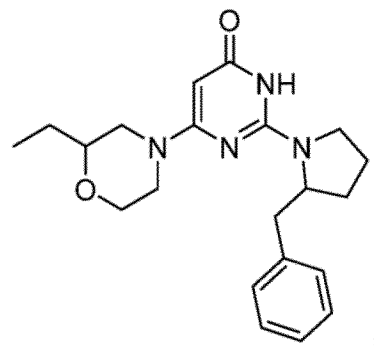
In Claim 30, Column 562, Lines 51-63, please replace " 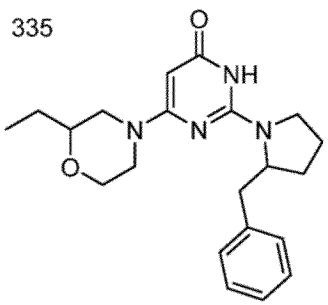 " with
-- 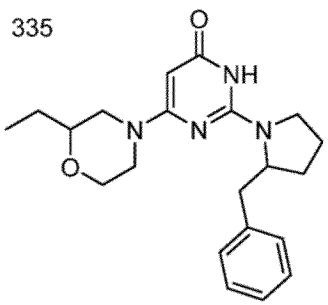 --.
stereoisomer 3
336
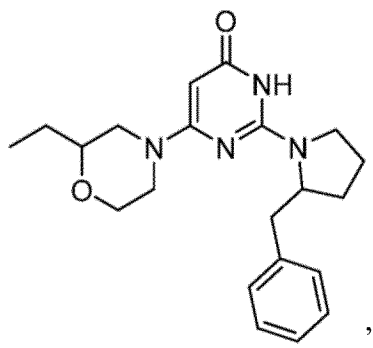
In Claim 30, Column 563, Lines 5-18, please replace " 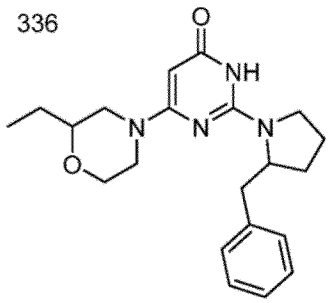 " with
-- 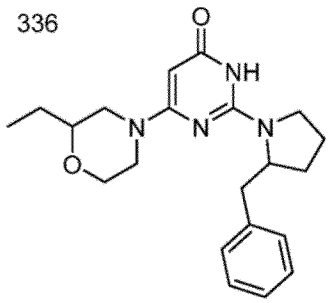 --.
stereoisomer 4

In Claim 30, Column 563, Lines 20-33, please replace " 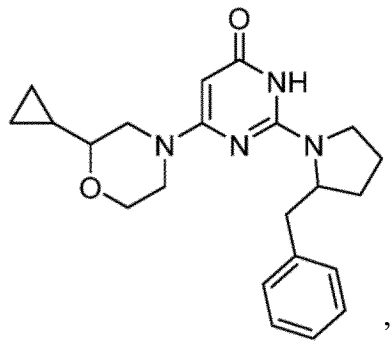 " with
337 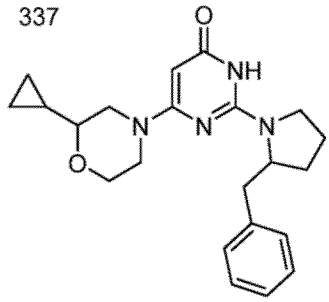
-- stereoisomer 1 --.
In Claim 30, Column 563, Lines 35-46, please replace " 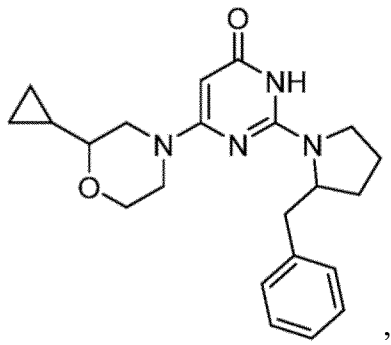 " with
338 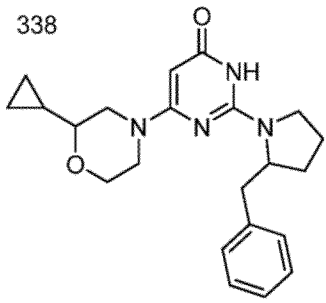
-- stereoisomer 2 --.

339
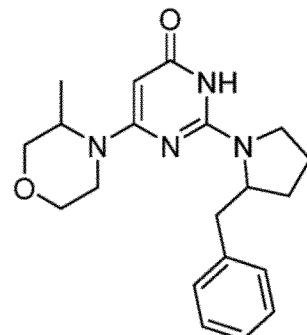
In Claim 30, Column 563, Lines 51-64, please replace " 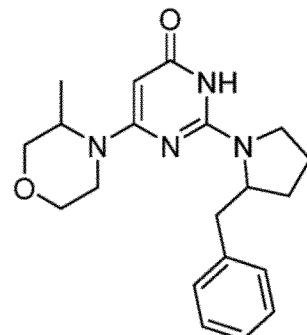 " with
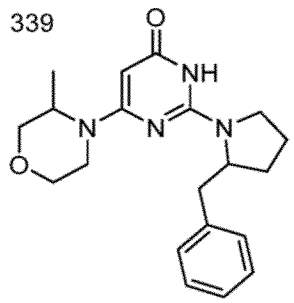
-- stereoisomer 1 --.
340
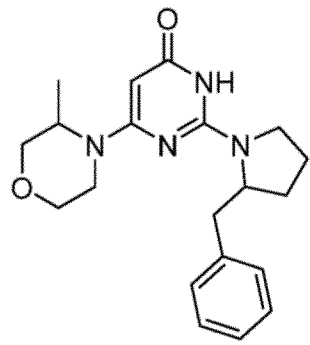
In Claim 30, Column 564, Lines 5-18, please replace " 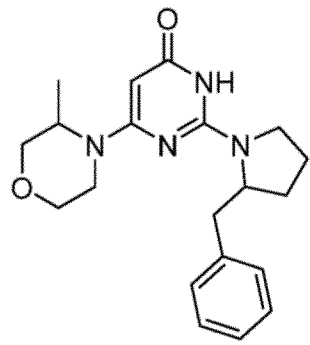 " with
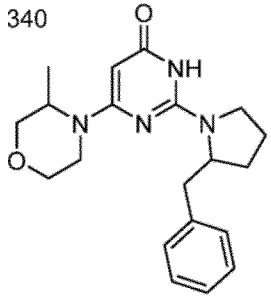
-- stereoisomer 2 --.

341
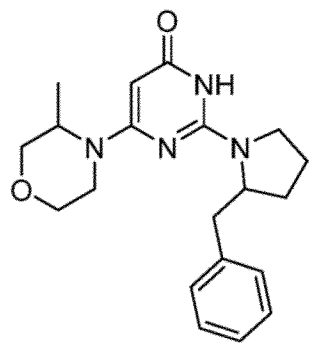
In Claim 30, Column 564, Lines 20-33, please replace " 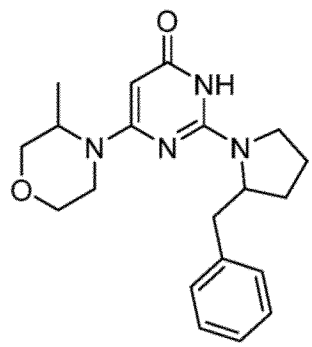 " with
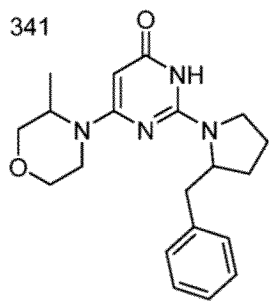
-- stereoisomer 3 --.
342
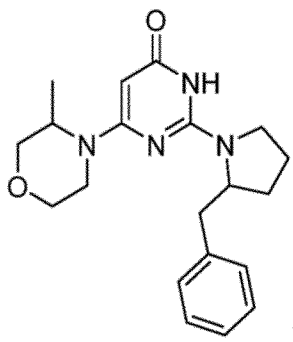
In Claim 30, Column 564, Lines 34-47, please replace " 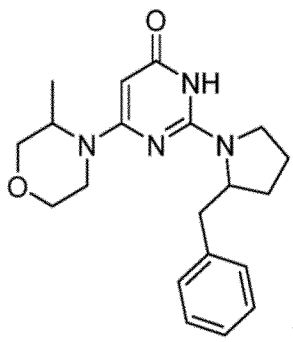 " with
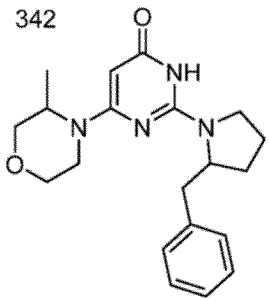
-- stereoisomer 4 --.

In Claim 30, Column 564, Lines 51-64, please replace " 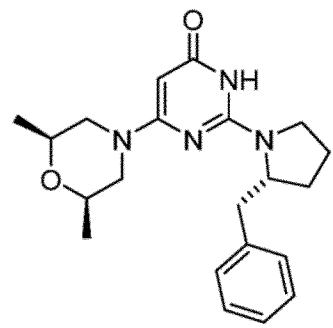 " with
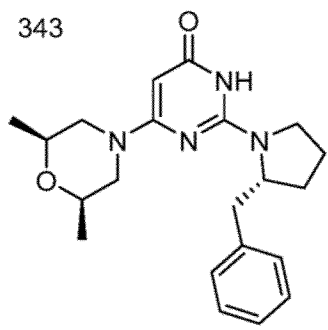 --.
In Claim 30, Column 565, Lines 20-32, please replace " 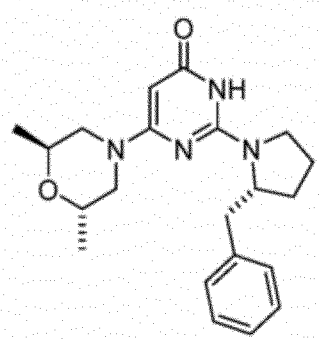 " with
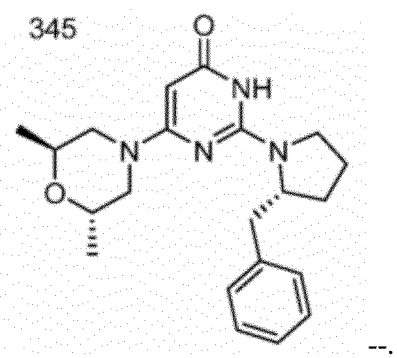 --.

CERTIFICATE OF CORRECTION (continued)
U.S. Pat. No. 11,685,734 B2

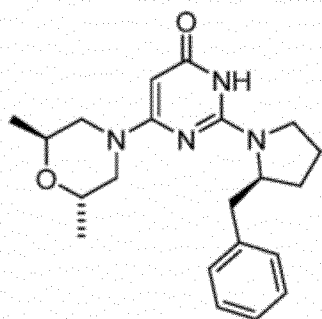

In Claim 30, Column 565, Lines 34-46, please replace " 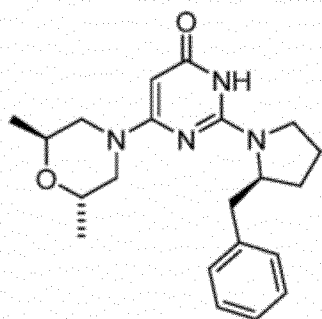 " with

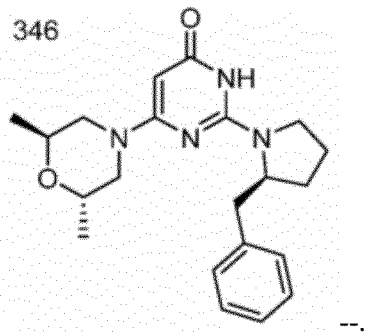

-- --.

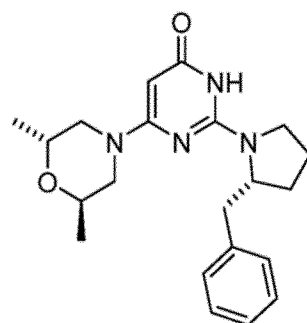

In Claim 30, Column 565, Lines 52-64, please replace " 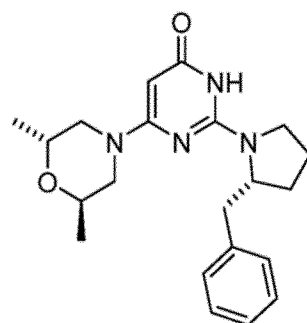 " with

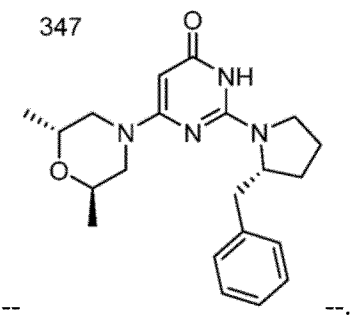

-- --.

In Claim 30, Column 566, Lines 5-18, please replace " 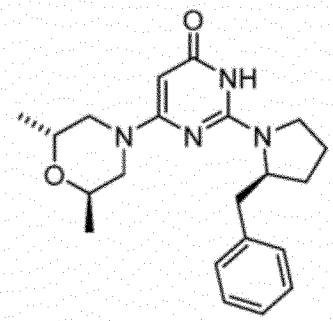 " with 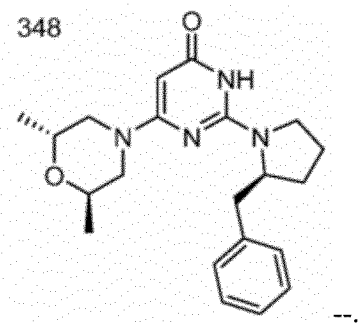 --.
In Claim 30, Column 566, Lines 20-33, please replace " 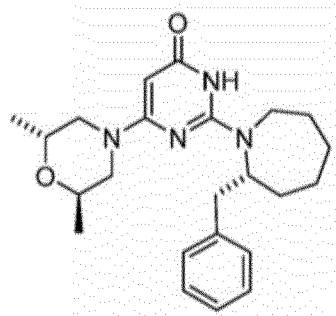 " with 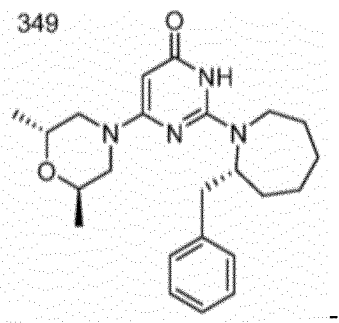 --.

In Claim 30, Column 566, Lines 34-46, please replace " 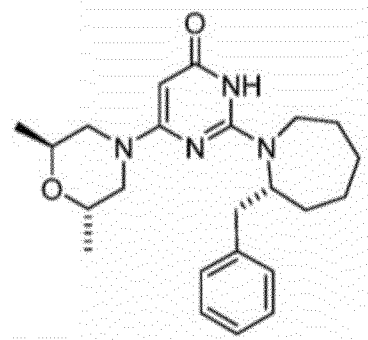 " with 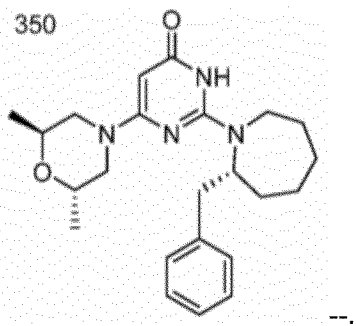 .
In Claim 30, Column 566, Lines 51-64, please replace " 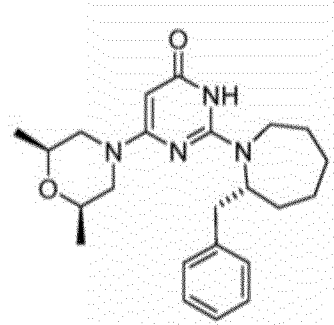 " with 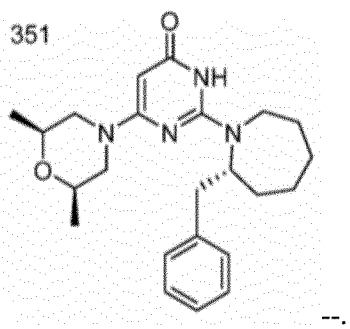 .

In Claim 30, Column 567, Lines 5-18, please replace " 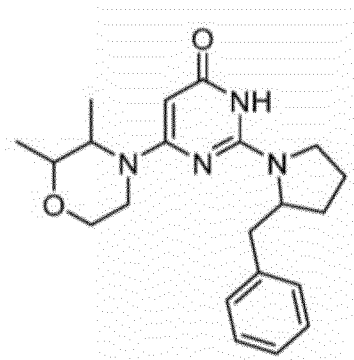 " with 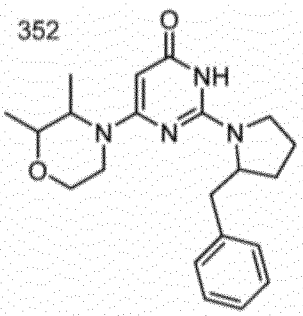 --.
In Claim 30, Column 567, Lines 20-33, please replace " 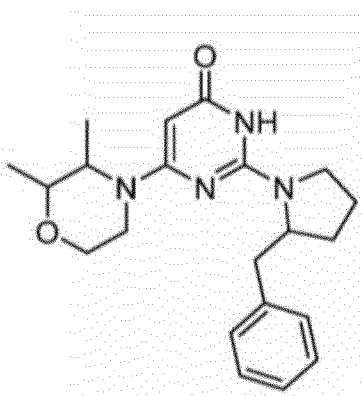 " with 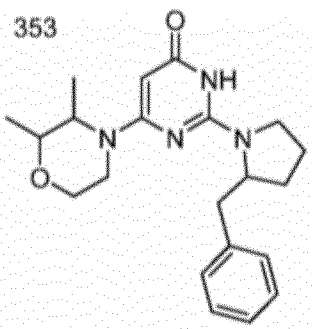 --.

CERTIFICATE OF CORRECTION (continued)
U.S. Pat. No. 11,685,734 B2

In Claim 30, Column 567, Lines 34-46, please replace " 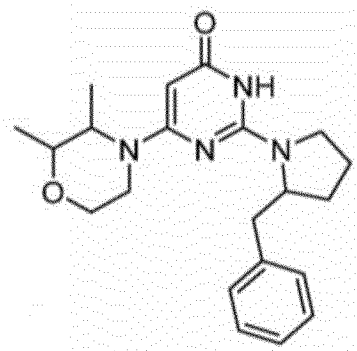 " with 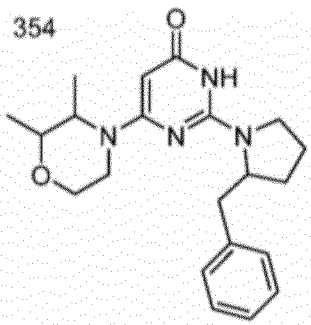 --.

In Claim 30, Column 567, Lines 52-63, please replace " 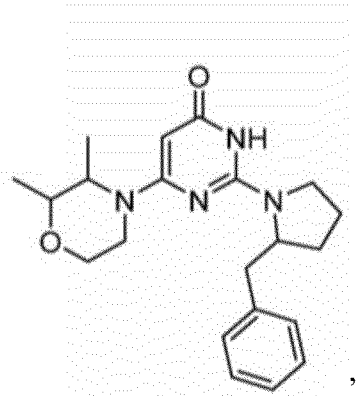 " with 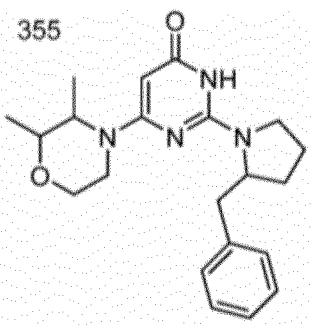 --.

CERTIFICATE OF CORRECTION (continued) Page 27 of 27
U.S. Pat. No. 11,685,734 B2

In Claim 33, Column 570, Lines 3-15, please replace " 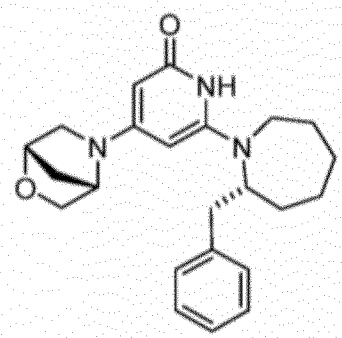 " with 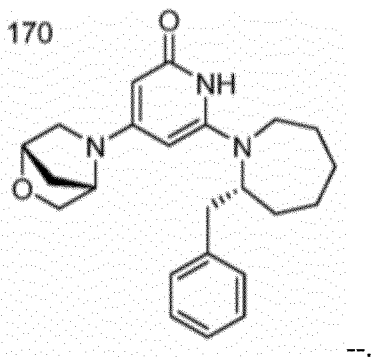 --.